US008952049B2

(12) United States Patent
Ruah et al.

(10) Patent No.: US 8,952,049 B2
(45) Date of Patent: *Feb. 10, 2015

(54) MODULATORS OF ATP-BINDING CASSETTE TRANSPORTERS

(71) Applicant: Vertex Pharmaceuticals Incorporated, Cambridge, MA (US)

(72) Inventors: Sara Sabina Hadida Ruah, La Jolla, CA (US); Peter Diederik Jan Grootenhuis, San Diego, CA (US); Fredrick F. Van Goor, San Diego, CA (US); Jinglan Zhou, San Diego, CA (US); Brian Richard Bear, Oceanside, CA (US); Mark Thomas Miller, San Diego, CA (US); Jason McCartney, Cardiff-by-the-Sea, CA (US); Mehdi Michel Djamel Numa, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/781,392

(22) Filed: Feb. 28, 2013

(65) Prior Publication Data

US 2013/0178471 A1    Jul. 11, 2013

Related U.S. Application Data

(60) Continuation of application No. 12/948,162, filed on Nov. 17, 2010, now Pat. No. 8,575,209, which is a continuation of application No. 12/767,472, filed on Apr. 26, 2010, now Pat. No. 8,623,905, which is a continuation of application No. 12/619,412, filed on Nov. 16, 2009, now Pat. No. 8,415,387, which is a division of application No. 11/975,297, filed on Oct. 18, 2007, now Pat. No. 7,645,789, which is a continuation-in-part of application No. 11/786,001, filed on Apr. 9, 2007, now Pat. No. 7,776,905.

(60) Provisional application No. 60/790,459, filed on Apr. 7, 2006.

(51) Int. Cl.
*A61K 31/36* (2006.01)
*C07D 405/12* (2006.01)
*C07D 209/08* (2006.01)
*C07D 471/04* (2006.01)
*C07D 233/64* (2006.01)
*C07D 403/12* (2006.01)

(52) U.S. Cl.
CPC ............ *C07D 405/12* (2013.01); *C07D 209/08* (2013.01); *C07D 471/04* (2013.01); *C07D 233/64* (2013.01); *C07D 403/12* (2013.01)
USPC .......................................... 514/414; 548/526

(58) Field of Classification Search
USPC .......................................... 548/526; 514/414
See application file for complete search history.

(56) References Cited

U.S. PATENT DOCUMENTS

| | | | |
|---|---|---|---|
| 5,304,121 A | 4/1994 | Sahatjian |
| 5,886,026 A | 3/1999 | Hunter et al. |
| 6,099,562 A | 8/2000 | Ding et al. |
| 6,777,400 B2 | 8/2004 | Biggadike et al. |
| 6,992,096 B2 | 1/2006 | Karp et al. |
| 7,202,262 B2 | 4/2007 | Karp et al. |
| 7,304,080 B2 | 12/2007 | Karp et al. |
| 7,407,976 B2 | 8/2008 | Miller et al. |
| 7,419,991 B2 | 9/2008 | Karp et al. |
| 7,495,103 B2 | 2/2009 | Hadida-Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,772,259 B2 | 8/2010 | Karp et al. |
| 7,776,905 B2 | 8/2010 | Hadida-Ruah et al. |
| 7,846,951 B2 | 12/2010 | Miller et al. |

(Continued)

FOREIGN PATENT DOCUMENTS

| | | |
|---|---|---|
| EP | 1380576 | 1/2004 |
| WO | WO 9506046 | 3/1995 |

(Continued)

OTHER PUBLICATIONS

Braun J., No association between the deltaF508 cystic fibrosis mutation and type 2 diabetes mellitus Exp Clin. Endocrinol Diabetes 107(8), (1999), 1.
Caira M R Crystalline Polymorphism of Organic Compounds—Topics of Current Chemistry Springer, Berlin, DE. vol. 198 (1998) pp. 163-208.
Cecil Textbook of Medicine, 20th Ed., 1996, vol. 2, pp. 1192-1996.
Cecil Textbook of Medicine, 20th Ed., 1996, vol. 2, pp. 2050-2057.
Dahl and Nordestgaard International Journal of COPD (2009) 4:157-167.
Definition of Amorphous in www.thefreedictionary.com/amorphous.
FDA mulls drug to slow late-stage Alzheimer's [online], [retrieved Sep. 23, 2003]. Retrieved from the internet, URL; http://www.cnn.com/2003/HEALTH/conditions/09/24/alzheimers.drug.ap/indexhtml.
Konno, et al., European Journal of Pharmaceuticals and Biopharmaceutics 70 (2308), pp. 493-499.
Stankovic, et al., Genetic Test Sep. 2008 12(3): 357-362.
Van Goor, et al., Am. J. Physiol. Lung Cell Mol. Physiol. (2006), 290: 1117-1130.
International Search Report, PCT/US20071008975, Aug. 18, 2011.

*Primary Examiner* — Shawquia Jackson
(74) *Attorney, Agent, or Firm* — Honigman Miller Schwartz and Cohn LLP; Heidi M. Berven; Jonathan P. O'Brien

(57) ABSTRACT

Compounds of the present invention and pharmaceutically acceptable compositions thereof, are useful as modulators of ATP-Binding Cassette ("ABC") transporters or fragments thereof, including Cystic Fibrosis Transmembrane Conductance Regulator ("CFTR"). The present invention also relates to methods of treating ABC transporter mediated diseases using compounds of the present invention.

3 Claims, No Drawings

(56) References Cited

U.S. PATENT DOCUMENTS

| | | |
|---|---|---|
| 7,956,052 B2 | 6/2011 | Hadida-Ruah et al. |
| 7,973,038 B2 | 7/2011 | Hadida-Ruah et al. |
| 7,973,169 B2 | 7/2011 | Hadida-Ruah et al. |
| 7,977,322 B2 | 7/2011 | Ruah et al. |
| 7,999,113 B2 | 8/2011 | Hadida-Ruah et al. |
| 8,012,699 B2 | 9/2011 | Ching |
| 8,039,491 B2 | 10/2011 | Hadida-Ruah et al. |
| 8,076,357 B2 | 12/2011 | Young et al. |
| 8,101,767 B2 | 1/2012 | Hadida-Ruah et al. |
| 8,124,781 B2 | 2/2012 | Siesel |
| 8,163,772 B2 | 4/2012 | Demattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Hadida-Ruah et al. |
| 8,299,099 B2 | 10/2012 | Hadida-Ruah et al. |
| 8,314,239 B2 | 11/2012 | Binch et al. |
| 8,314,256 B2 | 11/2012 | Ruah et al. |
| 8,318,733 B2 | 11/2012 | Hadida-Ruah et al. |
| 8,324,207 B2 | 12/2012 | Hadida-Ruah et al. |
| 8,324,242 B2 | 12/2012 | Hadida-Ruah et al. |
| 8,344,147 B2 | 1/2013 | Ambhaikar et al. |
| 8,354,427 B2 | 1/2013 | VanGoor et al. |
| 8,362,253 B2 | 1/2013 | De Mattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Hadida-Ruah et al. |
| 8,431,605 B2 | 4/2013 | Hadida-Ruah et al. |
| 8,436,014 B2 | 5/2013 | Zhang et al. |
| 2004/0105820 A1 | 6/2004 | Weers et al. |
| 2005/0059687 A1 | 3/2005 | Makings et al. |
| 2005/0113423 A1 | 5/2005 | VanGoor et al. |
| 2005/0215614 A1 | 9/2005 | Singh et al. |
| 2006/0052358 A1 | 3/2006 | Hadida-Ruah et al. |
| 2007/0105833 A1 | 5/2007 | Hadida-Ruah et al. |
| 2007/0244159 A1 | 10/2007 | Hadida-Ruah et al. |
| 2007/0264196 A1 | 11/2007 | Hadida-Ruah et al. |
| 2008/0009524 A1 | 1/2008 | Hadida-Ruah et al. |
| 2008/0044355 A1 | 2/2008 | Hadida-Ruah et al. |
| 2008/0071095 A1 | 3/2008 | Hadida-Ruah et al. |
| 2008/0113985 A1 | 5/2008 | Hadida-Ruah et al. |
| 2008/0132560 A1 | 6/2008 | Chow et al. |
| 2008/0176899 A1 | 7/2008 | Hadida-Ruah et al. |
| 2008/0286204 A1 | 11/2008 | Hadida-Ruah et al. |
| 2008/0305062 A1 | 12/2008 | Bui et al. |
| 2009/0099230 A1 | 4/2009 | DeMattei et al. |
| 2009/0105272 A1 | 4/2009 | Grootenhuis et al. |
| 2009/0131492 A1 | 5/2009 | Hadida-Ruah et al. |
| 2009/0143381 A1 | 6/2009 | Hadida-Ruah et al. |
| 2009/0170905 A1 | 7/2009 | Keshavarz-Shokri et al. |
| 2009/0176839 A1 | 7/2009 | Keshavarz-Shokri et al. |
| 2009/0221597 A1 | 9/2009 | Hadida-Ruah et al. |
| 2009/0227797 A1 | 9/2009 | Hadida-Ruah et al. |
| 2009/0246820 A1 | 10/2009 | Singh et al. |
| 2009/0253736 A1 | 10/2009 | Hadida-Ruah et al. |
| 2010/0036130 A1 | 2/2010 | Siesel |
| 2010/0074949 A1 | 3/2010 | Rowe et al. |
| 2010/0113508 A1 | 5/2010 | Binch et al. |
| 2010/0125090 A1 | 5/2010 | Hadida-Ruah et al. |
| 2010/0144798 A1 | 6/2010 | Van Goor et al. |
| 2010/0249113 A1 | 9/2010 | Hadida-Ruah et al. |
| 2010/0249180 A1 | 9/2010 | Gallardo-Godoy et al. |
| 2010/0256184 A1 | 10/2010 | Rowe et al. |
| 2010/0267768 A1 | 10/2010 | Demattei et al. |
| 2010/0331344 A1 | 12/2010 | Hadida-Ruah et al. |
| 2011/0008259 A1 | 1/2011 | Binch et al. |
| 2011/0060024 A1 | 3/2011 | Hadida-Ruah et al. |
| 2011/0064811 A1 | 3/2011 | Hurter et al. |
| 2011/0071206 A1 | 3/2011 | Hadida-Ruah et al. |
| 2011/0098311 A1 | 4/2011 | VanGoor et al. |
| 2011/0177999 A1 | 7/2011 | Singh et al. |
| 2011/0230519 A1 | 9/2011 | Arekar et al. |
| 2011/0251253 A1 | 10/2011 | Keshavarz-Shokri et al. |
| 2011/0256220 A1 | 10/2011 | Verwijs et al. |
| 2011/0257223 A1 | 10/2011 | VanGoor et al. |
| 2011/0263654 A1 | 10/2011 | Keshavarz-Shokri et al. |
| 2011/0288122 A1 | 11/2011 | VanGoor et al. |
| 2011/0306637 A1 | 12/2011 | Hadida-Ruah et al. |
| 2012/0010257 A1 | 1/2012 | Hadida-Ruah et al. |
| 2012/0015999 A1 | 1/2012 | Alargova et al. |
| 2012/0035179 A1 | 2/2012 | Hadida-Ruah et al. |
| 2012/0046330 A1 | 2/2012 | Alargova et al. |
| 2012/0064157 A1 | 3/2012 | Dokou et al. |
| 2012/0071504 A1 | 3/2012 | Yang et al. |
| 2012/0122921 A1 | 5/2012 | Demattei et al. |
| 2012/0122922 A1 | 5/2012 | Young et al. |
| 2012/0184583 A1 | 7/2012 | VanGoor et al. |
| 2012/0190856 A1 | 7/2012 | Siesel et al. |
| 2012/0203006 A1 | 8/2012 | Siesel et al. |
| 2012/0208841 A1 | 8/2012 | Binch et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2012/0259129 A1 | 10/2012 | Ambhaikar et al. |
| 2012/0270869 A1 | 10/2012 | Hadida-Ruah et al. |
| 2012/0277268 A1 | 11/2012 | Keshavarz-Shokri et al. |
| 2012/0309758 A1 | 12/2012 | Sheth et al. |
| 2012/0322798 A1 | 12/2012 | Hadida-Ruah et al. |
| 2013/0011923 A1 | 1/2013 | Hadida-Ruah et al. |
| 2013/0012536 A1 | 1/2013 | Hadida-Ruah et al. |
| 2013/0018071 A1 | 1/2013 | Arekar et al. |
| 2013/0023538 A1 | 1/2013 | Hadida-Ruah et al. |
| 2013/0035327 A1 | 2/2013 | Hadida-Ruah et al. |
| 2013/0040986 A1 | 2/2013 | Binch et al. |
| 2013/0072522 A1 | 3/2013 | Demattei et al. |
| 2013/0072687 A1 | 3/2013 | Ambhaikar et al. |
| 2013/0079367 A1 | 3/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0109717 A1 | 5/2013 | Demattei et al. |
| 2013/0116238 A1 | 5/2013 | Looker et al. |

FOREIGN PATENT DOCUMENTS

| | | |
|---|---|---|
| WO | WO 9619444 | 6/1996 |
| WO | WO 9847868 | 10/1998 |
| WO | WO 03002533 | 1/2003 |
| WO | WO 03007945 | 1/2003 |
| WO | WO 03055482 | 7/2003 |
| WO | WO 2004028480 | 4/2004 |
| WO | WO 2004034571 | 4/2004 |
| WO | WO 2004041277 | 5/2004 |
| WO | WO 2004056745 | 7/2004 |
| WO | WO 2004111014 | 12/2004 |
| WO | WO 2005016854 | 2/2005 |
| WO | WO 2005035514 | 4/2005 |
| WO | WO 2005049018 | 6/2005 |
| WO | WO 2005075435 | 8/2005 |
| WO | WO 2005094374 | 10/2005 |
| WO | WO 2005120497 | 12/2005 |
| WO | WO 2006044456 | 4/2006 |
| WO | WO 2006044502 | 4/2006 |
| WO | WO 2006044503 | 4/2006 |
| WO | WO 2006044505 | 4/2006 |
| WO | WO 2006044682 | 4/2006 |
| WO | WO 2006099258 | 9/2006 |
| WO | WO 2006101740 | 9/2006 |
| WO | WO 2006110483 | 10/2006 |
| WO | WO 2006127588 | 11/2006 |
| WO | WO 2007044560 | 4/2007 |
| WO | WO 2007117715 | 10/2007 |
| WO | WO 2006014012 | 2/2009 |
| WO | WO 2010053471 | 5/2010 |
| WO | WO 2010054138 | 5/2010 |

MODULATORS OF ATP-BINDING CASSETTE TRANSPORTERS

CROSS REFERENCE TO RELATED APPLICATIONS

The present application claims the benefit under 35 U.S.C. §120 of U.S. application Ser. No. 11/786,001, filed Apr. 9, 2007, which claims the benefit under 35 U.S.C. §119 of U.S. Provisional Application No. 60/790,459, filed Apr. 7, 2006, the entire contents of both applications being incorporated herein by reference.

TECHNICAL FIELD OF THE INVENTION

The present invention relates to modulators of ATP-Binding Cassette ("ABC") transporters or fragments thereof, including Cystic Fibrosis Transmembrane Conductance Regulator ("CFTR"), compositions thereof and methods therewith. The present invention also relates to methods of treating ABC transporter mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in Cystic Fibrosis ("CF"), the most common fatal genetic disease in humans. Cystic Fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 1234750). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial Na$^+$ channel, ENaC, Na$^+$/2Cl$^-$/K$^+$ co-transporter, Na$^+$—K$^+$-ATPase pump and the basolateral membrane K$^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the Na$^+$—K$^+$-ATPase pump and Cl– channels expressed on the basolateral surface of the cell. Secondary active transport of chloride from the luminal side leads to the accumulation of intracellular chloride, which can then passively leave the cell via Cl$^-$ channels, resulting in a vectorial transport. Arrangement of Na$^+$/2Cl$^-$/K$^+$ co-transporter, Na$^+$—K$^+$-ATPase pump and the basolateral membrane K$^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to Cystic Fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as Cystic Fibrosis and Sjögren's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögren's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al.; Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are Cystic fibrosis (due to misfolded ΔF508-CFTR as discussed above), Hereditary emphysema (due to al-antitrypsin; non Piz variants), Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses (due to Lysosomal processing enzymes), Sandhof/Tay-Sachs (due to β-Hexosaminidase), Crigler-Najjar type II (due to UDP-glucuronyl-sialyc-transferase), Polyendocrinopathy/Hyperinsulemia, Diabetes mellitus (due to Insulin receptor), Laron dwarfism (due to Growth hormone receptor), Myleoperoxidase deficiency, Primary hypoparathyroidism (due to Preproparathyroid hormone), Melanoma (due to Tyrosinase). The diseases associated with the latter class of ER malfunction are Glycanosis CDG type 1, Hereditary emphysema (due to α1-Antitrypsin (PiZ variant), Congenital hyperthyroidism, Osteogenesis imperfecta (due to Type I, II, IV procollagen), Hereditary hypofibrinogenemia (due to Fibrinogen), ACT deficiency (due to α1-Antichymotrypsin), Diabetes insipidus (DI), Neurophyseal DI (due to Vasopvessin hormone/V2-receptor), Neprogenic DI (due to Aquaporin II), Charcot-Marie Tooth syndrome (due to Peripheral myelin protein 22), Perlizaeus-Merzbacher disease, neurodegenerative diseases such as Alzheimer's disease (due to βAPP and presenilins), Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrhea causing bacteria is enterotoxogenic E-coli (ETEC) having the K99 pilus antigen. Common viral causes of diarrhea include rotavirus and coronavirus. Other infectious agents include cryptosporidium, *giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of ABC transporter activity, particularly CTFR activity. These compounds have the general formula I:

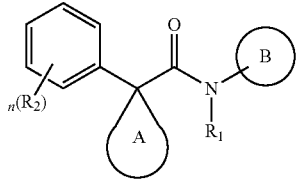

I or a pharmaceutically acceptable salt thereof, wherein $R_1$, $R_2$, ring A, ring B, and n are defined below.

It has also now been found that compounds of this invention, and pharmaceutically acceptable compositions thereof, are useful as modulators of ABC transporter activity. These compounds have the general formula II:

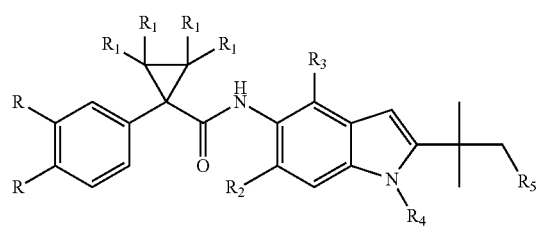

II or a pharmaceutically acceptable salt thereof, wherein R, $R_1$, $R_2$, $R_3$, $R_4$, and $R_5$ are defined below.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, diabetes mellitus, laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, diabetes insipidus, neurophysiol, nephrogenic, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjögren's disease.

DETAILED DESCRIPTION OF THE INVENTION

I. Definitions

As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing, e.g. activity, by a measurable amount. Compounds that modulate ABC Transporter activity, such as CFTR activity, by increasing the activity of the ABC Transporter, e.g., a CFTR anion channel, are called agonists. Compounds that modulate ABC Transporter activity, such as CFTR activity, by decreasing the activity of the ABC Transporter, e.g., CFTR anion channel, are called antagonists. An agonist interacts with an ABC Transporter, such as CFTR anion channel, to increase the ability of the receptor to transduce an intracellular signal in response to endogenous ligand binding. An antagonist interacts with an ABC Transporter, such as CFTR, and competes with the endogenous ligand(s) or substrate(s) for binding site(s) on the receptor to decrease the ability of the receptor to transduce an intracellular signal in response to endogenous ligand binding.

The phrase "treating or reducing the severity of an ABC Transporter mediated disease" refers both to treatments for diseases that are directly caused by ABC Transporter and/or CFTR activities and alleviation of symptoms of diseases not directly caused by ABC Transporter and/or CFTR anion channel activities. Examples of diseases whose symptoms may be affected by ABC Transporter and/or CFTR activity include, but are not limited to, Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophysiol DI, Nephrogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N(R$^X$)—C(O)—R$^Y$ or —C(O)—N(R$^X$)$_2$, when used terminally, and —C(O)—N(R$^X$)— or —N(R$^X$)—C(O)— when used internally, wherein R$^X$ and R$^y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyll)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C$_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S-]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a C$_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a C$_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "carbocycle" or "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S-], sulfoxy, urea, thiourea, sulfamoyl, sulfamide, oxo, or carbamoyl.

As used herein, the term "heterocycle" or "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1, 2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizinyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaralphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicaliphatic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[2.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, aralphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^XO(O)C$-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure -[CH$_2$]$_v$—, where v is 1-12. A branched aliphatic chain is a straight aliphatic chain that is substituted with one or more aliphatic groups. A branched aliphatic chain has the structure —[CQQ]$_v$- where each Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, and $R_3$, and other variables contained in formulae described herein encompass specific groups, such as alkyl and aryl. Unless otherwise noted, each of the specific groups for the variables $R_1$, $R_2$, and $R_3$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays, or as therapeutic agents.

Compounds of the present invention are useful modulators of ABC transporters and are useful in the treatment of ABC transporter mediated diseases.

II. Compounds

A. Generic Compounds

The present invention relates to compounds of formula I useful as modulators of ABC transporter activity:

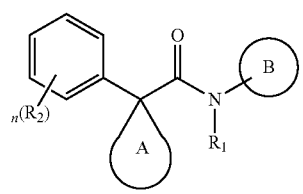

or a pharmaceutically acceptable salt thereof.

R₁ is —$Z^A R_4$, wherein each $Z^A$ is independently a bond or an optionally substituted branched or straight $C_{1-6}$ aliphatic chain wherein up to two carbon units of $Z^A$ are optionally and independently replaced by —CO—, —CS—, —$CONR^A$—, —$CONR^A NR^A$—, —$CO_2$—, —OCO—, —$NR^A CO_2$—, —O—, —$NR^A CONR^A$—, —$OCONR^A$—, —$NR^A NR^A$—, —$NR^A CO$—, —S—, —SO—, —$SO_2$—, —$NR^A$—, —$SO_2 NR^A$—, —$NR^A SO_2$—, or —$NR^A SO_2 NR^A$—. Each $R_4$ is independently $R^A$, halo, —OH, —$NH_2$, —$NO_2$, —CN, or —$OCF_3$. Each $R^A$ is independently hydrogen, an optionally substituted aliphatic, an optionally substituted cycloaliphatic, an optionally substituted heterocycloaliphatic, an optionally substituted aryl, or an optionally substituted heteroaryl.

R₂ is —$Z^B R_5$, wherein each $Z^B$ is independently a bond or an optionally substituted branched or straight $C_{1-6}$ aliphatic chain wherein up to two carbon units of $Z^B$ are optionally and independently replaced by —CO—, —CS—, —$CONR^B$—, —$CONR^B NR^B$—, —$CO_2$—, —OCO—, —$NR^B CO_2$—, —O—, —$NR^B CONR^B$—, —$OCONR^B$—, —$NR^B CO$—, —S—, —SO—, —$SO_2$—, —$NR^B$—, —$SO_2 NR^B$—, —$NR^B SO_2$—, or —$NR^B SO_2 NR^B$—. Each $R_5$ is independently $R^B$, halo, —OH, —$NH_2$, —$NO_2$, —CN, —$CF_3$, or —$OCF_3$. Each $R^B$ is independently hydrogen, an optionally substituted aliphatic, an optionally substituted cycloaliphatic, an optionally substituted heterocycloaliphatic, an optionally substituted aryl, or an optionally substituted heteroaryl. Alternatively, any two adjacent R₂ groups together with the atoms to which they are attached form an optionally substituted carbocycle or an optionally substituted heterocycle.

Ring A is an optionally substituted 3-7 membered monocyclic ring having 0-3 heteroatoms selected from N, O, and S.

Ring B is a group having formula Ia:

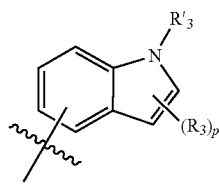

Ia or a pharmaceutically acceptable salt thereof, wherein p is 0-3 and each R₃ and R'₃ is independently —$Z^C R_6$, where each $Z^C$ is independently a bond or an optionally substituted branched or straight $C_{1-6}$ aliphatic chain wherein up to two carbon units of $Z^C$ are optionally and independently replaced by —CO—, —CS—, —$CONR^C$—, —$CONR^C NR^C$—, —$CO_2$—, —OCO—, —$NR^C CO_2$—, —O—, —$NR^C CONR^C$—, —$OCONR^C$—, —$NR^C NR^C$—, —$NR^C CO$—, —S—, —SO—, —$SO_2$—, —$SO_2 NR^C$—, —$NR^C SO_2$—, or —$NR^C SO_2 NR^C$—. Each $R_6$ is independently $R^C$, halo, —OH, —$NH_2$, —$NO_2$, —CN, or —$OCF_3$. Each $R^C$ is independently hydrogen, an optionally substituted aliphatic, an optionally substituted cycloaliphatic, an optionally substituted heterocycloaliphatic, an optionally substituted aryl, or an optionally substituted heteroaryl. Alternatively, any two adjacent R₃ groups together with the atoms to which they are attached form an optionally substituted carbocycle or an optionally substituted heterocycle. Furthermore, R'₃ and an adjacent R₃ group, together with the atoms to which they are attached, form an optionally substituted heterocycle.

n is 1-3.

However, in several embodiments, when ring A is unsubstituted cyclopentyl, n is 1, R₂ is 4-chloro, and R₁ is hydrogen, then ring B is not 2-(tertbutyl)indol-5-yl, or (2,6-dichlorophenyl(carbonyl))-3-methyl-1H-indol-5-yl; and when ring A is unsubstituted cyclopentyl, n is 0, and R₁ is hydrogen, then ring B is not

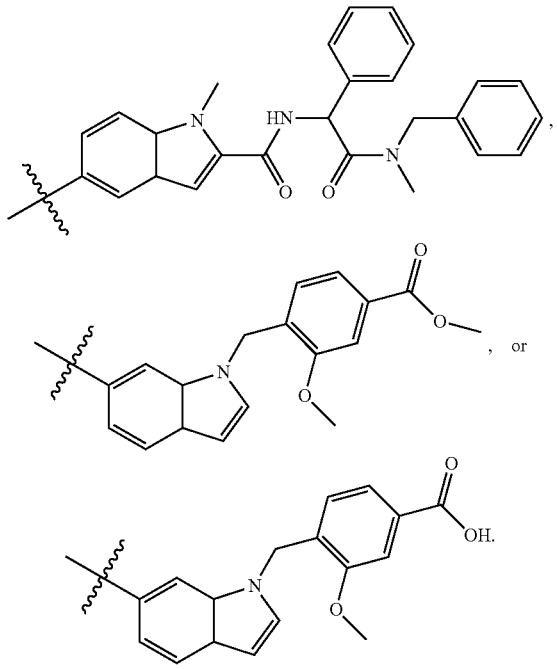

B. Specific Compounds

1. R₁ Groups

R₁ is —$Z^A R_4$, wherein each $Z^A$ is independently a bond or an optionally substituted branched or straight $C_{1-6}$ aliphatic chain wherein up to two carbon units of $Z^A$ are optionally and independently replaced by —CO—, —CS—, —$CONR^A$—, —$CONR^A NR^A$—, —$CO_2$—, —OCO—, —$NR^A CO_2$—, —O—, —$NR^A CONR^A$—, —$OCONR^A$—, —$NR^A NR^A$—, —$NR^A CO$—, —S—, —SO—, —$SO_2$—, —$NR^A$—, —$SO_2 NR^A$—, —$NR^A SO_2$—, or —$NR^A SO_2 NR^A$—. Each $R_4$ is independently $R^A$, halo, —OH, —$NH_2$, —$NO_2$, —CN, or —$OCF_3$. Each $R^A$ is independently hydrogen, an optionally substituted aliphatic, an optionally substituted cycloaliphatic, an optionally substituted heterocycloaliphatic, an optionally substituted aryl, or an optionally substituted heteroaryl.

In several embodiments, R₁ is —$Z^A R_4$, wherein each $Z^A$ is independently a bond or an optionally substituted branched or straight $C_{1-6}$ aliphatic chain and each $R_4$ is hydrogen.

In other embodiments, R₁ is —$Z^A R_4$, wherein each $Z^A$ is a bond and each $R_4$ is hydrogen.

2. R₂ Group

Each R₂ is independently —$Z^B R_5$, wherein each $Z^B$ is independently a bond or an optionally substituted branched or straight $C_{1-6}$ aliphatic chain wherein up to two carbon units of $Z^B$ are optionally and independently replaced by —CO—, —CS—, —$CONR^B$—, —$CONR^B NR^B$—, —$CO_2$—, —OCO—, —$NR^B CO_2$—, —O—, —$NR^B CONR^B$—, —$OCONR^B$—, —$NR^B NR^B$—, —$NR^B CO$—, —S—, —SO—, —$SO_2$—, —$NR^B$—, —$SO_2 NR^B$—, —$NR^B SO_2$—, or —$NR^B SO_2 NR^B$—. Each $R_5$ is independently $R^B$, halo, —OH, —$NH_2$, —$NO_2$, —CN, —$CF_3$, or —$OCF_3$. Each $R^B$ is independently hydrogen, an optionally substituted aliphatic, an optionally substituted cycloaliphatic, an optionally substituted heterocycloaliphatic, an optionally substituted aryl, or an optionally substituted heteroaryl. Alternatively, any two adjacent $R_2$ groups together with the atoms to which they are attached form an optionally substituted carbocycle or an optionally substituted heterocycle.

In several embodiments, $R_2$ is an optionally substituted aliphatic. For example, $R_2$ is an optionally substituted branched or straight $C_{1-6}$ aliphatic chain. In other examples, $R_2$ is an optionally substituted branched or straight $C_{1-6}$ alkyl chain, an optionally substituted branched or straight $C_{2-6}$ alkenyl chain, or an optionally substituted branched or straight $C_{2-6}$ alkynyl chain. In alternative embodiments, $R_2$ is a branched or straight $C_{1-6}$ aliphatic chain that is optionally substituted with 1-3 of halo, hydroxy, cyano, cycloaliphatic, heterocycloaliphatic, aryl, heteroaryl, or combinations thereof. For example, $R_2$ is a branched or straight $C_{1-6}$ alkyl that is optionally substituted with 1-3 of halo, hydroxy, cyano, cycloaliphatic, heterocycloaliphatic, aryl, heteroaryl, or combinations thereof. In still other examples, $R_2$ is a methyl, ethyl, propyl, butyl, isopropyl, or tert-butyl, each of which is optionally substituted with 1-3 of halo, hydroxy, cyano, aryl, heteroaryl, cycloaliphatic, or heterocycloaliphatic. In still other examples, $R_2$ is a methyl, ethyl, propyl, butyl, isopropyl, or tert-butyl, each of which is unsubstituted.

In several other embodiments, $R_2$ is an optionally substituted branched or straight $C_{1-5}$ alkoxy. For example, $R_2$ is a $C_{1-5}$ alkoxy that is optionally substituted with 1-3 of hydroxy, aryl, heteroaryl, cycloaliphatic, heterocycloaliphatic, or combinations thereof. In other examples, $R_2$ is a methoxy, ethoxy, propoxy, butoxy, or pentoxy, each of which is optionally substituted with 1-3 of hydroxy, aryl, heteroaryl, cycloaliphatic, heterocycloaliphatic, or combinations thereof.

In other embodiments, $R_2$ is hydroxy, halo, or cyano.

In several embodiments, $R_2$ is $-Z^B R_5$, and $Z^B$ is independently a bond or an optionally substituted branched or straight $C_{1-4}$ aliphatic chain wherein up to two carbon units of $Z^B$ are optionally and independently replaced by $-C(O)-$, $-O-$, $-S-$, $-S(O)_2-$, or $-NH-$, and $R_5$ is $R^B$, halo, $-OH$, $-NH_2$, $-NO_2$, $-CN$, $-CF_3$, or $-OCF_3$, and $R^B$ is hydrogen or aryl.

In several embodiments, two adjacent $R_2$ groups form an optionally substituted carbocycle or an optionally substituted heterocycle. For example, two adjacent $R_2$ groups form an optionally substituted carbocycle or an optionally substituted heterocycle, either of which is fused to the phenyl of formula I, wherein the carbocycle or heterocycle has formula Ib:

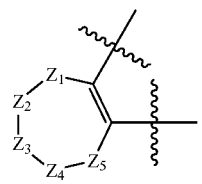

Ib

Each of $Z_1$, $Z_2$, $Z_3$, $Z_4$, and $Z_5$ is independently a bond, $-CR_7R'_7-$, $-NR_7-$, or $-O-$; each $R_7$ is independently $-Z^D R_8$, wherein each $Z^D$ is independently an optionally substituted branched or straight $C_1$ aliphatic chain wherein up to two carbon units of $Z^D$ are optionally and independently replaced by $-CO-$, $-CS-$, $-CONR^D-$, $-CO_2-$, $-OCO-$, $-NR^D CO_2-$, $-O-$, $-NR^D CONR^D-$, $-OCONR^D-$, $-NR^D NR^D-$, $-NR^D CO-$, $-S-$, $-SO-$, $-SO_2-$, $-NR^D-$, $-SO_2 NR^D-$, $-NR^D SO_2-$, or $-NR^D SO_2 NR^D-$. Each $R_8$ is independently $R^D$, halo, $-OH$, $-NH_2$, $-NO_2$, $-CN$, $-CF_3$, or $-OCF_3$. Each $R^D$ is independently hydrogen, an optionally substituted cycloaliphatic, an optionally substituted heterocycloaliphatic, an optionally substituted aryl, or an optionally substituted heteroaryl. Each $R'_7$ is independently hydrogen, optionally substituted $C_1$ aliphatic, hydroxy, halo, cyano, nitro, or combinations thereof. Alternatively, any two adjacent $R_7$ groups together with the atoms to which they are attached form an optionally substituted 3-7 membered carbocyclic ring, such as an optionally substituted cyclobutyl ring, or any two $R_7$ and $R'_7$ groups together with the atom or atoms to which they are attached form an optionally substituted 3-7 membered carbocyclic ring or a heterocarbocyclic ring.

In several other examples, two adjacent $R_2$ groups form an optionally substituted carbocycle. For example, two adjacent $R_2$ groups form an optionally substituted 5-7 membered carbocycle that is optionally substituted with 1-3 of halo, hydroxy, cyano, oxo, cyano, alkoxy, alkyl, or combinations thereof. In another example, two adjacent $R_2$ groups form a 5-6 membered carbocycle that is optionally substituted with 1-3 of halo, hydroxy, cyano, oxo, cyano, alkoxy, alkyl, or combinations thereof. In still another example, two adjacent $R_2$ groups form an unsubstituted 5-7 membered carbocycle.

In alternative examples, two adjacent $R_2$ groups form an optionally substituted heterocycle. For instance, two adjacent $R_2$ groups form an optionally substituted 5-7 membered heterocycle having 1-3 heteroatoms independently selected from N, O, and S. In several examples, two adjacent $R_2$ groups form an optionally substituted 5-6 membered heterocycle having 1-2 oxygen atoms. In other examples, two adjacent $R_2$ groups form an unsubstituted 5-7 membered heterocycle having 1-2 oxygen atoms. In other embodiments, two adjacent $R_2$ groups form a heterocyclic ring selected from:

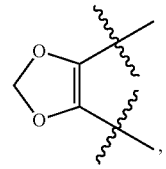

XA1

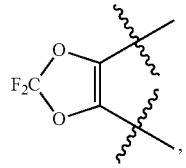

XA2

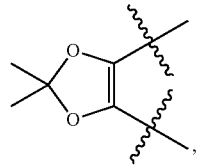

XA3

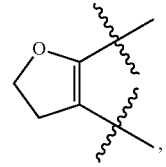

XA4

XA5 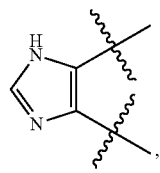

XA6 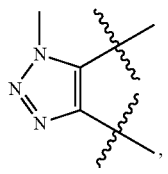

XA7 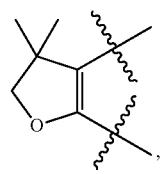

XA8 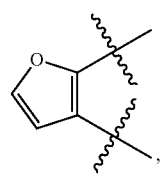

XA9 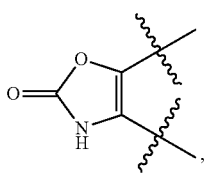

XA10 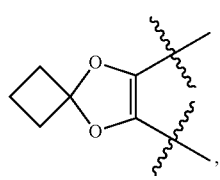

XA11 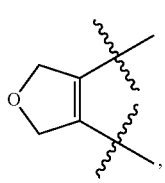

XA12 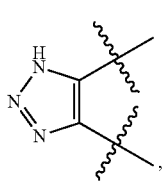

XA13 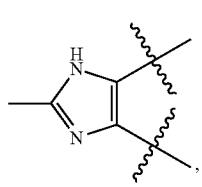

XA14 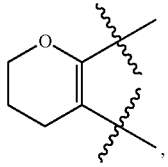

XA15 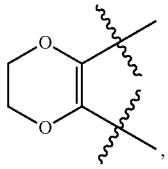

XA16 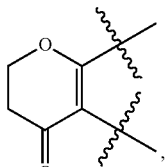

XA17 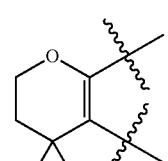

XA18 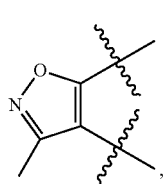

XA19 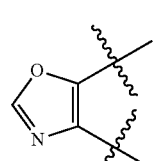

XA20 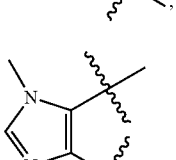

, and

XA21 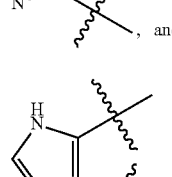

In alternative examples, two adjacent $R_2$ groups form an optionally substituted carbocycle or an optionally substituted heterocycle, and a third $R_2$ group is attached to any chemically feasible position on the phenyl of formula I. For instance, an optionally substituted carbocycle or an optionally substituted heterocycle, both of which is formed by two adjacent R₂ groups; a third R₂ group; and the phenyl of formula I form a group having formula Ic:

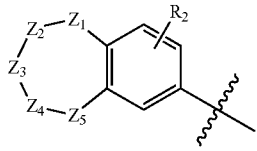
Ic $Z_1$, $Z_2$, $Z_3$, $Z_4$, and $Z_5$ has been defined above in formula Ib, and $R_2$ has been defined above in formula I.

In several embodiments, each $R_2$ group is independently selected from hydrogen, halo, —OCH₃, —OH, —CH₂OH, —CH₃, and —OCF₃, and/or two adjacent R₂ groups together with the atoms to which they are attached form XA1
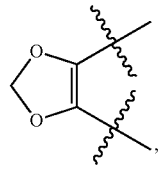, XA2
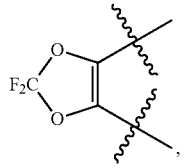, XA3
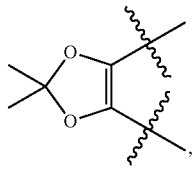, XA4
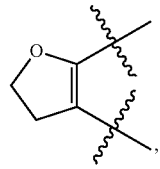, XA5
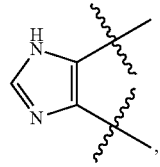, XA6
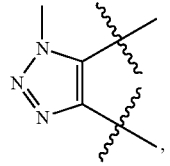, XA7
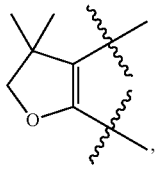, XA8
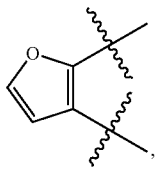, XA9
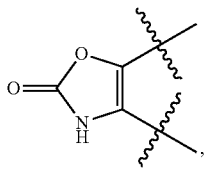, XA10
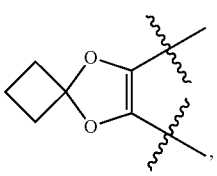, XA11
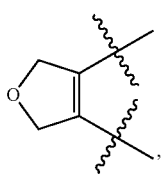, XA12
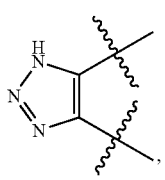, XA13
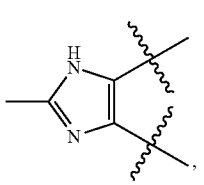, XA14
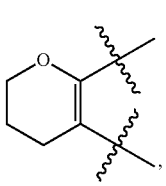, XA15
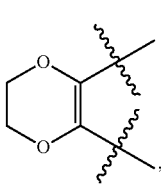,

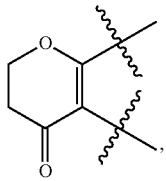
XA16,

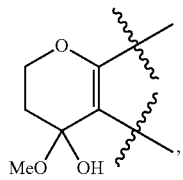
XA17,

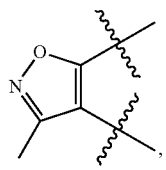
XA18,

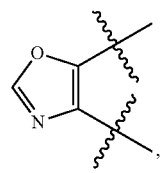
XA19,

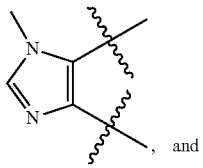
XA20, and

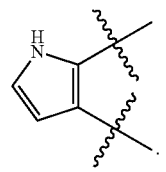
XA21.

In other embodiments, $R_2$ is at least one selected from hydrogen, halo, methoxy, phenylmethoxy, hydroxy, hydroxymethyl, trifluoromethoxy, and methyl.

In some embodiments, two adjacent $R_2$ groups, together with the atoms to which they are attached, form

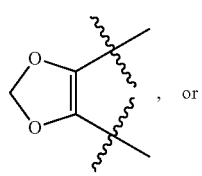
XA1, or

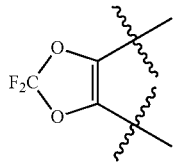
XA2.

3. Ring A

Ring A is an optionally substituted 3-7 membered monocyclic ring having 0-3 heteroatoms selected from N, O, and S.

In several embodiments, ring A is an optionally substituted 3-7 membered monocyclic cycloaliphatic. For example, ring A is a cyclopropyl, cyclobutyl, cyclopentyl, cyclohexyl, or cycloheptyl, each of which is optionally substituted with 1-3 of halo, hydroxy, $C_{1-5}$ aliphatic, or combinations thereof.

In other embodiments, ring A is an optionally substituted 3-7 membered monocyclic heterocycloaliphatic. For example, ring A is an optionally substituted 3-7 membered monocyclic heterocycloaliphatic having 1-2 heteroatoms independently selected from N, O, and S. In other examples, ring A is tetrahydrofuran-yl, tetrahydro-2H-pyran-yl, pyrrolidone-yl, or piperidine-yl, each of which is optionally substituted.

In still other examples, ring A is selected from

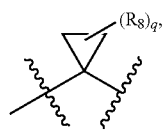
XB1,

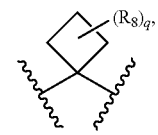
XB2,

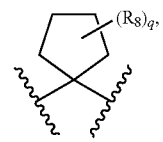
XB3,

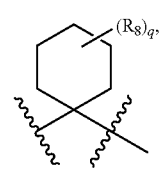
XB4,

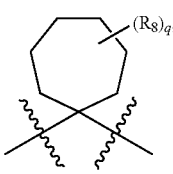
XB5,

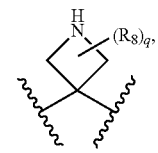
XB6,

-continued

XB7 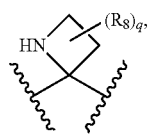

XB8 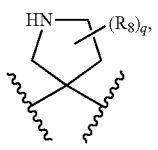

XB9 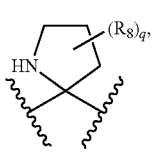

XB10 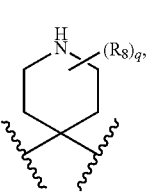

XB11 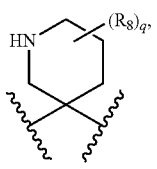

XB12 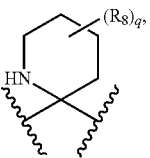

XB13 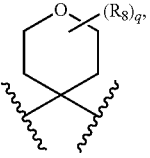

XB14 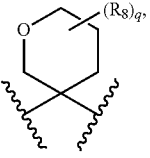

XB15 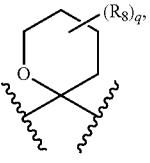

-continued

XB16 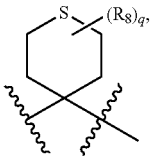

XB17 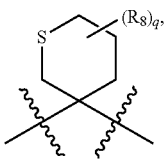

XB18 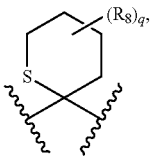

XB19 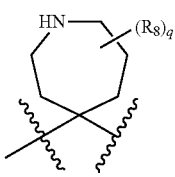

XB20 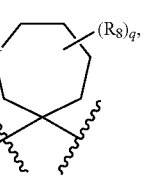

XB21 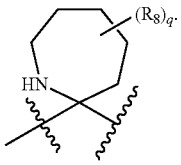

Each $R_8$ is independently —$Z^E R_9$, wherein each $Z^E$ is independently a bond or an optionally substituted branched or straight $C_{1-5}$ aliphatic chain wherein up to two carbon units of $Z^E$ are optionally and independently replaced by —CO—, —CS—, —CONR$^E$—, —CO$_2$—, —OCO—, —NR$^E$CO$_2$—, —O—, —NR$^E$CONR$^E$—, —OCONR$^E$—, —NR$^E$CO—, —S—, —SO—, —SO$_2$—, —NR$^E$—, —SO$_2$NR$^E$—, —NR$^E$SO$_2$—, or —NR$^E$SO$_2$NR$^E$—, each $R_9$ is independently R$^E$, —OH, —NH$_2$, —NO$_2$, —CN, —CF$_3$, oxo, or —OCF$_3$. Each R$^E$ is independently hydrogen, an optionally substituted cycloaliphatic, an optionally substituted heterocycloaliphatic, an optionally substituted aryl, or an optionally substituted heteroaryl.

q is 0-5.

In other embodiments, ring A is one selected from

XC1 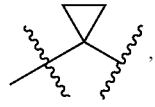

XC2
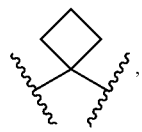

XC3
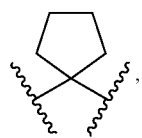

XC4
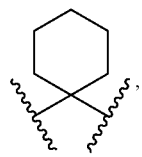

XC5
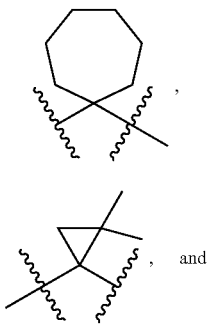

XC6
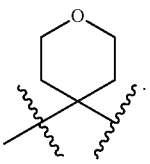

XC4
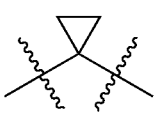, and

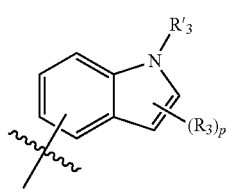

In several embodiments, ring A is

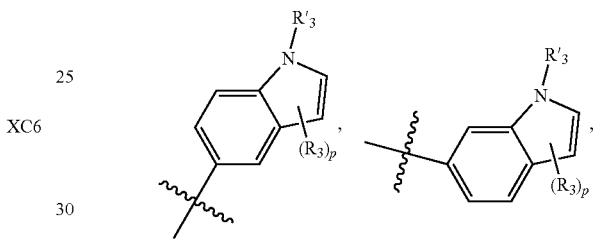

4. Ring B
Ring B is a group having formula Ia:

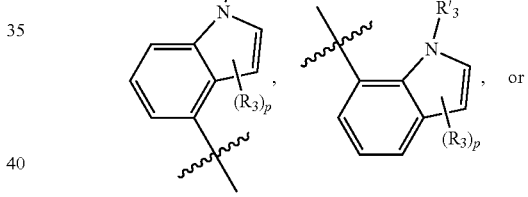

Ia or a pharmaceutically acceptable salt thereof, wherein p is 0-3.

Each $R_3$ and $R'_3$ is independently —$Z^C R_6$, where each $Z^C$ is independently a bond or an optionally substituted branched or straight $C_{1-6}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —SO—, —SO$_2$—, —NR$^C$—, —SO$_2$NR$^C$—, —NR$^C$SO$_2$—, or —NR$^C$SO$_2$NR$^C$—. Each $R_6$ is independently $R^C$, halo, —OH, —NH$_2$, —NO$_2$, —CN, or —OCF$_3$. Each $R^C$ is independently hydrogen, an optionally substituted aliphatic, an optionally substituted cycloaliphatic, an optionally substituted heterocycloaliphatic, an optionally substituted aryl, or an optionally substituted heteroaryl. Alternatively, any two adjacent $R_3$ groups together with the atoms to which they are attached form an optionally substituted carbocycle or an optionally substituted heterocycle, or $R'_3$ and an adjacent $R_3$, i.e., attached to the 2 position of the indole of formula Ia, together with the atoms to which they are attached form an optionally substituted heterocycle.

In several embodiments, ring B is wherein q is 0-3 and each $R_{20}$ is —$Z^G R_{21}$, where each $Z^G$ is independently a bond or an optionally substituted branched or straight $C_{1-5}$ aliphatic chain wherein up to two carbon units of $Z^G$ are optionally and independently replaced by —CO—, —CS—, —CONR$^G$—, —CO$_2$—, —OCO—, —NR$^G$CO$_2$—, —O—, —OCONR$^G$—, —NR$^G$NR$^G$—, —NR$^G$CO—, —S—, —SO—, —SO$_2$—, —NR$^G$—, —SO$_2$NR$^G$—, —NR$^G$SO$_2$—, or —NR$^G$SO$_2$NR$^G$—. Each $R_{21}$ is independently $R^G$, halo, —OH, —NH$_2$, —NO$_2$, —CN, or —OCF$_3$. Each $R^G$ is independently hydrogen, an optionally substituted aliphatic, an optionally substituted cycloaliphatic, an optionally substituted heterocycloaliphatic, an optionally substituted aryl, or an optionally substituted heteroaryl.

For example, ring B is

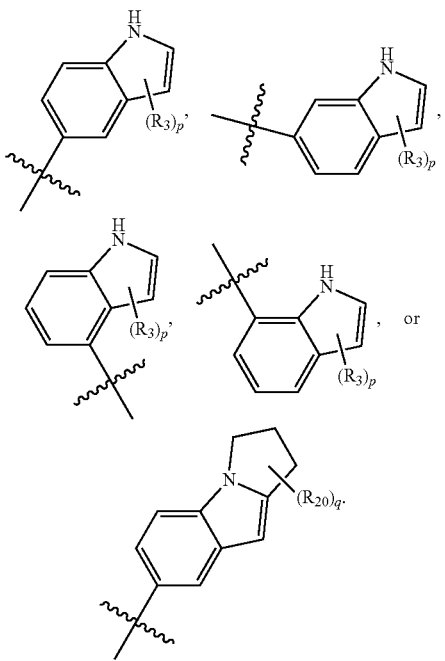

In several embodiments, R'$_3$ is hydrogen and R$_3$ is attached to the 2, 3, 4, 6, or 7 position of the indole of formula Ia. In several other examples, R$_3$ is attached to the 2 or 3 position of the indole of formula Ia, and R$_3$ is independently an optionally substituted aliphatic. For instance, R$_3$ is an optionally substituted acyl group. In several instances, R$_3$ is an optionally substituted (alkoxy)carbonyl. In other instances, R$_3$ is (methoxy)carbonyl, (ethoxy)carbonyl, (propoxy)carbonyl, or (butoxy)carbonyl, each of which is optionally substituted with 1-3 of halo, hydroxy, or combinations thereof. In other instances, R$_3$ is an optionally substituted (aliphatic)carbonyl. For example, R$_3$ is an optionally substituted (alkyl)carbonyl that is optionally substituted with 1-3 of halo, hydroxy, or combinations thereof. In other examples, R$_3$ is (methyl)carbonyl, (ethyl)carbonyl, (propyl)carbonyl, or (butyl)carbonyl, each of which is optionally substituted with 1-3 of halo, hydroxy, or combinations thereof.

In several embodiments, R$_3$ is an optionally substituted (cycloaliphatic)carbonyl or an optionally substituted (heterocycloaliphatic)carbonyl. In several examples, R$_3$ is an optionally substituted (C$_{3-7}$ cycloaliphatic)carbonyl. For example, R$_3$ is a (cyclopropyl)carbonyl, (cyclobutyl)carbonyl, (cyclopentyl)carbonyl, (cyclohexyl)carbonyl, or (cycloheptyl)carbonyl, each of which is optionally substituted with aliphatic, halo, hydroxy, nitro, cyano, or combinations thereof. In several alternative examples, R$_3$ is an optionally substituted (heterocycloaliphatic)carbonyl. For example, R$_3$ is an optionally substituted (heterocycloaliphatic)carbonyl having 1-3 heteroatoms independently selected from N, O, and S. In other examples, R$_3$ is an optionally substituted (heterocycloaliphatic)carbonyl having 1-3 heteroatoms independently selected from N and O. In still other examples, R$_3$ is an optionally substituted 4-7 membered monocyclic (heterocycloaliphatic) carbonyl having 1-3 heteroatoms independently selected from N and O. Alternatively, R$_3$ is (piperidine-1-yl)carbonyl, (pyrrolidine-1-yl)carbonyl, or (morpholine-4-yl)carbonyl, (piperazine-1-yl)carbonyl, each of which is optionally substituted with 1-3 of halo, hydroxy, cyano, nitro, or aliphatic.

In still other instances, R$_3$ is optionally substituted (aliphatic)amido such as (aliphatic(amino(carbonyl)) that is attached to the 2 or 3 position on the indole ring of formula Ia. In some embodiments, R$_3$ is an optionally substituted (alkyl (amino))carbonyl that is attached to the 2 or 3 position on the indole ring of formula Ia. In other embodiments, R$_3$ is an optionally substituted straight or branched (aliphatic(amino)) carbonyl that is attached to the 2 or 3 position on the indole ring of formula Ia. In several examples, R$_3$ is (N,N-dimethyl (amino))carbonyl, (methyl(amino))carbonyl, (ethyl(amino)) carbonyl, (propyl(amino))carbonyl, (prop-2-yl(amino))carbonyl, (dimethyl(but-2-yl(amino)))carbonyl, (tertbutyl (amino))carbonyl, (butyl(amino))carbonyl, each of which is optionally substituted with 1-3 of halo, hydroxy, cycloaliphatic, heterocycloaliphatic, aryl, heteroaryl, or combinations thereof.

In other embodiments, R$_3$ is an optionally substituted (alkoxy)carbonyl. For example, R$_3$ is (methoxy)carbonyl, (ethoxy)carbonyl, (propoxy)carbonyl, or (butoxy)carbonyl, each of which is optionally substituted with 1-3 of halo, hydroxy, or combinations thereof. In several instances, R$_3$ is an optionally substituted straight or branched C$_1$ aliphatic. For example, R$_3$ is an optionally substituted straight or branched C$_{1-6}$ alkyl. In other examples, R$_3$ is independently an optionally substituted methyl, ethyl, propyl, butyl, isopropyl, or tertbutyl, each of which is optionally substituted with 1-3 of halo, hydroxy, cyano, nitro, or combination thereof. In other embodiments, R$_3$ is an optionally substituted C$_{3-6}$ cycloaliphatic. Exemplary embodiments include cyclopropyl, 1-methyl-cycloprop-1-yl, etc. In other examples, p is 2 and the two R$_3$ substituents are attached to the indole of formula Ia at the 2,4- or 2,6- or 2,7-positions. Exemplary embodiments include 6-F, 3-(optionally substituted C$_{1-6}$ aliphatic or C$_{3-6}$ cycloaliphatic); 7-F-2-(-(optionally substituted C$_{1-6}$ aliphatic or C$_{3-6}$ cycloaliphatic)), 4F-2-(optionally substituted C$_{1-6}$ aliphatic or C$_{3-6}$ cycloaliphatic); 7-CN-2-(optionally substituted C$_{1-6}$ aliphatic or C$_{3-6}$ cycloaliphatic); 7-Me-2-(optionally substituted C$_{1-6}$ aliphatic or C$_{3-6}$ cycloaliphatic) and 7-OMe-2-(optionally substituted C$_{1-6}$ aliphatic or C$_{3-6}$ cycloaliphatic).

In several embodiments, R$_3$ is hydrogen.
In several embodiments, R$_3$ is one selected from:
—H, —CH$_3$, —CH$_2$OH, —CH$_2$CH$_3$, —CH$_2$CH$_2$OH, —CH$_2$CH$_2$CH$_3$, —NH$_2$, halo, —OCH$_3$, —CN, —CF$_3$, —C(O)OCH$_2$CH$_3$, —S(O)$_2$CH$_3$, —CH$_2$NH$_2$, —C(O)NH$_2$,

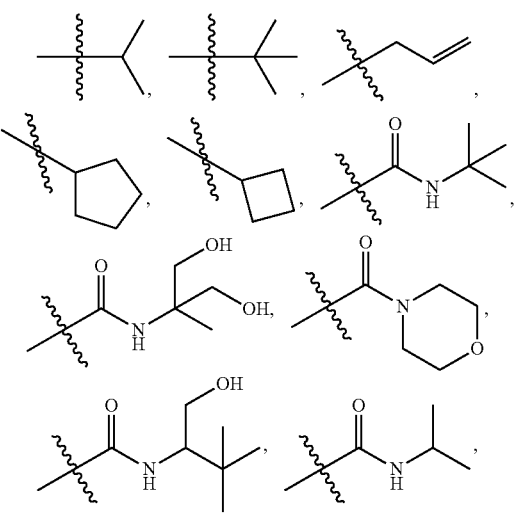

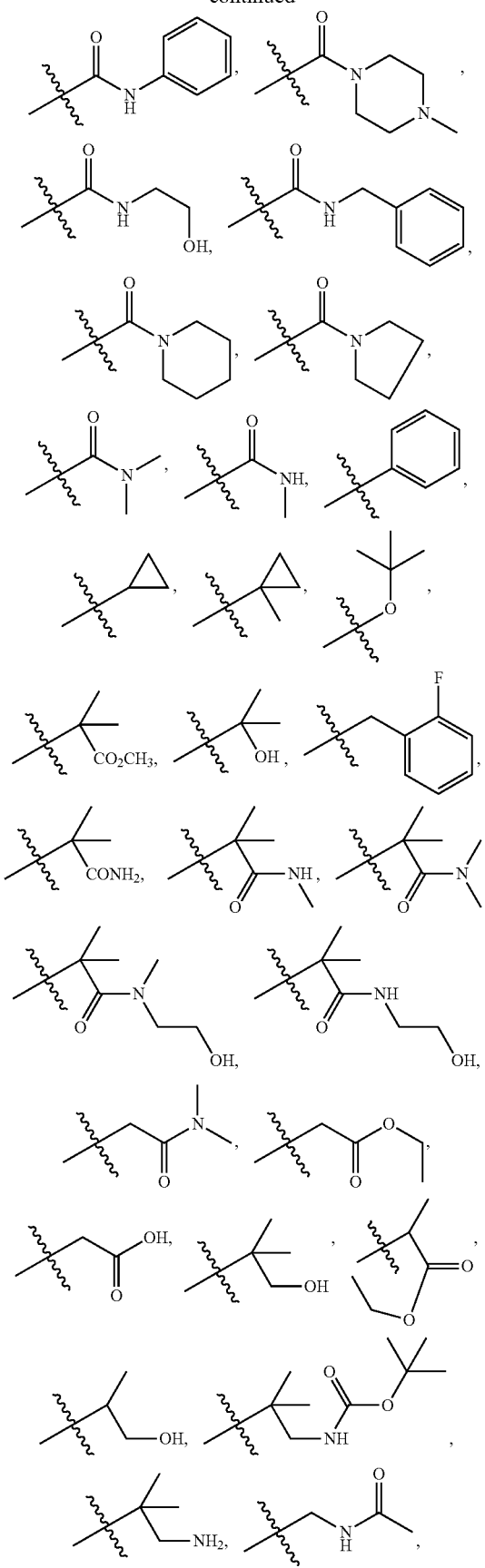
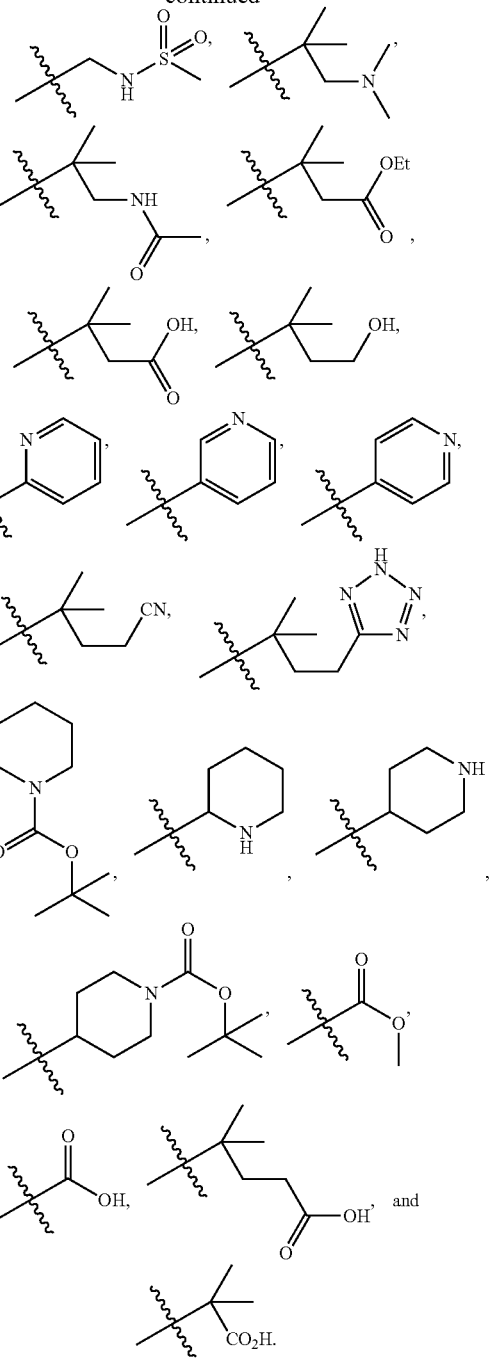
In another embodiment, two adjacent $R_3$ groups form
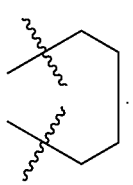 [SMILES: *CCCC*]
In several embodiments, $R'_3$ is independently $-Z^C R_6$, where each $Z^C$ is independently a bond or an optionally substituted branched or straight $C_{1-6}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, NR$^C$CO—, —S—, —SO—, —SO$_2$—, —SO$_2$NR$^C$—, —NR$^C$SO$_2$—, or —NR$^C$SO$_2$NR$^C$—. Each $R_6$ is independently $R^C$, halo, —OH, —NH$_2$, —NO$_2$, —CN, or —OCF$_3$. Each $R^C$ is independently hydrogen, an optionally substituted aliphatic, an optionally substituted cycloaliphatic, an optionally substituted heterocycloaliphatic, or an optionally substituted heteroaryl. In one embodiment, each $R^C$ is hydrogen, $C_{1-6}$ aliphatic, or $C_{3-6}$ cycloaliphatic, wherein either of the aliphatic or cycloaliphatic is optionally substituted with up to 4-OH substituents. In another embodiment, $R^C$ is hydrogen, or $C_{1-6}$ alkyl optionally substituted with up to 4-OH substituents.

For example, in many embodiments, $R'_3$ is independently —$Z^C R_6$, where each $Z^C$ is independently a bond or an optionally substituted branched or straight $C_{1-6}$ aliphatic chain wherein up to two carbon units of $Z^C$ are optionally and independently replaced by —C(O)—, —C(O)NR$^C$—, —C(O)O—, —NR$^C$C(O)O—, —O—, —NR$^C$S(O)$_2$—, or —NR$^C$—. Each $R_6$ is independently $R^C$, —OH, or —NH$_2$. Each $R^C$ is independently hydrogen, an optionally substituted cycloaliphatic, an optionally substituted heterocycloaliphatic, or an optionally substituted heteroaryl. In one embodiment, each $R^C$ is hydrogen, $C_{1-6}$ aliphatic, or $C_{3-6}$ cycloaliphatic, wherein either of the aliphatic or cycloaliphatic is optionally substituted with up to 4-OH substituents. In another embodiment, $R^C$ is hydrogen, or $C_{1-6}$ alkyl optionally substituted with up to 4-OH substituents.

In other embodiments, $R'_3$ is hydrogen or

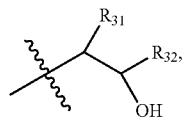

wherein $R_{31}$ is H or a $C_{1-2}$ aliphatic that is optionally substituted with 1-3 of halo, —OH, or combinations thereof. $R_{32}$ is -L-$R_{33}$, wherein L is a bond, —CH$_2$—, —CH$_2$O—, —CH$_2$NHS(O)$_2$—, —CH$_2$C(O)—, —CH$_2$NHC(O)—, or —CH$_2$NH—; and $R_{33}$ is hydrogen, or $C_{1-2}$ aliphatic, cycloaliphatic, heterocycloaliphatic, or heteroaryl, each of which is optionally substituted with 1 of —OH, —NH$_2$, or —CN. For example, in one embodiment, $R_{31}$ is hydrogen and $R_{32}$ is $C_{1-2}$ aliphatic optionally substituted with —OH, —NH$_2$, or —CN.

In several embodiments, $R'_3$ is independently selected from one of the following:
—H, —CH$_3$, —CH$_2$CH$_3$, —C(O)CH$_3$, —CH$_2$CH$_2$OH, —C(O)OCH$_3$,

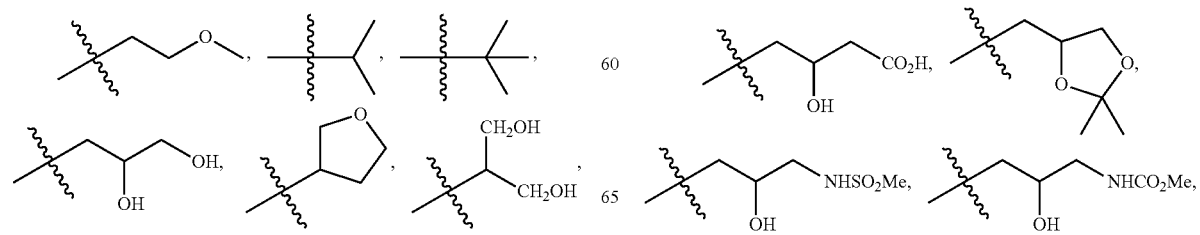

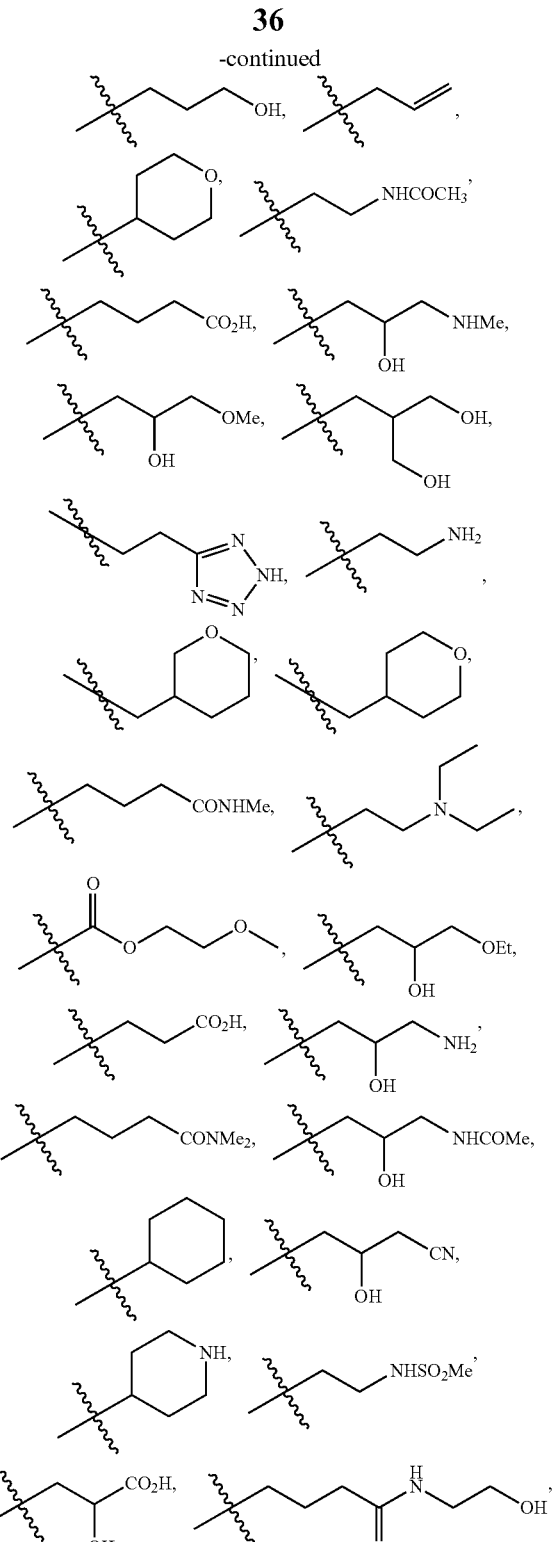

-continued
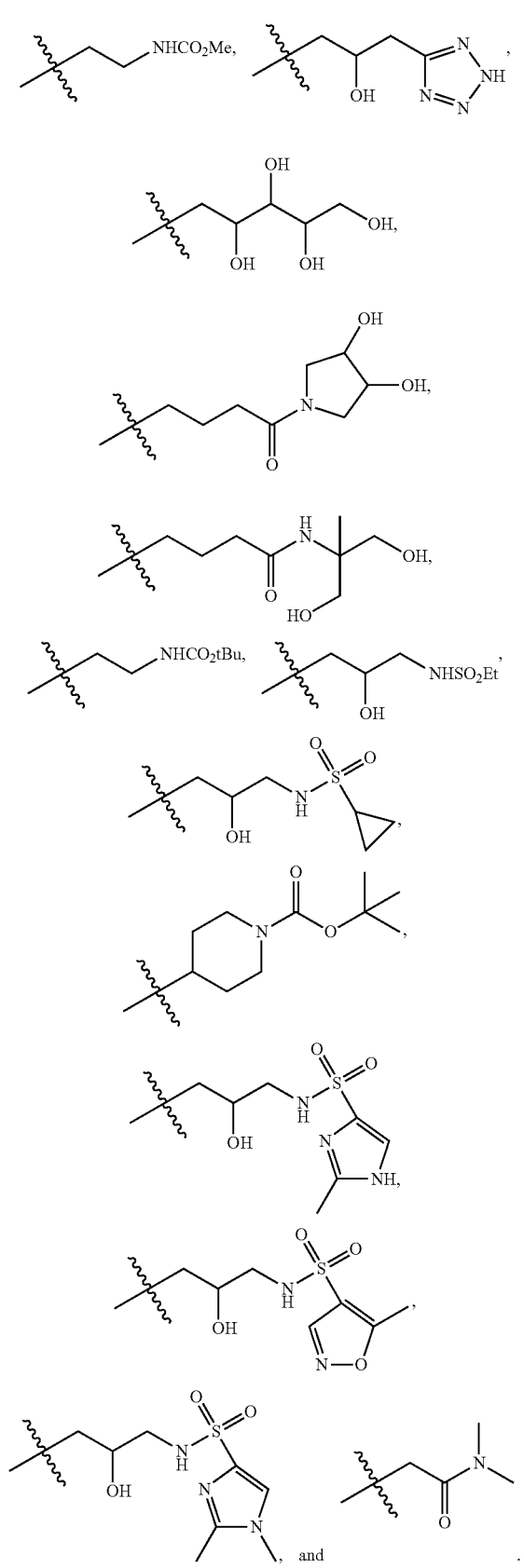
In several embodiments, ring B is one selected from:
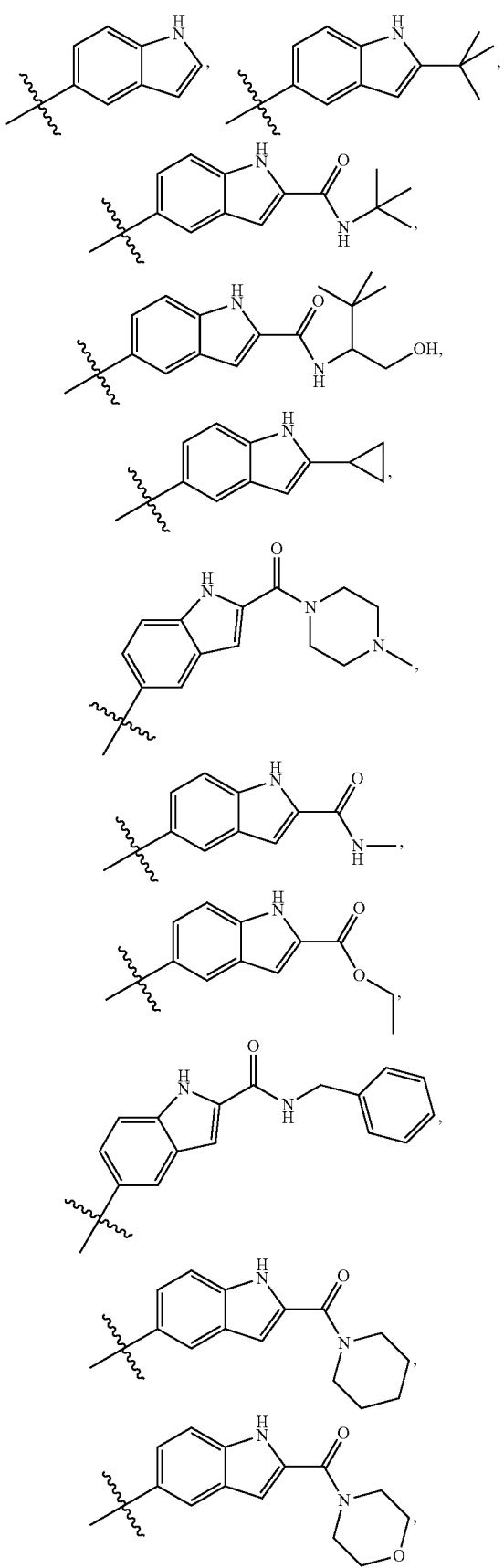

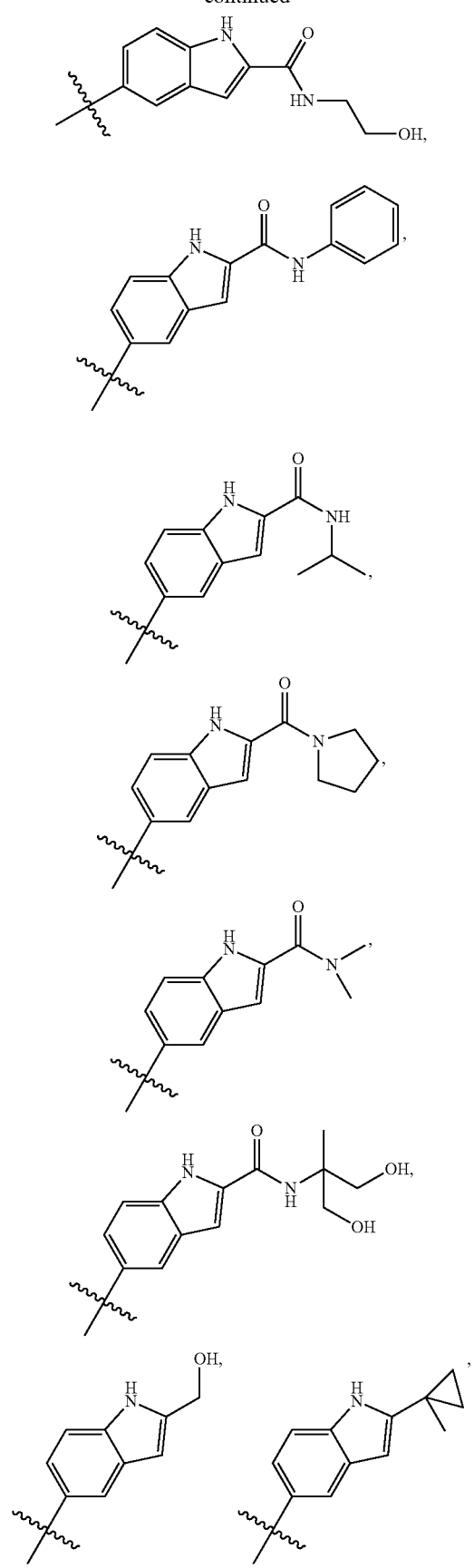
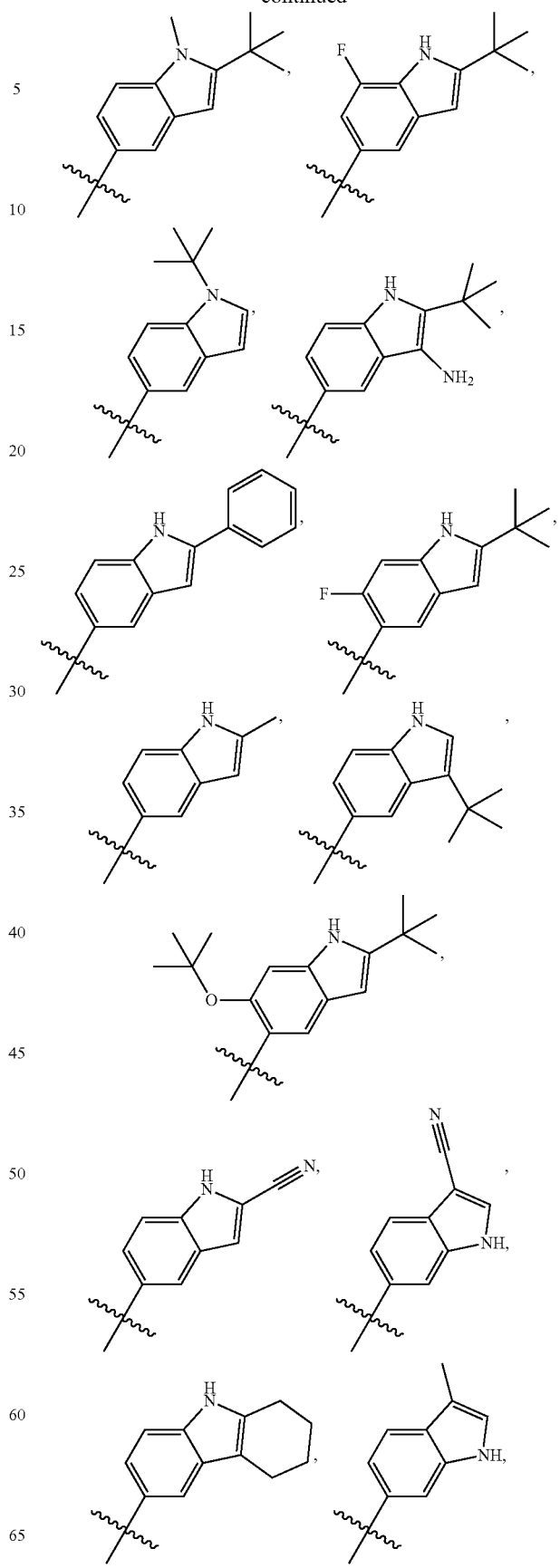

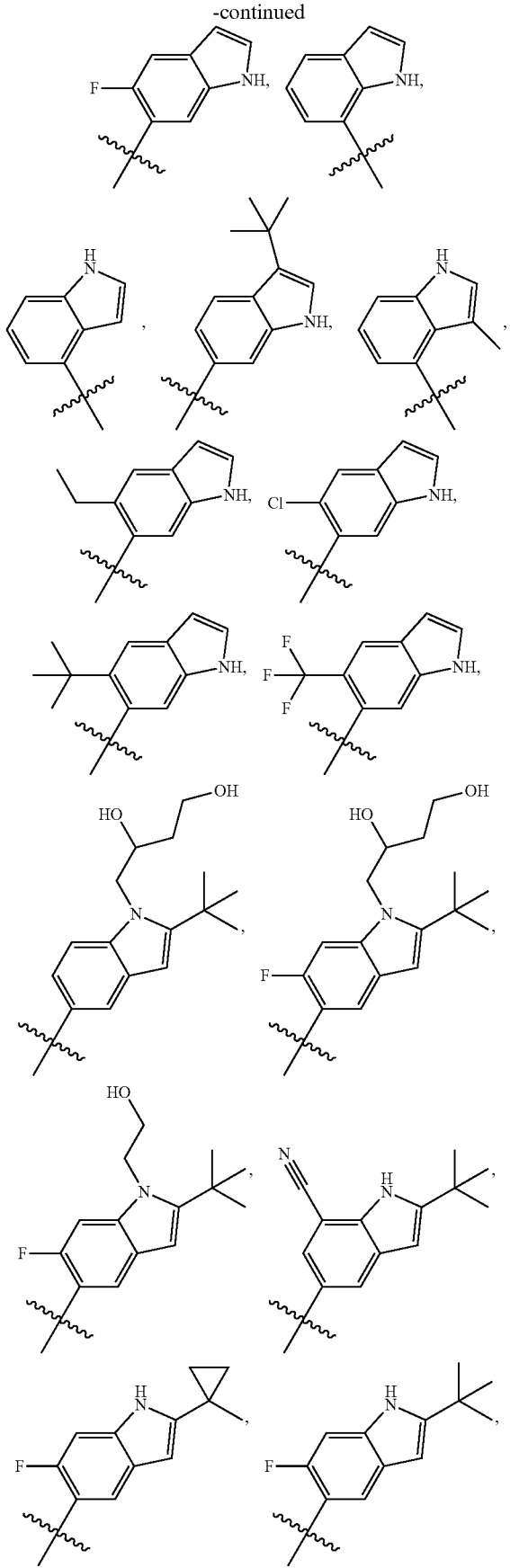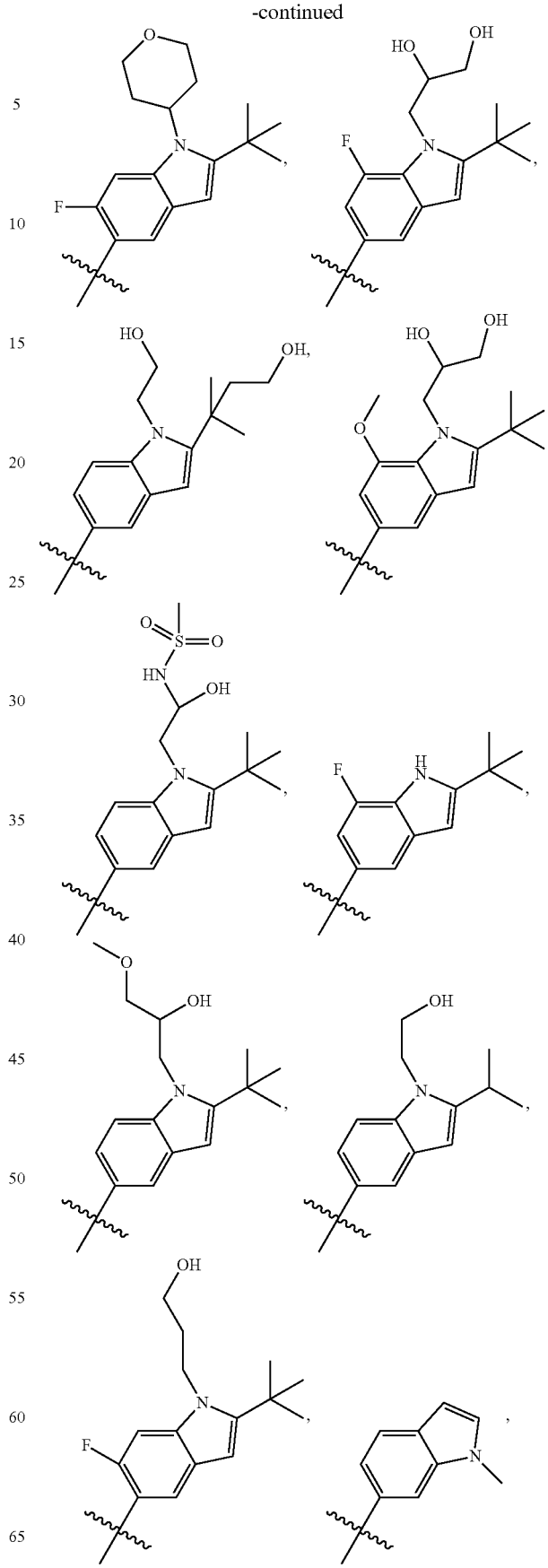

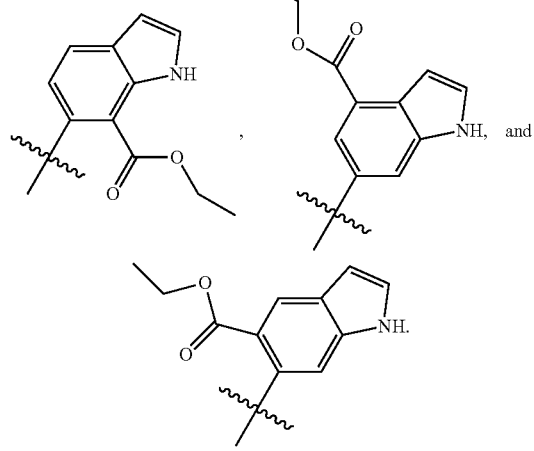

, and

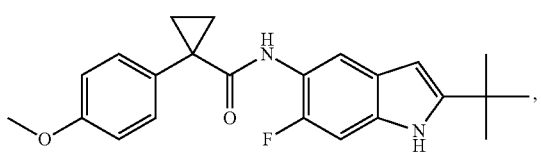

5. n term n is 1-3.

In several embodiments, n is 1. In other embodiments, n is 2. In still other embodiments, n is 3.

In one aspect, the present invention relates to compounds of formula II useful as modulators of ABC transporter activity:

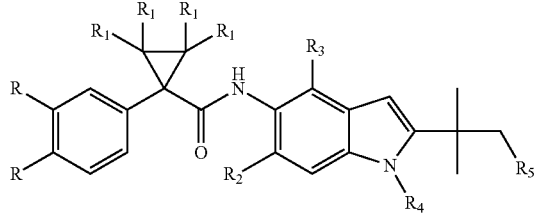

or a pharmaceutically acceptable salt thereof, wherein independently for each occurrence:

R is H, OH, OCH$_3$ or two R taken together form —OCH$_2$O— or —OCF$_2$O—;

R$_1$ is H or alkyl;

R$_2$ is H or F;

R$_3$ is H or CN;

R$_4$ is H, —CH$_2$OCH$_2$CH(OH)CH$_2$OH, —CH$_2$CH$_2$N(CH$_3$)$_3$, or —CH$_2$CH$_2$OH;

R$_5$ is H, OH, —CH$_2$OCH$_2$CH(OH)CH$_2$OH, —CH$_2$OH, or R$_4$ and R$_5$ taken together form a five membered ring.

In one embodiment, the present invention provides compounds of formula II, wherein the compounds set forth below are excluded:

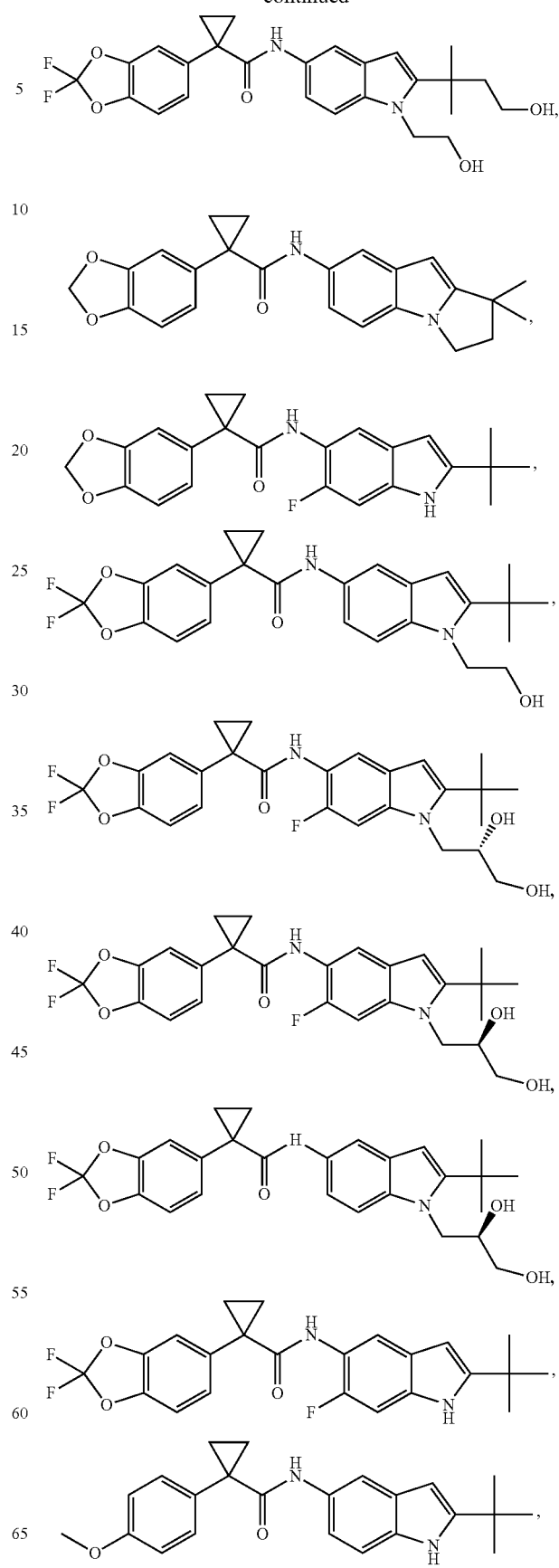

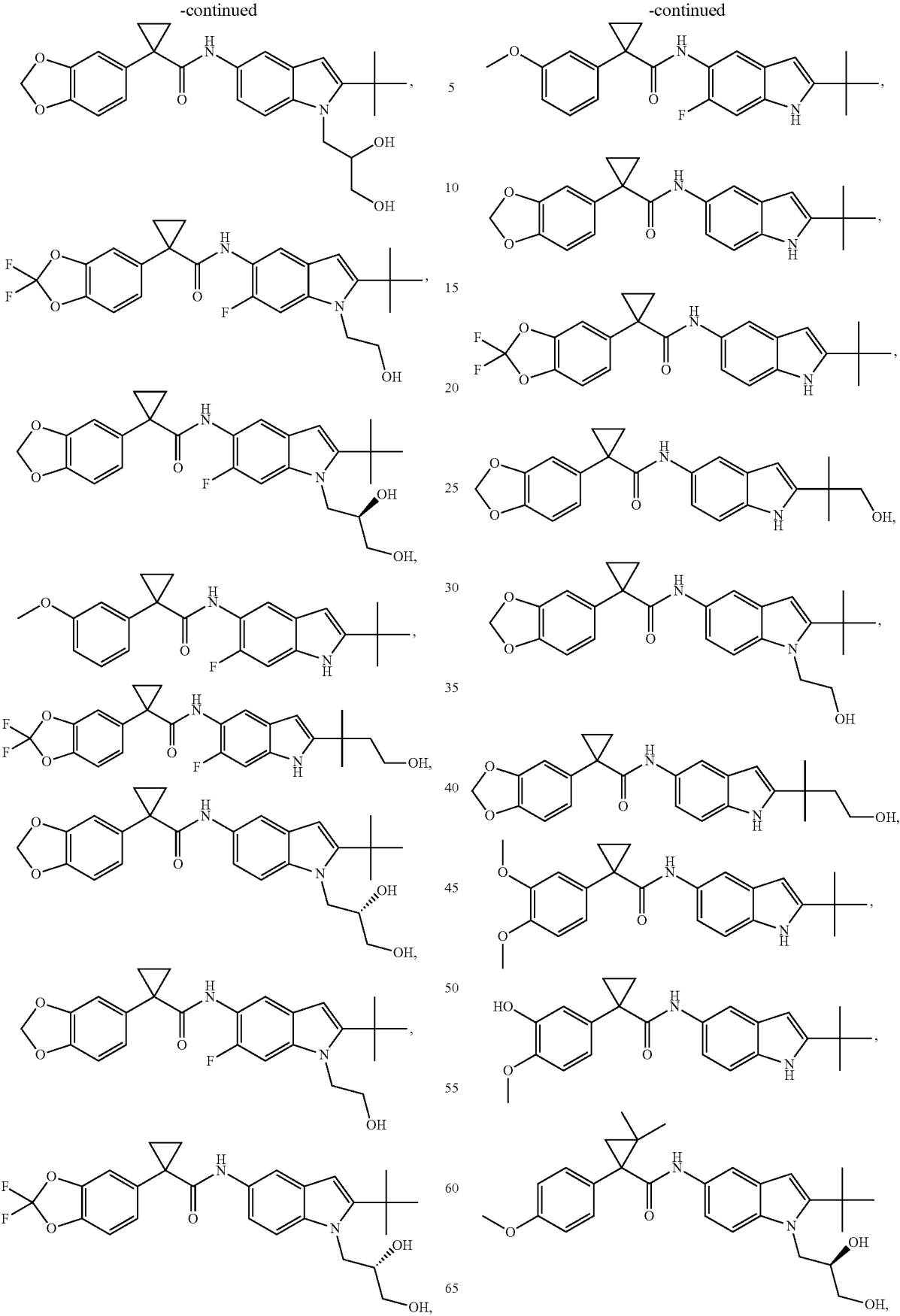

-continued

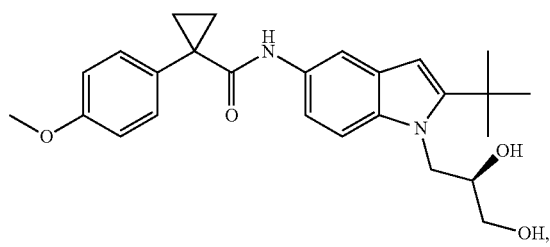

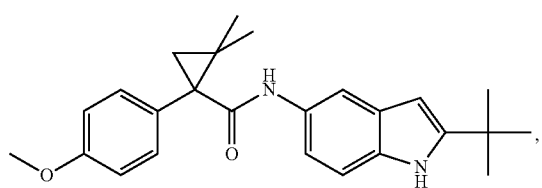

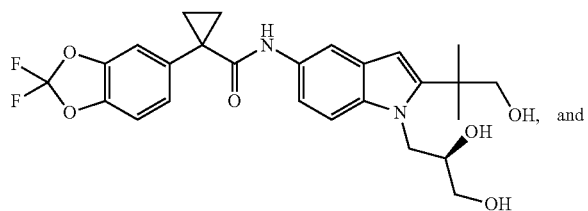

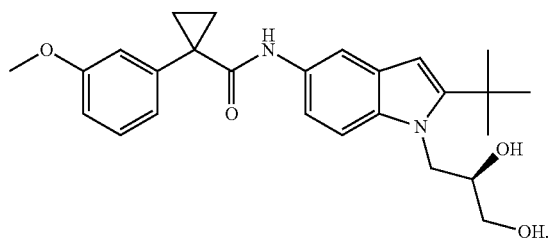

In one embodiment of the compounds, two R taken together form —OCF$_2$O—, R$_1$ is H, and R$_2$ is F. In another embodiment, two R taken together form —OCF$_2$O—, R$_1$ is H, R$_2$ is F, and R$_3$ is H. In another embodiment, two R taken together form —OCF$_2$O—, R$_1$ is H, R$_2$ is F, R$_3$ is H, and R$_4$ is H. In another embodiment, two R taken together form —OCF$_2$O—, R$_1$ is H, R$_2$ is F, R$_3$ is H, and R$_4$ is —CH$_2$CH$_2$N$^+$(CH$_3$)$_3$. In another embodiment, two R taken together form —OCF$_2$O—, R$_1$ is H, R$_2$ is F, R$_3$ is H, and R$_4$ is —CH$_2$OCH$_2$CH(OH)CH$_2$OH. In another embodiment, two R taken together form —OCF$_2$O—, R$_1$ is H, R$_2$ is F, R$_3$ is H, and R$_4$ and R$_5$ taken together form a five membered ring.

In one embodiment of the compounds, two R taken together form —OCH$_2$O—, R$_1$ is H, and R$_2$ is F. In another embodiment, two R taken together form —OCH$_2$O—, R$_1$ is H, R$_2$ is F, and R$_3$ is H. In another embodiment, two R taken together form —OCH$_2$O—, R$_1$ is H, R$_2$ is F, R$_3$ is H, and R$_4$ is —CH$_2$OCH$_2$CH(OH)CH$_2$OH.

In one embodiment of the compounds, R is OH, R$_1$ is H, R$_2$ is H, R$_3$ is H, and R$_4$ is —CH$_2$OCH$_2$CH(OH)CH$_2$OH.

In one embodiment of the compounds, at least one R is OCH$_3$, at least two R$_1$ are methyl, R$_2$ is H, R$_3$ is H, and R$_4$ is H. In another embodiment, at least one R is OCH$_3$, at least two R$_1$ are methyl, R$_2$ is H, R$_3$ is H, and R$_4$ is —CH$_2$OCH$_2$CH(OH)CH$_2$OH.

In one embodiment of the compounds, two R taken together form —CH$_2$CH$_2$CH$_2$—, R$_1$ is H, R$_2$ is H, R$_3$ is H, and R$_4$ is —CH$_2$OCH$_2$CH(OH)CH$_2$OH.

In one embodiment, the compound is represented by formula IIa:

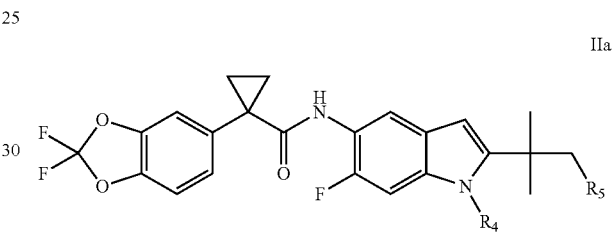

IIa or a pharmaceutically acceptable salt thereof, wherein:
R$_4$ is H, —CH$_2$OCH$_2$CH(OH)CH$_2$OH, —CH$_2$CH$_2$N$^+$(CH$_3$)$_3$, or —CH$_2$CH$_2$OH; and
R$_5$ is H, OH, —CH$_2$OCH$_2$CH(OH)CH$_2$OH, —CH$_2$OH, or R$_4$ and R$_5$ taken together form a five membered ring.

In one embodiment of the compounds, R$_4$ is —CH$_2$OCH$_2$CH(OH)CH$_2$OH, —CH$_2$CH$_2$N$^+$(CH$_3$)$_3$, or —CH$_2$CH$_2$OH. In another embodiment, R$_5$ is OH, —CH$_2$OCH$_2$CH(OH)CH$_2$OH, or —CH$_2$OH. In another embodiment, R$_4$ is —CH$_2$OCH$_2$CH(OH)CH$_2$OH, —CH$_2$CH$_2$N$^+$(CH$_3$)$_3$, or —CH$_2$CH$_2$OH; and R$_5$ is OH, —CH$_2$OCH$_2$CH(OH)CH$_2$OH, or —CH$_2$OH.

C. Exemplary Compounds of the Present Invention

Exemplary compounds of the present invention include, but are not limited to, those illustrated in Table 1 below.

TABLE 1

Exemplary compounds of the present invention.

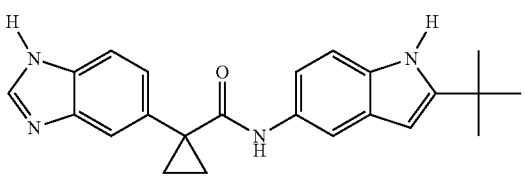 [SMILES: CC(C)(C)c1cc2cc(NC(=O)C3(c4ccc5[nH]cnc5c4)CC3)ccc2[nH]1]

1

TABLE 1-continued
Exemplary compounds of the present invention.
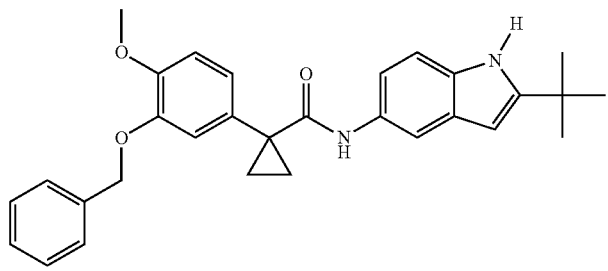 [SMILES: COc1ccc(C2(C(=O)Nc3ccc4[nH]c(C(C)(C)C)cc4c3)CC2)cc1OCc1ccccc1]
2
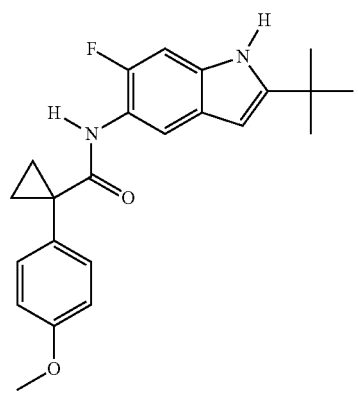 [SMILES: COc1ccc(C2(C(=O)Nc3cc4cc(C(C)(C)C)[nH]c4cc3F)CC2)cc1]
3
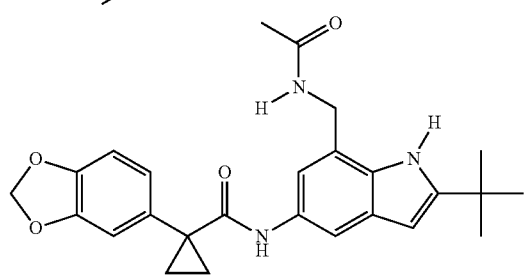
4
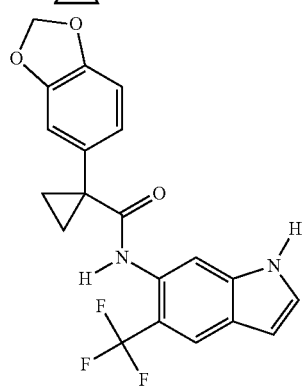
5
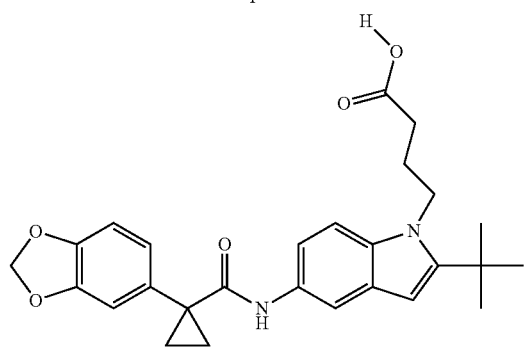
6

TABLE 1-continued
Exemplary compounds of the present invention.
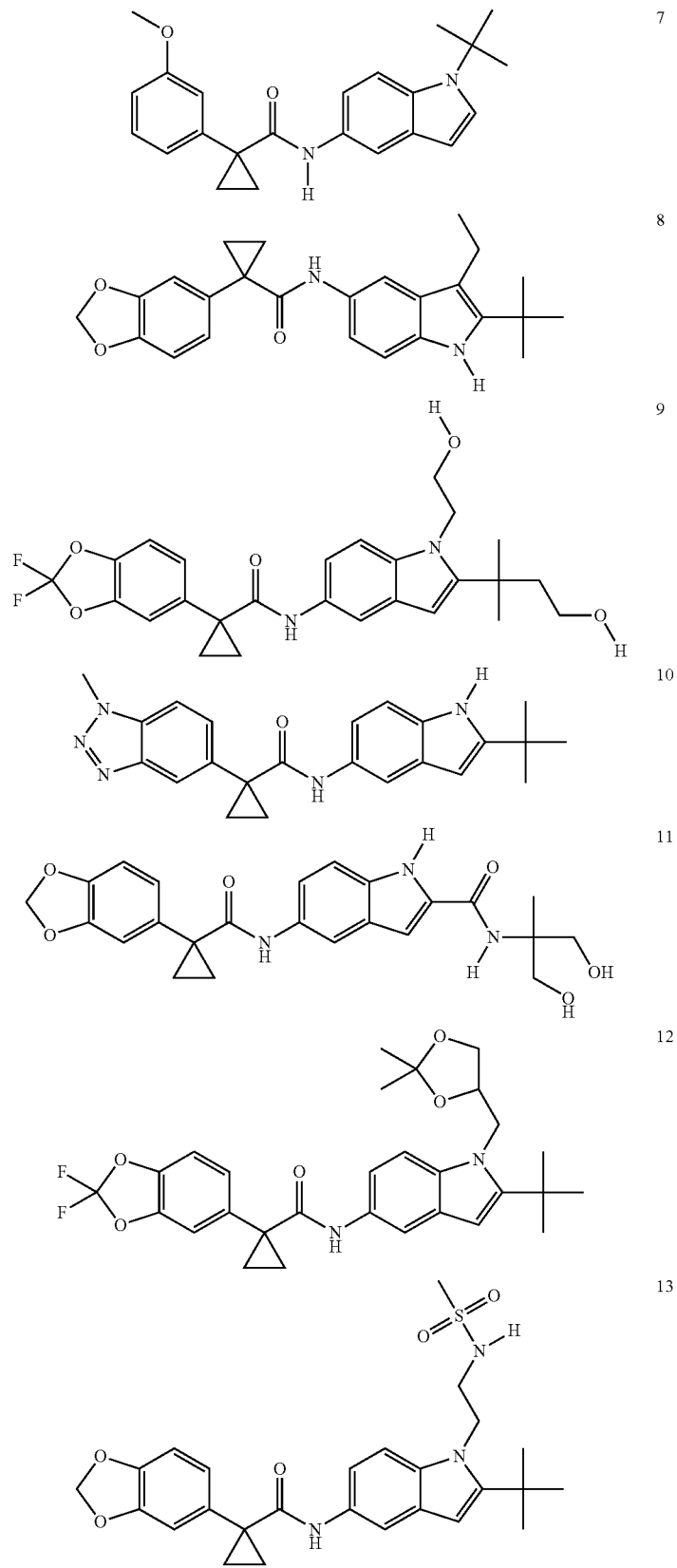

TABLE 1-continued
Exemplary compounds of the present invention.
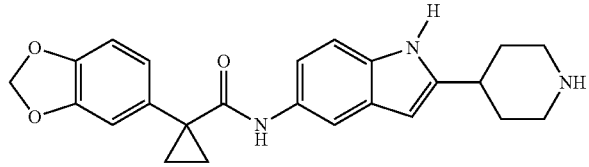 [SMILES: O=C(Nc1ccc2[nH]c(C3CCNCC3)cc2c1)C1(c2ccc3c(c2)OCO3)CC1]
14
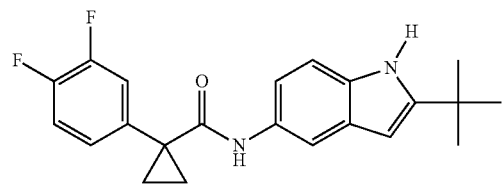 [SMILES: CC(C)(C)c1cc2cc(NC(=O)C3(c4ccc(F)c(F)c4)CC3)ccc2[nH]1]
15
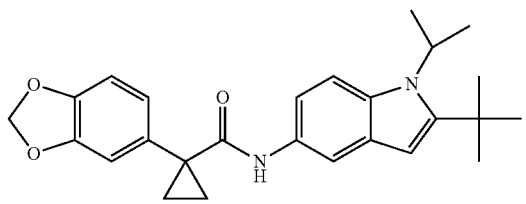 [SMILES: CC(C)n1c(C(C)(C)C)cc2cc(NC(=O)C3(c4ccc5c(c4)OCO5)CC3)ccc21]
16
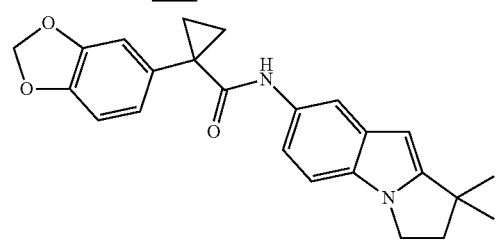
17
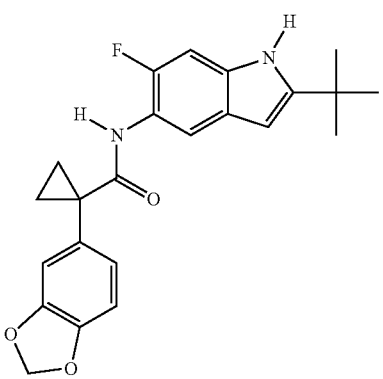 [SMILES: CC(C)(C)c1cc2cc(NC(=O)C3(c4ccc5c(c4)OCO5)CC3)c(F)cc2[nH]1]
18
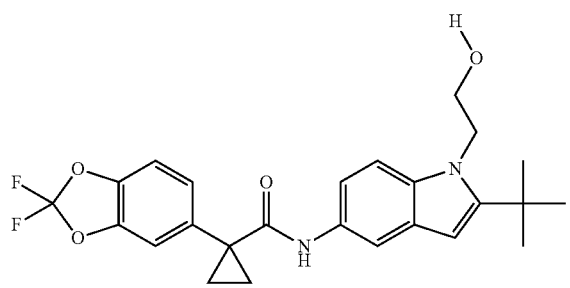 [SMILES: CC(C)(C)c1cc2cc(NC(=O)C3(c4ccc5c(c4)OC(F)(F)O5)CC3)ccc2n1CCO]
19
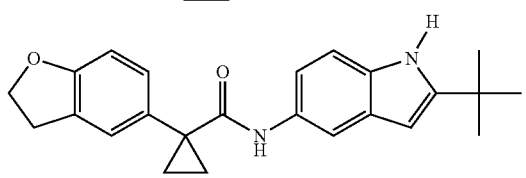
20

TABLE 1-continued
Exemplary compounds of the present invention.
21
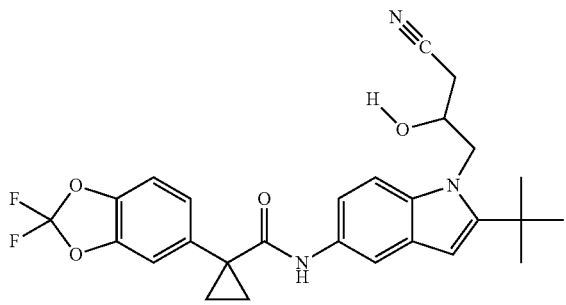 [SMILES: CC(C)(C)c1cc2cc(NC(=O)C3(c4ccc5c(c4)OC(F)(F)O5)CC3)ccc2n1CC(O)CC#N]
22
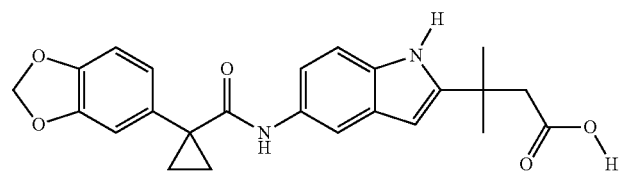 [SMILES: CC(C)(CC(=O)O)c1cc2cc(NC(=O)C3(c4ccc5c(c4)OCO5)CC3)ccc2[nH]1]
23
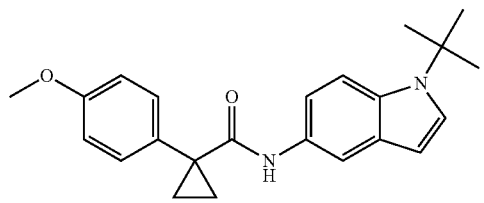 [SMILES: COc1ccc(C2(C(=O)Nc3ccc4c(ccn4C(C)(C)C)c3)CC2)cc1]
24
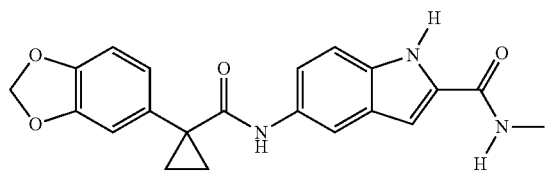
25
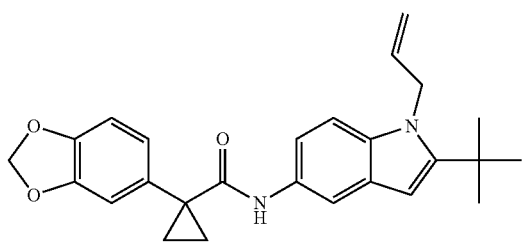 [SMILES: C=CCn1c(C(C)(C)C)cc2cc(NC(=O)C3(c4ccc5c(c4)OCO5)CC3)ccc21]
26
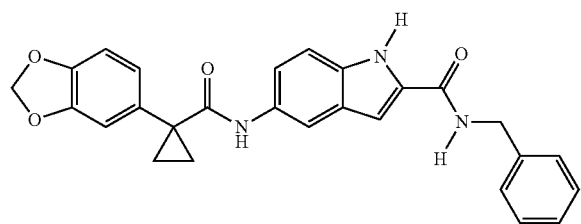 [SMILES: O=C(NCc1ccccc1)c1cc2cc(NC(=O)C3(c4ccc5c(c4)OCO5)CC3)ccc2[nH]1]

TABLE 1-continued
Exemplary compounds of the present invention.
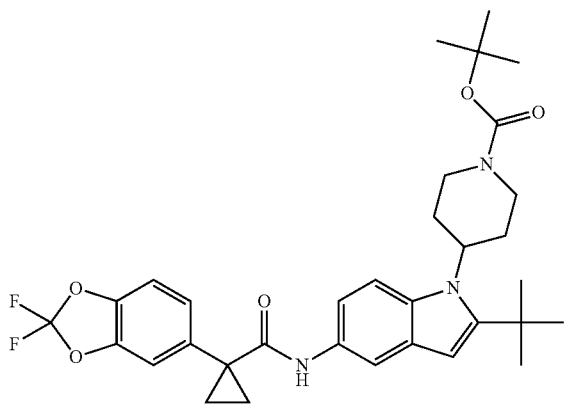 [SMILES: CC(C)(C)OC(=O)N1CCC(n2c(C(C)(C)C)cc3cc(NC(=O)C4(c5ccc6c(c5)OC(F)(F)O6)CC4)ccc32)CC1]
27
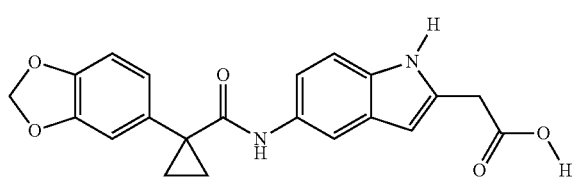 [SMILES: O=C(O)Cc1cc2cc(NC(=O)C3(c4ccc5c(c4)OCO5)CC3)ccc2[nH]1]
28
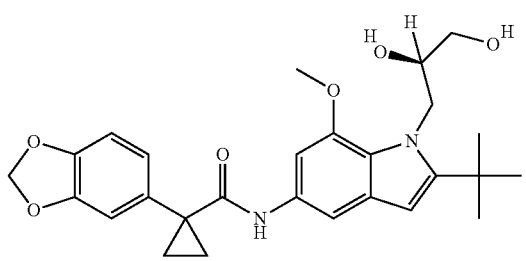
29
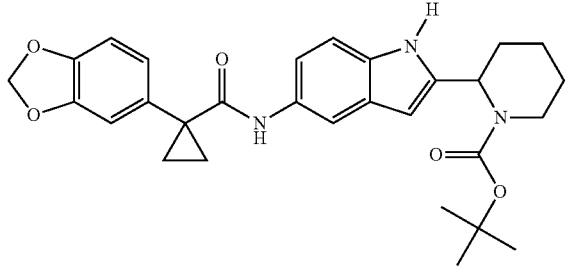 [SMILES: CC(C)(C)OC(=O)N1CCCCC1c1cc2cc(NC(=O)C3(c4ccc5c(c4)OCO5)CC3)ccc2[nH]1]
30
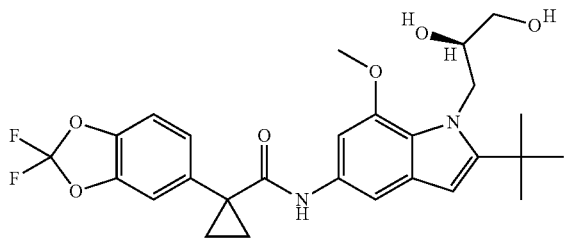
31
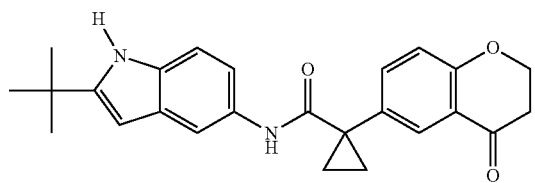 [SMILES: CC(C)(C)c1cc2cc(NC(=O)C3(c4ccc5c(c4)C(=O)CCO5)CC3)ccc2[nH]1]
32

TABLE 1-continued
Exemplary compounds of the present invention.
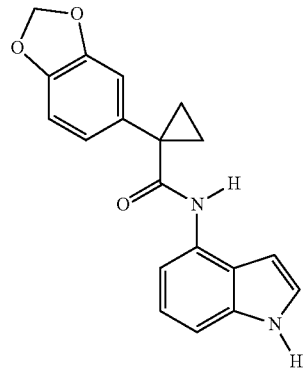 [SMILES: O=C(Nc1cccc2[nH]ccc12)C1(c2ccc3c(c2)OCO3)CC1]
33
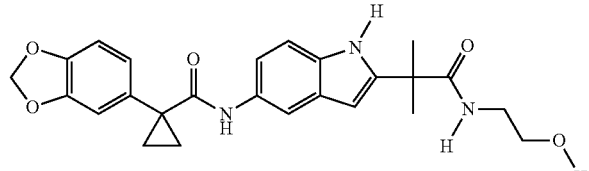
34
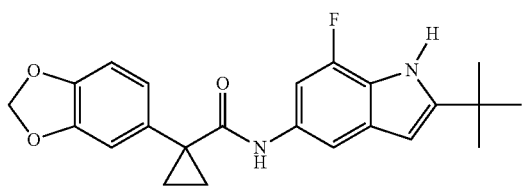 [SMILES: CC(C)(C)c1cc2cc(NC(=O)C3(c4ccc5c(c4)OCO5)CC3)cc(F)c2[nH]1]
35
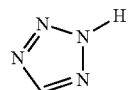
36
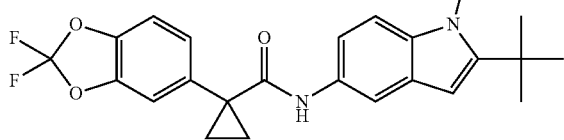
37
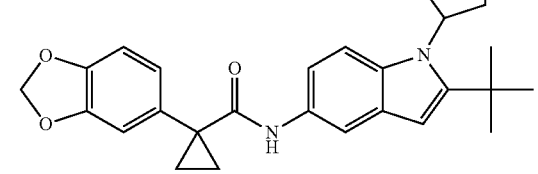
38
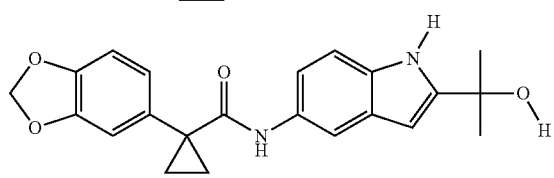
39

TABLE 1-continued
Exemplary compounds of the present invention.
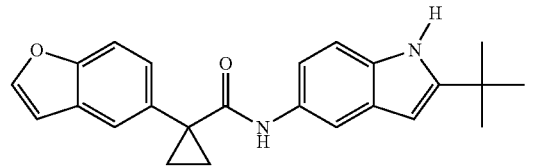 [SMILES: CC(C)(C)c1cc2cc(NC(=O)C3(c4ccc5occc5c4)CC3)ccc2[nH]1]
40
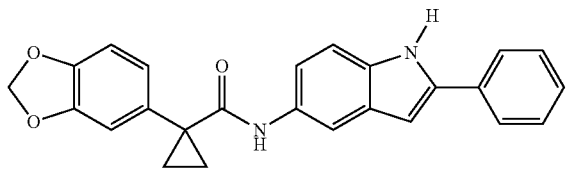
41
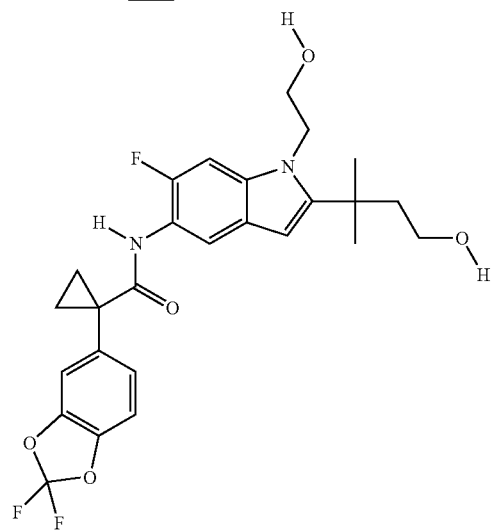
42
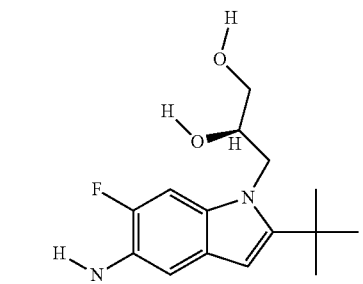
43
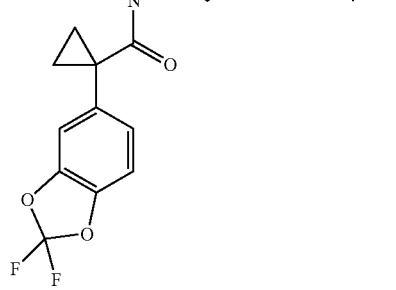
44

TABLE 1-continued
Exemplary compounds of the present invention.
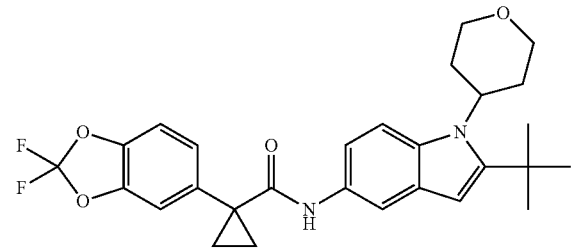 [SMILES: CC(C)(C)c1cc2cc(NC(=O)C3(c4ccc5c(c4)OC(F)(F)O5)CC3)ccc2n1C1CCOCC1]
45
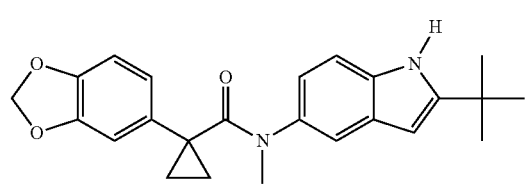 [SMILES: CN(C(=O)C1(c2ccc3c(c2)OCO3)CC1)c1ccc2[nH]c(C(C)(C)C)cc2c1]
46
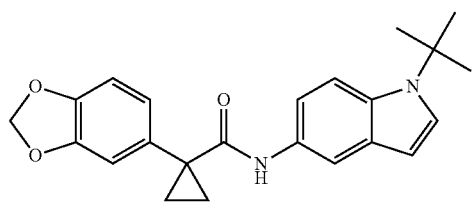 [SMILES: CC(C)(C)n1ccc2cc(NC(=O)C3(c4ccc5c(c4)OCO5)CC3)ccc21]
47
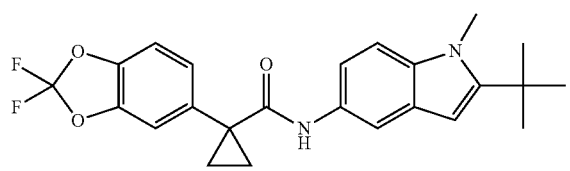 [SMILES: Cn1c(C(C)(C)C)cc2cc(NC(=O)C3(c4ccc5c(c4)OC(F)(F)O5)CC3)ccc21]
48
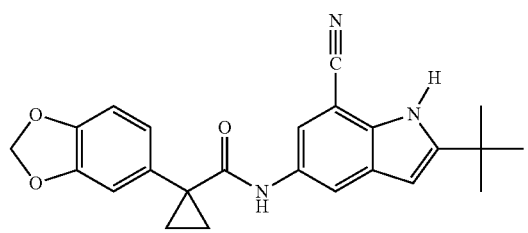 [SMILES: CC(C)(C)c1cc2cc(NC(=O)C3(c4ccc5c(c4)OCO5)CC3)cc(C#N)c2[nH]1]
49
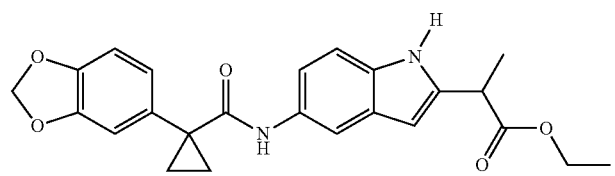 [SMILES: CCOC(=O)C(C)c1cc2cc(NC(=O)C3(c4ccc5c(c4)OCO5)CC3)ccc2[nH]1]
50
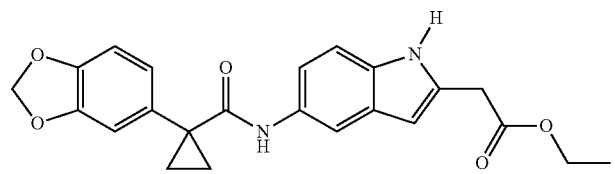 [SMILES: CCOC(=O)Cc1cc2cc(NC(=O)C3(c4ccc5c(c4)OCO5)CC3)ccc2[nH]1]
51
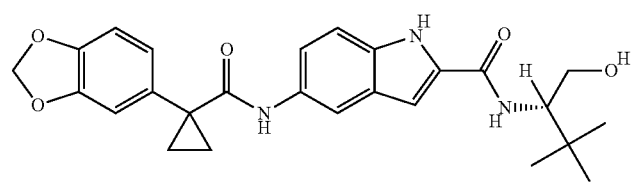
52

TABLE 1-continued
Exemplary compounds of the present invention.
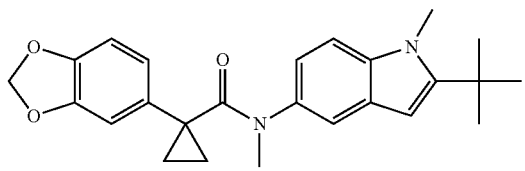 [SMILES: CN(C(=O)C1(c2ccc3c(c2)OCO3)CC1)c1ccc2c(c1)cc(C(C)(C)C)n2C]
53
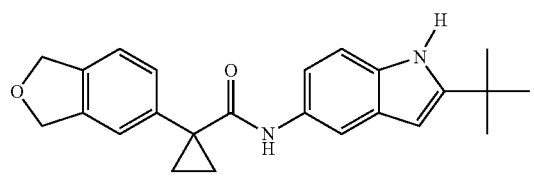 [SMILES: CC(C)(C)c1cc2cc(NC(=O)C3(c4ccc5c(c4)COC5)CC3)ccc2[nH]1]
54
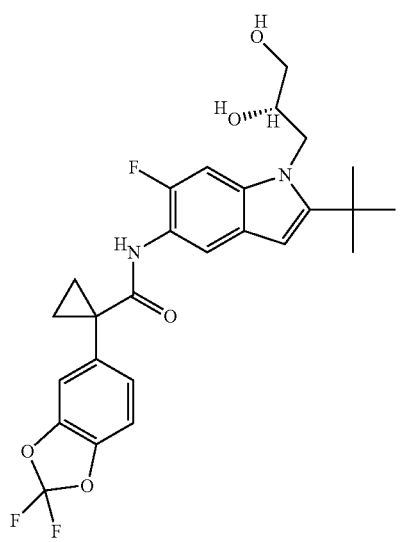
55
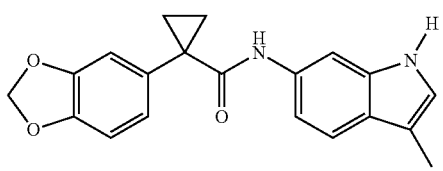 [SMILES: Cc1c[nH]c2cc(NC(=O)C3(c4ccc5c(c4)OCO5)CC3)ccc12]
56
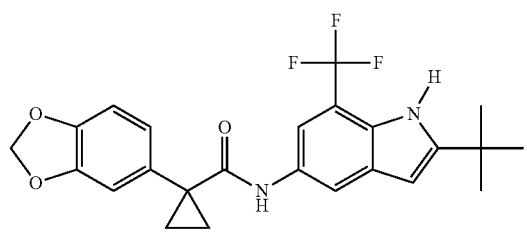 [SMILES: CC(C)(C)c1cc2cc(NC(=O)C3(c4ccc5c(c4)OCO5)CC3)cc(C(F)(F)F)c2[nH]1]
57

TABLE 1-continued
Exemplary compounds of the present invention.
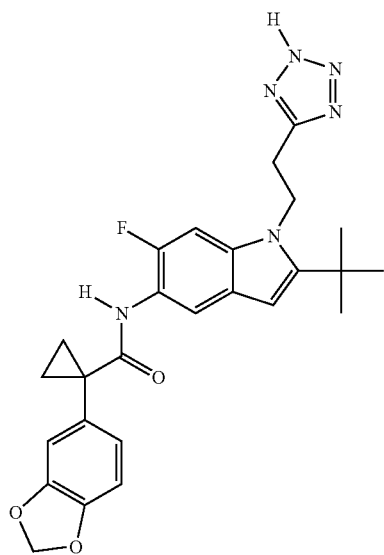 [SMILES: CC(C)(C)c1cc2cc(NC(=O)C3(c4ccc5c(c4)OCO5)CC3)c(F)cc2n1CCc1nn[nH]n1] 58
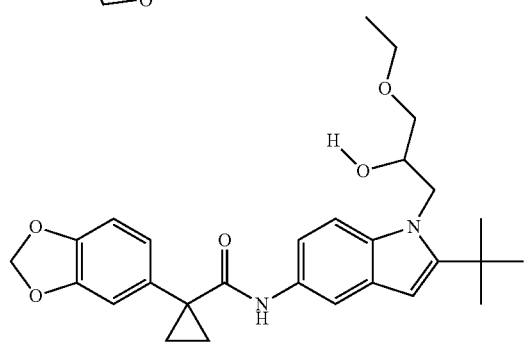 59
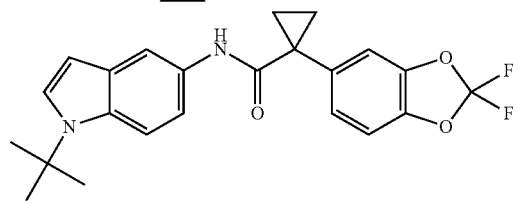 60
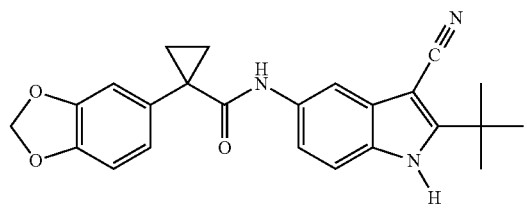 [SMILES: CC(C)(C)c1[nH]c2ccc(NC(=O)C3(c4ccc5c(c4)OCO5)CC3)cc2c1C#N] 61
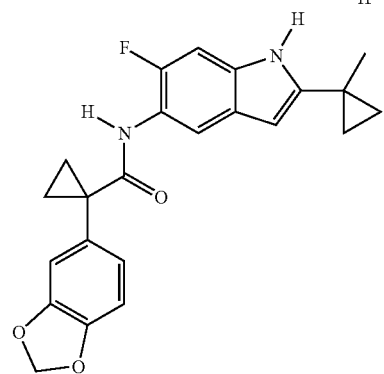 62

TABLE 1-continued
Exemplary compounds of the present invention.
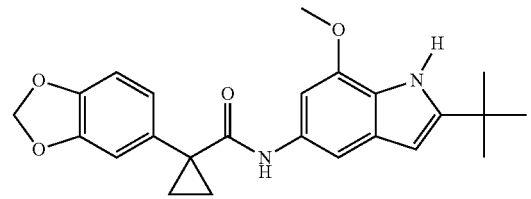 [SMILES: COc1cc(NC(=O)C2(c3ccc4c(c3)OCO4)CC2)cc2cc(C(C)(C)C)[nH]c12]
63
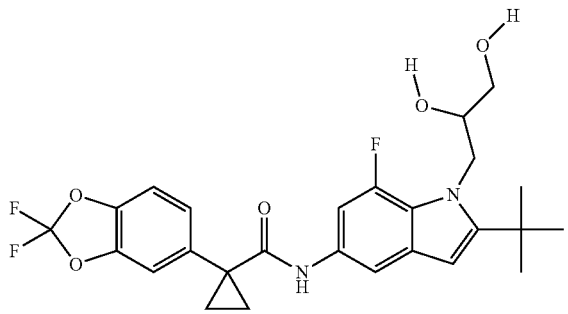 [SMILES: CC(C)(C)c1cc2cc(NC(=O)C3(c4ccc5c(c4)OC(F)(F)O5)CC3)cc(F)c2n1CC(O)CO]
64
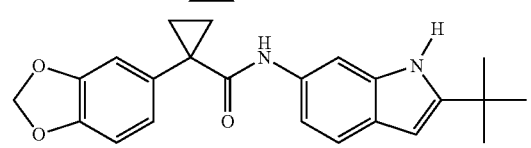
65
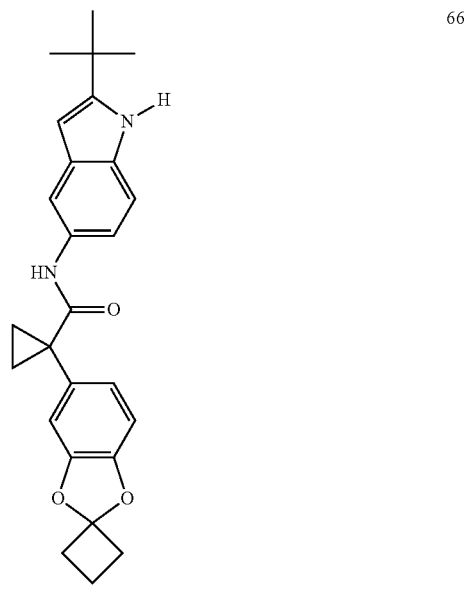
66
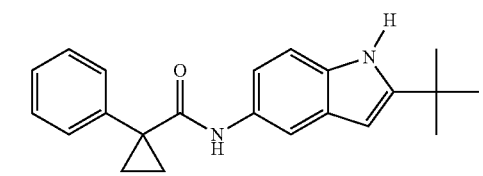 [SMILES: CC(C)(C)c1cc2cc(NC(=O)C3(c4ccccc4)CC3)ccc2[nH]1]
67
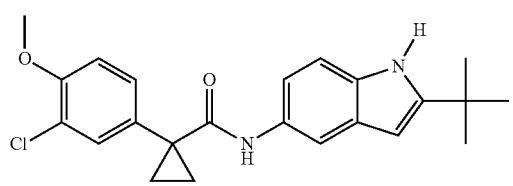 [SMILES: COc1ccc(C2(C(=O)Nc3ccc4[nH]c(C(C)(C)C)cc4c3)CC2)cc1Cl]
68

TABLE 1-continued
Exemplary compounds of the present invention.
| | |
|---|---|
| 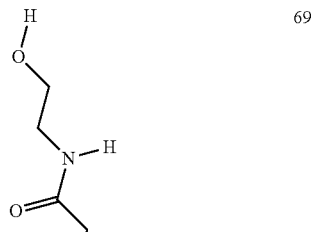 | 69 |
| 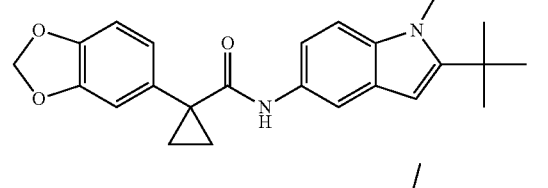 | 70 |
| 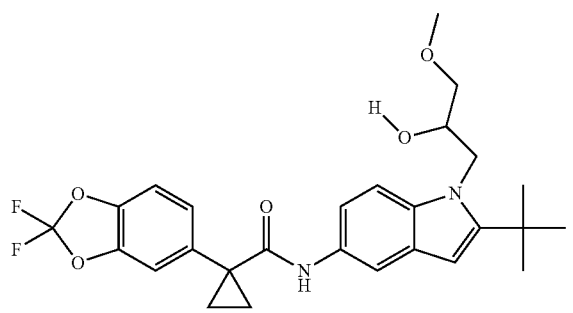 [SMILES: COCC(O)Cn1c(C(C)(C)C)cc2cc(NC(=O)C3(c4ccc5c(c4)OC(F)(F)O5)CC3)ccc21] | 71 |
| 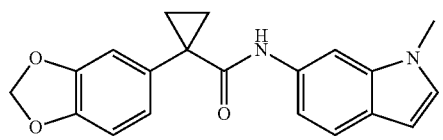 [SMILES: Cn1ccc2ccc(NC(=O)C3(c4ccc5c(c4)OCO5)CC3)cc21] | 72 |
| 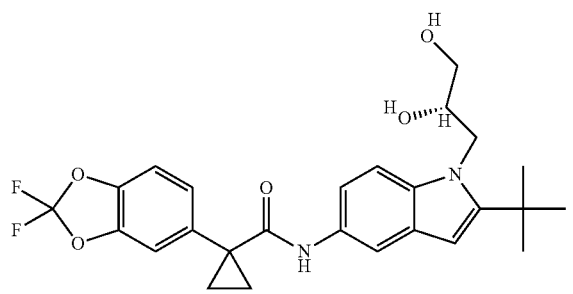 | 72 |
| 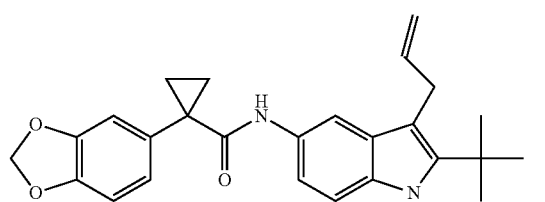 | 73 |
| 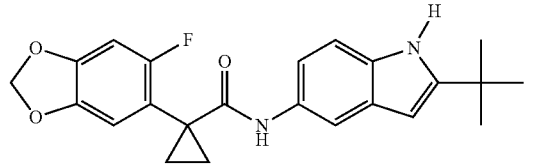 [SMILES: CC(C)(C)c1cc2cc(NC(=O)C3(c4cc5c(cc4F)OCO5)CC3)ccc2[nH]1] | 74 |

TABLE 1-continued
Exemplary compounds of the present invention.
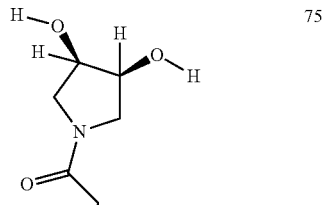
75
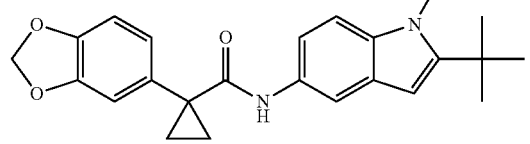
76
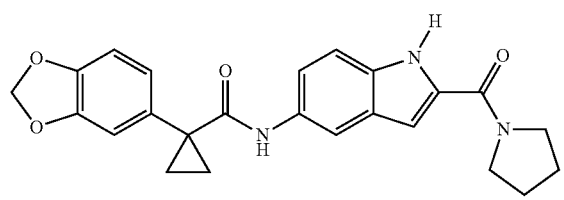 [SMILES: O=C(c1cc2cc(NC(=O)C3(c4ccc5c(c4)OCO5)CC3)ccc2[nH]1)N1CCCC1]
77
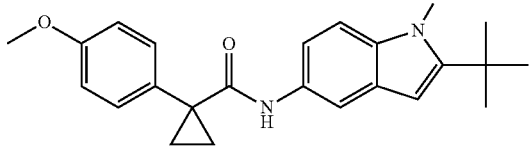
78
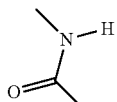
79
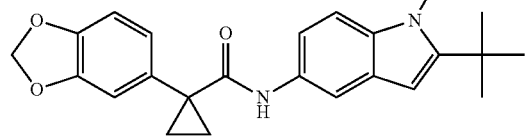
80

TABLE 1-continued
Exemplary compounds of the present invention.
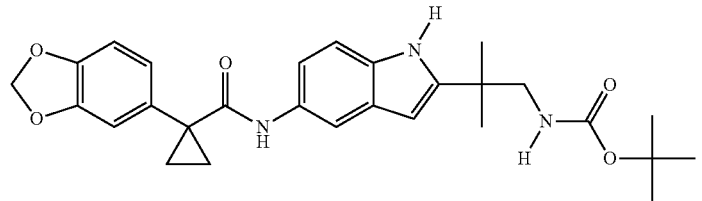 [SMILES: CC(C)(C)OC(=O)NCC(C)(C)c1cc2cc(NC(=O)C3(c4ccc5c(c4)OCO5)CC3)ccc2[nH]1]
81
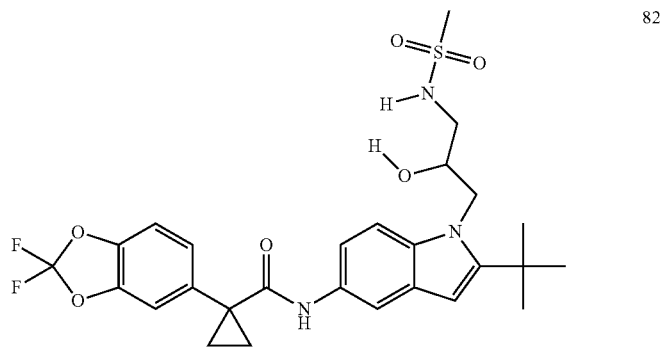
82
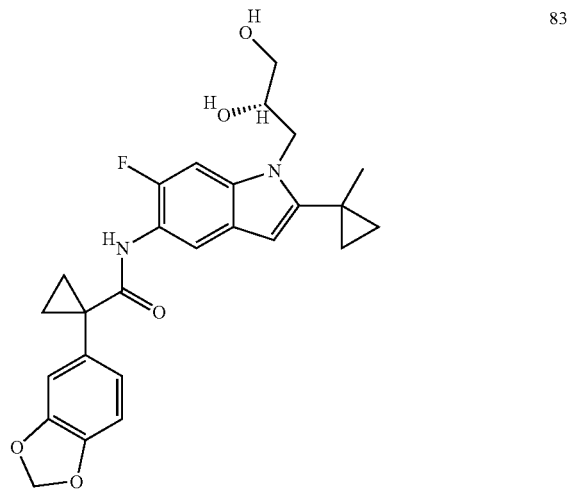
83
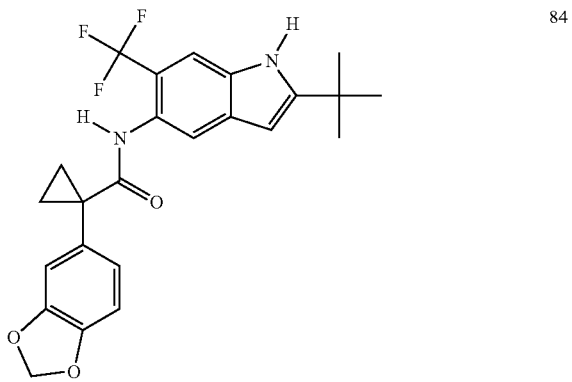
84
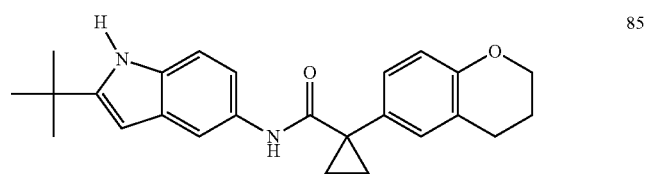
85

TABLE 1-continued
Exemplary compounds of the present invention.
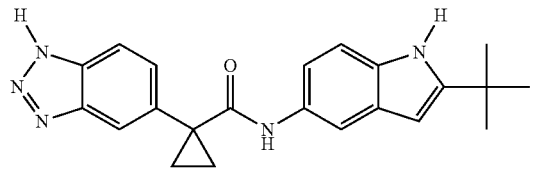 [SMILES: CC(C)(C)c1cc2cc(NC(=O)C3(c4ccc5[nH]nnc5c4)CC3)ccc2[nH]1]
86
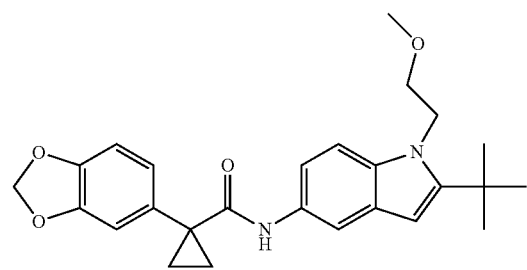 [SMILES: COCCn1c(C(C)(C)C)cc2cc(NC(=O)C3(c4ccc5c(c4)OCO5)CC3)ccc21]
87
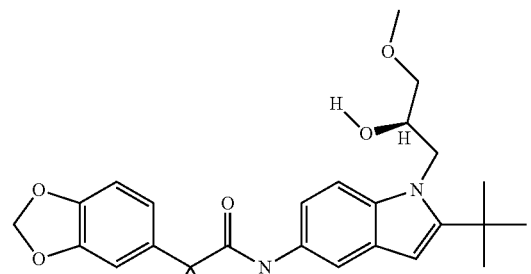
88
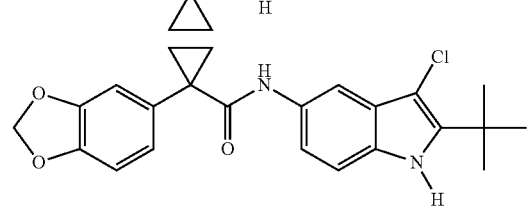
89
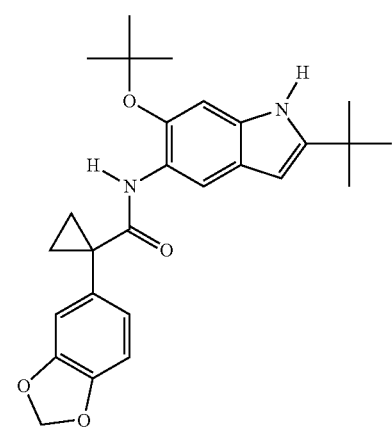 [SMILES: CC(C)(C)Oc1cc2[nH]c(C(C)(C)C)cc2cc1NC(=O)C1(c2ccc3c(c2)OCO3)CC1]
90
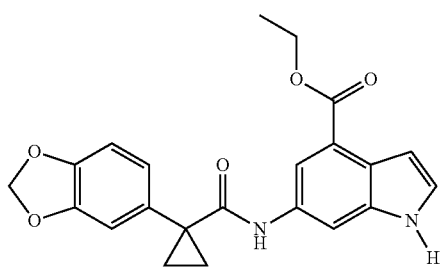 [SMILES: CCOC(=O)c1cc(NC(=O)C2(c3ccc4c(c3)OCO4)CC2)cc2[nH]ccc12]
91

TABLE 1-continued
Exemplary compounds of the present invention.
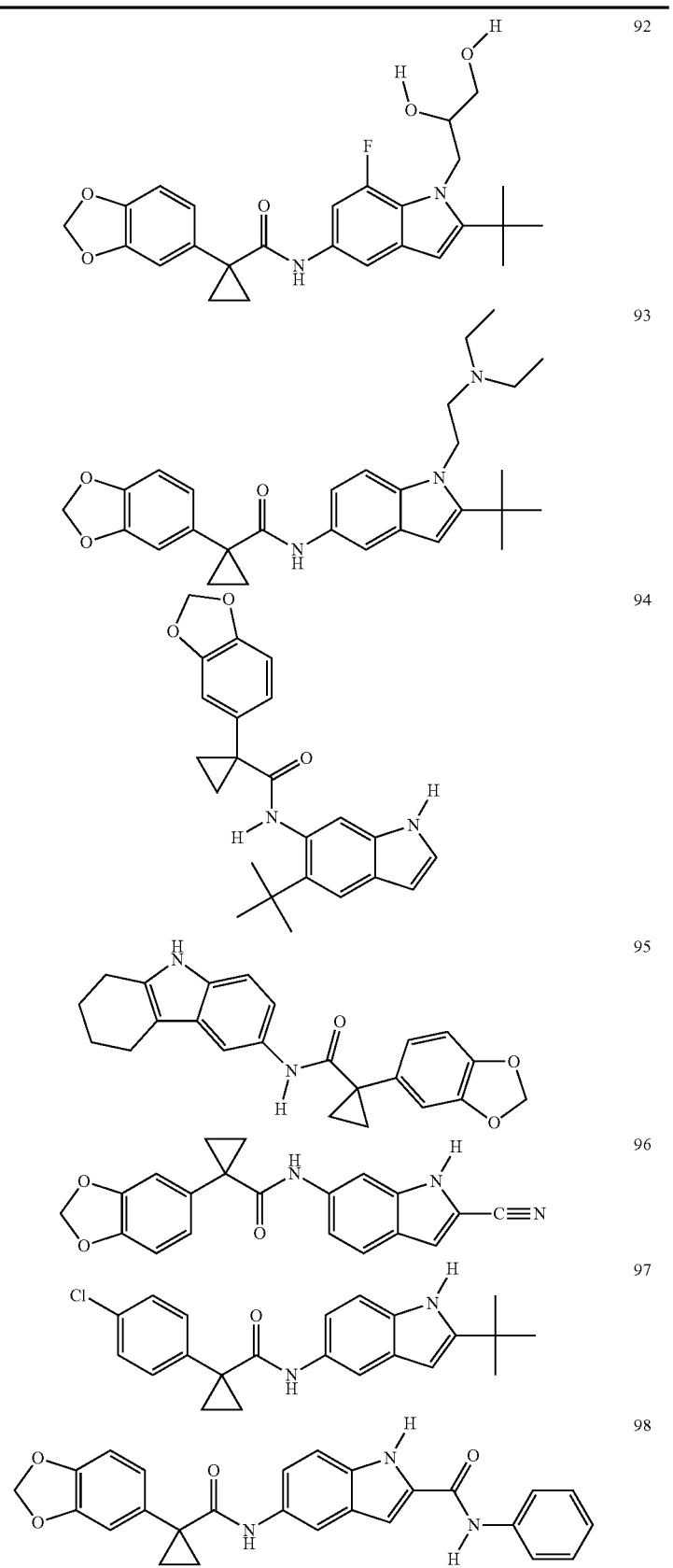

TABLE 1-continued
Exemplary compounds of the present invention.
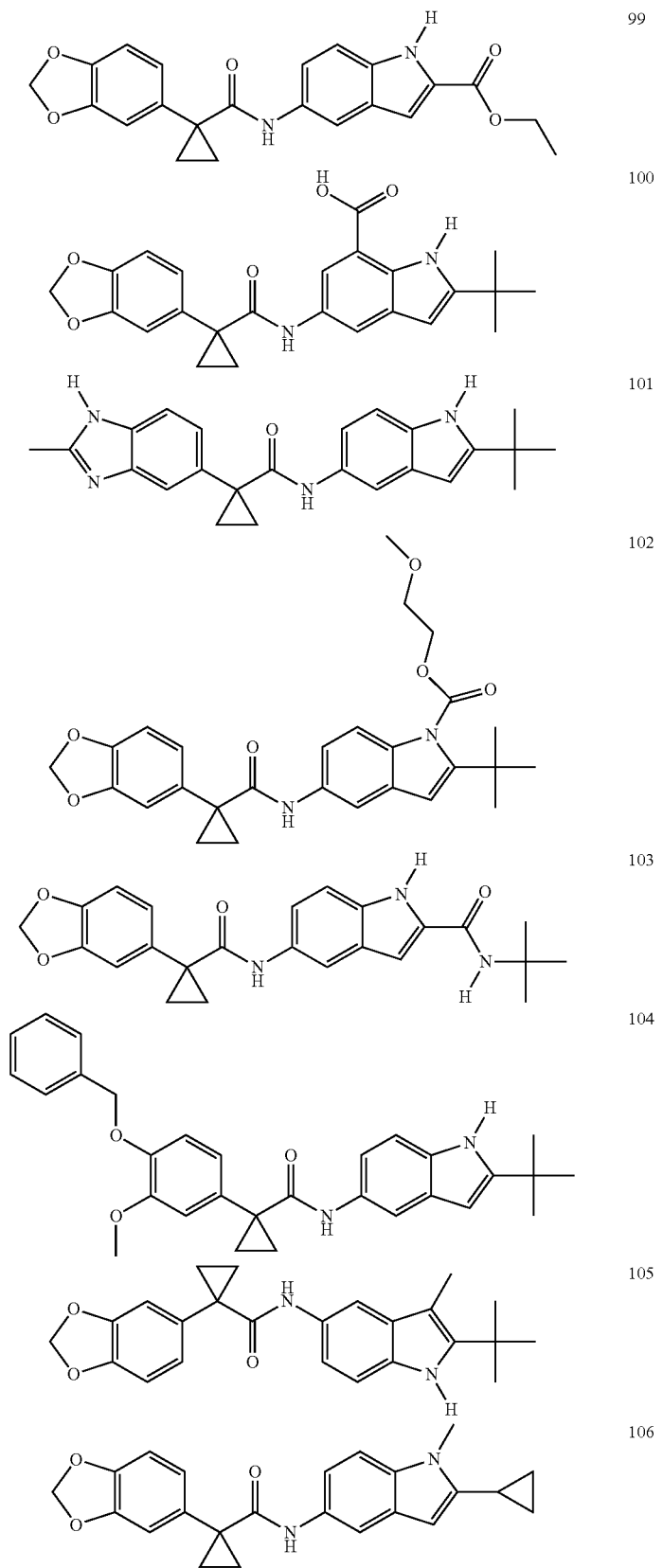

TABLE 1-continued

Exemplary compounds of the present invention.

| | |
|---|---|
| (structure) | 107 |
| (structure) | 108 |
| (structure) | 109 |
| (structure) | 110 |
| (structure) | 111 |
| (structure) | 112 |

TABLE 1-continued
Exemplary compounds of the present invention.
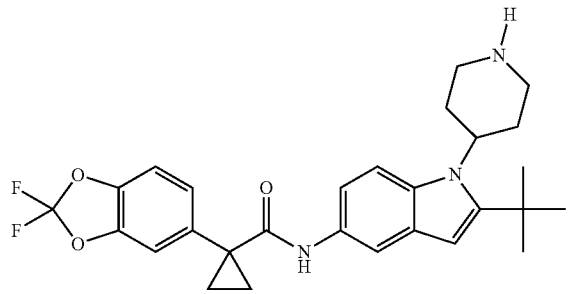 [SMILES: CC(C)(C)c1cc2cc(NC(=O)C3(c4ccc5c(c4)OC(F)(F)O5)CC3)ccc2n1C1CCNCC1] 113
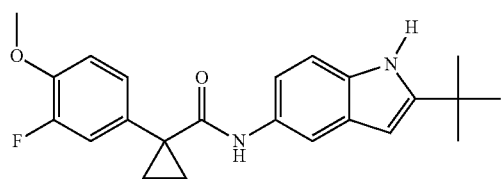 [SMILES: COc1ccc(C2(C(=O)Nc3ccc4[nH]c(C(C)(C)C)cc4c3)CC2)cc1F] 114
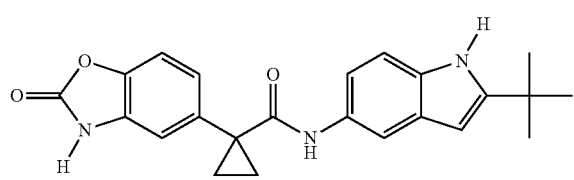 [SMILES: CC(C)(C)c1cc2cc(NC(=O)C3(c4ccc5oc(=O)[nH]c5c4)CC3)ccc2[nH]1] 115
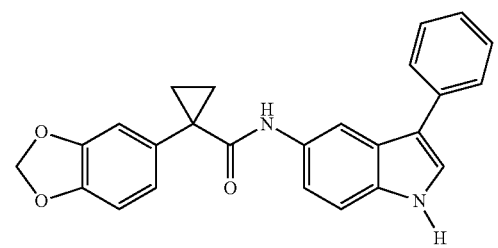 [SMILES: O=C(Nc1ccc2[nH]cc(-c3ccccc3)c2c1)C1(c2ccc3c(c2)OCO3)CC1] 116
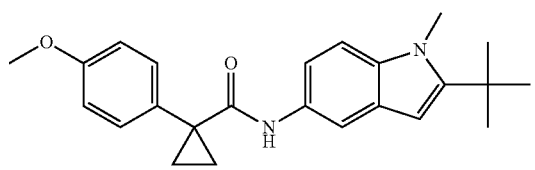 [SMILES: COc1ccc(C2(C(=O)Nc3ccc4c(c3)cc(C(C)(C)C)n4C)CC2)cc1] 117
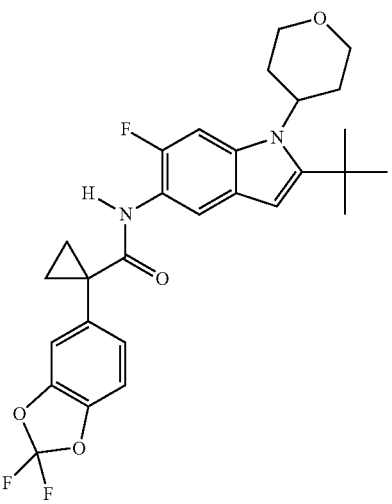 [SMILES: CC(C)(C)c1cc2cc(NC(=O)C3(c4ccc5c(c4)OC(F)(F)O5)CC3)c(F)cc2n1C1CCOCC1] 118

TABLE 1-continued

Exemplary compounds of the present invention.

| | |
|---|---|
| [structure] | 119 |
| [structure] | 120 |
| [structure] | 121 |
| [structure] | 122 |
| [structure] | 123 |
| [structure] | 124 |
| [structure] | 125 |
| [structure] | 126 |

TABLE 1-continued
Exemplary compounds of the present invention.
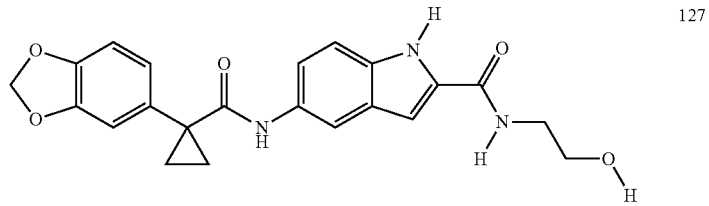 127
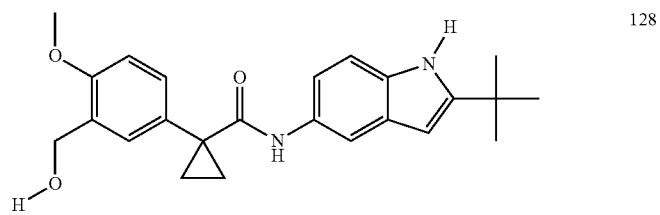 128
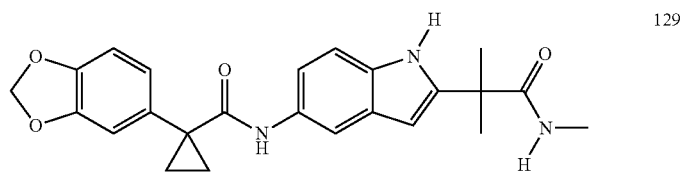 129
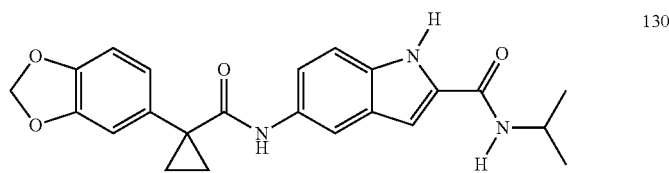 130
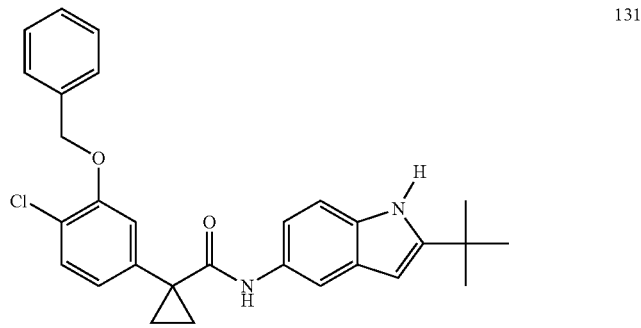 131
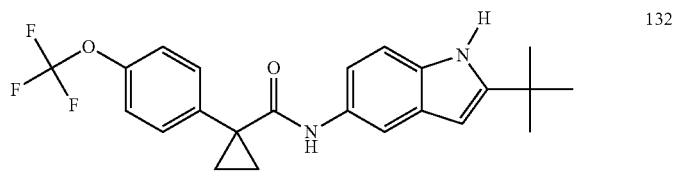 132
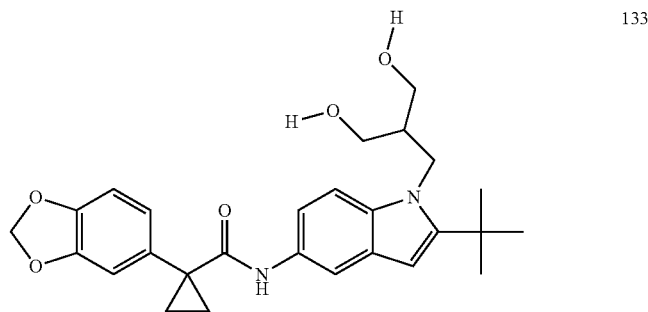 133

TABLE 1-continued
Exemplary compounds of the present invention.
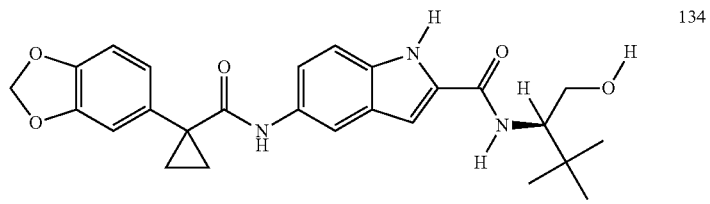
134
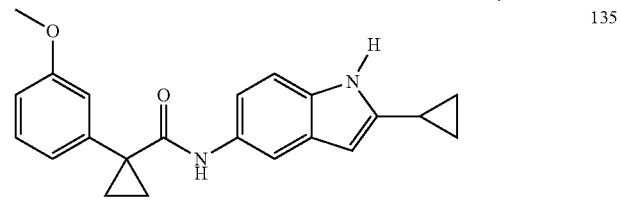
135
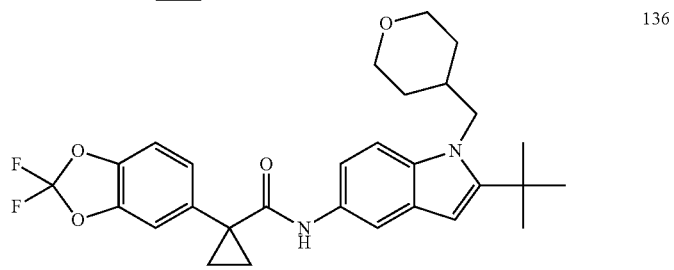
136
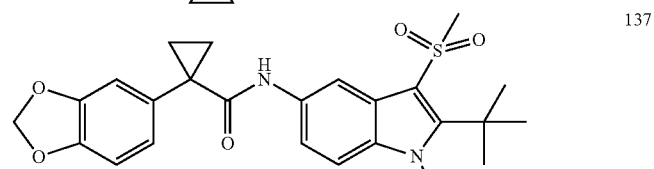
137
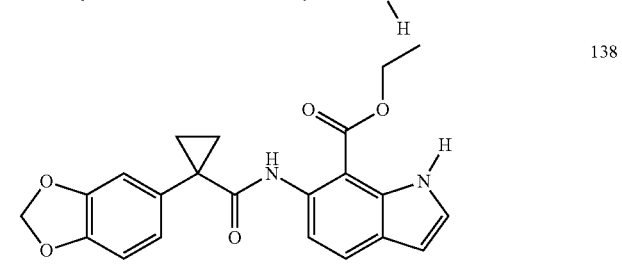
138
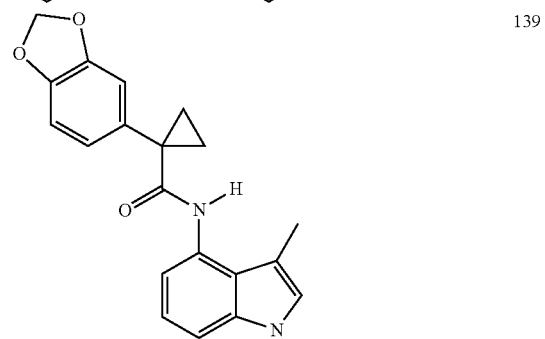
139
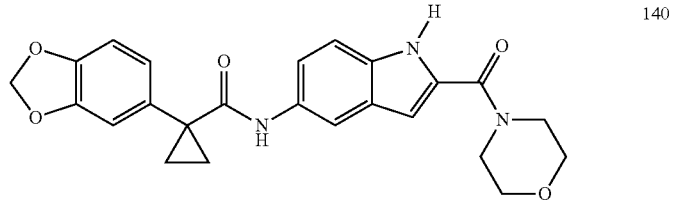
140

TABLE 1-continued
Exemplary compounds of the present invention.
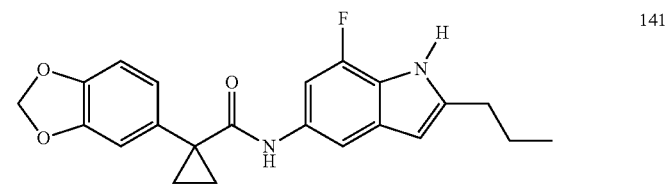
141
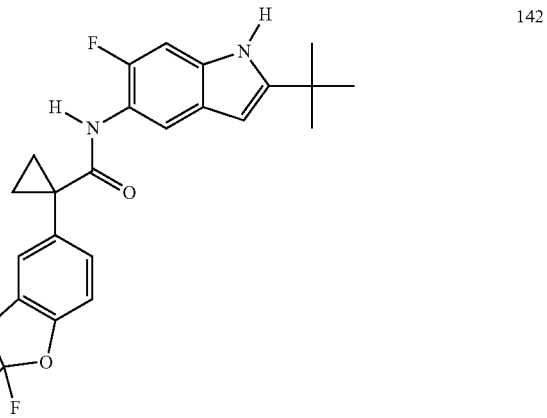
142
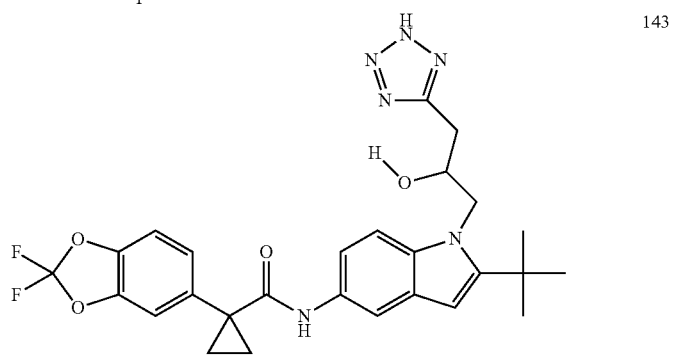
143
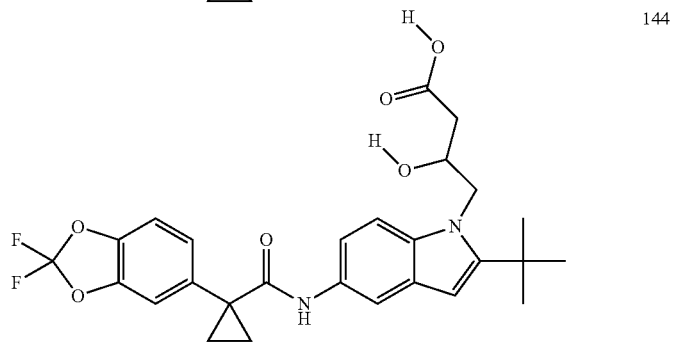
144
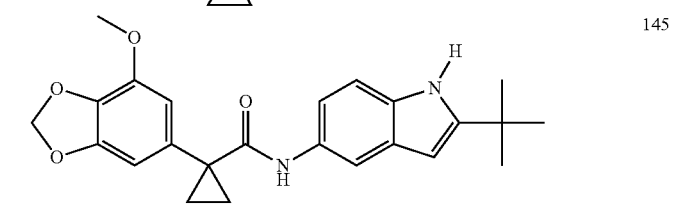
145
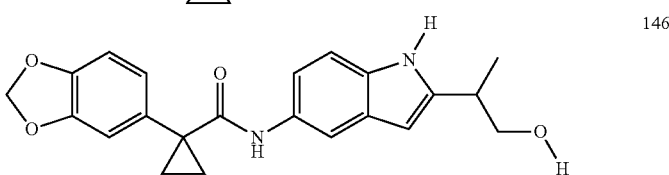
146

TABLE 1-continued
Exemplary compounds of the present invention.
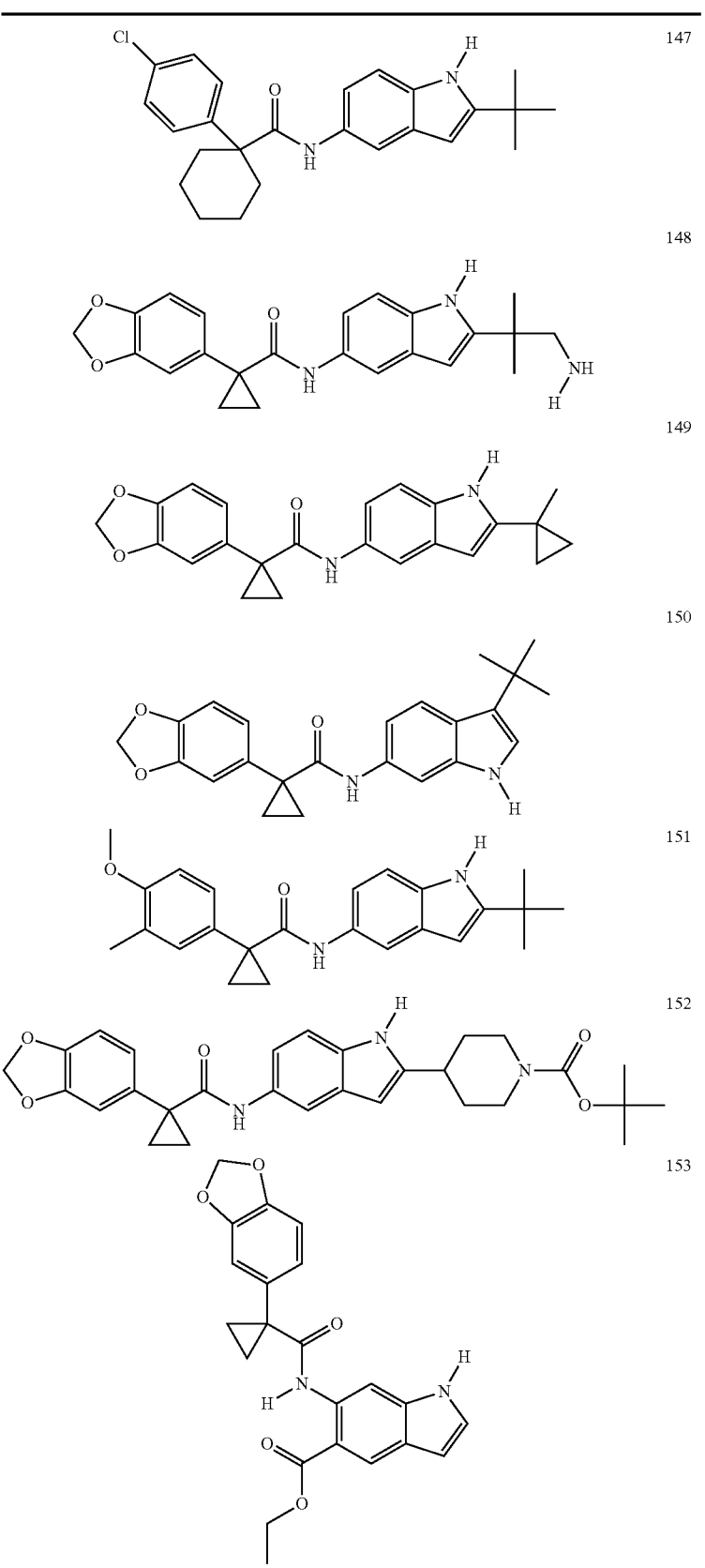

TABLE 1-continued
Exemplary compounds of the present invention.
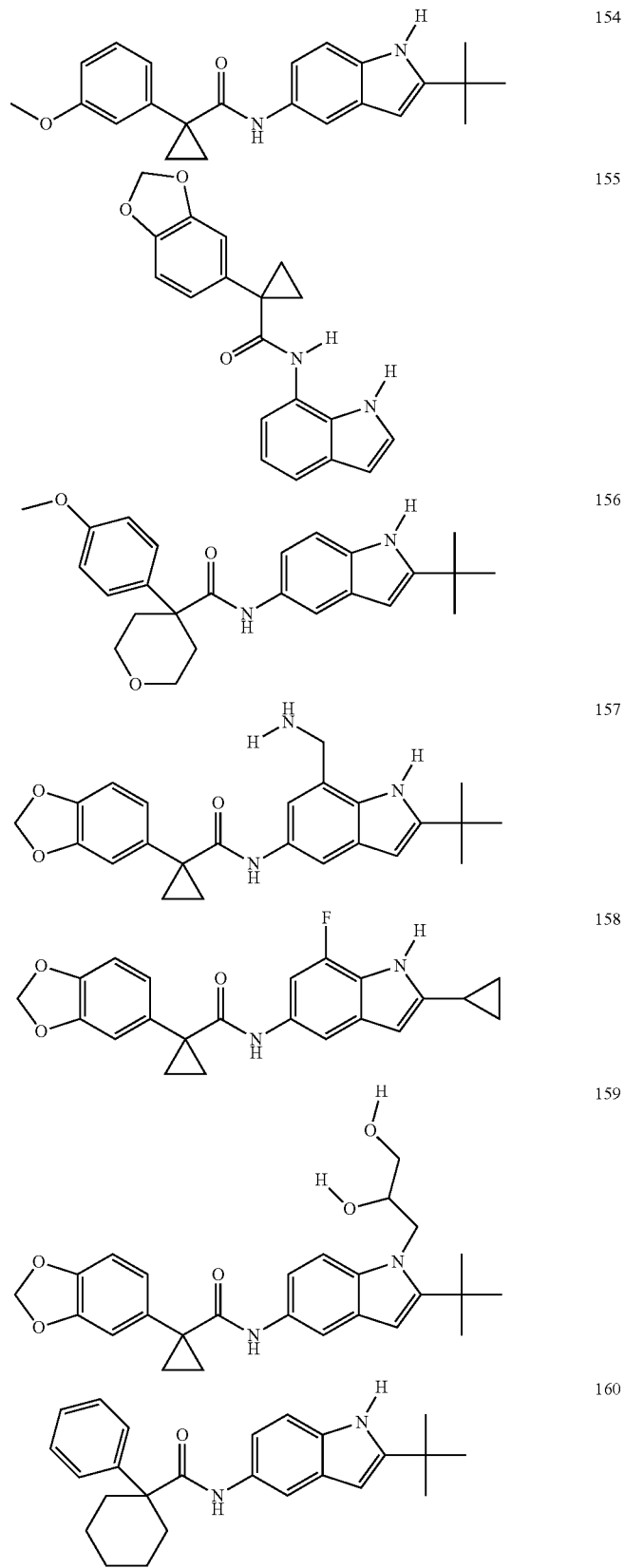

TABLE 1-continued
Exemplary compounds of the present invention.
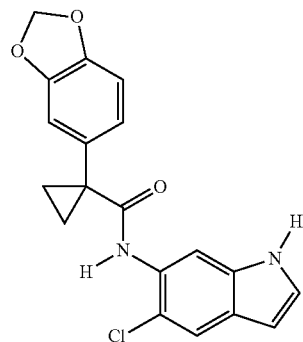 [SMILES: O=C(Nc1cc2[nH]ccc2cc1Cl)C1(c2ccc3c(c2)OCO3)CC1]
161
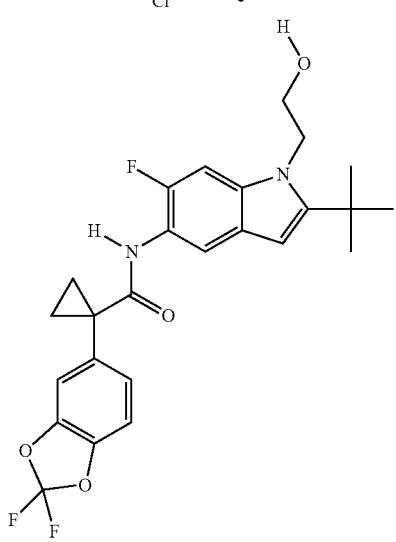
162
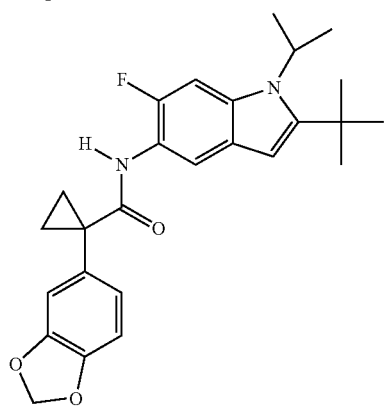
163
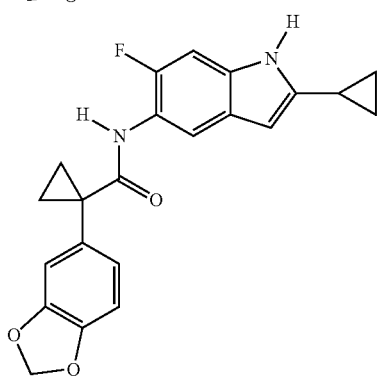
164

TABLE 1-continued
Exemplary compounds of the present invention.
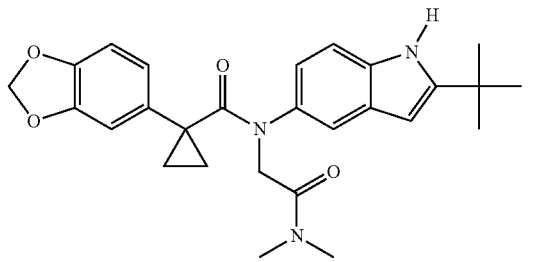 [SMILES: CN(C)C(=O)CN(C(=O)C1(c2ccc3c(c2)OCO3)CC1)c1ccc2[nH]c(C(C)(C)C)cc2c1]
165
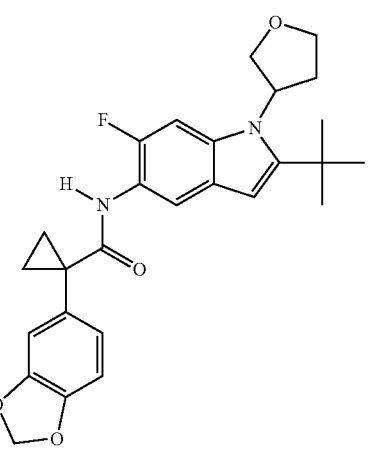
166
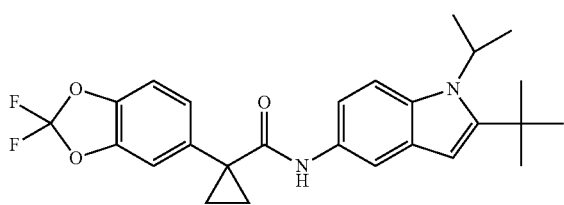 [SMILES: CC(C)n1c(C(C)(C)C)cc2cc(NC(=O)C3(c4ccc5c(c4)OC(F)(F)O5)CC3)ccc21]
167
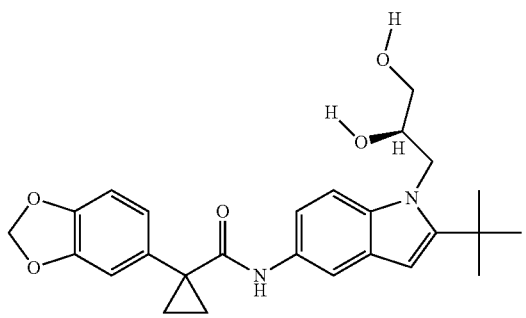
168
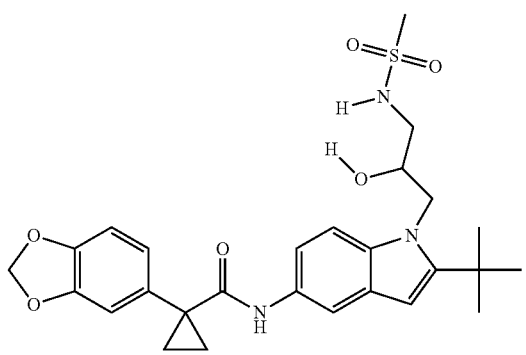 [SMILES: CC(C)(C)c1cc2cc(NC(=O)C3(c4ccc5c(c4)OCO5)CC3)ccc2n1CC(O)CNS(C)(=O)=O]
169

TABLE 1-continued
Exemplary compounds of the present invention.
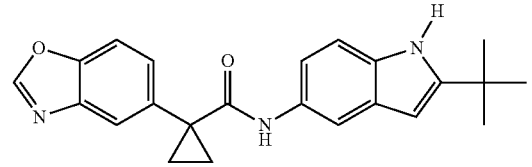
170
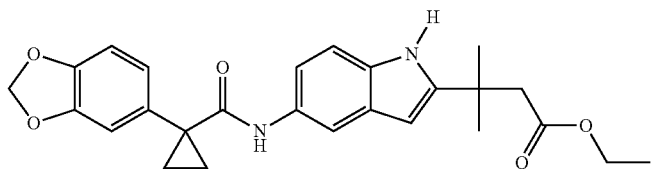 [SMILES: CCOC(=O)CC(C)(C)c1cc2cc(NC(=O)C3(c4ccc5c(c4)OCO5)CC3)ccc2[nH]1]
171
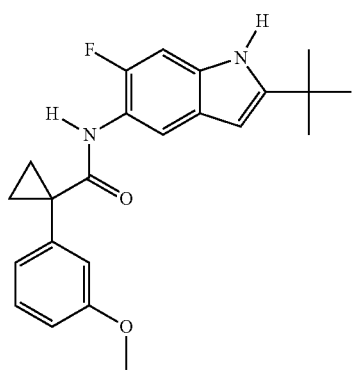 [SMILES: COc1cccc(C2(C(=O)Nc3cc4cc(C(C)(C)C)[nH]c4cc3F)CC2)c1]
172
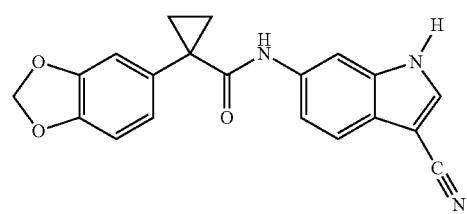 [SMILES: N#Cc1c[nH]c2cc(NC(=O)C3(c4ccc5c(c4)OCO5)CC3)ccc12]
173
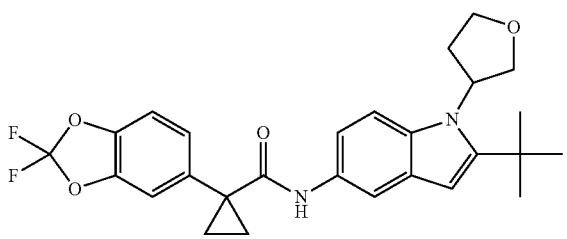 [SMILES: CC(C)(C)c1cc2cc(NC(=O)C3(c4ccc5c(c4)OC(F)(F)O5)CC3)ccc2n1C1CCOC1]
174
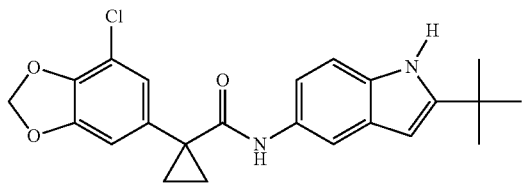 [SMILES: CC(C)(C)c1cc2cc(NC(=O)C3(c4cc(Cl)c5c(c4)OCO5)CC3)ccc2[nH]1]
175
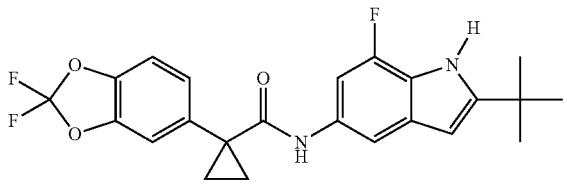 [SMILES: CC(C)(C)c1cc2cc(NC(=O)C3(c4ccc5c(c4)OC(F)(F)O5)CC3)cc(F)c2[nH]1]
176

TABLE 1-continued
Exemplary compounds of the present invention.
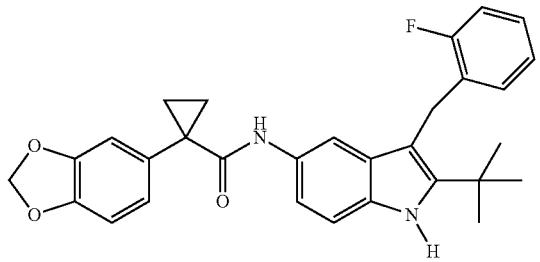 [SMILES: CC(C)(C)c1[nH]c2ccc(NC(=O)C3(c4ccc5c(c4)OCO5)CC3)cc2c1Cc1ccccc1F]
177
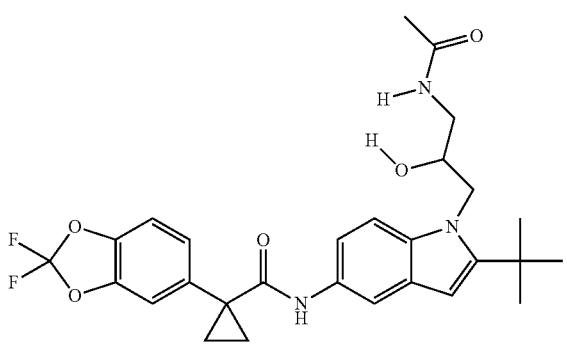 [SMILES: CC(=O)NCC(O)Cn1c(C(C)(C)C)cc2cc(NC(=O)C3(c4ccc5c(c4)OC(F)(F)O5)CC3)ccc21]
178
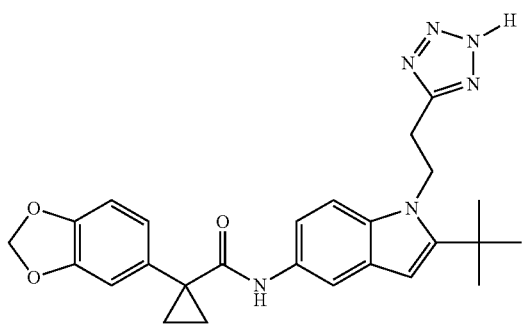 [SMILES: CC(C)(C)c1cc2cc(NC(=O)C3(c4ccc5c(c4)OCO5)CC3)ccc2n1CCc1nn[nH]n1]
179
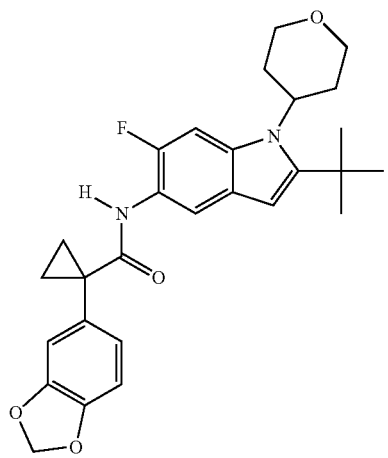 [SMILES: CC(C)(C)c1cc2cc(NC(=O)C3(c4ccc5c(c4)OCO5)CC3)c(F)cc2n1C1CCOCC1]
180
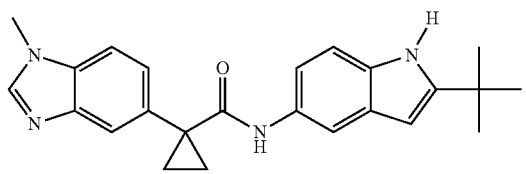
181

TABLE 1-continued
Exemplary compounds of the present invention.
182
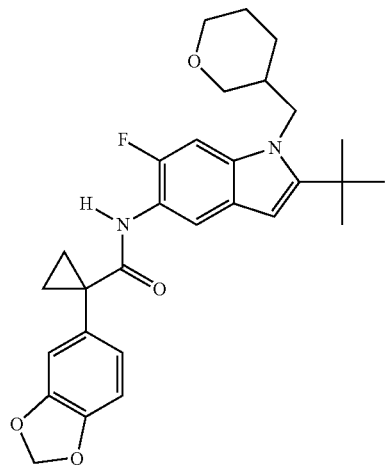 [SMILES: CC(C)(C)c1cc2cc(NC(=O)C3(c4ccc5c(c4)OCO5)CC3)c(F)cc2n1CC1CCCOC1]
183
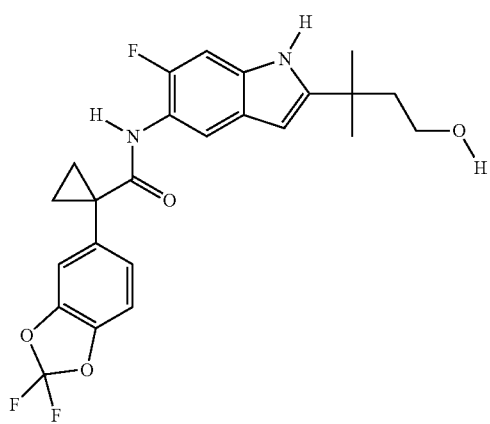 [SMILES: CC(C)(CCO)c1cc2cc(NC(=O)C3(c4ccc5c(c4)OC(F)(F)O5)CC3)c(F)cc2[nH]1]
184
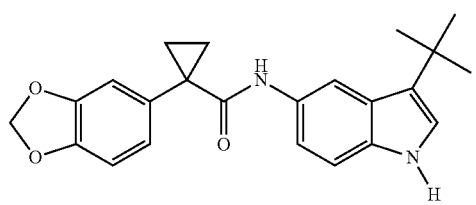 [SMILES: CC(C)(C)c1c[nH]c2ccc(NC(=O)C3(c4ccc5c(c4)OCO5)CC3)cc12]
185
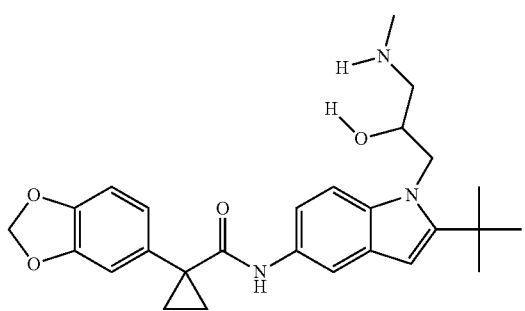 [SMILES: CNCC(O)Cn1c(C(C)(C)C)cc2cc(NC(=O)C3(c4ccc5c(c4)OCO5)CC3)ccc21]
186

TABLE 1-continued
Exemplary compounds of the present invention.
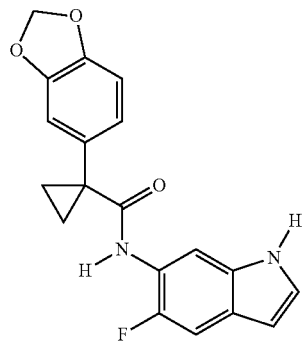
187
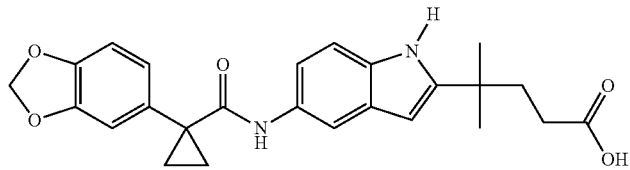 [SMILES: CC(C)(CCC(=O)O)c1cc2cc(NC(=O)C3(c4ccc5c(c4)OCO5)CC3)ccc2[nH]1]
188
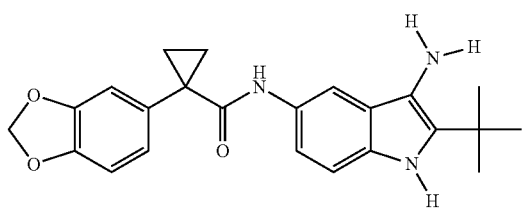 [SMILES: CC(C)(C)c1[nH]c2ccc(NC(=O)C3(c4ccc5c(c4)OCO5)CC3)cc2c1N]
189
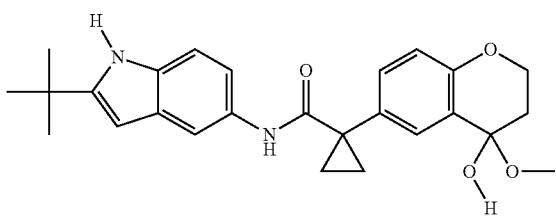 [SMILES: COC1(O)CCOc2ccc(C3(C(=O)Nc4ccc5[nH]c(C(C)(C)C)cc5c4)CC3)cc21]
190
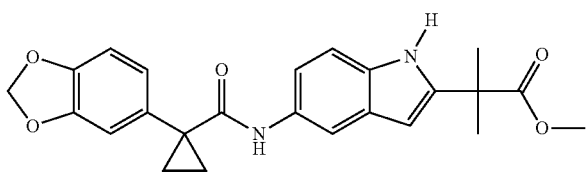 [SMILES: COC(=O)C(C)(C)c1cc2cc(NC(=O)C3(c4ccc5c(c4)OCO5)CC3)ccc2[nH]1]
191
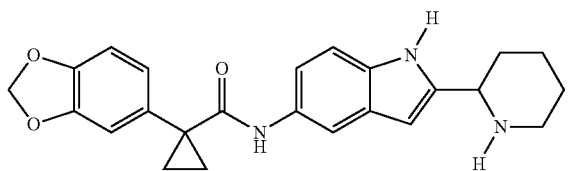 [SMILES: O=C(Nc1ccc2[nH]c(C3CCCCN3)cc2c1)C1(c2ccc3c(c2)OCO3)CC1]
192
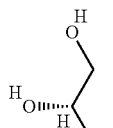
193

TABLE 1-continued
Exemplary compounds of the present invention.
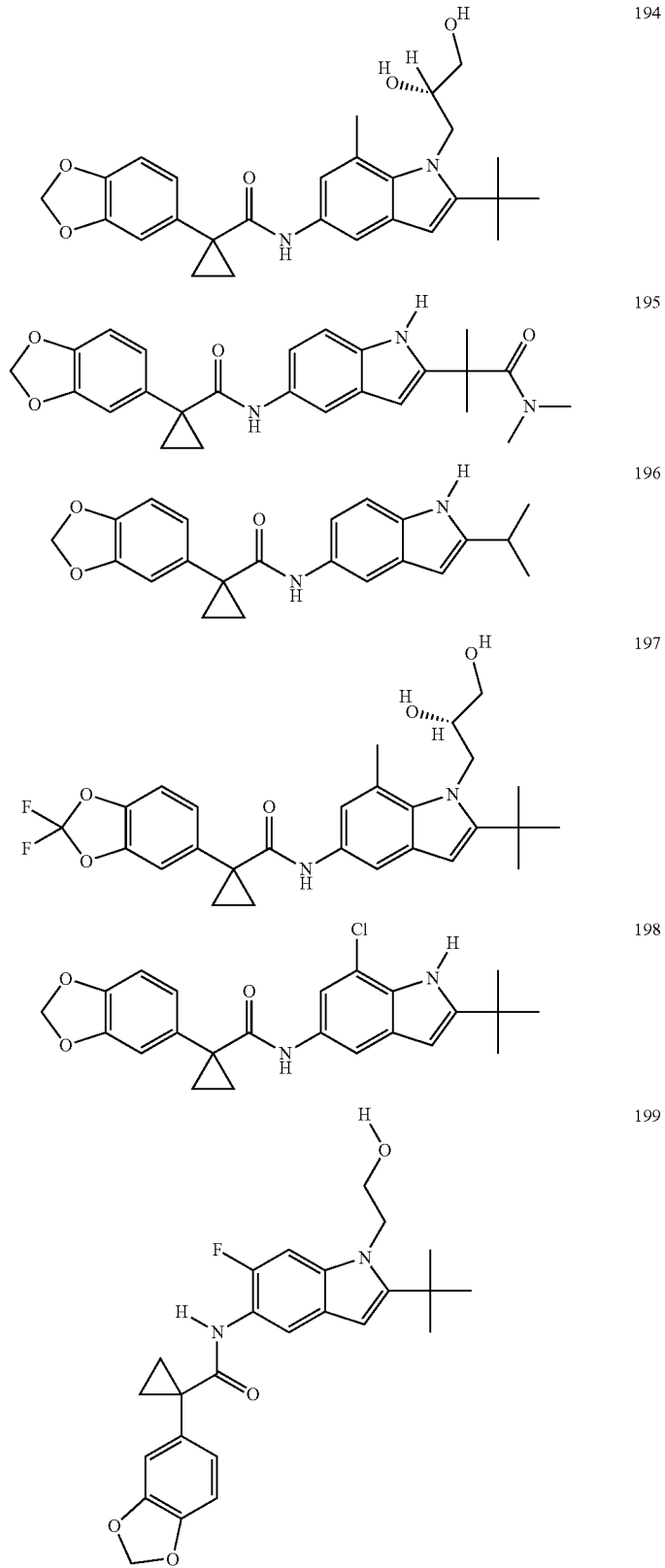

TABLE 1-continued
Exemplary compounds of the present invention.
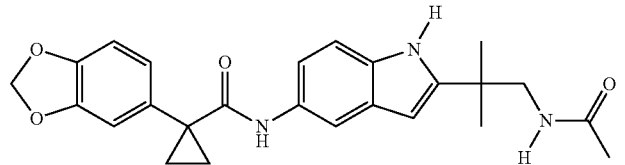 [SMILES: CC(=O)NCC(C)(C)c1cc2cc(NC(=O)C3(c4ccc5c(c4)OCO5)CC3)ccc2[nH]1]
200
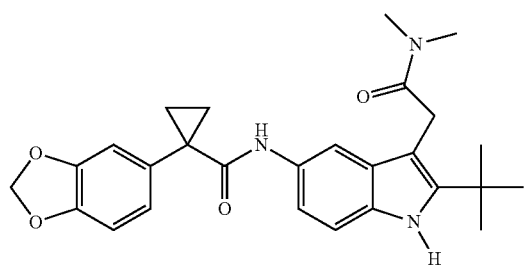 [SMILES: CN(C)C(=O)Cc1c(C(C)(C)C)[nH]c2ccc(NC(=O)C3(c4ccc5c(c4)OCO5)CC3)cc12]
201
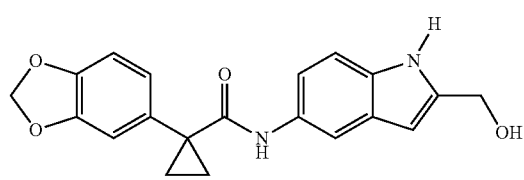 [SMILES: O=C(Nc1ccc2[nH]c(CO)cc2c1)C1(c2ccc3c(c2)OCO3)CC1]
202
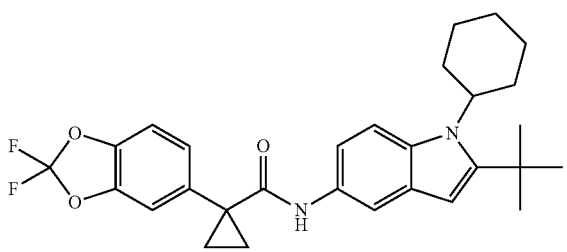 [SMILES: CC(C)(C)c1cc2cc(NC(=O)C3(c4ccc5c(c4)OC(F)(F)O5)CC3)ccc2n1C1CCCCC1]
203
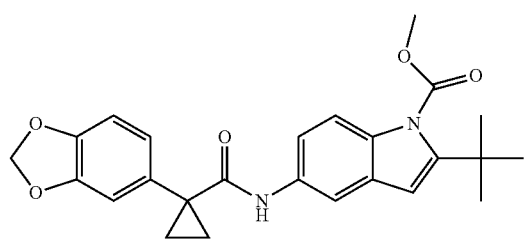 [SMILES: COC(=O)n1c(C(C)(C)C)cc2cc(NC(=O)C3(c4ccc5c(c4)OCO5)CC3)ccc21]
204
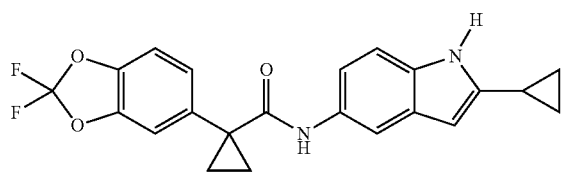 [SMILES: O=C(Nc1ccc2[nH]c(C3CC3)cc2c1)C1(c2ccc3c(c2)OC(F)(F)O3)CC1]
205

TABLE 1-continued
Exemplary compounds of the present invention.
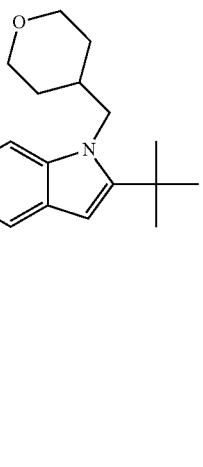
206
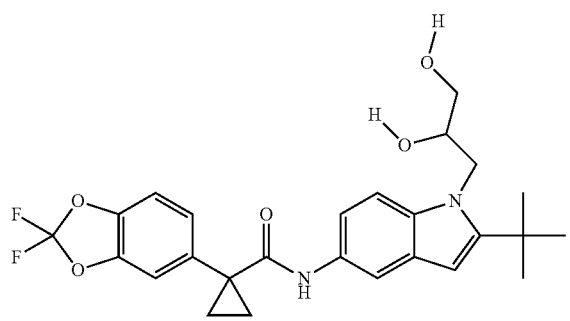
207
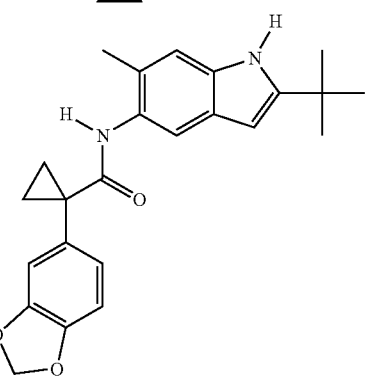
208
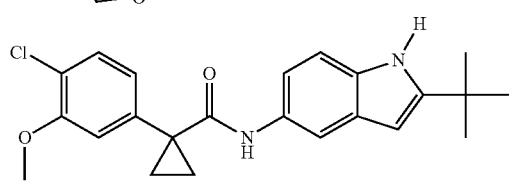
209
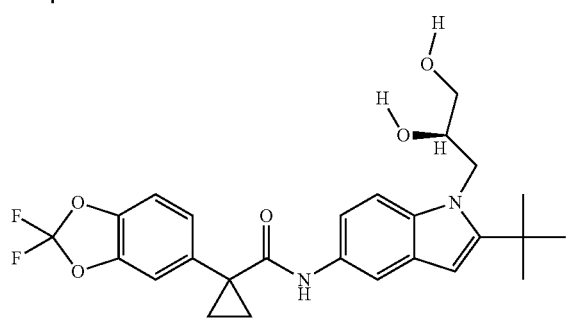
210

TABLE 1-continued
Exemplary compounds of the present invention.
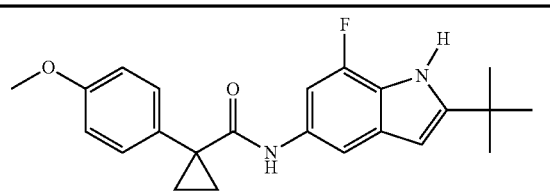 211
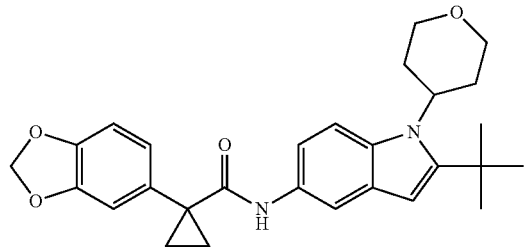 [SMILES: CC(C)(C)c1cc2cc(NC(=O)C3(c4ccc5c(c4)OCO5)CC3)ccc2n1C1CCOCC1] 212
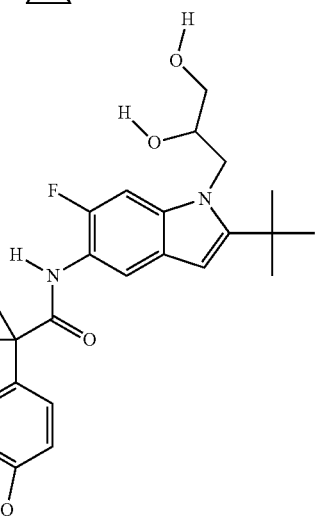 213
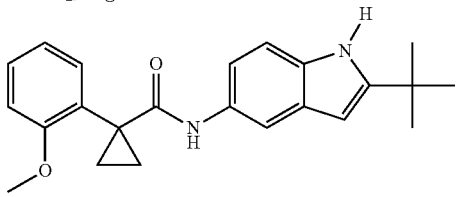 214
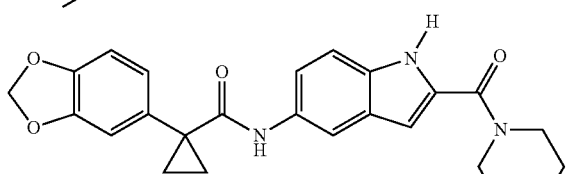 215
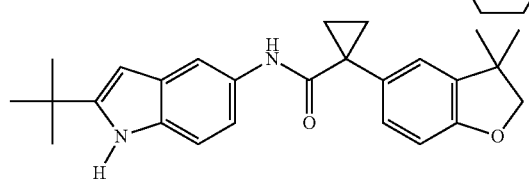 216
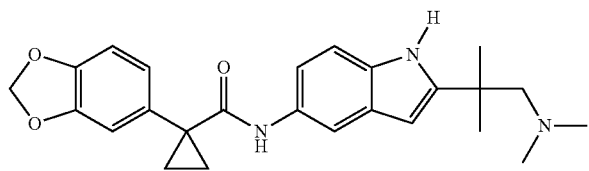 217

TABLE 1-continued
Exemplary compounds of the present invention.
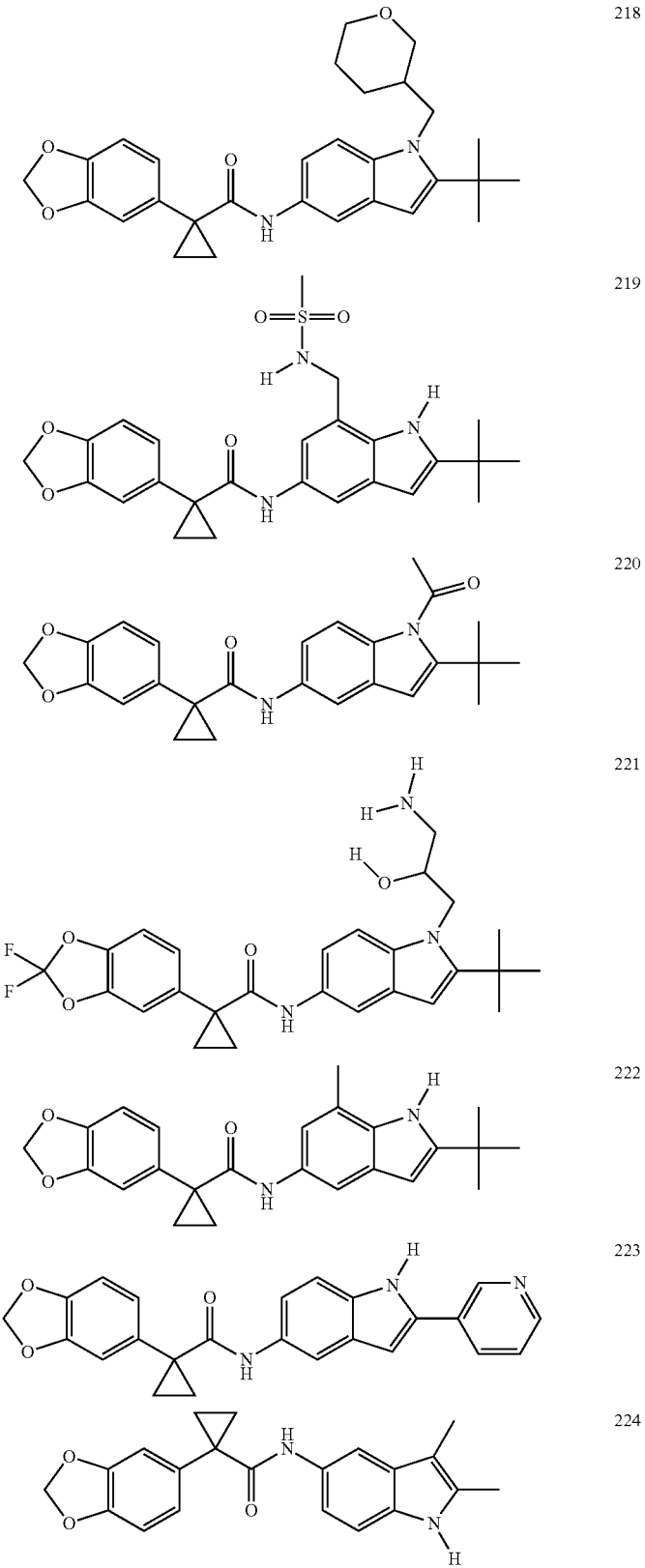

TABLE 1-continued
Exemplary compounds of the present invention.
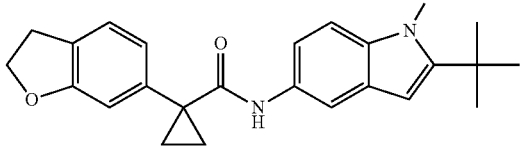 225
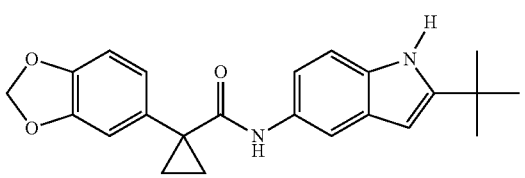 [SMILES: CC(C)(C)c1cc2cc(NC(=O)C3(c4ccc5c(c4)OCO5)CC3)ccc2[nH]1] 226
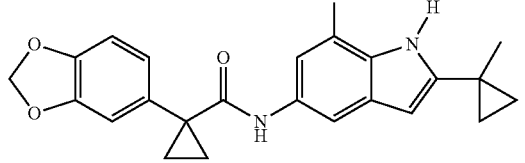 227
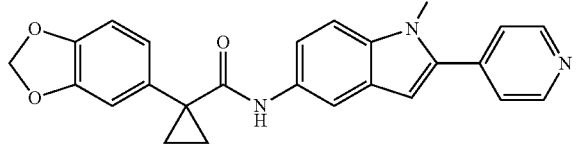 228
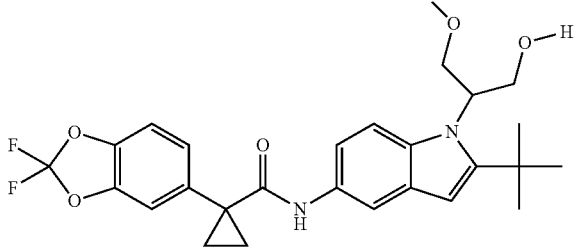 229
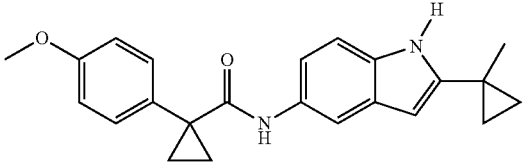 [SMILES: COc1ccc(C2(C(=O)Nc3ccc4[nH]c(C5(C)CC5)cc4c3)CC2)cc1] 230
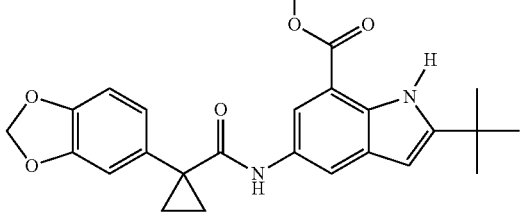 231
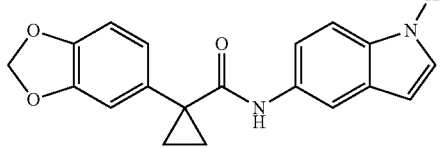 232

TABLE 1-continued
Exemplary compounds of the present invention.
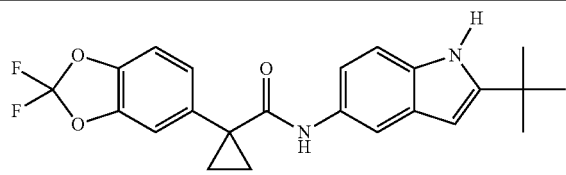
233
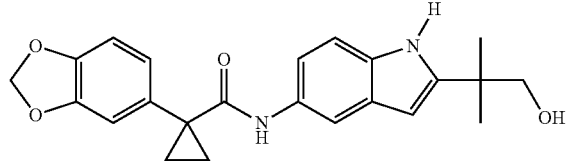 [SMILES: CC(C)(CO)c1cc2cc(NC(=O)C3(c4ccc5c(c4)OCO5)CC3)ccc2[nH]1]
234
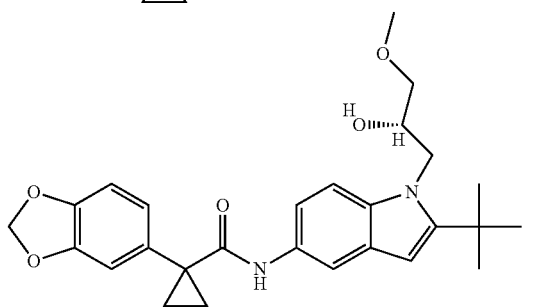
235
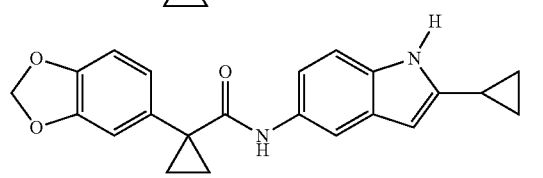
236
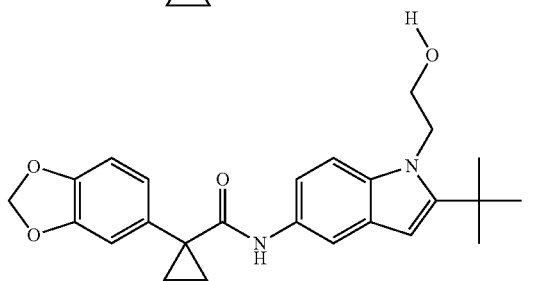
237
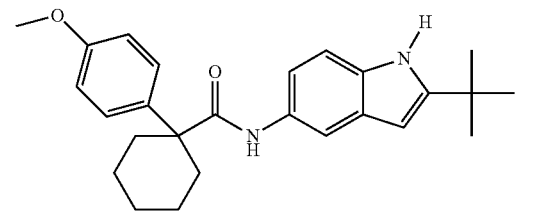 [SMILES: COc1ccc(C2(C(=O)Nc3ccc4[nH]c(C(C)(C)C)cc4c3)CCCCC2)cc1]
238
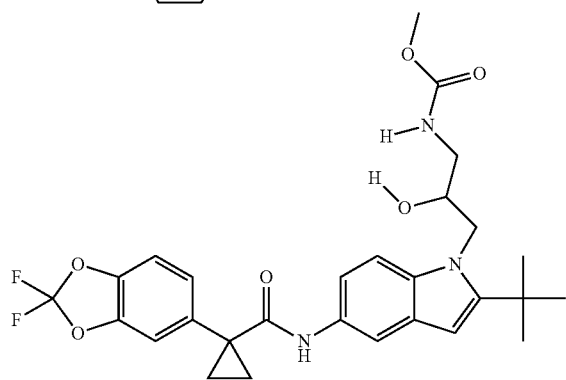
239

TABLE 1-continued
Exemplary compounds of the present invention.
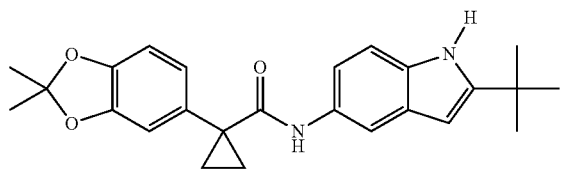 [SMILES: CC1(C)Oc2ccc(C3(C(=O)Nc4ccc5[nH]c(C(C)(C)C)cc5c4)CC3)cc2O1]
240
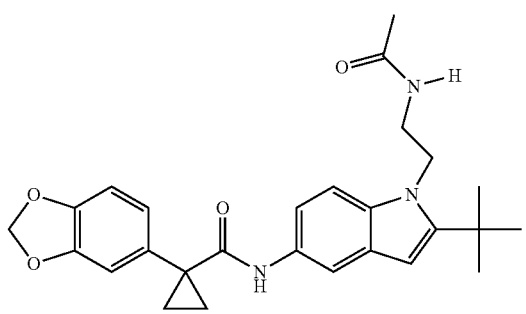 [SMILES: CC(=O)NCCn1c(C(C)(C)C)cc2cc(NC(=O)C3(c4ccc5c(c4)OCO5)CC3)ccc21]
241
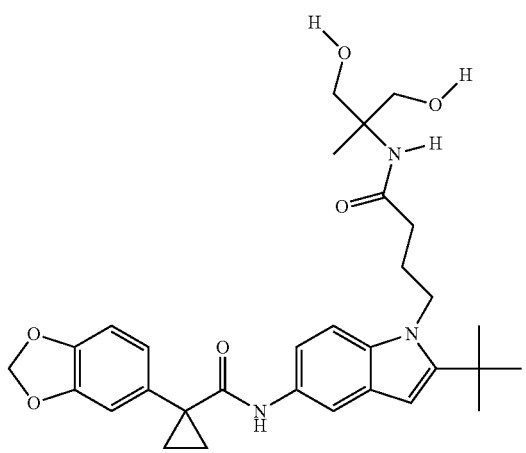 [SMILES: CC(CO)(CO)NC(=O)CCCn1c(C(C)(C)C)cc2cc(NC(=O)C3(c4ccc5c(c4)OCO5)CC3)ccc21]
242
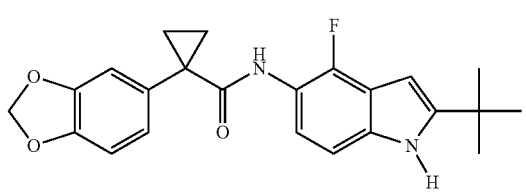 [SMILES: CC(C)(C)c1cc2c(F)c(NC(=O)C3(c4ccc5c(c4)OCO5)CC3)ccc2[nH]1]
243
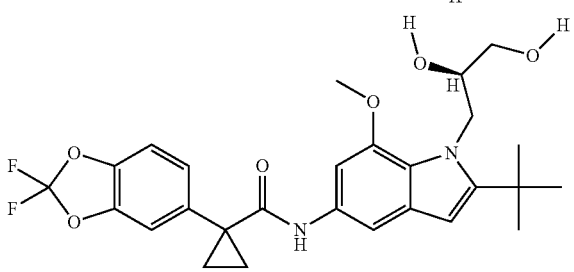
244
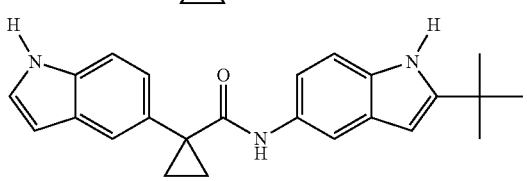
245

TABLE 1-continued
Exemplary compounds of the present invention.
| | |
|---|---|
| 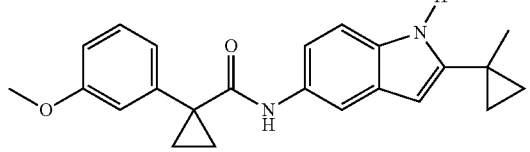 | 246 |
| 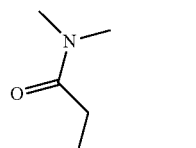 | 247 |
| 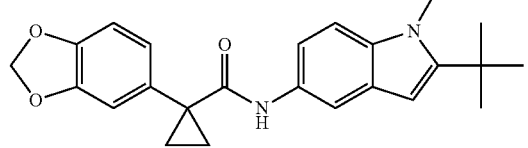 | 248 |
| 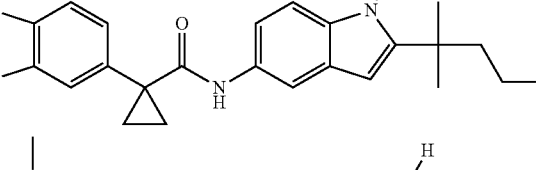 | 249 |
| 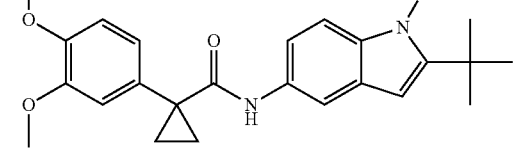 | 250 |
| 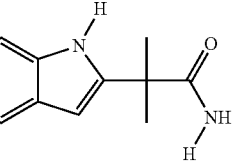 | 251 |
|  | 252 |
| 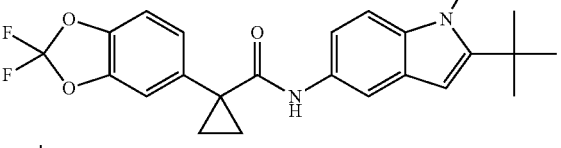 | 253 |

TABLE 1-continued
Exemplary compounds of the present invention.
254
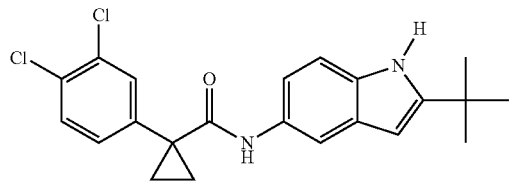 [SMILES: CC(C)(C)c1cc2cc(NC(=O)C3(c4ccc(Cl)c(Cl)c4)CC3)ccc2[nH]1]
255
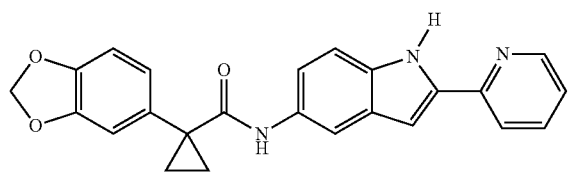
256
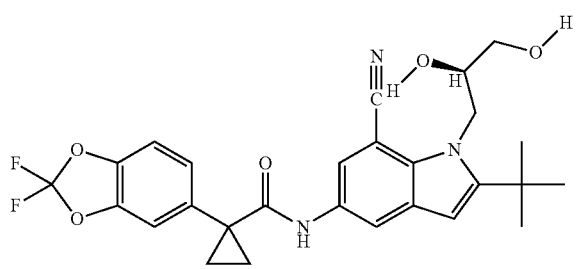
257
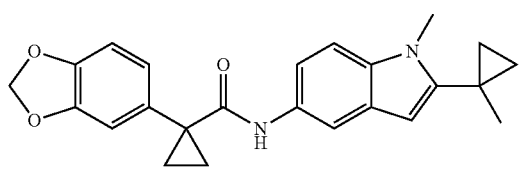 [SMILES: Cn1c(C2(C)CC2)cc2cc(NC(=O)C3(c4ccc5c(c4)OCO5)CC3)ccc21]
258
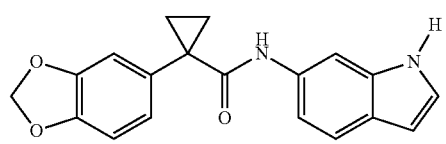 [SMILES: O=C(Nc1ccc2cc[nH]c2c1)C1(c2ccc3c(c2)OCO3)CC1]
259
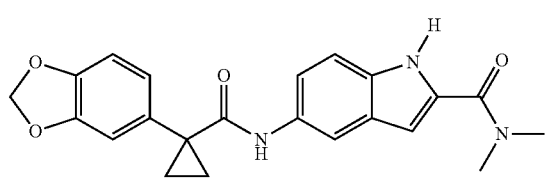 [SMILES: CN(C)C(=O)c1cc2cc(NC(=O)C3(c4ccc5c(c4)OCO5)CC3)ccc2[nH]1]
260
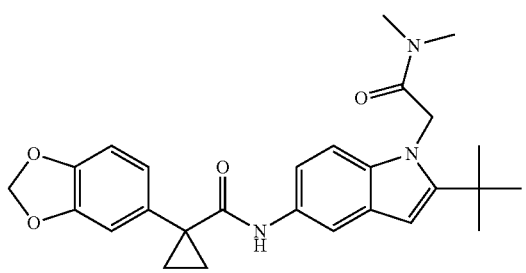 [SMILES: CN(C)C(=O)Cn1c(C(C)(C)C)cc2cc(NC(=O)C3(c4ccc5c(c4)OCO5)CC3)ccc21]

TABLE 1-continued
Exemplary compounds of the present invention.
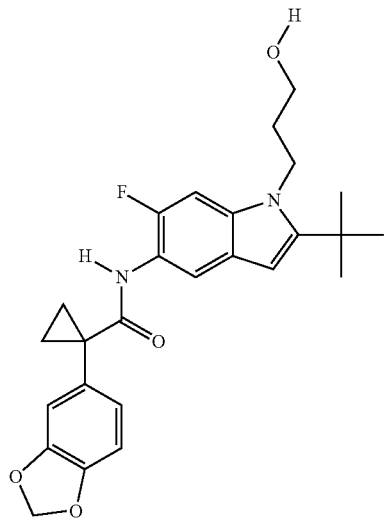 [SMILES: CC(C)(C)c1cc2cc(NC(=O)C3(c4ccc5c(c4)OCO5)CC3)c(F)cc2n1CCCO]
261
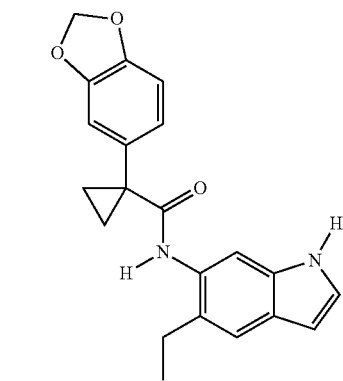 [SMILES: CCc1cc2cc[nH]c2cc1NC(=O)C1(c2ccc3c(c2)OCO3)CC1]
262
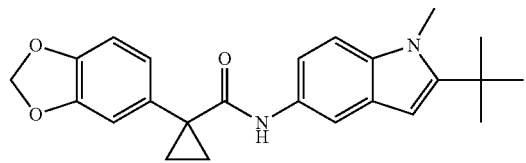 [SMILES: Cn1c(C(C)(C)C)cc2cc(NC(=O)C3(c4ccc5c(c4)OCO5)CC3)ccc21]
263
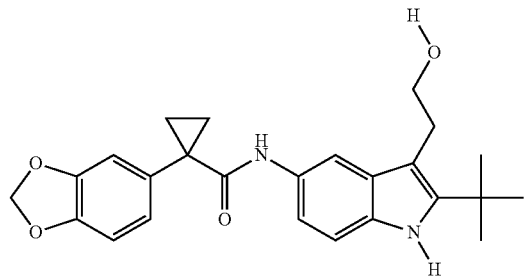 [SMILES: CC(C)(C)c1[nH]c2ccc(NC(=O)C3(c4ccc5c(c4)OCO5)CC3)cc2c1CCO]
264
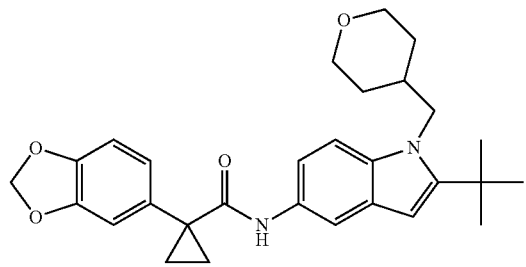 [SMILES: CC(C)(C)c1cc2cc(NC(=O)C3(c4ccc5c(c4)OCO5)CC3)ccc2n1CC1CCOCC1]
265

TABLE 1-continued
Exemplary compounds of the present invention.
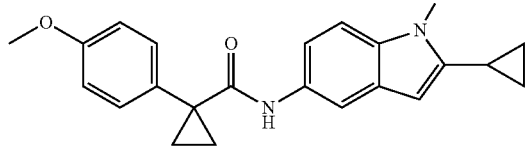 266
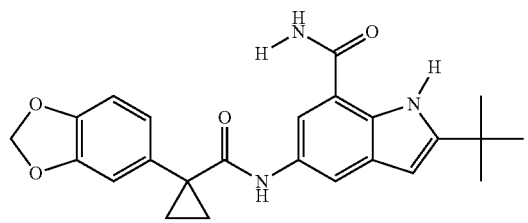 [SMILES: CC(C)(C)c1cc2cc(NC(=O)C3(c4ccc5c(c4)OCO5)CC3)cc(C(N)=O)c2[nH]1] 267
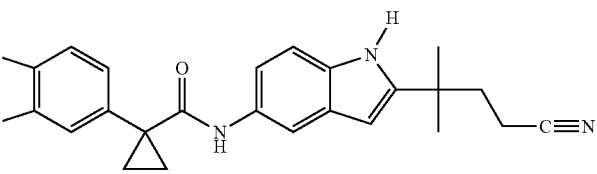 268
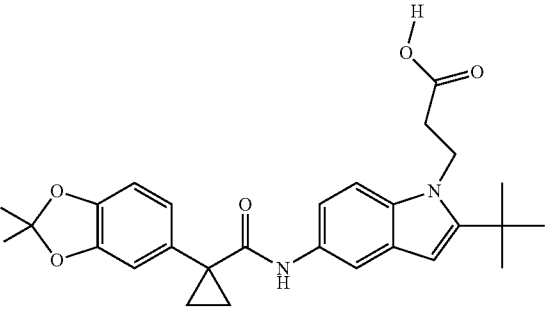 269
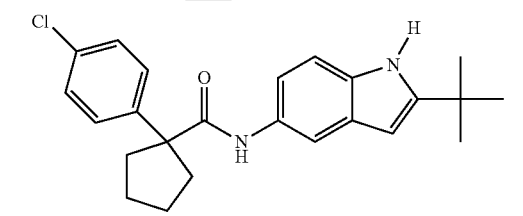 [SMILES: CC(C)(C)c1cc2cc(NC(=O)C3(c4ccc(Cl)cc4)CCCC3)ccc2[nH]1] 270
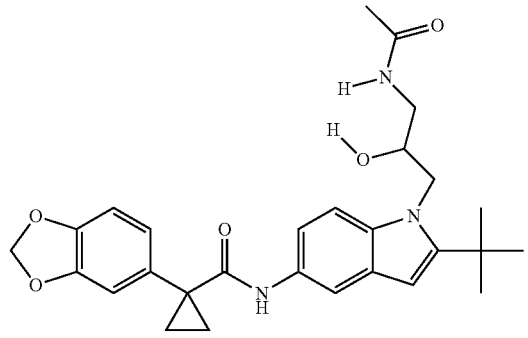 [SMILES: CC(=O)NCC(O)Cn1c(C(C)(C)C)cc2cc(NC(=O)C3(c4ccc5c(c4)OCO5)CC3)ccc21] 271
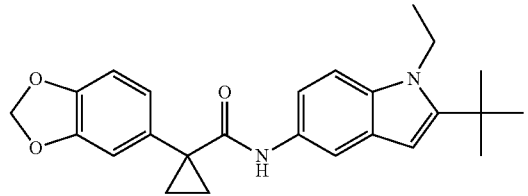 [SMILES: CCn1c(C(C)(C)C)cc2cc(NC(=O)C3(c4ccc5c(c4)OCO5)CC3)ccc21] 272

TABLE 1-continued
Exemplary compounds of the present invention.
| | |
|---|---|
| 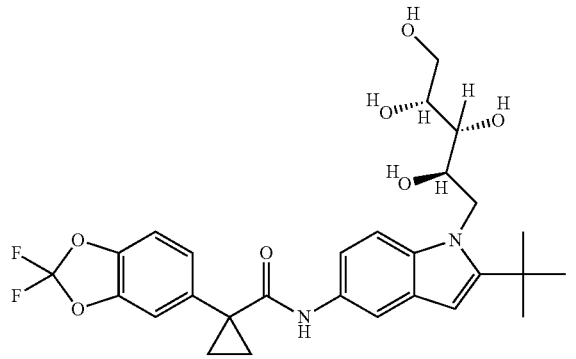 | 273 |
| 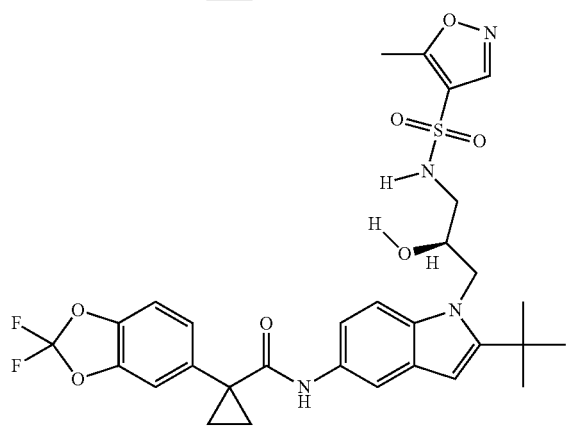 | 274 |
| 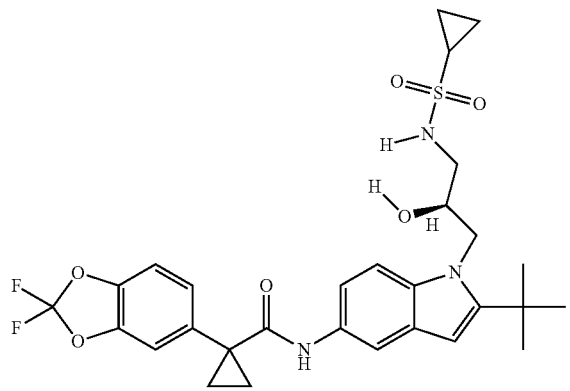 | 275 |
| 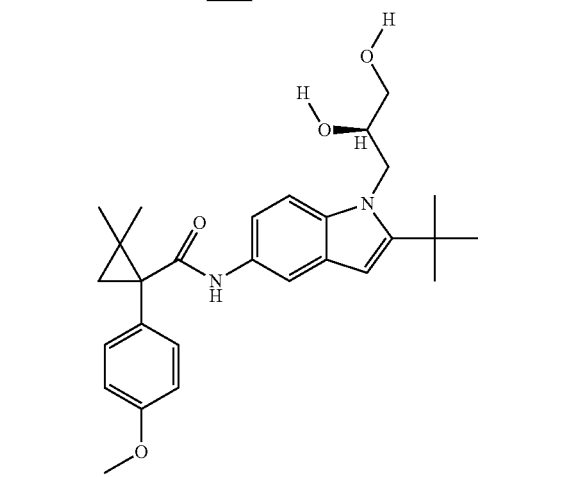 | 276 |

TABLE 1-continued
Exemplary compounds of the present invention.
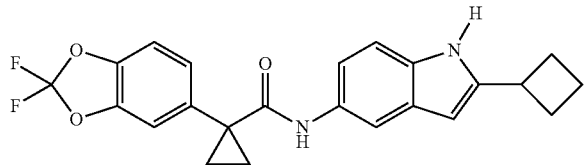 [SMILES: O=C(Nc1ccc2[nH]c(C3CCC3)cc2c1)C1(c2ccc3c(c2)OC(F)(F)O3)CC1] 277
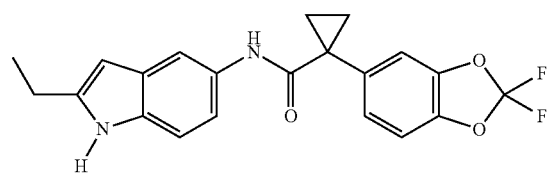 [SMILES: CCc1cc2cc(NC(=O)C3(c4ccc5c(c4)OC(F)(F)O5)CC3)ccc2[nH]1] 278
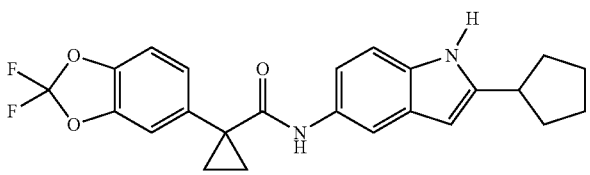 [SMILES: O=C(Nc1ccc2[nH]c(C3CCCC3)cc2c1)C1(c2ccc3c(c2)OC(F)(F)O3)CC1] 279
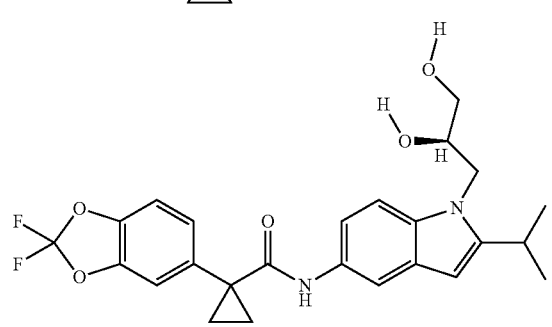 280
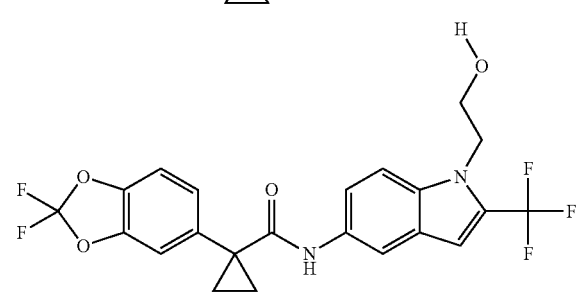 281
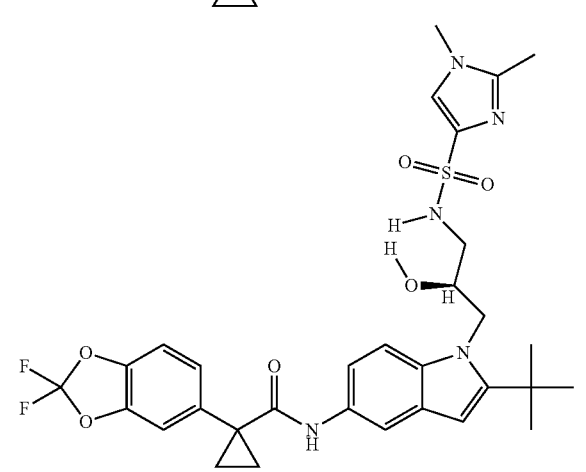 282

TABLE 1-continued
Exemplary compounds of the present invention.
283
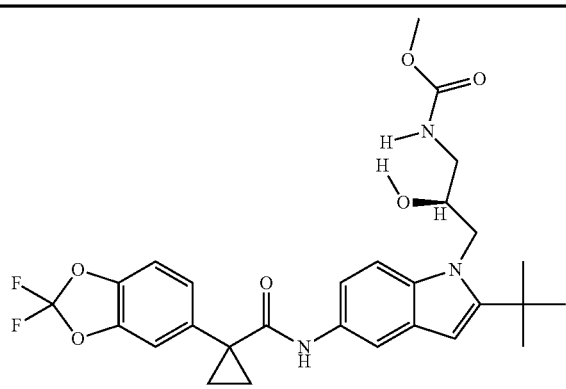
284
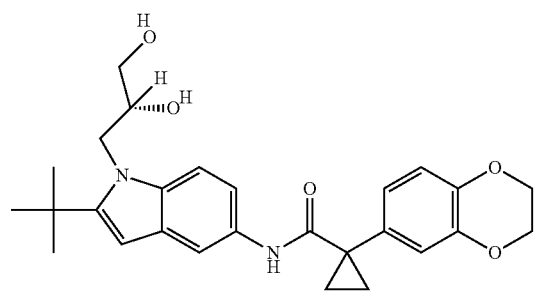
285
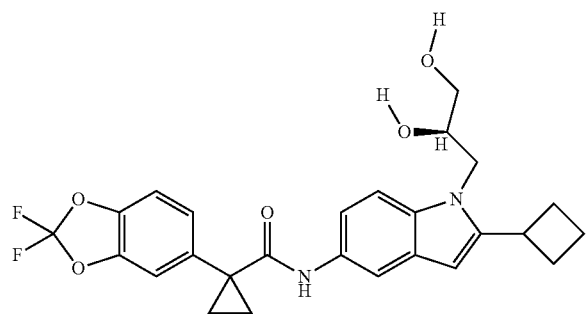
286
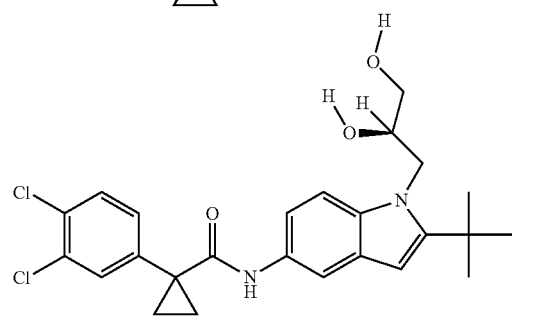
287
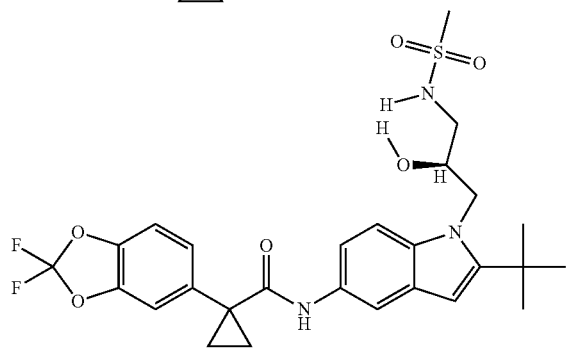

TABLE 1-continued
Exemplary compounds of the present invention.
288
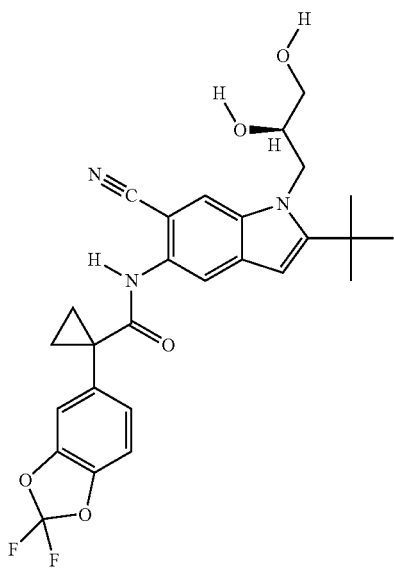
289
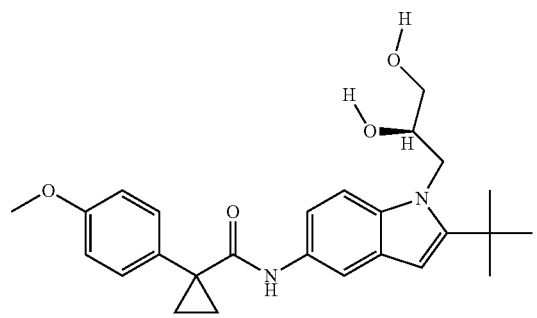
290
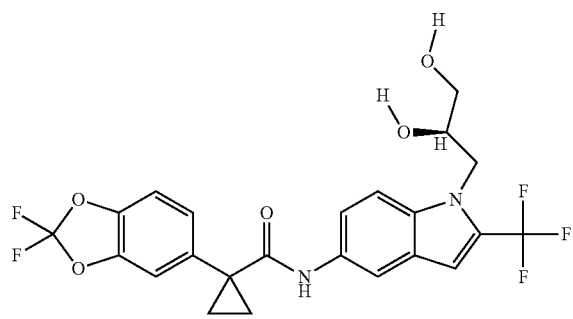
291
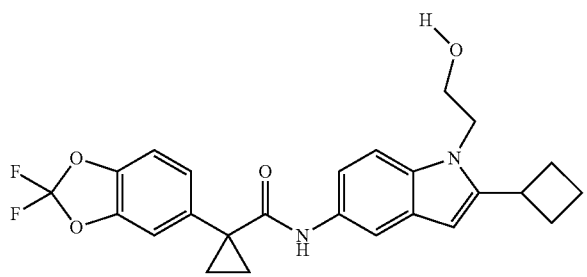 [SMILES: O=C(Nc1ccc2c(c1)cc(C1CCC1)n2CCO)C1(c2ccc3c(c2)OC(F)(F)O3)CC1]

TABLE 1-continued
Exemplary compounds of the present invention.
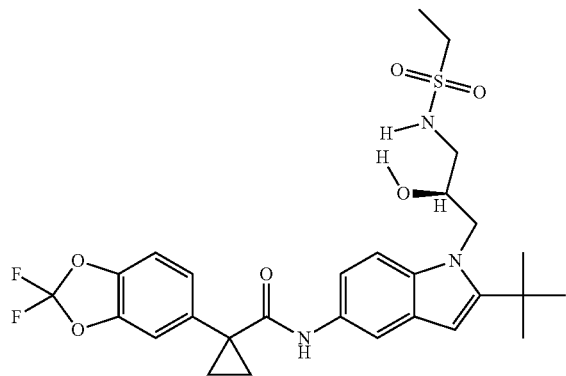
292
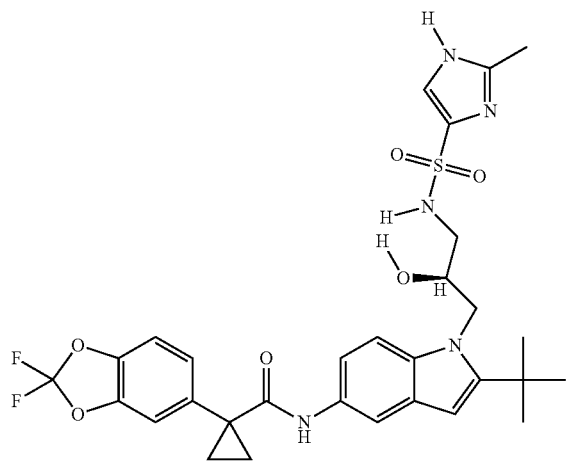
293
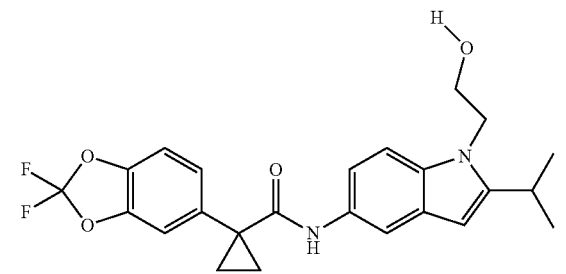 [SMILES: CC(C)c1cc2cc(NC(=O)C3(c4ccc5c(c4)OC(F)(F)O5)CC3)ccc2n1CCO]
294
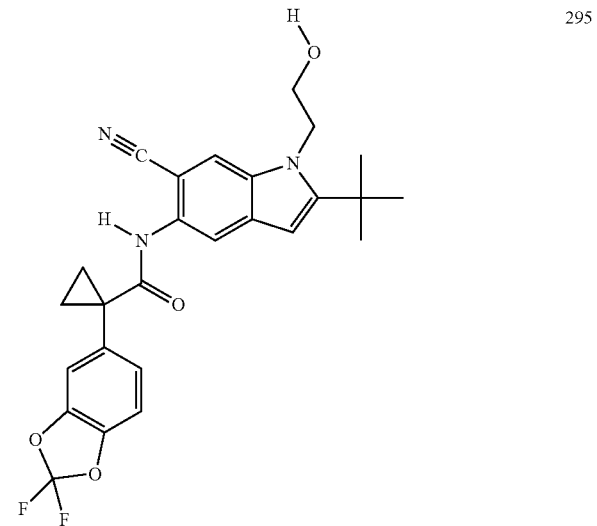
295

TABLE 1-continued
Exemplary compounds of the present invention.
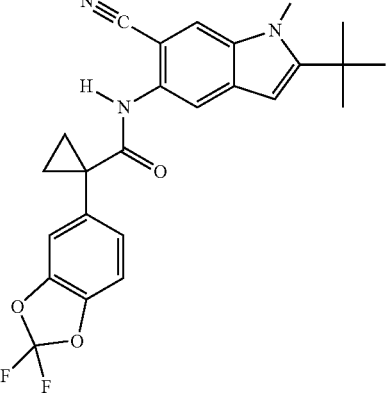
296
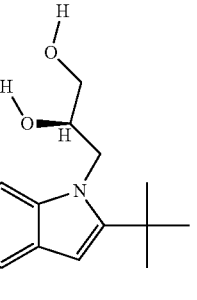
297
298
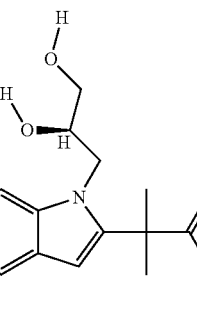
299
300

TABLE 1-continued
Exemplary compounds of the present invention.
301
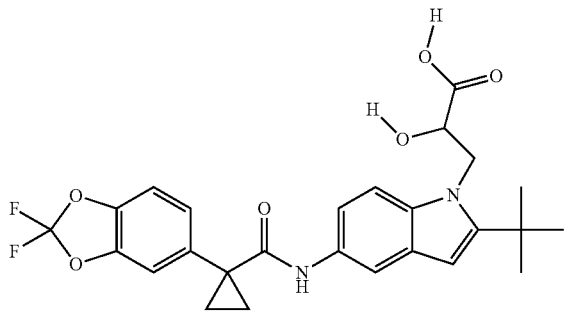 [SMILES: CC(C)(C)c1cc2cc(NC(=O)C3(c4ccc5c(c4)OC(F)(F)O5)CC3)ccc2n1CC(O)C(=O)O]
302
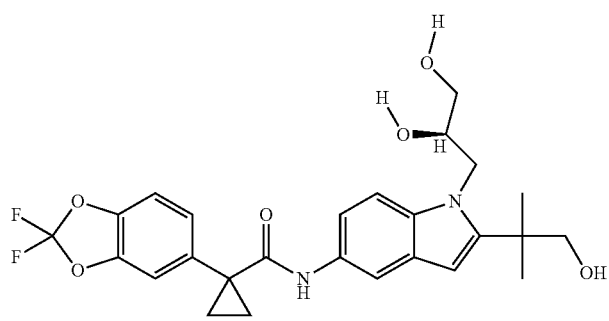
303
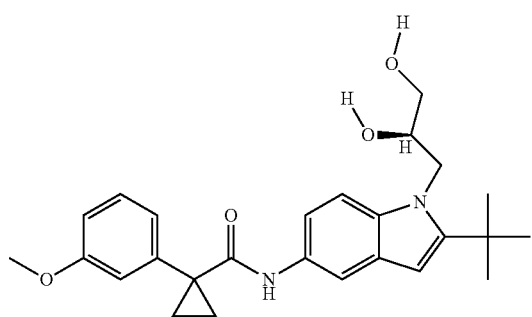
304
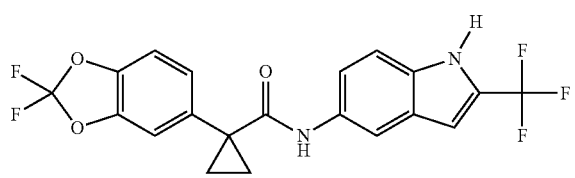 [SMILES: O=C(Nc1ccc2[nH]c(C(F)(F)F)cc2c1)C1(c2ccc3c(c2)OC(F)(F)O3)CC1]
305
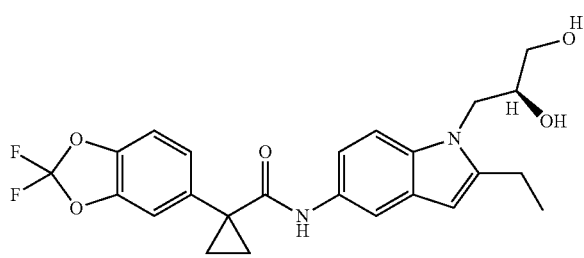

TABLE 1-continued
Exemplary compounds of the present invention.
306
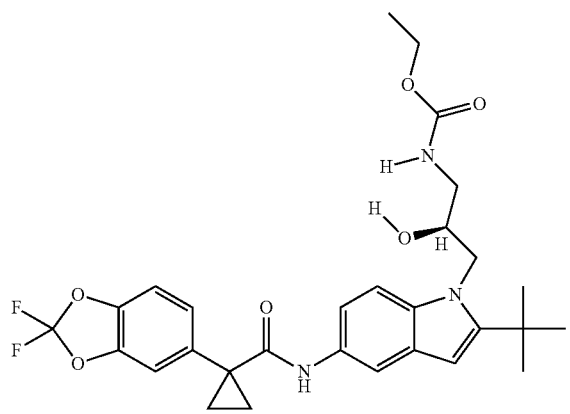
307
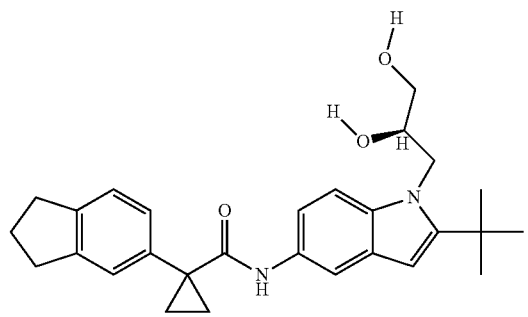
308
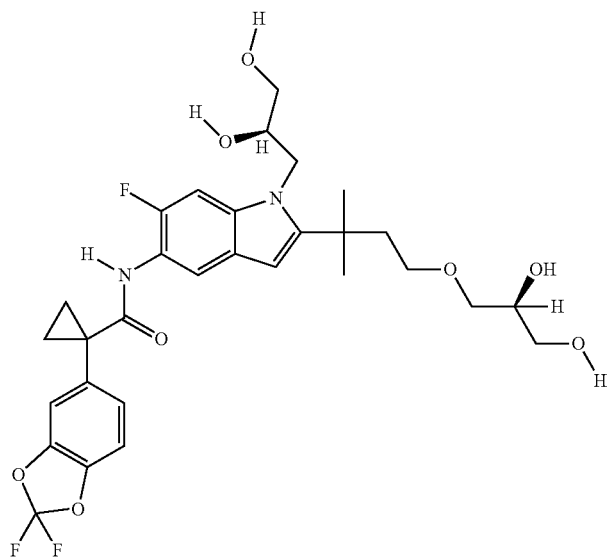

TABLE 1-continued
Exemplary compounds of the present invention.
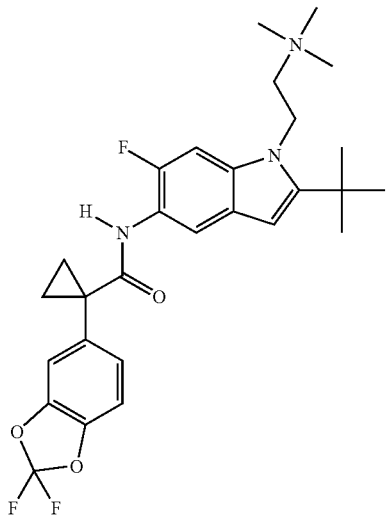
309
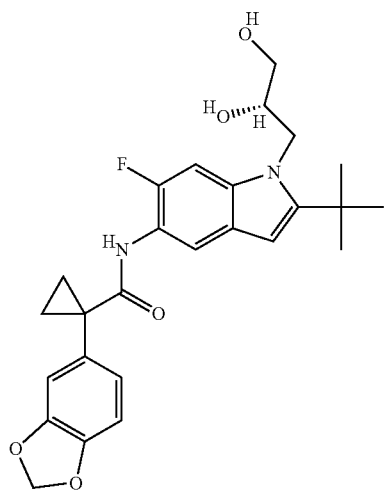
310
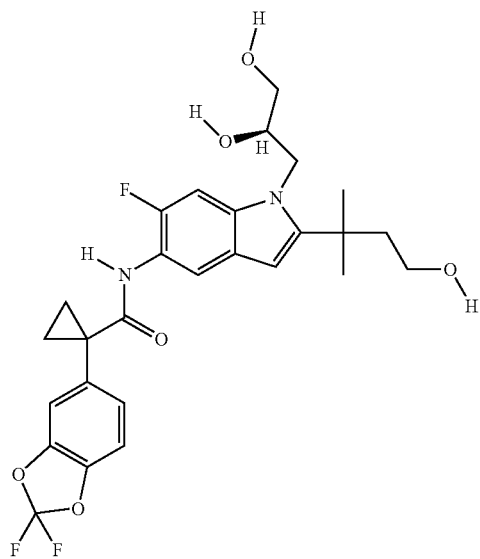
311

TABLE 1-continued
Exemplary compounds of the present invention.
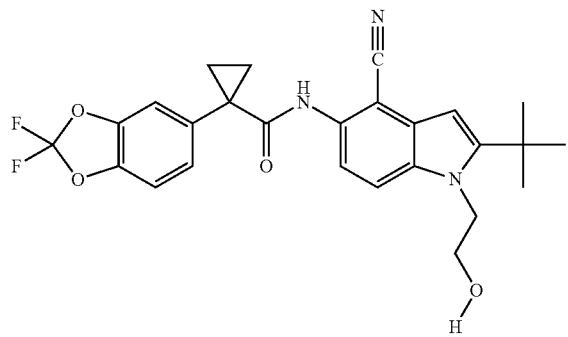 [SMILES: CC(C)(C)c1cc2c(C#N)c(NC(=O)C3(c4ccc5c(c4)OC(F)(F)O5)CC3)ccc2n1CCO]
312
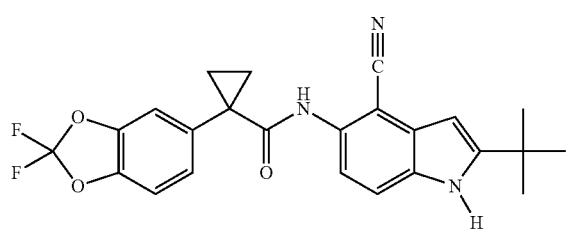 [SMILES: CC(C)(C)c1cc2c(C#N)c(NC(=O)C3(c4ccc5c(c4)OC(F)(F)O5)CC3)ccc2[nH]1]
313
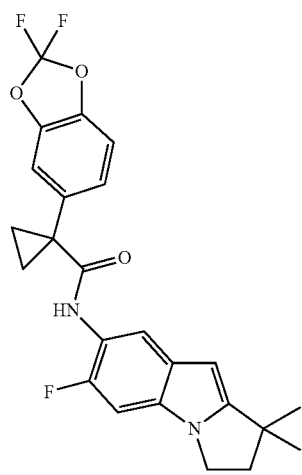 [SMILES: CC1(C)CCn2c1cc1cc(NC(=O)C3(c4ccc5c(c4)OC(F)(F)O5)CC3)c(F)cc12]
314
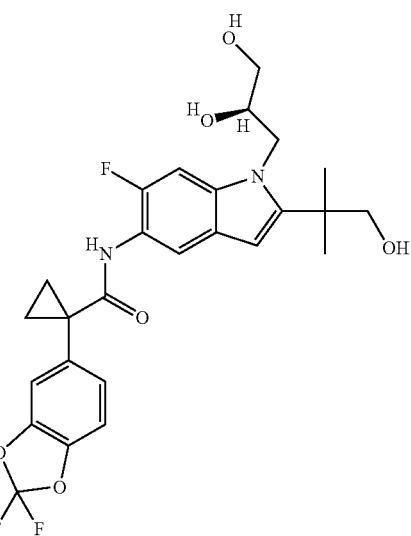
315

TABLE 1-continued
Exemplary compounds of the present invention.
316
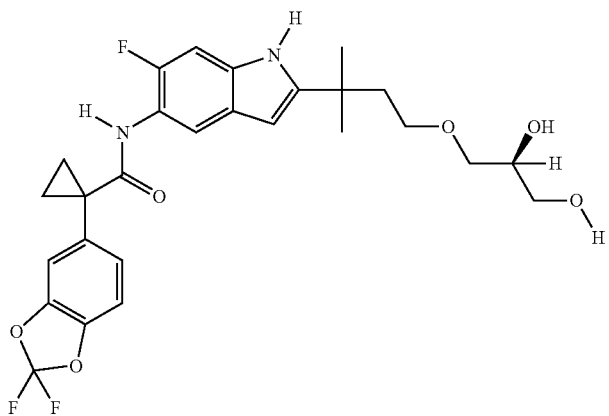 [SMILES: CC(C)(CCOC[C@@H](O)CO)c1cc2cc(NC(=O)C3(c4ccc5c(c4)OC(F)(F)O5)CC3)c(F)cc2[nH]1]
317
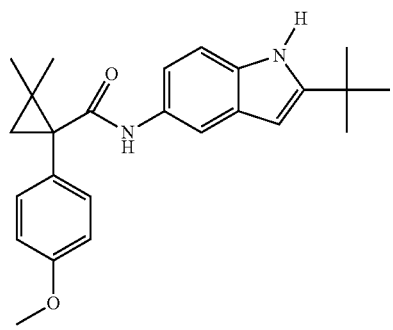 [SMILES: COc1ccc(C2(C(=O)Nc3ccc4[nH]c(C(C)(C)C)cc4c3)CC2(C)C)cc1]
318
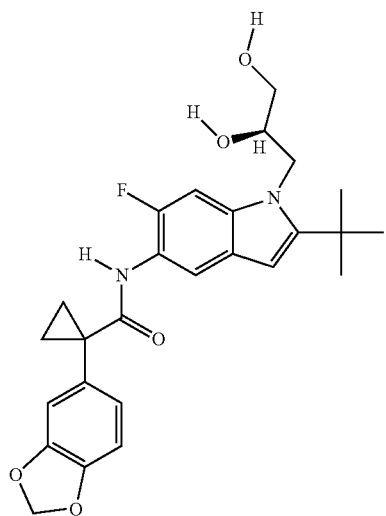

TABLE 1-continued
Exemplary compounds of the present invention.
319
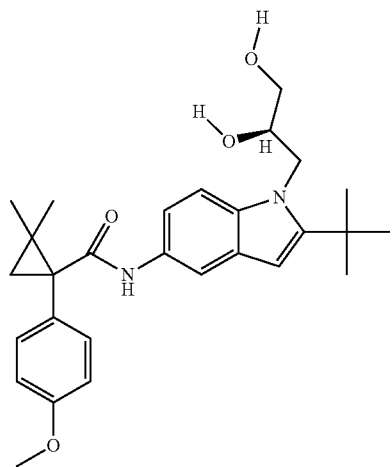
320
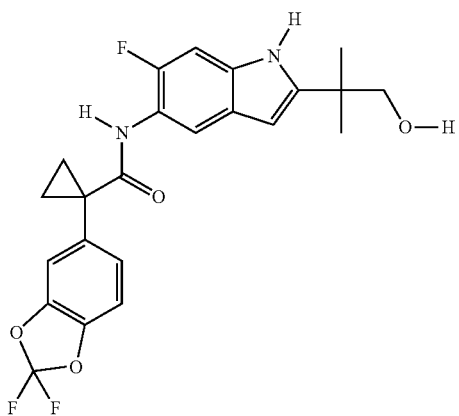 [SMILES: CC(C)(CO)c1cc2cc(NC(=O)C3(c4ccc5c(c4)OC(F)(F)O5)CC3)c(F)cc2[nH]1]
321
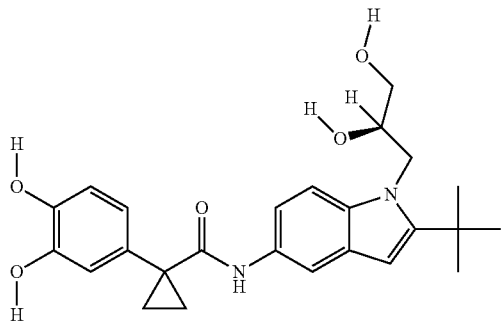 [SMILES: CC(C)(C)c1cc2cc(NC(=O)C3(c4ccc(O)c(O)c4)CC3)ccc2n1C[C@@H](O)CO]

TABLE 1-continued

Exemplary compounds of the present invention.

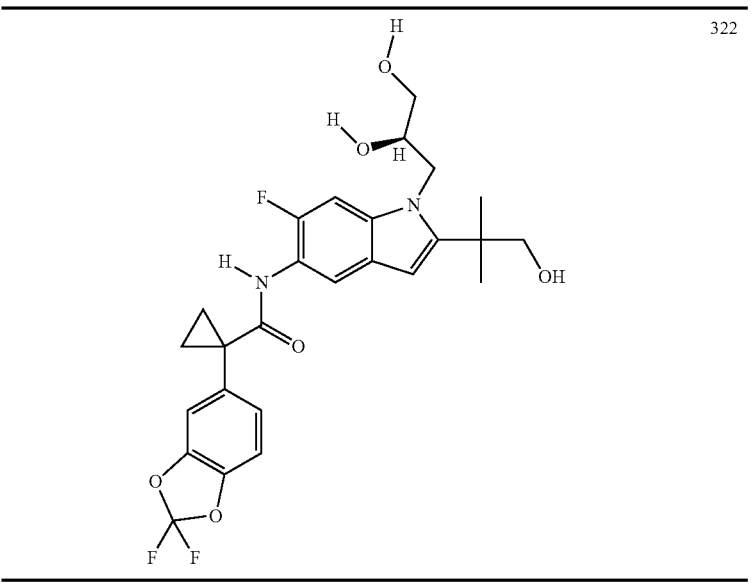

322

In another aspect, the present invention relates to a pharmaceutical composition comprising (i) a compound of the present invention; and (ii) a pharmaceutically acceptable carrier. In another embodiment, the composition further comprises an additional agent selected from a mucolytic agent, bronchodialator, an anti-biotic, an anti-infective agent, an anti-inflammatory agent, CFTR corrector, or a nutritional agent. In another embodiment, the composition further comprises an additional agent selected from compounds disclosed in U.S. patent application Ser. No. 11/165,818, published as U.S. Published Patent Application No. 2006/0074075, filed Jun. 24, 2005, and hereby incorporated by reference in its entirety. In another embodiment, the composition further comprises N-(5-hydroxy-2,4-ditert-butyl-phenyl)-4-oxo-1H-quinoline-3-carboxamide. These compositions are useful for treating the diseases described below including cystic fibrosis. These compositions are also useful in the kits described below.

In another aspect, the present invention relates to a method of increasing the number of functional ABC transporters in a membrane of a cell, comprising the step of contacting said cell with a compound of formula II:

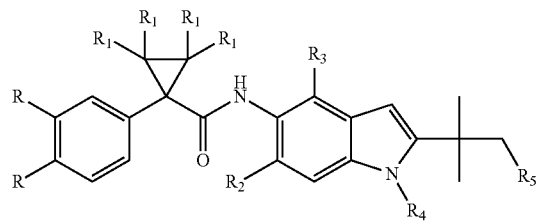

II wherein independently for each occurrence:
R is H, OH, OCH$_3$ or two R taken together form —CH$_2$CH$_2$CH$_2$—, —OCH$_2$O— or —OCF$_2$O—;
R$_1$ is H or alkyl;
R$_2$ is H or F;
R$_3$ is H or CN;
R$_4$ is H, —CH$_2$OCH$_2$CH(OH)CH$_2$OH, —CH$_2$CH$_2$N$^+$(CH$_3$)$_3$, or —CH$_2$CH$_2$OH; and
R$_5$ is H, OH, —CH$_2$OCH$_2$CH(OH)CH$_2$OH, —CH$_2$OH, or R$_4$ and R$_5$ taken together form a five membered ring.

In one embodiment of this method, the ABC transporter is CFTR.

In one embodiment of this method, two R taken together form —OCF$_2$O—, R$_1$ is H, and R$_2$ is F. In another embodiment, two R taken together form —OCF$_2$O—, R$_1$ is H, R$_2$ is F, and R$_3$ is H.

In another embodiment, two R taken together form —OCF$_2$O—, R$_1$ is H, R$_2$ is F, R$_3$ is H, and R$_4$ is H. In another embodiment, two R taken together form —OCF$_2$O—, R$_1$ is H, R$_2$ is F, R$_3$ is H, and R$_4$ is —CH$_2$CH$_2$N$^+$(CH$_3$)$_3$. In another embodiment, two R taken together form —OCF$_2$O—, R$_1$ is H, R$_2$ is F, R$_3$ is H, and R$_4$ is —CH$_2$OCH$_2$CH(OH)CH$_2$OH. In another embodiment, two R taken together form —OCF$_2$O—, R$_1$ is H, R$_2$ is F, R$_3$ is H, and R$_4$ and R$_5$ taken together form a five membered ring.

In one embodiment of this method, two R taken together form —OCH$_2$O—, R$_1$ is H, and R$_2$ is F. In another embodiment, two R taken together form —OCH$_2$O—, R$_1$ is H, R$_2$ is F, and R$_3$ is H. In another embodiment, two R taken together form —OCH$_2$O—, R$_1$ is H, R$_2$ is F, R$_3$ is H, and R$_4$ is —CH$_2$OCH$_2$CH(OH)CH$_2$OH.

In one embodiment of this method, R is OH, R$_1$ is H, R$_2$ is H, R$_3$ is H, and R$_4$ is —CH$_2$OCH$_2$CH(OH)CH$_2$OH.

In one embodiment of this method, at least one R is OCH$_3$, at least two R$_1$ are methyl, R$_2$ is H, R$_3$ is H, and R$_4$ is H. In another embodiment, at least one R is OCH$_3$, at least two R$_1$ are methyl, R$_2$ is H, R$_3$ is H, and R$_4$ is —CH$_2$OCH$_2$CH(OH)CH$_2$OH.

In one embodiment of this method, two R taken together form —CH$_2$CH$_2$CH$_2$—, R$_1$ is H, R$_2$ is H, R$_3$ is H, and R$_4$ is —CH$_2$OCH$_2$CH(OH)CH$_2$OH.

In one embodiment of this method, the compound is represented by formula IIa:

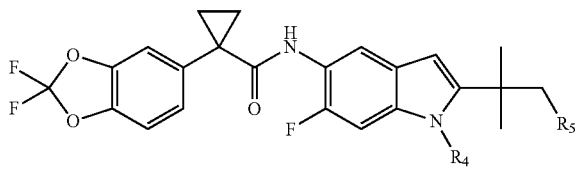

or a pharmaceutically acceptable salt thereof, wherein:

$R_4$ is H, —$CH_2OCH_2CH(OH)CH_2OH$, —$CH_2CH_2N^+(CH_3)_3$, or —$CH_2CH_2OH$; and $R_5$ is H, OH, —$CH_2OCH_2CH(OH)CH_2OH$, —$CH_2OH$, or $R_4$ and $R_5$ taken together form a five membered ring.

In one embodiment of this method, $R_4$ is —$CH_2OCH_2CH(OH)CH_2OH$, —$CH_2CH_2N^+(CH_3)_3$, or —$CH_2CH_2OH$. In another embodiment, $R_5$ is OH, —$CH_2OCH_2CH(OH)CH_2OH$, or —$CH_2OH$. In another embodiment, $R_4$ is —$CH_2OCH_2CH(OH)CH_2OH$, —$CH_2CH_2N^+(CH_3)_3$, or —$CH_2CH_2OH$; and $R_5$ is OH, —$CH_2OCH_2CH(OH)CH_2OH$, or —$CH_2OH$.

In one embodiment of this method, the compound is selected from Table 1.

In another aspect, the present invention relates to a method of treating a condition, disease, or disorder in a patient implicated by ABC transporter activity, comprising the step of administering to said patient a compound having formula II:

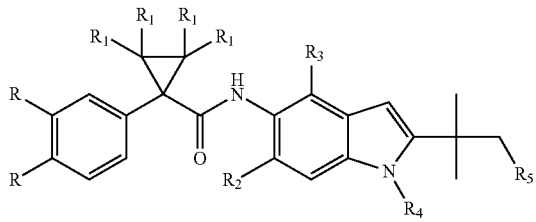

or a pharmaceutically acceptable salt thereof, wherein independently for each occurrence:

R is H, OH, $OCH_3$ or two R taken together form —$CH_2CH_2CH_2$—, —$OCH_2O$— or —$OCF_2O$—;

$R_1$ is H or alkyl;

$R_2$ is H or F;

$R_3$ is H or CN;

$R_4$ is H, —$CH_2OCH_2CH(OH)CH_2OH$, —$CH_2CH_2N^+(CH_3)_3$, or —$CH_2CH_2OH$; and $R_5$ is H, OH, —$CH_2OCH_2CH(OH)CH_2OH$, —$CH_2OH$, or $R_4$ and $R_5$ taken together form a five membered ring.

In one embodiment of this method, two R taken together form —$OCF_2O$—, $R_1$ is H, and $R_2$ is F. In another embodiment, two R taken together form —$OCF_2O$—, $R_1$ is H, $R_2$ is F, and $R_3$ is H. In another embodiment, two R taken together form —$OCF_2O$—, $R_1$ is H, $R_2$ is F, $R_3$ is H, and $R_4$ is H. In another embodiment, two R taken together form —$OCF_2O$—, $R_1$ is H, $R_2$ is F, $R_3$ is H, and $R_4$ is —$CH_2CH_2N^+(CH_3)_3$. In another embodiment, two R taken together form —$OCF_2O$—, $R_1$ is H, $R_2$ is F, $R_3$ is H, and $R_4$ is —$CH_2OCH_2CH(OH)CH_2OH$. In another embodiment, two R taken together form —$OCF_2O$—, $R_1$ is H, $R_2$ is F, $R_3$ is H, and $R_4$ and $R_5$ taken together form a five membered ring.

In one embodiment of this method, two R taken together form —$OCH_2O$—, $R_1$ is H, and $R_2$ is F. In another embodiment, two R taken together form —$OCH_2O$—, $R_1$ is H, $R_2$ is F, and $R_3$ is H. In another embodiment, two R taken together form —$OCH_2O$—, $R_1$ is H, $R_2$ is F, $R_3$ is H, and $R_4$ is —$CH_2OCH_2CH(OH)CH_2OH$.

In one embodiment of this method, R is OH, $R_1$ is H, $R_2$ is H, $R_3$ is H, and $R_4$ is —$CH_2OCH_2CH(OH)CH_2OH$.

In one embodiment of this method, at least one R is $OCH_3$, at least two $R_1$ are methyl, $R_2$ is H, $R_3$ is H, and $R_4$ is H. In another embodiment, at least one R is $OCH_3$, at least two $R_1$ are methyl, $R_2$ is H, $R_3$ is H, and $R_4$ is —$CH_2OCH_2CH(OH)CH_2OH$.

In one embodiment of this method, two R taken together form —$CH_2CH_2CH_2$—, $R_1$ is H, $R_2$ is H, $R_3$ is H, and $R_4$ is —$CH_2OCH_2CH(OH)CH_2OH$.

In one embodiment of this method, the compound is represented by formula IIa:

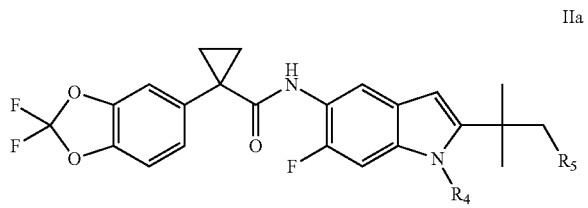

or a pharmaceutically acceptable salt thereof, wherein:

$R_4$ is H, —$CH_2OCH_2CH(OH)CH_2OH$, —$CH_2CH_2N^+(CH_3)_3$, or —$CH_2CH_2OH$; and $R_5$ is H, OH, —$CH_2OCH_2CH(OH)CH_2OH$, —$CH_2OH$, or $R_4$ and $R_5$ taken together form a five membered ring.

In one embodiment of this method, $R_4$ is —$CH_2OCH_2CH(OH)CH_2OH$, —$CH_2CH_2N^+(CH_3)_3$, or —$CH_2CH_2OH$. In another embodiment, $R_5$ is OH, —$CH_2OCH_2CH(OH)CH_2OH$, or —$CH_2OH$. In another embodiment, $R_4$ is —$CH_2OCH_2CH(OH)CH_2OH$, —$CH_2CH_2N^+(CH_3)_3$, or —$CH_2CH_2OH$; and $R_5$ is OH, —$CH_2OCH_2CH(OH)CH_2OH$, or —$CH_2OH$.

In one embodiment of this method, the compound is selected from Table 1.

In one embodiment of this method, said condition, disease, or disorder is selected from cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, diabetes mellitus, laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, diabetes insipidus (di), neurophyseal di, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjögren's disease.

In another aspect, the present invention relates to a kit for use in measuring the activity of a ABC transporter or a fragment thereof in a biological sample in vitro or in vivo, comprising:

(i) a first composition comprising a compound of formula II:

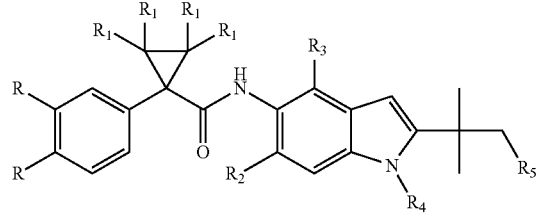

wherein independently for each occurrence:

R is H, OH, OCH$_3$ or two R taken together form —CH$_2$CH$_2$CH$_2$—, —OCH$_2$O— or —OCF$_2$O—;

R$_1$ is H or alkyl;

R$_2$ is H or F;

R$_3$ is H or CN;

R$_4$ is H, —CH$_2$OCH$_2$CH(OH)CH$_2$OH, —CH$_2$CH$_2$N$^+$(CH$_3$)$_3$, or —CH$_2$CH$_2$OH; and R$_5$ is H, OH, —CH$_2$OCH$_2$CH(OH)CH$_2$OH, —CH$_2$OH, or R$_4$ and R$_5$ taken together form a five membered ring; and (ii) instructions for: a) contacting the composition with the biological sample; and b) measuring activity of said ABC transporter or a fragment thereof.

In one embodiment, the kit further comprises instructions for a) contacting an additional composition with the biological sample; b) measuring the activity of said ABC transporter or a fragment thereof in the presence of said additional compound, and c) comparing the activity of the ABC transporter in the presence of the additional compound with the density of the ABC transporter in the presence of said first composition.

In one embodiment, the kit is used to measure the density of CFTR.

In one embodiment of this kit, two R taken together form —OCF$_2$O—, R$_1$ is H, and R$_2$ is F. In another embodiment, two R taken together form —OCF$_2$O—, R$_1$ is H, R$_2$ is F, and R$_3$ is H. In another embodiment, two R taken together form —OCF$_2$O—, R$_1$ is H, R$_2$ is F, R$_3$ is H, and R$_4$ is H. In another embodiment, two R taken together form —OCF$_2$O—, R$_1$ is H, R$_2$ is F, R$_3$ is H, and R$_4$ is —CH$_2$CH$_2$N$^+$(CH$_3$)$_3$. In another embodiment, two R taken together form —OCF$_2$O—, R$_1$ is H, R$_2$ is F, R$_3$ is H, and R$_4$ is —CH$_2$OCH$_2$CH(OH)CH$_2$OH. In another embodiment, two R taken together form —OCF$_2$O—, R$_1$ is H, R$_2$ is F, R$_3$ is H, and R$_4$ and R$_5$ taken together form a five membered ring.

In one embodiment of this kit, two R taken together form —OCH$_2$O—, R$_1$ is H, and R$_2$ is F. In another embodiment, two R taken together form —OCH$_2$O—, R$_1$ is H, R$_2$ is F, and R$_3$ is H. In another embodiment, two R taken together form —OCH$_2$O—, R$_1$ is H, R$_2$ is F, R$_3$ is H, and R$_4$ is —CH$_2$OCH$_2$CH(OH)CH$_2$OH. In another embodiment, R is OH, R$_1$ is H, R$_2$ is H, R$_3$ is H, and R$_4$ is —CH$_2$OCH$_2$CH(OH)CH$_2$OH. In another embodiment, at least one R is OCH$_3$, at least two R$_1$ are methyl, R$_2$ is H, R$_3$ is H, and R$_4$ is H. In another embodiment, at least one R is OCH$_3$, at least two R$_1$ are methyl, R$_2$ is H, R$_3$ is H, and R$_4$ is —CH$_2$OCH$_2$CH(OH)CH$_2$OH. In another embodiment, two R taken together form —CH$_2$CH$_2$CH$_2$—, R$_1$ is H, R$_2$ is H, R$_3$ is H, and R$_4$ is —CH$_2$OCH$_2$CH(OH)CH$_2$OH.

In one embodiment of this kit, the compound is represented by formula IIa:

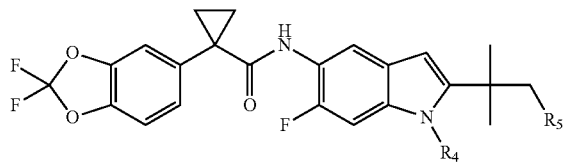

or a pharmaceutically acceptable salt thereof, wherein:

R$_4$ is H, —CH$_2$OCH$_2$CH(OH)CH$_2$OH, —CH$_2$CH$_2$N$^+$(CH$_3$)$_3$, or —CH$_2$CH$_2$OH; and R$_5$ is H, OH, —CH$_2$OCH$_2$CH(OH)CH$_2$OH, —CH$_2$OH, or R$_4$ and R$_5$ taken together form a five membered ring.

In one embodiment of this kit, R$_4$ is —CH$_2$OCH$_2$CH(OH)CH$_2$OH, —CH$_2$CH$_2$N$^+$(CH$_3$)$_3$, or —CH$_2$CH$_2$OH. In another embodiment, R$_5$ is OH, —CH$_2$OCH$_2$CH(OH)CH$_2$OH, or —CH$_2$OH. In another embodiment, R$_4$ is —CH$_2$OCH$_2$CH(OH)CH$_2$OH, —CH$_2$CH$_2$N$^+$(CH$_3$)$_3$, or —CH$_2$CH$_2$OH; and R$_5$ is OH, —CH$_2$OCH$_2$CH(OH)CH$_2$OH, or —CH$_2$OH.

In one embodiment of this kit, the compound is selected from Table 1.

III. Subgeneric Compounds of the Present Invention

Another aspect of the present invention provides a compound that is useful for modulating ABC transporter activity. The compound has formula Id:

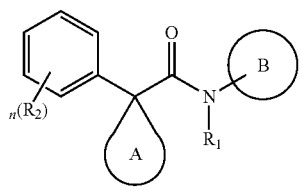

or a pharmaceutically acceptable salt thereof.

R$_1$, R$_2$, and ring A are defined above in formula I, and ring B, R$_3$ and p are defined in formula Ia. Furthermore, when ring A is unsubstituted cyclopentyl, n is 1, R$_2$ is 4-chloro, and R$_1$ is hydrogen, then ring B is not 2-(tertbutyl)indol-5-yl, or (2,6-dichlorophenyl(carbonyl))-3-methyl-1H-indol-5-yl;

and when ring A is unsubstituted cyclopentyl, n is 0, and R$_1$ is hydrogen, then ring B is not

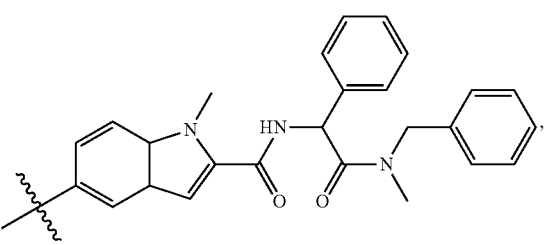 [SMILES: *C1=CC2C=C(C(=O)NC(C(=O)N(C)Cc3ccccc3)c3ccccc3)N(C)C2C=C1]

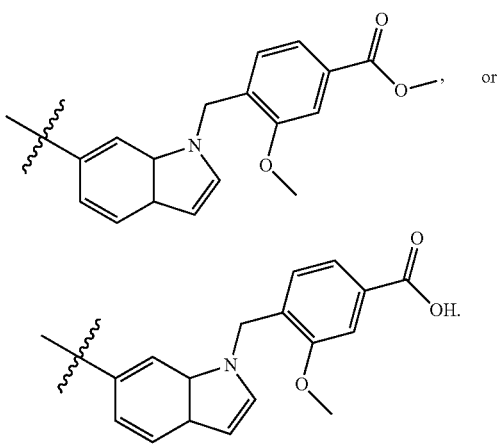

Another aspect of the present invention provides a compound that is useful for modulating ABC transporter activity. The compound has formula Id:

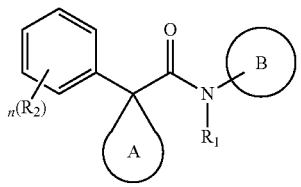

Id or a pharmaceutically acceptable salt thereof.

$R_1$, $R_2$, and ring A are defined above in formula I, and ring B, $R_3$ and p are defined in formula Ia.

However, when $R_1$ is H, n is 0, ring A is an unsubstituted cyclopentyl, and ring B is an indole-5-yl substituted with 1-2 of $R_3$, then each $R_3$ is independently —$Z^G R_{12}$, where each $Z^G$ is independently a bond or an unsubstituted branched or straight $C_{1-6}$ aliphatic chain wherein up to two carbon units of $Z^G$ are optionally and independently replaced by —CS—, —CONR$^G$NR$^G$—, —CO$_2$—, —OCO—, —NR$^G$CO$_2$—, —O—, —NR$^G$CONR$^G$—, —OCONR$^G$—, —NR$^G$NR$^G$—, —S—, —SO—, —SO$_2$—, —NR$^G$—, —SO$_2$NR$^G$—, —NR$^G$SO$_2$—, or —NR$^G$SO$_2$NR$^G$—, each $R_{12}$ is independently R$^G$, halo, —OH, —NH$_2$, —NO$_2$, —CN, or —OCF$_3$, and each R$^G$ is independently hydrogen, an unsubstituted aliphatic, an optionally substituted cycloaliphatic, an optionally substituted heterocycloaliphatic, an unsubstituted aryl, or an optionally substituted heteroaryl; or any two adjacent $R_3$ groups together with the atoms to which they are attached form an optionally substituted heterocycle. Furthermore, when $R_1$ is H, n is 1, $R_2$ is 4-chloro, ring A is an unsubstituted cyclopentyl, and ring B is an indole-5-yl substituted with 1-2 of $R_3$, then each $R_3$ is independently —$Z^H R_{22}$, where each $Z^H$ is independently a bond or an unsubstituted branched or straight $C_{1-3}$ aliphatic chain wherein up to two carbon units of $Z^H$ are optionally and independently replaced by —CS—, —CONR$^H$NR$^H$—, —CO$_2$—, —OCO—, —NR$^H$CO$_2$—, —O—, —NR$^H$CONR$^H$—, —OCONR$^H$—, —NR$^H$NR$^H$—, —S—, —SO—, —SO$_2$—, —NR$^H$—, —SO$_2$NR$^H$—, —NR$^H$SO$_2$—, or —NR$^H$SO$_2$NR$^H$—, each $R_{22}$ is independently R$^H$, halo, —OH, —NH$_2$, —NO$_2$, —CN, or —OCF$_3$, and each R$^H$ is independently hydrogen, a substituted $C_4$ alkyl, an optionally substituted $C_{2-6}$ alkenyl, an optionally substituted $C_{2-6}$ alkynyl, an optionally substituted $C_4$ alkenyl, an optionally substituted $C_4$ alkynyl, an optionally substituted cycloaliphatic, an optionally substituted heterocycloaliphatic, an optionally substituted heteroaryl, an unsubstituted phenyl, or a mono-substituted phenyl, or any two adjacent $R_3$ groups together with the atoms to which they are attached form an optionally substituted heterocycle.

Another aspect of the present invention provides a compound that is useful for modulating ABC transporter activity. The compound has formula II:

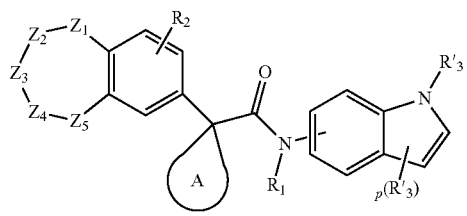

II or a pharmaceutically acceptable salt thereof.

$R_1$, $R_2$, and ring A are defined above in formula I; $R_3$, $R'_3$, and p are defined above in formula Ia; and $Z_1$, $Z_2$, $Z_3$, $Z_4$, and $Z_5$ are defined above in formula Ib.

Another aspect of the present invention provides a compound that is useful for modulating ABC transporter activity. The compound has formula IIa:

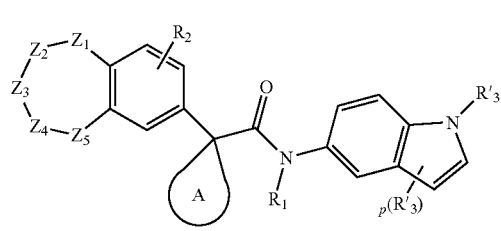

IIa or a pharmaceutically acceptable salt thereof.

$R_1$, $R_2$, and ring A are defined above in formula I; $R_3$, $R'_3$, and p are defined above in formula Ia; and $Z_1$, $Z_2$, $Z_3$, $Z_4$, and $Z_5$ are defined above in formula Ib.

Another aspect of the present invention provides a compound that is useful for modulating ABC transporter activity. The compound has formula IIb:

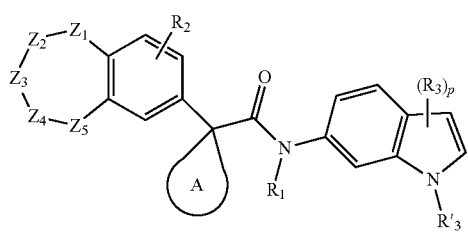

IIb or a pharmaceutically acceptable salt thereof.

$R_1$, $R_2$, and ring A, are defined above in formula I; $R_3$, $R'_3$, and p are defined above in formula Ia; and $Z_1$, $Z_2$, $Z_3$, $Z_4$, and $Z_5$ are defined above in formula Ib.

Another aspect of the present invention provides a compound that is useful for modulating ABC transporter activity. The compound has formula IIc:

IIc

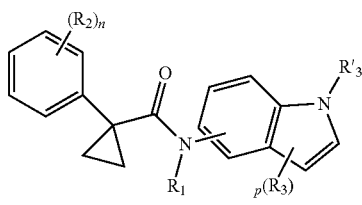

or a pharmaceutically acceptable salt thereof.

$R_1$, $R_2$ and n are defined above in formula I; and $R_3$, $R'_3$, and p are defined in formula Ia.

Another aspect of the present invention provides a compound that is useful for modulating ABC transporter activity. The compound has formula IId:

IId

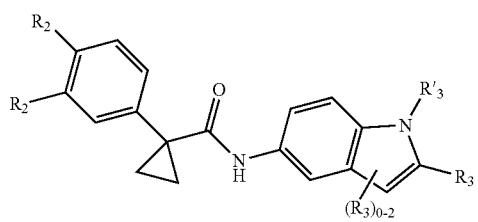

or a pharmaceutically acceptable salt thereof.

Both $R_2$ groups, together with the atoms to which they are attached form a group selected from:

XA1

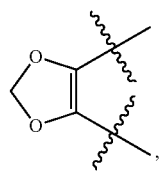

XA2

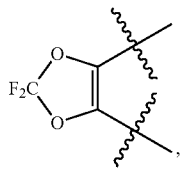

XA3

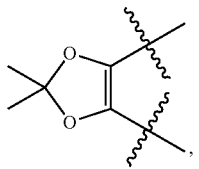

XA4

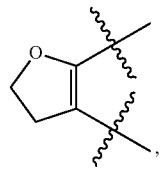

XA5

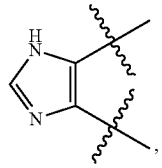

XA6

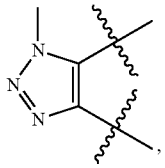

XA7

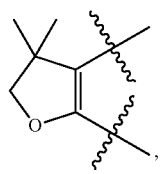

XA8

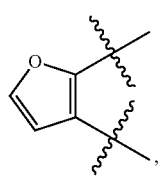

XA9

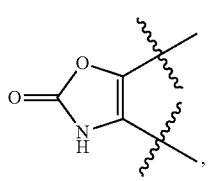

XA10

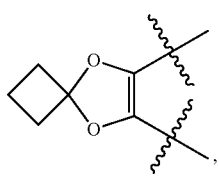

XA11

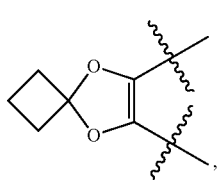

XA12

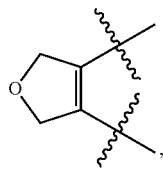

XA13

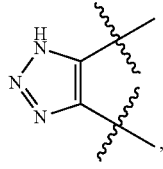

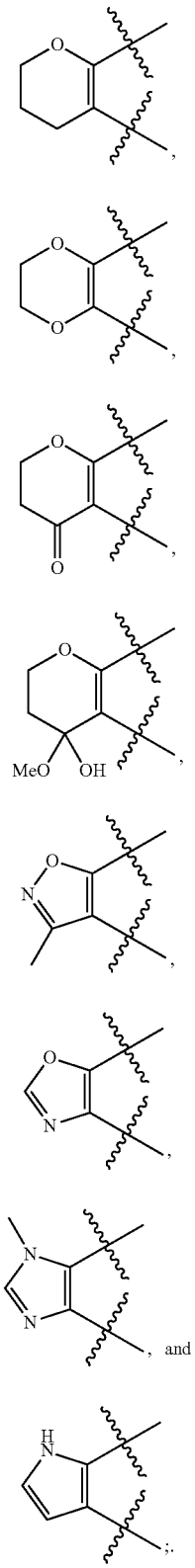
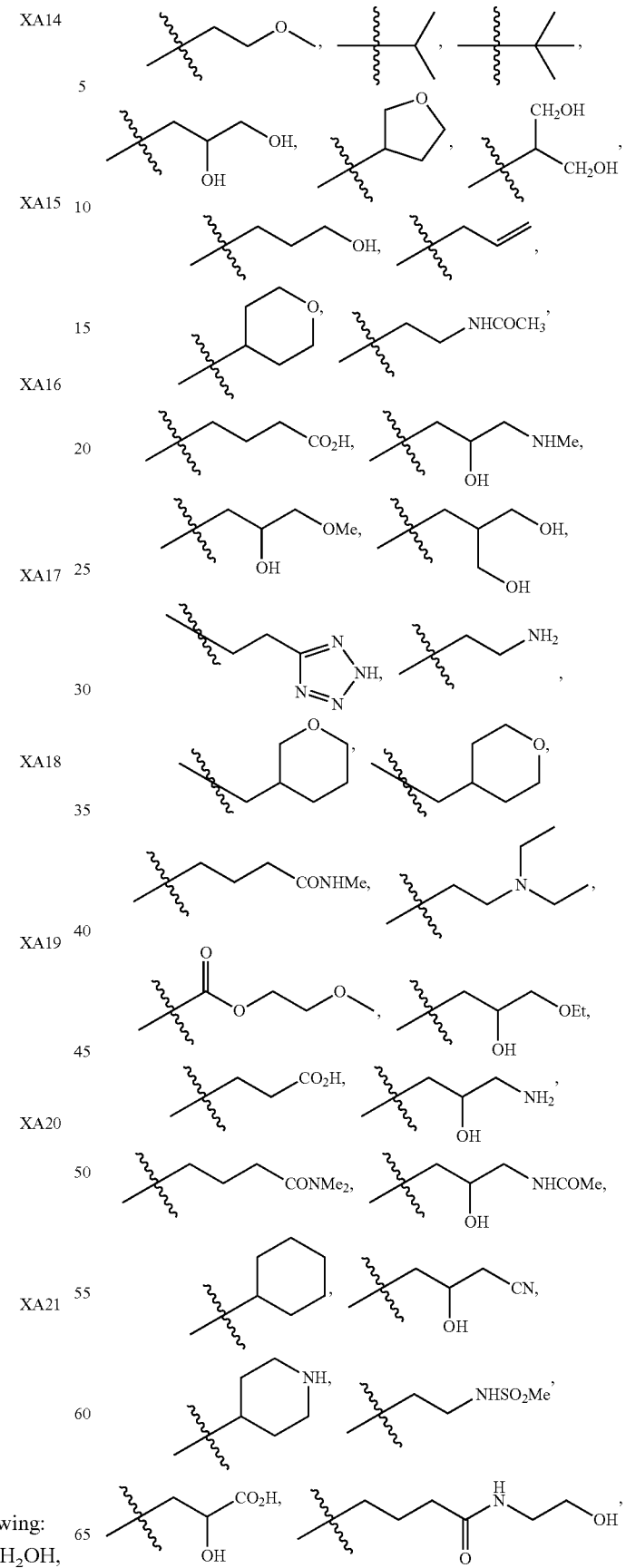
R'₃ is independently selected from one of the following:
—H, —CH₃, —CH₂CH₃, —C(O)CH₃, —CH₂CH₂OH, —C(O)OCH₃,

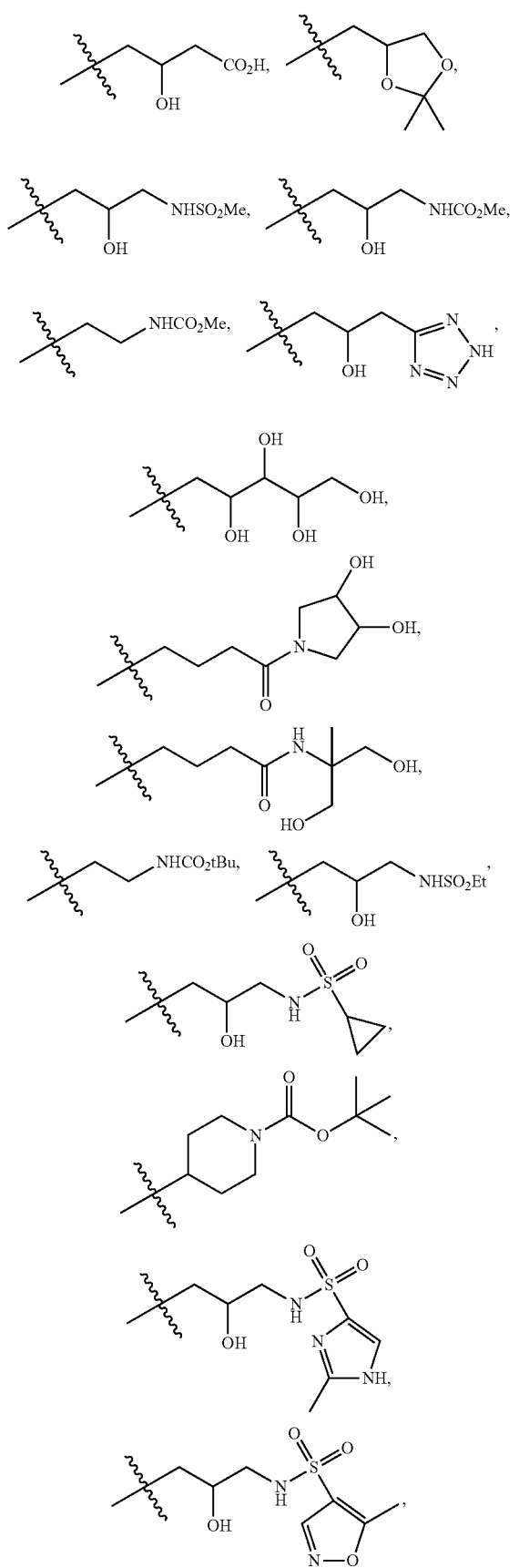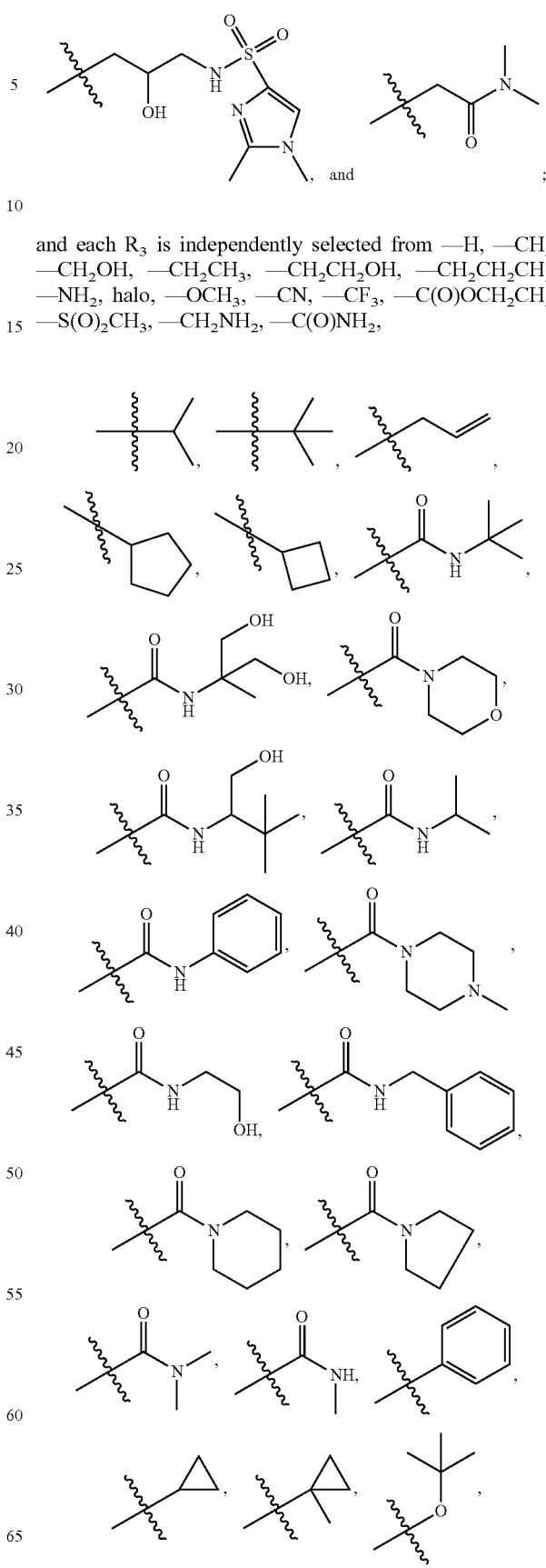
and each $R_3$ is independently selected from —H, —$CH_3$, —$CH_2OH$, —$CH_2CH_3$, —$CH_2CH_2OH$, —$CH_2CH_2CH_3$, —$NH_2$, halo, —$OCH_3$, —CN, —$CF_3$, —$C(O)OCH_2CH_3$, —$S(O)_2CH_3$, —$CH_2NH_2$, —$C(O)NH_2$, -continued

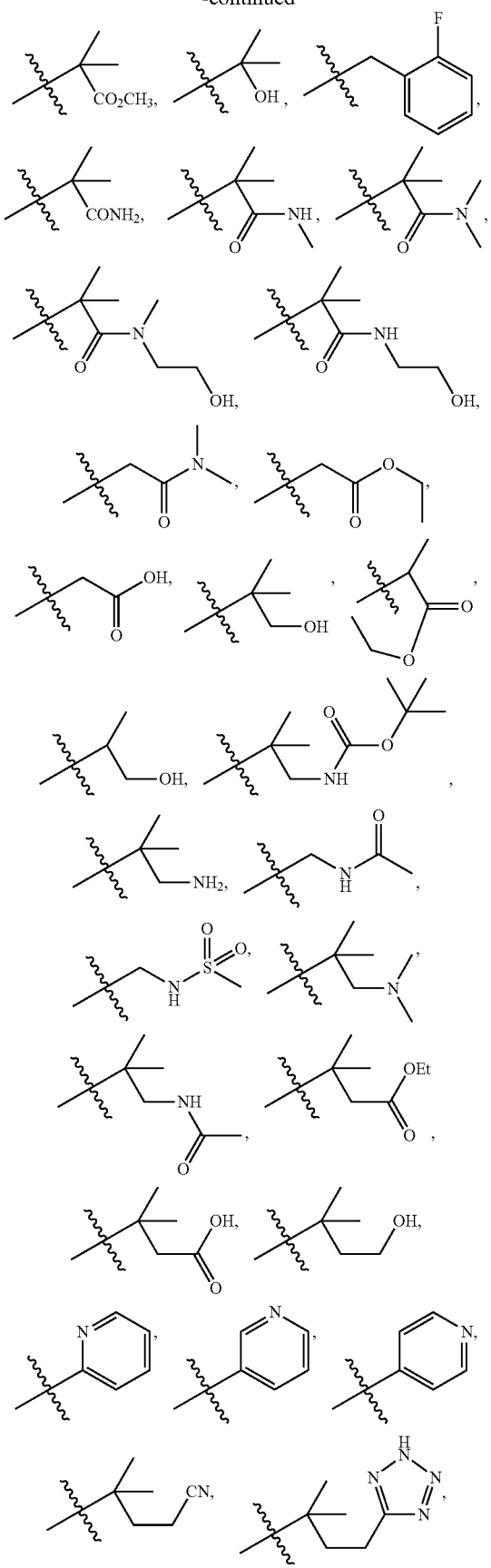

-continued

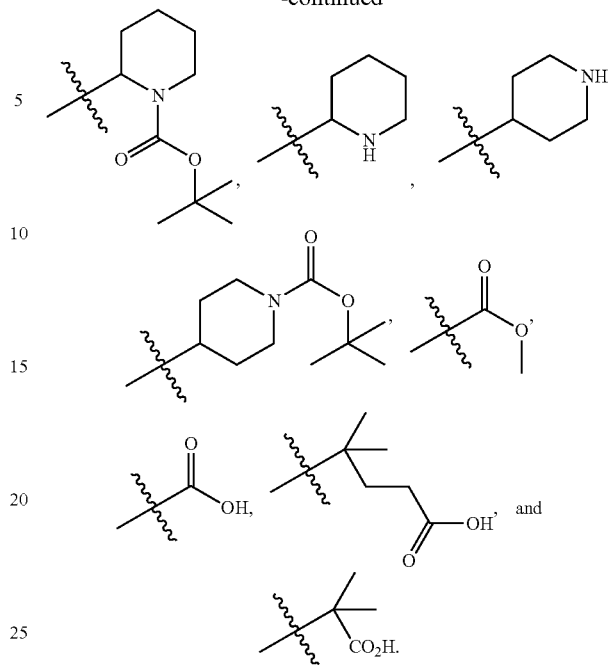

IV. Generic Synthetic Schemes

The compounds of formulae (I, Ic, Id, II, IIa, IIb, IIc, and IId) may be readily synthesized from commercially available or known starting materials by known methods. Exemplary synthetic routes to produce compounds of formulae (I, Ic, Id, II, IIa, IIb, IIc, and IId) are provided below in Schemes 1-22 below.

Preparation of the compounds of the invention is achieved by the coupling of a ring B amine with a ring A carboxylic acid as illustrated in Scheme 1.

Scheme 1:

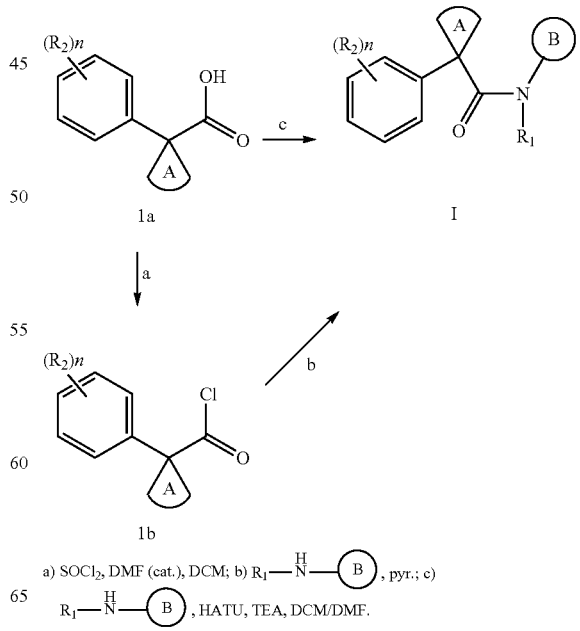

a) $SOCl_2$, DMF (cat.), DCM; b) $R_1$—NH—B, pyr.; c) $R_1$—NH—B, HATU, TEA, DCM/DMF.

Referring to Scheme 1, the acid 1a may be converted to the corresponding acid chloride 1b using thionyl chloride in the presence of a catalystic amount of dimethylformamide. Reaction of the acid chloride with the amine

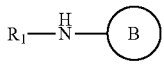

provides compounds of the invention I. Alternatively, the acid 1a may be directly coupled to the amine using known coupling reagents such as, for example, HATU in the presence of triethylamine.

Preparation of the acids 1a may be achieved as illustrated in Scheme 2.

Scheme 2:

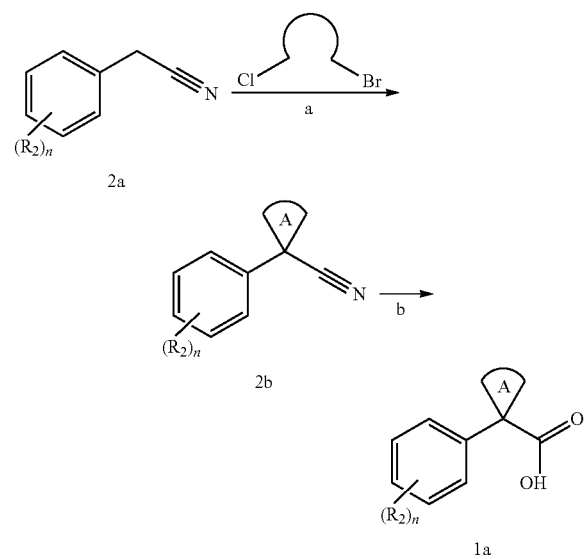

a) NaOH, BTEAC; b) NaOH, Δ

Referring to Scheme 2, the nitrile 2a reacts with a suitable bromochloroalkane in the presence of sodium hydroxide and a phase tranfer catalyst such as butyltriethylammonium chloride to provide the intermediate 2b. Hydrolysis of the nitrite of 2b provides the acid 1a. In some instances, isolation of the intermediate 2b is unnecessary.

The phenylacetonitriles 2a are commercially available or may be prepared as illustrated in Scheme 3.

Scheme 3

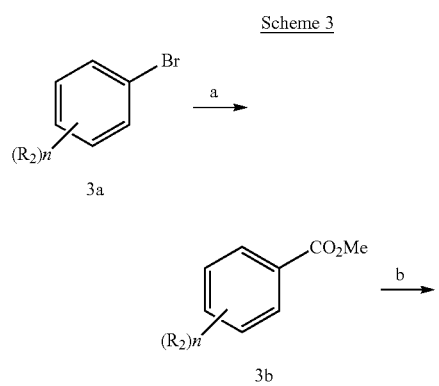

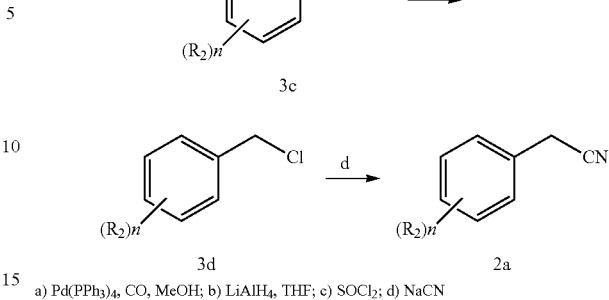

a) Pd(PPh$_3$)$_4$, CO, MeOH; b) LiAlH$_4$, THF; c) SOCl$_2$; d) NaCN

Referring to Scheme 3, reaction of an aryl bromide 3a with carbon monoxide in the presence of methanol and tetrakis(triphenylphosphine)palladium (0) provides the ester 3b. Reduction of 3b with lithium aluminum hydride provides the alcohol 3c which is converted to the halide 3d with thionyl chloride. Reaction of 3d with sodium cyanide provides the nitrile 2a.

Other methods of producing the nitrile 2a are illustrated in schemes 4 and 5 below.

Scheme 4

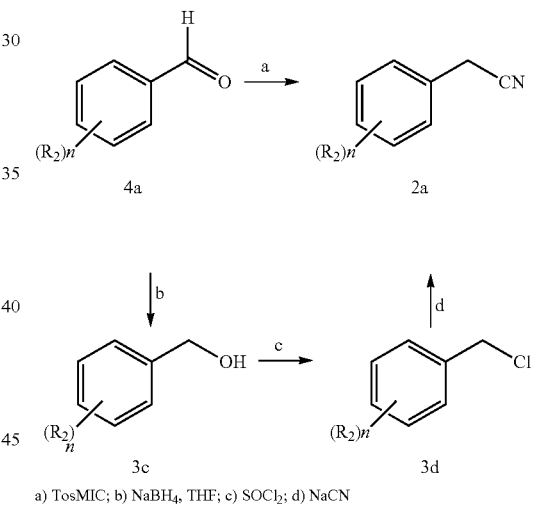

a) TosMIC; b) NaBH$_4$, THF; c) SOCl$_2$; d) NaCN

Scheme 5

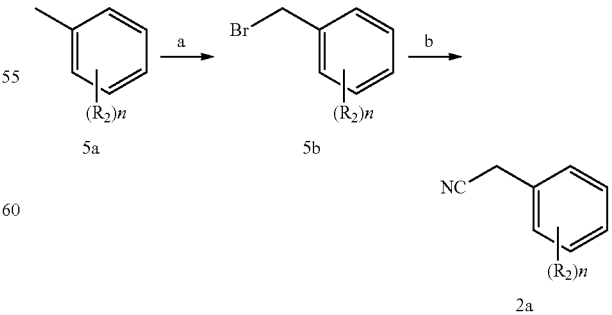

a) NBS, AIBN, CCl$_4$; b) NaCN, EtOH

Preparation of

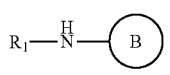

components is illustrated in the schemes that follow. A number of methods for preparing ring B compounds wherein ring B is an indole have been reported. See for example Angew. Chem. 2005, 44, 606; J. Am. Chem. Soc. 2005, 127, 5342,); J. Comb. Chem. 2005, 7, 130; Tetrahedron 2006, 62, 3439; J. Chem. Soc. Perkin Trans. 1, 2000, 1045.

One method for preparing

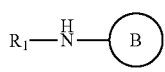

is illustrated in Scheme 6.

Scheme 6

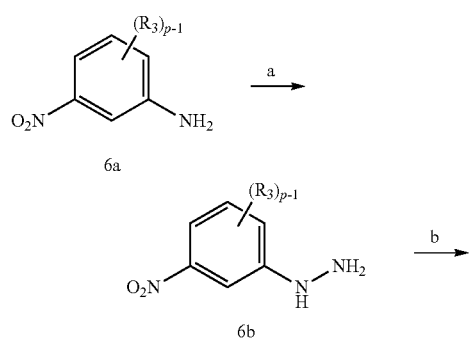

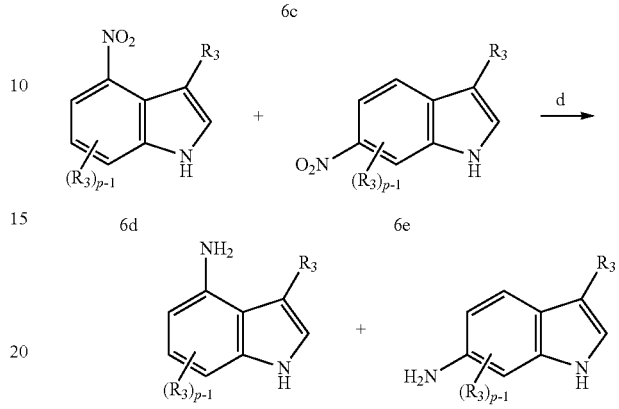

a) $NaNO_2$, HCl, $SnCl_2$; b) NaOH, $R_3CH_2C(O)R_3$, EtOH; c) $H_3PO_4$, toluene; d) $H_2$, Pd-C, EtOH Referring to Scheme 6, a nitroaniline 6a is converted to the hydrazine 6b using nitrous acid in the presence of HCl and stannous chloride. Reaction of 6b with an aldehyde or ketone $CH_3C(O)R_3$ provides the hydrazone 6c which on treatment with phosphoric acid in toluene leads to a mixture of nitro indoles 6d and 6e. Catalytic hydrogenation in the presence of palladium on carbon provides a mixture of the amino indoles 6f and 6g which may be separated using know methods such as, for example, chromatography.

An alternative method is illustrated in scheme 7.

Scheme 7

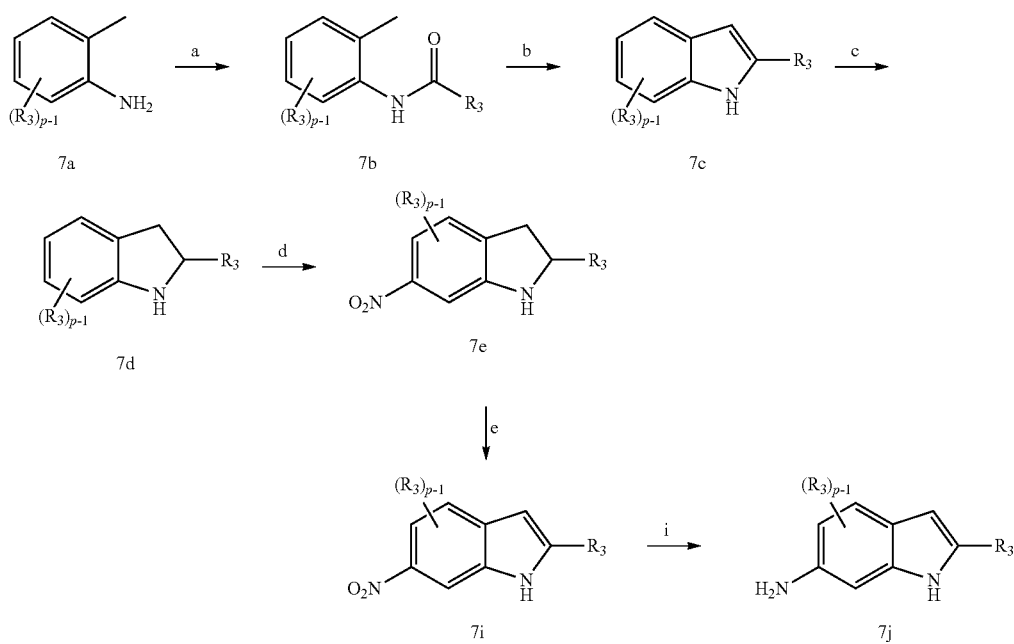

-continued

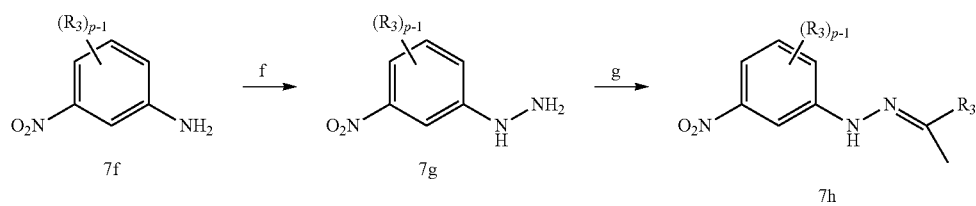

a) $R_{3a}COCl$, $Et_3N$, $CH_2Cl_2$; b) n-BuLi, THF; c) $NaBH_4$, AcOH; d) $KNO_3$, $H_2SO_4$; e) DDQ, 1,4-dioxane; f) $NaNO_2$, HCl, $SnCl_2·2H_2O$, $H_2O$; g) $MeCOR_3$, EtOH; h) PPA; i) Pd/C, EtOH or $H_2$, Raney Ni, EtOH or MeOH Scheme 8

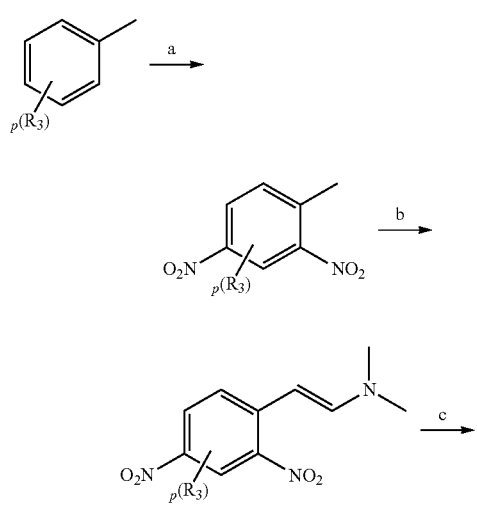

a) $HNO_3$, $H_2SO_4$; b) $Me_2NCH(OMe)_2$, DMF; c) $H_2$, Raney Ni, EtOH

Scheme 9

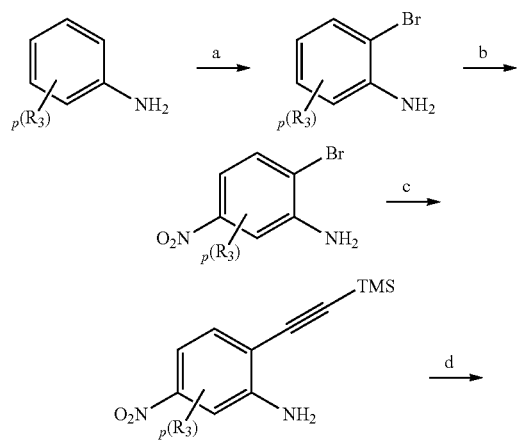

a) NBS, DMF; b) $KNO_3$, $H_2SO_4$; c) HC≡C-TMS, $Pd(PPh_3)_2Cl_2$, CuI, $Et_3N$, toluene, $H_2O$; d) CuI, DMF; e) $H_2$, Raney Ni, MeOH Scheme 10

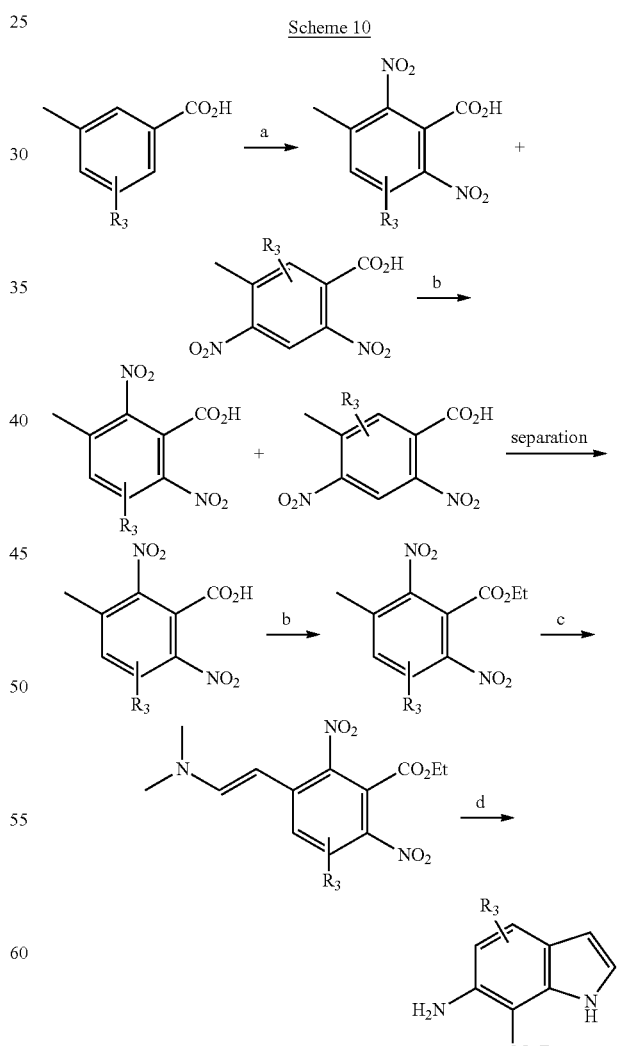

a) $HNO_3$, $H_2SO_4$; b) $SOCl_2$; EtOH; c) DMA, DMF; d) Raney Ni, $H_2$, MeOH

Scheme 11

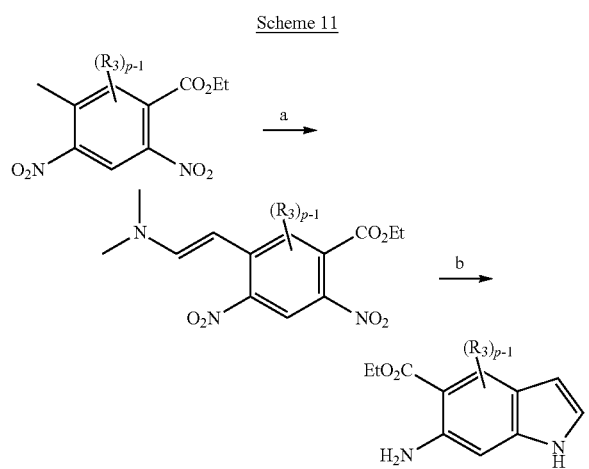

a) DMA, DMF; b) Raney Ni, H$_2$, MeOH

Scheme 12

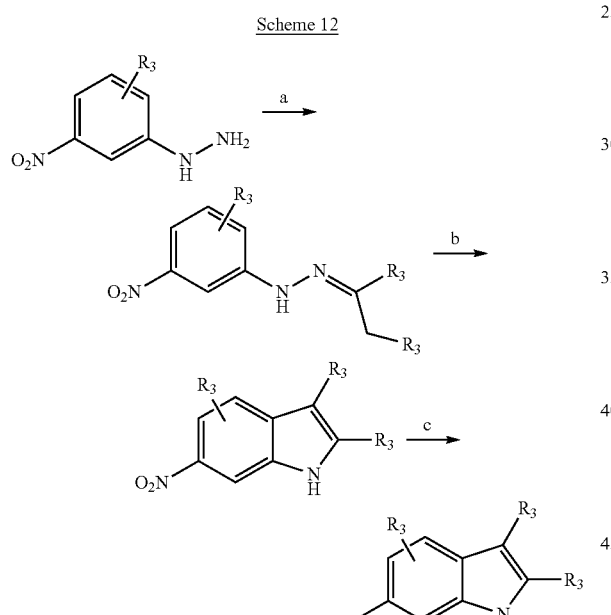

a) R$_{3a}$CH$_2$COR$_{3b}$, AcOH, EtOH;
b) H$_3$PO$_4$, toluene;
c) H$_2$, Pd/C, EtOH

Scheme 14

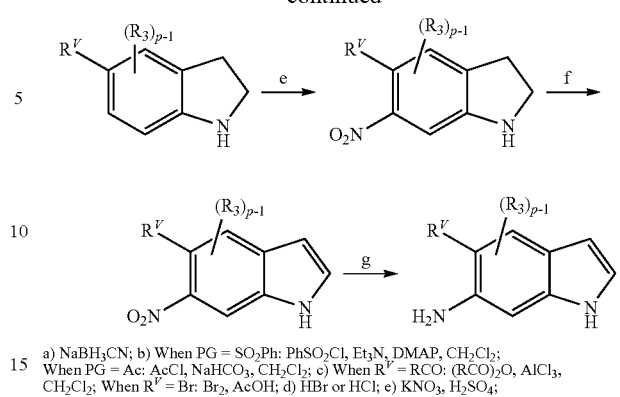

a) NaBH$_3$CN; b) When PG = SO$_2$Ph: PhSO$_2$Cl, Et$_3$N, DMAP, CH$_2$Cl$_2$;
When PG = Ac: AcCl, NaHCO$_3$, CH$_2$Cl$_2$; c) When R$^V$ = RCO: (RCO)$_2$O, AlCl$_3$,
CH$_2$Cl$_2$; When R$^V$ = Br: Br$_2$, AcOH; d) HBr or HCl; e) KNO$_3$, H$_2$SO$_4$;
f) MnO$_2$, CH$_2$Cl$_2$ or DDQ, 1,4-dioxane; g) H$_2$, Raney Ni, EtOH.

Scheme 14

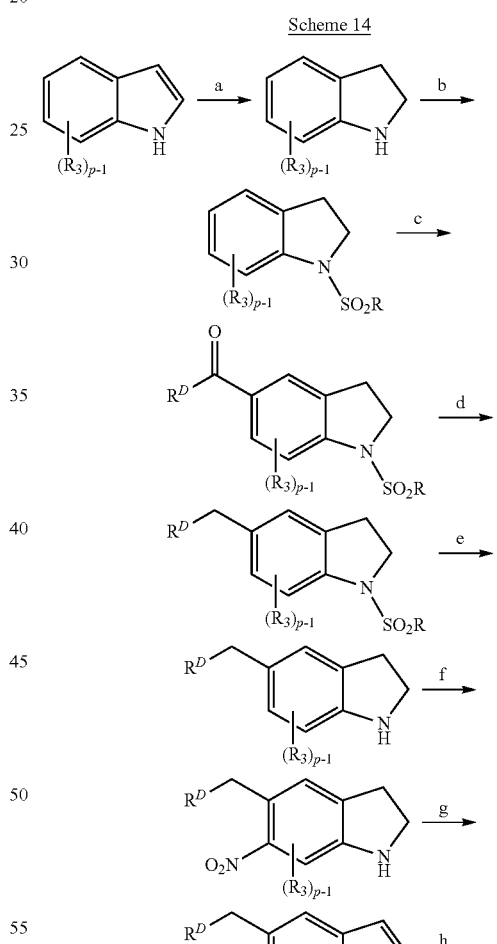

a) NaBH$_3$CN; b) RSO$_2$Cl, DMAP, Et$_3$N, CH$_2$Cl$_2$;
c) R$^D$C(O)Cl, AlCl$_3$, CH$_2$Cl$_2$; d) NaBH$_4$, THF;
e) HBr; f) KNO$_3$, H$_2$SO$_2$; g) MnO$_2$; g) Raney Ni, H$_2$, EtOH Scheme 15

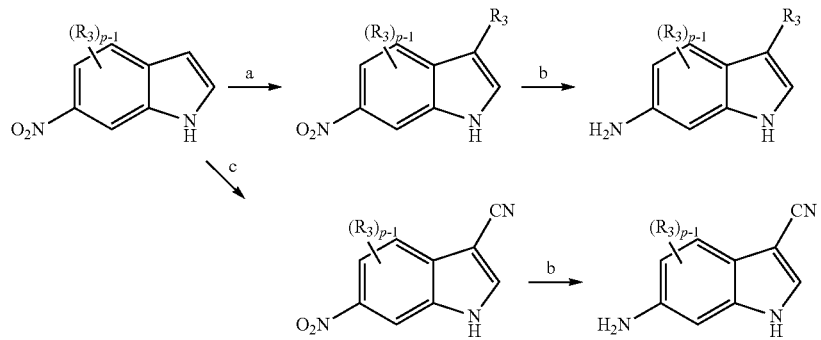

a) R$_3$X (X=BR, I), zinc triflate, TBAI, DIEA, toluene;
b) H$_2$, Raney Ni, EtOH or H$_2$, Pd/C, EtOH or SnCl$_2$•2H$_2$O, EtOH;
c) ClSO$_2$NCO, DMF, CH$_3$CN Scheme 16

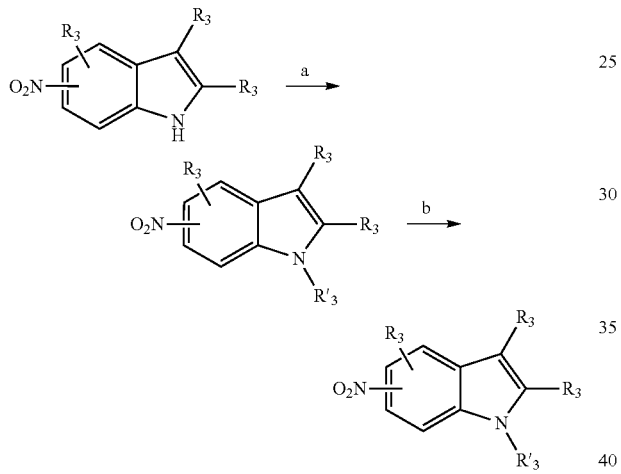

a) when X=Cl, Br, I, or OTs: R′$_3$X, K$_2$CO$_3$, DMF or CH$_3$CN; b) H$_2$, Pd/C, EtOH or SnCl$_2$•2H$_2$O, EtOH or SnCl$_2$•2H$_2$O, DIEA, EtOH.

Scheme 17

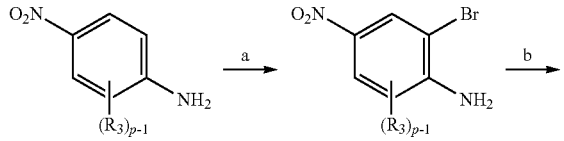

-continued

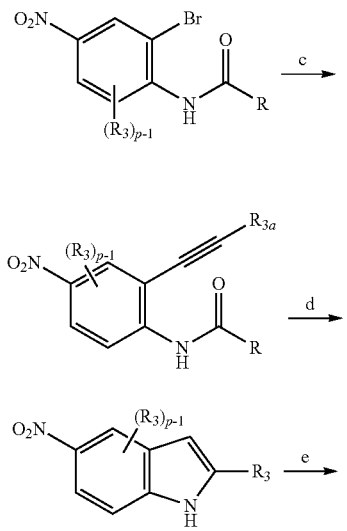

a) Br$_2$, AcOH; b) RC(O)Cl, Et$_3$N, CH$_2$Cl$_2$;
c) HC≡CR$_{3a}$, Pd(PPh$_3$)$_2$Cl$_2$, CuI, Et$_3$N;
d) TBAF, THF or tBuOK, DMF or Pd(PPh$_3$)$_2$Cl$_2$, CuI, DMF;
e) H$_2$, Pd/C, EtOH or SnCl$_2$, MeOH or HCO$_2$NH$_4$, Pd/C, EtOH

Scheme 18

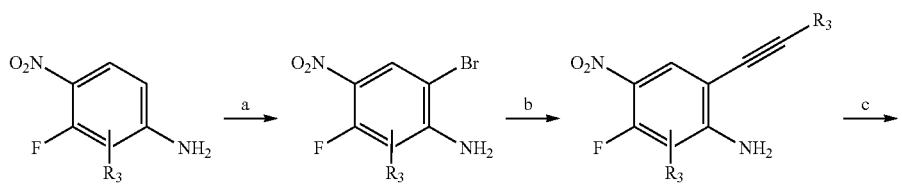

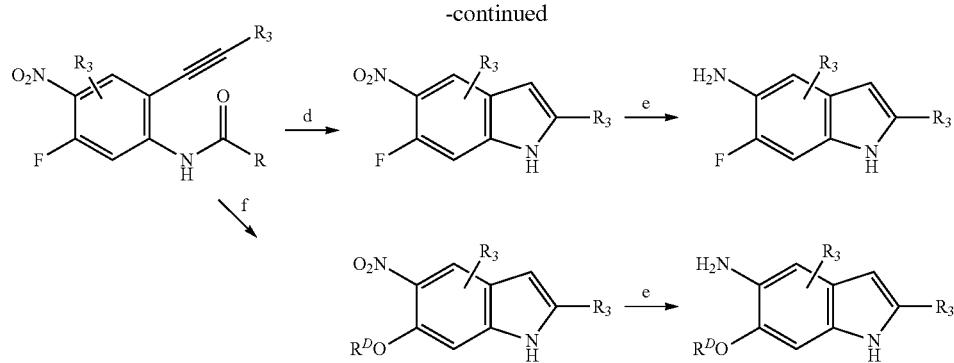

a) Br$_2$, AcOH, CHCl$_3$; b) R$_{3a}$C≡CH, CuI, Et$_3$N, Pd(PPh$_3$)$_2$Cl$_2$;
c) RCOCl, Et$_3$N, CH$_2$Cl$_2$; d) TBAF, DMF; e) Raney Ni, H$_2$, MeOH;
f) ROK, DMF

Scheme 19

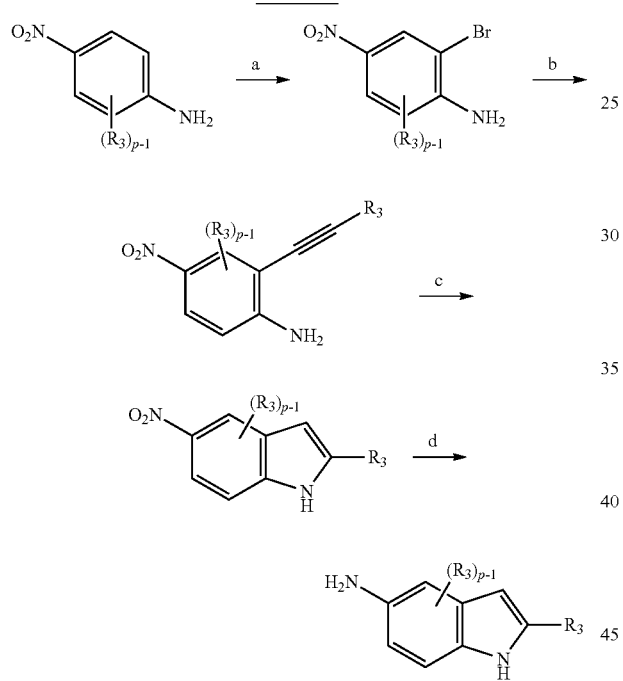

a) Br$_2$, AcOH; b) HC≡CR$_{3a}$, Pd(PPh$_3$)$_2$Cl$_2$, CuI, Et$_3$N; c) Pd(PPh$_3$)$_2$Cl$_2$, CuI, DMF; d) H$_2$, Pd/C, EtOH or SnCl$_2$, MeOH or HCO$_2$NH$_4$, Pd/C, EtOH

Scheme 20

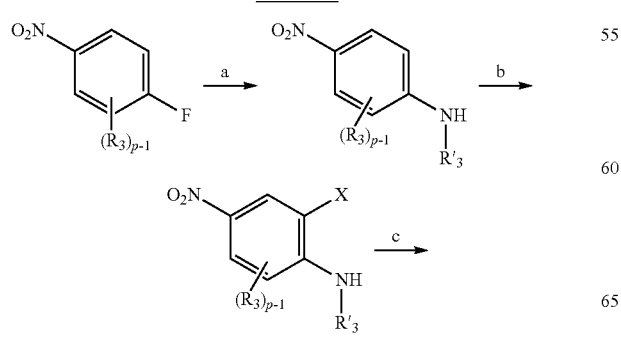

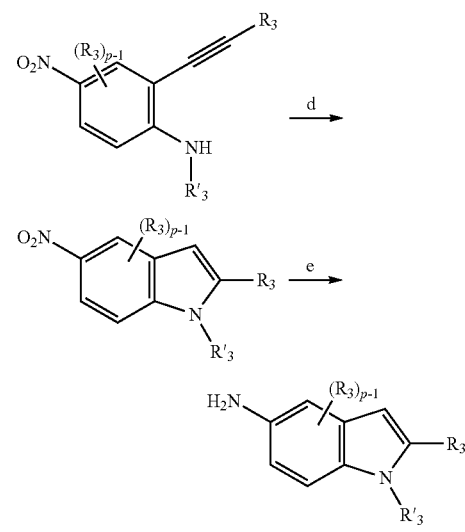

a) H$_2$NR'$_3$; b) X=Br: HOAc; X=I: NIS;
c) HC≡CR$_3$, Pd(PPh$_3$)$_2$Cl$_2$, CuI, Et$_3$N;
d) CuI, DMF or TBAF, THF;
e) H$_2$, Pd/C, EtOH or SnCl$_2$, MeOH or HCO$_2$NH$_4$, Pd/C, EtOH

Scheme 21

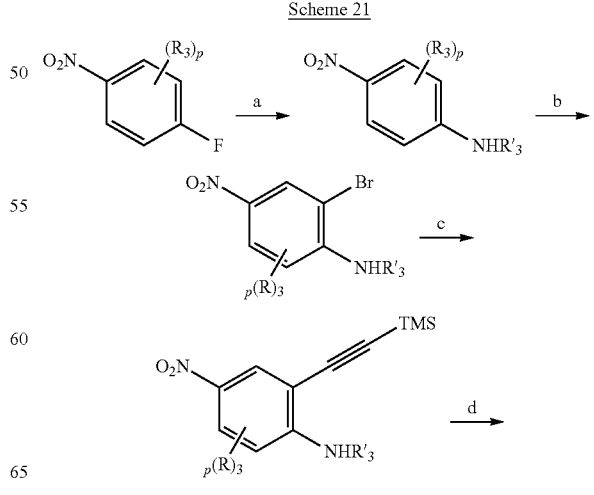

187
-continued
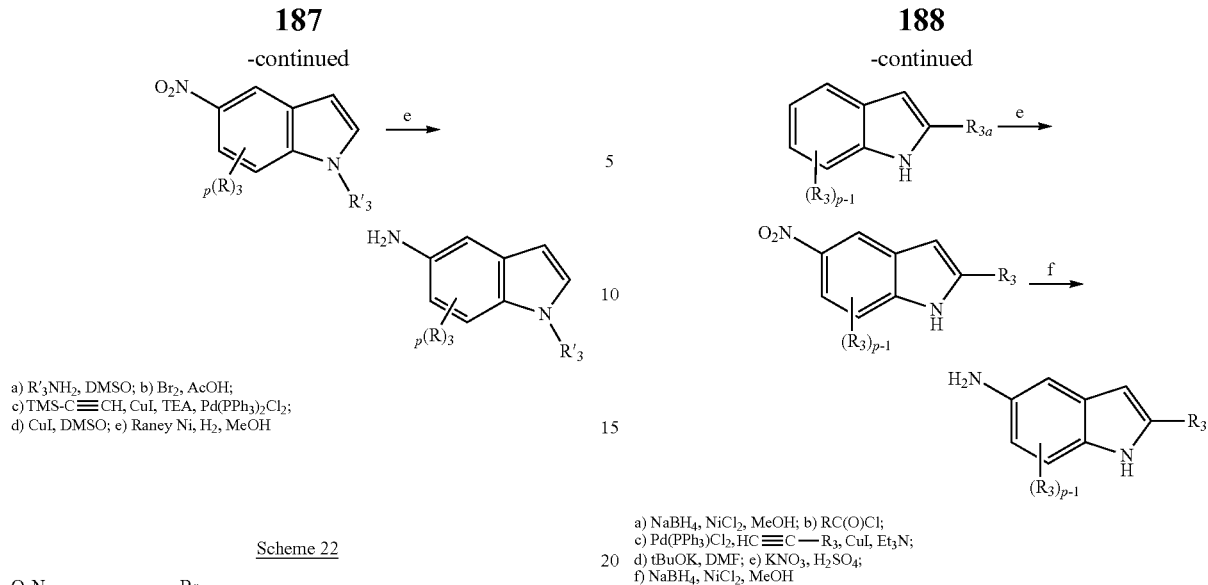
a) R′₃NH₂, DMSO; b) Br₂, AcOH;
c) TMS-C≡CH, CuI, TEA, Pd(PPh₃)₂Cl₂;
d) CuI, DMSO; e) Raney Ni, H₂, MeOH
Scheme 22
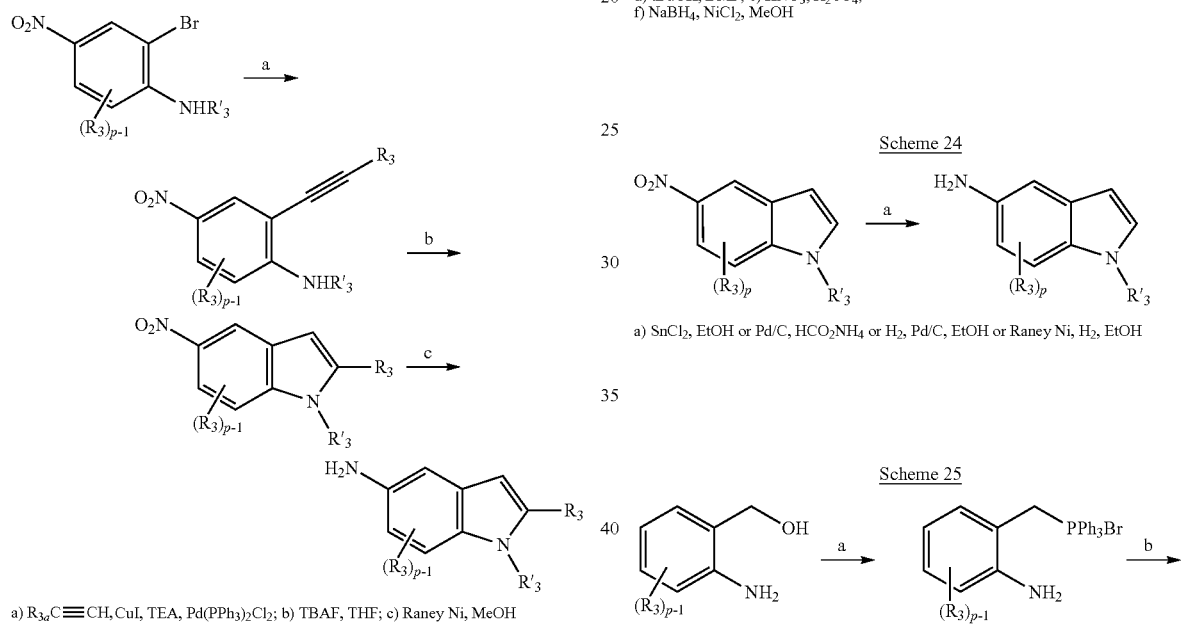
a) R₃ₐC≡CH, CuI, TEA, Pd(PPh₃)₂Cl₂; b) TBAF, THF; c) Raney Ni, MeOH
Scheme 23
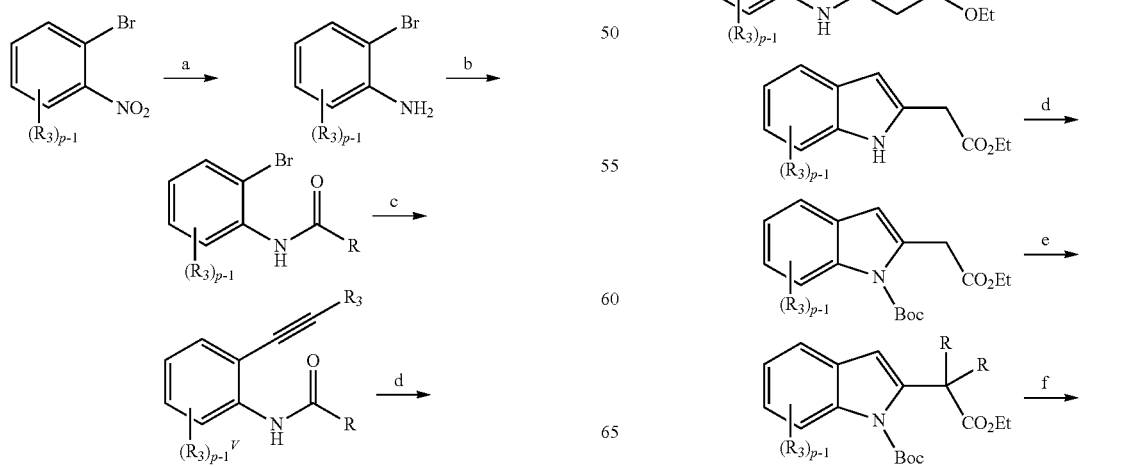
188
-continued
a) NaBH₄, NiCl₂, MeOH; b) RC(O)Cl;
c) Pd(PPh₃)₂Cl₂, HC≡C—R₃, CuI, Et₃N;
d) tBuOK, DMF; e) KNO₃, H₂SO₄;
f) NaBH₄, NiCl₂, MeOH
Scheme 24
a) SnCl₂, EtOH or Pd/C, HCO₂NH₄ or H₂, Pd/C, EtOH or Raney Ni, H₂, EtOH
Scheme 25

-continued

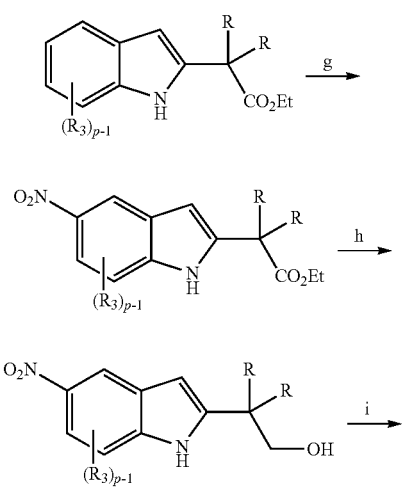

a) PPh$_3$, HBr; b) Cl(O)CCH$_2$CO$_2$Et; c) tBuOK;
d) (Boc)$_2$O, DMAP; e) KHMDS, R—X; KHMDS, R—X;
f) TFA; g) NaNO$_3$, H$_2$SO$_4$; h) LiAlH$_4$, THF;
i) SnCl$_2$, EtOH

Scheme 26

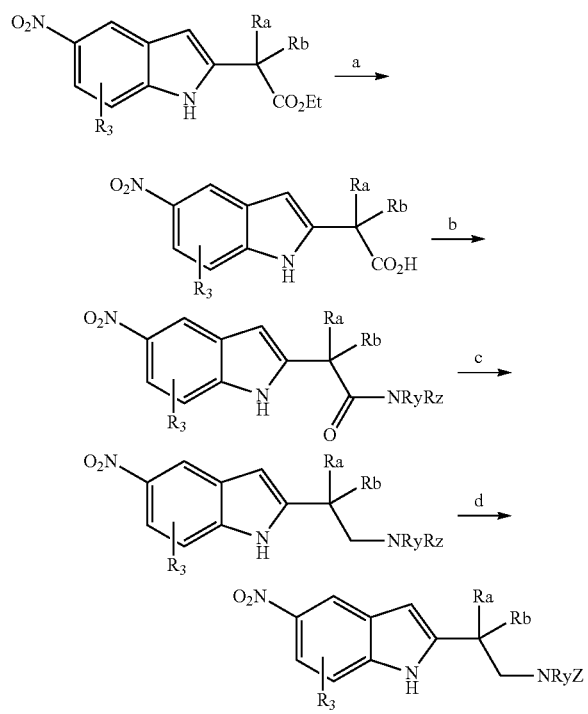

a) LiOH; b) EDC, HOBt, Et$_3$N, HNRyRz;
c) BH$_3$—THF;
d) if Rz═H, RC(O)Cl (Z═RC(O)-) or RSO$_2$Cl (Z═RSO$_2$-)
or RO(CO)Cl (Z═RO(CO)-) or RO(CO))$_2$O (Z═Z═RO(CO)-),
Et$_3$N, CH$_2$Cl$_2$

Scheme 27

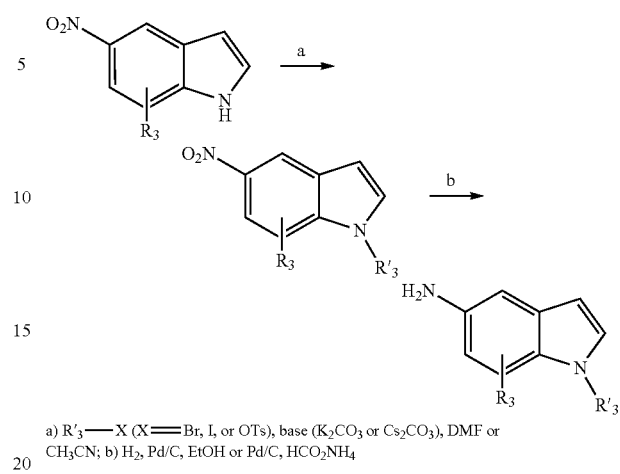

a) R'$_3$—X (X═Br, I, or OTs), base (K$_2$CO$_3$ or Cs$_2$CO$_3$), DMF or CH$_3$CN; b) H$_2$, Pd/C, EtOH or Pd/C, HCO$_2$NH$_4$ Scheme 28

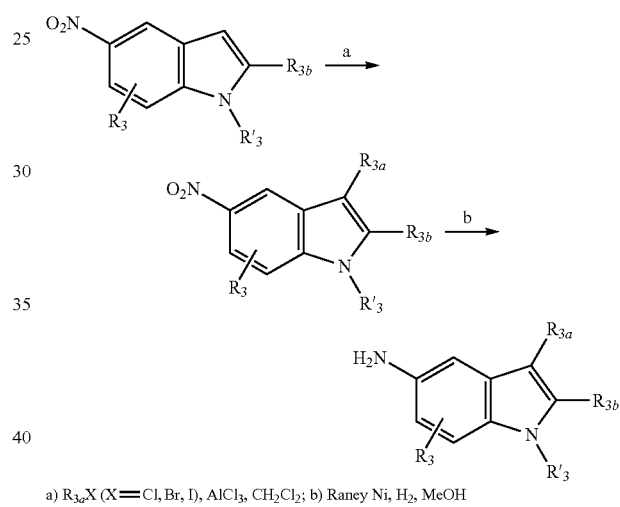

a) R$_{3a}$X (X═Cl, Br, I), AlCl$_3$, CH$_2$Cl$_2$; b) Raney Ni, H$_2$, MeOH

Scheme 29

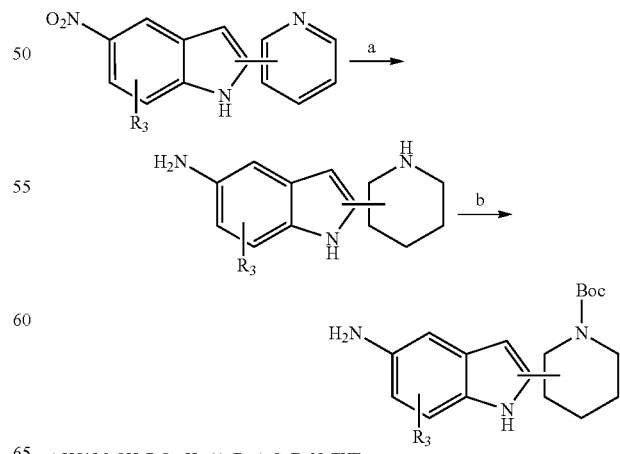

a) HCl/MeOH; PtO$_2$, H$_2$; b) (Boc)$_2$O, Et$_3$N, THF

Scheme 30
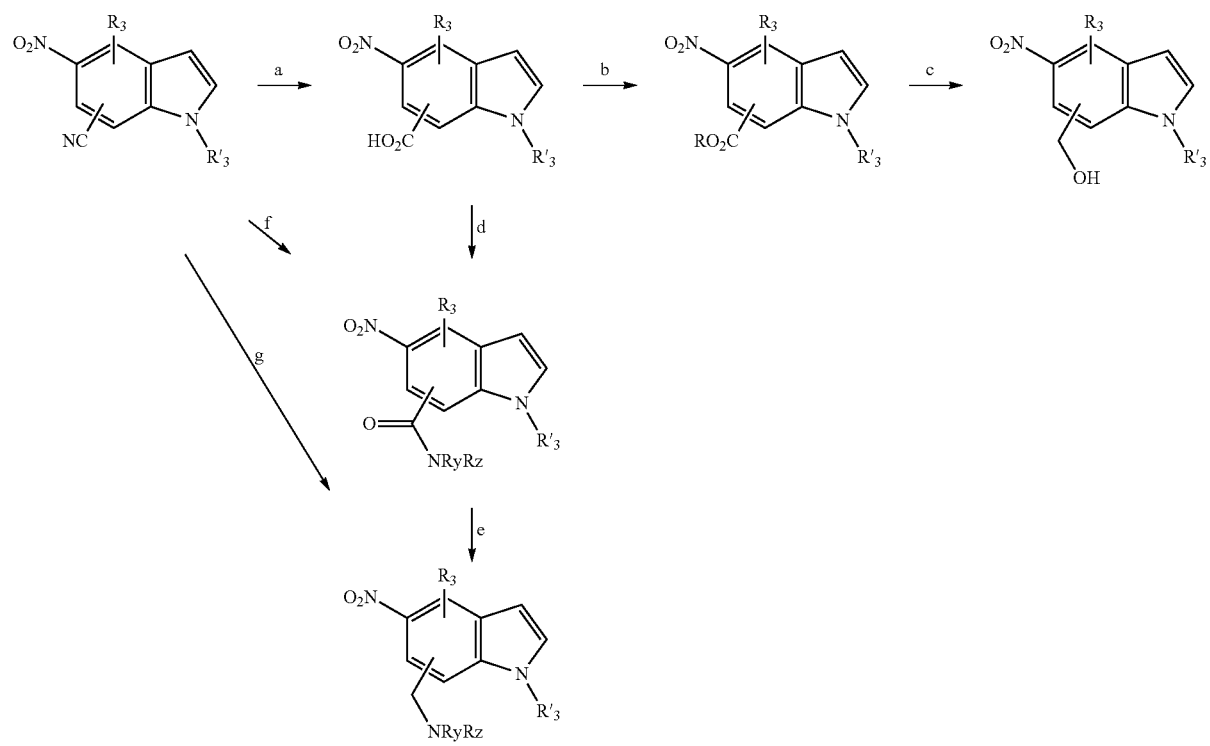
a) NaOH or LiOH; b) ROH, HCl; c) NaBH$_4$ or LiAlH$_4$ or DIBAL-H, THF; d) HNRyRz, HATU, Et$_3$N, EtOH or DMF; e) LiAlH$_4$, THF or BH$_3$·THF; f) H$_2$O$_2$, H$_2$O (Ry═Rz═H); g) H$_2$, Pd/C
Scheme 31
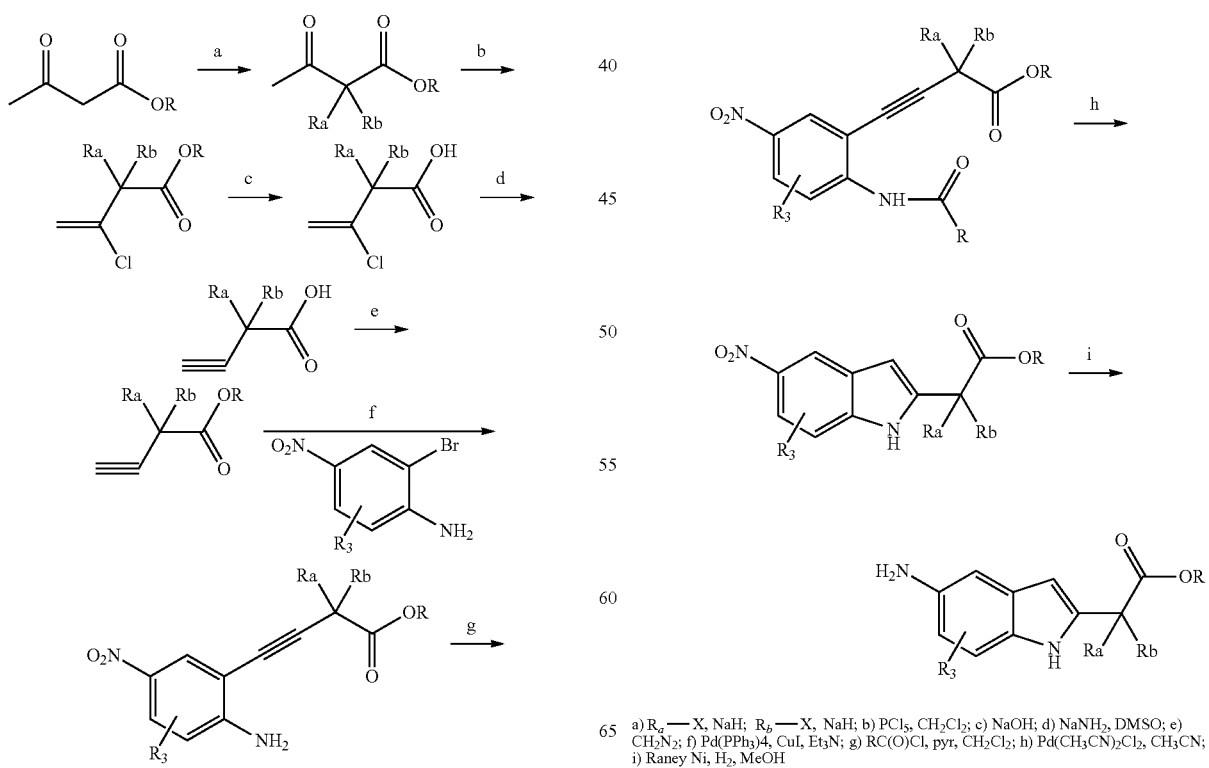
a) R$_a$—X, NaH; R$_b$—X, NaH; b) PCl$_5$, CH$_2$Cl$_2$; c) NaOH; d) NaNH$_2$, DMSO; e) CH$_2$N$_2$; f) Pd(PPh$_3$)$_4$, CuI, Et$_3$N; g) RC(O)Cl, pyr, CH$_2$Cl$_2$; h) Pd(CH$_3$CN)$_2$Cl$_2$, CH$_3$CN; i) Raney Ni, H$_2$, MeOH Scheme 32
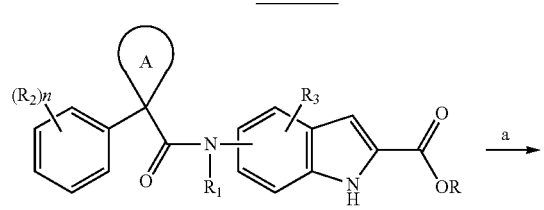
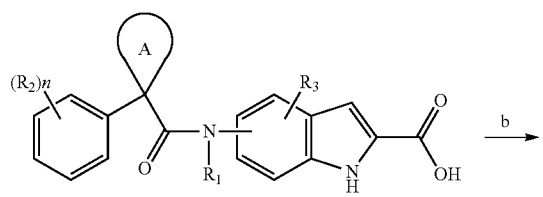
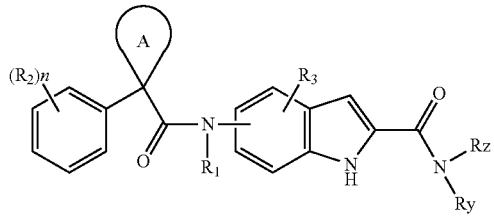
a) LiOH, THF/H₂O; b) HNRyRz, HATU, TEA, DMF/CH₂Cl₂
Scheme 33
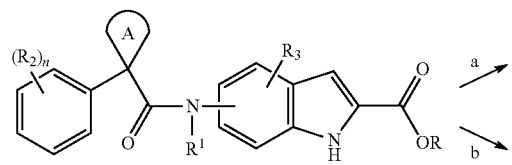
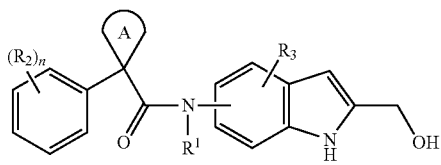
a) LiBH₄, THF/H₂O or LiAlH₄, THF; b) Rₐ—Li, THF
Scheme 34
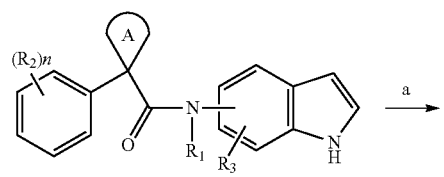
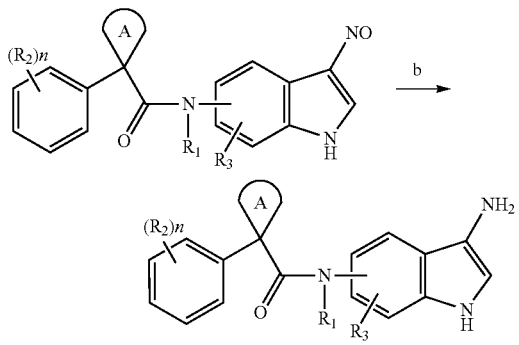
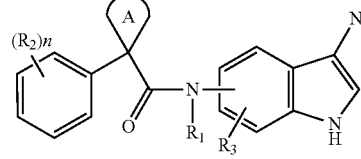
a) NaNO₂, AcOH/H₂O; b) Zn, AcOH
Scheme 35
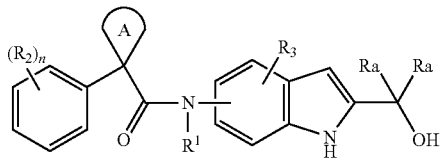
-continued
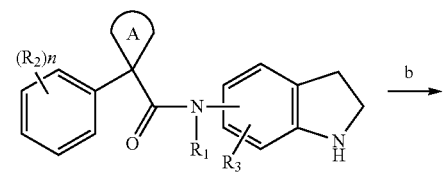

195
-continued
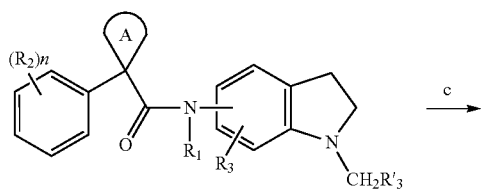
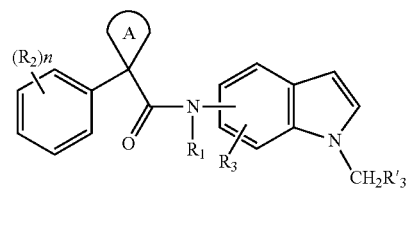
a) NaBH₃CN; b) R′₃CHO, NaHB(OAc)₃, TFA, DCE; c) chloranil or CDCl₃, light or DDQ
Scheme 36
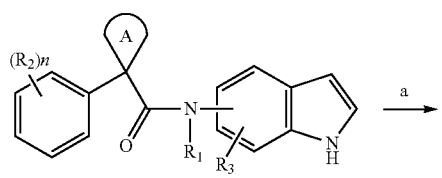
196
-continued
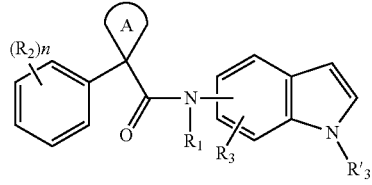
a) NaH, DMF—THF; R₃—X (X = Cl, Br, I, or OTs)
Scheme 37
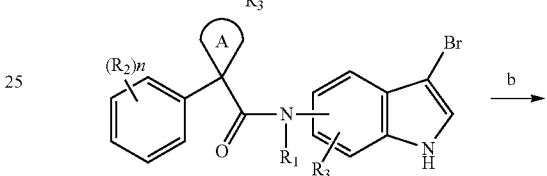
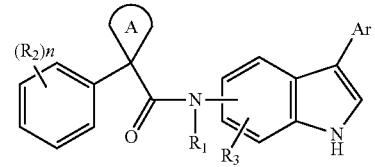
a) NBS; b) Ar—B(OR)₂, Pd-FibreCat 1007, K₂CO₃, EtOH
Scheme 38
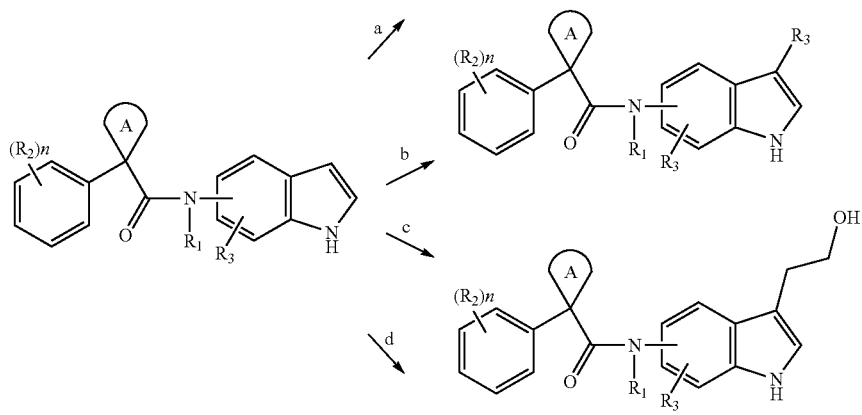

-continued
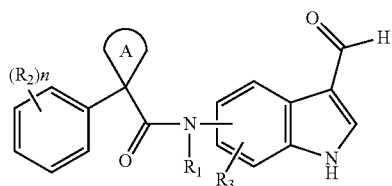
↓ e
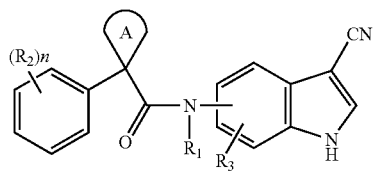
a) RSO₂Cl, NaH, THF—DMF; b) R₃—X (X = Br, I, or OTs), NaH, THF—DMF; c) ethylene dioxide, InCl₃; d) POCl₃, DMF; e) H₂N—OH, CH₂Cl₂; Ac₂O
Scheme 39
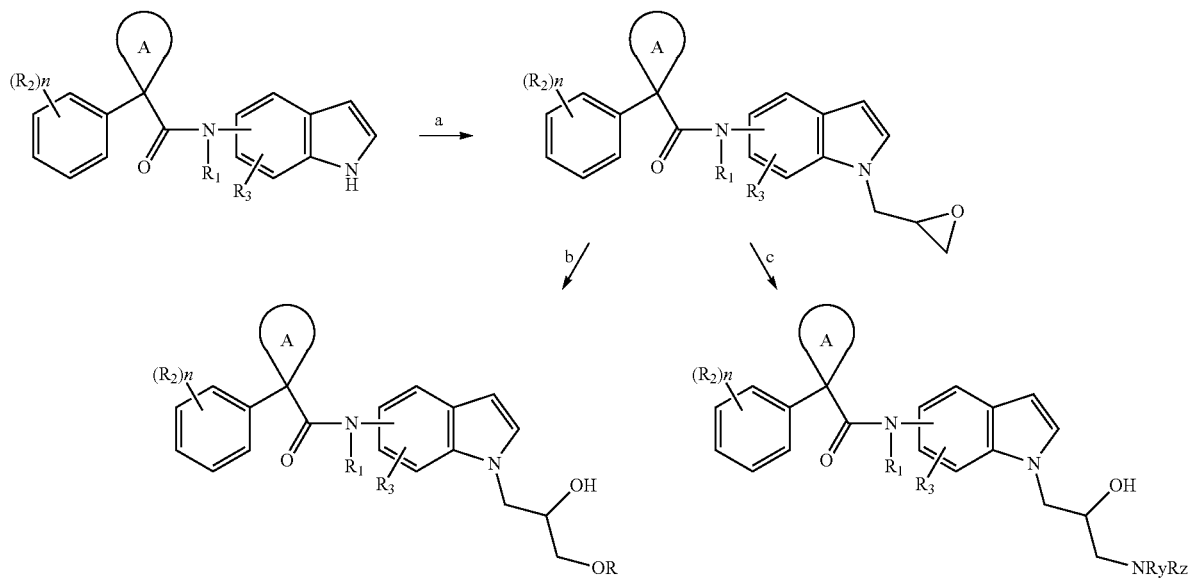
a) NaH, THF-DMF; epichlorohydrin; b) ROH; c) HNRyRz
Scheme 40
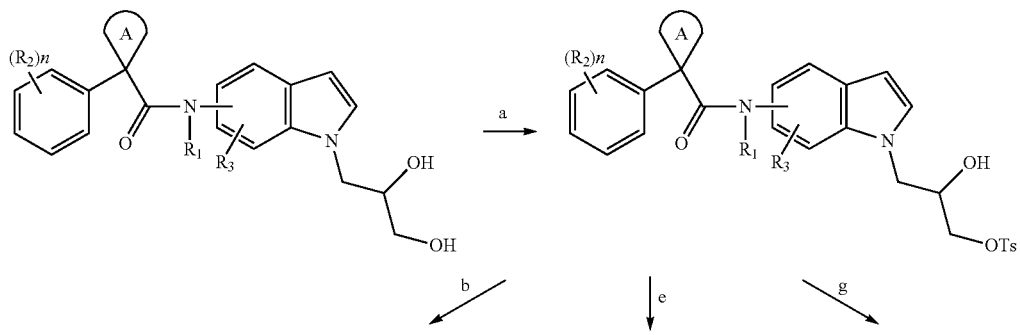

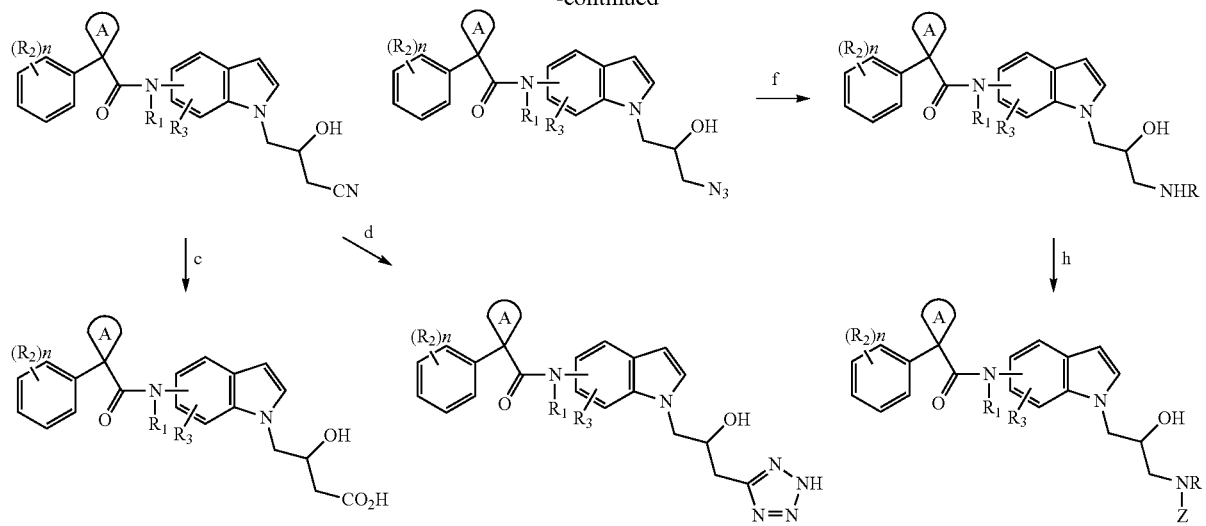
a) TsCl, Et₃N, CH₂Cl₂; b) NaCN, DMF; c) NaOH, MeOH; d) NaN₃, NH₄Cl; e) NaN₃, DMF; f) Pd/C, H₂, MeOH (R = H); h) R^xC(O)Cl (Z = R^xC(O)—) or R^xSO₂Cl (Z = R^xSO₂—) or R^yO(CO)Cl (Z = R^yO(CO)—) or (R^yO(CO))₂O (Z = R^yO(CO)—), Et₃N, CH₂Cl₂
Scheme 41
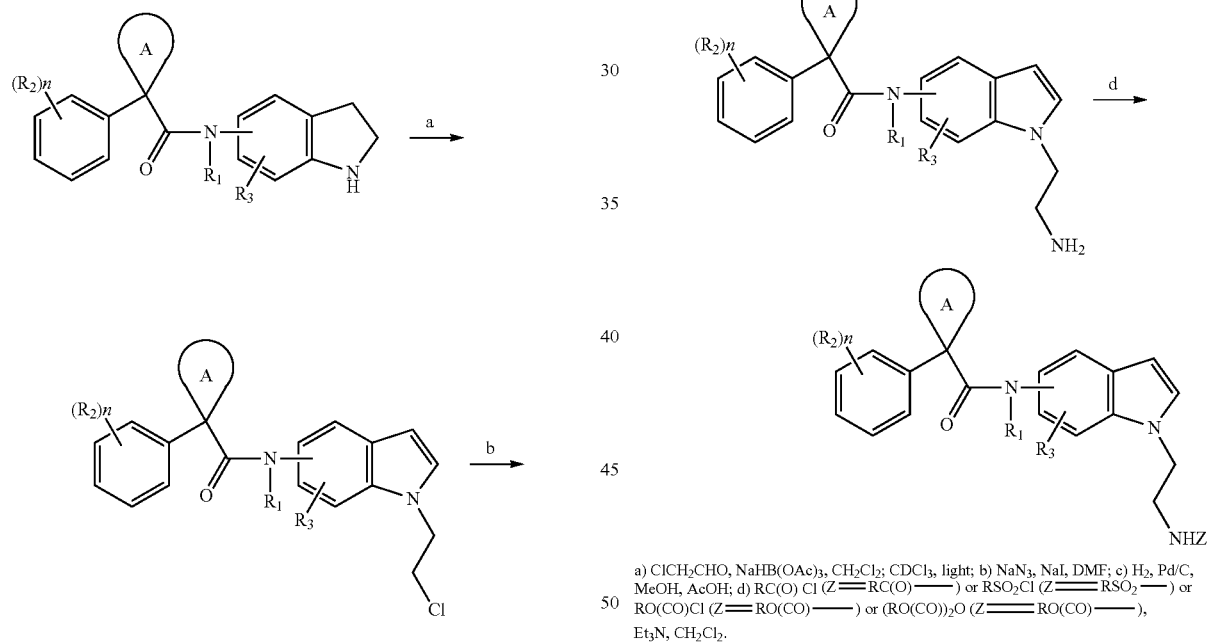
a) ClCH₂CHO, NaHB(OAc)₃, CH₂Cl₂; CDCl₃, light; b) NaN₃, NaI, DMF; c) H₂, Pd/C, MeOH, AcOH; d) RC(O)Cl (Z═RC(O)—) or RSO₂Cl (Z═RSO₂—) or RO(CO)Cl (Z═RO(CO)—) or (RO(CO))₂O (Z═RO(CO)—), Et₃N, CH₂Cl₂.
Scheme 42
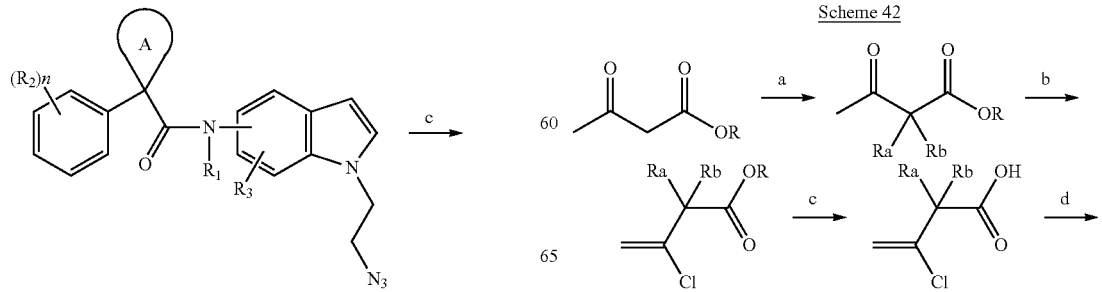

-continued

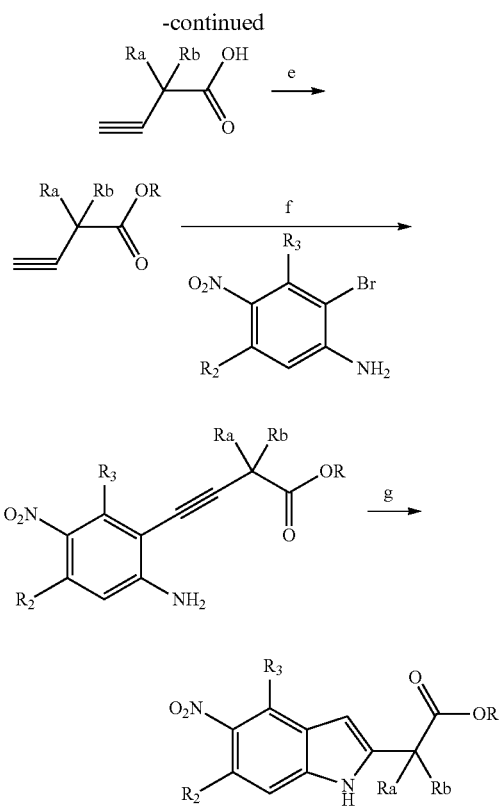

a) R$_a$—X, NaH; R$_b$—X, NaH; b) PCl$_5$, CH$_2$Cl$_2$; c) NaOH; d) NaNH$_2$, DMSO; e) R-OH, DCC; f) Pd(PPh$_3$)$_2$Cl$_2$, CuI, Et$_3$N; g) PdCl$_2$, CH$_3$CN

Scheme 43

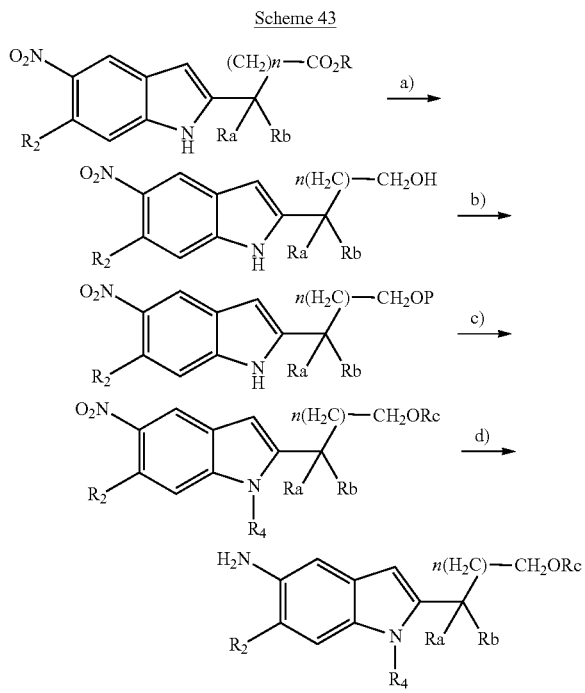

n = 0 or 1 a) DIBAL-H; b) P-LG; P = protecting group like TBDMS and LG = leaving group like Cl; c) R$_4$-LG, base like Cs$_2$CO$_3$; R$_4$ is alkyl and LG is tosylate, Rc = H or R$_4$; d) reducing conditions like Pd/C, H$_2$ or ammonium formate.

Scheme 43

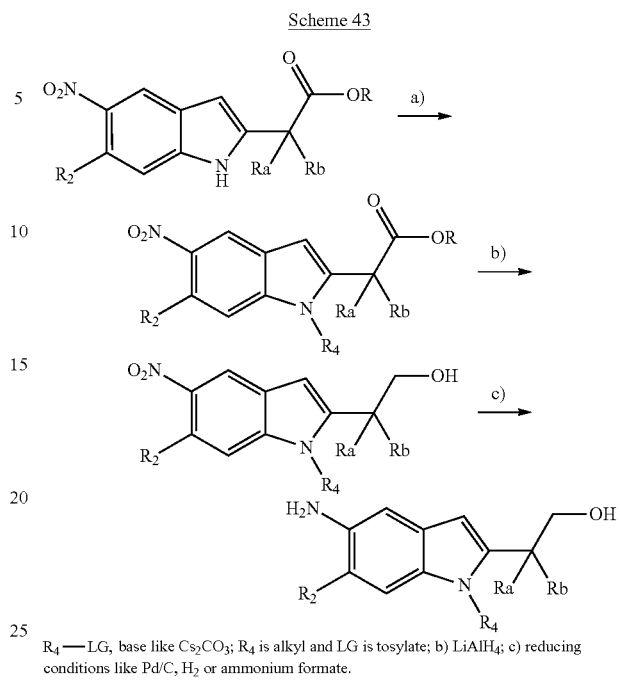

R$_4$—LG, base like Cs$_2$CO$_3$; R$_4$ is alkyl and LG is tosylate; b) LiAlH$_4$; c) reducing conditions like Pd/C, H$_2$ or ammonium formate.

In the schemes above, the radical R employed therein is a substituent, e.g., RW as defined hereinabove. One of skill in the art will readily appreciate that synthetic routes suitable for various substituents of the present invention are such that the reaction conditions and steps employed do not modify the intended substituents.

V. Formulations, Administrations, and Uses

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, the present invention provides a method of treating a condition, disease, or disorder implicated by ABC transporter activity. In certain embodiments, the present invention provides a method of treating a condition, disease, or disorder implicated by a deficiency of ABC transporter activity, the method comprising administering a composition comprising a compound of formulae (I, Ic, Id, II, IIa, IIb, IIc, and IId) to a subject, preferably a mammal, in need thereof.

In certain preferred embodiments, the present invention provides a method of treating Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease, Straussler-Scheinker disease, secretory diarrhea, polycystic kidney disease, chronic obstructive pulmonary disease (COPD), dry eye disease, and Sjögren's Syndrome, comprising the step of administering to said mammal an effective amount of a composition comprising a compound of formulae (I, Ic, Id, II, IIa, IIb, IIc, and IId), or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of formulae (I, Ic, Id, II, IIa, IIb, IIc, and IId), or a preferred embodiment thereof as set forth above.

According to the invention an "effective amount" of the compound or pharmaceutically acceptable composition is that amount effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The compounds and compositions, according to the method of the present invention, may be administered using any amount and any route of administration effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formulae (I, Ic, Id, II, IIa, IIb, IIc, and IId). In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formulae (I, Ic, Id, II, IIa, IIb, IIc, and IId). The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" Drug Discov Today 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formulae (I, Ic, Id, II, IIa, IIb, IIc, and IId) or any of the above embodiments; and (ii) instructions for a.) contacting the composition with the biological sample and b.) measuring activity of said ABC transporter or a fragment thereof. In one embodiment, the kit further comprises instructions for a.) contacting an additional composition with the biological sample; b.) measuring the activity of said ABC transporter or a fragment thereof in the presence of said additional compound, and c.) comparing the activity of the ABC transporter in the presence of the additional compound with the density of the ABC transporter in the presence of a composition of formulae (I, Ic, Id, II, IIa, IIb, IIc, and IId). In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

VI. Preparations and Examples

General Procedure I: Carboxylic Acid Building Block

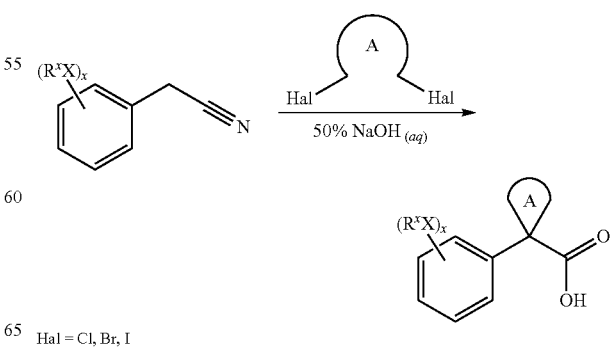

Hal = Cl, Br, I

Benzyltriethylammonium chloride (0.025 equivalents) and the appropriate dihalo compound (2.5 equivalents) were added to a substituted phenyl acetonitrile. The mixture was heated at 70° C. and then 50% sodium hydroxide (10 equivalents) was slowly added to the mixture. The reaction was stirred at 70° C. for 12-24 hours to ensure complete formation of the cycloalkyl moiety and then heated at 130° C. for 24-48 hours to ensure complete conversion from the nitrile to the carboxylic acid. The dark brown/black reaction mixture was diluted with water and extracted with dichloromethane three times to remove side products. The basic aqueous solution was acidified with concentrated hydrochloric acid to pH less than one and the precipitate which began to form at pH 4 was filtered and washed with 1 M hydrochloric acid two times. The solid material was dissolved in dichloromethane and extracted two times with 1 M hydrochloric acid and one time with a saturated aqueous solution of sodium chloride. The organic solution was dried over sodium sulfate and evaporated to dryness to give the cycloalkylcarboxylic acid. Yields and purities were typically greater than 90%.

Example 1

1-Benzo[1,3]dioxol-5-yl-cyclopropanecarboxylic acid

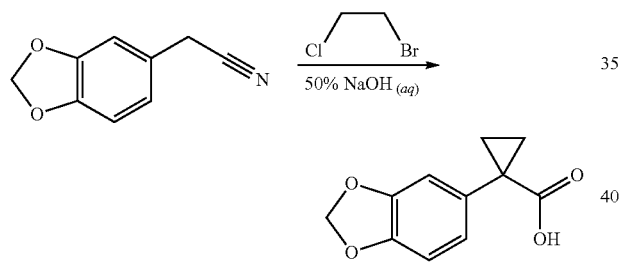

A mixture of 2-(benzo[d][1,3]dioxol-5-yl)acetonitrile (5.10 g 31.7 mmol), 1-bromo-2-chloro-ethane (9.00 mL 109 mmol), and benzyltriethylammonium chloride (0.181 g, 0.795 mmol) was heated at 70° C. and then 50% (wt./wt.) aqueous sodium hydroxide (26 mL) was slowly added to the mixture. The reaction was stirred at 70° C. for 24 hours and then heated at 130° C. for 48 hours. The dark brown reaction mixture was diluted with water (400 mL) and extracted once with an equal volume of ethyl acetate and once with an equal volume of dichloromethane. The basic aqueous solution was acidified with concentrated hydrochloric acid to pH less than one and the precipitate filtered and washed with 1 M hydrochloric acid. The solid material was dissolved in dichloromethane (400 mL) and extracted twice with equal volumes of 1 M hydrochloric acid and once with a saturated aqueous solution of sodium chloride. The organic solution was dried over sodium sulfate and evaporated to dryness to give a white to slightly off-white solid (5.23 g, 80%) ESI-MS m/z calc. 206.1. found 207.1 (M+1)$^+$. Retention time 2.37 minutes. $^1$H NMR (400 MHz, DMSO-$d_6$) δ 1.07-1.11 (m, 2H), 1.38-1.42 (m, 2H), 5.98 (s, 2H), 6.79 (m, 2H), 6.88 (m, 1H), 12.26 (s, 1H).

General Procedure II: Carboxylic Acid Building Block

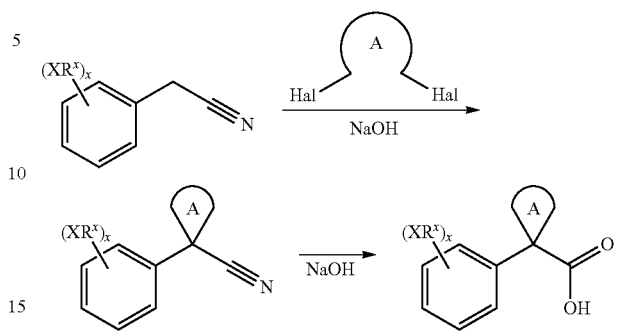

Hal = Cl, Br, I, all other variables are as defined in the text.

Sodium hydroxide (50% aqueous solution, 7.4 equivalents) was slowly added to a mixture of the appropriate phenyl acetonitrile, benzyltriethylammonium chloride (1.1 equivalents), and the appropriate dihalo compound (2.3 equivalents) at 70° C. The mixture was stirred overnight at 70° C. and the reaction mixture was diluted with water (30 mL) and extracted with ethyl acetate. The combined organic layers were dried over sodium sulfate and evaporated to dryness to give the crude cyclopropanecarbonitrile, which was used directly in the next step.

The crude cyclopropanecarbonitrile was refluxed in 10% aqueous sodium hydroxide (7.4 equivalents) for 2.5 hours. The cooled reaction mixture was washed with ether (100 mL) and the aqueous phase was acidified to pH 2 with 2M hydrochloric acid. The precipitated solid was filtered to give the cyclopropanecarboxylic acid as a white solid.

General Procedure III: Carboxylic Acid Building Block

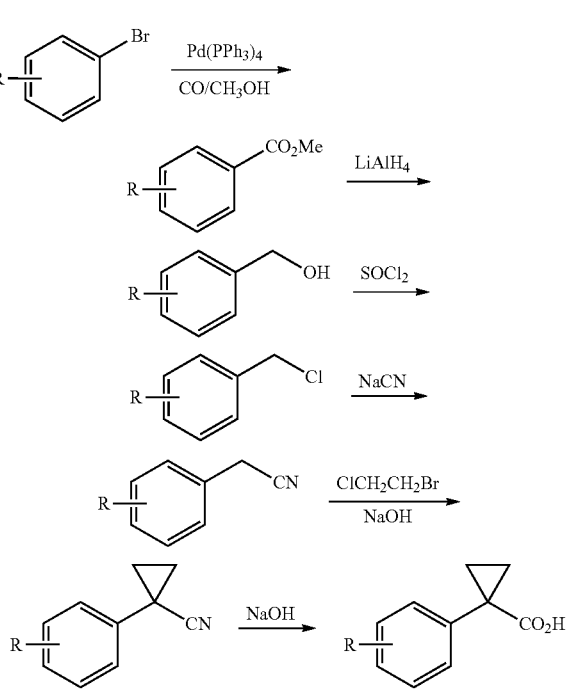

Example 2

1-(2,2-Difluoro-benzo[1,3]dioxol-5-yl)-cyclopropanecarboxylic acid

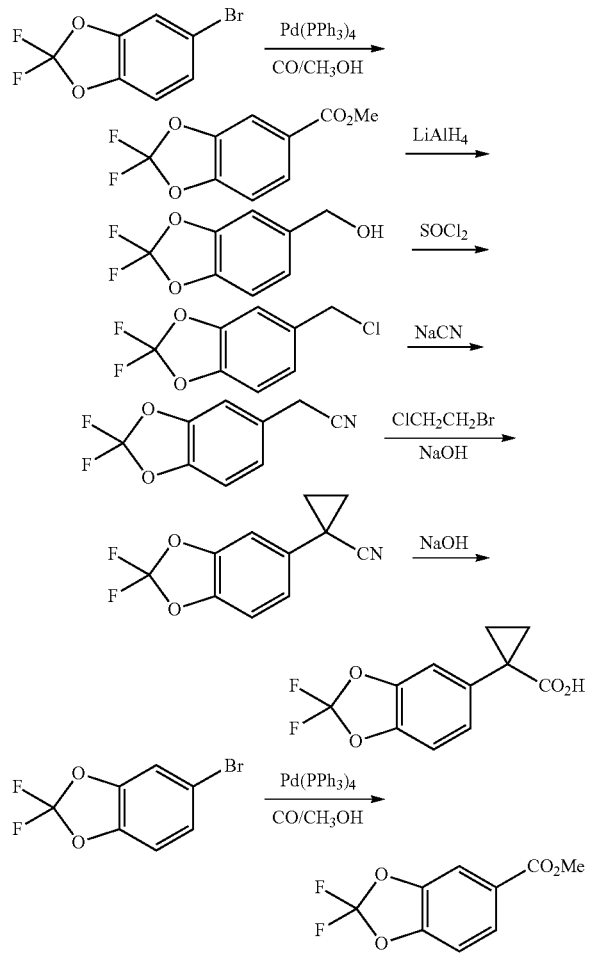

2,2-Difluoro-benzo[1,3]dioxole-5-carboxylic acid methyl ester

A solution of 5-bromo-2,2-difluoro-benzo[1,3]dioxole (11.8 g, 50.0 mmol) and tetrakis(triphenylphosphine)palladium (0) [Pd(PPh$_3$)$_4$, 5.78 g, 5.00 mmol] in methanol (20 mL) containing acetonitrile (30 mL) and triethylamine (10 mL) was stirred under a carbon monoxide atmosphere (55 PSI) at 75° C. (oil bath temperature) for 15 hours. The cooled reaction mixture was filtered and the filtrate was evaporated to dryness. The residue was purified by silica gel column chromatography to give crude 2,2-difluoro-benzo[1,3]dioxole-5-carboxylic acid methyl ester (11.5 g), which was used directly in the next step.

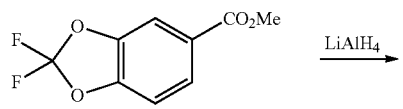

(2,2-Difluoro-benzo[1,3]dioxol-5-yl)-methanol

Crude 2,2-difluoro-benzo[1,3]dioxole-5-carboxylic acid methyl ester (11.5 g) dissolved in 20 mL of anhydrous tetrahydrofuran (THF) was slowly added to a suspension of lithium aluminum hydride (4.10 g, 106 mmol) in anhydrous THF (100 mL) at 0° C. The mixture was then warmed to room temperature. After being stirred at room temperature for 1 hour, the reaction mixture was cooled to 0° C. and treated with water (4.1 g), followed by sodium hydroxide (10% aqueous solution, 4.1 mL). The resulting slurry was filtered and washed with THF. The combined filtrate was evaporated to dryness and the residue was purified by silica gel column chromatography to give (2,2-difluoro-benzo[1,3]dioxol-5-yl)-methanol (7.2 g, 38 mmol, 76% over two steps) as a colorless oil.

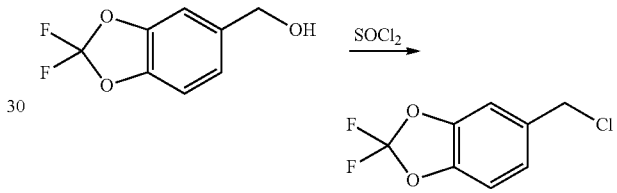

5-Chloromethyl-2,2-difluoro-benzo[1,3]dioxole

Thionyl chloride (45 g, 38 mmol) was slowly added to a solution of (2,2-difluoro-benzo[1,3]dioxol-5-yl)-methanol (7.2 g, 38 mmol) in dichloromethane (200 mL) at 0° C. The resulting mixture was stirred overnight at room temperature and then evaporated to dryness. The residue was partitioned between an aqueous solution of saturated sodium bicarbonate (100 mL) and dichloromethane (100 mL). The separated aqueous layer was extracted with dichloromethane (150 mL) and the organic layer was dried over sodium sulfate, filtrated, and evaporated to dryness to give crude 5-chloromethyl-2,2-difluoro-benzo[1,3]dioxole (4.4 g) which was used directly in the next step.

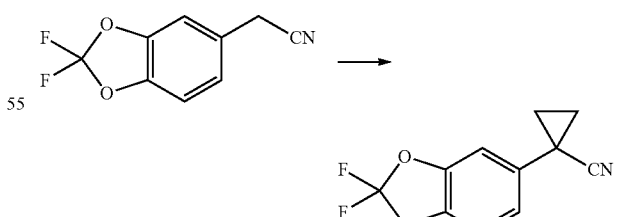

(2,2-Difluoro-benzo[1,3]dioxol-5-yl)-acetonitrile

A mixture of crude 5-chloromethyl-2,2-difluoro-benzo[1,3]dioxole (4.4 g) and sodium cyanide (1.36 g, 27.8 mmol) in dimethylsulfoxide (50 mL) was stirred at room temperature overnight. The reaction mixture was poured into ice and extracted with ethyl acetate (300 mL). The organic layer was dried over sodium sulfate and evaporated to dryness to give crude (2,2-difluoro-benzo[1,3]dioxol-5-yl)-acetonitrile (3.3 g) which was used directly in the next step.

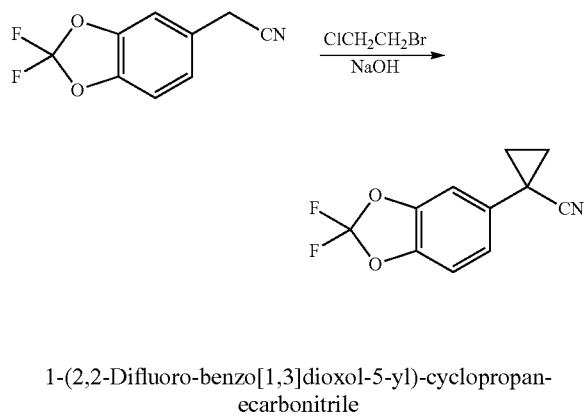

1-(2,2-Difluoro-benzo[1,3]dioxol-5-yl)-cyclopropanecarbonitrile

Sodium hydroxide (50% aqueous solution, 10 mL) was slowly added to a mixture of crude (2,2-difluoro-benzo[1,3]dioxol-5-yl)-acetonitrile, benzyltriethylammonium chloride (3.00 g, 15.3 mmol), and 1-bromo-2-chloroethane (4.9 g, 38 mmol) at 70° C.

The mixture was stirred overnight at 70° C. before the reaction mixture was diluted with water (30 mL) and extracted with ethyl acetate. The combined organic layers were dried over sodium sulfate and evaporated to dryness to give crude 1-(2,2-difluoro-benzo[1,3]dioxol-5-yl)-cyclopropanecarbonitrile, which was used directly in the next step.

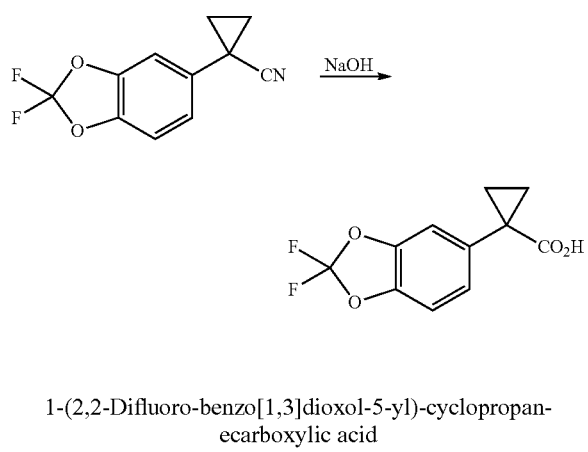

1-(2,2-Difluoro-benzo[1,3]dioxol-5-yl)-cyclopropanecarboxylic acid 1-(2,2-Difluoro-benzo[1,3]dioxol-5-yl)-cyclopropanecarbonitrile (crude from the last step) was refluxed in 10% aqueous sodium hydroxide (50 mL) for 2.5 hours. The cooled reaction mixture was washed with ether (100 mL) and the aqueous phase was acidified to pH 2 with 2M hydrochloric acid. The precipitated solid was filtered to give 1-(2,2-difluoro-benzo[1,3]dioxol-5-yl)-cyclopropanecarboxylic acid as a white solid (0.15 g, 1.6% over four steps). ESI-MS m/z calc. 242.04. found 241.58 (M+1)$^+$; $^1$H NMR (CDCl$_3$) δ 7.14-7.04 (m, 2H), 6.98-6.96 (m, 1H), 1.74-1.64 (m, 2H), 1.26-1.08 (m, 2H).

Example 3

2-(2,2-Dimethylbenzo[d][1,3]dioxol-5-yl)acetonitrile

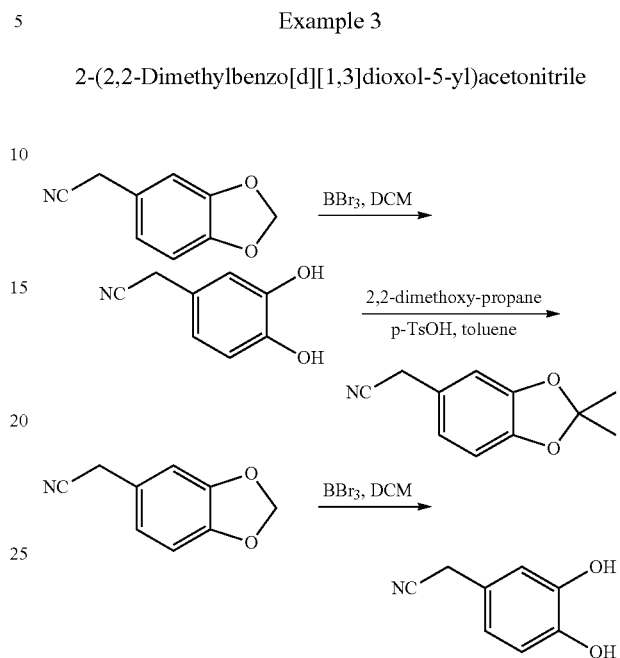

(3,4-Dihydroxy-phenyl)-acetonitrile

To a solution of benzo[1,3]dioxol-5-yl-acetonitrile (0.50 g, 3.1 mmol) in CH$_2$Cl$_2$ (15 mL) was added dropwise BBr$_3$ (0.78 g, 3.1 mmol) at −78° C. under N$_2$. The mixture was slowly warmed to room temperature and stirred overnight. H$_2$O (10 mL) was added to quench the reaction and the CH$_2$Cl$_2$ layer was separated. The aqueous phase was extracted with CH$_2$Cl$_2$ (2×7 mL). The combined organics were washed with brine, dried over Na$_2$SO$_4$ and purified by column chromatography on silica gel (petroleum ether/ethyl acetate 5:1) to give (3,4-dihydroxy-phenyl)-acetonitrile (0.25 g, 54%) as a white solid. $^1$H NMR (DMSO-d$_6$, 400 MHz) δ 9.07 (s, 1H), 8.95 (s, 1H), 6.68-6.70 (m, 2H), 6.55 (dd, J=8.0, 2.0 Hz, 1H), 3.32 (s, 2H).

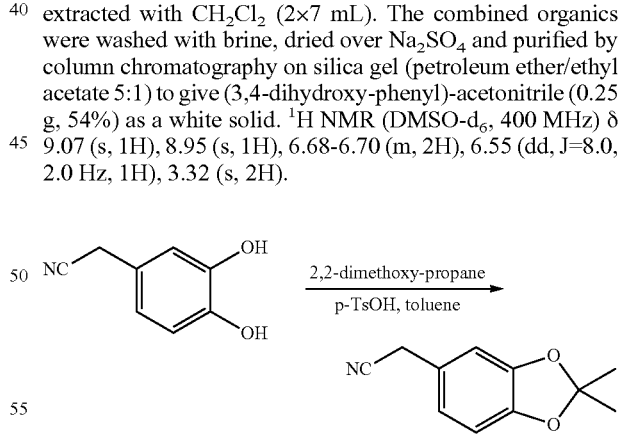

2-(2,2-Dimethylbenzo[d][1,3]dioxol-5-yl)acetonitrile

To a solution of (3,4-dihydroxy-phenyl)-acetonitrile (0.20 g, 1.3 mmol) in toluene (4 mL) was added 2,2-dimethoxypropane (0.28 g, 2.6 mmol) and TsOH (0.010 g, 0.065 mmol). The mixture was heated at reflux overnight. The reaction mixture was evaporated to remove the solvent and the residue was dissolved in ethyl acetate. The organic layer was washed with NaHCO$_3$ solution, H$_2$O, brine, and dried over Na$_2$SO$_4$.

The solvent was evaporated under reduced pressure to give a residue, which was purified by column chromatography on silica gel (petroleum ether/ethyl acetate 10:1) to give 2-(2,2-dimethylbenzo[d][1,3]dioxol-5-yl)acetonitrile (40 mg, 20%). $^1$H NMR (CDCl$_3$, 400 MHz) δ 6.68-6.71 (m, 3H), 3.64 (s, 2H), 1.67 (s, 6H).

Example 4

1-(3,4-Dihydroxy-phenyl)cyclopropanecarboxylic acid

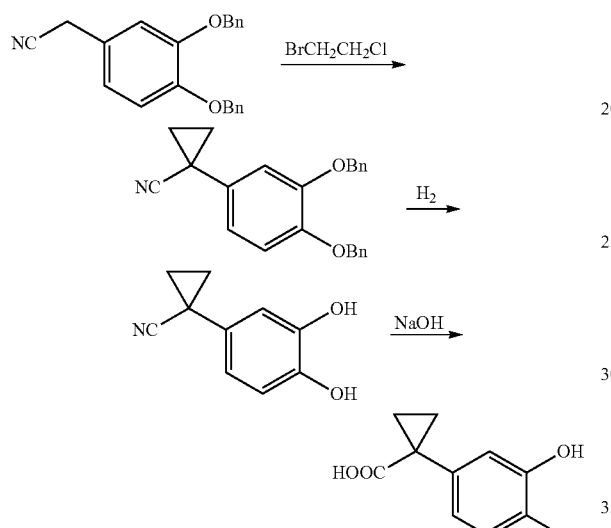

1-(3,4-Bis-benzyloxy-phenyl)-cyclopropanecarbonitrile

To a mixture of (n-C$_4$H$_9$)$_4$NBr (0.50 g, 1.5 mmol), toluene (7 mL) and (3,4-bis-benzyloxy-phenyl)-acetonitrile (14 g, 42 mmol) in NaOH (50 g) and H$_2$O (50 mL) was added BrCH$_2$CH$_2$Cl (30 g, 0.21 mol). The reaction mixture was stirred at 50° C. for 5 h before being cooled to room temperature. Toluene (30 mL) was added and the organic layer was separated and washed with H$_2$O, brine, dried over anhydrous MgSO$_4$, and concentrated. The residue was purified by column on silica gel (petroleum ether/ethyl acetate 10:1) to give 1-(3,4-bis-benzyloxy-phenyl)-cyclopropanecarbonitrile (10 g, 66%). $^1$H NMR (DMSO 300 MHz) δ 7.46-7.30 (m, 10H), 7.03 (d, J=8.4 Hz, 1H), 6.94 (d, J=2.4 Hz, 1H), 6.89 (dd, J=2.4, 8.4 Hz, 1H), 5.12 (d, J=7.5 Hz, 4H), 1.66-1.62 (m, 2H), 1.42-1.37 (m, 2H).

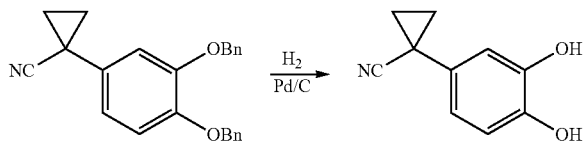 [SMILES: N#CC1(c2ccc(OCc3ccccc3)c(OCc3ccccc3)c2)CC1 ; "H2" ; "Pd/C" ; N#CC1(c2ccc(O)c(O)c2)CC1]

1-(3,4-Dihydroxy-phenyl)-cyclopropanecarbonitrile

To a solution of 1-(3,4-bis-benzyloxy-phenyl)-cyclopropanecarbonitrile (10 g, 28 mmol) in MeOH (50 mL) was added Pd/C (0.5 g) under nitrogen atmosphere. The mixture was stirred under hydrogen atmosphere (1 atm) at room temperature for 4 h. The catalyst was filtered off through a celite pad and the filtrate was evaporated under vacuum to give 1-(3,4-dihydroxy-phenyl)-cyclopropanecarbonitrile (4.5 g, 92%). $^1$H NMR (DMSO 400 MHz) δ 9.06 (br s, 2H), 6.67-6.71 (m, 2H), 6.54 (dd, J=2.4, 8.4 Hz, 1H), 1.60-1.57 (m, 2H), 1.30-1.27 (m, 2H).

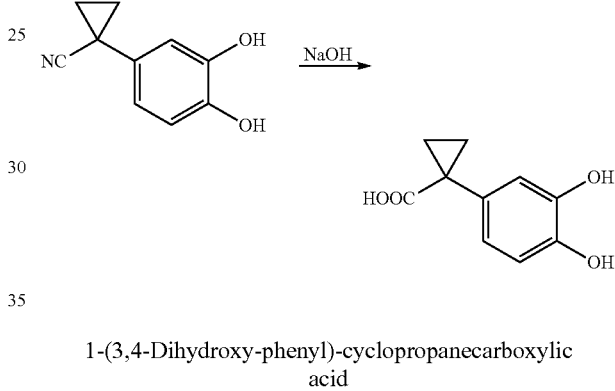

1-(3,4-Dihydroxy-phenyl)-cyclopropanecarboxylic acid

To a solution of NaOH (20 g, 0.50 mol) in H$_2$O (20 mL) was added 1-(3,4-dihydroxy-phenyl)-cyclopropanecarbonitrile (4.4 g, 25 mmol). The mixture was heated at reflux for 3 h before being cooled to room temperature. The mixture was neutralized with HCl (0.5 N) to pH 3-4 and extracted with ethyl acetate (20 mL×3). The combined organic layers were washed with water, brine, dried over anhydrous MgSO$_4$, and concentrated under vacuum to obtain 1-(3,4-dihydroxy-phenyl)-cyclopropanecarboxylic acid (4.5 g crude). From 900 mg crude, 500 mg pure 1-(3,4-dihydroxy-phenyl)-cyclopropanecarboxylic acid was obtained by preparatory HPLC. $^1$H NMR (DMSO, 300 MHz) δ 12.09 (br s, 1H), 8.75 (br s, 2H), 6.50-6.67 (m, 3H), 1.35-1.31 (m, 2H), 1.01-0.97 (m, 2H).

Example 5

1-(2-Oxo-2,3-dihydrobenzo[d]oxazol-5-yl)cyclopropane-carboxylic acid

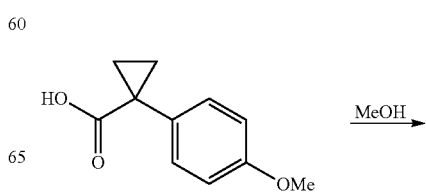

219

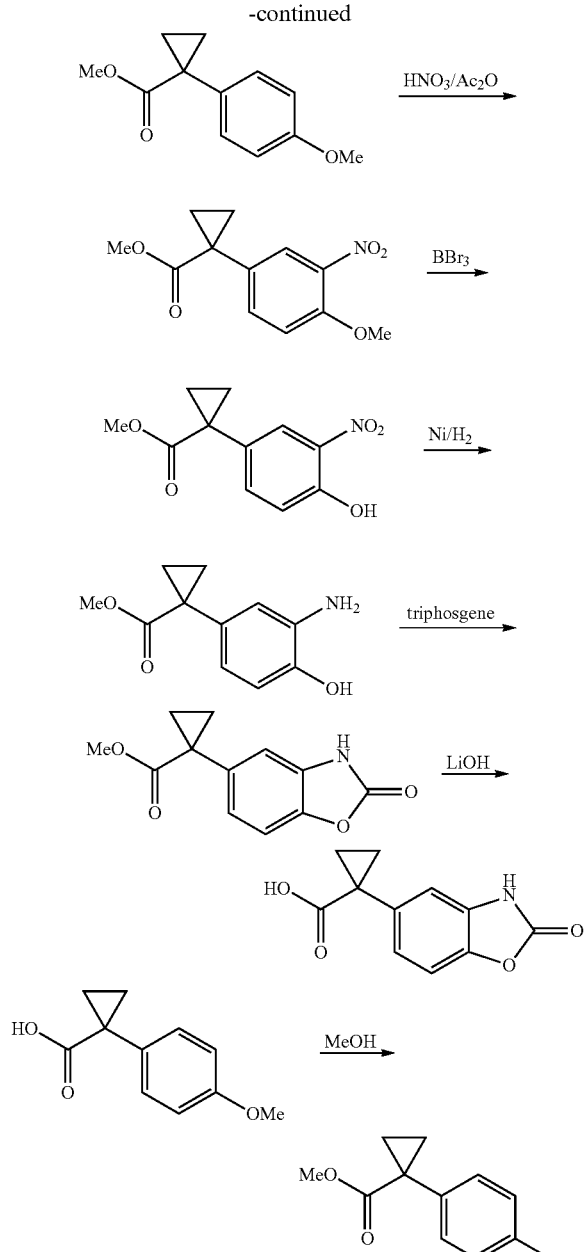

1-(4-Methoxy-phenyl)-cyclopropanecarboxylic acid methyl ester

To a solution of 1-(4-methoxy-phenyl)-cyclopropanecarboxylic acid (50 g, 0.26 mol) in MeOH (500 mL) was added toluene-4-sulfonic acid monohydrate (2.5 g, 13 mmol) at room temperature. The reaction mixture was heated at reflux for 20 hours. MeOH was removed by evaporation under vacuum and EtOAc (200 mL) was added. The organic layer was washed with sat. aq. NaHCO$_3$ (100 mL) and brine, dried over anhydrous Na$_2$SO$_4$ and evaporated under vacuum to give 1-(4-methoxy-phenyl)-cyclopropanecarboxylic acid methyl ester (53 g, 99%). $^1$H NMR (CDCl$_3$, 400 MHz) δ 7.25-7.27 (m, 2H), 6.85 (d, J=8.8 Hz, 2H), 3.80 (s, 3H), 3.62 (s, 3H), 1.58 (q, J=3.6 Hz, 2H), 1.15 (q, J=3.6 Hz, 2H).

220

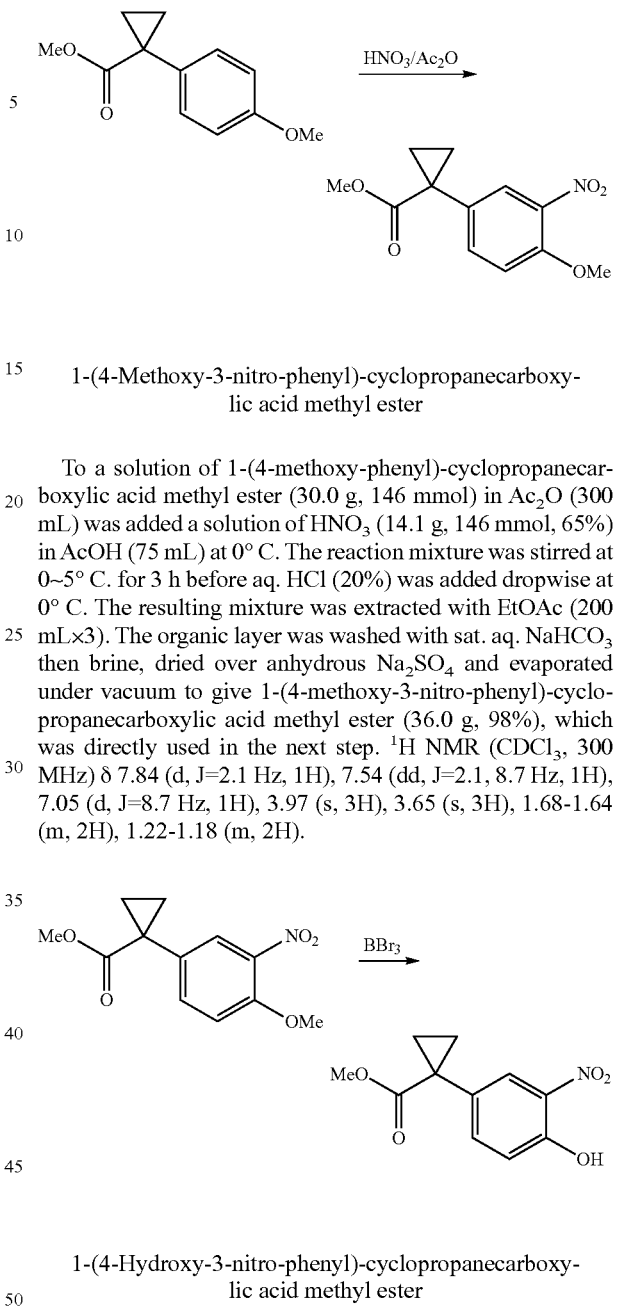

1-(4-Methoxy-3-nitro-phenyl)-cyclopropanecarboxylic acid methyl ester

To a solution of 1-(4-methoxy-phenyl)-cyclopropanecarboxylic acid methyl ester (30.0 g, 146 mmol) in Ac$_2$O (300 mL) was added a solution of HNO$_3$ (14.1 g, 146 mmol, 65%) in AcOH (75 mL) at 0° C. The reaction mixture was stirred at 0~5° C. for 3 h before aq. HCl (20%) was added dropwise at 0° C. The resulting mixture was extracted with EtOAc (200 mL×3). The organic layer was washed with sat. aq. NaHCO$_3$ then brine, dried over anhydrous Na$_2$SO$_4$ and evaporated under vacuum to give 1-(4-methoxy-3-nitro-phenyl)-cyclopropanecarboxylic acid methyl ester (36.0 g, 98%), which was directly used in the next step. $^1$H NMR (CDCl$_3$, 300 MHz) δ 7.84 (d, J=2.1 Hz, 1H), 7.54 (dd, J=2.1, 8.7 Hz, 1H), 7.05 (d, J=8.7 Hz, 1H), 3.97 (s, 3H), 3.65 (s, 3H), 1.68-1.64 (m, 2H), 1.22-1.18 (m, 2H).

1-(4-Hydroxy-3-nitro-phenyl)-cyclopropanecarboxylic acid methyl ester

To a solution of 1-(4-methoxy-3-nitro-phenyl)-cyclopropane-carboxylic acid methyl ester (10.0 g, 39.8 mmol) in CH$_2$Cl$_2$ (100 mL) was added BBr$_3$ (12.0 g, 47.8 mmol) at −70° C. The mixture was stirred at −70° C. for 1 hour, then allowed to warm to −30° C. and stirred at this temperature for 3 hours. Water (50 mL) was added dropwise at −20° C., and the resulting mixture was allowed to warm room temperature before it was extracted with EtOAc (200 mL×3). The combined organic layers were dried over anhydrous Na$_2$SO$_4$ and evaporated under vacuum to give the crude product, which was purified by column chromatography on silica gel (petroleum ether/ethyl acetate 15:1) to afford 1-(4-hydroxy-3-nitro-phenyl)-cyclopropanecarboxylic acid methyl ester (8.3 g, 78%). $^1$H NMR (CDCl$_3$, 400 MHz) δ 10.5 (s, 1H), 8.05 (d, J=2.4 Hz, 1H), 7.59 (dd, J=2.0, 8.8 Hz, 1H), 7.11 (d, J=8.4 Hz, 1H), 3.64 (s, 3H), 1.68-1.64 (m, 2H), 1.20-1.15 (m, 2H).

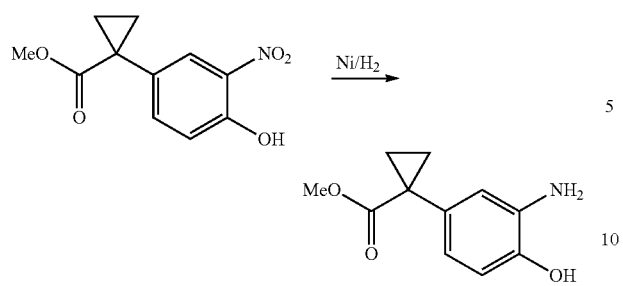

1-(3-Amino-4-hydroxy-phenyl)-cyclopropanecarboxylic acid methyl ester

To a solution of 1-(4-hydroxy-3-nitro-phenyl)-cyclopropanecarboxylic acid methyl ester (8.3 g, 35 mmol) in MeOH (100 mL) was added Raney Nickel (0.8 g) under nitrogen atmosphere. The mixture was stirred under hydrogen atmosphere (1 atm) at 35° C. for 8 hours. The catalyst was filtered off through a Celite pad and the filtrate was evaporated under vacuum to give crude product, which was purified by column chromatography on silica gel (petroleum ether/ethyl acetate 1:1) to give 1-(3-amino-4-hydroxy-phenyl)-cyclopropanecarboxylic acid methyl ester (5.3 g, 74%). $^1$H NMR (CDCl$_3$, 400 MHz) δ 6.77 (s, 1H), 6.64 (d, J=2.0 Hz, 2H), 3.64 (s, 3H), 1.55-1.52 (m, 2H), 1.15-1.12 (m, 2H).

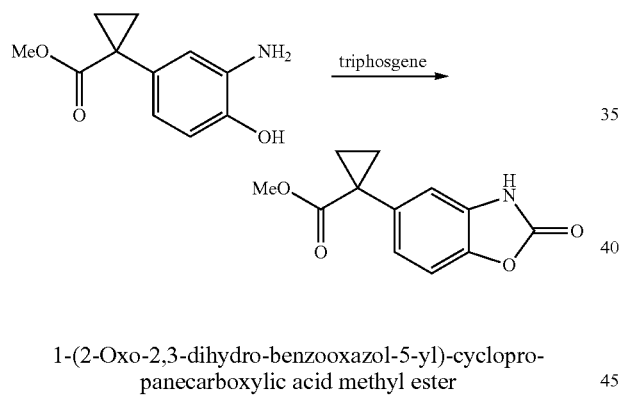

1-(2-Oxo-2,3-dihydro-benzooxazol-5-yl)-cyclopropanecarboxylic acid methyl ester To a solution of 1-(3-amino-4-hydroxy-phenyl)-cyclopropanecarboxylic acid methyl ester (2.0 g, 9.6 mmol) in THF (40 mL) was added triphosgene (4.2 g, 14 mmol) at room temperature. The mixture was stirred for 20 minutes at this temperature before water (20 mL) was added dropwise at 0° C. The resulting mixture was extracted with EtOAc (100 mL×3). The combined organic layers were dried over anhydrous Na$_2$SO$_4$ and evaporated under vacuum to give 1-(2-oxo-2,3-dihydro-benzooxazol-5-yl)-cyclopropanecarboxylic acid methyl ester (2.0 g, 91%), which was directly used in the next step. $^1$H NMR (CDCl$_3$, 300 MHz) δ 8.66 (s, 1H), 7.13-7.12 (m, 2H), 7.07 (s, 1H), 3.66 (s, 3H), 1.68-1.65 (m, 2H), 1.24-1.20 (m, 2H).

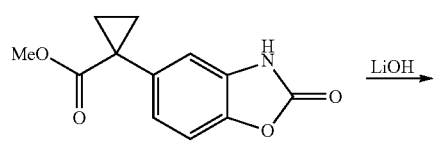

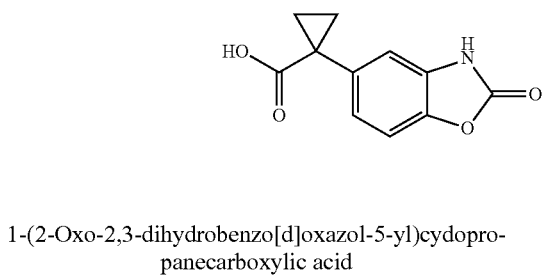

1-(2-Oxo-2,3-dihydrobenzo[d]oxazol-5-yl)cyclopropanecarboxylic acid

To a solution of 1-(2-oxo-2,3-dihydro-benzooxazol-5-yl)-cyclopropanecarboxylic acid methyl ester (1.9 g, 8.1 mmol) in MeOH (20 mL) and water (2 mL) was added LiOH.H$_2$O (1.7 g, 41 mmol) in portions at room temperature. The reaction mixture was stirred for 20 hours at 50° C. MeOH was removed by evaporation under vacuum before water (100 mL) and EtOAc (50 mL) were added. The aqueous layer was separated, acidified with HCl (3 mol/L) and extracted with EtOAc (100 mL×3). The combined organic layers were dried over anhydrous Na$_2$SO$_4$ and evaporated under vacuum to give 1-(2-oxo-2,3-dihydrobenzo[d]oxazol-5-yl)cyclopropanecarboxylic acid (1.5 g, 84%). $^1$H NMR (DMSO, 400 MHz) δ 12.32 (brs, 1H), 11.59 (brs, 1H), 7.16 (d, J=8.4 Hz, 1H), 7.00 (d, J=8.0 Hz, 1H), 1.44-1.41 (m, 2H), 1.13-1.10 (m, 2H). MS (ESI) m/e (M+H$^+$) 218.1.

Example 6

1-(6-Fluoro-benzo[1,3]dioxol-5-yl)-cyclopropanecarboxylic acid

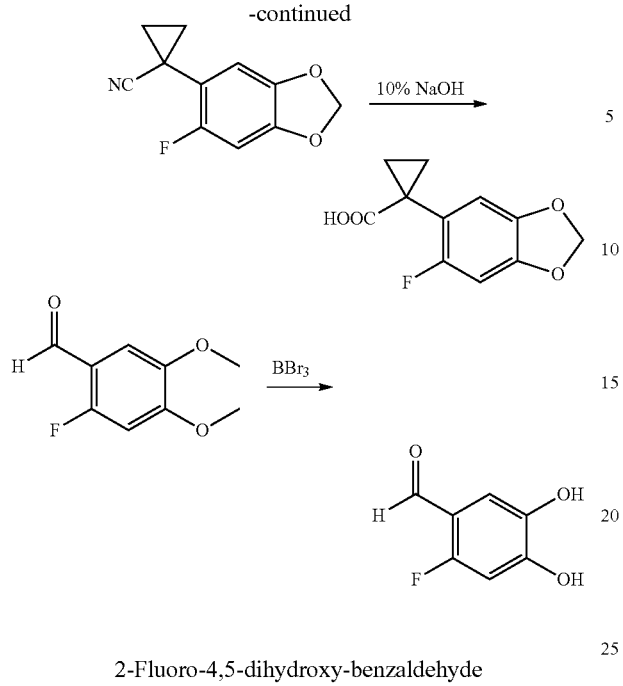

2-Fluoro-4,5-dihydroxy-benzaldehyde

To a stirred suspension of 2-fluoro-4,5-dimethoxy-benzaldehyde (3.00 g, 16.3 mmol) in dichloromethane (100 mL) was added BBr$_3$ (12.2 mL, 130 mmol) dropwise at −78° C. under nitrogen atmosphere. After addition, the mixture was warmed to −30° C. and stirred at this temperature for 5 h. The reaction mixture was poured into ice water and the precipitated solid was collected by filtration and washed with dichloromethane to afford 2-fluoro-4,5-dihydroxy-benzaldehyde (8.0 g), which was used directly in the next step.

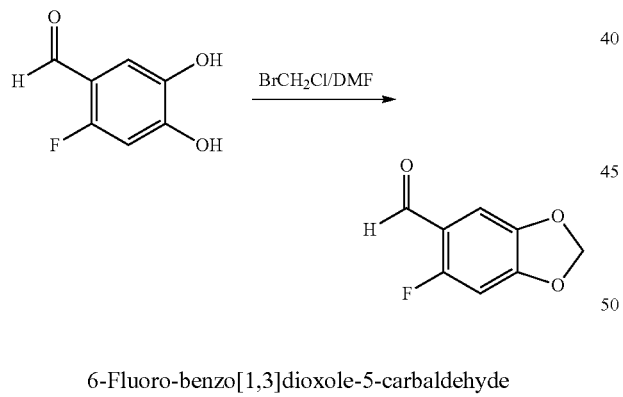

6-Fluoro-benzo[1,3]dioxole-5-carbaldehyde

To a stirred solution of 2-fluoro-4,5-dihydroxy-benzaldehyde (8.0 g) and BrClCH$_2$ (24.8 g, 190 mmol) in dry DMF (50 mL) was added Cs$_2$CO$_3$ (62.0 g, 190 mmol) in portions. The resulting mixture was stirred at 60° C. overnight and then poured into water. The mixture was extracted with EtOAc (200 mL×3). The combined organic layers were washed with brine (200 mL), dried over Na$_2$SO$_4$, and evaporated in vacuo to give crude product, which was purified by column chromatography on silica gel (5-20% ethyl acetate/petroleum ether) to afford 6-fluoro-benzo[1,3]dioxole-5-carbaldehyde (700 mg, two steps yield: 24%). $^1$H-NMR (400 MHz, CDCl$_3$) δ 10.19 (s, 1H), 7.23 (d, J=5.6, 1H), 6.63 (d, J=9.6, 1H), 6.08 (s, 2H).

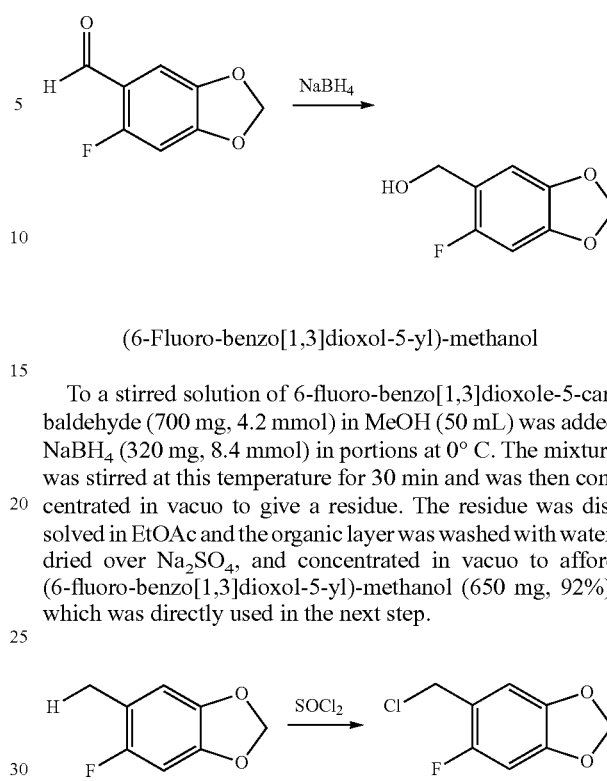

(6-Fluoro-benzo[1,3]dioxol-5-yl)-methanol

To a stirred solution of 6-fluoro-benzo[1,3]dioxole-5-carbaldehyde (700 mg, 4.2 mmol) in MeOH (50 mL) was added NaBH$_4$ (320 mg, 8.4 mmol) in portions at 0° C. The mixture was stirred at this temperature for 30 min and was then concentrated in vacuo to give a residue. The residue was dissolved in EtOAc and the organic layer was washed with water, dried over Na$_2$SO$_4$, and concentrated in vacuo to afford (6-fluoro-benzo[1,3]dioxol-5-yl)-methanol (650 mg, 92%), which was directly used in the next step.

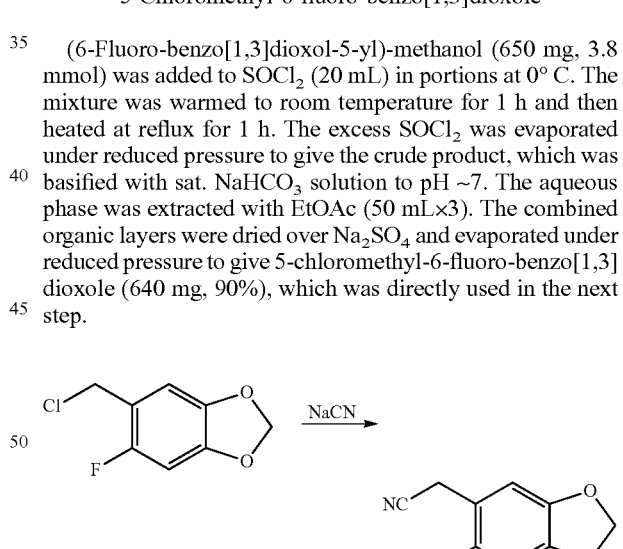

5-Chloromethyl-6-fluoro-benzo[1,3]dioxole (6-Fluoro-benzo[1,3]dioxol-5-yl)-methanol (650 mg, 3.8 mmol) was added to SOCl$_2$ (20 mL) in portions at 0° C. The mixture was warmed to room temperature for 1 h and then heated at reflux for 1 h. The excess SOCl$_2$ was evaporated under reduced pressure to give the crude product, which was basified with sat. NaHCO$_3$ solution to pH ~7. The aqueous phase was extracted with EtOAc (50 mL×3). The combined organic layers were dried over Na$_2$SO$_4$ and evaporated under reduced pressure to give 5-chloromethyl-6-fluoro-benzo[1,3]dioxole (640 mg, 90%), which was directly used in the next step.

(6-Fluoro-benzo[1,3]dioxol-5-yl)-acetonitrile

A mixture of 5-chloromethyl-6-fluoro-benzo[1,3]dioxole (640 mg, 3.4 mmol) and NaCN (340 mg, 6.8 mmol) in DMSO (20 mL) was stirred at 30° C. for 1 h and then poured into water. The mixture was extracted with EtOAc (50 mL×3). The combined organic layers were washed with water (50 mL) and brine (50 mL), dried over Na$_2$SO$_4$, and evaporated under reduced pressure to give the crude product, which was purified by column chromatography on silica gel (5-10% ethyl acetate/petroleum ether) to afford (6-fluoro-benzo[1,3]dioxol-5-yl)-acetonitrile (530 mg, 70%). ¹H-NMR (300 MHz, CDCl₃) δ 6.82 (d, J=4.8, 1H), 6.62 (d, J=5.4, 1H), 5.99 (s, 2H), 3.65 (s, 2H).

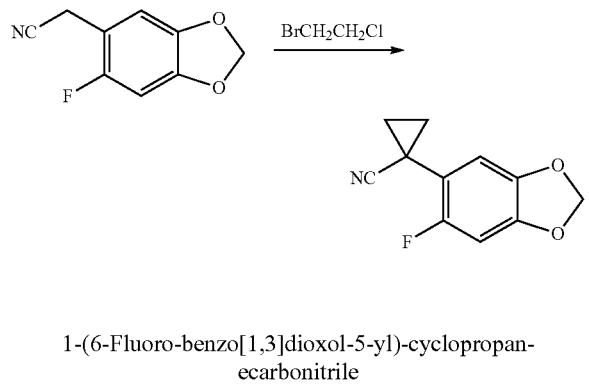

1-(6-Fluoro-benzo[1,3]dioxol-5-yl)-cyclopropanecarbonitrile

A flask was charged with water (10 mL), followed by a rapid addition of NaOH (10 g, 0.25 mol) in three portions over a 5 min period. The mixture was allowed to cool to room temperature. Subsequently, the flask was charged with toluene (6 mL), tetrabutyl-ammonium bromide (50 mg, 0.12 mmol), (6-fluoro-benzo[1,3]dioxol-5-yl)-acetonitrile (600 mg, 3.4 mmol) and 1-bromo-2-chloroethane (1.7 g, 12 mmol). The mixture stirred vigorously at 50° C. overnight. The cooled flask was charged with additional toluene (20 mL). The organic layer was separated and washed with water (30 mL) and brine (30 mL). The organic layer was removed in vacuo to give the crude product, which was purified by column chromatography on silica gel (5-10% ethyl acetate/petroleum ether) to give 1-(6-fluoro-benzo[1,3]dioxol-5-yl)-cyclopropanecarbonitrile (400 mg, 60%). ¹H NMR (300 MHz, CDCl₃) δ 6.73 (d, J=3.0 Hz, 1H), 6.61 (d, J=9.3 Hz, 1H), 5.98 (s, 2H), 1.67-1.62 (m, 2H), 1.31-1.27 (m, 2H).

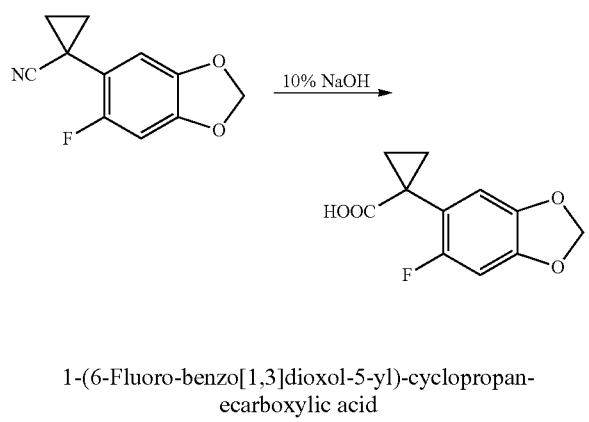

1-(6-Fluoro-benzo[1,3]dioxol-5-yl)-cyclopropanecarboxylic acid

A mixture of 1-(6-fluoro-benzo[1,3]dioxol-5-yl)-cyclopropanecarbonitrile (400 mg, 0.196 mmol) and 10% NaOH (10 mL) was stirred at 100° C. overnight. After the reaction was cooled, 5% HCl was added until the pH<5 and then EtOAc (30 mL) was added to the reaction mixture. The layers were separated and combined organic layers were evaporated in vacuo to afford 1-(6-fluoro-benzo[1,3]dioxol-5-yl)-cyclopropanecarboxylic acid (330 mg, 76%). ¹H NMR (400 MHz, DMSO) δ 12.2 (s, 1H), 6.87-6.85 (m, 2H), 6.00 (s, 1H), 1.42-1.40 (m, 2H), 1.14-1.07 (m, 2H).

Example 7

1-(Benzofuran-5-yl)cyclopropanecarboxylic acid

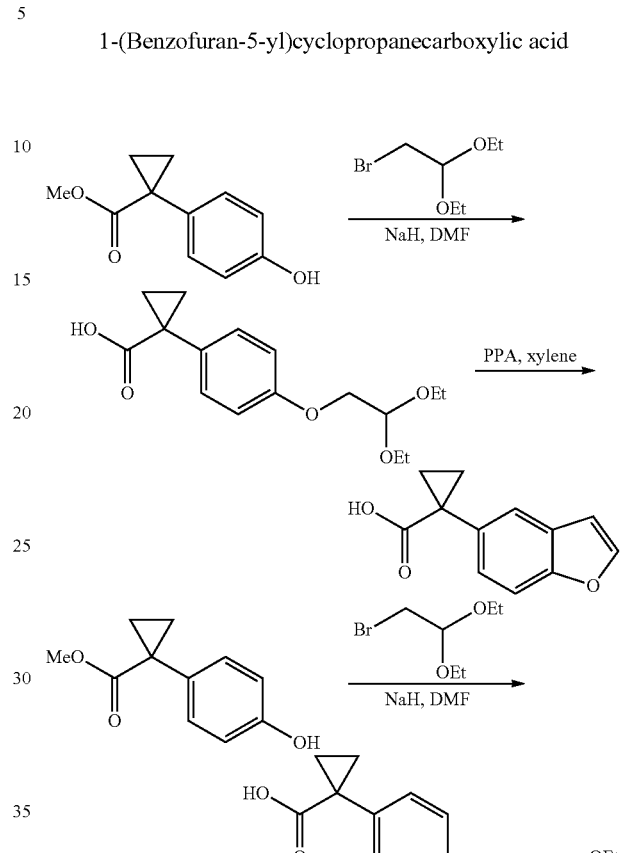

1-[4-(2,2-Diethoxy-ethoxy)-phenyl]-cyclopropanecarboxylic acid

To a stirred solution of 1-(4-hydroxy-phenyl)-cyclopropanecarboxylic acid methyl ester (15.0 g, 84.3 mmol) in DMF (50 mL) was added sodium hydride (6.7 g, 170 mmol, 60% in mineral oil) at 0° C. After hydrogen evolution ceased, 2-bromo-1,1-diethoxy-ethane (16.5 g, 84.3 mmol) was added dropwise to the reaction mixture. The reaction was stirred at 160° C. for 15 hours. The reaction mixture was poured onto ice (100 g) and was extracted with CH₂Cl₂. The combined organics were dried over Na₂SO₄. The solvent was evaporated under vacuum to give 1-[4-(2,2-diethoxy-ethoxy)-phenyl]-cyclopropanecarboxylic acid (10 g), which was used directly in the next step without purification.

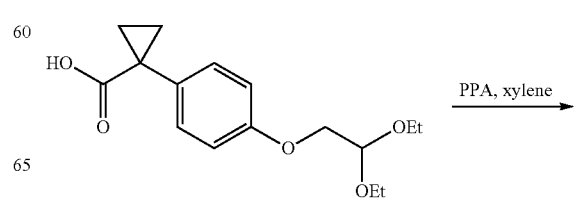

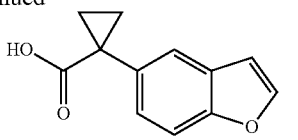

1-Benzofuran-5-yl-cyclopropanecarboxylic acid

To a suspension of 1-[4-(2,2-diethoxy-ethoxy)phenyl]-cyclopropanecarboxylic acid (20 g, ~65 mmol) in xylene (100 mL) was added PPA (22.2 g, 64.9 mmol) at room temperature. The mixture was heated at reflux (140° C.) for 1 hour before it was cooled to room temperature and decanted from the PPA. The solvent was evaporated under vacuum to obtain the crude product, which was purified by preparative HPLC to provide 1-(benzofuran-5-yl)cyclopropanecarboxylic acid (1.5 g, 5%). $^1$H NMR (400 MHz, DMSO-$d_6$) δ 12.25 (br s, 1H), 7.95 (d, J=2.8 Hz, 1H), 7.56 (d, J=2.0 Hz, 1H), 7.47 (d, J=11.6 Hz, 1H), 7.25 (dd, J=2.4, 11.2 Hz, 1H), 6.89 (d, J=1.6 Hz, 1H), 1.47-1.44 (m, 2H), 1.17-1.14 (m, 2H).

Example 8

1-(2,3-Dihydrobenzofuran-6-yl)cyclopropanecarboxylic acid

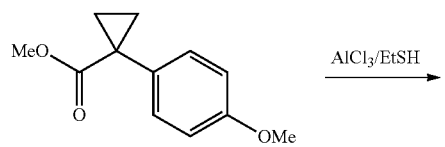

To a solution of 1-(benzofuran-6-yl)cyclopropanecarboxylic acid (370 mg, 1.8 mmol) in MeOH (50 mL) was added PtO$_2$ (75 mg, 20%) at room temperature. The reaction mixture was stirred under hydrogen atmosphere (1 atm) at 20° C. for 3 d. The reaction mixture was filtered and the solvent was evaporated in vacuo to afford the crude product, which was purified by prepared HPLC to give 1-(2,3-dihydrobenzofuran-6-yl)cyclopropanecarboxylic acid (155 mg, 42%). $^1$H NMR (300 MHz, MeOD) δ 7.13 (d, J=7.5 Hz, 1H), 6.83 (d, J=7.8 Hz, 1H), 6.74 (s, 1H), 4.55 (t, J=8.7 Hz, 2H), 3.18 (t, J=8.7 Hz, 2H), 1.56-1.53 (m, 2H), 1.19-1.15 (m, 2H).

Example 9

1-(3,3-Dimethyl-2,3-dihydrobenzofuran-5-yl)cyclopropanecarboxylic acid

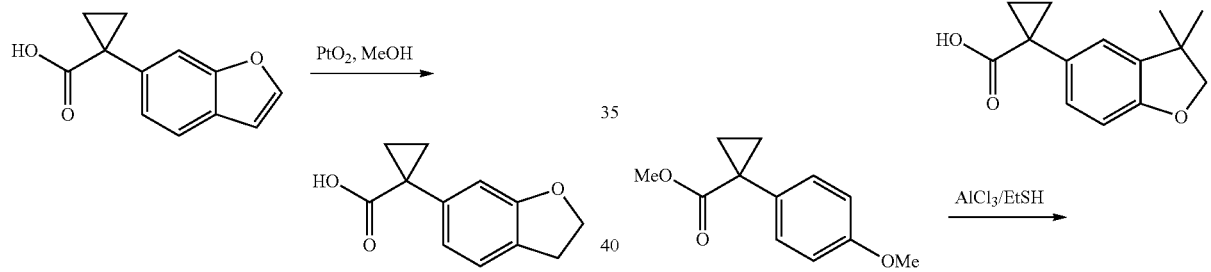

1-(4-Hydroxy-phenyl)-cyclopropanecarboxylic acid methyl ester

To a solution of methyl 1-(4-methoxyphenyl)cyclopropanecarboxylate (10.0 g, 48.5 mmol) in dichloromethane (80 mL) was added EtSH (16 mL) under ice-water bath. The mixture was stirred at 0° C. for 20 min before AlCl$_3$ (19.5 g, 0.15 mmol) was added slowly at 0° C. The mixture was stirred at 0° C. for 30 min. The reaction mixture was poured into ice-water, the organic layer was separated, and the aqueous phase was extracted with dichloromethane (50 mL×3). The combined organic layers were washed with H$_2$O, brine, dried over Na$_2$SO$_4$ and evaporated under vacuum to give 1-(4-hydroxy-phenyl)-cyclopropanecarboxylic acid methyl ester (8.9 g, 95%). $^1$H NMR (400 MHz, CDCl$_3$) δ 7.20-7.17 (m, 2H), 6.75-6.72 (m, 2H), 5.56 (s, 1H), 3.63 (s, 3H), 1.60-1.57 (m, 2H), 1.17-1.15 (m, 2H).

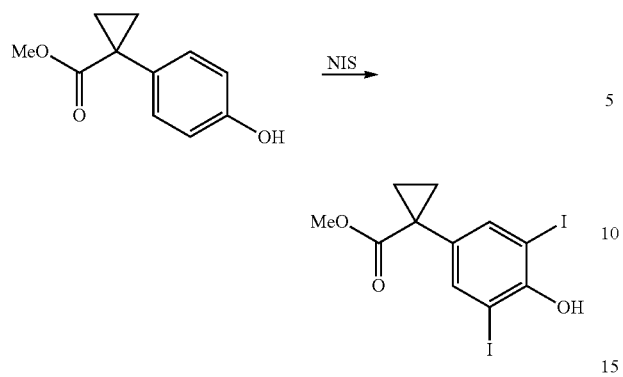

1-(4-Hydroxy-3,5-diiodo-phenyl)-cyclopropanecarboxylic acid methyl ester

To a solution of 1-(4-hydroxy-phenyl)-cyclopropanecarboxylic acid methyl ester (8.9 g, 46 mmol) in CH$_3$CN (80 mL) was added NIS (15.6 g, 69 mmol). The mixture was stirred at room temperature for 1 hour. The reaction mixture was concentrated and the residue was purified by column chromatography on silica gel (petroleum ether/ethyl acetate 10:1) to give 1-(4-hydroxy-3,5-diiodo-phenyl)-cyclopropanecarboxylic acid methyl ester (3.5 g, 18%). $^1$H NMR (400 MHz, CDCl$_3$) δ 7.65 (s, 2H), 5.71 (s, 1H), 3.63 (s, 3H), 1.59-1.56 (m, 2H), 1.15-1.12 (m, 2H).

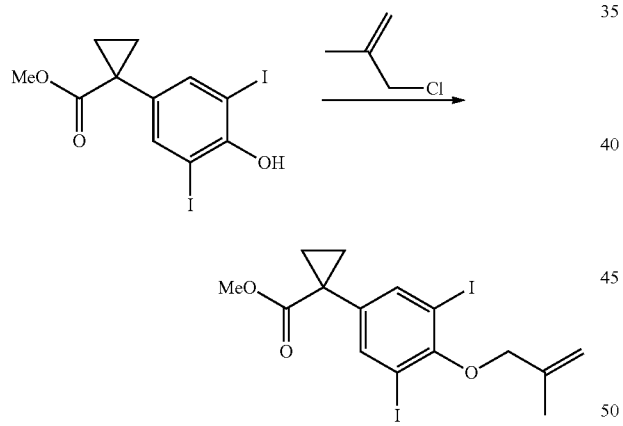

1-[3,5-Diiodo-4-(2-methyl-allyloxy)-phenyl]-cyclopropanecarboxylic acid methyl ester A mixture of 1-(4-hydroxy-3,5-diiodo-phenyl)-cyclopropanecarboxylic acid methyl ester (3.2 g, 7.2 mmol), 3-chloro-2-methyl-propene (1.0 g, 11 mmol), K$_2$CO$_3$ (1.2 g, 8.6 mmol), NaI (0.1 g, 0.7 mmol) in acetone (20 mL) was stirred at 20° C. overnight. The solid was filtered off and the filtrate was concentrated under vacuum to give 1-[3,5-diiodo-4-(2-methyl-allyloxy)-phenyl]-cyclopropane-carboxylic acid methyl ester (3.5 g, 97%). $^1$H NMR (300 MHz, CDCl$_3$) δ 7.75 (s, 2H), 5.26 (s, 1H), 5.06 (s, 1H), 4.38 (s, 2H), 3.65 (s, 3H), 1.98 (s, 3H), 1.62-1.58 (m, 2H), 1.18-1.15 (m, 2H).

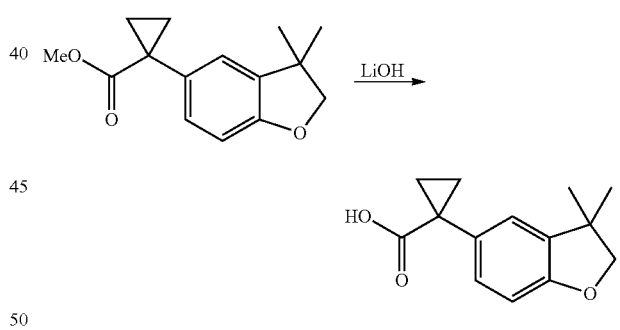

1-(3,3-Dimethyl-2,3-dihydro-benzofuran-5-yl)-cyclopropanecarboxylic acid methyl ester To a solution of 1-[3,5-diiodo-4-(2-methyl-allyloxy)-phenyl]-cyclopropane-carboxylic acid methyl ester (3.5 g, 7.0 mmol) in toluene (15 mL) was added Bu$_3$SnH (2.4 g, 8.4 mmol) and AIBN (0.1 g, 0.7 mmol). The mixture was heated at reflux overnight. The reaction mixture was concentrated under vacuum and the residue was purified by column chromatography on silica gel (petroleum ether/ethyl acetate 20:1) to give 1-(3,3-dimethyl-2,3-dihydro-benzofuran-5-yl)-cyclopropanecarboxylic acid methyl ester (1.05 g, 62%). $^1$H NMR (400 MHz, CDCl$_3$) δ 7.10-7.07 (m, 2H), 6.71 (d, J=8 Hz, 1H), 4.23 (s, 2H), 3.62 (s, 3H), 1.58-1.54 (m, 2H), 1.34 (s, 6H), 1.17-1.12 (m, 2H).

1-(3,3-Dimethyl-2,3-dihydrobenzofuran-5-yl)cyclopropanecarboxylic acid

To a solution of 1-(3,3-dimethyl-2,3-dihydro-benzofuran-5-yl)-cyclopropanecarboxylic acid methyl ester (1.0 g, 4.0 mmol) in MeOH (10 mL) was added LiOH (0.40 g, 9.5 mmol). The mixture was stirred at 40° C. overnight. HCl (10%) was added slowly to adjust the pH to 5. The resulting mixture was extracted with ethyl acetate (10 mL×3). The extracts were washed with brine and dried over Na$_2$SO$_4$. The solvent was removed under vacuum and the crude product was purified by preparative HPLC to give 1-(3,3-dimethyl-2,3-dihydrobenzofuran-5-yl)cyclopropanecarboxylic acid (0.37 g, 41%). $^1$H NMR (400 MHz, CDCl$_3$) δ 7.11-7.07 (m, 2H), 6.71 (d, J=8 Hz, 1H), 4.23 (s, 2H), 1.66-1.63 (m, 2H), 1.32 (s, 6H), 1.26-1.23 (m, 2H).

Example 10

2-(7-Methoxybenzo[d][1,3]dioxol-5-yl)acetonitrile

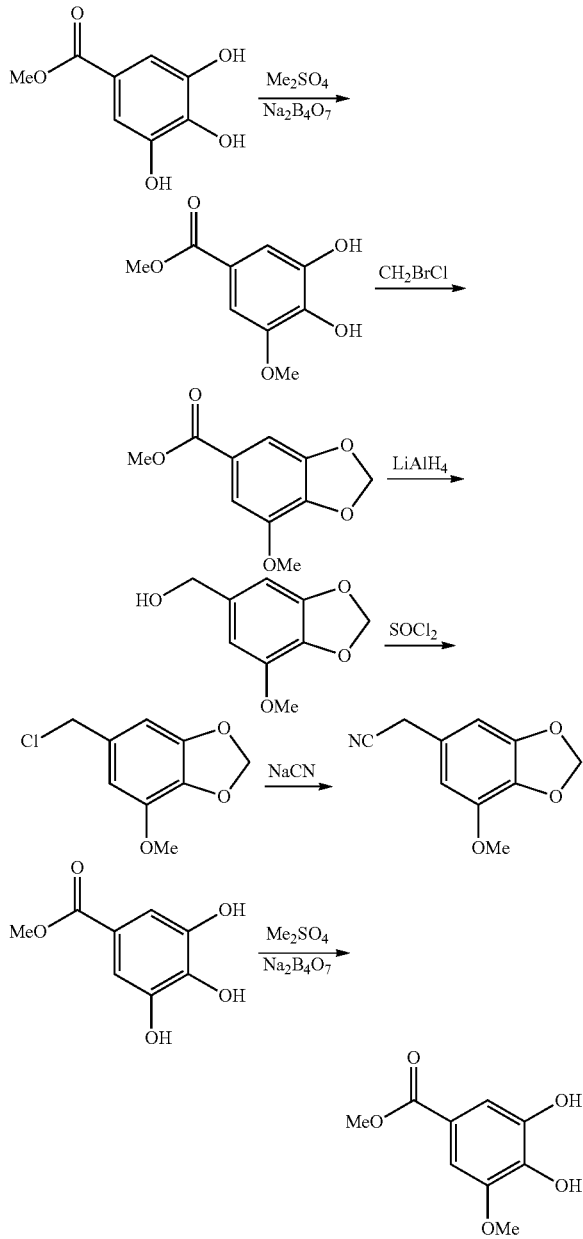

3,4-Dihydroxy-5-methoxybenzoate

To a solution of 3,4,5-trihydroxy-benzoic acid methyl ester (50 g, 0.27 mol) and Na$_2$B$_4$O$_7$ (50 g) in water (1000 mL) was added Me$_2$SO$_4$ (120 mL) and aqueous NaOH solution (25%, 200 mL) successively at room temperature. The mixture was stirred at room temperature for 6 h before it was cooled to 0° C. The mixture was acidified to pH ~2 by adding conc. H$_2$SO$_4$ and then filtered. The filtrate was extracted with EtOAc (500 mL×3). The combined organic layers were dried over anhydrous Na$_2$SO$_4$ and evaporated under reduced pressure to give methyl 3,4-dihydroxy-5-methoxybenzoate (15.3 g 47%), which was used in the next step without further purification.

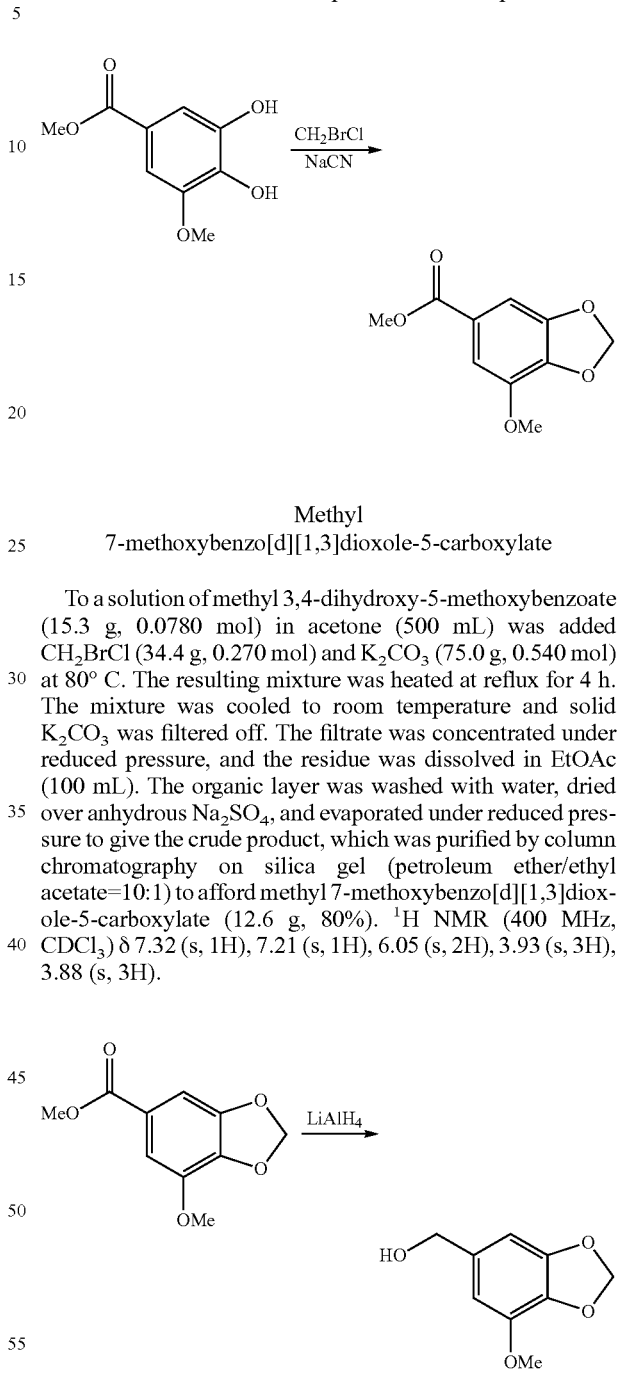

Methyl 7-methoxybenzo[d][1,3]dioxole-5-carboxylate

To a solution of methyl 3,4-dihydroxy-5-methoxybenzoate (15.3 g, 0.0780 mol) in acetone (500 mL) was added CH$_2$BrCl (34.4 g, 0.270 mol) and K$_2$CO$_3$ (75.0 g, 0.540 mol) at 80° C. The resulting mixture was heated at reflux for 4 h. The mixture was cooled to room temperature and solid K$_2$CO$_3$ was filtered off. The filtrate was concentrated under reduced pressure, and the residue was dissolved in EtOAc (100 mL). The organic layer was washed with water, dried over anhydrous Na$_2$SO$_4$, and evaporated under reduced pressure to give the crude product, which was purified by column chromatography on silica gel (petroleum ether/ethyl acetate=10:1) to afford methyl 7-methoxybenzo[d][1,3]dioxole-5-carboxylate (12.6 g, 80%). $^1$H NMR (400 MHz, CDCl$_3$) δ 7.32 (s, 1H), 7.21 (s, 1H), 6.05 (s, 2H), 3.93 (s, 3H), 3.88 (s, 3H).

(7-Methoxybenzo[d][1,3]dioxol-5-yl)methanol

To a solution of methyl 7-methoxybenzo[d][1,3]dioxole-5-carboxylate (14 g, 0.040 mol) in THF (100 mL) was added LiAlH$_4$ (3.1 g, 0.080 mol) in portions at room temperature. The mixture was stirred for 3 h at room temperature. The reaction mixture was cooled to 0° C. and treated with water (3.1 g) and NaOH (10%, 3.1 mL) successively. The slurry was filtered off and washed with THF. The combined filtrates were evaporated under reduced pressure to give (7-methoxy-benzo[d][1,3]dioxol-5-yl)methanol (7.2 g, 52%). $^1$H NMR (400 MHz, CDCl$_3$) δ 6.55 (s, 1H), 6.54 (s, 1H), 5.96 (s, 2H), 4.57 (s, 2H), 3.90 (s, 3H).

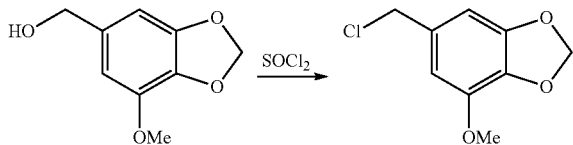

6-(Chloromethyl)-4-methoxybenzo[d][1,3]dioxole

To a solution of SOCl$_2$ (150 mL) was added (7-methoxy-benzo[d][1,3]dioxol-5-yl)methanol (9.0 g, 54 mmol) in portions at 0° C. The mixture was stirred for 0.5 h. The excess SOCl$_2$ was evaporated under reduced pressure to give the crude product, which was basified with sat. aq. NaHCO$_3$ to pH ~7. The aqueous phase was extracted with EtOAc (100 mL×3). The combined organic layers were dried over anhydrous Na$_2$SO$_4$ and evaporated to give 6-(chloromethyl)-4-methoxybenzo[d][1,3]dioxole (10 g 94%), which was used in the next step without further purification. $^1$H NMR (400 MHz, CDCl$_3$) δ 6.58 (s, 1H), 6.57 (s, 1H), 5.98 (s, 2H), 4.51 (s, 2H), 3.90 (s, 3H).

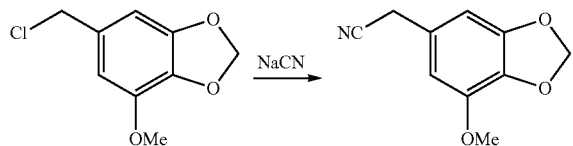

2-(7-Methoxybenzo[d][1,3]-dioxol-5-yl)acetonitrile

To a solution of 6-(chloromethyl)-4-methoxybenzo[d][1,3]dioxole (10 g, 40 mmol) in DMSO (100 mL) was added NaCN (2.4 g, 50 mmol) at room temperature. The mixture was stirred for 3 h and poured into water (500 mL). The aqueous phase was extracted with EtOAc (100 mL×3). The combined organic layers were dried over anhydrous Na$_2$SO$_4$ and evaporated to give the crude product, which was washed with ether to afford 2-(7-methoxybenzo[d][1,3]dioxol-5-yl)acetonitrile (4.6 g, 45%). $^1$H NMR (400 MHz, CDCl$_3$) δ 6.49 (s, 2H), 5.98 (s, 2H), 3.91 (s, 3H), 3.65 (s, 2H). $^{13}$C NMR (400 MHz, CDCl$_3$) δ 148.9, 143.4, 134.6, 123.4, 117.3, 107.2, 101.8, 101.3, 56.3, 23.1.

Example 11

2-(3-(Benzyloxy)-4-methoxyphenyl)acetonitrile

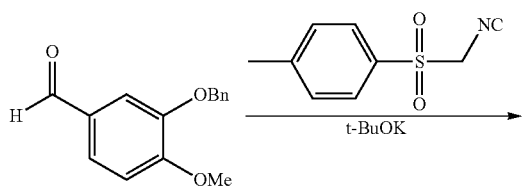

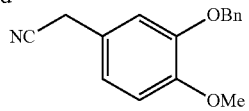

To a suspension of t-BuOK (20.2 g, 0.165 mol) in THF (250 mL) was added a solution of TosMIC (16.1 g, 82.6 mmol) in THF (100 mL) at −78° C. The mixture was stirred for 15 minutes, treated with a solution of 3-benzyloxy-4-methoxy-benzaldehyde (10.0 g, 51.9 mmol) in THF (50 mL) dropwise, and continued to stir for 1.5 hours at −78° C. To the cooled reaction mixture was added methanol (50 mL). The mixture was heated at reflux for 30 minutes. Solvent was removed to give a crude product, which was dissolved in water (300 mL). The aqueous phase was extracted with EtOAc (100 mL×3). The combined organic layers were dried and evaporated under reduced pressure to give crude product, which was purified by column chromatography (petroleum ether/ethyl acetate 10:1) to afford 2-(3-(benzyloxy)-4-methoxyphenyl)-acetonitrile (5.0 g, 48%). $^1$H NMR (300 MHz, CDCl$_3$) δ 7.48-7.33 (m, 5H), 6.89-6.86 (m, 3H), 5.17 (s, 2H), 3.90 (s, 3H), 3.66 (s, 2H). $^{13}$C NMR (75 MHz, CDCl$_3$) 149.6, 148.6, 136.8, 128.8, 128.8, 128.2, 127.5, 127.5, 122.1, 120.9, 118.2, 113.8, 112.2, 71.2, 56.2, 23.3.

Example 12

2-(3-(Benzyloxy)-4-chlorophenyl)acetonitrile

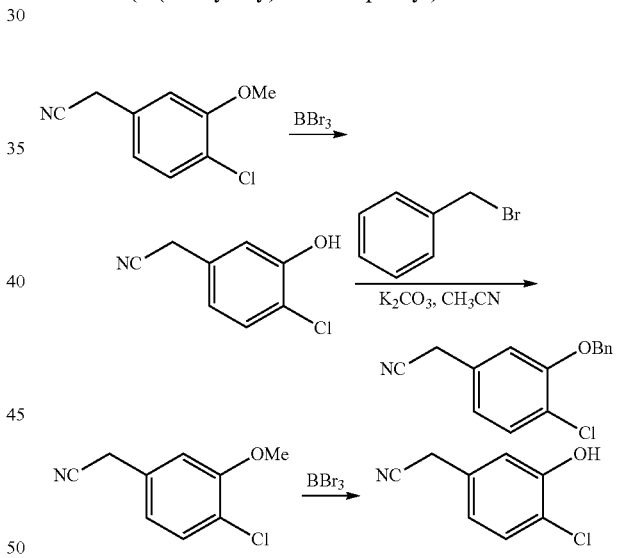

(4-Chloro-3-hydroxy-phenyl)acetonitrile

BBr$_3$ (17 g, 66 mmol) was slowly added to a solution of 2-(4-chloro-3-methoxyphenyl)acetonitrile (12 g, 66 mmol) in dichloromethane (120 mL) at −78° C. under N$_2$. The reaction temperature was slowly increased to room temperature. The reaction mixture was stirred overnight and then poured into ice and water. The organic layer was separated, and the aqueous layer was extracted with dichloromethane (40 mL×3). The combined organic layers were washed with water, brine, dried over Na$_2$SO$_4$, and concentrated under vacuum to give (4-chloro-3-hydroxy-phenyl)-acetonitrile (9.3 g, 85%). $^1$H NMR (300 MHz, CDCl$_3$) δ 7.34 (d, J=8.4 Hz, 1H), 7.02 (d, J=2.1 Hz, 1H), 6.87 (dd, J=2.1, 8.4 Hz, 1H), 5.15 (brs, 1H), 3.72 (s, 2H).

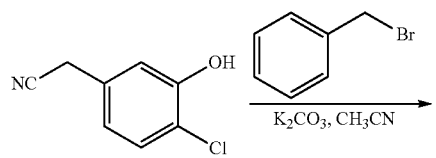

2-(3-(Benzyloxy)-4-chlorophenyl)acetonitrile

To a solution of (4-chloro-3-hydroxy-phenyl)acetonitrile (6.2 g, 37 mmol) in $CH_3CN$ (80 mL) was added $K_2CO_3$ (10 g, 74 mmol) and BnBr (7.6 g, 44 mmol). The mixture was stirred at room temperature overnight. The solids were filtered off and the filtrate was evaporated under vacuum. The residue was purified by column chromatography on silica gel (petroleum ether/ethyl acetate 50:1) to give 2-(3-(benzyloxy)-4-chlorophenyl)-acetonitrile (5.6 g, 60%). $^1H$ NMR (400 MHz, $CDCl_3$) δ 7.48-7.32 (m, 6H), 6.94 (d, J=2 Hz, 2H), 6.86 (dd, J=2.0, 8.4 Hz, 1H), 5.18 (s, 2H), 3.71 (s, 2H).

Example 13

2-(3-(Benzyloxy)-4-methoxyphenyl)acetonitrile

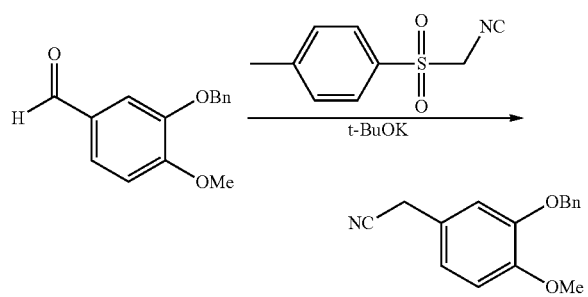

To a suspension of t-BuOK (20.2 g, 0.165 mol) in THF (250 mL) was added a solution of TosMIC (16.1 g, 82.6 mmol) in THF (100 mL) at −78° C. The mixture was stirred for 15 minutes, treated with a solution of 3-benzyloxy-4-methoxy-benzaldehyde (10.0 g, 51.9 mmol) in THF (50 mL) dropwise, and continued to stir for 1.5 hours at −78° C. To the cooled reaction mixture was added methanol (50 mL). The mixture was heated at reflux for 30 minutes. Solvent of the reaction mixture was removed to give a crude product, which was dissolved in water (300 mL). The aqueous phase was extracted with EtOAc (100 mL×3). The combined organic layers were dried and evaporated under reduced pressure to give crude product, which was purified by column chromatography (petroleum ether/ethyl acetate 10:1) to afford 2-(3-(benzyloxy)-4-methoxyphenyl)acetonitril (5.0 g, 48%). $^1H$ NMR (300 MHz, $CDCl_3$) δ 7.48-7.33 (m, 5H), 6.89-6.86 (m, 3H), 5.17 (s, 2H), 3.90 (s, 3H), 3.66 (s, 2H). $^{13}C$ NMR (75 MHz, $CDCl_3$) δ 149.6, 148.6, 136.8, 128.8, 128.8, 128.2, 127.5, 127.5, 122.1, 120.9, 118.2, 113.8, 112.2, 71.2, 56.2, 23.3.

Example 14

2-(3-Chloro-4-methoxyphenyl)acetonitrile

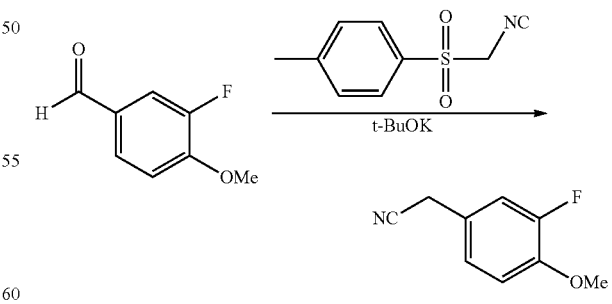

To a suspension of t-BuOK (4.8 g, 40 mmol) in THF (30 mL) was added a solution of TosMIC (3.9 g, 20 mmol) in THF (10 mL) at −78° C. The mixture was stirred for 10 minutes, treated with a solution of 3-chloro-4-methoxy-benzaldehyde (1.7 g, 10 mmol) in THF (10 mL) dropwise, and continued to stir for 1.5 hours at −78° C. To the cooled reaction mixture was added methanol (10 mL). The mixture was heated at reflux for 30 minutes. Solvent of the reaction mixture was removed to give a crude product, which was dissolved in water (20 mL). The aqueous phase was extracted with EtOAc (20 mL×3). The combined organic layers were dried and evaporated under reduced pressure to give crude product, which was purified by column chromatography (petroleum ether/ethyl acetate 10:1) to afford 2-(3-chloro-4-methoxyphenyl)acetonitrile (1.5 g, 83%). $^1H$ NMR (400 MHz, $CDCl_3$) δ 7.33 (d, J=2.4 Hz, 1H), 7.20 (dd, J=2.4, 8.4 Hz, 1H), 6.92 (d, J=8.4 Hz, 1H), 3.91 (s, 3H), 3.68 (s, 2H). $^{13}C$ NMR (100 MHz, $CDCl_3$) δ 154.8, 129.8, 127.3, 123.0, 122.7, 117.60, 112.4, 56.2, 22.4.

Example 15

2-(3-Fluoro-4-methoxyphenyl)acetonitrile

To a suspension of t-BuOK (25.3 g, 0.207 mol) in THF (150 mL) was added a solution of TosMIC (20.3 g, 0.104 mol) in THF (50 mL) at −78° C. The mixture was stirred for 15 minutes, treated with a solution of 3-fluoro-4-methoxy-benzaldehyde (8.00 g, 51.9 mmol) in THF (50 mL) dropwise, and continued to stir for 1.5 hours at −78° C. To the cooled reaction mixture was added methanol (50 mL). The mixture was heated at reflux for 30 minutes. Solvent of the reaction mixture was removed to give a crude product, which was dissolved in water (200 mL). The aqueous phase was extracted with EtOAc (100 mL×3). The combined organic layers were dried and evaporated under reduced pressure to give crude product, which was purified by column chromatography (petroleum ether/ethyl acetate 10:1) to afford 2-(3-fluoro-4-methoxyphenyl)acetonitrile (5.0 g, 58%). $^1$H NMR (400 MHz, CDCl$_3$) δ 7.02-7.05 (m, 2H), 6.94 (t, J=8.4 Hz, 1H), 3.88 (s, 3H), 3.67 (s, 2H). $^{13}$C NMR (100 MHz, CDCl$_3$) δ 152.3, 147.5, 123.7, 122.5, 117.7, 115.8, 113.8, 56.3, 22.6.

Example 16

2-(4-Chloro-3-methoxyphenyl)acetonitrile

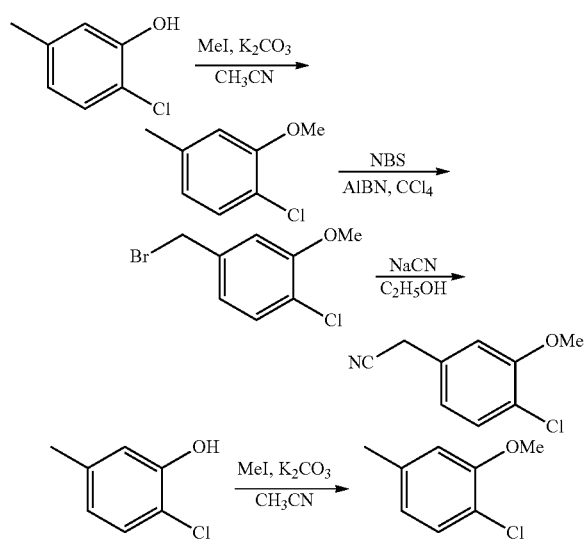

Chloro-2-methoxy-4-methyl-benzene

To a solution of 2-chloro-5-methyl-phenol (93 g, 0.65 mol) in CH$_3$CN (700 mL) was added CH$_3$I (110 g, 0.78 mol) and K$_2$CO$_3$ (180 g, 1.3 mol). The mixture was stirred at 25° C. overnight. The solid was filtered off and the filtrate was evaporated under vacuum to give 1-chloro-2-methoxy-4-methyl-benzene (90 g, 89%). $^1$H NMR (300 MHz, CDCl$_3$) δ 7.22 (d, J=7.8 Hz, 1H), 6.74-6.69 (m, 2H), 3.88 (s, 3H), 2.33 (s, 3H).

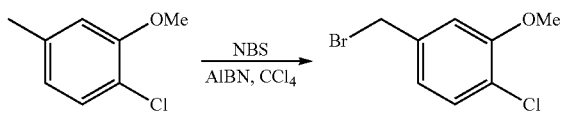

4-Bromomethyl-1-chloro-2-methoxy-benzene

To a solution of 1-chloro-2-methoxy-4-methyl-benzene (50 g, 0.32 mol) in CCl$_4$ (350 mL) was added NBS (57 g, 0.32 mol) and AIBN (10 g, 60 mmol). The mixture was heated at reflux for 3 hours. The solvent was evaporated under vacuum and the residue was purified by column chromatography on silica gel (petroleum ether/ethyl acetate=20:1) to give 4-bromomethyl-1-chloro-2-methoxy-benzene (69 g, 92%). $^1$H NMR (400 MHz, CDCl$_3$) δ 7.33-7.31 (m, 1H), 6.95-6.91 (m, 2H), 4.46 (s, 2H), 3.92 (s, 3H).

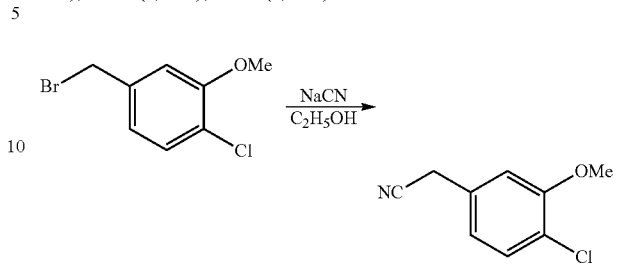

2-(4-Chloro-3-methoxyphenyl)acetonitrile

To a solution of 4-bromomethyl-1-chloro-2-methoxy-benzene (68.5 g, 0.290 mol) in C$_2$H$_5$OH (90%, 500 mL) was added NaCN (28.5 g, 0.580 mol). The mixture was stirred at 60° C. overnight. Ethanol was evaporated and the residue was dissolved in H$_2$O. The mixture was extracted with ethyl acetate (300 mL×3). The combined organic layers were washed with brine, dried over Na$_2$SO$_4$ and purified by column chromatography on silica gel (petroleum ether/ethyl acetate 30:1) to give 2-(4-chloro-3-methoxyphenyl)acetonitrile (25 g, 48%). $^1$H NMR (400 MHz, CDCl$_3$) δ 7.36 (d, J=8 Hz, 1H), 6.88-6.84 (m, 2H), 3.92 (s, 3H), 3.74 (s, 2H). $^{13}$C NMR (100 MHz, CDCl$_3$) δ 155.4, 130.8, 129.7, 122.4, 120.7, 117.5, 111.5, 56.2, 23.5.

Example 17

1-(3-(Hydroxymethyl)-4-methoxyphenyl)cyclopropanecarboxylic acid

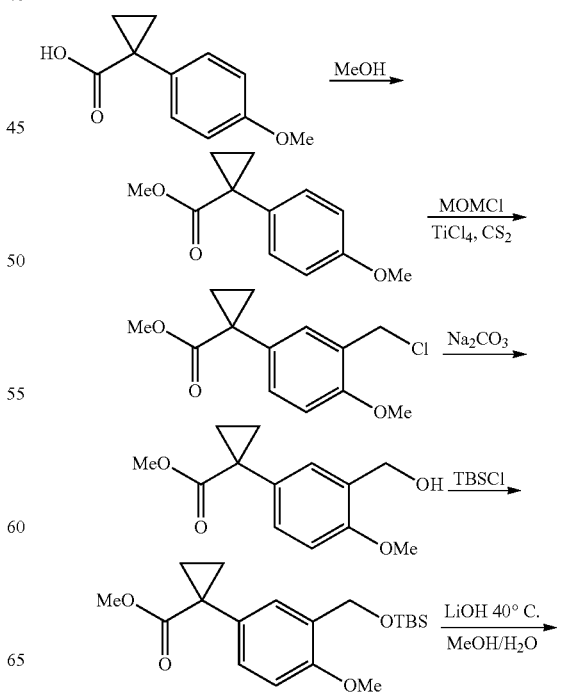

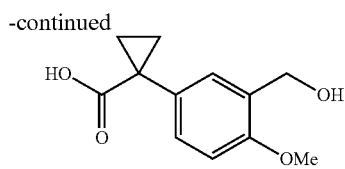

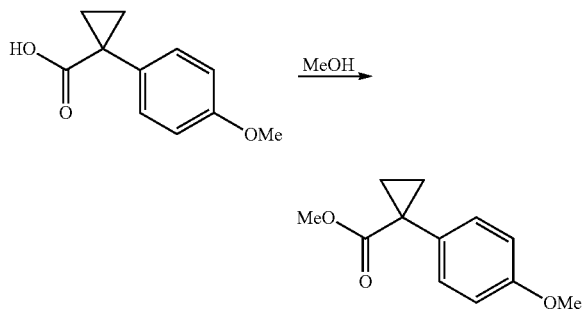

1-(4-Methoxy-phenyl)-cyclopropanecarboxylic acid methyl ester

To a solution of 1-(4-methoxy-phenyl)-cyclopropanecarboxylic acid (50 g, 0.26 mol) in MeOH (500 mL) was added toluene-4-sulfonic acid monohydrate (2.5 g, 13 mmol) at room temperature. The reaction mixture was heated at reflux for 20 hours. MeOH was removed by evaporation under vacuum and EtOAc (200 mL) was added. The organic layer was washed with sat. aq. NaHCO$_3$ (100 mL) and brine, dried over anhydrous Na$_2$SO$_4$ and evaporated under vacuum to give 1-(4-methoxy-phenyl)cyclopropanecarboxylic acid methyl ester (53 g, 99%). $^1$H NMR (CDCl$_3$, 400 MHz) δ 7.25-7.27 (m, 2H), 6.85 (d, J=8.8 Hz, 2H), 3.80 (s, 3H), 3.62 (s, 3H), 1.58 (m, 2H), 1.15 (m, 2H).

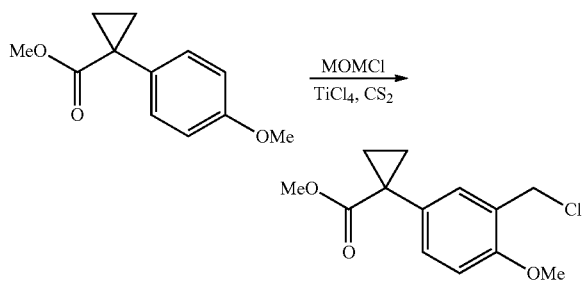

1-(3-Chloromethyl-4-methoxy-phenyl)-cyclopropanecarboxylic acid methyl ester To a solution of 1-(4-methoxy-phenyl)-cyclopropanecarboxylic acid methyl ester (30.0 g, 146 mmol) and MOMCl (29.1 g, 364 mmol) in CS$_2$ (300 mL) was added TiCl$_4$ (8.30 g, 43.5 mmol) at 5° C. The reaction mixture was heated at 30° C. for 1 d and poured into ice-water. The mixture was extracted with CH$_2$Cl$_2$ (150 mL×3). The combined organic extracts were evaporated under vacuum to give 1-(3-chloromethyl-4-methoxy-phenyl)-cyclopropanecarboxylic acid methyl ester (38.0 g), which was used in the next step without further purification.

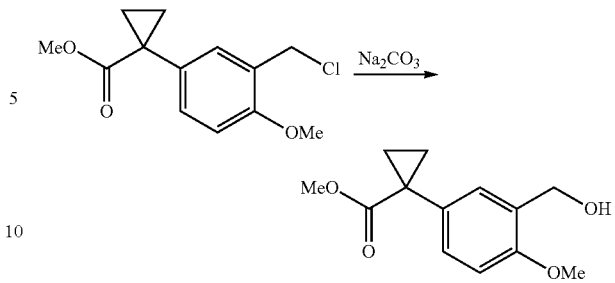

1-(3-Hydroxymethyl-4-methoxy-phenyl)cyclopropanecarboxylic acid methyl ester To a suspension of 1-(3-chloromethyl-4-methoxy-phenyl)-cyclopropanecarboxylic acid methyl ester (20 g) in water (350 mL) was added Bu$_4$NBr (4.0 g) and Na$_2$CO$_3$ (90 g, 0.85 mol) at room temperature. The reaction mixture was heated at 65° C. overnight. The resulting solution was acidified with aq. HCl (2 mol/L) and extracted with EtOAc (200 mL×3). The organic layer was washed with brine, dried over anhydrous Na$_2$SO$_4$ and evaporated under vacuum to give crude product, which was purified by column (petroleum ether/ethyl acetate 15:1) to give 1-(3-hydroxymethyl-4-methoxy-phenyl)-cyclopropanecarboxylic acid methyl ester (8.0 g, 39%). $^1$H NMR (CDCl$_3$. 400 MHz) δ 7.23-7.26 (m, 2H), 6.83 (d, J=8.0 Hz, 1H), 4.67 (s, 2H), 3.86 (s, 3H), 3.62 (s, 3H), 1.58 (q, J=3.6 Hz, 2H), 1.14-1.17 (m, 2H).

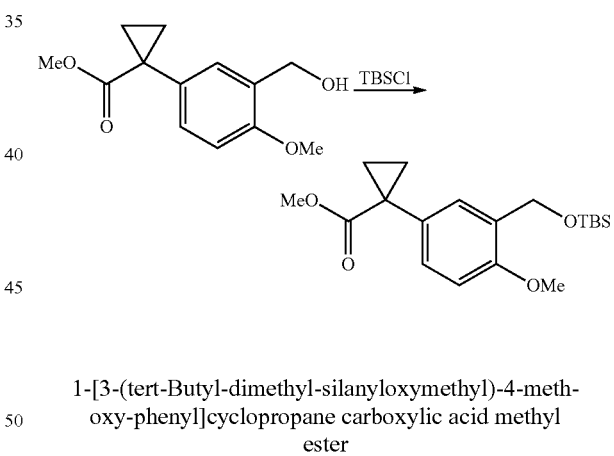

1-[3-(tert-Butyl-dimethyl-silanyloxymethyl)-4-methoxy-phenyl]cyclopropane carboxylic acid methyl ester To a solution of 1-(3-hydroxymethyl-4-methoxy-phenyl)-cyclopropanecarboxylic acid methyl ester (8.0 g, 34 mmol) in CH$_2$Cl$_2$ (100 mL) were added imidazole (5.8 g, 85 mmol) and TBSCl (7.6 g, 51 mmol) at room temperature. The mixture was stirred overnight at room temperature. The mixture was washed with brine, dried over anhydrous Na$_2$SO$_4$ and evaporated under vacuum to give crude product, which was purified by column (petroleum ether/ethyl acetate 30:1) to give 1-[3-(tert-butyl-dimethyl-silanyloxymethyl)-4-methoxy-phenyl]-cyclopropanecarboxylic acid methyl ester (6.7 g, 56%). $^1$H NMR (CDCl$_3$, 400 MHz) δ 7.44-7.45 (m, 1H), 7.19 (dd, J=2.0, 8.4 Hz, 1H), 6.76 (d, J=8.4 Hz, 1H), 4.75 (s, 2H), 3.81 (s, 3H), 3.62 (s, 3H), 1.57-1.60 (m, 2H), 1.15-1.18 (m, 2H), 0.96 (s, 9H), 0.11 (s, 6H).

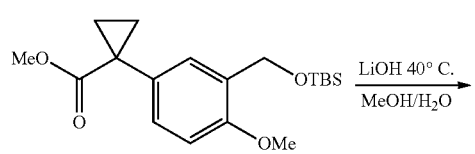
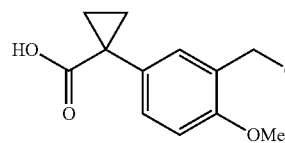

1-(3-Hydroxymethyl-4-methoxy-phenyl)-cyclopropanecarboxylic acid

To a solution of 1-[3-(tert-butyl-dimethyl-silanyloxymethyl)-4-methoxy-phenyl]-cyclopropane carboxylic acid methyl ester (6.2 g, 18 mmol) in MeOH (75 mL) was added a solution of LiOH.H$_2$O (1.5 g, 36 mmol) in water (10 mL) at 0° C. The reaction mixture was stirred overnight at 40° C. MeOH was removed by evaporation under vacuum. AcOH (1 mol/L, 40 mL) and EtOAc (200 mL) were added. The organic layer was separated, washed with brine, dried over anhydrous Na$_2$SO$_4$ and evaporated under vacuum to provide 1-(3-hydroxymethyl-4-methoxy-phenyl)-cyclopropanecarboxylic acid (5.3 g).

Example 18

2-(7-Chlorobenzo[d][1,3]dioxol-5-yl)acetonitrile

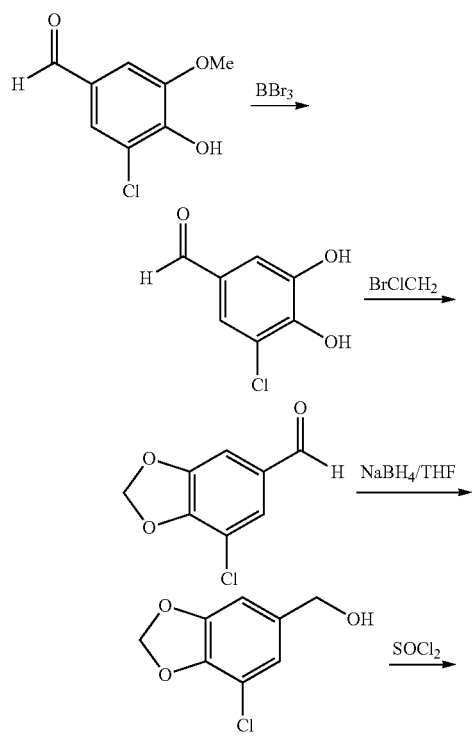

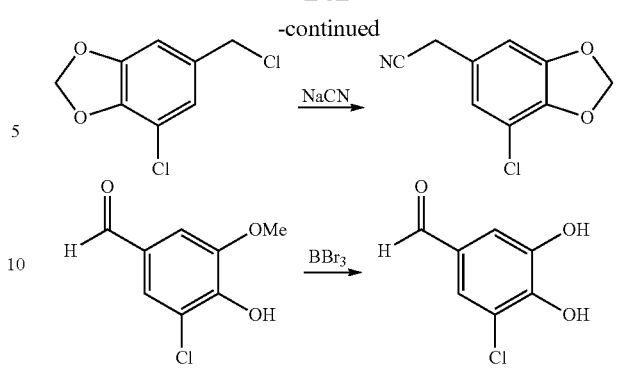

3-Chloro-4,5-dihydroxybenzaldehyde

To a suspension of 3-chloro-4-hydroxy-5-methoxy-benzaldehyde (10 g, 54 mmol) in dichloromethane (300 mL) was added BBr$_3$ (26.7 g, 107 mmol) dropwise at −40° C. under N$_2$. After addition, the mixture was stirred at this temperature for 5 h and then was poured into ice water. The precipitated solid was filtered and washed with petroleum ether. The filtrate was evaporated under reduced pressure to afford 3-chloro-4,5-dihydroxybenzaldehyde (9.8 g, 89%), which was directly used in the next step.

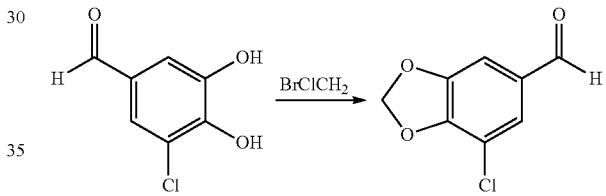

7-Chlorobenzo[d][1,3]dioxole-5-carbaldehyde

To a solution of 3-chloro-4,5-dihydroxybenzaldehyde (8.0 g, 46 mmol) and BrClCH$_2$ (23.9 g, 185 mmol) in dry DMF (100 mL) was added Cs$_2$CO$_3$ (25 g, 190 mmol). The mixture was stirred at 60° C. overnight and was then poured into water. The resulting mixture was extracted with EtOAc (50 mL×3). The combined extracts were washed with brine (100 mL), dried over Na$_2$SO$_4$ and concentrated under reduced pressure to afford 7-chlorobenzo[d][1,3]dioxole-5-carbaldehyde (6.0 g, 70%). $^1$H NMR (400 MHz, CDCl$_3$) δ 9.74 (s, 1H), 7.42 (d, J=0.4 Hz, 1H), 7.26 (d, J=3.6 Hz, 1H), 6.15 (s, 2H).

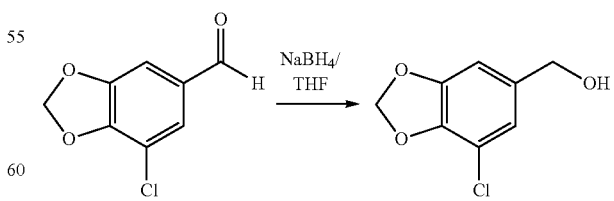

(7-Chlorobenzo[d][1,3]dioxol-5-yl)methanol

To a solution of 7-chlorobenzo[d][1,3]dioxole-5-carbaldehyde (6.0 g, 33 mmol) in THF (50 mL) was added NaBH$_4$ (2.5 g, 64 mmol)) in portions at 0° C. The mixture was stirred at this temperature for 30 min and then poured into aqueous NH₄Cl solution. The organic layer was separated, and the aqueous phase was extracted with EtOAc (50 mL×3). The combined extracts were dried over Na₂SO₄ and evaporated under reduced pressure to afford (7-chlorobenzo[d][1,3]dioxol-5-yl)methanol, which was directly used in the next step.

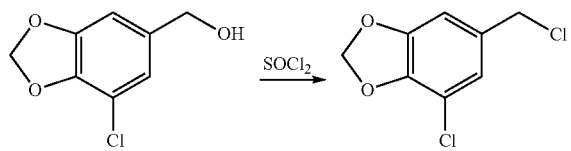

4-Chloro-6-(chloromethyl)benzo[d][1,3]dioxole

A mixture of (7-chlorobenzo[d][1,3]-dioxol-5-yl)methanol (5.5 g, 30 mmol) and SOCl₂ (5.0 mL, 67 mmol) in dichloromethane (20 mL) was stirred at room temperature for 1 h and was then poured into ice water. The organic layer was separated and the aqueous phase was extracted with dichloromethane (50 mL×3). The combined extracts were washed with water and aqueous NaHCO₃ solution, dried over Na₂SO₄ and evaporated under reduced pressure to afford 4-chloro-6-(chloromethyl)benzo[d][1,3]dioxole, which was directly used in the next step.

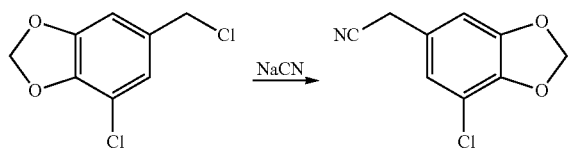

2-(7-Chlorobenzo[d][1,3]dioxol-5-yl)acetonitrile

A mixture of 4-chloro-6-(chloromethyl)benzo[d][1,3]dioxole (6.0 g, 29 mmol) and NaCN (1.6 g, 32 mmol) in DMSO (20 mL) was stirred at 40° C. for 1 h and was then poured into water. The mixture was extracted with EtOAc (30 mL×3). The combined organic layers were washed with water and brine, dried over Na₂SO₄ and evaporated under reduced pressure to afford 2-(7-chlorobenzo[d][1,3]dioxol-5-yl)acetonitrile (3.4 g, 58%). ¹H NMR δ 6.81 (s, 1H), 6.71 (s, 1H), 6.07 (s, 2H), 3.64 (s, 2H). ¹³C-NMR δ149.2, 144.3, 124.4, 122.0, 117.4, 114.3, 107.0, 102.3, 23.1.

Example 19

1-(Benzo[d]oxazol-5-yl)cyclopropanecarboxylic acid

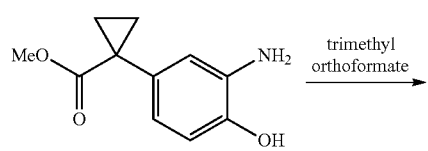

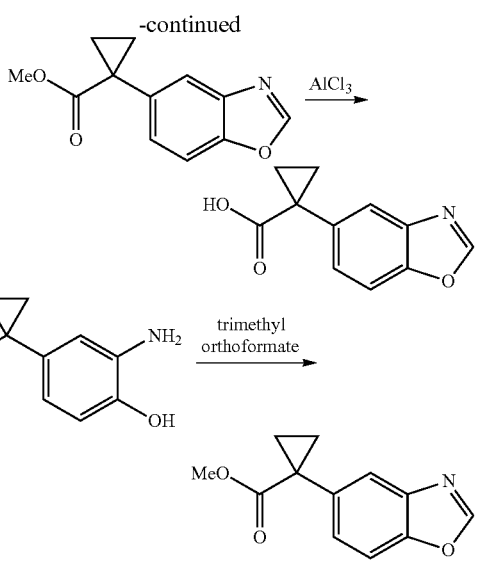

1-Benzooxazol-5-yl-cyclopropanecarboxylic acid methyl ester

To a solution of 1-(3-amino-4-hydroxyphenyl)cyclopropanecarboxylic acid methyl ester (3.00 g, 14.5 mmol) in DMF were added trimethyl orthoformate (5.30 g, 14.5 mmol) and a catalytic amount of p-tolueneslufonic acid monohydrate (0.3 g) at room temperature. The mixture was stirred for 3 hours at room temperature. The mixture was diluted with water and extracted with EtOAc (100 mL×3). The combined organic layers were dried over anhydrous Na₂SO₄ and evaporated under vacuum to give 1-benzooxazol-5-yl-cyclopropanecarboxylic acid methyl ester (3.1 g), which was directly used in the next step. ¹H NMR (CDCl₃, 400 MHz) δ 8.09 (s, 1), 7.75 (d, J=1.2 Hz, 1H), 7.53-7.51 (m, 1H), 7.42-7.40 (m, 1H), 3.66 (s, 3H), 1.69-1.67 (m, 2H), 1.27-1.24 (m, 2H).

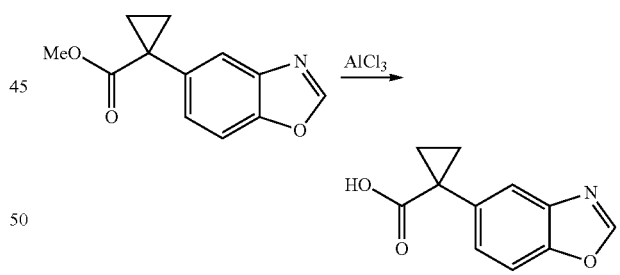

1-(Benzo[d]oxazol-5-yl)cyclopropanecarboxylic acid

To a solution of 1-benzooxazol-5-yl-cyclopropanecarboxylic acid methyl ester (2.9 g) in EtSH (30 mL) was added AlCl₃ (5.3 g, 40 mmol) in portions at 0° C. The reaction mixture was stirred for 18 hours at room temperature. Water (20 mL) was added dropwise at 0° C. The resulting mixture was extracted with EtOAc (100 mL×3). The combined organic layers were dried over anhydrous Na₂SO₄ and evaporated under vacuum to give the crude product, which was purified by column chromatography on silica gel (petroleum ether/ethyl acetate 1:2) to give 1-(benzo[d]oxazol-5-yl)cyclopropanecarboxylic acid (280 mg, 11% over two steps). ¹H NMR (DMSO, 400 MHz) δ12.25 (brs, 1H), 8.71 (s, 1H), 7.70-7.64 (m, 2H), 7.40 (dd, J=1.6, 8.4 Hz, 1H), 1.49-1.46 (m, 2H), 1.21-1.18 (m, 2H). MS (ESI) m/e (M+H⁺) 204.4.

Example 20

2-(7-Fluorobenzo[d][1,3]dioxol-5-yl)acetonitrile

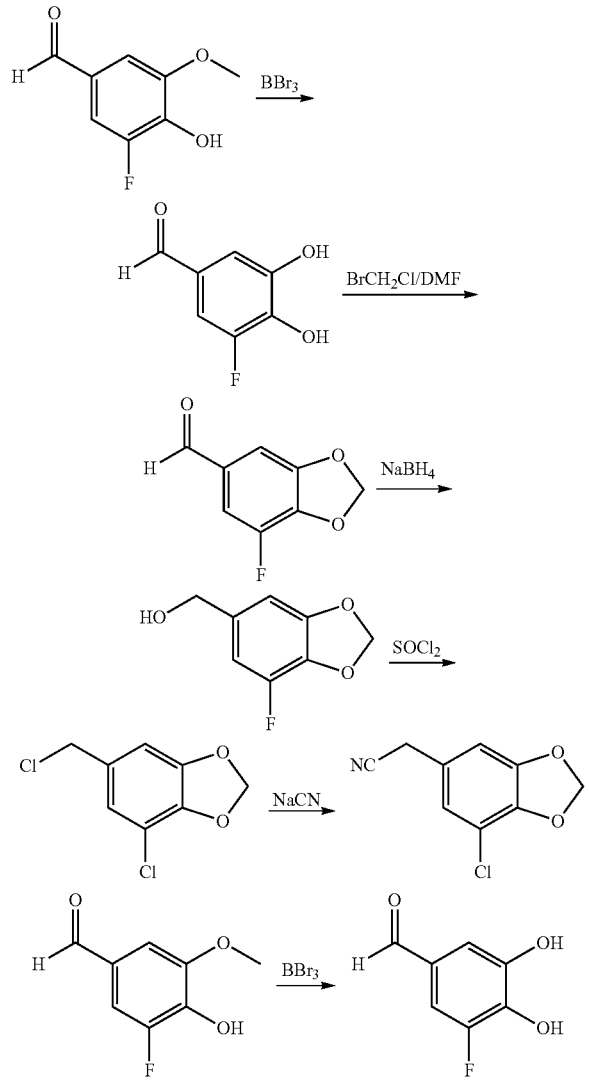

3-Fluoro-4,5-dihydroxy-benzaldehyde

To a suspension of 3-fluoro-4-hydroxy-5-methoxy-benzaldehyde (1.35 g, 7.94 mmol) in dichloromethane (100 mL) was added BBr₃ (1.5 mL, 16 mmol) dropwise at −78° C. under N₂. After addition, the mixture was warmed to −30° C. and it was stirred at this temperature for 5 h. The reaction mixture was poured into ice water. The precipitated solid was collected by filtration and washed with dichloromethane to afford 3-fluoro-4,5-dihydroxy-benzaldehyde (1.1 g, 89%), which was directly used in the next step.

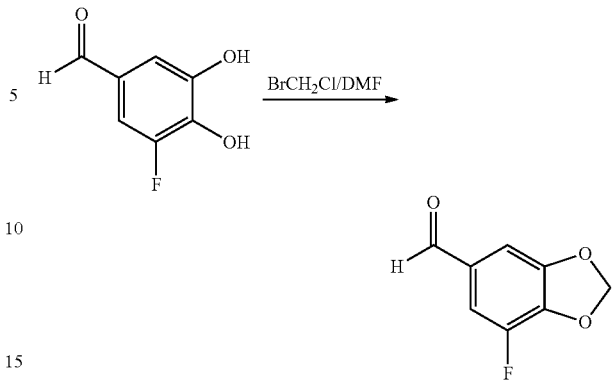

7-Fluoro-benzo[1,3]dioxole-5-carbaldehyde

To a solution of 3-fluoro-4,5-dihydroxy-benzaldehyde (1.5 g, 9.6 mmol) and BrClCH₂ (4.9 g, 38.5 mmol) in dry DMF (50 mL) was added Cs₂CO₃ (12.6 g, 39 mmol). The mixture was stirred at 60° C. overnight and was then poured into water. The resulting mixture was extracted with EtOAc (50 mL×3). The combined organic layers were washed with brine (100 mL), dried over Na₂SO₄ and evaporated under reduced pressure to give the crude product, which was purified by column chromatography on silica gel (petroleum ether/ethyl acetate=10/1) to afford 7-fluoro-benzo[1,3]dioxole-5-carbaldehyde (0.80 g, 49%). ¹H NMR (300 MHz, CDCl₃) δ 9.78 (d, J=0.9 Hz, 1H), 7.26 (dd, J=1.5, 9.3 Hz, 1H), 7.19 (d, J=1.2 Hz, 1H), 6.16 (s, 2H).

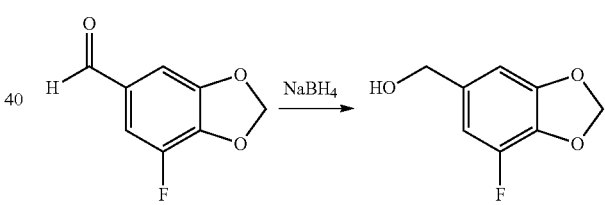

(7-Fluoro-benzo[1,3]dioxol-5-yl)-methanol

To a solution of 7-fluoro-benzo[1,3]clioxole-5-carbaldehyde (0.80 g, 4.7 mmol) in MeOH (50 mL) was added NaBH₄ (0.36 g, 9.4 mmol) in portions at 0° C. The mixture was stirred at this temperature for 30 min and was then concentrated to dryness. The residue was dissolved in EtOAc. The EtOAc layer was washed with water, dried over Na₂SO₄ and concentrated to dryness to afford (7-fluoro-benzo[1,3]dioxol-5-yl)-methanol (0.80 g, 98%), which was directly used in the next step.

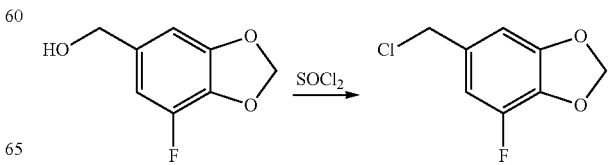

6-Chloromethyl-4-fluoro-benzo[1,3]dioxole

To SOCl$_2$ (20 mL) was added (7-fluoro-benzo[1,3]dioxol-5-yl)-methanol (0.80 g, 4.7 mmol) in portions at 0° C. The mixture was warmed to room temperature over 1 h and then was heated at reflux for 1 h. The excess SOCl$_2$ was evaporated under reduced pressure to give the crude product, which was basified with saturated aqueous NaHCO$_3$ to pH ~7. The aqueous phase was extracted with EtOAc (50 mL×3). The combined organic layers were dried over Na$_2$SO$_4$ and evaporated under reduced pressure to give 6-chloromethyl-4-fluoro-benzo[1,3]dioxole (0.80 g, 92%), which was directly used in the next step.

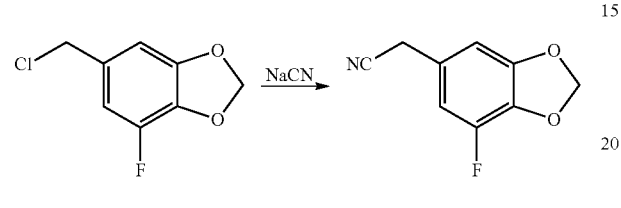

2-(7-Fluorobenzo[d][1,3]dioxol-5-yl)acetonitrile

A mixture of 6-chloromethyl-4-fluoro-benzo[1,3]dioxole (0.80 g, 4.3 mmol) and NaCN (417 mg, 8.51 mmol) in DMSO (20 mL) was stirred at 30° C. for 1 h and was then poured into water. The mixture was extracted with EtOAc (50 mL×3). The combined organic layers were washed with water (50 mL) and brine (50 mL), dried over Na$_2$SO$_4$ and evaporated under reduced pressure to give the crude product, which was purified by column chromatography on silica gel (petroleum ether/ethyl acetate=10/1) to afford 2-(7-fluorobenzo[d][1,3]dioxol-5-yl)acetonitrile (530 mg, 70%). $^1$H NMR (300 MHz, CDCl$_3$) δ 6.68-6.64 (m, 2H), 6.05 (s, 2H), 3.65 (s, 2H). $^{13}$C-NMR δ151.1, 146.2, 134.1, 124.2, 117.5, 110.4, 104.8, 102.8, 23.3.

Example 21

1-(1H-Indol-5-yl)cyclopropanecarboxylic acid

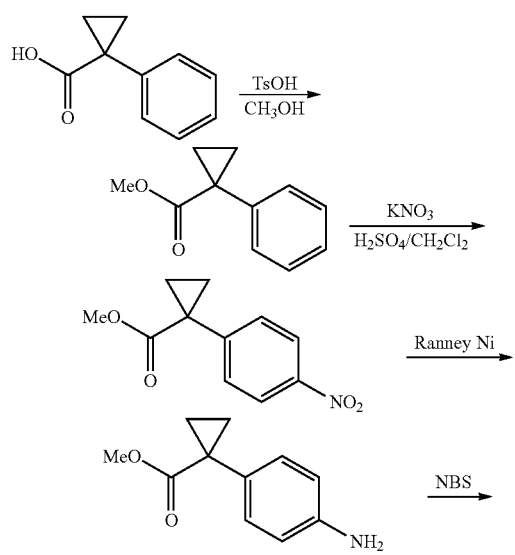

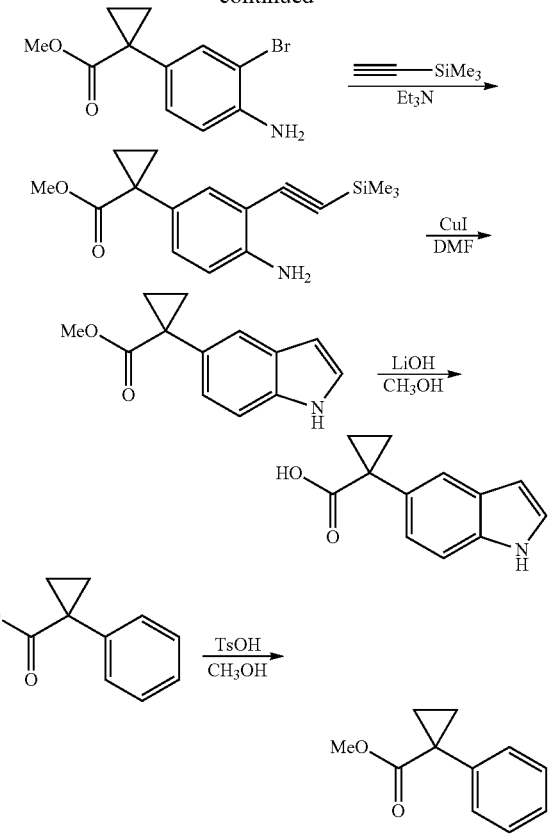

Methyl 1-phenylcyclopropanecarboxylate

To a solution of 1-phenylcyclopropanecarboxylic acid (25 g, 0.15 mol) in CH$_3$OH (200 mL) was added TsOH (3 g, 0.1 mol) at room temperature. The mixture was refluxed overnight. The solvent was evaporated under reduced pressure to give crude product, which was dissolved into EtOAc. The EtOAc layer was washed with aq. sat. NaHCO$_3$. The organic layer was dried over anhydrous Na$_2$SO$_4$ and evaporated under reduced pressure to give methyl 1-phenylcyclopropanecarboxylate (26 g, 96%), which was used directly in the next step. $^1$H NMR (400 MHz, CDCl$_3$) δ 7.37-7.26 (m, 5H), 3.63 (s, 3H), 1.63-1.60 (m, 2H), 1.22-1.19 (m, 2H).

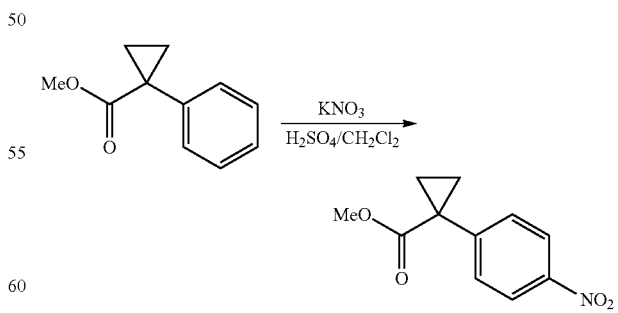

Methyl 1-(4-nitrophenyl)cyclopropanecarboxylate

To a solution of 1-phenylcyclopropanecarboxylate (20.62 g, 0.14 mol) in H$_2$SO$_4$/CH$_2$Cl$_2$ (40 mL/40 mL) was added KNO₃ (12.8 g, 0.13 mol) in portion at 0° C. The mixture was stirred for 0.5 hr at 0° C. Ice water was added and the mixture was extracted with EtOAc (100 mL×3). The organic layers were dried with anhydrous Na₂SO₄ and evaporated to give methyl 1-(4-nitrophenyl)cyclopropanecarboxylate (21 g, 68%), which was used directly in the next step. ¹H NMR (300 MHz, CDCl₃) δ 8.18 (dd, J=2.1, 6.9 Hz, 2H), 7.51 (dd, J=2.1, 6.9 Hz, 2H), 3.64 (s, 3H), 1.72-1.69 (m, 2H), 1.25-1.22 (m, 2H).

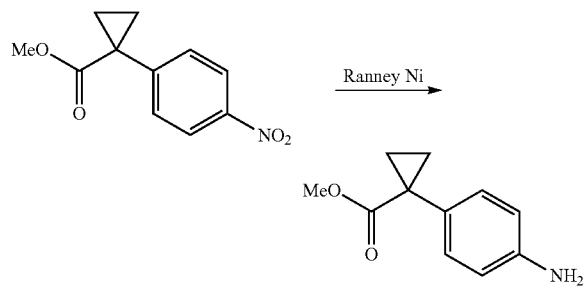

Methyl 1-(4-aminophenyl)cyclopropanecarboxylate

To a solution of methyl 1-(4-nitrophenyl)cyclopropanecarboxylate (20 g, 0.09 mol) in MeOH (400 mL) was added Ni (2 g) under nitrogen atmosphere. The mixture was stirred under hydrogen atmosphere (1 atm) at room temperature overnight. The catalyst was filtered off through a pad of Celite and the filtrate was evaporated under vacuum to give crude product, which was purified by chromatography column on silica gel (petroleum ether/ethyl acetate=10:1) to give methyl 1-(4-aminophenyl)cyclopropanecarboxylate (11.38 g, 66%). ¹H NMR (300 MHz, CDCl₃) δ 7.16 (d, J=8.1 Hz, 2H), 6.86 (d, J=7.8 Hz, 2H), 4.31 (br, 2H), 3.61 (s, 3H), 1.55-1.50 (m, 2H), 1.30-1.12 (m, 2H).

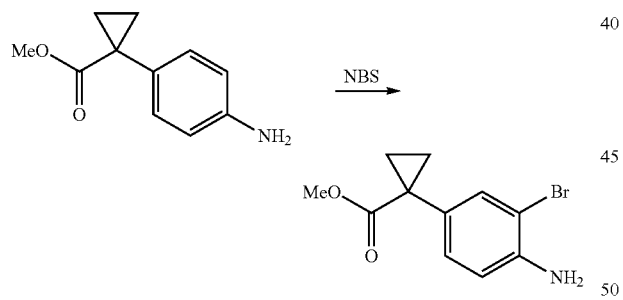

Methyl 1-(4-amino-3-bromophenyl)cyclopropanecarboxylate

To a solution of methyl 1-(4-aminophenyl)cyclopropanecarboxylate (10.38 g, 0.05 mol) in acetonitrile (200 mL) was added NBS (9.3 g, 0.05 mol) at room temperature. The mixture was stirred overnight. Water (200 mL) was added. The organic layer was separated and the aqueous phase was extracted with EtOAc (80 mL×3). The organic layers were dried with anhydrous Na₂SO₄ and evaporated to give methyl 1-(4-amino-3-bromophenyl)cyclopropanecarboxylate (10.6 g, 78%), which was used directly in the next step. ¹H NMR (400 MHz, CDCl₃) δ 7.38 (d, J=2.0 Hz, 1H), 7.08 (dd, J=1.6, 8.4 Hz, 1H), 6.70 (d, J=8.4 Hz, 1H), 3.62 (s, 3H), 1.56-1.54 (m, 2H), 1.14-1.11 (m, 2H).

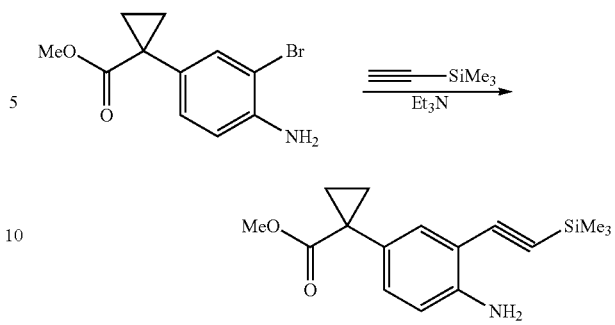

Methyl 1-(4-amino-3-((trimethylsilyl)ethynyl)phenyl)cyclopropane carboxylate To a degassed solution of methyl 1-(4-amino-3-bromophenyl)cyclopropane carboxylate (8 g, 0.03 mol) in Et₃N (100 mL) was added ethynyl-trimethyl-silane (30 g, 0.3 mol), DMAP (5% mol) and Pd(PPh₃)₂Cl₂ (5% mol) under N₂. The mixture was refluxed at 70° C. overnight. The insoluble solid was filtered off and washed with EtOAc (100 mL×3). The filtrate was evaporated under reduced pressure to give a residue, which was purified by chromatography column on silica gel (petroleum ether/ethyl acetate=20:1) to give methyl 1-(4-amino-3-((trimethylsilyl)ethynyl)phenyl)cyclopropanecarboxylate (4.8 g, 56%). ¹H NMR (300 MHz, CDCl₃) δ 7.27 (s, 1H), 7.10 (dd, J=2.1, 8.4 Hz, 1H), 6.64 (d, J=8.4 Hz, 1H), 3.60 (s, 3H), 1.55-1.51 (m, 2H), 1.12-1.09 (m, 2H), 0.24 (s, 9H).

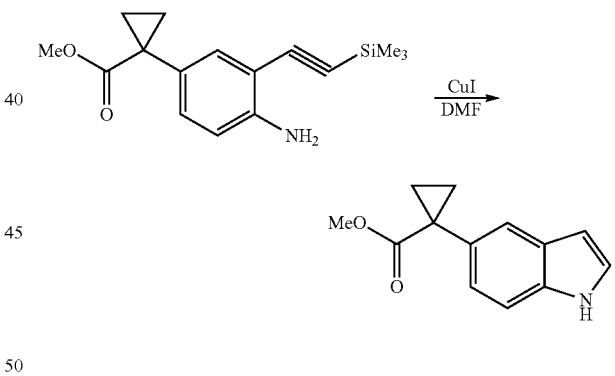

Methyl 1-(1H-indol-5-yl)cyclopropanecarboxylate

To a degassed solution of methyl 1-(4-amino-3-((trimethylsilyl)ethynyl)phenyl)cyclopropanecarboxylate (4.69 g, 0.02 mol) in DMF (20 mL) was added CuI (1.5 g, 0.008 mol) under N₂ at room temperature. The mixture was stirred for 3 hr at room temperature. The insoluble solid was filtered off and washed with EtOAc (50 mL×3). The filtrate was evaporated under reduced pressure to give a residue, which was purified by chromatography column on silica gel (petroleum ether/ethyl acetate=20:1) to give methyl 1-(1H-indol-5-yl)cyclopropanecarboxylate (2.2 g, 51%). ¹H NMR (400 MHz, CDCl₃) δ 7.61 (s, 1H), 7.33 (d, J=8.4 Hz, 1H), 7.23-7.18 (m, 2H), 6.52-6.51 (m, 1H) 3.62 (s, 3H), 1.65-1.62 (m, 2H), 1.29-1.23 (m, 2H).

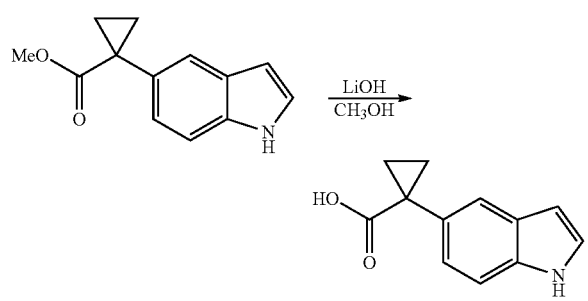

1-(1H-Indol-5-yl)cyclopropanecarboxylic acid

To a solution of methyl 1-(1H-indol-5-yl)cyclopropanecarboxylate (1.74 g, 8 mmol) in CH$_3$OH (50 mL) and water (20 mL) was added LiOH (1.7 g, 0.04 mol). The mixture was heated at 45° C. for 3 hr. Water was added and the mixture was acidified with concentrated HCl to pH ~3 before being extracted with EtOAc (20 mL×3). The organic layers were dried over anhydrous Na$_2$SO$_4$ and evaporated to give 1-(1H-indol-5-yl)cyclopropanecarboxylic acid (1.4 g, 87%). $^1$H NMR (300 MHz, DMSO-d$_6$) 7.43 (s, 1H), 7.30-7.26 (m, 2H), 7.04 (dd, J=1.5, 8.4 Hz, 1H), 6.35 (s, 1H); 1.45-1.41 (m, 2H), 1.14-1.10 (m, 2H).

Example 22

1-(4-Oxochroman-6-yl)cyclopropanecarboxylic acid

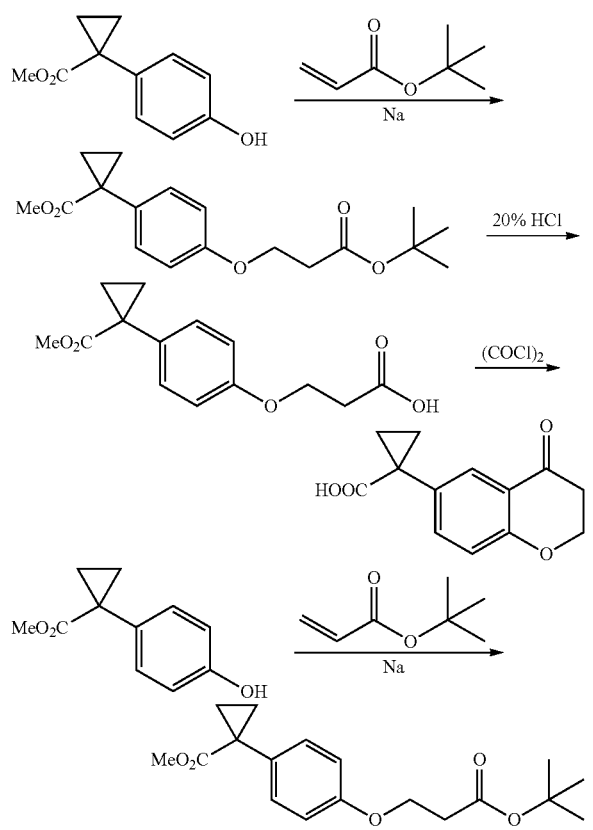

1-[4-(2-tert-Butoxycarbonyl-ethoxy)-phenyl]-cyclopropanecarboxylic methyl ester

To a solution of 1-(4-hydroxy-phenyl)-cyclopropanecarboxylic methyl ester (7.0 g, 3.6 mmol) in acrylic tert-butyl ester (50 mL) was added Na (42 mg, 1.8 mmol) at room temperature. The mixture was heated at 110° C. for 1 h. After cooling to room temperature, the resulting mixture was quenched with water and extracted with EtOAc (100 mL×3). The combined organic extracts were dried over anhydrous Na$_2$SO$_4$ and evaporated under vacuum to give the crude product, which was purified by column chromatography on silica gel (petroleum ether/ethyl acetate 20:1) to give 1-[4-(2-tert-butoxycarbonyl-ethoxy)-phenyl]-cyclopropanecarboxylic methyl ester (6.3 g, 54%) and unreacted start material (3.0 g). $^1$H NMR (300 MHz, CDCl$_3$) δ 7.24 (d, J=8.7 Hz, 2H), 6.84 (d, J=8.7 Hz, 2H), 4.20 (t, J=6.6 Hz, 2H), 3.62 (s, 3H), 2.69 (t, J=6.6 Hz, 2H), 1.59-1.56 (m, 2H), 1.47 (s, 9H), 1.17-1.42 (m, 2H).

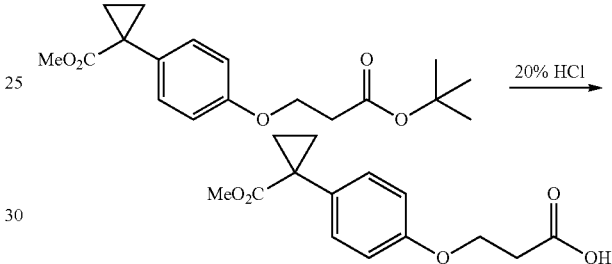

1-[4-(2-Carboxy-ethoxy)phenyl]-cyclopropanecarboxylic methyl ester

A solution of 1-[4-(2-tert-butoxycarbonyl-ethoxy)-phenyl]-cyclopropanecarboxylic methyl ester (6.3 g, 20 mmol) in HCl (20%, 200 mL) was heated at 110° C. for 1 h. After cooling to room temperature, the resulting mixture was filtered. The solid was washed with water and dried under vacuum to give 1-[4-(2-carboxy-ethoxy)-phenyl]-cyclopropanecarboxylic methyl ester (5.0 g, 96%). $^1$H NMR (300 MHz, DMSO) δ 7.23-7.19 (m, 2H), 6.85-6.81 (m, 2H), 4.13 (t, J=6.0 Hz, 2H), 3.51 (s, 3H), 2.66 (t, J=6.0 Hz, 2H), 1.43-1.39 (m, 2H), 1.14-1.10 (m, 2H).

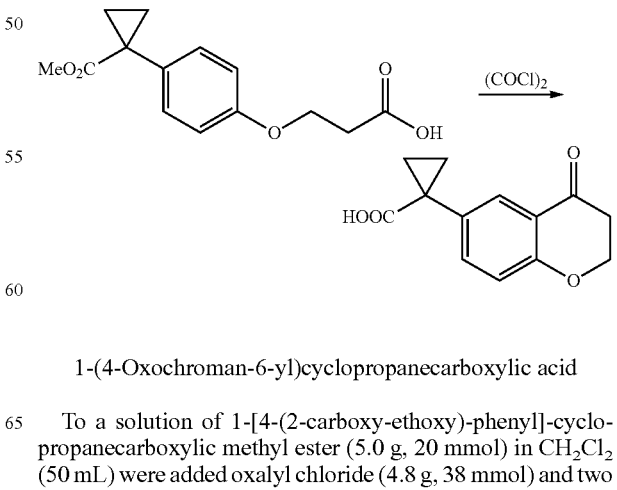

1-(4-Oxochroman-6-yl)cyclopropanecarboxylic acid

To a solution of 1-[4-(2-carboxy-ethoxy)-phenyl]-cyclopropanecarboxylic methyl ester (5.0 g, 20 mmol) in CH$_2$Cl$_2$ (50 mL) were added oxalyl chloride (4.8 g, 38 mmol) and two drops of DMF at 0° C. The mixture was stirred at 0-5° C. for 1 h and then evaporated under vacuum. To the resulting mixture was added CH$_2$Cl$_2$ (50 mL) at 0° C. and stirring was continued at 0-5° C. for 1 h. The reaction was slowly quenched with water and was extracted with EtOAc (50 mL×3). The combined organic extracts were dried over anhydrous Na$_2$SO$_4$ and evaporated under vacuum to give the crude product, which was purified by column chromatography on silica gel (petroleum ether/ethyl acetate 20:1-2:1) to give 1-(4-oxochroman-6-yl)cyclopropanecarboxylic acid (830 mg, 19%) and methyl 1-(4-oxochroman-6-yl)cyclopropanecarboxylate (1.8 g, 38%). 1-(4-Oxochroman-6-yl)cyclopropane-carboxylic acid: $^1$H NMR (400 MHz, DMSO) δ 12.33 (br s, 1H), 7.62 (d, J=2.0 Hz, 1H), 7.50 (dd, J=2.4, 8.4 Hz, 1H), 6.95 (d, J=8.4 Hz, 1H), 4.50 (t, J=6.4 Hz, 2H), 2.75 (t, J=6.4 Hz, 2H), 1.44-1.38 (m, 2H), 1.10-1.07 (m, 2H). MS (ESI) m/z (M+H$^+$) 231.4. 1-(4-Oxochroman-6-yl)cyclopropanecarboxylate: $^1$H NMR (400 MHz, CDCl$_3$) δ 7.83 (d, J=2.4 Hz, 1H), 7.48 (dd, J=2.4, 8.4 Hz, 1H), 6.93 (d, J=8.4 Hz, 1H), 4.55-4.52 (m, 2H), 3.62 (s, 3H), 2.80 (t, J=6.4 Hz, 2H), 1.62-1.56 (m, 2H), 1.18-1.15 (m, 2H).

Example 23

1-(4-Hydroxy-4-methoxychroman-6-yl)cyclopropanecarboxylic acid

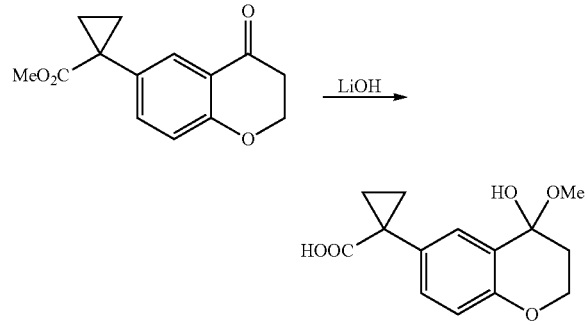

1-(4-Hydroxy-4-methoxychroman-6-yl)cyclopropanecarboxylic acid

To a solution of methyl 1-(4-oxochroman-6-yl)cyclopropanecarboxylate (1.0 g, 4.1 mmol) in MeOH (20 mL) and water (20 mL) was added LiOH.H$_2$O (0.70 g, 16 mmol) in portions at room temperature. The mixture was stirred overnight at room temperature before the MeOH was removed by evaporation under vacuum. Water and Et$_2$O were added to the residue and the aqueous layer was separated, acidified with HCl and extracted with EtOAc (50 mL×3). The combined organic extracts dried over anhydrous Na$_2$SO$_4$ and evaporated under vacuum to give 1-(4-hydroxy-4-methoxychroman-6-yl)cyclopropanecarboxylic acid (480 mg, 44%). $^1$H NMR (400 MHz, CDCl$_3$) δ 12.16 (s, 1H), 7.73 (d, J=2.0 Hz, 1H), 7.47 (dd, J=2.0, 8.4 Hz, 1H), 6.93 (d, J=8.8 Hz, 1H), 3.83-3.80 (m, 2H), 3.39 (s, 3H), 3.28-3.25 (m, 2H), 1.71-1.68 (m, 2H), 1.25-1.22 (m, 2H). MS (ESI) m/z (M+H$^+$) 263.1.

Example 24

1-(4-Hydroxy-4-methoxychroman-6-yl)cyclopropanecarboxylic acid

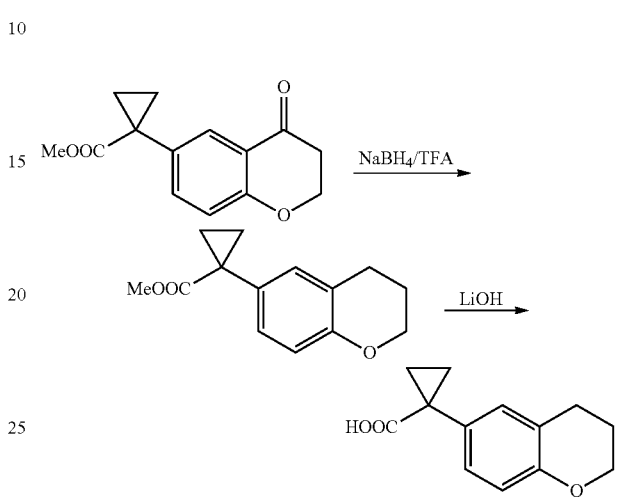

1-Chroman-6-yl-cyclopropanecarboxylic methyl ester

To trifluoroacetic acid (20 mL) was added NaBH$_4$ (0.70 g, 130 mmol) in portions at 0° C. under N$_2$ atmosphere. After stirring for 5 min, a solution of 1-(4-oxo-chroman-6-yl)-cyclopropanecarboxylic methyl ester (1.6 g, 6.5 mmol) was added at 15° C. The reaction mixture was stirred for 1 h at room temperature before being slowly quenched with water. The resulting mixture was extracted with EtOAc (50 mL×3). The combined organic extracts dried over anhydrous Na$_2$SO$_4$ and evaporated under vacuum to give 1-chroman-6-yl-cyclopropanecarboxylic methyl ester (1.4 g, 92%), which was used directly in the next step. $^1$H NMR (300 MHz, CDCl$_3$) δ 7.07-7.00 (m, 2H), 6.73 (d, J=8.4 Hz, 1H), 4.17 (t, J=5.1 Hz, 2H), 3.62 (s, 3H), 2.79-2.75 (m, 2H), 2.05-1.96 (m, 2H), 1.57-1.54 (m, 2H), 1.16-1.13 (m, 2H).

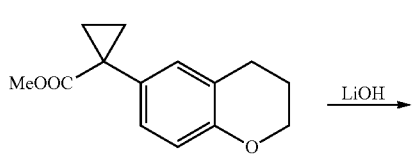

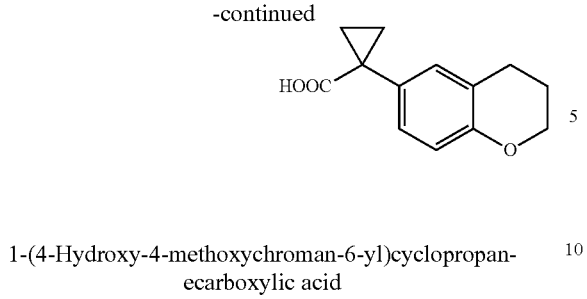

1-(4-Hydroxy-4-methoxychroman-6-yl)cyclopropanecarboxylic acid

To a solution of 1-chroman-6-yl-cyclopropanecarboxylic methyl ester (1.4 g, 60 mmol) in MeOH (20 mL) and water (20 mL) was added LiOH.H$_2$O (1.0 g, 240 mmol) in portions at room temperature. The mixture was stirred overnight at room temperature before the MeOH was removed by evaporation under vacuum. Water and Et$_2$O were added and the aqueous layer was separated, acidified with HCl and extracted with EtOAc (50 mL×3). The combined organic extracts dried over anhydrous Na$_2$SO$_4$ and evaporated under vacuum to give 1-(4-Hydroxy-4-methoxychroman-6-yl)cyclopropanecarboxylic acid (1.0 g, 76%). $^1$H NMR (400 MHz, DMSO) δ 12.10 (br s, 1H), 6.95 (d, J=2.4 Hz, 2H), 6.61-6.59 (m, 1H), 4.09-4.06 (m, 2H), 2.70-2.67 (m, 2H), 1.88-1.86 (m, 2H), 1.37-1.35 (m, 2H), 1.04-1.01 (m, 2H). MS (ESI) m/z (M+H$^+$) 217.4.

Example 25

1-(3-Methylbenzo[d]isoxazol-5-yl)cyclopropanecarboxylic acid

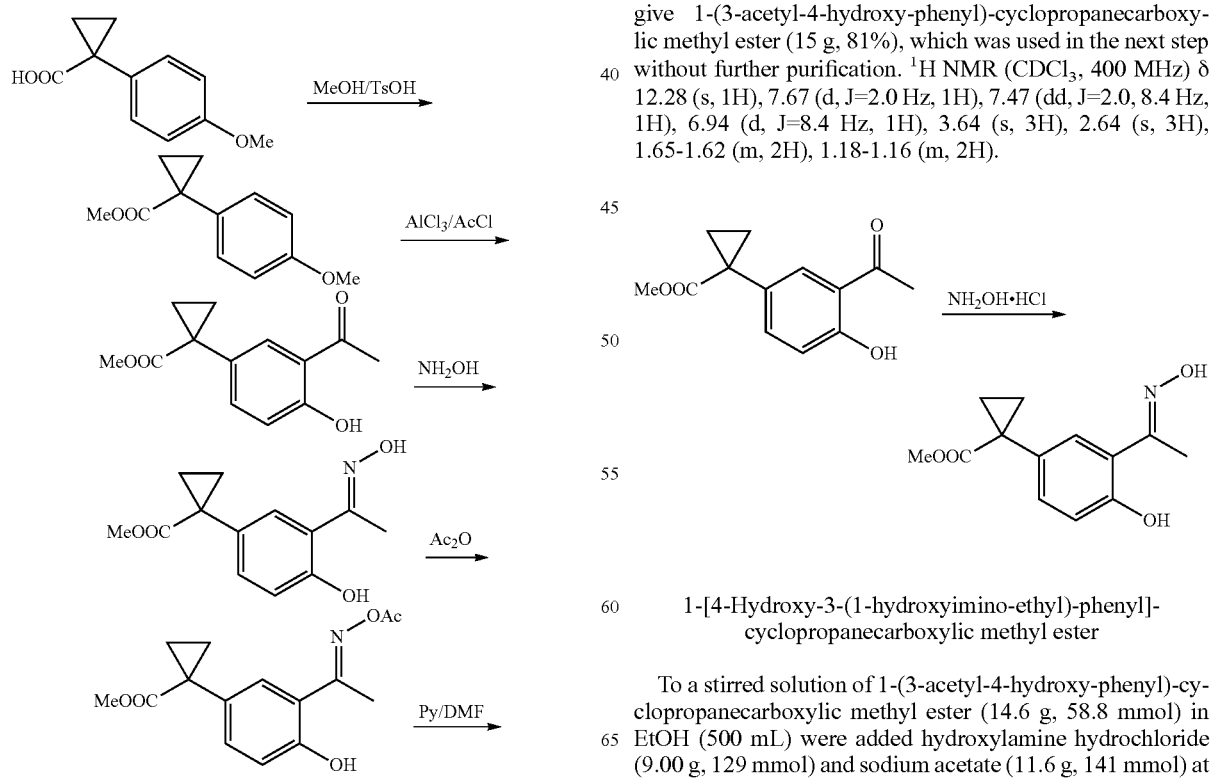

1-(3-Acetyl-4-hydroxy-phenyl)-cyclopropanecarboxylic methyl ester

To a stirred suspension of AlCl$_3$ (58 g, 440 mmol) in CS$_2$ (500 mL) was added acetyl chloride (7.4 g, 95 mmol) at room temperature. After stirring for 5 min, methyl 1-(4-methoxyphenyl)cyclopropanecarboxylate (15 g, 73 mmol) was added. The reaction mixture was heated at reflux for 2 h before ice water was added carefully to the mixture at room temperature. The resulting mixture was extracted with EtOAc (150 mL×3). The combined organic extracts were dried over anhydrous Na$_2$SO$_4$ and evaporated under reduced pressure to give 1-(3-acetyl-4-hydroxy-phenyl)-cyclopropanecarboxylic methyl ester (15 g, 81%), which was used in the next step without further purification. $^1$H NMR (CDCl$_3$, 400 MHz) δ 12.28 (s, 1H), 7.67 (d, J=2.0 Hz, 1H), 7.47 (dd, J=2.0, 8.4 Hz, 1H), 6.94 (d, J=8.4 Hz, 1H), 3.64 (s, 3H), 2.64 (s, 3H), 1.65-1.62 (m, 2H), 1.18-1.16 (m, 2H).

1-[4-Hydroxy-3-(1-hydroxyimino-ethyl)-phenyl]-cyclopropanecarboxylic methyl ester To a stirred solution of 1-(3-acetyl-4-hydroxy-phenyl)-cyclopropanecarboxylic methyl ester (14.6 g, 58.8 mmol) in EtOH (500 mL) were added hydroxylamine hydrochloride (9.00 g, 129 mmol) and sodium acetate (11.6 g, 141 mmol) at room temperature. The resulting mixture was heated at reflux overnight. After removal of EtOH under vacuum, water (200 mL) and EtOAc (200 mL) were added. The organic layer was separated and the aqueous layer was extracted with EtOAc (100 mL×3). The combined organic layers were dried over anhydrous $Na_2SO_4$ and evaporated under vacuum to give 1-[4-hydroxy-3-(1-hydroxyimino-ethyl)-phenyl]-cyclopropanecarboxylic methyl ester (14.5 g, 98%), which was used in the next step without further purification. $^1$H NMR ($CDCl_3$, 400 MHz) δ 11.09 (s, 1H), 7.39 (d, J=2.0 Hz, 1H), 7.23 (d, J=2.0 Hz, 1H), 7.14 (s, 1H), 6.91 (d, J=8.4 Hz, 1H), 3.63 (s, 3H), 2.36 (s, 3H), 1.62-1.59 (m, 2H), 1.18-1.15 (m, 2H).

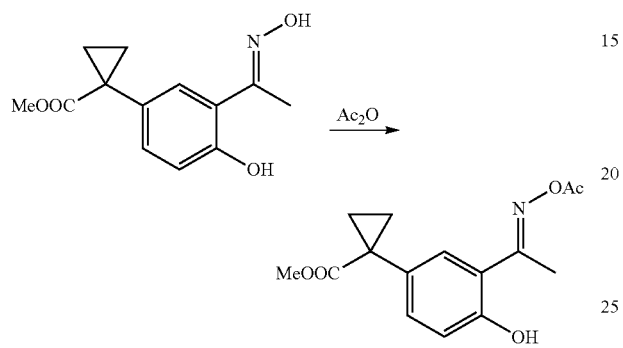

(E)-Methyl 1-(3-(1-(acetoxyimino)ethyl)-4-hydroxyphenyl)cyclopropane carboxylate The solution of 1-[4-hydroxy-3-(1-hydroxyimino-ethyl)-phenyl]-cyclopropanecarboxylic methyl ester (10.0 g, 40.1 mmol) in $Ac_2O$ (250 mL) was heated at 45° C. for 4 h. The $Ac_2O$ was removed by evaporation under vacuum before water (100 mL) and EtOAc (100 mL) were added. The organic layer was separated and the aqueous layer was extracted with EtOAc (100 mL×2). The combined organic layers were dried over anhydrous $Na_2SO_4$ and evaporated under vacuum to give (E)-methyl 1-(3-(1-(acetoxyimino) ethyl)-4-hydroxyphenyl)cyclopropanecarboxylate (10.5 g, 99%), which was used in the next step without further purification.

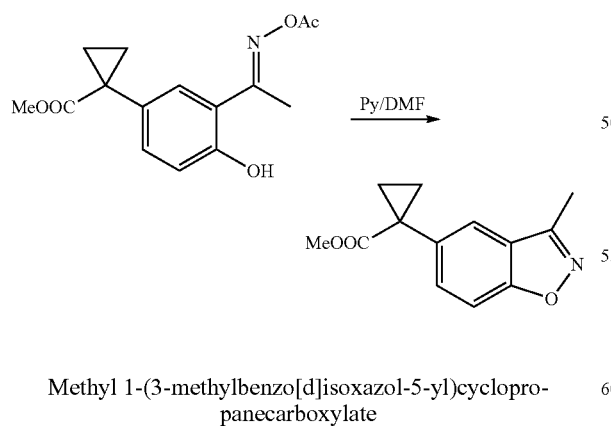

Methyl 1-(3-methylbenzo[d]isoxazol-5-yl)cyclopropanecarboxylate

A solution of (E)-methyl 1-(3-(1-(acetoxyimino)ethyl)-4-hydroxyphenyl)cyclopropane carboxylate (10.5 g, 39.6 mmol) and pyridine (31.3 g, 396 mmol) in DMF (150 mL) was heated at 125° C. for 10 h. The cooled reaction mixture was poured into water (250 mL) and was extracted with EtOAc (100 mL×3). The combined organic layers were dried over anhydrous $Na_2SO_4$ and evaporated under vacuum to give the crude product, which was purified by column chromatography on silica gel (petroleum ether/ethyl acetate 50:1) to give methyl 1-(3-methylbenzo[d]isoxazol-5-yl)cyclopropanecarboxylate (7.5 g, 82%). $^1$H NMR ($CDCl_3$ 300 MHz) δ 738-7.54 (m, 2H), 7.48 (dd, J=1.5, 8.1 Hz, 1H), 3.63 (s, 3H), 2.58 (s, 3H), 1.71-1.68 (m, 2H), 1.27-1.23 (m, 2H).

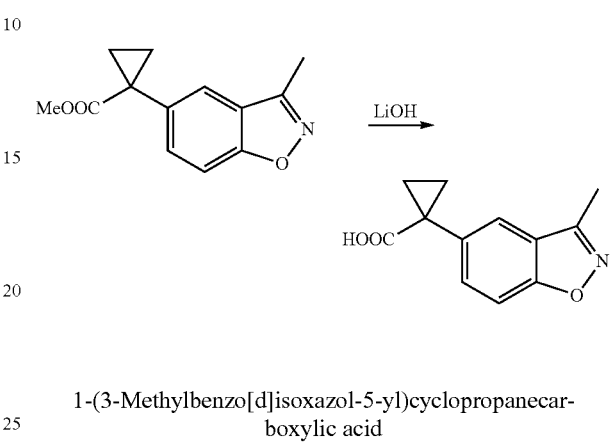

1-(3-Methylbenzo[d]isoxazol-5-yl)cyclopropanecarboxylic acid

To a solution of methyl 1-(3-methylbenzo[d]isoxazol-5-yl) cyclopropanecarboxylate (1.5 g, 6.5 mmol) in MeOH (20 mL) and water (2 mL) was added $LiOH.H_2O$ (0.80 g, 19 mmol) in portions at room temperature. The reaction mixture was stirred at room temperature overnight before the MeOH was removed by evaporation under vacuum. Water and $Et_2O$ were added and the aqueous layer was separated, acidified with HCl and extracted with EtOAc (50 mL×3). The combined organic extracts were dried over anhydrous $Na_2SO_4$ and evaporated under vacuum to give 1-(3-methylbenzo[d] isoxazol-5-yl)cyclopropanecarboxylic acid (455 mg, 32%). $^1$H NMR (400 MHz, DMSO) δ 12.40 (br s, 1H), 7.76 (s, 1H), 7.60-7.57 (m, 2H), 2.63 (s, 3H), 1.52-1.48 (m, 2H), 1.23-1.19 (m, 2H). MS (ESI) m/z (M+H$^+$) 218.1.

Example 26

1-(Spiro[benzo[d][1,3]dioxole-2,1'-cyclobutane]-5-yl)cyclopropane carboxylic acid

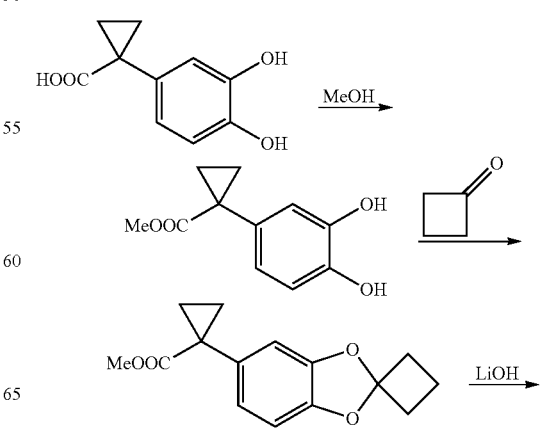

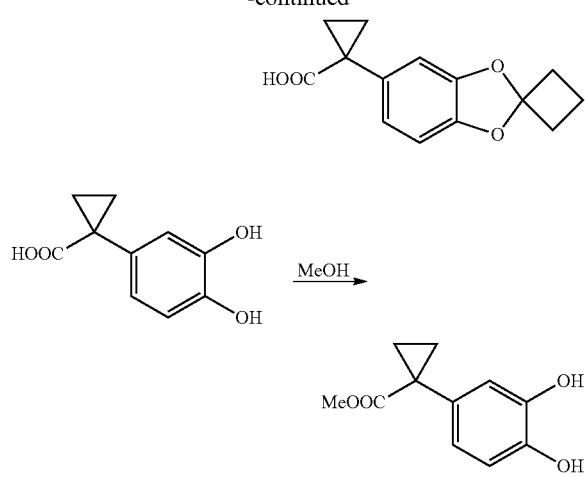

1-(3,4-Dihydroxy-phenyl)-cyclopropanecarboxylic methyl ester

To a solution of 1-(3,4-dihydroxyphenyl)cyclopropanecarboxylic acid (4.5 g) in MeOH (30 mL) was added TsOH (0.25 g, 1.3 mmol). The stirring was continued at 50° C. overnight before the mixture was cooled to room temperature. The mixture was concentrated under vacuum and the residue was purified by column chromatography on silica gel (petroleum ether/ethyl acetate 3:1) to give 1-(3,4-dihydroxy-phenyl)-cyclopropanecarboxylic methyl ester (2.1 g). $^1$H NMR (DMSO 300 MHz) δ 8.81 (brs, 2H), 6.66 (d, J=2.1 Hz, 1H), 6.61 (d, J=8.1 Hz, 1H), 6.53 (dd, J=2.1, 8.1 Hz, 1H), 3.51 (s, 3H), 1.38-1.35 (m, 2H), 1.07-1.03 (m, 2H).

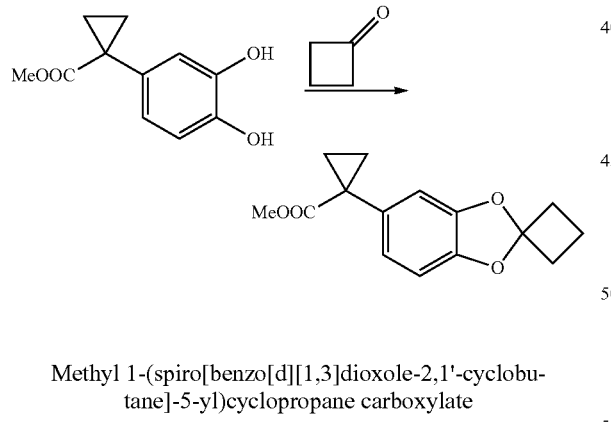

Methyl 1-(spiro[benzo[d][1,3]dioxole-2,1'-cyclobutane]-5-yl)cyclopropane carboxylate To a solution of 1-(3,4-dihydroxy-phenyl)-cyclopropanecarboxylic methyl ester (1.0 g, 4.8 mmol) in toluene (30 mL) was added TsOH (0.10 g, 0.50 mmol) and cyclobutanone (0.70 g, 10 mmol). The reaction mixture was heated at reflux for 2 h before being concentrated under vacuum. The residue was purified by chromatography on silica gel (petroleum ether/ethyl acetate 15:1) to give methyl 1-(spiro[benzo[d][1,3]dioxole-2,1'-cyclobutane]-5-yl)cyclopropanecarboxylate (0.6 g, 50%). $^1$H NMR (CDCl$_3$ 300 MHz) δ 6.78-6.65 (m, 3H), 3.62 (s, 3H), 2.64-2.58 (m, 4H), 1.89-1.78 (m, 2H), 1.56-1.54 (m, 2H), 1.53-1.12 (m, 2H).

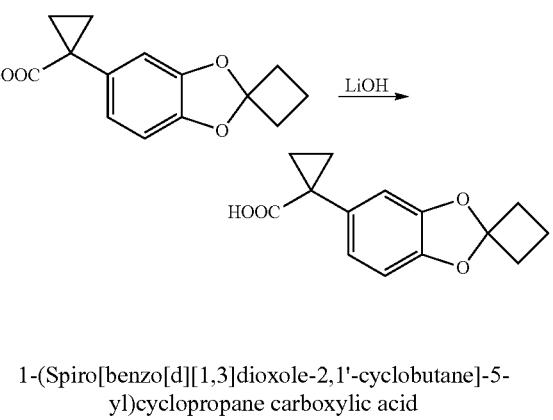

1-(Spiro[benzo[d][1,3]dioxole-2,1'-cyclobutane]-5-yl)cyclopropane carboxylic acid To a mixture of methyl 1-(spiro[benzo[d][1,3]dioxole-2,1'-cyclobutane]-5-yl)cyclopropanecarboxylate (0.60 g, 2.3 mmol) in THF/H$_2$O (4:1, 10 mL) was added LiOH (0.30 g, 6.9 mmol). The mixture was stirred at 60° C. for 24 h. HCl (0.5 N) was added slowly to the mixture at 0° C. until pH 2-3. The mixture was extracted with EtOAc (10 mL×3). The combined organic phases were washed with brine, dried over anhydrous MgSO$_4$, and washed with petroleum ether to give 1-(spiro[benzo[d][1,3]-dioxole-2,1'-cyclobutane]-5-yl)cyclopropane carboxylic acid (330 mg, 59%). $^1$H NMR (400 MHz, CDCl$_3$) δ 6.78-6.65 (m, 3H), 2.65-2.58 (m, 4H), 1.86-1.78 (m, 2H), 1.63-1.60 (m, 2H), 1.26-1.19 (m, 2H).

Example 27

2-(2,3-Dihydrobenzo[b][1,4]dioxin-6-yl)acetonitrile

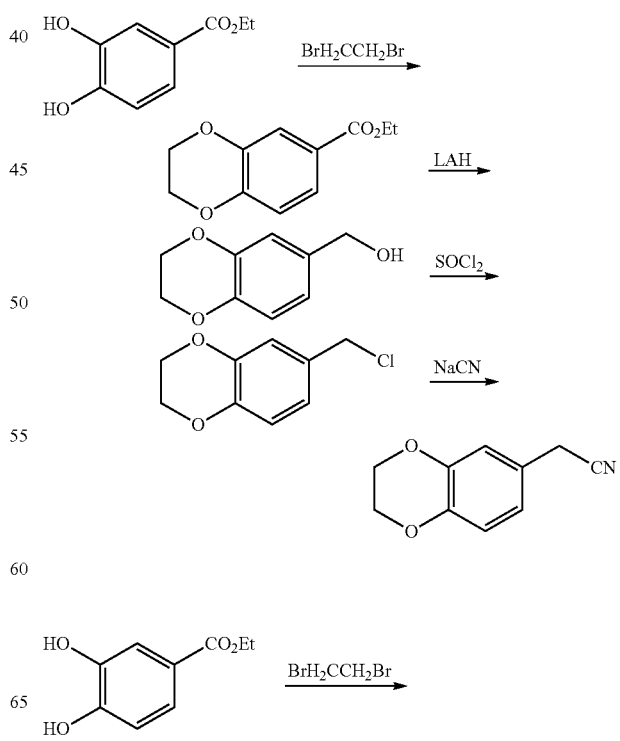

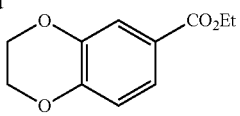

2,3-Dihydro-benzo[1,4]dioxine-6-carboxylic acid ethyl ester

To a suspension of Cs$_2$CO$_3$ (270 g, 1.49 mol) in DMF (1000 mL) were added 3,4-dihydroxybenzoic acid ethyl ester (54.6 g, 0.3 mol) and 1,2-dibromoethane (54.3 g, 0.29 mol) at room temperature. The resulting mixture was stirred at 80° C. overnight and then poured into ice-water. The mixture was extracted with EtOAc (200 mL×3). The combined organic layers were washed with water (200 mL×3) and brine (100 mL), dried over Na$_2$SO$_4$ and concentrated to dryness. The residue was purified by column (petroleum ether/ethyl acetate 50:1) on silica gel to obtain 2,3-dihydro-benzo[1,4]dioxine-6-carboxylic acid ethyl ester (18 g, 29%). $^1$H NMR (300 MHz, CDCl$_3$) δ 7.53 (dd, J=1.8, 7.2 Hz, 2H), 6.84-6.87 (m, 1H), 4.22-4.34 (m, 6H), 1.35 (t, J=7.2 Hz, 3H).

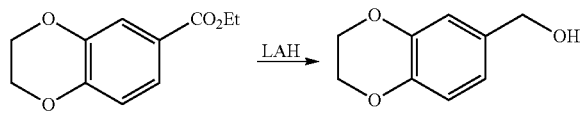 [SMILES: CCOC(=O)c1ccc2c(c1)OCCO2 ; "LAH" ; OCc1ccc2c(c1)OCCO2]

(2,3-Dihydro-benzo[1,4]dioxin-6-yl)-methanol

To a suspension of LiAlH$_4$ (2.8 g, 74 mmol) in THF (20 mL) was added dropwise a solution of 2,3-dihydro-benzo[1,4]dioxine-6-carboxylic acid ethyl ester (15 g, 72 mmol) in THF (10 mL) at 0° C. under N$_2$. The mixture was stirred at room temperature for 1 h and then quenched carefully with addition of water (2.8 mL) and NaOH (10%, 28 mL) with cooling. The precipitated solid was filtered off and the filtrate was evaporated to dryness to obtain (2,3-dihydro-benzo[1,4]dioxin-6-yl)-methanol (10.6 g). $^1$H NMR (300 MHz, DMSO-d$_6$) δ 6.73-6.78 (m, 3H), 5.02 (t, J=5.7 Hz, 1H), 4.34 (d, J=6.0 Hz, 2H), 4.17-4.20 (m, 4H).

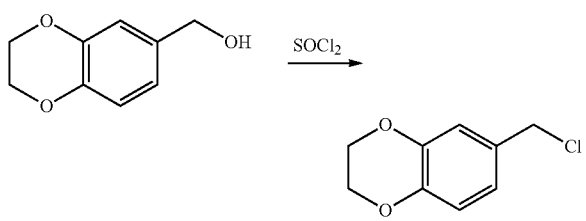

6-Chloromethyl-2,3-dihydro-benzo[1,4]dioxine

A mixture of (2,3-dihydro-benzo[1,4]dioxin-6-yl)methanol (10.6 g) in SOCl$_2$ (10 mL) was stirred at room temperature for 10 min and then poured into ice-water. The organic layer was separated and the aqueous phase was extracted with dichloromethane (50 mL×3). The combined organic layers were washed with NaHCO$_3$ (sat solution), water and brine, dried over Na$_2$SO$_4$ and concentrated to dryness to obtain 6-chloromethyl-2,3-dihydro-benzo[1,4]dioxine (12 g, 88% over two steps), which was used directly in next step.

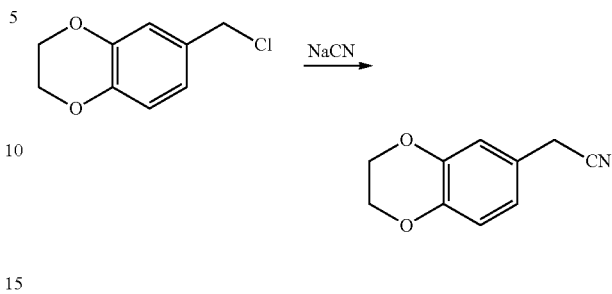

2-(2,3-Dihydrobenzo[b][1,4]dioxin-6-yl)acetonitrile

A mixture of 6-chloromethyl-2,3-dihydro-benzo[1,4]dioxine (12.5 g, 67.7 mmol) and NaCN (4.30 g, 87.8 mmol) in DMSO (50 mL) was stirred at rt for 1 h. The mixture was poured into water (150 mL) and then extracted with dichloromethane (50 mL×4). The combined organic layers were washed with water (50 mL×2) and brine (50 mL), dried over Na$_2$SO$_4$ and concentrated to dryness. The residue was purified by column (petroleum ether/ethyl acetate 50:1) on silica gel to obtain 2-(2,3-dihydrobenzo[b][1,4]dioxin-6-yl)acetonitrile as a yellow oil (10.2 g, 86%). $^1$H-NMR (300 MHz, CDCl$_3$) δ 6.78-6.86 (m, 3H), 4.25 (s, 4H), 3.63 (s, 2H).

The following Table 2 contains a list of carboxylic acid building blocks that were commercially available, or prepared by one of the three methods described above:

TABLE 2

Carboxylic acid building blocks.

| Name | Structure |
| --- | --- |
| 1-benzo[1,3]dioxol-5-ylcyclopropane-1-carboxylic acid | 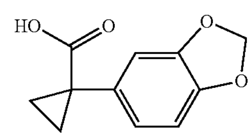 [SMILES: O=C(O)C1(c2ccc3c(c2)OCO3)CC1] |
| 1-(2,2-difluorobenzo[1,3]dioxol-5-yl)cyclopropane-1-carboxylic acid | 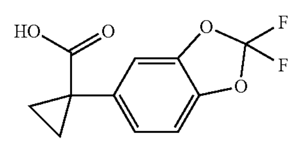 [SMILES: O=C(O)C1(c2ccc3c(c2)OC(F)(F)O3)CC1] |
| 1-(3,4-dihydroxyphenyl)cyclopropanecarboxylic acid | 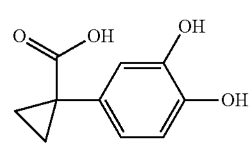 |
| 1-(3-methoxyphenyl)cyclopropane-1-carboxylic acid | 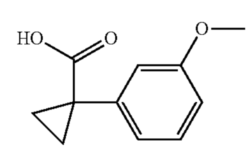 |

TABLE 2-continued

Carboxylic acid building blocks.

| Name | Structure |
|---|---|
| 1-(2-methoxyphenyl)cyclopropane-1-carboxylic acid | |
| 1-[4-(trifluoromethoxy)phenyl]cyclopropane-1-carboxylic acid | |
| 1-(2,2-dimethylbenzo[d][1,3]dioxol-5-yl)cyclopropanecarboxylic acid | |
| tetrahydro-4-(4-methoxyphenyl)-2H-pyran-4-carboxylic acid | |
| 1-phenylcyclopropane-1-carboxylic acid | |
| 1-(4-methoxyphenyl)cyclopropane-1-carboxylic acid | |
| 1-(4-chlorophenyl)cyclopropane-1-carboxylic acid | |
| 1-(3-hydroxyphenyl)cyclopropanecarboxylic acid | |
| 1-phenylcyclopentanecarboxylic acid | |
| 1-(2-oxo-2,3-dihydrobenzo[d]oxazol-5-yl)cyclopropanecaxboxylic acid | 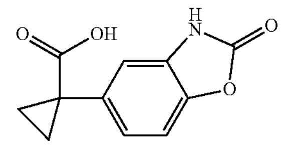 [SMILES: O=C(O)C1(c2ccc3oc(=O)[nH]c3c2)CC1] |
| 1-(benzofuran-5-yl)cyclopropanecarboxylic acid | 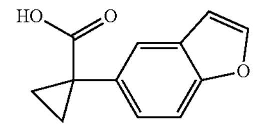 [SMILES: O=C(O)C1(c2ccc3occc3c2)CC1] |
| 1-(4-methoxyphenyl)cyclohexanecarboxylic acid | 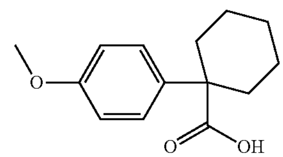 |
| 1-(4-chlorophenyl)cyclohexanecarboxylic acid | 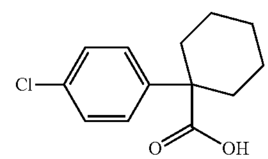 [SMILES: O=C(O)C1(c2ccc(Cl)cc2)CCCCC1] |
| 1-(2,3-dihydrobenzofuran-5-yl)cyclopropanecarboxylic acid | 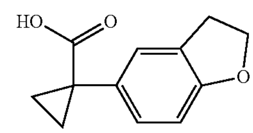 [SMILES: O=C(O)C1(c2ccc3c(c2)CCO3)CC1] |
| 1-(3,3-dimethyl-2,3-dihydrobenzofuran-5-yl)cyclopropanecarboxylic acid | 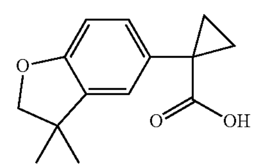 [SMILES: CC1(C)COc2ccc(C3(C(=O)O)CC3)cc21] |
| 1-(7-methoxybenzo[d][1,3]dioxol-5-yl)cyclopropanecarboxylic acid | 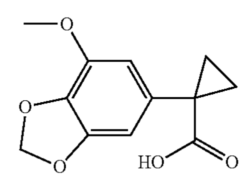 [SMILES: COc1cc(C2(C(=O)O)CC2)cc2c1OCO2] |
| 1-(3-hydroxy-4-methoxyphenyl)cyclopropanecarboxylic acid | 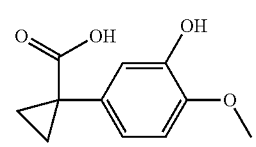 |
| 1-(4-chloro-3-hydroxyphenyl)cyclopropanecarboxylic acid | 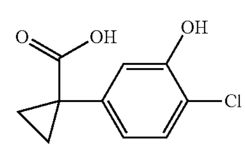 [SMILES: O=C(O)C1(c2ccc(Cl)c(O)c2)CC1] |
| 1-(3-(benzyloxy)-4-chlorophenyl)cyclopropanecarboxylic acid | 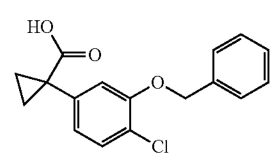 [SMILES: O=C(O)C1(c2ccc(Cl)c(OCc3ccccc3)c2)CC1] |

TABLE 2-continued

Carboxylic acid building blocks.

| Name | Structure |
|---|---|
| 1-(4-chlorophenyl)cyclopentanecarboxylic acid | 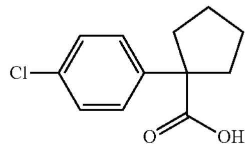 [SMILES: O=C(O)C1(c2ccc(Cl)cc2)CCCC1] |
| 1-(3-(benzyloxy)-4-methoxyphenyl)cyclopropanecarboxylic acid | 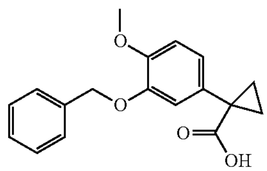 [SMILES: COc1ccc(C2(C(=O)O)CC2)cc1OCc1ccccc1] |
| 1-(3-chloro-4-methoxyphenyl)cyclopropanecarboxylic acid | 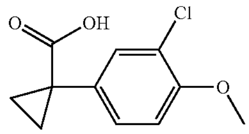 |
| 1-(3-fluoro-4-methoxyphenyl)cyclopropanecarboxylic acid | 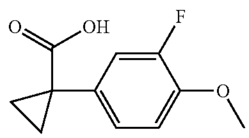 |
| 1-(4-methoxy-3-methylphenyl)cyclopropanecarboxylic acid | 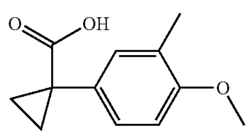 |
| 1-(4-(benzyloxy)-3-thoxyphenyl)cyclopropanecarboxylic acid | 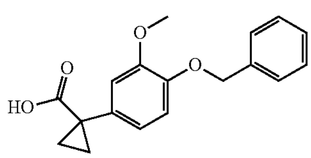 [SMILES: COc1cc(C2(C(=O)O)CC2)ccc1OCc1ccccc1] |
| 1-(4-chloro-3-methoxyphenyl)cyclopropanecarboxylic acid | 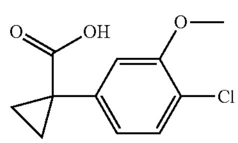 |
| 1-(3-chloro-4-hydroxyphenyl)cyclopropanecarboxylic acid | 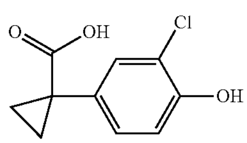 [SMILES: O=C(O)C1(c2ccc(O)c(Cl)c2)CC1] |
| 1-(3-(hydroxymethyl)-4-methoxyphenyl)cyclopropanecarboxylic acid | 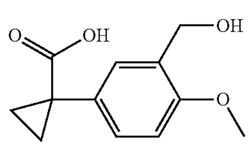 [SMILES: COc1ccc(C2(C(=O)O)CC2)cc1CO] |
| 1-(4-methoxyphenyl)cyclopentanecarboxylic acid | 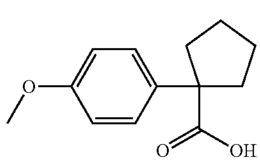 [SMILES: COc1ccc(C2(C(=O)O)CCCC2)cc1] |
| 1-phenylcyclohexanecarboxylic acid | |
| 1-(3,4-dimethoxyphenyl)cyclopropanecarboxylic acid | |
| 1-(7-chlorobenzo[d][1,3]dioxol-5-yl)cyclopropanecarboxylic acid | |
| 1-(benzo[d]oxazol-5-yl)cyclopropanecarboxylic acid | |
| 1-(7-fluorobenzo[d][1,3]dioxol-5-yl)cyclopropanecarboxylic acid | |
| 1-(3,4-difluorophenyl)cyclopropanecarboxylic acid | |
| 1-(1H-indol-5-yl)cyclopropanecarboxylic acid | |
| 1-(1H-benzo[d]imidazol-5-yl)cyclopropanecarboxylic acid | |
| 1-(2-methyl-1H-benzo[d]imidazol-5-yl)cyclopropanecarboxylic acid | |
| 1-(1-methyl-1H-benzo[d]imidazol-5-yl)cyclopropanecarboxylic acid | |

TABLE 2-continued

Carboxylic acid building blocks.

| Name | Structure |
|---|---|
| 1-(3-methylbenzo[d]isoxazol-5-yl)cyclopropanecarboxylic acid | 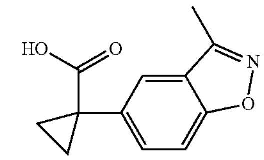 [SMILES: Cc1noc2ccc(C3(C(=O)O)CC3)cc12] |
| 1-(spiro[benzo[d][1,3]dioxole-2,1'-cyclobutane]-5-yl)cyclopropanecarboxylic acid | 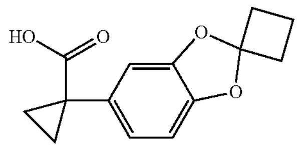 [SMILES: O=C(O)C1(c2ccc3c(c2)OC2(CCC2)O3)CC1] |
| 1-(1H-benzo[d][1,2,3]triazol-5-yl)cyclopropanecarboxylic acid | 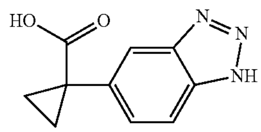 [SMILES: O=C(O)C1(c2ccc3[nH]nnc3c2)CC1] |
| 1-(1-methyl-1H-benzo[d][1,2,3]triazol-5-yl)cyclopropanecarboxylic acid | 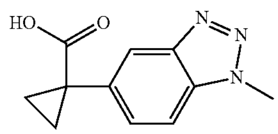 [SMILES: Cn1nnc2cc(C3(C(=O)O)CC3)ccc21] |
| 1-(1,3-dihydroisobenzofuran-5-yl)cyclopropanecarboxylic acid | 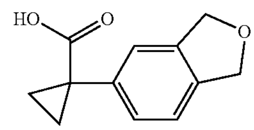 [SMILES: O=C(O)C1(c2ccc3c(c2)COC3)CC1] |
| 1-(6-fluorobenzo[d][1,3]dioxol-5-yl)cyclopropanecarboxylic acid | 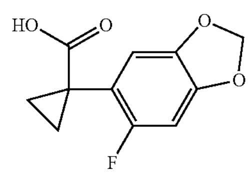 [SMILES: O=C(O)C1(c2cc3c(cc2F)OCO3)CC1] |
| 1-(2,3-dihydrobenzofuran-6-yl)cyclopropanecarboxylic acid | 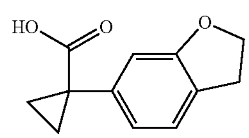 [SMILES: O=C(O)C1(c2ccc3c(c2)OCC3)CC1] |
| 1-(chroman-6-yl)cyclopropanecarboxylic acid | 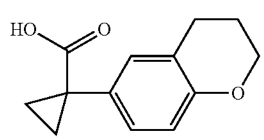 [SMILES: O=C(O)C1(c2ccc3c(c2)CCCO3)CC1] |
| 1-(4-hydroxy-4-methoxychroman-6-yl)cyclopropanecarboxylic acid | 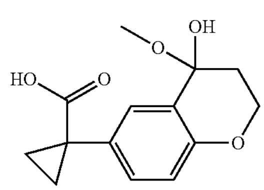 [SMILES: COC1(O)CCOc2ccc(C3(C(=O)O)CC3)cc21] |
| 1-(4-oxochroman-6-yl)cyclopropanecarboxylic acid | 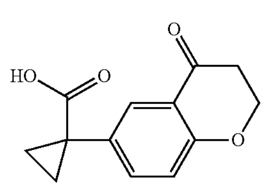 [SMILES: O=C1CCOc2ccc(C3(C(=O)O)CC3)cc21] |
| 1-(3,4-dichlorophenyl)cyclopropanecarboxylic acid | |
| 1-(2,3-dihydrobenzo[b][1,4]dioxin-6-yl)cyclopropanecarboxylic acid | |
| 1-(benzofuran-6-yl)cyclopropanecarboxylic acid | |

Specific Procedures

Synthesis of Aminoindole Building Blocks

Example 28

3-Methyl-1H-indol-6-amine

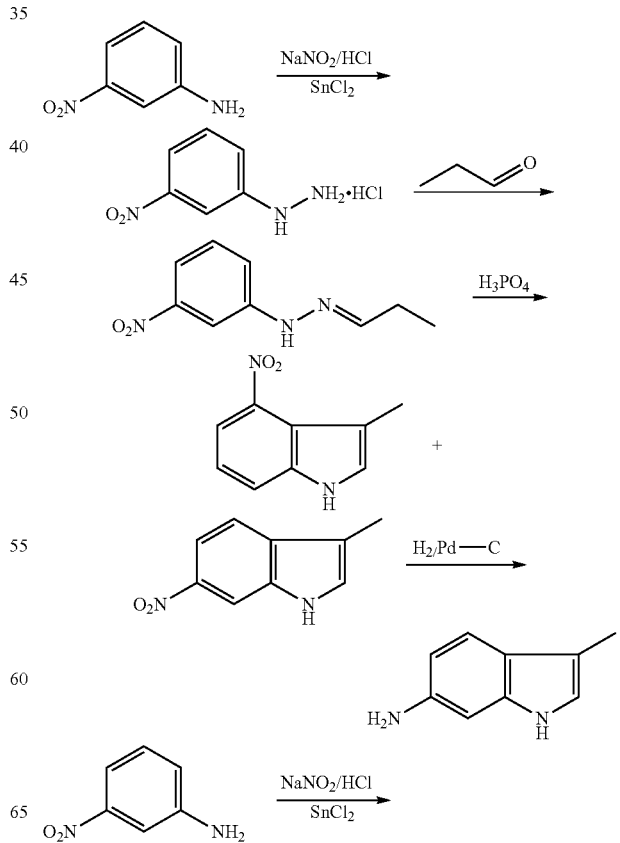

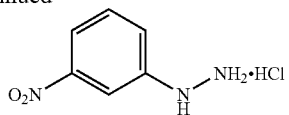

(3-Nitro-phenyl)-hydrazine hydrochloride salt

3-Nitro-phenylamine (27.6 g, 0.2 mol) was dissolved in the mixture of $H_2O$ (40 mL) and 37% HCl (40 mL). A solution of $NaNO_2$ (13.8 g, 0.2 mol) in $H_2O$ (60 mL) was added to the mixture at 0° C., and then a solution of $SnCl_2 \cdot H_2O$ (135.5 g, 0.6 mol) in 37% HCl (100 mL) was added at that temperature. After stirring at 0° C. for 0.5 h, the insoluble material was isolated by filtration and was washed with water to give (3-nitrophenyl)hydrazine hydrochloride (27.6 g, 73%).

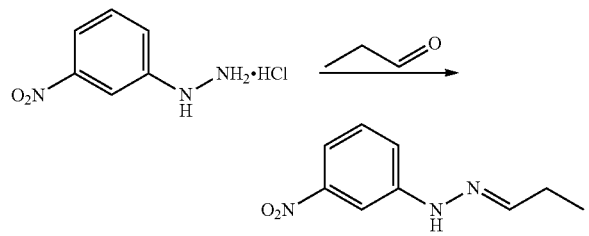

N-(3-Nitro-phenyl)-N'-propylidene-hydrazine

Sodium hydroxide solution (10%, 15 mL) was added slowly to a stirred suspension of (3-nitrophenyl)hydrazine hydrochloride (1.89 g, 10 mmol) in ethanol (20 mL) until pH 6. Acetic acid (5 mL) was added to the mixture followed by propionaldehyde (0.7 g, 12 mmol). After stirring for 3 h at room temperature, the mixture was poured into ice-water and the resulting precipitate was isolated by filtration, washed with water and dried in air to obtain (E)-1-(3-nitrophenyl)-2-propylidenehydrazine, which was used directly in the next step.

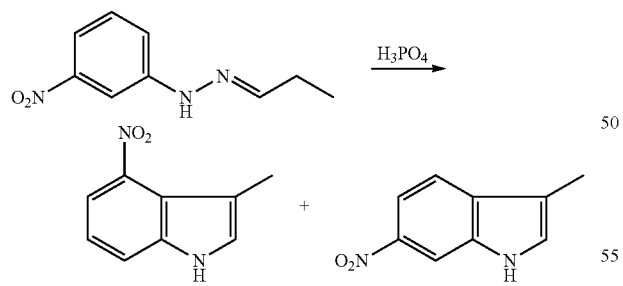

3-Methyl-4-nitro-1H-indole 3 and 3-methyl-6-nitro-1H-indole

A mixture of (E)-1-(3-nitrophenyl)-2-propylidenehydrazine dissolved in 85% $H_3PO_4$ (20 mL) and toluene (20 mL) was heated at 90-100° C. for 2 h. After cooling, toluene was removed under reduced pressure. The resultant oil was basified to pH 8 with 10% NaOH. The aqueous layer was extracted with EtOAc (100 mL×3). The combined organic layers were dried, filtered and concentrated under reduced pressure to afford the mixture of 3-methyl-4-nitro-1H-indole and 3-methyl-6-nitro-1H-indole [1.5 g in total, 86%, two steps from (3-nitrophenyl)hydrazine hydrochloride] which was used to the next step without further purification.

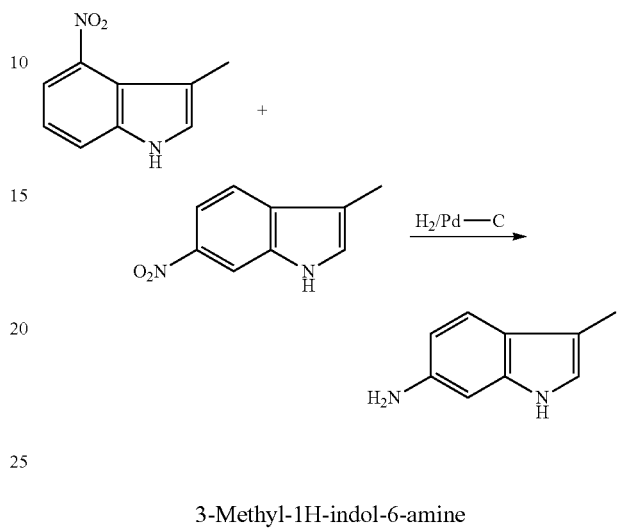

3-Methyl-1H-indol-6-amine

The crude mixture from previous steps (3 g, 17 mmol) and 10% Pd—C (0.5 g) in ethanol (30 mL) was stirred overnight under $H_2$ (1 atm) at room temperature. Pd—C was filtered off and the filtrate was concentrated under reduced pressure. The solid residue was purified by column to give 3-methyl-1H-indol-6-amine (0.6 g, 24%). $^1$H NMR ($CDCl_3$) δ 7.59 (br s. 1H), 7.34 (d, J=8.0 Hz, 1H), 6.77 (s, 1H), 6.64 (s, 1H), 6.57 (m, 1H), 3.57 (brs, 2H), 2.28 (s, 3H); MS (ESI) m/e (M+H$^+$) 147.2.

Example 29

3-tert-Butyl-1H-indol-5-amine

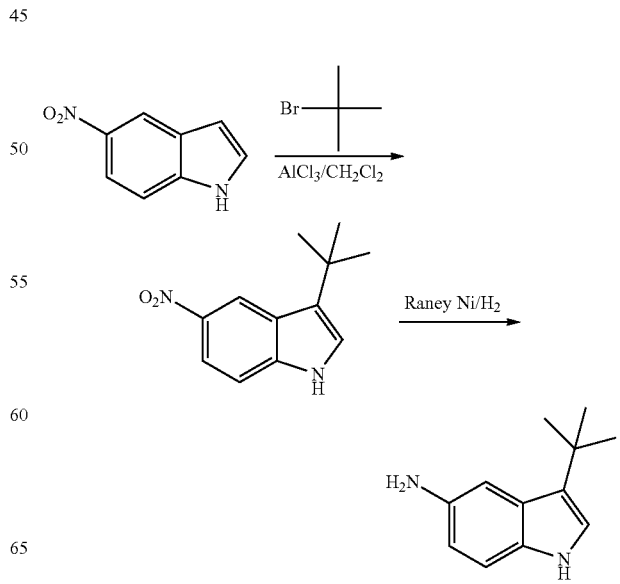

-continued

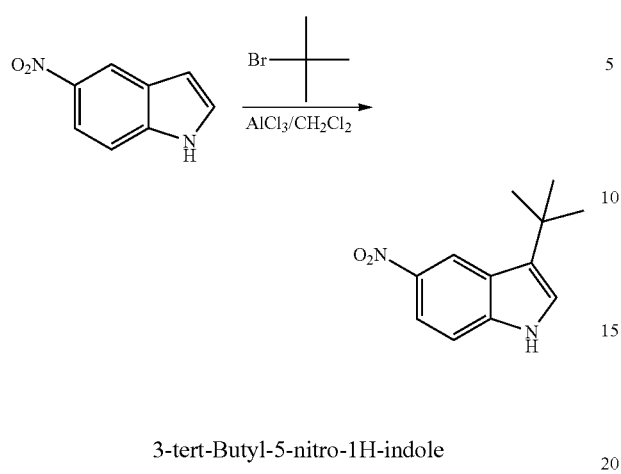

3-tert-Butyl-5-nitro-1H-indole

To a mixture of 5-nitro-1H-indole (6.0 g, 37 mmol) and AlCl₃ (24 g, 0.18 mol) in CH₂Cl₂ (100 mL) at 0° C. was added 2-bromo-2-methyl-propane (8.1 g, 37 mmol) dropwise. After being stirred at 15° C. overnight, the mixture was poured into ice (100 mL). The precipitated salts were removed by filtration and the aqueous layer was extracted with CH₂Cl₂ (30 mL×3). The combined organic layers were washed with water, brine, dried over Na₂SO₄ and concentrated under vacuum to obtain the crude product, which was purified by column chromatography on silica gel (petroleum ether/ethyl acetate=20:1) to give 3-tert-butyl-5-nitro-1H-indole (2.5 g, 31%). $^1$H NMR (CDCl₃, 400 MHz) δ 8.49 (d, J=1.6 Hz, 1H), 8.31 (brs, 1H), 8.05 (dd, J=2.0, 8.8 Hz, 1H), 7.33 (d, J=8.8 Hz, 1H), 6.42 (d, J=1.6 Hz, 1H), 1.42 (s, 9H).

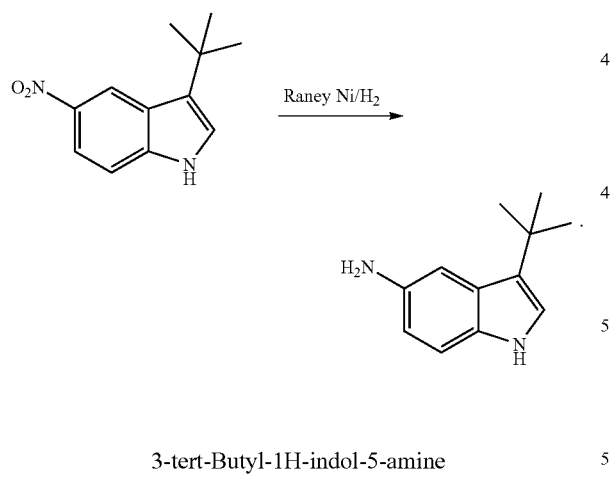

3-tert-Butyl-1H-indol-5-amine

To a solution of 3-tert-butyl-5-nitro-1H-indole (2.5 g, 12 mmol) in MeOH (30 mL) was added Raney Nickel (0.2 g) under N₂ protection. The mixture was stirred under hydrogen atmosphere (1 atm) at 15° C. for 1 h. The catalyst was filtered off and the filtrate was concentrated to dryness under vacuum. The residue was purified by preparative HLPC to afford 3-tert-butyl-1H-indol-5-amine (0.43 g, 19%). $^1$H NMR (CDCl₃, 400 MHz) δ 7.72 (br.s, 1H), 7.11 (d, J=8.4 Hz, 1H), 6.86 (d, J=2.0 Hz, 1H), 6.59 (dd, J=2.0, 8.4 Hz, 1H), 6.09 (d, J=1.6 Hz, 1H), 1.37 (s, 9H); MS (ESI) m/e (M+H⁺) 189.1.

Example 30

2-tert-Butyl-6-fluoro-1H-indol-5-amine and 6-tert-butoxy-2-tert-butyl-1H-indol-5-amine

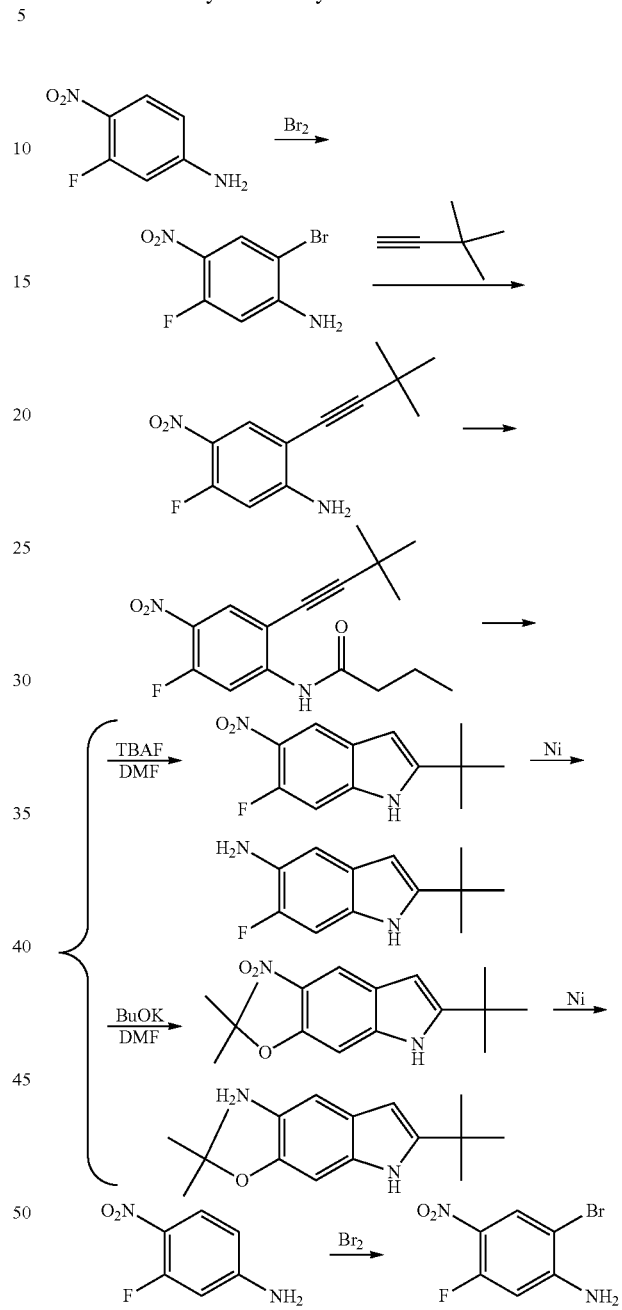

2-Bromo-5-fluoro-4-nitroaniline

To a mixture of 3-fluoro-4-nitroaniline (6.5 g, 42.2 mmol) in AcOH (80 mL) and chloroform (25 mL) was added dropwise Br₂ (2.15 mL, 42.2 mmol) at 0° C. After addition, the resulting mixture was stirred at room temperature for 2 h and then poured into ice water. The mixture was basified with aqueous NaOH (10%) to pH ~8.0-9.0 under cooling and then extracted with EtOAc (50 mL×3). The combined organic layers were washed with water (80 mL×2) and brine (100 mL), dried over Na₂SO₄ and concentrated under reduced pressure to give 2-bromo-5-fluoro-4-nitroaniline (9 g, 90%). $^1$H-NMR (400 MHz, DMSO-d$_6$) δ 8.26 (d, J=8.0, Hz, 1H), 7.07 (brs, 2H), 6.62 (d, J=9.6 Hz, 1H).

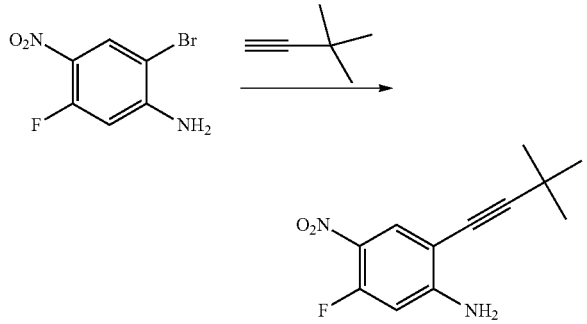

2-(3,3-Dimethylbut-1-ynyl)-5-fluoro-4-nitroaniline

A mixture of 2-bromo-5-fluoro-4-nitroaniline (9.0 g, 38.4 mmol), 3,3-dimethyl-but-1-yne (9.95 g, 121 mmol), CuI (0.5 g 2.6 mmol), Pd(PPh$_3$)$_2$Cl$_2$ (3.4 g, 4.86 mmol) and Et$_3$N (14 mL, 6.9 mmol) in toluene (100 mL) and water (50 mL) was heated at 70° C. for 4 h. The aqueous layer was separated and the organic layer was washed with water (80 mL×2) and brine (100 mL), dried over Na$_2$SO$_4$ and concentrated under reduced pressure to dryness. The residue was recrystallized with ether to afford 2-(3,3-dimethylbut-1-ynyl)-5-fluoro-4-nitroaniline (4.2 g, 46%). $^1$H-NMR (400 MHz, DMSO-d$_6$) δ 7.84 (d, J=8.4 Hz, 0.1H), 6.84 (brs, 2H), 6.54 (d, J=14.4 Hz, 1H), 1.29 (s, 9H).

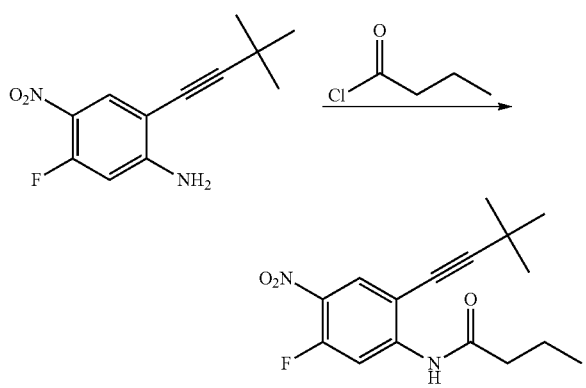

N-(2-(3,3-Dimethylbut-1-ynyl)-5-fluoro-4-nitrophenyl)butyramide

To a solution of 2-(3,3-dimethylbut-1-ynyl)-5-fluoro-4-nitroaniline (4.2 g, 17.8 mmol) in dichloromethane (50 mL) and Et$_3$N (10.3 mL, 71.2 mmol) was added butyryl chloride (1.9 g, 17.8 mmol) at 0° C. The mixture was stirred at room temperature for 1 h and then poured into water. The aqueous phase was separated and the organic layer was washed with water (50 mL×2) and brine (100 mL), dried over Na$_2$SO$_4$ and concentrated under reduced pressure to dryness. The residue was washed with ether to give N-(2-(3,3-dimethylbut-1-ynyl)-5-fluoro-4-nitrophenyl)butyramide (3.5 g, 67%), which was used in the next step without further purification.

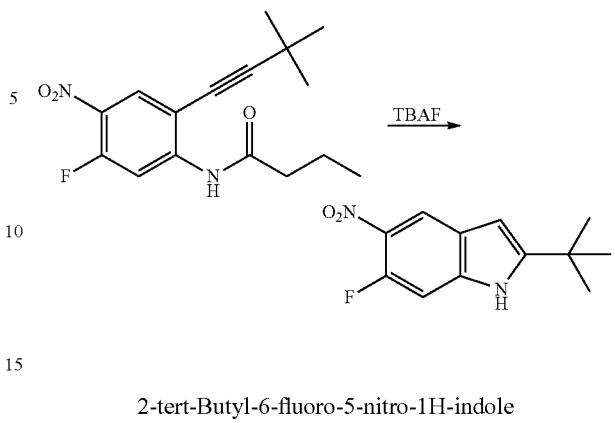

2-tert-Butyl-6-fluoro-5-nitro-1H-indole

A solution of N-(2-(3,3-dimethylbut-1-ynyl)-5-fluoro-4-nitrophenyl)butyramide (3.0 g, 9.8 mmol) and TBAF (4.5 g, 17.2 mmol) in DMF (25 mL) was heated at 100° C. overnight. The mixture was poured into water and then extracted with EtOAc (80 mL×3). The combined extracts were washed with water (50 mL) and brine (50 mL), dried over Na$_2$SO$_4$ and concentrated under reduced pressure to dryness. The residue was purified by column chromatography on silica gel (petroleum ether/ethyl acetate 20:1) to give compound 2-tert-butyl-6-fluoro-5-nitro-1H-indole (1.5 g, 65%). $^1$H-NMR (400 MHz, CDCl$_3$) δ 8.30 (d, J=7.2 Hz, 1H), 7.12 (d, J=11.6 Hz, 1H), 6.35 (d, J=1.2 Hz, 1H), 1.40 (s, 9H).

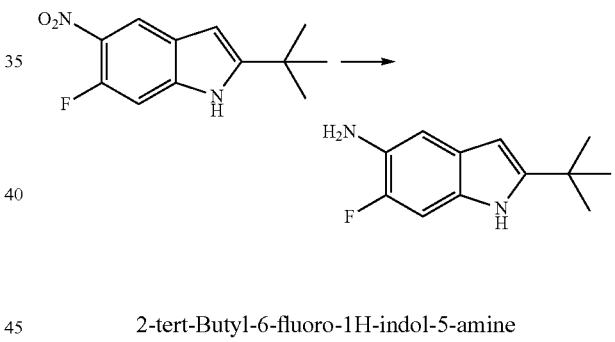

2-tert-Butyl-6-fluoro-1H-indol-5-amine

A suspension of 2-tert-butyl-6-fluoro-5-nitro-1H-indole (1.5 g, 6.36 mmol) and Ni (0.5 g) in MeOH (20 mL) was stirred under H$_2$ atmosphere (1 atm) at the room temperature for 3 h. The catalyst was filtered off and the filtrate was concentrated under reduced pressure to dryness. The residue was recrystallized in ether to give 2-tert-butyl-6-fluoro-1H-indol-5-amine (520 mg, 38%). $^1$H-NMR (300 MHz, DMSO-d$_6$) δ 10.46 (brs, 1H), 6.90 (d, J=8.7 Hz, 1H), 6.75 (d, J=9.0 Hz, 1H), 5.86 (s, 1H), 4.37 (brs, 2H), 1.29 (s, 9H); MS (ESI) m/e 206.6.

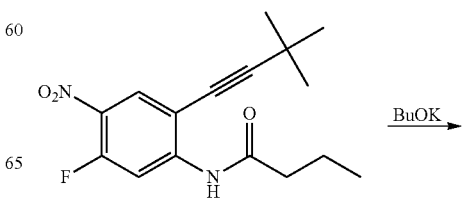

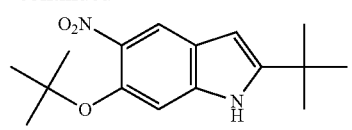

6-tert-Butoxy-2-tert-butyl-5-nitro-1H-indole

A solution of N-(2-(3,3-dimethylbut-1-ynyl)-5-fluoro-4-nitrophenyl)butyramide (500 mg, 1.63 mmol) and t-BuOK (0.37 g, 3.26 mmol) in DMF (10 mL) was heated at 70° C. for 2 h. The mixture was poured into water and then extracted with EtOAc (50 mL×3). The combined extracts were washed with water (50 mL) and brine (50 mL), dried over $Na_2SO_4$ and concentrated under reduced pressure to give 6-tert-butoxy-2-tert-butyl-5-nitro-1H-indole (100 mg, 21%). $^1$H-NMR (300 MHz, DMSO-$d_6$) δ 11.35 (brs, 1H), 7.99 (s, 1H), 7.08 (s, 1H), 6.25 (s, 1H), 1.34 (s, 9H), 1.30 (s, 9H).

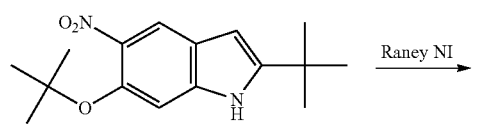

6-tert-Butoxy-2-tert-butyl-1H-indol-5-amine

A suspension of 6-tert-butoxy-2-tert-butyl-5-nitro-1H-indole (100 mg, 0.36 mmol) and Raney Ni (0.5 g) in MeOH (15 mL) was stirred under $H_2$ atmosphere (1 atm) at the room temperature for 2.5 h. The catalyst was filtered off and the filtrate was concentrated under reduced pressure to dryness. The residue was recrystallized in ether to give 6-tert-butoxy-2-tert-butyl-1H-indol-5-amine (30 mg, 32%). $^1$H-NMR (300 MHz, MeOD) 6.98 (s, 1H), 6.90 (s, 1H), 5.94 (d, J=0.6 Hz, 1H), 1.42 (s, 9H), 1.36 (s, 9H); MS (ESI) m/e 205.0.

Example 31

1-tert-Butyl-1H-indol-5-amine

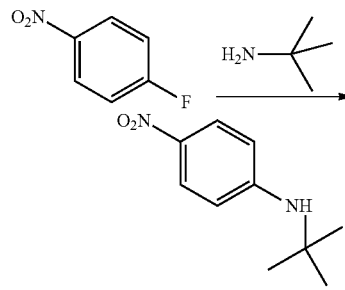

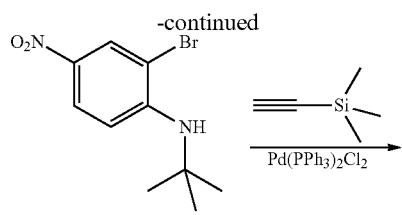

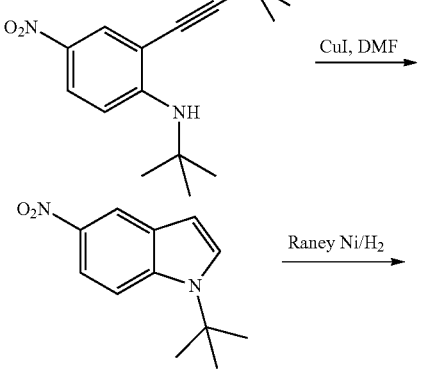

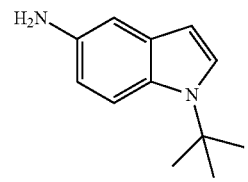

N-tert-Butyl-4-nitroaniline

A solution of 1-fluoro-4-nitro-benzene (1 g, 7.1 mmol) and tert-butylamine (1.5 g, 21 mmol) in DMSO (5 mL) was stirred at 75° C. overnight. The mixture was poured into water (10 mL) and extracted with EtOAc (7 mL×3). The combined organic layers were washed with water, brine, dried over $Na_2SO_4$ and concentrated under vacuum to dryness. The residue was purified by column chromatography on silica gel (petroleum ether/ethyl acetate 30:1) to afford N-tert-butyl-4-nitroaniline (1 g, 73%). $^1$H NMR (CDCl$_3$, 400 MHz) δ 8.03-8.00 (m, 2H), 6.61-6.57 (m, 2H), 4.67 (brs, 1H), 1.42 (s, 9H).

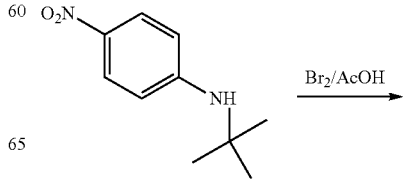

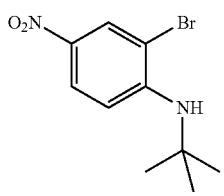

(2-Bromo-4-nitro-phenyl)tert-butyl-amine

To a solution of N-tert-butyl-4-nitroaniline (1 g, 5.1 mmol) in AcOH (5 mL) was added Br$_2$ (0.86 g, 54 mmol) dropwise at 15° C. After addition, the mixture was stirred at 30° C. for 30 min and then filtered. The filter cake was basified to pH 8-9 with aqueous NaHCO$_3$. The aqueous layer was extracted with EtOAc (10 mL×3). The combined organic layers were washed with water, brine, dried over Na$_2$SO$_4$ and concentrated under vacuum to give (2-bromo-4-nitro-phenyl)-tert-butyl-amine (0.6 g, 43%). $^1$H-NMR (CDCl$_3$, 400 MHz) δ 8.37 (dd, J=2.4 Hz, 1H), 8.07 (dd, J=2.4, 9.2 Hz, 1H), 6.86 (d, J=9.2 Hz, 1H), 5.19 (brs, 1H), 1.48 (s, 9H).

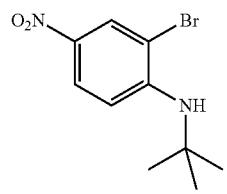 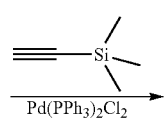

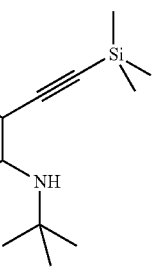

tert-Butyl-(4-nitro-2-trimethylsilanylethynyl-phenyl)-amine

To a solution of (2-bromo-4-nitro-phenyl)-tert-butyl-amine (0.6 g, 2.2 mmol) in Et$_3$N (10 mL) was added Pd(PPh$_3$)$_2$ Cl$_2$ (70 mg, 0.1 mmol), CuI (20.9 mg, 0.1 mmol) and ethynyl-trimethyl-silane (0.32 g, 3.3 mmol) successively under N$_2$ protection. The reaction mixture was heated at 70° C. overnight. The solvent was removed under vacuum and the residue was washed with EtOAc (10 mL×3). The combined organic layers were washed with water, brine, dried over Na$_2$SO$_4$ and concentrated under vacuum to dryness. The residue was purified by column chromatography on silica gel (petroleum ether/ethyl acetate 20:1) to afford tert-butyl-(4-nitro-2-trimethylsilanylethynyl-phenyl)-amine (100 mg, 16%). $^1$H-NMR (CDCl$_3$, 400 MHz) δ 8.20 (d, J=2.4, Hz, 1H), 8.04 (dd, J=2.4, 9.2 Hz, 1H), 6.79 (d, J=9.6 Hz, 1H), 5.62 (brs, 1H), 1.41 (s, 9H), 0.28 (s, 9H).

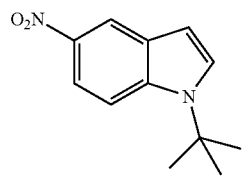

1-tert-Butyl-5-nitro-1H-indole

To a solution of tert-butyl-(4-nitro-2-trimethylsilanylethynyl-phenyl)-amine (10 mg, 0.035 mmol) in DMF (2 mL), was added CuI (13 mg, 0.07 mmol) under N$_2$ protection. The reaction mixture was stirred at 100° C. overnight. At this time, EtOAc (4 mL) was added to the mixture. The mixture was filtered and the filtrate was washed with water, brine, dried over Na$_2$SO$_4$ and concentrated under vacuum to obtain 1-tert-butyl-5-nitro-1H-indole (7 mg, 93%). $^1$H-NMR (CDCl$_3$, 300 MHz) δ 8.57 (d, J=2.1 Hz, 1H), 8.06 (dd, J=2.4, 9.3 Hz, 1H), 7.65 (d, J=9.3 Hz, 1H), 7.43 (d, J=3.3 Hz, 1H), 6.63 (d, J=3.3 Hz, 1H), 1.76 (s, 9H).

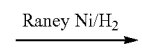

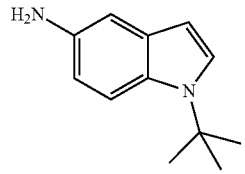

1-tert-Butyl-1H-indol-5-amine

To a solution of 1-tert-butyl-5-nitro-1H-indole (6.5 g, 0.030 mol) in MeOH (100 mL) was added Raney Nickel (0.65 g, 10%) under N$_2$ protection. The mixture was stirred under hydrogen atmosphere (1 atm) at 30° C. for 1 h. The catalyst was filtered off and the filtrate was concentrated under vacuum to dryness. The residue was purified by column chromatography on silica gel (PE/EtOAc 1:2) to give 1-tert-butyl-1H-indol-5-amine (2.5 g, 45%). $^1$H-NMR (CDCl$_3$, 400 MHz) δ 7.44 (d, J=8.8 Hz, 1H), 7.19 (dd, J=3.2 Hz, 1H), 6.96 (d, J=2.0 Hz, 1H), 6.66 (d, J=2.0, 8.8 Hz, 1H), 6.26 (d, J=3.2 Hz, 1H), 1.67 (s, 9H). MS (ESI) m/e (M+H⁺) 189.2.

Example 32

2-tert-Butyl-1-methyl-1H-indol-5-amine

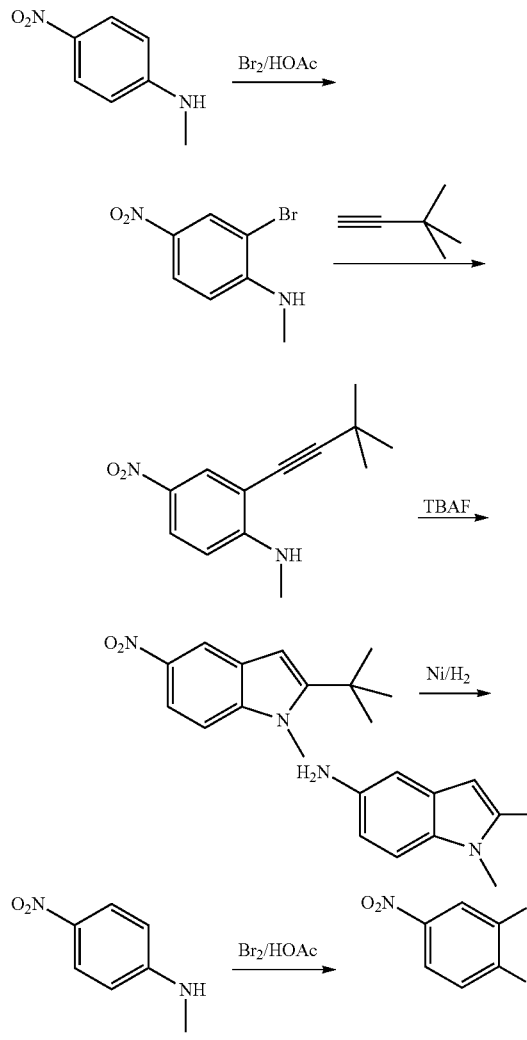

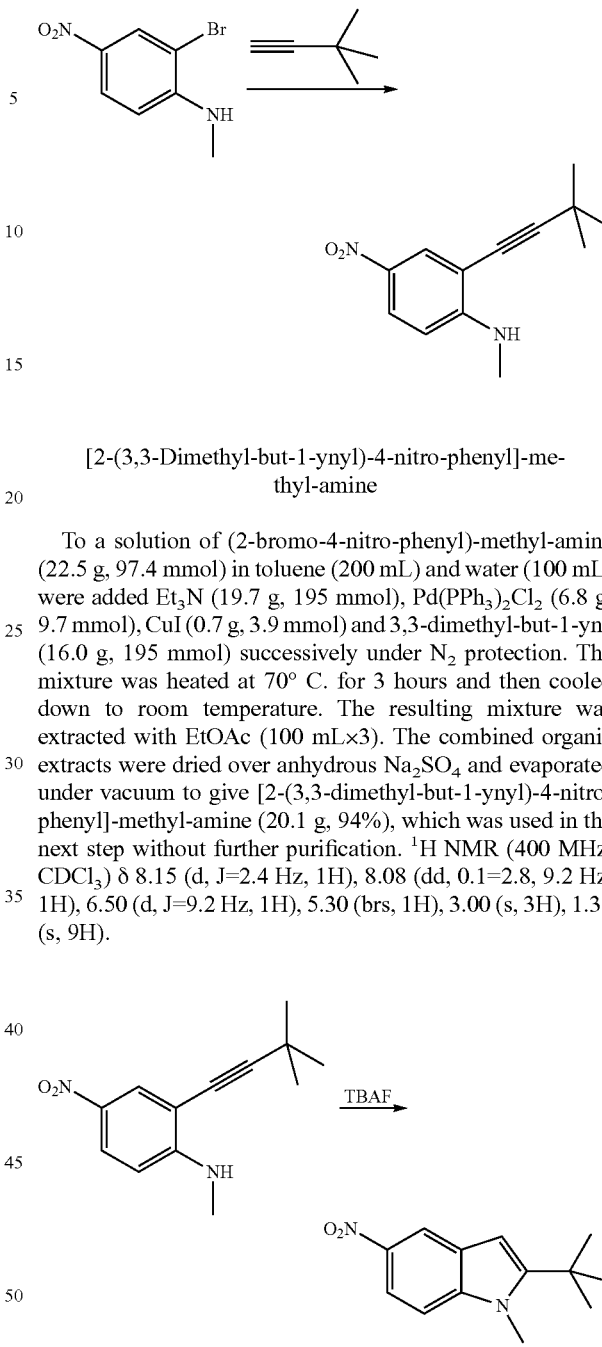

[2-(3,3-Dimethyl-but-1-ynyl)-4-nitro-phenyl]-methyl-amine

To a solution of (2-bromo-4-nitro-phenyl)-methyl-amine (22.5 g, 97.4 mmol) in toluene (200 mL) and water (100 mL) were added Et₃N (19.7 g, 195 mmol), Pd(PPh₃)₂Cl₂ (6.8 g, 9.7 mmol), CuI (0.7 g, 3.9 mmol) and 3,3-dimethyl-but-1-yne (16.0 g, 195 mmol) successively under N₂ protection. The mixture was heated at 70° C. for 3 hours and then cooled down to room temperature. The resulting mixture was extracted with EtOAc (100 mL×3). The combined organic extracts were dried over anhydrous Na₂SO₄ and evaporated under vacuum to give [2-(3,3-dimethyl-but-1-ynyl)-4-nitrophenyl]-methyl-amine (20.1 g, 94%), which was used in the next step without further purification. ¹H NMR (400 MHz, CDCl₃) δ 8.15 (d, J=2.4 Hz, 1H), 8.08 (dd, 0.1=2.8, 9.2 Hz, 1H), 6.50 (d, J=9.2 Hz, 1H), 5.30 (brs, 1H), 3.00 (s, 3H), 1.35 (s, 9H).

(2-Bromo-4-nitro-phenyl)-methyl-amine

To a solution of methyl-(4-nitro-phenyl)-amine (15.2 g, 0.1 mol) in AcOH (150 mL) and CHCl₃ (50 mL) was added Br₂ (16.0 g, 0.1 mol) dropwise at 5° C. The mixture was stirred at 10° C. for 1 h and then basified with sat. aq. NaHCO₃. The resulting mixture was extracted with EtOAc (100 mL×3), and the combined organics were dried over anhydrous Na₂SO₄ and evaporated under vacuum to give (2-bromo-4-nitro-phenyl)-methyl-amine(2-bromo-4-nitro-phenyl)-methyl-amine (23.0 g, 99%), which was used in the next step without further purification. ¹H NMR (300 MHz, CDCl₃) δ 8.37 (d, J=2.4 Hz, 1H), 8.13 (dd, J=2.4, 9.0 Hz, 1H), 6.58 (d, J=9.0 Hz, 1H), 5.17 (brs, 1H), 3.01 (d, J=5.4 Hz, 3H).

2-tert-Butyl-1-methyl-5-nitro-1H-indole

A solution of [2-(3,3-dimethyl-but-1-ynyl)-4-nitro-phenyl]methyl-amine (5.0 g, 22.9 mmol) and TBAF (23.9 g, 91.6 mmol) in THF (50 mL) was heated at reflux overnight. The solvent was removed by evaporation under vacuum and the residue was dissolved in brine (100 mL) and EtOAc (100 mL). The organic phase was separated, dried over Na₂SO₄ and evaporated under vacuum to give 2-tert-butyl-1-methyl-5-nitro-1H-indole (5.0 g, 99%), which was used in the next step without further purification. ¹H NMR (CDCl₃, 400 MHz) δ 8.47 (d, J=2.4 Hz, 1H), 8.07 (dd, J=2.4, 9.2 Hz, 1H), 7.26-7.28 (m, 1H), 6.47 (s, 1H), 3.94 (s, 3H), 1.50 (s, 9H).

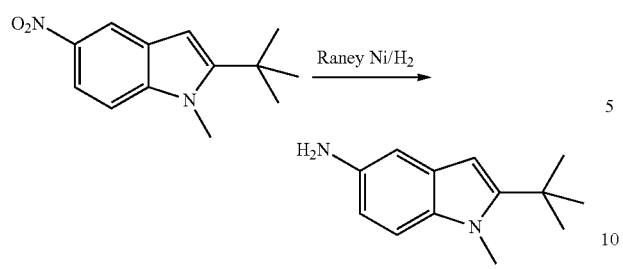

2-tert-Butyl-1-methyl-1H-indol-5-amine

To a solution of 2-tert-butyl-1-methyl-5-nitro-1H-indole (3.00 g, 13.7 mmol) in MeOH (30 mL) was added Raney Ni (0.3 g) under nitrogen atmosphere. The mixture was stirred under hydrogen atmosphere (1 atm) at room temperature overnight. The mixture was filtered through a Celite pad and the filtrate was evaporated under vacuum. The crude residue was purified by column chromatography on silica gel (P.E/EtOAc 20:1) to give 2-tert-butyl-1-methyl-1H-indol-5-amine (1.7 g, 66%). $^1$H NMR (300 MHz, CDCl$_3$) δ 7.09 (d, J=8.4 Hz, 1H), 6.89-6.9 (m, 1H), 6.66 (dd, J=2.4, 8.7 Hz, 1H), 6.14 (d, J=0.6 Hz, 1H), 3.83 (s, 3H), 3.40 (brs, 2H), 1.45 (s, 9H); MS (ESI) m/e (M+H$^+$) 203.1.

Example 33

2-Cyclopropyl-1H-indol-5-amine

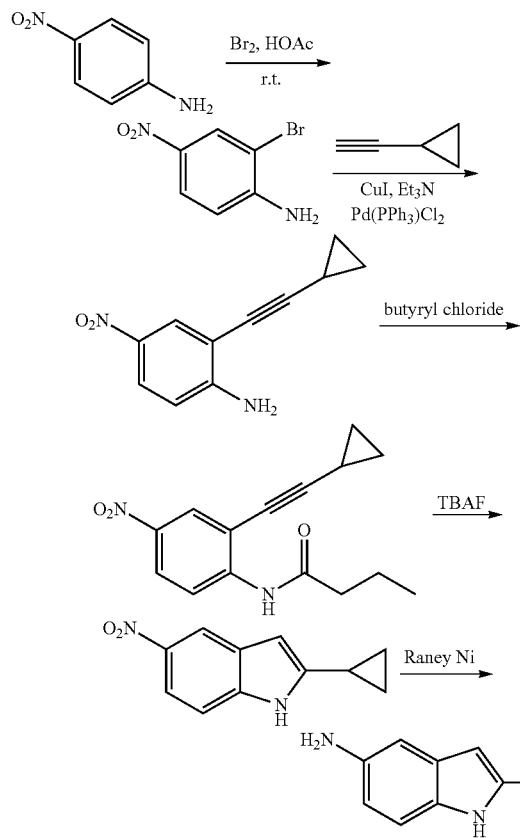

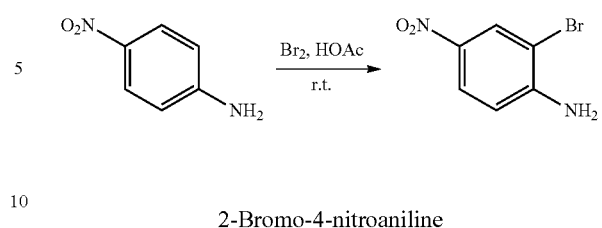

2-Bromo-4-nitroaniline

To a solution of 4-nitro-aniline (25 g, 0.18 mol) in HOAc (150 mL) was added liquid Br$_2$ (30 g, 0.19 mol) dropwise at room temperature. The mixture was stirred for 2 hours. The solid was collected by filtration and poured into water (100 mL), which was basified with sat. aq. NaHCO$_3$ to pH 7 and extracted with EtOAc (300 mL×3). The combined organic layers were dried over anhydrous Na$_2$SO$_4$ and evaporated under reduced pressure to give 2-bromo-4-nitroaniline (30 g, 80%), which was directly used in the next step.

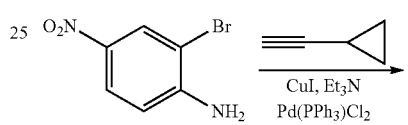

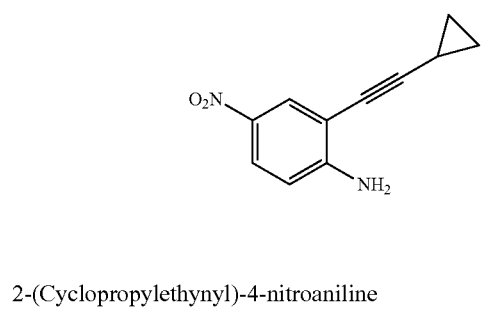

2-(Cyclopropylethynyl)-4-nitroaniline

To a deoxygenated solution of 2-bromo-4-nitroaniline (2.17 g, 0.01 mmol), ethynyl-cyclopropane (1 g, 15 mmol) and CuI (10 mg, 0.05 mmol) in triethylamine (20 mL) was added Pd(PPh$_3$)$_2$Cl$_2$ (210 mg, 0.3 mmol) under N$_2$. The mixture was heated at 70° C. and stirred for 24 hours. The solid was filtered off and washed with EtOAc (50 mL×3). The filtrate was evaporated under reduced pressure, and the residue was purified by column chromatography on silica gel (petroleum ether/ethyl acetate=10/1) to give 2-(cyclopropylethynyl)-4-nitroaniline (470 mg, 23%). $^1$H NMR (300 MHz, CDCl$_3$) δ 8.14 (d, J=2.7 Hz, 1H), 7.97 (dd, J=2.7, 9.0 Hz, 1H), 6.63 (d, J=9.0 Hz, 1H), 4.81 (brs, 2H), 1.55-1.46 (m, 1H), 0.98-0.90 (m, 2H), 0.89-0.84 (m, 2H).

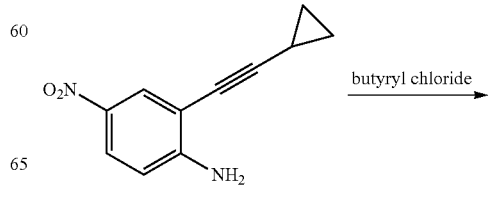

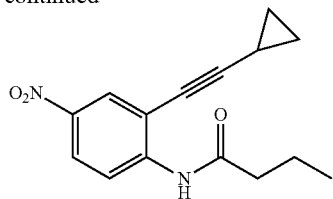

N-(2-(Cyclopropylethynyl)phenyl)-4-nitrobutyramide

To a solution of 2-(cyclopropylethynyl)-4-nitroaniline (3.2 g, 15.8 mmol) and pyridine (2.47 g, 31.7 mmol) in $CH_2Cl_2$ (60 mL) was added butyryl chloride (2.54 g, 23.8 mmol) at 0° C. The mixture was warmed to room temperature and stirred for 3 hours. The resulting mixture was poured into ice-water. The organic layer was separated. The aqueous phase was extracted with $CH_2Cl_2$ (30 m L×3). The combined organic layers were dried over anhydrous $Na_2SO_4$ and evaporated under reduced pressure to give the crude product, which was purified by column chromatography on silica gel (petroleum ether/ethyl acetate=10/1) to give N-(2-(cyclopropylethynyl)phenyl)-4-nitrobutyramide (3.3 g, 76%). $^1$H NMR (400 MHz, $CDCl_3$) δ 8.61 (d, J=9.2 Hz, 1H), 8.22 (d, J=2.8 Hz, 1H), 8.18 (brs, 1H), 8.13 (dd, J=2.4, 9.2 Hz, 1H), 2.46 (t, J=7.2 Hz, 2H), 1.83-1.76 (m, 2H), 1.59-1.53 (m, 1H), 1.06 (t, J=7.2 Hz, 3H), 1.03-1.01 (m, 2H), 0.91-0.87 (m, 2H).

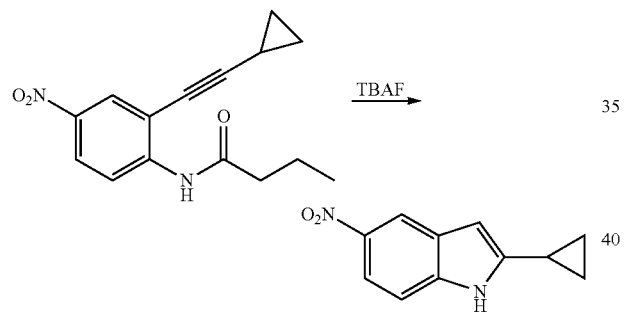

2-Cyclopropyl-5-nitro-1H-indole

A mixture of N-(2-(cyclopropylethynyl)phenyl)-4-nitrobutyramide (3.3 g, 0.01 mol) and TBAF (9.5 g, 0.04 mol) in THF (100 mL) was heated at reflux for 24 hours. The mixture was cooled to the room temperature and poured into ice water. The mixture was extracted with $CH_2Cl_2$ (50 m L×3). The combined organic layers were dried over anhydrous $Na_2SO_4$ and evaporated under reduced pressure. The residue was purified by column chromatography on silica gel (petroleum ether/ethyl acetate=10/1) to give 2-cyclopropyl-5-nitro-1H-indole (1.3 g, 64%). $^1$H NMR (400 MHz, $CDCl_3$) δ 8.44 (d, J=2.0 Hz, 1H), 8.40 (brs, 1H), 8.03 (dd, J=2.0, 8.8 Hz, 1H), 7.30 (d, J=8.8 Hz, 1H), 6.29 (d, J=0.8 Hz, 1H), 2.02-1.96 (m, 1H) 1.07-1.02 (m, 2H), 0.85-0.81 (m, 2H).

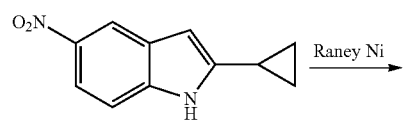

2-Cyclopropyl-1H-indol-5-amine

To a solution of 2-cyclopropyl-5-nitro-1H-indole (1.3 g, 6.4 mmol) in MeOH (30 mL) was added Raney Nickel (0.3 g) under nitrogen atmosphere. The mixture was stirred under hydrogen atmosphere (1 atm) at room temperature overnight. The catalyst was filtered through a Celite pad and the filtrate was evaporated under vacuum to give the crude product, which was purified by column chromatography on silica gel (petroleum ether/ethyl acetate=5/1) to give 2-cyclopropyl-1H-indol-5-amine (510 mg, 56%). $^1$H NMR (400 MHz, $CDCl_3$) δ 6.89 (d, J=8.4 Hz, 1H), 6.50 (d, J=1.6 Hz, 1H), 6.33 (dd, J=2.0, 8.4 Hz, 1H), 5.76 (s, 1H), 4.33 (brs, 2H), 1.91-1.87 (m, 1H), 0.90-0.85 (m, 2H), 0.70-0.66 (m, 2H); MS (ESI) m/e (M+H$^+$) 173.2.

Example 34

3-tert-Butyl-1H-indol-5-amine

3-tert-Butyl-5-nitro-1H-indole

To a mixture of 5-nitro-1H-indole (6 g, 36.8 mmol) and $AlCl_3$ (24 g, 0.18 mol) in $CH_2Cl_2$ (100 mL) was added 2-bromo-2-methyl-propane (8.1 g, 36.8 mmol) dropwise at 0° C. After being stirred at 15° C. overnight, the reaction mixture was poured into ice (100 mL). The precipitated salts were removed by filtration and the aqueous layer was extracted with CH₂Cl₂ (30 mL×3). The combined organic layers were washed with water, brine, dried over Na₂SO₄ and concentrated under vacuum to obtain the crude product, which was purified by column chromatography on silica gel (petroleum ether/ethyl acetate 20:1) to give 3-tert-butyl-5-nitro-1H-indole (2.5 g, 31%). ¹H NMR (CDCl₃, 400 MHz) δ 8.49 (d, J=1.6 Hz, 1H), 8.31 (brs, 1H), 8.05 (dd, J=2.0, 8.8 Hz, 1H), 7.33 (d, J=8.8 Hz, 1H), 6.42 (d, J=1.6 Hz, 1H), 1.42 (s, 9H).

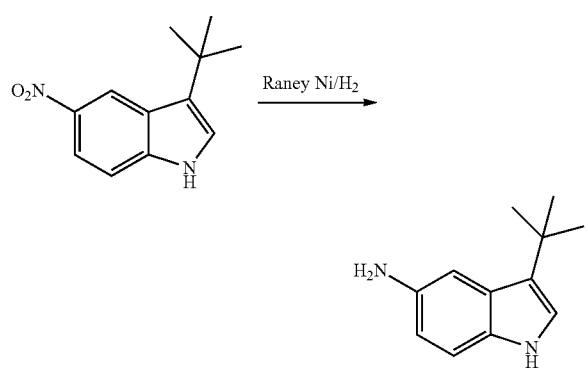

3-tert-Butyl-1H-indol-5-amine

To a solution of 3-tert-butyl-5-nitro-1H-indole (2.5 g, 11.6 mmol) in MeOH (30 mL) was added Raney Nickel (0.2 g) under N₂ protection. The mixture was stirred under hydrogen atmosphere (1 atm) at 15° C. for 1 hr. The catalyst was filtered off and the filtrate was concentrated under vacuum to dryness. The residue was purified by preparative HLPC to afford 3-tert-butyl-1H-indol-5-amine (0.43 g, 19%). ¹H NMR (CDCl₃, 400 MHz) δ 7.72 (brs, 1H), 7.11 (d, J=8.4 Hz, 1H), 6.86 (d, J=2.0 Hz, 1H), 6.59 (dd, J=2.0, 8.4 Hz, 1H), 6.09 (d, J=1.6 Hz, 1H), 1.37 (s, 9H); MS (ESI) (M+H⁺) 189.1.

Example 35

2-Phenyl-1H-indol-5-amine

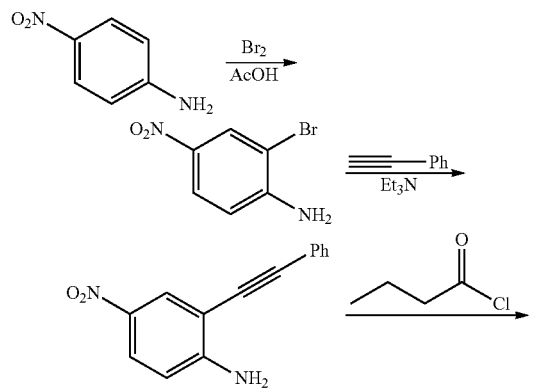

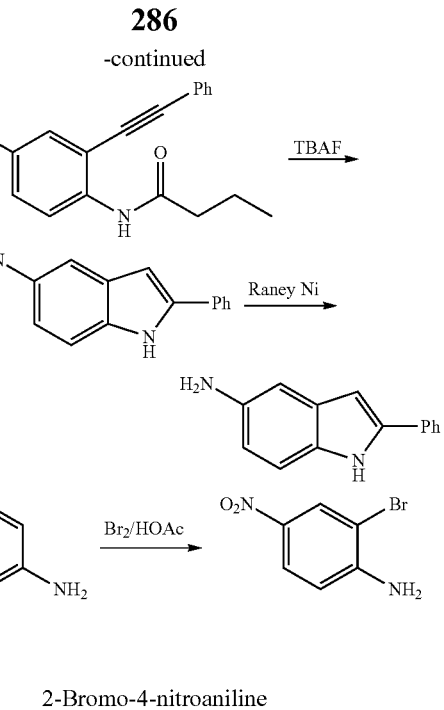

2-Bromo-4-nitroaniline

To a solution of 4-nitroaniline (50 g, 0.36 mol) in AcOH (500 mL) was added liquid Br₂ (60 g, 0.38 mol) dropwise at 5° C. The mixture was stirred for 30 min at that temperature. The insoluble solid was collected by filtration and poured into EtOAc (200 mL). The mixture was basified with saturated aqueous NaHCO₃ to pH 7. The organic layer was separated. The aqueous phase was extracted with EtOAc (300 mL×3). The combined organic layers were dried and evaporated under reduced pressure to give 2-bromo-4-nitroaniline (56 g, 72%), which was directly used in the next step.

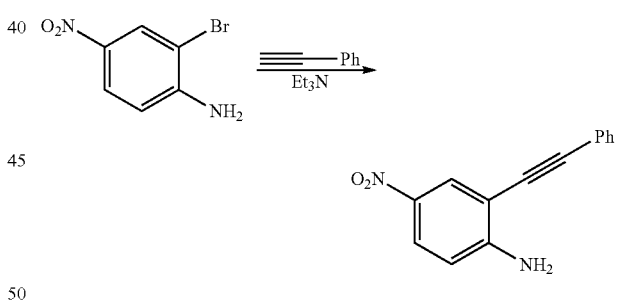

4-Nitro-2-(phenylethynyl)aniline

To a deoxygenated solution of 2-bromo-4-nitroaniline (2.17 g, 0.01 mmol), ethynyl-benzene (1.53 g, 0.015 mol) and CuI (10 mg, 0.05 mmol) in triethylamine (20 mL) was added Pd(PPh₃)₂Cl₂ (210 mg, 0.2 mmol) under N₂. The mixture was heated at 70° C. and stirred for 24 hours. The solid was filtered off and washed with EtOAc (50 mL×3). The filtrate was evaporated under reduced pressure and the residue was purified by column chromatography on silica gel (petroleum ether/ethyl acetate=10/1) to give 4-nitro-2-(phenylethynyl) aniline (340 mg, 14%). ¹H NMR (300 MHz, CDCl₃) δ 8.37-8.29 (m, 1H), 8.08-8.00 (m, 1H), 7.56-7.51 (m, 2H), 7.41-7.37 (m, 3H), 6.72 (m, 1H), 4.95 (brs, 2H).

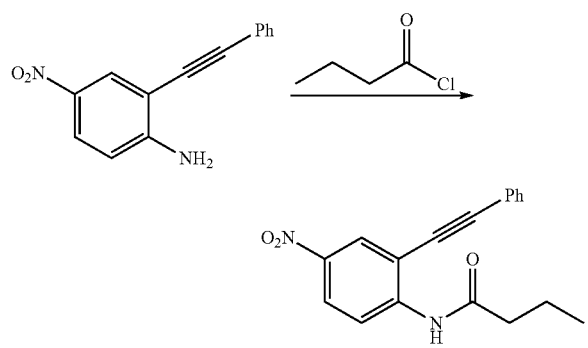

N-(2-(Phenylethynyl)phenyl)-4-nitrobutyramide

To a solution of 4-nitro-2-(phenylethynyl)aniline (17 g, 0.07 mmol) and pyridine (11.1 g, 0.14 mol) in CH$_2$Cl$_2$ (100 mL) was added butyryl chloride (11.5 g, 0.1 mol) at 0° C. The mixture was warmed to room temperature and stirred for 3 hours. The resulting mixture was poured into ice-water. The organic layer was separated. The aqueous phase was extracted with CH$_2$Cl$_2$ (30 m L×3). The combined organic layers were dried over anhydrous Na$_2$SO$_4$ and evaporated under reduced pressure. The residue was purified by column chromatography on silica gel (petroleum ether/ethyl acetate=10/1) to give N-(2-(phenylethynyl)phenyl)-4-nitrobutyramide (12 g, 55%). $^1$H NMR (400 MHz, CDCl$_3$) δ 8.69 (d, J=9.2 Hz, 1H), 8.39 (d, J=2.8 Hz, 1H), 8.25-8.20 (m, 2H), 7.58-7.55 (m, 2H), 7.45-7.42 (m, 3H), 2.49 (t, J=7.2 Hz, 2H), 1.85-1.79 (m, 2H), 1.06 (t, J=7.2 Hz, 3H).

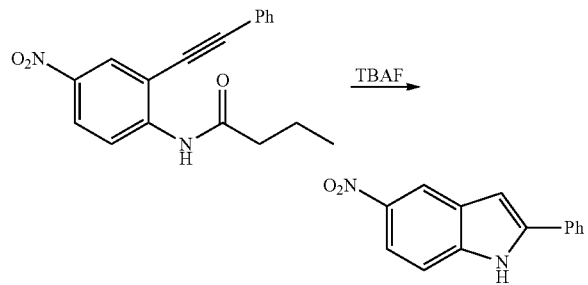

5-Nitro-2-phenyl-1H-indole

A mixture of N-(2-(phenylethynyl)phenyl)-4-nitrobutyramide (5.0 g, 0.020 mol) and TBAF (12.7 g, 0.050 mol) in THF (30 mL) was heated at reflux for 24 h. The mixture was cooled to room temperature and poured into ice water. The mixture was extracted with CH$_2$Cl$_2$ (50 m L×3). The combined organic layers were dried over anhydrous Na$_2$SO$_4$ and evaporated under reduced pressure. The residue was purified by column chromatography on silica gel (petroleum ether/ethyl acetate=10/1) to give 5-nitro-2-phenyl-1H-indole (3.3 g, 69%). $^1$H NMR (400 MHz, CDCl$_3$) δ 8.67 (s, 1H), 8.06 (dd, J=2.0, 8.8 Hz, 1H), 7.75 (d, J=7.6 Hz, 2H), 7.54 (d, J=8.8 Hz, 1H), 7.45 (t, J=7.6 Hz, 2H), 7.36 (t, J=7.6 Hz, 1H). 6.95 (s, 1H).

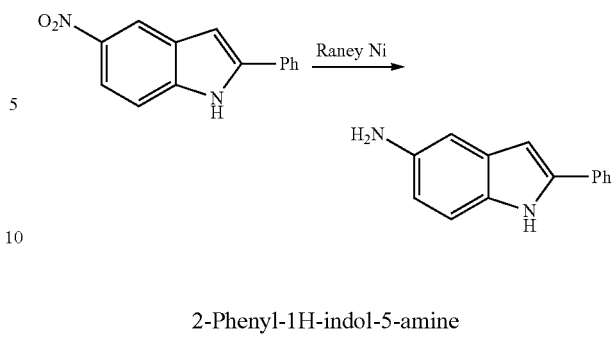

2-Phenyl-1H-indol-5-amine

To a solution of 5-nitro-2-phenyl-1H-indole (2.83 g, 0.01 mol) in MeOH (30 mL) was added Raney Ni (510 mg) under nitrogen atmosphere. The mixture was stirred under hydrogen atmosphere (1 atm) at room temperature overnight. The catalyst was filtered through a Celite pad and the filtrate was evaporated under vacuum to give the crude product, which was purified by column chromatography on silica gel (petroleum ether/ethyl acetate=5/1) to give 2-phenyl-1H-indol-5-amine (1.6 g, 77%). $^1$H NMR (400 MHz, CDCl$_3$) δ 7.76 (d, J=7.6 Hz, 2H), 7.39 (t, J=7.6 Hz, 2H), 7.24 (t, J=7.6 Hz, 1H), 7.07 (d, J=8.4 Hz, 1H), 6.64 (d, J=1.6 Hz, 1H), 6.60 (d, J=1.2 Hz, 1H), 6.48 (dd, J=2.0, 8.4 Hz, 1H), 4.48 (brs, 2H); MS (ESI) m/e (M+H$^+$) 209.0.

Example 36

2-tert-Butyl-4-fluoro-1H-indol-5-amine

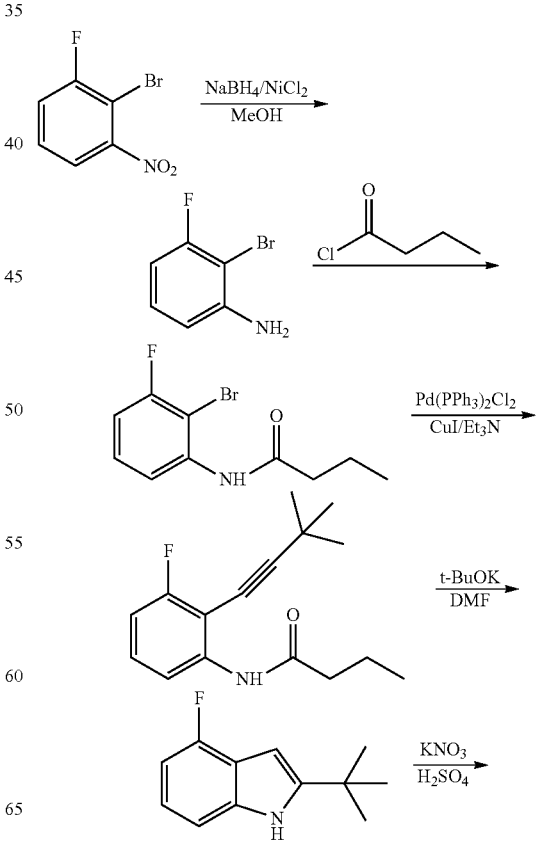

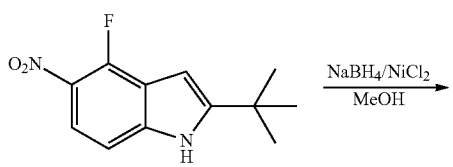

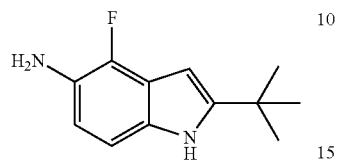

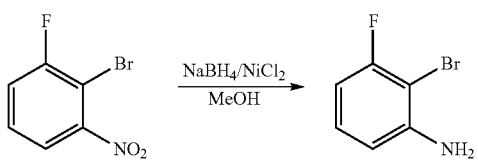

2-Bromo-3-fluoroaniline

To a solution of 2-bromo-1-fluoro-3-nitrobenzene (1.0 g, 5.0 mmol) in CH₃OH (50 mL) was added NiCl₂ (2.2 g 10 mmol) and NaBH₄ (0.50 g 14 mmol) at 0° C. After the addition, the mixture was stirred for 5 min. Water (20 mL) was added and the mixture was extracted with EtOAc (20 mL×3). The organic layers were dried over anhydrous Na₂SO₄ and evaporated under vacuum to give 2-bromo-3-fluoroaniline (600 mg, 70%). ¹H NMR (400 MHz, CDCl₃) δ 7.07-7.02 (m, 1H), 6.55-6.49 (m, 1H), 4.22 (br s, 2H).

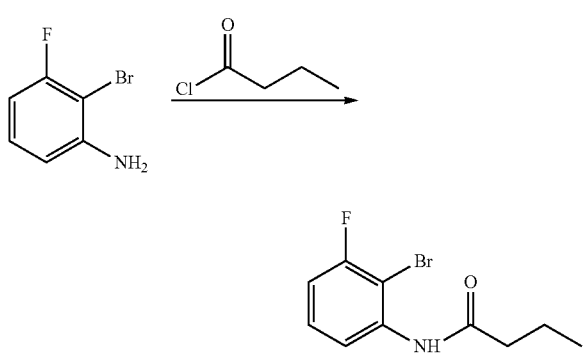

N-(2-Bromo-3-fluorophenyl)butyramide

To a solution of 2-bromo-3-fluoroaniline (2.0 g, 11 mmol) in CH₂Cl₂ (50 mL) was added butyryl chloride (1.3 g, 13 mmol) and pyridine (1.7 g, 21 mmol) at 0° C. The mixture was stirred at room temperature for 24 h. Water (20 mL) was added and the mixture was extracted with CH₂Cl₂ (50 mL×3). The organic layers were dried anhydrous over Na₂SO₄ and evaporated under vacuum to give N-(2-bromo-3-fluorophenyl)butyramide (2.0 g, 73%), which was directly used in the next step.

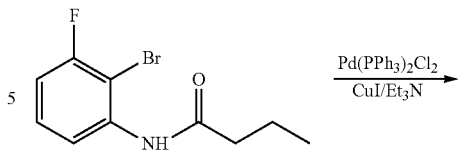

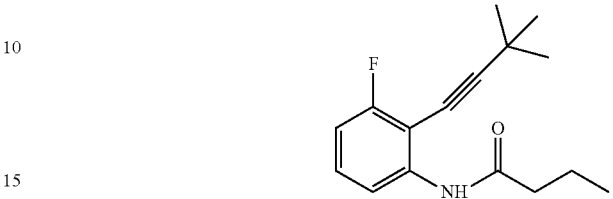

N-(2-(3,3-Dimethylbut-1-ynyl)-3-fluorophenyl)butyramide

To a solution of N-(2-bromo-3-fluorophenyl)butyramide (2.0 g, 7.0 mmol) in Et₃N (100 mL) was added 4,4-dimethylpent-2-yne (6.0 g, 60 mmol), CuI (70 mg, 3.8 mmol), and Pd(PPh₃)₂Cl₂ (500 mg) successively at room temperature under N₂. The mixture was heated at 80° C. overnight. The cooled mixture was filtered and the filtrate was extracted with EtOAc (40 mL×3). The organic layers were washed with sat. NaCl, dried over anhydrous Na₂SO₄, and evaporated under vacuum. The crude compound was purified by column chromatography on silica gel (10% EtOAc in petroleum ether) to give N-(2-(3,3-dimethylbut-1-ynyl)-3-fluorophenyl)butyramide (1.1 g, 55%). ¹H NMR (400 MHz, CDCl₃) δ 8.20 (d, J=7.6, 1H), 7.95 (s, 1H), 7.21 (m, 1H), 6.77 (t, J=7.6 Hz, 1H), 2.39 (t, J=7.6 Hz, 2H), 1.82-1.75 (m, 2H), 1.40 (s, 9H), 1.12 (t, J=7.2 Hz, 3H).

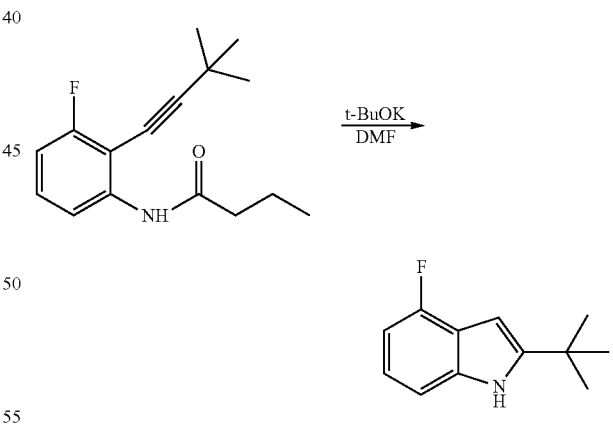

2-tert-Butyl-4-fluoro-1H-indole

To a solution of N-(2-(3,3-dimethylbut-1-ynyl)-3-fluorophenyl)butyramide (6.0 g, 20 mmol) in DMF (100 mL) was added t-BuOK (5.0 g, 50 mmol) at room temperature. The mixture was heated at 90° C. overnight before it was poured into water and extracted with EtOAc (100 mL×3). The organic layers were washed with sat. NaCl and water, dried over anhydrous Na₂SO₄ and evaporated under vacuum to give 2-tert-butyl-4-fluoro-1H-indole (5.8 g, 97%). ¹H NMR (400 MHz, CDCl$_3$) δ 8.17 (br s, 1H), 7.11 (d, J=7.2 Hz, 1H), 7.05-6.99 (m, 1H), 6.76-6.71 (m, 1H), 6.34 (m, 1H), 1.41 (s, 9H).

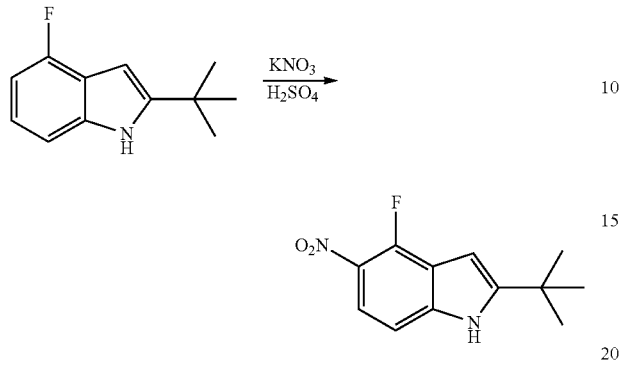

2-tert-Butyl-4-fluoro-5-nitro-1H-indole

To a solution of 2-tert-butyl-4-fluoro-1H-indole (2.5 g, 10 mmol) in H$_2$SO$_4$ (30 mL) was added KNO$_3$ (1.3 g, 10 mmol) at 0° C. The mixture was stirred for 0.5 h at −10° C. The mixture was poured into water and extracted with EtOAc (100 mL×3). The organic layers were washed with sat. NaCl and water, dried over anhydrous Na$_2$SO$_4$, and evaporated under vacuum. The crude compound was purified by column chromatography on silica gel (10% EtOAc in petroleum ether) to give 2-tert-butyl-4-fluoro-5-nitro-1H-indole (900 mg, 73%). $^1$H NMR (400 MHz, CDCl$_3$) δ 8.50 (br s, 1H), 7.86 (dd, J=7.6, 8.8 Hz, 1H), 7.13 (d, J=8.8 Hz, 1H), 6.52 (dd, J=0.4, 2.0 Hz, 1H), 1.40 (s, 9H).

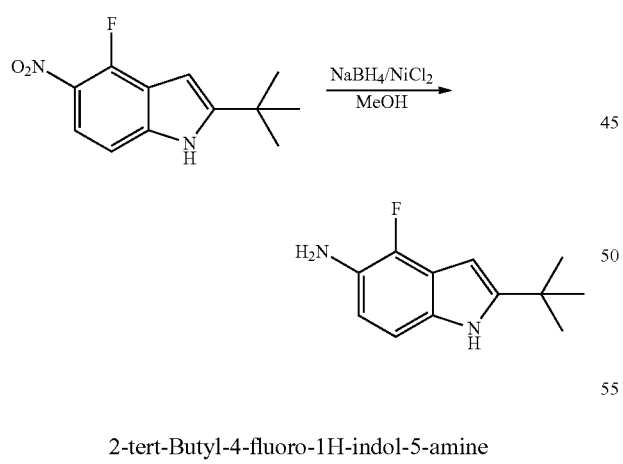

2-tert-Butyl-4-fluoro-1H-indol-5-amine

To a solution of 2-tert-butyl-4-fluoro-5-nitro-1H-indole (2.1 g, 9.0 mmol) in methanol (50 mL) was added NiCl$_2$ (4.2 g, 18 mmol) and NaBH$_4$ (1.0 g, 27 mmol) at 0° C. After the addition, the mixture was stirred for 5 min. Water (20 mL) was added and the mixture was extracted with EtOAc (30 mL×3). The organic layers were washed with sat. NaCl and water, dried over anhydrous Na$_2$SO$_4$, evaporated under vacuum to give 2-tert-butyl-4-fluoro-1H-indol-5-amine (900 mg, 50%). $^1$H NMR (300 MHz, CDCl$_3$) δ 7.80 (brs, 1H), 6.91 (d, J=8.4 Hz, 1H), 6.64 (dd, J=0.9, 2.4 Hz, 1H), 6.23 (s, 1H), 1.38 (s, 9H).

Example 37

2,3,4,9-Tetrahydro-1H-carbazol-6-amine

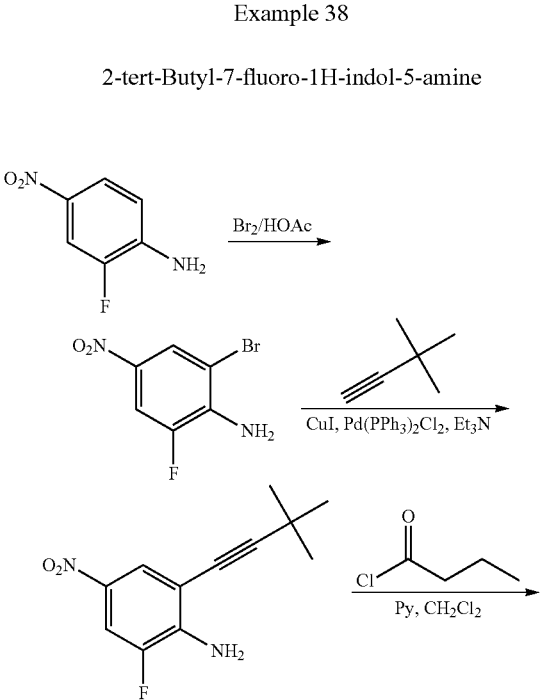

2,3,4,9-Tetrahydro-1H-carbazol-6-amine

6-Nitro-2,3,4,9-tetrahydro-1H-carbazole (0.100 g, 0.462 mmol) was dissolved in a 40 mL scintillation vial containing a magnetic stir bar and 2 mL of ethanol. Tin(II) chloride dihydrate (1.04 g, 4.62 mmol) was added to the reaction mixture and the resulting suspension was heated at 70° C. for 16 h. The crude reaction mixture was then diluted with 15 mL of a saturated aqueous solution of sodium bicarbonate and extracted three times with an equivalent volume of ethyl acetate. The ethyl acetate extracts were combined, dried over sodium sulfate, and evaporated to dryness to yield 2,3,4,9-tetrahydro-1H-carbazol-6-amine (82 mg, 95%) which was used without further purification.

Example 38

2-tert-Butyl-7-fluoro-1H-indol-5-amine

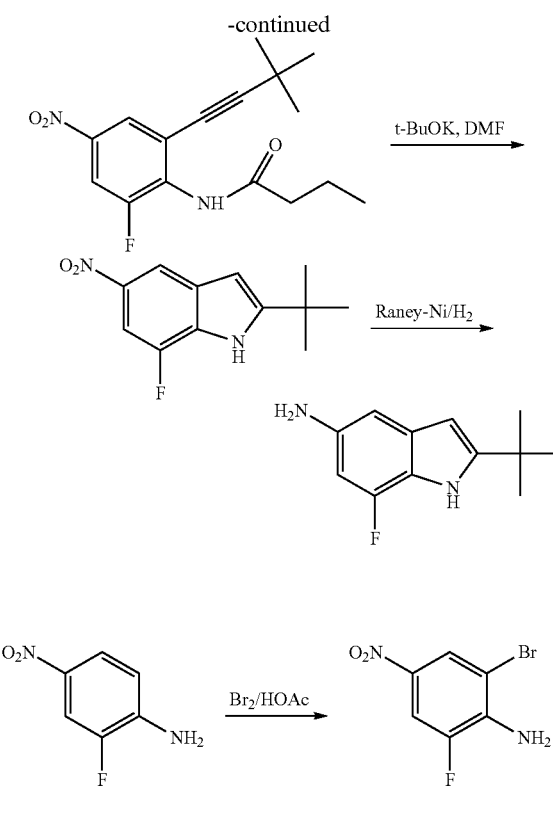

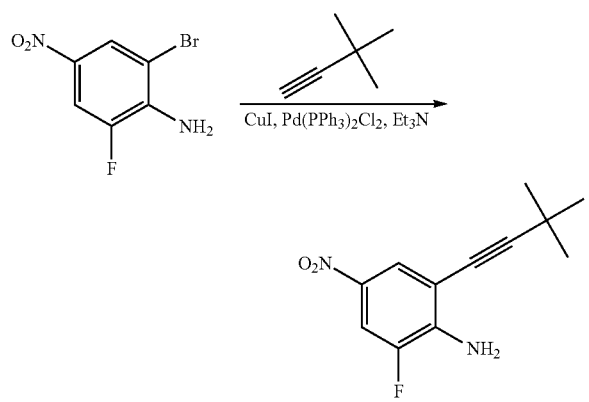

2-Bromo-6-fluoro-4-nitro-phenylamine

To a solution of 2-fluoro-4-nitro-phenylamine (12 g, 77 mmol) in AcOH (50 mL) was added Br$_2$ (3.9 mL, 77 mmol) dropwise at 0° C. The mixture was stirred at 20° C. for 3 h. The reaction mixture was basified with sat. aq. NaHCO$_3$, and extracted with EtOAc (100 mL×3). The combined organics were dried over anhydrous Na$_2$SO$_4$ and evaporated under vacuum to give 2-bromo-6-fluoro-4-nitro-phenylamine (18 g, 97%). $^1$H NMR (400 MHz, CDCl$_3$) δ 8.22 (m, 1H), 7.90 (dd, J=2.4, 10.8 Hz, 1H), 4.88 (brs, 2H).

2-(3,3-Dimethyl-but-1-ynyl)-6-fluoro-4-nitro-phenylamine

To a solution of 2-bromo-6-fluoro-4-nitro-phenylamine (11 g, 47 mmol) in dry Et$_3$N (100 mL) was added CuI (445 mg, 5% mol), Pd(PPh$_3$)$_2$Cl$_2$ (550 mg, 5% mol) and 3,3-dimethyl-but-1-yne (9.6 g, 120 mmol) under N$_2$ protection. The mixture was stirred at 80° C. for 10 h. The reaction mixture was filtered, poured into ice (100 g), and extracted with EtOAc (50 mL×3). The combined organic extracts were dried over anhydrous Na$_2$SO$_4$ and evaporated under vacuum to give the crude product, which was purified by column chromatography on silica gel (petroleum ether/ethyl acetate 50:1) to give 2-(3,3-dimethyl-but-1-ynyl)-6-fluoro-4-nitro-phenylamine (4.0 g, 36%). $^1$H NMR (400 MHz, CDCl$_3$) δ 8.02 (d, J=1.2 Hz, 1H), 7.84 (dd, J=2.4, 10.8 Hz, 1H), 4.85 (brs, 2H), 1.36 (s, 9H).

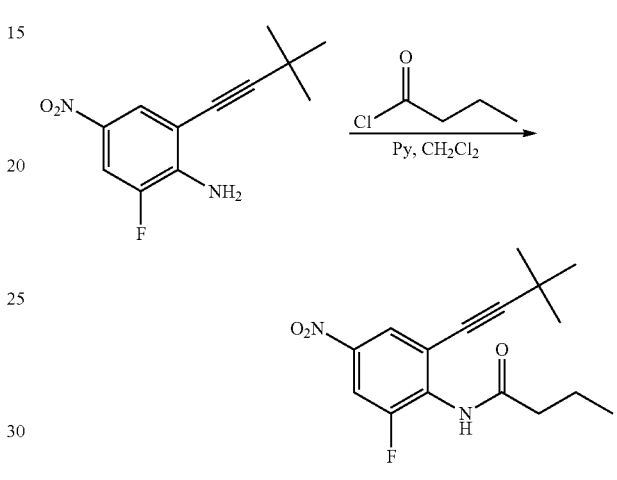

N-[2-(3,3-Dimethyl-but-1-ynyl)-6-fluoro-4-nitro-phenyl]-butyramide

To a solution of 2-(3,3-dimethyl-but-1-ynyl)-6-fluoro-4-nitro-phenylamine (4.0 g, 17 mmol) and pyridine (2.7 g, 34 mmol) in anhydrous CH$_2$Cl$_2$ (30 mL) was added and butyryl chloride (1.8 g, 17 mmol) dropwise at 0° C. After stirring for 5 h at 0° C., the reaction mixture was poured into ice (50 g) and extracted with CH$_2$Cl$_2$ (30 mL×3). The combined organic extracts were dried over anhydrous Na$_2$SO$_4$ and evaporated under vacuum to give N-[2-(3,3-dimethyl-but-1-ynyl)-6-fluoro-4-nitro-phenyl]-butyramide (3.2 g, 62%), which was used in the next step without further purification. $^1$H NMR (300 MHz, DMSO) δ 8.10 (dd, J=1.5, 2.7 Hz, 1H), 7.95 (dd, J=2.4, 9.6 Hz, 1H), 7.22 (brs, 1H), 2.45 (t, J=7.5 Hz, 2H), 1.82 (m, 2H), 1.36 (s, 9H), 1.06 (t, J=7.5 Hz, 3H).

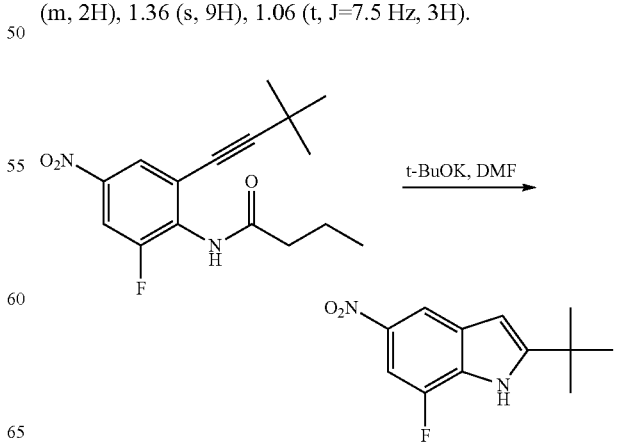

2-tert-Butyl-7-fluoro-5-nitro-1H-indole

To a solution of N-[2-(3,3-dimethyl-but-1-ynyl)-6-fluoro-4-nitro-phenyl]-butyramide (3.2 g, 10 mmol) in DMF (20 mL) was added t-BuOK (2.3 g, 21 mmol) at room temperature. The mixture was heated at 120° C. for 2 g before being cooled down to room temperature. Water (50 mL) was added to the reaction mixture and the resulting mixture was extracted with $CH_2Cl_2$ (30 mL×3). The combined organic extracts were dried over anhydrous $Na_2SO_4$ and evaporated under vacuum to give 2-tert-butyl-7-fluoro-5-nitro-1H-indole (2.0 g, 81%), which was used in the next step without further purification. $^1$H NMR (300 MHz, $CDCl_3$) δ 9.95 (brs, 1H), 8.30 (d, J=2.1 Hz, 1H), 7.74 (dd, J=1.8, 11.1 Hz, 1H), 6.43 (dd, J=2.4, 3.3 Hz, 1H), 1.43 (s, 9H).

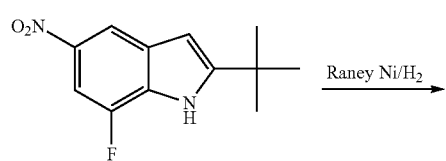

2-tert-Butyl-7-fluoro-1H-indol-5-amine

To a solution of 2-tert-butyl-7-fluoro-5-nitro-1H-indole (2.0 g, 8.5 mmol) in MeOH (20 mL) was added Ni (0.3 g) under nitrogen atmosphere. The reaction mixture was stirred under hydrogen atmosphere (1 atm) at room temperature overnight. The catalyst was filtered off through the celite pad and the filtrate was evaporated under vacuum. The crude product was purified by column chromatography on silica gel (petroleum ether/ethyl acetate 100:1) to give 2-tert-butyl-7-fluoro-1H-indol-5-amine (550 mg, 24%). $^1$H NMR (300 MHz, $CDCl_3$) δ 7.87 (brs, 1H), 6.64 (d, J=1.5 Hz, 1H), 6.37 (dd, J=1.8, 12.3 Hz, 1H), 6.11 (dd, J=2.4, 3.6 Hz, 1H), 1.39 (s, 9H). MS (ESI) m/z (M+H$^+$) 207.

Example 39

5-Amino-2-tert-butyl-1H-indole-7-carbonitrile

2-Amino-3-(3,3-dimethylbut-1-ynyl)-5-nitrobenzonitrile

To a stirred solution of 2-amino-3-bromo-5-nitrobenzonitrile (2.4 g, 10 mmol) in dry $Et_3N$ (60 mL) was added CuI (380 mg, 5% mol) and $Pd(PPh_3)_2Cl_2$ (470 mg, 5% mol) at room temperature. 3,3-dimethyl-but-1-yne (2.1 g, 25 mmol) was added dropwise to the mixture at room temperature. The reaction mixture was stirred at 80° C. for 10 h. The reaction mixture was filtered and the filtrate was poured into ice (60 g), extracted with ethyl acetate. The phases were separated and the organic phase was dried over $Na_2SO_4$. The solvent was removed under vacuum to obtain the crude product, which was purified by column chromatography (2-10% EtOAc in petroleum ether) to obtain 2-amino-3-(3,3-dimethylbut-1-ynyl)-5-nitrobenzonitrile (1.7 g, 71%). $^1$H NMR (300 MHz, $CDCl_3$) δ 8.28 (d, J=2.7 Hz, 1H), 8.27 (d, J=2.7 Hz, 1H), 5.56 (br s, 2H), 1.37 (s, 9H).

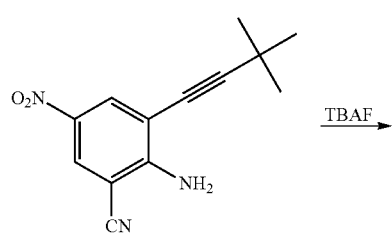

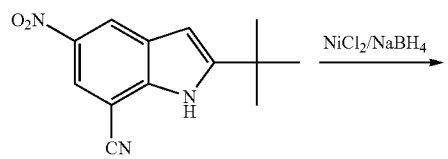

2-tert-Butyl-5-nitro-1H-indole-7-carbonitrile

To a solution of 2-amino-3-(3,3-dimethylbut-1-ynyl)-5-nitrobenzonitrile (1.7 g, 7.0 mmol) in THF (35 mL) was added TBAF (9.5 g, 28 mmol) at room temperature. The mixture was heated at reflux overnight. The reaction mixture was cooled and the THF was removed under reduced pressure. Water (50 ml) was added to the residue and the mixture was extracted with EtOAc. The organics were dried over Na₂SO₄ and the solvent was evaporated under vacuum to obtain 0.87 g of crude product 2-tert-butyl-5-nitro-1H-indole-7-carbonitrile which was used directly in the next step without purification.

5-Amino-2-tert-butyl-1H-indol-7-carbonitrile

To a solution of crude product 2-tert-butyl-5-nitro-1H-indole-7-carbonitrile (0.87 g, 3.6 mmol) in MeOH (10 mL) was added NiCl₂·6H₂O (1.8 g, 7.2 mmol) at −5° C. The reaction mixture was stirred for 30 min, then NaBH₄ (0.48 g, 14.32 mmol) was added to the reaction mixture at 0° C. After 5 min, the reaction mixture was quenched with water, filtered and extracted with EtOAc. The combined organic layers were dried over Na₂SO₄ and concentrated under vacuum to obtain the crude product, which was purified by column chromatography (5-20% EtOAc in petroleum ether) to obtain 5-amino-2-tert-butyl-1H-indol-7-carbonitrile (470 mg, 32% over two steps). $^1$H NMR (400 MHz, CDCl₃) δ 8.25 (s, 1H), 7.06 (d, J=2.4 Hz, 1H), 6.84 (d, J=2.4 Hz, 1H), 6.14 (d, J=2.4 Hz, 1H), 3.57 (br s, 2H), 1.38 (s, 9H). MS (ESI) m/z: 214 (M+H⁺).

Example 40

Methyl 5-amino-2-tert-butyl-1H-indole-7-carboxylate

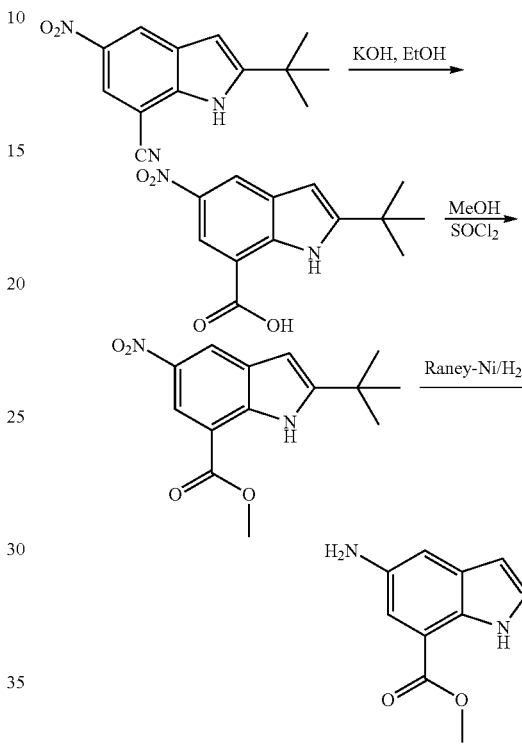

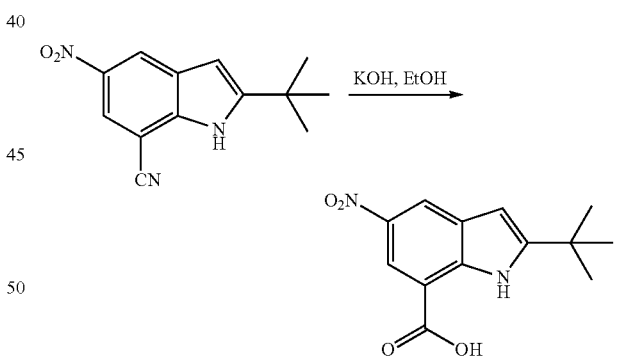

2-tert-Butyl-5-nitro-1H-indole-7-carboxylic acid 2-tert-Butyl-5-nitro-1H-indole-7-carbonitrile (4.6 g, 19 mmol) was added to a solution of KOH in EtOH (10%, 100 mL) and the mixture was heated at reflux overnight. The solution was evaporated to remove alcohol, a small amount of water was added, and then the mixture was acidified with dilute hydrochloric acid. Upon standing in the refrigerator, an orange-yellow solid precipitated, which was purified by chromatography on silica gel (15% EtOAc in petroleum ether) to afford 2-tert-butyl-5-nitro-1H-indole-7-carboxylic acid (4.0 g, 77%). $^1$H NMR (CDCl₃, 300 MHz) δ 10.79 (brs, 1H), 8.66 (s, 1H), 8.45 (s, 1H), 6.57 (s, 1H), 1.39 (s, 9H).

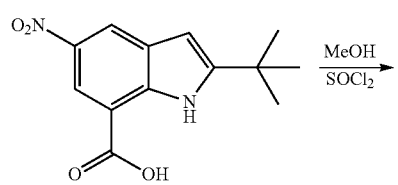

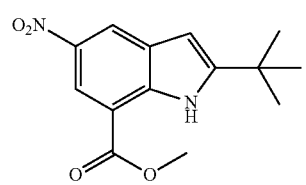

Methyl 2-tert-butyl-5-nitro-1H-indole-7-carboxylate

SOCl$_2$ (3.6 g, 30 mol) was added dropwise to a solution of 2-tert-butyl-5-nitro-1H-indole-7-carboxylic acid (4.0 g, 15 mol) and methanol (30 mL) at 0° C. The mixture was stirred at 80° C. for 12 h. The solvent was evaporated under vacuum and the residue was purified by column chromatography on silica gel (5% EtOAc in petroleum ether) to afford methyl 2-tert-butyl-5-nitro-1H-indole-7-carboxylate (2.95 g, 70%). $^1$H NMR (CDCl$_3$, 300 MHz) δ 9.99 (brs, 1H), 8.70 (d, J=2.1 Hz, 1H), 8.65 (d, J=2.1 Hz, 1H), 6.50 (d, J=2.4 Hz, 1H), 4.04 (s, 3H), 1.44 (s, 9H).

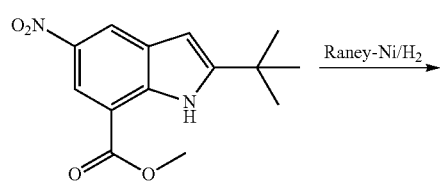

Methyl 5-amino-2-tert-butyl-1H-indole-7-carboxylate

A solution of 2-tert-butyl-5-nitro-1H-indole-7-carboxylate (2.0 g, 7.2 mmol) and Raney Nickel (200 mg) in CH$_3$OH (50 mL) was stirred for 5 h at the room temperature under H$_2$ atmosphere. The catalyst was filtered off through a celite pad and the filtrate was evaporated under vacuum to give methyl 5-amino-2-tert-butyl-1H-indole-7-carboxylate (1.2 g, 68%) $^1$H NMR (CDCl$_3$, 400 MHz) δ 9.34 (brs, 1H), 7.24 (d, J=1.6 Hz, 1H), 7.10 (s, 1H), 6.12 (d, J=1.6 Hz, 1H), 3.88 (s, 3H), 1.45 (s, 9H).

Example 41

(5-Amino-2-tert-butyl-1H-indol-7-yl)methanol

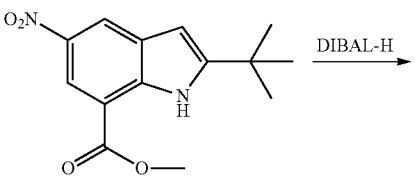

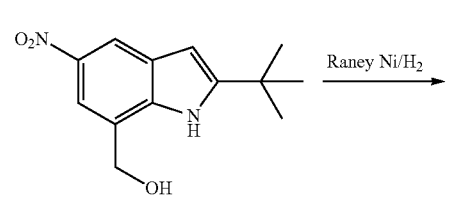

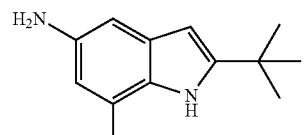

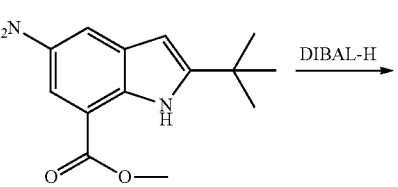

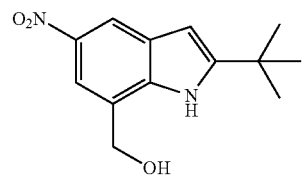

(2-tert-Butyl-5-nitro-1H-indol-7-yl)methanol

To a solution of methyl 2-tert-butyl-5-nitro-1H-indole-7-carboxylate (6.15 g, 22.3 mmol) and dichloromethane (30 ml) was added DIBAL-H (1.0 M, 20 mL, 20 mmol) at 78° C. The mixture was stirred for 1 h before water (10 mL) was added slowly. The resulting mixture was extracted with EtOAc (120 mL×3). The combined organic extracts were dried over anhydrous Na$_2$SO$_4$ and evaporated under vacuum to give (2-tert-butyl-5-nitro-1H-indol-7-yl)methanol (4.0 g, 73%), which was used in the next step directly.

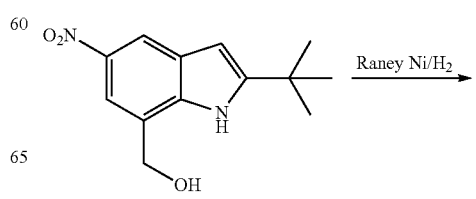

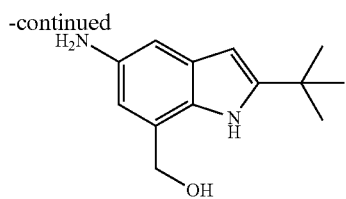

(5-Amino-2-tert-butyl-1H-indol-7-yl)methanol

A mixture of (2-tert-butyl-5-nitro-1H-indol-7-yl)methanol (4.0 g, 16 mmol) and Raney Nickel (400 mg) in CH$_3$OH (100 mL) was stirred for 5 g at room temperature under H$_2$. The catalyst was filtered off through a celite pad and the filtrate was evaporated under vacuum to give (5-amino-2-tert-butyl-1H-indol-7-yl)methanol (3.4 g, 80%). $^1$H NMR (CDCl$_3$, 400 MHz) δ 8.53 (br s, 1H), 6.80 (d, J=2.0 Hz, 1H), 6.38 (d, J=1.6 Hz, 1H), 4.89 (s, 2H), 1.37 (s, 9H).

Example 42

2-(1-Methykyclopropyl)-1H-indol-5-amine

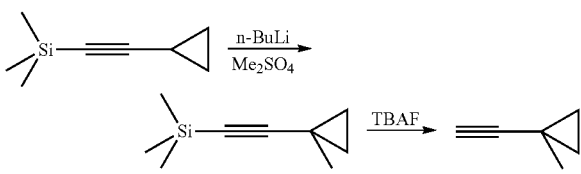

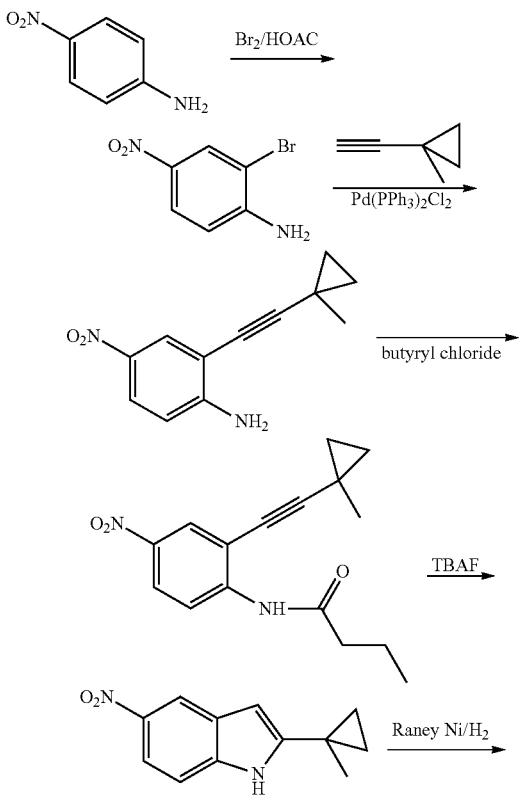

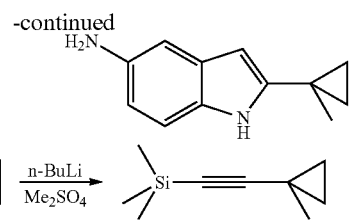

Trimethyl-(1-methyl-cyclopropylethynyl)-silane

To a solution of cyclopropylethynyl-trimethyl-silane (3.0 g, 22 mmol) in ether (20 mL) was added dropwise n-BuLi (8.6 mL, 21.7 mol, 2.5 M solution in hexane) at 0° C. The reaction mixture was stirred at ambient temperature for 24 h before dimethyl sulfate (6.85 g, 54.3 mmol) was added dropwise at −10° C. The resulting solution was stirred at 10° C. and then at 20° C. for 30 min each. The reaction was quenched by adding a mixture of sat. aq. NH$_4$Cl and 25% aq. ammonia (1:3, 100 mL). The mixture was then stirred at ambient temperature for 1 h. The aqueous phase was extracted with diethyl ether (3×50 mL) and the combined organic layers were washed successively with 5% aqueous hydrochloric acid (100 mL), 5% aq. NaHCO$_3$ solution (100 mL), and water (100 mL). The organics were dried over anhydrous NaSO$_4$ and concentrated at ambient pressure. After fractional distillation under reduced pressure, trimethyl-(1-methyl-cyclopropylethynyl)-silane (1.7 g, 52%) was obtained as a colorless liquid. $^1$H NMR (400 MHz, CDCl$_3$) δ 1.25 (s, 3H), 0.92-0.86 (m, 2H), 0.58-0.56 (m, 2H), 0.15 (s, 9H).

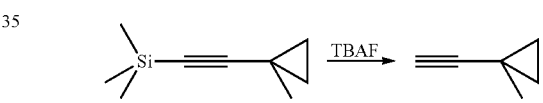

1-Ethynyl-1-methyl-cyclopropane

To a solution of trimethyl-(1-methyl-cyclopropylethynyl)-silane (20 g, 0.13 mol) in THF (250 mL) was added TBAF (69 g, 0.26 mol). The mixture was stirred overnight at 20° C. The mixture was poured into water and the organic layer was separated. The aqueous phase was extracted with THF (50 mL). The combined organic layers were dried over anhydrous Na$_2$SO$_4$ and distilled under atmospheric pressure to obtain 1-ethynyl-1-methyl-cyclopropane (7.0 g, contained ½ THF, 34%). $^1$H NMR (400 MHz, CDCl$_3$) δ 1.82 (s, 1H), 1.26 (s, 3H), 0.90-0.88 (m, 2H), 0.57-0.55 (m, 2H).

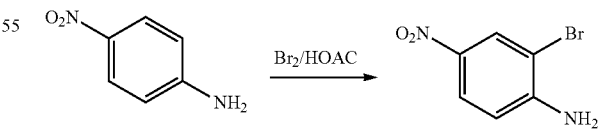

2-Bromo-4-nitroaniline

To a solution of 4-nitro-phenylamine (50 g, 0.36 mol) in AcOH (500 mL) was added Br$_2$ (60 g, 0.38 mol) dropwise at 5° C. The mixture was stirred for 30 min at that temperature. The insoluble solid was collected by filtration and basified with saturated aqueous NaHCO₃ to pH 7. The aqueous phase was extracted with EtOAc (300 mL×3). The combined organic layers were dried and evaporated under reduced pressure to obtain compound 2-bromo-4-nitroaniline (56 g, 72%), which was directly used in the next step.

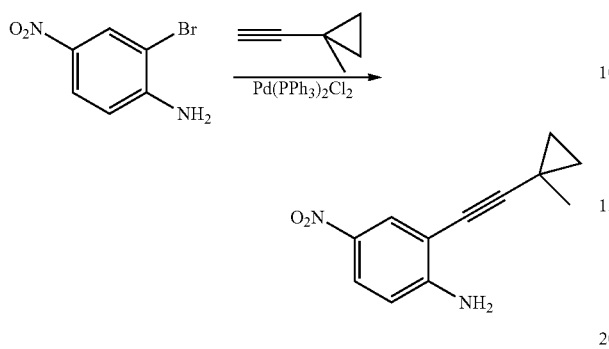

2-((1-Methylcyclopropyl)ethynyl)-4-nitroaniline

To a deoxygenated solution of 2-bromo-4-nitroaniline (430 mg, 2.0 mmol) and 1-ethynyl-1-methyl-cyclopropane (630 mg, 8.0 mmol) in triethylamine (20 mL) was added CuI (76 mg, 0.40 mmol) and Pd(PPh₃)₂Cl₂ (140 mg, 0.20 mmol) under N₂. The mixture was heated at 70° C. and stirred for 24 h. The solid was filtered off and washed with EtOAc (50 mL×3). The filtrate was evaporated under reduced pressure and the residue was purified by column chromatography on silica gel (petroleum ether/ethyl acetate=10/1) to give 2-((1-methylcyclopropyl)ethynyl)-4-nitroaniline (340 mg, 79%). ¹H NMR (300 MHz, CDCl₃) δ 8.15-8.14 (m, 1H), 7.98-7.95 (m, 1H), 6.63 (d, J=6.9 Hz, 1H), 4.80 (brs, 2H), 1.38 (s, 3H), 1.04-1.01 (m, 2H), 0.76-0.73 (m, 2H).

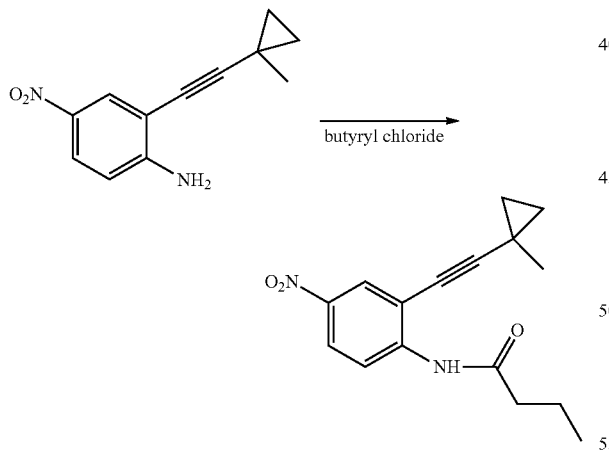

N-[2-(1-Methyl-cyclopropylethynyl)-4-nitro-phenyl]-butyramide

To a solution of 2-((1-methylcyclopropyl)ethynyl)-4-nitroaniline (220 mg, 1.0 mmol) and pyridine (160 mg, 2.0 mol) in CH₂Cl₂ (20 mL) was added butyryl chloride (140 mg, 1.3 mmol) at 0° C. The mixture was warmed to room temperature and stirred for 3 h. The mixture was poured into ice-water. The organic layer was separated and the aqueous phase was extracted with CH₂Cl₂ (30 mL×3). The combined organic layers were dried over anhydrous Na₂SO₄ and evaporated under reduced pressure to obtain N-[2-(1-methyl-cyclopropyl-ethynyl)-4-nitro-phenyl]-butyramide (230 mg, 82%), which was directly used in the next step.

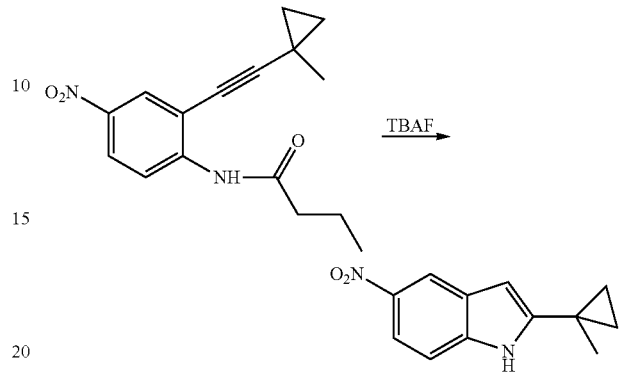

2-(1-Methylcyclopropyl)-5-nitro-1H-indole

A mixture of N-[2-(1-methyl-cyclopropylethynyl)-4-nitro-phenyl]-butyramide (1.3 g, 4.6 mmol) and TBAF (2.4 g, 9.2 mmol) in THF (20 mL) was heated at reflux for 24 h. The mixture was cooled to room temperature and poured into ice water. The mixture was extracted with CH₂Cl₂ (30 mL×3). The combined organic layers were dried over anhydrous Na₂SO₄ and evaporated under reduced pressure. The residue was purified by column chromatography on silica gel (petroleum ether/ethyl acetate=10/1) to afford 2-(1-methylcyclopropyl)-5-nitro-1H-indole (0.70 g, 71%). ¹H NMR (400 MHz, CDCl₃) δ 8.56 (brs, 1H), 8.44 (d, J=2.0 Hz, 1H), 8.01 (dd, J=2.4, 8.8 Hz, 1H), 7.30 (d, J=8.8 Hz, 1H), 6.34 (d, J=1.6 Hz, 1H), 1.52 (s, 3H), 1.03-0.97 (m, 2H), 0.89-0.83 (m, 2H).

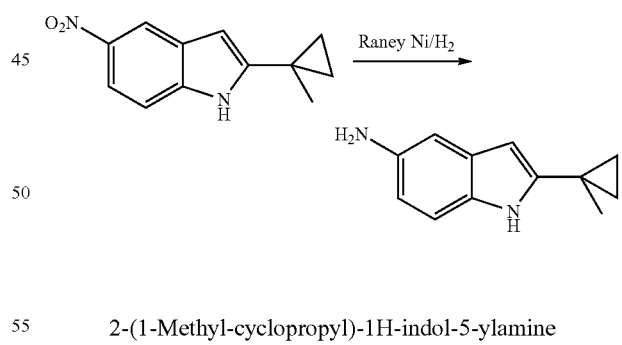

2-(1-Methyl-cyclopropyl)-1H-indol-5-ylamine

To a solution of 2-(1-methylcyclopropyl)-5-nitro-1H-indole (0.70 g, 3.2 mmol) in EtOH (20 mL) was added Raney Nickel (100 mg) under nitrogen atmosphere. The mixture was stirred under hydrogen atmosphere (1 atm) at room temperature overnight. The catalyst was filtered off through a celite pad and the filtrate was evaporated under vacuum. The residue was purified by column chromatography on silica gel (petroleum ether/ethyl acetate=5/1) to afford 2-(1-methyl-cyclopropyl)-1H-indol-5-ylamine (170 mg, 28%). ¹H NMR (400 MHz, CDCl₃) δ 7.65 (brs, 1H), 7.08 (d, J=8.4 Hz, 1H), 6.82 (s, 1H), 6.57 (d, J=8.4 Hz, 1H), 6.14 (s, 1H), 3.45 (brs, 2H), 1.47 (s, 3H), 0.82-0.78 (m, 2H), 0.68-0.63 (m, 2H).

Example 43

Methyl 2-(5-amino-1H-indol-2-yl)-2-methylpropanoate

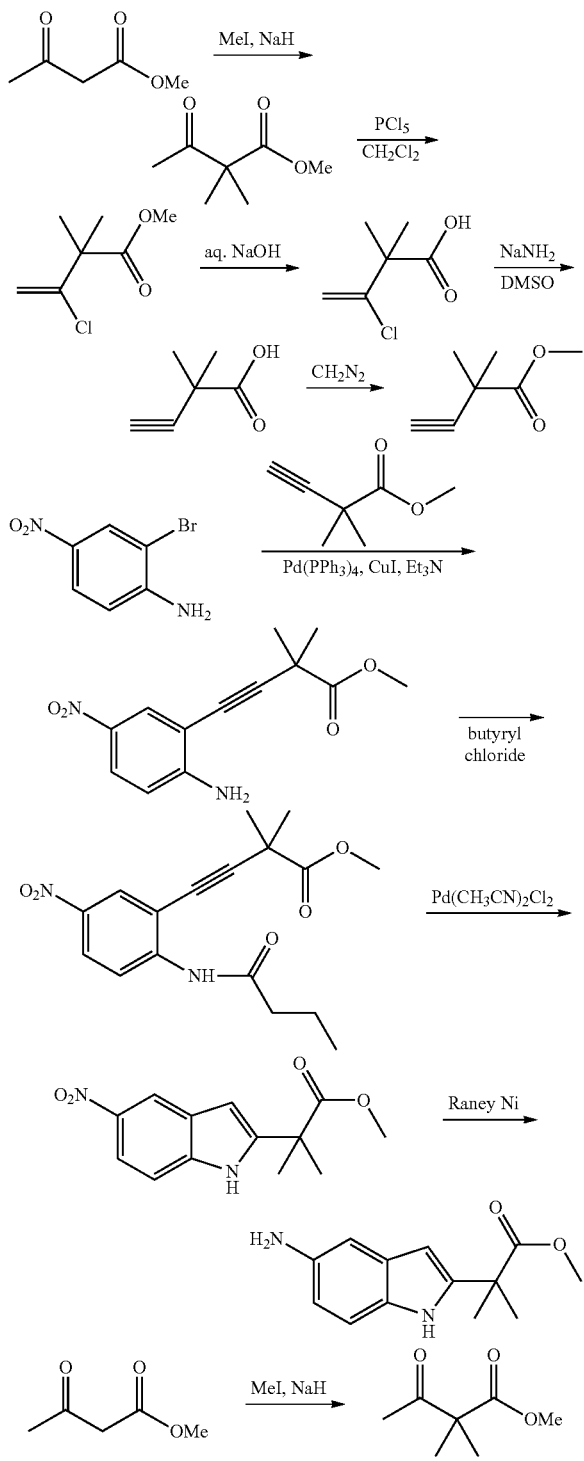

Methyl 2,2-dimethyl-3-oxobutanoate

To a suspension of NaH (42 g, 1.1 mol, 60%) in THF (400 mL) was added dropwise a solution of methyl 3-oxobutanoate (116 g, 1.00 mol) in THF (100 mL) at 0° C. The mixture was stirred for 0.5 h at that temperature before MeI (146 g, 1.1 mol) was added dropwise at 0° C. The resultant mixture was warmed to room temperature and stirred for 1 h. NaH (42 g, 1.05 mol, 60%) was added in portions at 0° C. and the resulting mixture was continued to stir for 0.5 h at this temperature. Me (146 g, 1.05 mol) was added dropwise at 0° C. The reaction mixture was warmed to room temperature and stirred overnight. The mixture was poured into ice water and the organic layer was separated. The aqueous phase was extracted with EtOAc (500 mL×3). The combined organic layers were dried and evaporated under reduced pressure to give methyl 2,2-dimethyl-3-oxobutanoate (85 g), which was used directly in the next step.

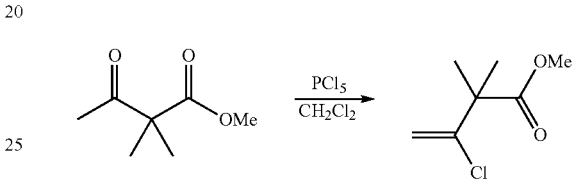

Methyl 3-chloro-2,2-dimethylbut-3-enoate

To a suspension of $PCl_5$ (270 g, 1.3 mol) in $CH_2Cl_2$ (1000 mL) was added dropwise methyl 2,2-dimethyl-3-oxobutanoate (85 g) at 0° C., following by addition of approximately 30 drops of dry DMF. The mixture was heated at reflux overnight. The reaction mixture was cooled to ambient temperature and slowly poured into ice water. The organic layer was separated and the aqueous phase was extracted with $CH_2Cl_2$ (500 mL×3). The combined organic layers were washed with saturated aqueous $NaHCO_3$ and dried over anhydrous $Na_2SO_4$. The solvent was evaporated and the residue was distilled under reduced pressure to give methyl 3-chloro-2,2-dimethylbut-3-enoate (37 g, 23%). $^1$H NMR (400 MHz, $CDCl_3$) δ 5.33 (s, 1H), 3.73 (s, 3H), 1.44 (s, 6H).

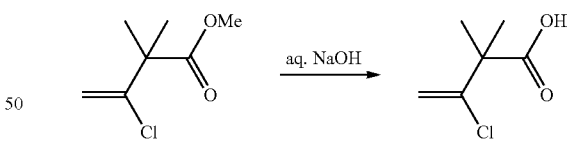

3-Chloro-2,2-dimethylbut-3-enoic acid

A mixture of methyl 3-chloro-2,2-dimethylbut-3-enoate (33 g, 0.2 mol) and NaOH (9.6 g, 0.24 mol) in water (200 mL) was heated at reflux for 5 h. The mixture was cooled to ambient temperature and extracted with ether. The organic layer was discarded. The aqueous layer was acidified with cold 20% HCl solution and extracted ether (200 mL×3). The combined organic layers were dried and evaporated under reduced pressure to give 3-chloro-2,2-dimethyl-but-3-enoic acid (21 g, 70%), which was used directly in the next step. $^1$H NMR (400 MHz, $CDCl_3$) δ 7.90 (brs, 1H), 5.37 (dd, J=2.4, 6.8 Hz, 2H), 1.47 (s, 6H).

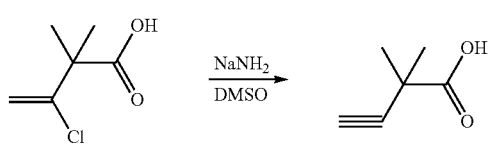

2,2-Dimethyl-but-3-ynoic acid

Liquid NH$_3$ was condensed in a 3-neck, 250 mL round bottom flask at −78° C. Na (3.98 g, 0.173 mol) was added to the flask in portions. The mixture was stirred for 2 h at −78° C. before anhydrous DMSO (20 mL) was added dropwise at −78° C. The mixture was stirred at room temperature until no more NH$_3$ was given off. A solution of 3-chloro-2,2-dimethyl-but-3-enoic acid (6.5 g, 43 mmol) in DMSO (10 mL) was added dropwise at −40° C. The mixture was warmed and stirred at 50° C. for 5 h, then stirred at room temperature overnight. The cloudy, olive green solution was poured into cold 20% HCl solution and then extracted three times with ether. The ether extracts were dried over anhydrous Na$_2$SO$_4$ and concentrated to give crude 2,2-dimethyl-but-3-ynoic acid (2 g), which was used directly in the next step. $^1$H NMR (400 MHz, CDCl$_3$) δ 2.30 (s, 1H), 1.52 (s, 6H).

Methyl 2,2-dimethylbut-3-ynoate

To a solution of diazomethane (~10 g) in ether (400 mL) was added dropwise 2,2-dimethyl-but-3-ynoic acid (10.5 g, 93.7 mmol) at 0° C. The mixture was warmed to room temperature and stirred overnight. The mixture was distilled under atmospheric pressure to give crude methyl 2,2-dimethylbut-3-ynoate (14 g), which was used directly in the next step. $^1$H NMR (400 MHz, CDCl$_3$) δ 3.76 (s, 3H), 2.28 (s, 1H), 1.50 (s, 6H).

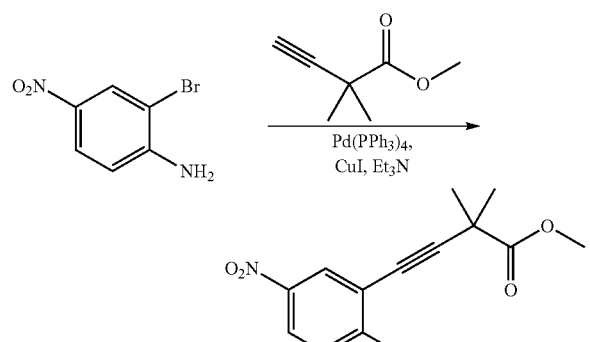

Methyl 4-(2-amino-5-nitrophenyl)-2,2-dimethylbut-3-ynoate

To a deoxygenated solution of compound 2-bromo-4-nitroaniline (9.43 g, 43.7 mmol), methyl 2,2-dimethylbut-3-ynoate (5.00 g, 39.7 mmol), CuI (754 mg, 3.97 mmol) and triethylamine (8.03 g, 79.4 mmol) in toluene/H$_2$O (100/30 mL) was added Pd(PPh$_3$)$_4$ (6.17 g, 3.97 mmol) under N$_2$. The mixture was heated at 70° C. and stirred for 24 h. After cooling, the solid was filtered off and washed with EtOAc (50 mL×3). The organic layer was separated and the aqueous phase was washed with EtOAc (50 mL×3). The combined organic layers were dried and evaporated under reduced pressure to give a residue, which was purified by column chromatography on silica gel (petroleum ether/ethyl acetate=10/1) to obtain methyl 4-(2-amino-5-nitrophenyl)-2,2-dimethylbut-3-ynoate (900 mg, 9%). $^1$H NMR (400 MHz, CDCl$_3$) δ 8.17 (d, J=2.8 Hz, 1H), 8.01 (dd, J=2.8, 9.2 Hz, 1H), 6.65 (d, J=9.2 Hz, 1H), 5.10 (brs, 2H), 3.80 (s, 3H), 1.60 (s, 6H).

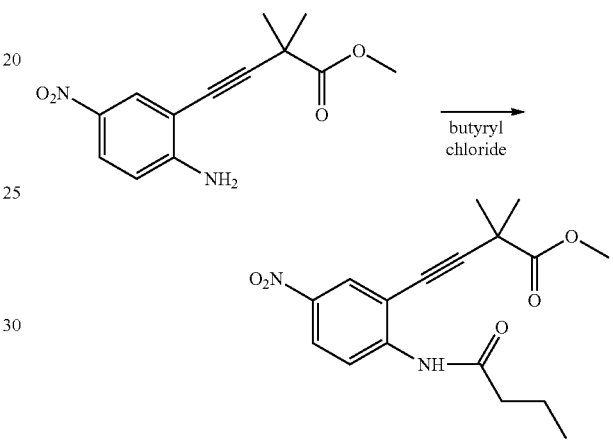

Methyl 4-(2-butyramido-5-nitrophenyl)-2,2-dimethylbut-3-ynoate

To a solution of methyl 4-(2-amino-5-nitrophenyl)-2,2-dimethylbut-3-ynoate (260 mg, 1.0 mmol) and pyridine (160 mg, 2.0 mol) in CH$_2$Cl$_2$ (20 mL) was added butyryl chloride (140 mg, 1.3 mmol) at 0° C. The reaction mixture was warmed to room temperature and stirred for 3 h before the mixture was poured into ice-water. The organic layer was separated and the aqueous phase was extracted with CH$_2$Cl$_2$ (30 mL×3). The combined organic layers were dried over anhydrous Na$_2$SO$_4$ and evaporated under reduced pressure to obtain methyl 4-(2-butyramido-5-nitrophenyl)-2,2-dimethylbut-3-ynoate (150 mg, 45%), which was used directly in the next step. $^1$H NMR (400 MHz, CDCl$_3$) δ 8.79 (brs, 1H), 8.71 (d, J=9.2 Hz, 1H), 8.24 (d, J=2.8 Hz, 1H), 8.17 (dd, J=2.8, 9.2 Hz, 1H), 3.82 (s, 3H), 2.55 (t, J=7.2 Hz, 2H), 1.85-1.75 (m, 2H), 1.63 (s, 6H), 1.06 (t, J=6.8 Hz, 3H).

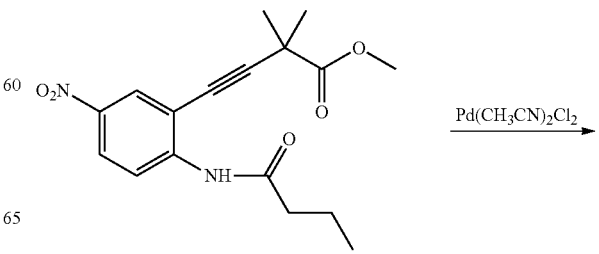

-continued

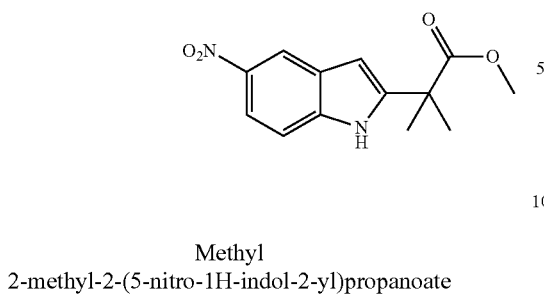

Methyl 2-methyl-2-(5-nitro-1H-indol-2-yl)propanoate

To a deoxygenated solution of methyl 4-(2-butyramido-5-nitrophenyl)-2,2-dimethylbut-3-ynoate (1.8 g, 5.4 mmol) in acetonitrile (30 mL) was added Pd(CH$_3$CN)$_2$Cl$_2$ (0.42 g, 1.6=mmol) under N$_2$. The mixture was heated at reflux for 24 h. After cooling the mixture to ambient temperature, the solid was filtered off and washed with EtOAc (50 mL×3). The filtrate was evaporated under reduced pressure to give a residue, which was purified by column chromatography on silica gel (petroleum ether/ethyl acetate=30/1) to give methyl 2-methyl-2-(5-nitro-1H-indol-2-yl)propanoate (320 mg, 23%). $^1$H NMR (400 MHz, CDCl$_3$) δ 9.05 (brs, 1H), 8.52 (d, J=2.0 Hz, 1H), 8.09 (dd, J=2.0, 8.8 Hz, 1H), 7.37 (d, J=8.8 Hz, 1H), 6.54 (d, J=1.6 Hz, 1H), 3.78 (d, J=9.6 Hz, 3H), 1.70 (s, 6H).

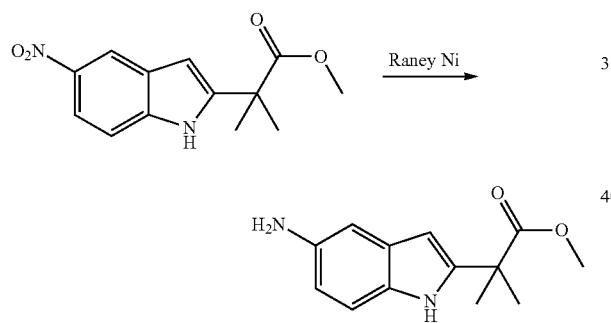

Methyl 2-(5-amino-1H-indol-2-yl)-2-methylpropanoate

A suspension of methyl 2-methyl-2-(5-nitro-1H-indol-2-yl)propanoate (60 mg, 0.23 mmol) and Raney Nickel (10 mg) in MeOH (5 mL) was hydrogenated under hydrogen (1 atm) at room temperature overnight. The catalyst was filtered off through a celite pad and the filtrate was evaporated under vacuum to give a residue, which was purified by column chromatography on silica gel (petroleum ether/ethyl acetate=5/1) to give methyl 2-(5-amino-1H-indol-2-yl)-2-methylpropanoate (20 mg, 38%). $^1$H NMR (400 MHz, CDCl$_3$) δ 8.37 (br s, 1H), 7.13 (d, J=8.4 Hz, 1H), 6.87 (d, J=2.0 Hz, 1H), 6.63 (dd, J=2.0, 8.4 Hz, 1H), 6.20 (d, J=1.2 Hz, 1H), 3.72 (d, J=7.6 Hz, 3H), 3.43 (br s, 1H), 1.65 (s, 6H); MS (ESI) m/e (M+H$^+$) 233.2.

Example 44

2-Isopropyl-1H-indol-5-amine

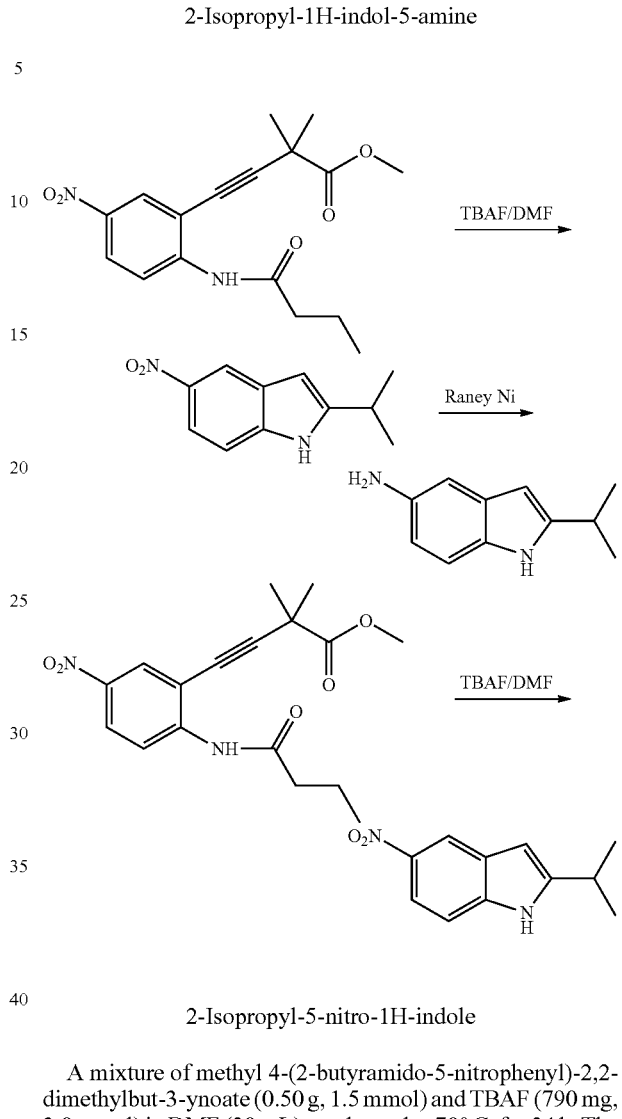

2-Isopropyl-5-nitro-1H-indole

A mixture of methyl 4-(2-butyramido-5-nitrophenyl)-2,2-dimethylbut-3-ynoate (0.50 g, 1.5 mmol) and TBAF (790 mg, 3.0 mmol) in DMF (20 mL) was heated at 70° C. for 24 h. The reaction mixture was cooled to room temperature and poured into ice water. The mixture was extracted with ether (30 mL×3). The combined organic layers were dried over anhydrous Na$_2$SO$_4$ and evaporated under reduced pressure to give a residue, which was purified by column chromatography on silica gel (petroleum ether/ethyl acetate=20/1) to give 2-isopropyl-5-nitro-1H-indole (100 mg, 33%). $^1$H NMR (400 MHz, CDCl$_3$) δ 8.68 (s, 1H), 8.25 (br s, 1H), 8.21 (dd, J=2.4, 10.0 Hz, 1H), 7.32 (d, J=8.8 Hz, 1H), 6.41 (s, 1H), 3.07-3.14 (m, 1H), 1.39 (d, J=6.8 Hz, 6H).

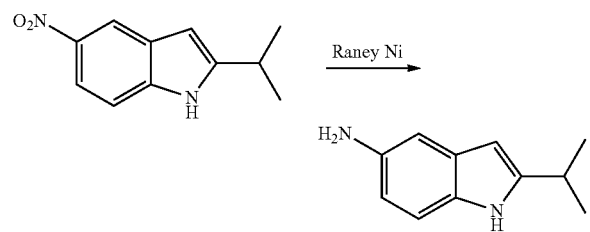

311

2-Isopropyl-1H-indol-5-amine

A suspension of 2-isopropyl-5-nitro-1H-indole (100 mg, 0.49 mmol) and Raney Nickel (10 mg) in MeOH (10 mL) was hydrogenated under hydrogen (1 atm) at the room temperature overnight. The catalyst was filtered off through a celite pad and the filtrate was evaporated under vacuum to give a residue, which was purified by column (petroleum ether/ethyl acetate=5/1) to give 2-isopropyl-1H-indol-5-amine (35 mg, 41%). $^1$H NMR (400 MHz, CDCl$_3$) δ 7.69 (br s, 1H), 7.10 (d, J=8.4 Hz, 1H), 6.86 (d, J=2.4 Hz, 1H), 6.58 (dd, J=2.4, 8.8 Hz, 1H), 6.07 (t, J=1.2 Hz, 1H), 3.55 (br s, 2H), 3.06-2.99 (m, 1H), 1.33 (d, J=7.2 Hz, 6H); MS (ESI) m/e (M+H$^+$) 175.4.

Example 45

1-(Benzo[d][1,3]dioxol-5-yl)-N-(2-(1-hydroxy-2-methylpropan-2-yl)-1H-indol-5-yl)cyclopropanecarboxamide

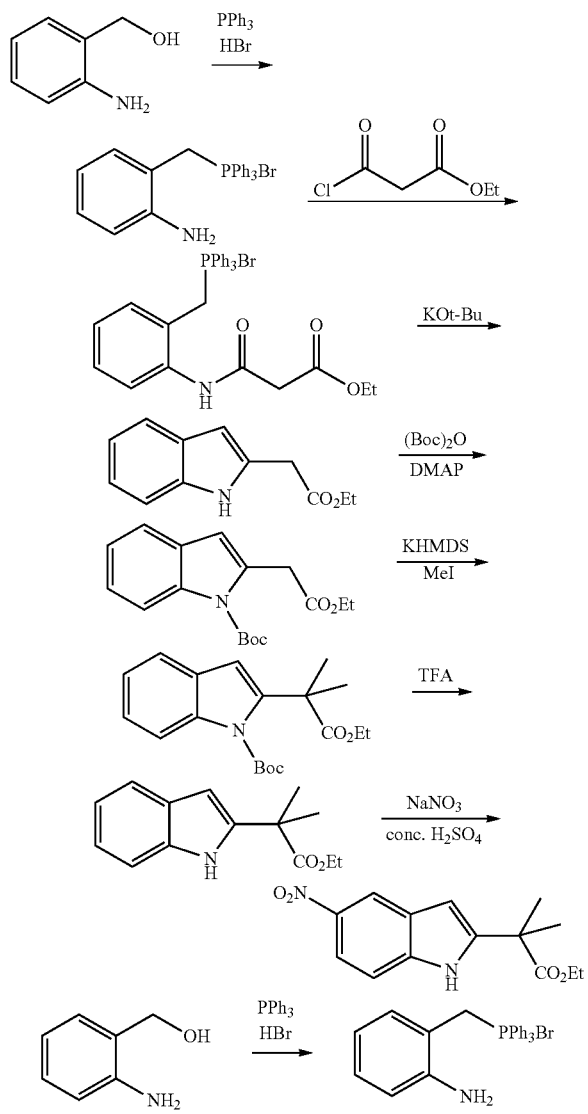

312

Triphenyl(2-aminobenzyl)phosphonium bromide

2-Aminobenzyl alcohol (60.0 g, 0.487 mol) was dissolved in acetonitrile (2.5 L) and brought to reflux. Triphenylphosphine hydrobromide (167 g, 0.487 mol) was added and the mixture was heated at reflux for 3 h. The reaction mixture was concentrated to approximately 500 mL and left at room temperature for 1 h. The precipitate was filtered and washed with cold acetonitrile followed by hexane. The solid was dried overnight at 40° C. under vacuum to give triphenyl(2-aminobenzyl)phosphonium bromide (193 g, 88%).

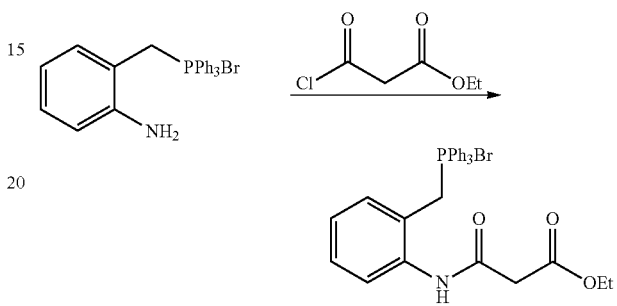

Triphenyl((ethyl(2-carbamoyl)acetate)-2-benzyl)phosphonium bromide

To a suspension of triphenyl(2-aminobenzyl)phosphonium bromide (190 g, 0.43 mol) in anhydrous dichloromethane (1 L) was added ethyl malonyl chloride (55 ml, 0.43 mol). The reaction was stirred for 3 h at room temperature. The mixture was evaporated to dryness before ethanol (400 mL) was added. The mixture was heated at reflux until a clear solution was obtained. The solution was left at room temperature for 3 h. The precipitate was filtered, washed with cold ethanol followed by hexane and dried. A second crop was obtained from the mother liquor in the same way. In order to remove residual ethanol both crops were combined and dissolved in dichloromethane (approximately 700 mL) under heating and evaporated. The solid was dried overnight at 50° C. under vacuum to give triphenyl((ethyl(2-carbamoyl)acetate)-2-benzyl)-phosphonium bromide (139 g, 58%).

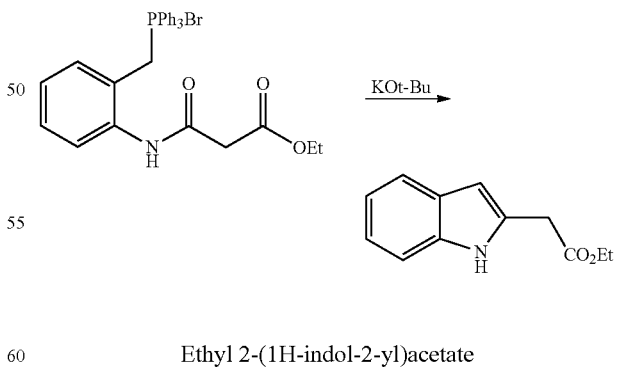

Ethyl 2-(1H-indol-2-yl)acetate

Triphenyl((ethyl(2-carbamoyl)acetate)-2-benzyl)phosphonium bromide (32.2 g, 57.3 mmol) was added to anhydrous toluene (150 mL) and the mixture was heated at reflux. Fresh potassium tert-butoxide (7.08 g, 63.1 mmol) was added in portions over 15 minutes. Reflux was continued for another 30 minutes. The mixture was filtered hot through a plug of celite and evaporated under reduced pressure. The residue was purified by column chromatography on silica gel (0-30% ethyl acetate in hexane over 45 min) to give ethyl 2-(1H-indol-2-yl)acetate (9.12 g, 78%).

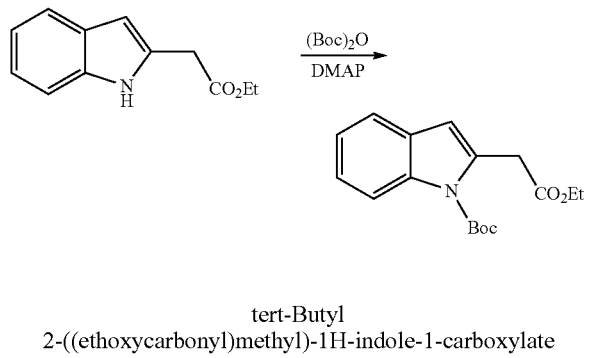

tert-Butyl 2-((ethoxycarbonyl)methyl)-1H-indole-1-carboxylate

To a solution of ethyl 2-(1H-indol-2-yl)acetate (14.7 g, 72.2 mmol) in dichloromethane (150 mL) was added 4-dimethylaminopyridine (8.83 g, 72.2 mmol) and di-tert-butyl carbonate (23.7 g, 108 mmol) in portions. After stirring for 2 h at room temperature, the mixture was diluted with dichloromethane, washed with water, dried over magnesium sulfate and purified by silica gel chromatography (0 to 20% EtOAc in hexane) to give tert-butyl 2-((ethoxycarbonyl)methyl)-1H-indole-1-carboxylate (20.0 g, 91%).

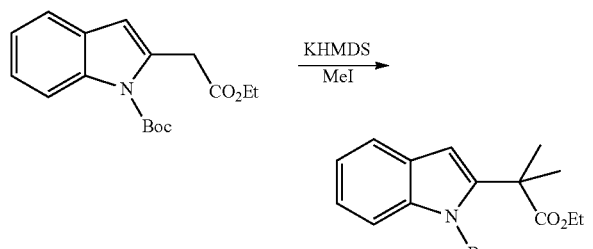

tert-Butyl 2-(2-(ethoxycarbonyl)propan-2-yl)-1H-indole-1-carboxylate tert-Butyl 2-((ethoxycarbonyl)methyl)-1H-indole-1-carboxylate (16.7 g, 54.9 mmol) was added to anhydrous THF (100 mL) and cooled to −78° C. A 0.5M solution of potassium hexamethyldisilazane (165 mL, 82 mmol) was added slowly such that the internal temperature stayed below −60° C. Stirring was continued for 30 minutes at −78° C. To this mixture, methyl iodide (5.64 mL, 91 mmol) was added. The mixture was stirred for 30 min at room temperature and then cooled to −78° C. A 0.5M solution of potassium hexamethyldisilazane (210 mL, 104 mmol) was added slowly and the mixture was stirred for another 30 minutes at −78° C. More methyl iodide (8.6 mL, 137 mmol) was added and the mixture was stirred for 1.5 h at room temperature. The reaction was quenched with sat. aq. ammonium chloride and partitioned between water and dichloromethane. The aqueous phase was extracted with dichloromethane and the combined organic phases were dried over magnesium sulfate and evaporated under reduced pressure. The residue was purified by column chromatography on silica gel (0 to 20% ethylacetate in hexane) to give tert-butyl 2-(2-(ethoxycarbonyl)propan-2-yl)-1H-indole-1-carboxylate (17.1 g, 94%).

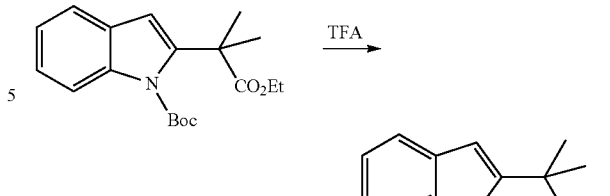

Ethyl 2-(1H-indol-2-yl)-2-methylpropanoate tert-Butyl 2-(2-(ethoxycarbonyl)propan-2-yl)-1H-indole-1-carboxylate (22.9 g, 69.1 mmol) was dissolved in dichloromethane (200 mL) before TFA (70 mL) was added. The mixture was stirred for 5 h at room temperature. The mixture was evaporated to dryness, taken up in dichloromethane and washed with saturated sodium bicarbonate solution, water, and brine. The product was purified by column chromatography on silica gel (0-20% EtOAc in hexane) to give ethyl 2-(1H-indol-2-yl)-2-methylpropanoate (12.5 g, 78%).

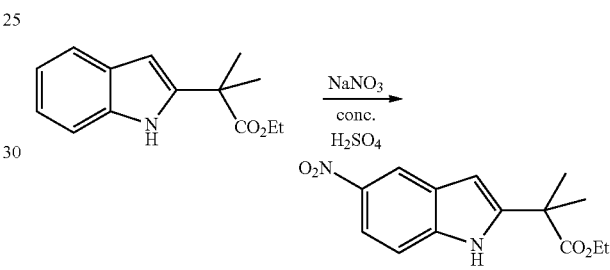

Ethyl 2-methyl-2-(5-nitro-1H-indol-2-yl)propanoate

Ethyl 2-(1H-indol-2-yl)-2-methylpropanoate (1.0 g, 4.3 mmol) was dissolved in concentrated sulfuric acid (6 mL) and cooled to −10° C. (salt/ice-mixture). A solution of sodium nitrate (370 mg, 4.33 mmol) in concentrated sulfuric acid (3 mL) was added dropwise over 30 min. Stirring was continued for another 30 min at −10° C. The mixture was poured into ice and the product was extracted with dichloromethane. The combined organic phases were washed with a small amount of sat. aq. sodium bicarbonate. The product was purified by column chromatography on silica gel (5-30% EtOAc in hexane) to give ethyl 2-methyl-2-(5-nitro-1H-indol-2-yl)propanoate (0.68 g, 57%).

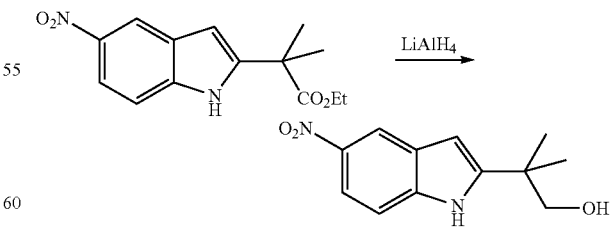

2-Methyl-2-(5-nitro-1H-indol-2-yl)propan-1-ol

To a cooled solution of LiAlH$_4$ (1.0 M in THF, 1.1 mL, 1.1 mmol) in THF (5 mL) at 0° C. was added a solution of ethyl 2-methyl-2-(5-nitro-1H-indol-2-yl)propanoate (0.20 g, 0.72 mmol) in THF (3.4 mL) dropwise. After addition, the mixture was allowed to warm up to room temperature and was stirred for 3 h. The mixture was cooled to 0° C. before water (2 mL) was slowly added followed by careful addition of 15% NaOH (2 mL) and water (4 mL). The mixture was stirred at room temperature for 0.5 h and was filtered through a short plug of celite using ethyl acetate. The organic layer was separated from the aqueous layer, dried over $Na_2SO_4$, filtered and evaporated under reduced pressure. The residue was purified by column chromatography on silica gel (ethyl acetate/hexane=1/1) to give 2-methyl-2-(5-nitro-1H-indol-2-yl)propan-1-ol (0.098 g, 58%).

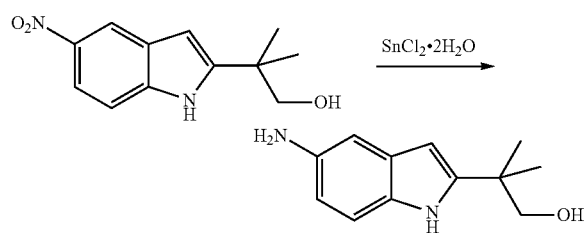

2-(5-Amino-1H-indol-2-yl)-2-methylpropan-1-ol

To a solution of 2-methyl-2-(5-nitro-1H-indol-2-yl)propan-1-ol (0.094 g, 0.40 mmol) in ethanol (4 mL) was added tin chloride dihydrate (0.451 g, 2.0 mmol). The mixture was heated in the microwave at 120° C. for 1 h. The mixture was diluted with ethyl acetate and water before being quenched with saturated aqueous $NaHCO_3$. The reaction mixture was filtered through a plug of celite using ethyl acetate. The organic layer was separated from the aqueous layer, dried over $Na_2SO_4$, filtered and evaporated under reduced pressure to give 2-(5-amino-1H-indol-2-yl)-2-methylpropan-1-ol (0.080 g, 98%).

Example 46

2-(Pyridin-2-yl)-1H-indol-5-amine

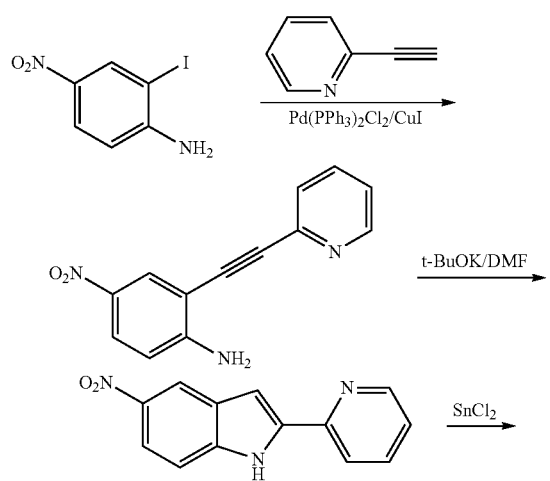

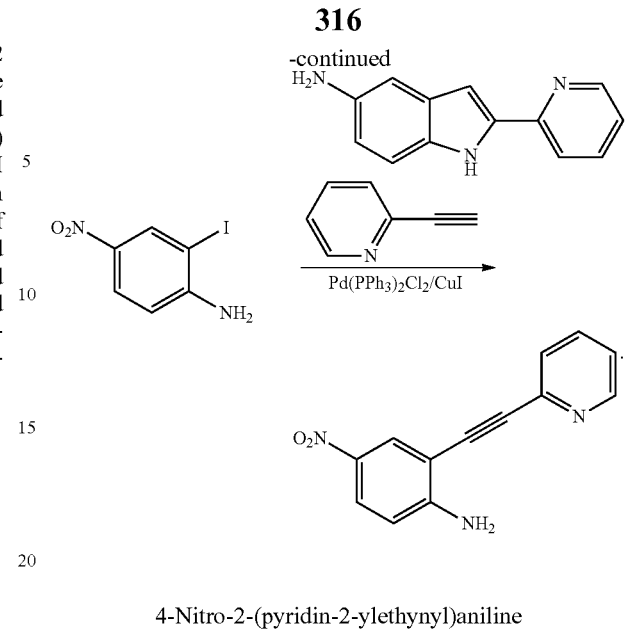

4-Nitro-2-(pyridin-2-ylethynyl)aniline

To the solution of 2-iodo-4-nitroaniline (3.0 g, 11 mmol) in DMF (60 mL) and $Et_3N$ (60 mL) was added 2-ethynylpyridine (3.0 g, 45 mmol), $Pd(PPh_3)_2Cl_2$ (600 mg) and CuI (200 mg) under $N_2$. The reaction mixture was stirred at 60° C. for 12 h. The mixture was diluted with water and extracted with dichloromethane (3×100 mL). The combined organic layers were washed with brine, dried over anhydrous $Na_2SO_4$ and concentrated in vacuum. The residue was purified by chromatography on silica gel (5-10% ethyl acetate/petroleum ether) to afford 4-nitro-2-(pyridin-2-ylethynyl)aniline (1.5 g, 60%). $^1$H NMR (300 MHz, $CDCl_3$) δ 8.60 (s, 1H), 8.13 (d, J=2.1 Hz, 1H), 7.98 (d, J=1.8, 6.9 Hz, 1H), 7.87-7.80 (m, 2H), 7.42-7.39 (m, 1H), 7.05 (brs, 2H), 6.80 (d, J=6.9 Hz, 1H).

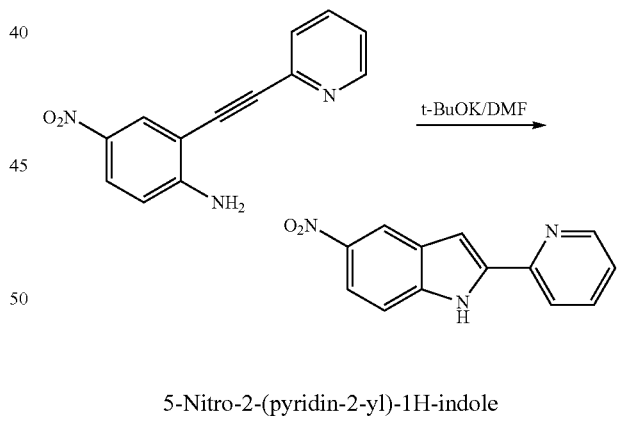

5-Nitro-2-(pyridin-2-yl)-1H-indole

To the solution of 4-nitro-2-(pyridin-2-ylethynyl)aniline (1.5 g, 6.3 mmol) in DMF (50 mL) was added t-BuOK (1.5 g, 13 mmol). The reaction mixture was stirred at 90° C. for 2 h. The mixture was diluted with water and extracted with dichloromethane (3×50 mL). The combined organic layers were washed with brine, dried over anhydrous $Na_2SO_4$ and concentrated in vacuum. The residue was purified by chromatography on silica gel (5-10% ethyl acetate/petroleum ether) to afford 5-nitro-2-(pyridin-2-yl)-1H-indole (1.0 g, 67% yield). $^1$H NMR (300 MHz, d-DMSO) δ 12.40 (s, 1H), 8.66 (d, J=2.1 Hz, 1H), 8.58 (d, J=1.8 Hz, 1H), 8.07-7.91 (m, 3H), 7.59 (d, J=6.6 Hz, 1H), 7.42-7.37 (m, 2H).

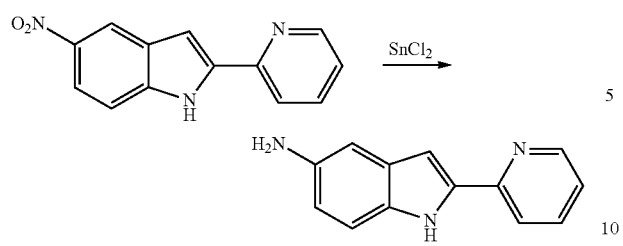

2-(Pyridin-2-yl)-1H-indol-5-amine

To a solution of 5-nitro-2-(pyridin-2-yl)-1H-indole (700 mg, 2.9 mmol) in EtOH (20 mL) was added SnCl$_2$ (2.6 g, 12 mmol). The mixture was heated at reflux for 10 h. Water was added and the mixture was extracted with EtOAc (50 mL×3). The combined organic layers were washed with brine, dried over anhydrous Na$_2$SO$_4$ and concentrated in vacuum. The residue was purified by chromatography on silica gel (5-10% ethyl acetate/petroleum ether) to afford 2-(pyridin-2-yl)-1H-indol-5-amine (120 mg, 20%). $^1$H NMR (400 MHz, CDCl$_3$) δ 9.33 (brs, 1H), 8.55 (dd, J=1.2, 3.6 Hz, 1H), 7.76-7.67 (m, 2H), 7.23 (d, J=6.4 Hz, 1H), 7.16-7.12 (m, 1H), 6.94 (d, J=2.0 Hz, 1H), 6.84 (d, J=2.4 Hz, 1H), 6.71-6.69 (dd, J=2.0, 8.4 Hz, 1H).

Example 47

2-(Pyridin-2-yl)-1H-indol-5-amine

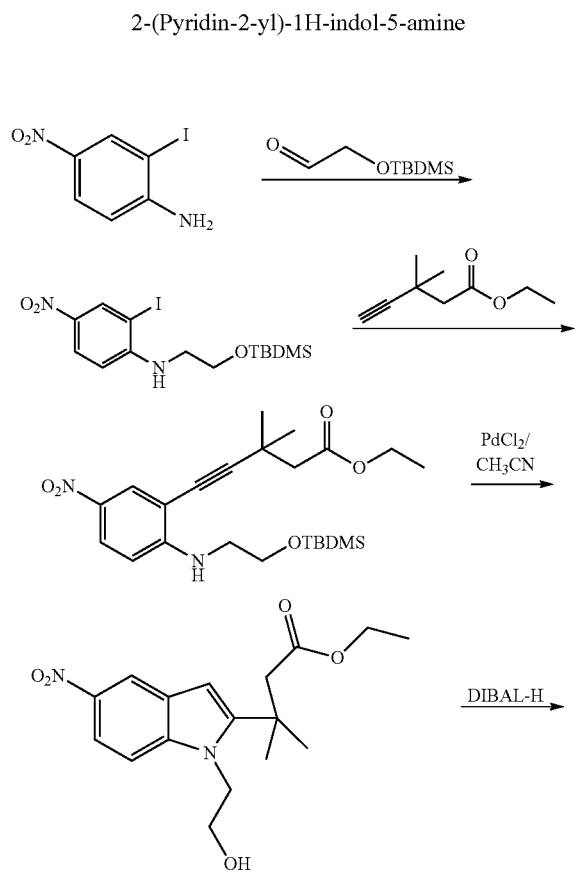

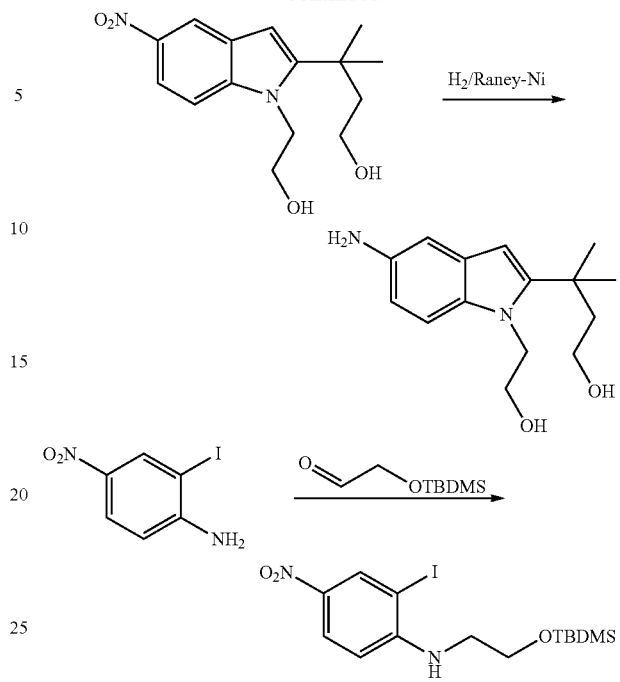

[2-(tert-Butyl-dimethyl-silanyloxy)-ethyl]-(2-iodo-4-nitro-phenyl)-amine

To a solution of 2-iodo-4-nitroaniline (2.0 g, 7.6 mmol) and 2-(tert-butyldimethylsilyloxy)-acetaldehyde (3.5 g, 75% purity, 15 mmol) in methanol (30 mL) was added TFA (1.5 mL) at 0° C. The reaction mixture was stirred at this temperature for 30 min before NaCNBH$_3$ (900 mg, 15 mmol) was added in portions. The mixture was stirred for 2 h and was then quenched with water. The resulting mixture was extracted with EtOAc (30 mL×3), the combined organic extracts were dried over anhydrous Na$_2$SO$_4$ and evaporated under vacuum, and the residue was purified by chromatography on silica gel (5% ethyl acetate/petroleum) to afford [2-(tert-butyl-dimethyl-silanyloxy)-ethyl]-(2-iodo-4-nitro-phenyl)-amine (800 mg, 25%). $^1$H NMR (300 MHz, CDCl$_3$) δ 8.57 (d, J=2.7 Hz, 1H), 8.12 (dd, J=2.4, 9.0 Hz, 1H), 6.49 (d, J=9.3 Hz, 1H), 5.46 (br s, 1H), 3.89 (t, J=5.4 Hz, 2H), 3.35 (q, J=5.4 Hz, 2H), 0.93 (s, 9H), 0.10 (s, 6H).

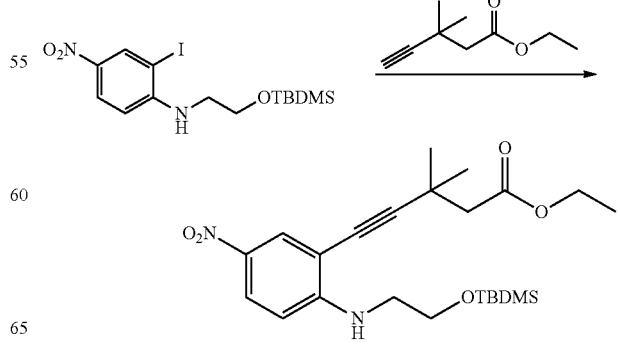

5-{2-[2-(tert-Butyl-dimethyl-silanyloxy)-ethylamino]-5-nitro-phenyl}-3,3-dimethyl-pent-4-ynoic acid ethyl ester To a solution of [2-(tert-butyl-dimethyl-silanyloxy)-ethyl]-(2-iodo-4-nitro-phenyl)-amine (800 mg, 1.9 mmol) in Et$_3$N (20 mL) was added Pd(PPh$_3$)$_2$Cl$_2$ (300 mg, 0.040 mmol), CuI (76 mg, 0.040 mmol) and 3,3-dimethyl-but-1-yne (880 mg, 5.7 mmol) successively under N$_2$ protection. The reaction mixture was heated at 80° C. for 6 h and allowed to cool down to room temperature. The resulting mixture was extracted with EtOAc (30 mL×3). The combined organic extracts were dried over anhydrous Na$_2$SO$_4$ and evaporated under vacuum to give 5-{2-[2-(tert-butyl-dimethyl-silanyloxy)-ethylamino]-5-nitro-phenyl}-3,3-dimethyl-pent-4-ynoic acid ethyl ester (700 mg, 82%), which was used in the next step without further purification. $^1$H NMR (400 MHz, CDCl$_3$) δ 8.09 (s, 1H), 8.00 (d, J=9.2 Hz, 1H), 6.54 (d, J=9.2 Hz, 1H), 6.45 (brs, 1H), 4.17-4.10 (m, 4H), 3.82 (t, J=5.6 Hz, 2H), 3.43 (q, J=5.6 Hz, 2H), 2.49 (s, 2H), 1.38 (s, 6H), 1.28 (t, J=7.2 Hz, 3H), 0.84 (s, 9H), 0.00 (s, 6H).

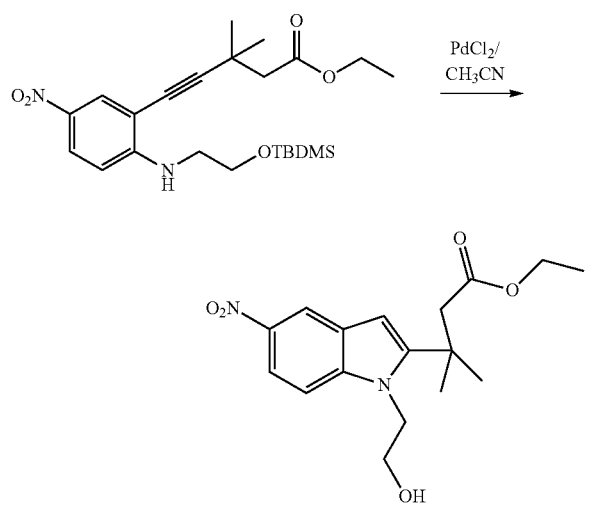

3-[1-(2-Hydroxy-ethyl)-5-nitro-1H-indol-2-yl]-3-methyl-butyric acid ethyl ester A solution of 5-{2-[2-(tert-butyl-dimethyl-silanyloxy)-ethylamino]-5-nitro-phenyl}-3,3-dimethyl-pent-4-ynoic acid ethyl ester (600 mg, 1.34 mmol) and PdCl$_2$ (650 mg) in CH$_3$CN (30 mL) was heated at reflux overnight. The resulting mixture was extracted with EtOAc (30 mL×3). The combined organic extracts were dried over anhydrous Na$_2$SO$_4$ and evaporated under vacuum. The residue was dissolved in THF (20 mL) and TBAF (780 mg, 3.0 mmol) was added. The mixture was stirred at room temperature for 1 h, the solvent was removed under vacuum, and the residue was purified by chromatography on silica gel (10% ethyl acetate/petroleum) to afford 3-[1-(2-hydroxy-ethyl)-5-nitro-1H-indol-2-yl]-3-methyl-butyric acid ethyl ester (270 mg, 60%). $^1$H NMR (300 MHz, CDCl$_3$) δ 8.45 (d, J=2.1 Hz, 1H), 8.05 (dd, J=2.1, 9.0 Hz, 1H), 6.36 (d, J=9.0 Hz, 1H), 6.48 (s, 1H), 4.46 (t, J=6.6 Hz, 2H), 4.00-3.91 (m, 4H), 2.76 (s, 2H), 1.61 (s, 6H), 0.99 (t, J=7.2 Hz, 1H), 0.85 (s, 9H), 0.03 (s, 6H).

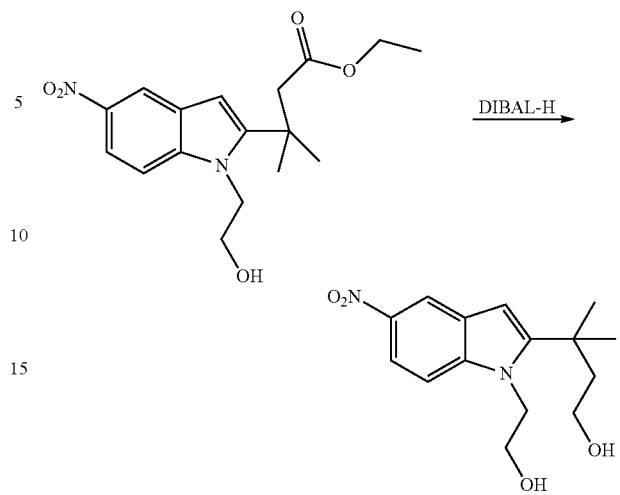

3-[1-(2-Hydroxy-ethyl)-5-nitro-1,1-indol-2-yl]-3-methyl-butan-1-ol

To a solution of 3-[1-(2-hydroxy-ethyl)-5-nitro-1H-indol-2-yl]-3-methyl-butyric acid ethyl ester (700 mg, 2.1 mmol) in THF (25 mL) was added DIBAL-H (1.0 M, 4.2 mL, 4.2 mmol) at −78° C. The mixture was stirred at room temperature for 1 h. Water (2 mL) was added and the resulting mixture was extracted with EtOAc (15 mL×3). The combined organic layers were dried over anhydrous Na$_2$SO$_4$ and evaporated under vacuum. The residue was purified by chromatography on silica gel (15% ethyl acetate/petroleum) to afford 3-[1-(2-hydroxy-ethyl)-5-nitro-1H-indol-2-yl]-3-methyl-butan-1-ol (300 mg, 49%). $^1$H NMR (300 MHz, d-DMSO) δ 8.42 (d, J=1.5 Hz, 1H), 7.95 (dd, J=1.2, 8.7 Hz, 1H), 6.36 (d, J=9.3 Hz, 1H), 6.50 (s, 1H), 5.25 (br s, 1H), 4.46-4.42 (m, 4H), 3.69-3.66 (m, 2H), 3.24-3.21 (m, 2H), 1.42 (s, 6H).

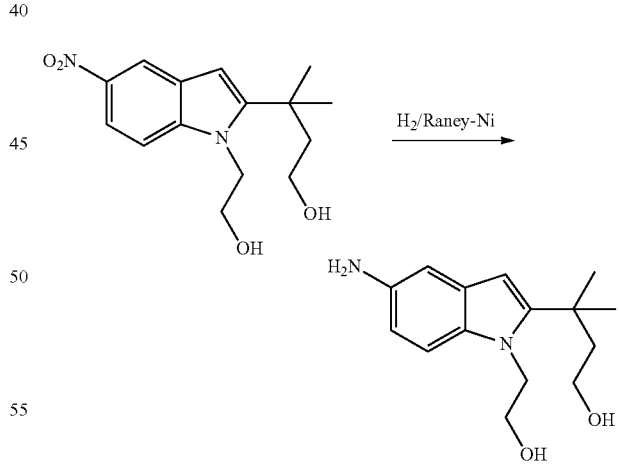

3-[5-Amino-1-(2-hydroxy-ethyl)-1H-indol-2-yl]-3-methyl-butan-1-ol

A solution of 3-[1-(2-hydroxy-ethyl)-5-nitro-1H-indol-2-yl]-3-methyl-butan-1-ol (300 mg, 1.03 mmol) and Raney Nickel (200 mg) in CH$_3$OH (30 mL) was stirred for 5 h at room temperature under a H$_2$ atmosphere. The catalyst was filtered through a celite pad and the filtrate was evaporated under vacuum to give a residue, which was purified by preparative TLC to afford 3-[5-amino-1-(2-hydroxy-ethyl)-1H-indol-2-yl]-3-methyl-butan-1-ol (70 mg, 26%). $^1$H NMR (300 MHz, CDCl$_3$) δ 7.07 (d, J=8.7 Hz, 1H), 6.83 (d, J=2.1 Hz, 1H), 6.62 (dd, J=2.1, 8.4 Hz, 1H), 6.15 (s, 1H), 4.47 (t, J=5.4 Hz, 2H), 4.07 (t, J=5.4 Hz, 2H), 3.68 (t, J=5.7 Hz, 2H), 2.16 (t, J=5.7 Hz, 2H), 4.00-3.91 (m, 4H), 2.76 (s, 2H), 1.61 (s, 6H), 1.42 (s, 6H).

Example 48 tert-Butyl 2-(5-amino-1H-indol-2-yl)piperidine-1-carboxylate

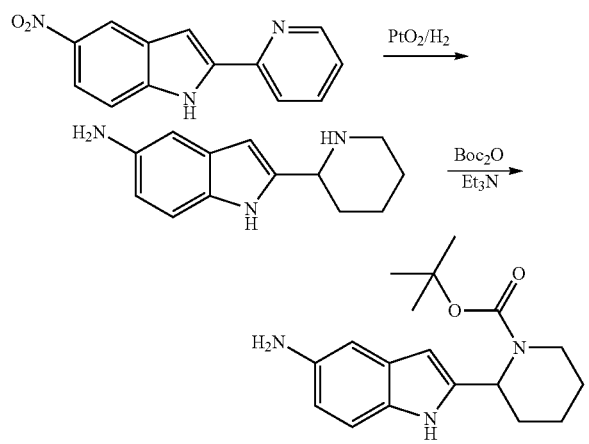

2-(Piperidin-2-yl)-1H-indol-5-amine

5-Nitro-2-(pyridin-2-yl)-1H-indole (1.0 g, 4.2 mmol) was added to HCl/MeOH (2 M, 50 mL). The reaction mixture was stirred at room temperature for 1 h and the solvent was evaporated under vacuum. PtO$_2$ (200 mg) was added to a solution of the residue in MeOH (50 mL) and the reaction mixture was stirred under hydrogen atmosphere (1 atm) at room temperature for 2 h. The catalyst was filtered through a celite pad and the solvent was evaporated under vacuum to afford 2-(piperidin-2-yl)-1H-indol-5-amine (1.0 g), which was directly used in the next step.

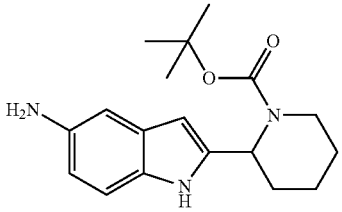

tert-Butyl 2-(5-amino-1H-indol-2-yl)piperidine-1-carboxylate

To a solution of 2-(piperidin-2-yl)-1H-indol-5-amine (1.0 g) in Et$_3$N (25 mL) and THF (25 mL) was added Boc$_2$O (640 mg, 2.9 mmol). The reaction mixture was stirred at room temperature overnight. The mixture was diluted with water and extracted with dichloromethane (3×25 mL). The combined organic layers were washed with brine, dried over anhydrous Na$_2$SO$_4$ and concentrated in vacuum. The residue was purified by chromatography on silica gel (5-10% ethyl acetate/petroleum ether) followed by preparative HPLC to afford tert-butyl 2-(5-amino-1H-indol-2-yl)piperidine-1-carboxylate (15 mg, 1% over 2 steps). $^1$H NMR (400 MHz, CDCl$_3$) δ 8.82 (s, 1H), 7.58 (s, 1H), 7.22 (d, J=8.8 Hz, 1H), 7.02 (d, J=1.6, 8.0 Hz, 1H), 6.42 (s, 1H), 6.25 (s, 1H), 3.91-3.88 (m, 1H), 3.12-3.10 (m, 1H), 2.81-2.76 (m, 1H), 2.06-1.97 (m, 4H), 1.70-1.58 (m, 2H), 1.53 (s, 9H).

Example 49

6-amino-1H-indole-2-carbonitrile

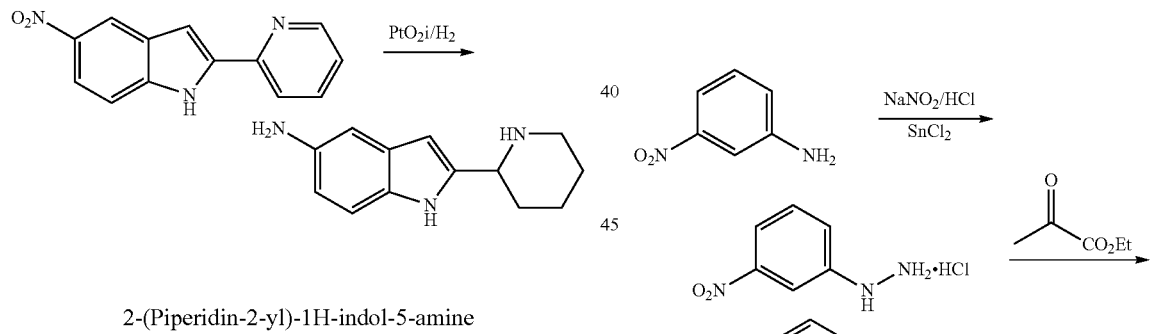

-continued

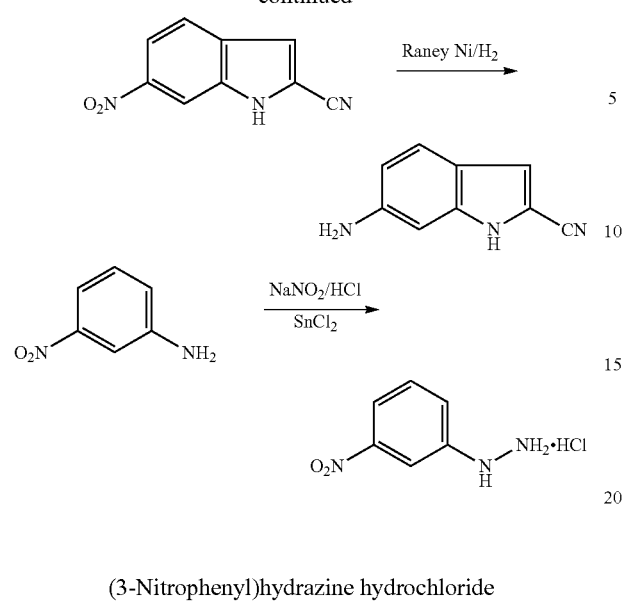

(3-Nitrophenyl)hydrazine hydrochloride

3-Nitroaniline (28 g, 0.20 mol) was dissolved in a mixture of $H_2O$ (40 mL) and 37% HCl (40 mL). A solution of $NaNO_2$ (14 g, 0.20 mol) in $H_2O$ (60 mL) was added to the mixture at 0° C., and then a solution of $SnCl_2.H_2O$ (140 g, 0.60 mol) in 37% HCl (100 mL) was added. After stirring at 0° C. for 0.5 h, the insoluble material was isolated by filtration and was washed with water to give (3-nitrophenyl)hydrazine hydrochloride (28 g, 73%).

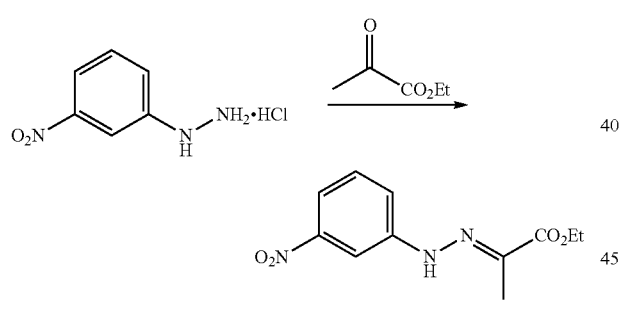

(E)-Ethyl 2-(2-(3-nitrophenyl)hydrazono)propanoate (3-Nitrophenyl)hydrazine hydrochloride (30 g, 0.16 mol) and 2-oxo-propionic acid ethyl ester (22 g, 0.19 mol) were dissolved in ethanol (300 mL). The mixture was stirred at room temperature for 4 h before the solvent was evaporated under reduced pressure to give (E)-ethyl 2-(2-(3-nitrophenyl) hydrazono)propanoate, which was used directly in the next step.

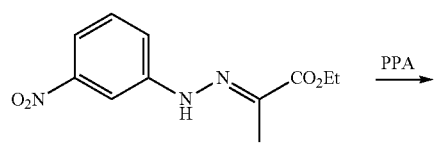

-continued

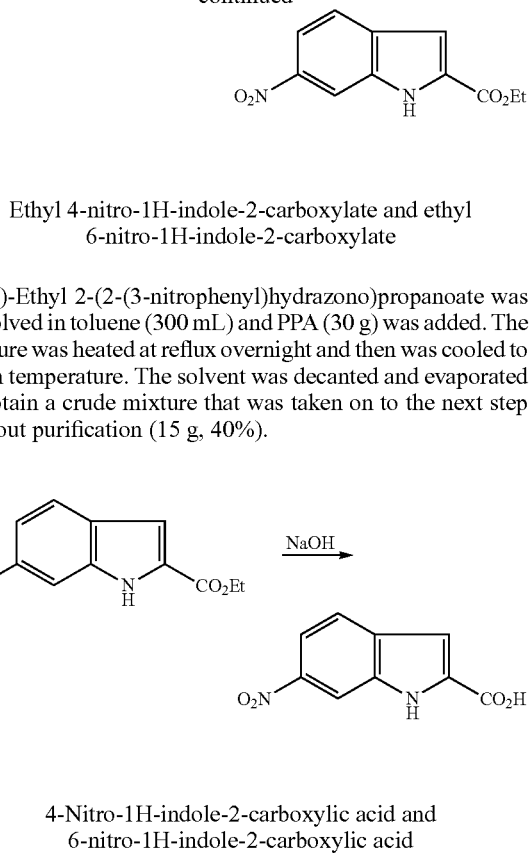

Ethyl 4-nitro-1H-indole-2-carboxylate and ethyl 6-nitro-1H-indole-2-carboxylate (E)-Ethyl 2-(2-(3-nitrophenyl)hydrazono)propanoate was dissolved in toluene (300 mL) and PPA (30 g) was added. The mixture was heated at reflux overnight and then was cooled to room temperature. The solvent was decanted and evaporated to obtain a crude mixture that was taken on to the next step without purification (15 g, 40%).

4-Nitro-1H-indole-2-carboxylic acid and 6-nitro-1H-indole-2-carboxylic acid

A mixture of ethyl 6-nitro-1H-indole-2-carboxylate (0.5 g) and 10% NaOH (20 mL) was heated at reflux overnight and then was cooled to room temperature. The mixture was extracted with ether and the aqueous phase was acidified with HCl to pH 1-2. The insoluble solid was isolated by filtration to give a crude mixture that was taken on to the next step without purification (0.3 g, 68%).

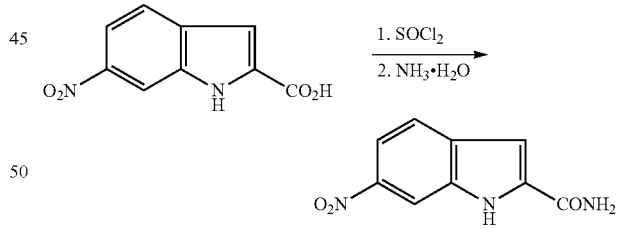

4-Nitro-1H-indole-2-carboxamide and 6-nitro-1H-indole-2-carboxamide

A mixture of 6-nitro-1H-indole-2-carboxylic acid (12 g, 58 mmol) and $SOCl_2$ (50 mL, 64 mmol) in benzene (150 mL) was heated at reflux for 2 h. The benzene and excess $SOCl_2$ was removed under reduced pressure. The residue was dissolved in anhydrous $CH_2Cl_2$ (250 mL) and $NH_3.H_2O$ (22 g, 0.32 mol) was added dropwise at 0° C. The mixture was stirred at room temperature for 1 h. The insoluble solid was isolated by filtration to obtain crude mixture (9.0 g, 68%), which was used directly in the next step.

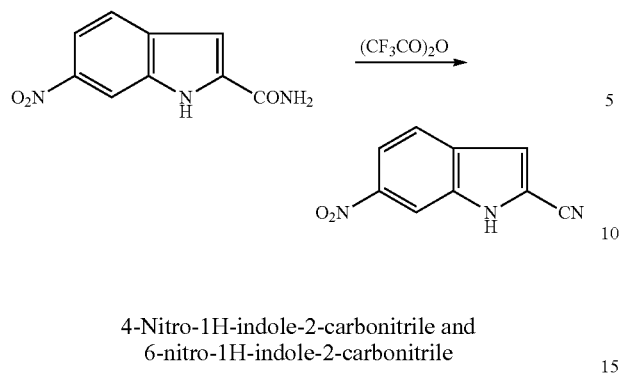

4-Nitro-1H-indole-2-carbonitrile and 6-nitro-1H-indole-2-carbonitrile

6-Nitro-1H-indole-2-carboxamide (5.0 g, 24 mmol) was dissolved in $CH_2Cl_2$ (200 mL). $Et_3N$ (24 g, 0.24 mol) and $(CF_3CO)_2O$ (51 g, 0.24 mol) were added dropwise to the mixture at room temperature. The mixture was continued to stir for 1 h and was then poured into water (100 mL). The organic layer was separated and the aqueous layer was extracted with EtOAc (100 mL×3). The combined organic layers were dried over $Na_2SO_4$, filtered and concentrated under reduced pressure to obtain crude product which was purified by column chromatography on silica gel to give a impure sample of 4-nitro-1H-indole-2-carbonitrile (2.5 g, 55%).

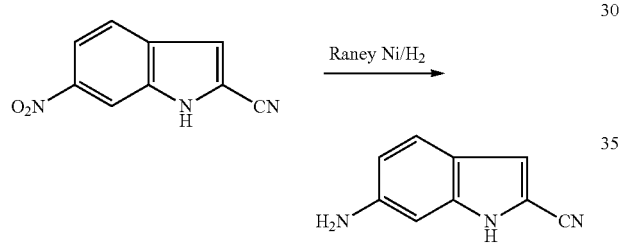

6-Amino-1H-indole-2-carbonitrile

A mixture of 6-nitro-1H-indole-2-carbonitrile (2.5 g, 13 mmol) and Raney Nickel (500 mg) in EtOH (50 mL) was stirred at room temperature under $H_2$ (1 atm) for 1 h. Raney Nickel was removed via filtration and the filtrate was evaporated under reduced pressure to give a residue, which was purified by column chromatograpy on silica get to give 6-amino-1H-indole-2-carbonitrile (1.0 g, 49%). $^1$H NMR (DMSO-$d_6$) δ 12.75 (br s, 1H), 7.82 (d, J=8 Hz, 1H), 7.57 (s, 1H), 7.42 (s, 1H), 7.15 (d, J=8 Hz, 1H); MS (ESI) m/e (M+H$^+$) 158.2.

Example 50

6-Amino-1H-indole-3-carbonitrile

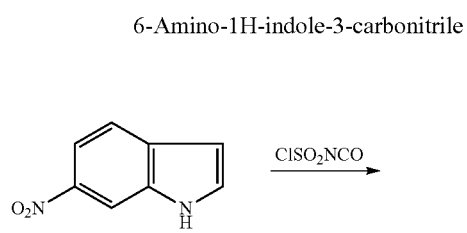

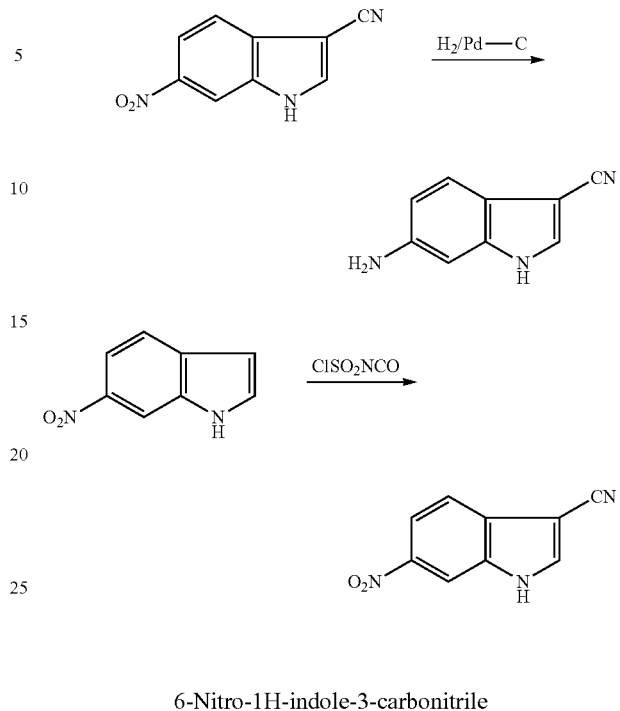

6-Nitro-1H-indole-3-carbonitrile

To a solution of 6-nitroindole (4.9 g 30 mmol) in DMF (24 mL) and $CH_3CN$ (240 mL) was added dropwise a solution of $ClSO_2NCO$ (5.0 mL) in $CH_3CN$ (39 mL) at 0° C. After addition, the reaction was allowed to warm to room temperature and was stirred for 2 h. The mixture was then poured into ice-water and basified with sat. $NaHCO_3$ solution to pH 7-8. The mixture was extracted with ethyl acetate. The organics were washed with brine, dried over $Na_2SO_4$ and concentrated to give 6-nitro-1H-indole-3-carbonitrile (4.6 g, 82%).

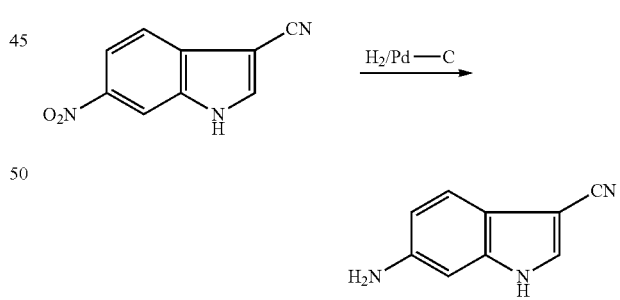

6-Amino-1H-indole-3-carbonitrile

A suspention of 6-nitro-1H-indole-3-carbonitrile (4.6 g, 25 mmol) and 10% Pd—C (0.46 g) in EtOH (50 mL) was stirred under $H_2$ (1 atm) at room temperature overnight. After filtration, the filtrate was concentrated and the residue was purified by column chromatography on silica gel (petroleum ether/ethyl acetate=3/1) to give 6-amino-1H-indole-3-carbonitrile (1.0 g, 98%) as a pink solid. $^1$H NMR (DMSO-$d_6$) δ 11.51 (s, 1H), 7.84 (d, J=2.4 Hz, 1H), 7.22 (d, J=8.4 Hz, 1H), 6.62 (s, 1H), 6.56 (d, J=8.4 Hz, 1H), 5.0 (s, 2H); MS (ESI) m/e (M+H+) 157.1.

Example 51

2-tert-Butyl-1H-indol-6-amine

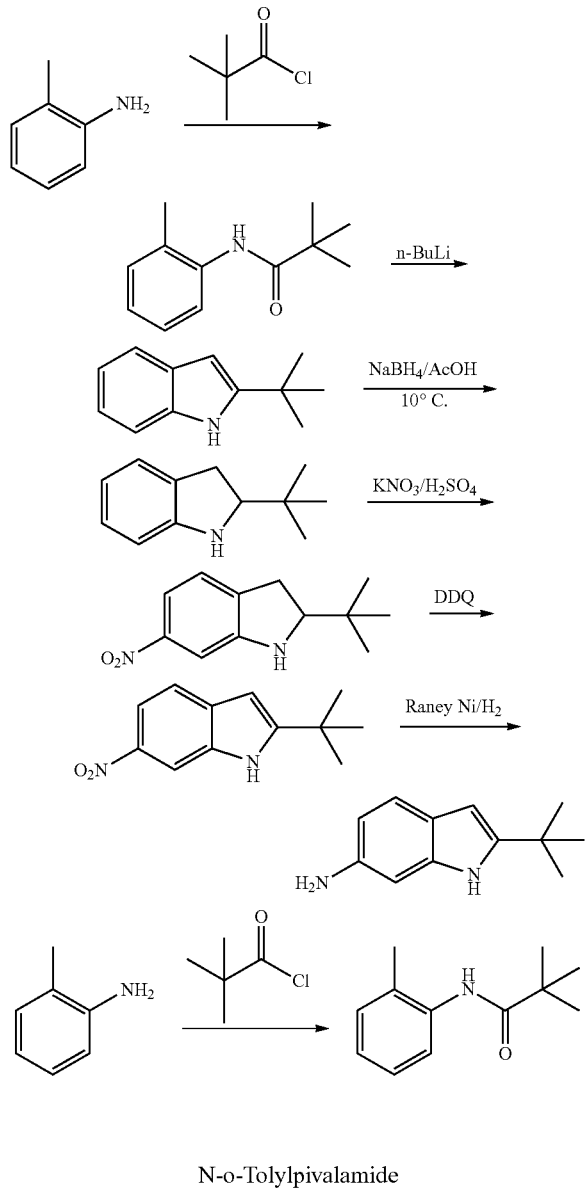

N-o-Tolylpivalamide

To a solution of o-tolylamine (21 g, 0.20 mol) and Et$_3$N (22 g, 0.22 mol) in CH$_2$Cl$_2$ was added 2,2-dimethyl-propionyl chloride (25 g, 0.21 mol) at 10° C. After addition, the mixture was stirred overnight at room temperature. The mixture was washed with aq. HCl (5%, 80 mL), saturated aq. NaHCO$_3$ and brine. The organic layer was dried over Na$_2$SO$_4$ and concentrated under vacuum to give N-o-tolylpivalamide (35 g, 91%). $^1$H NMR (300 MHz, CDCl$_3$) δ 7.88 (d, J=7.2 Hz, 1H), 7.15-7.25 (m, 2H), 7.05 (t, J=7.2 Hz, 1H), 2.26 (s, 3H), 1.34 (s, 9H).

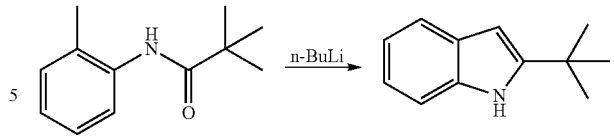

2-tert-Butyl-1H-indole

To a solution of N-o-tolylpivalamide (30.0 g, 159 mmol) in dry THF (100 mL) was added dropwise n-BuLi (2.5 M in hexane, 190 mL) at 15° C. After addition, the mixture was stirred overnight at 15° C. The mixture was cooled in an ice-water bath and treated with saturated NH$_4$Cl. The organic layer was separated and the aqueous layer was extracted with ethyl acetate. The combined organic layers were dried over anhydrous Na$_2$SO$_4$, filtered, and concentrated in vacuum. The residue was purified by column chromatography on silica gel to give 2-tert-butyl-1H-indole (24 g, 88%). $^1$H NMR (300 MHz, CDCl$_3$) δ 7.99 (br. s, 1H), 7.54 (d, J=7.2 Hz, 1H), 7.05 (d, J=7.8 Hz, 1H), 7.06-7.13 (m, 2H), 6.26 (s, 1H), 1.39 (s, 9H).

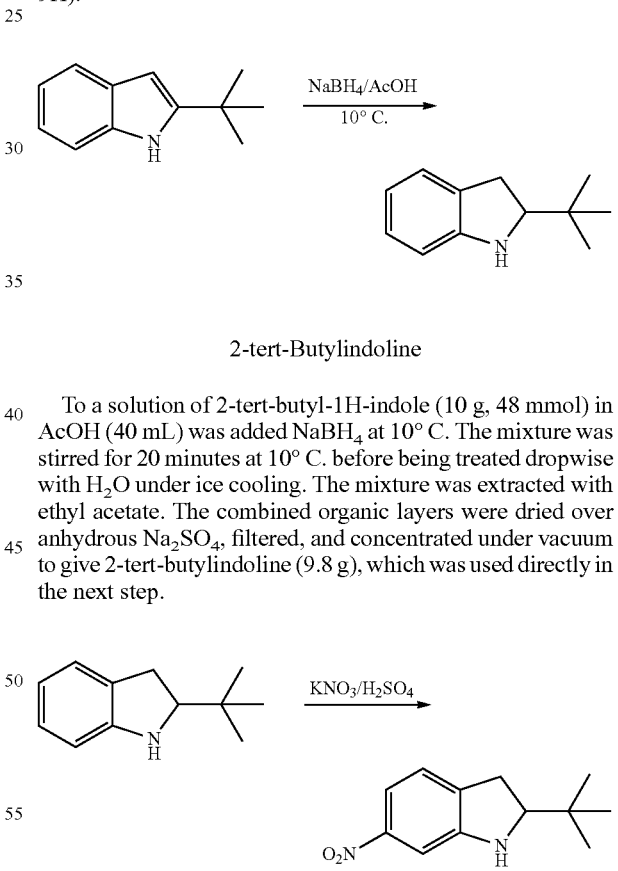

2-tert-Butylindoline

To a solution of 2-tert-butyl-1H-indole (10 g, 48 mmol) in AcOH (40 mL) was added NaBH$_4$ at 10° C. The mixture was stirred for 20 minutes at 10° C. before being treated dropwise with H$_2$O under ice cooling. The mixture was extracted with ethyl acetate. The combined organic layers were dried over anhydrous Na$_2$SO$_4$, filtered, and concentrated under vacuum to give 2-tert-butylindoline (9.8 g), which was used directly in the next step.

2-tert-butyl-6-nitroindoline and
2-tert-butyl-5-nitro-1H-indole

To a solution of 2-tert-butylindoline (9.7 g) in H$_2$SO$_4$ (98%, 80 mL) was slowly added KNO$_3$ (5.6 g, 56 mmol) at 0° C. After addition, the reaction mixture was stirred at room temperature for 1 h. The mixture was carefully poured into cracked ice, basified with Na$_2$CO$_3$ to pH 8 and extracted with ethyl acetate. The combined extracts were washed with brine, dried over anhydrous Na₂SO₄ and concentrated under vacuum. The residue was purified by column chromatography to give 2-tert-butyl-6-nitroindoline (4.0 g, 31% over two steps). ¹H NMR (300 MHz, CDCl₃) δ 7.52 (dd, J=1.8, 8.1 Hz, 1H), 7.30 (s, 1H), 7.08 (d, J=7.8 Hz, 1H), 3.76 (t, J=9.6 Hz, 1H), 2.98-3.07 (m, 1H), 2.82-2.91 (m, 1H), 0.91 (s, 9H).

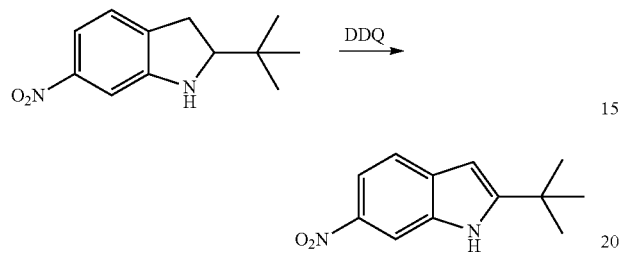

2-tert-Butyl-6-nitro-1H-indole

To a solution of 2-tert-butyl-6-nitroindoline (2.0 g, 9.1 mmol) in 1,4-dioxane (20 mL) was added DDQ (6.9 g, 30 mmol) at room temperature. The mixture was heated at reflux for 2.5 h before being filtered and concentrated under vacuum. The residue was purified by column chromatography to give 2-tert-butyl-6-nitro-1H-indole (1.6 g, 80%). ¹H NMR (300 MHz, CDCl₃) δ 8.30 (br. s, 1H), 8.29 (s, 1H), 8.00 (dd, J=2.1, 8.7 Hz, 1H), 7.53 (d, J=9.3 Hz, 1H), 6.38 (s, 1H), 1.43 (s, 9H).

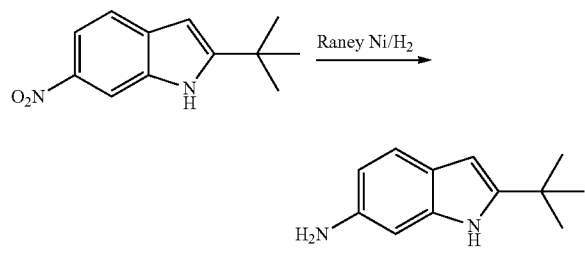

2-tert-Butyl-1H-indol-6-amine

To a solution of 2-tert-butyl-6-nitro-1H-indole (1.3 g, 6.0 mmol) in MeOH (10 mL) was added Raney Nickel (0.2 g). The mixture was hydrogenated under 1 atm of hydrogen at room temperature for 3 h. The reaction mixture was filtered and the filtrate was concentrated. The residue was washed with petroleum ether to give 2-tert-butyl-1H-indol-6-amine (1.0 g, 89%). ¹H NMR (300 MHz, DMSO-d₆) δ 10.19 (s, 1H), 6.99 (d, J=8.1 Hz, 1H), 6.46 (s, 1H), 6.25 (dd, J=1.8, 8.1 Hz, 1H), 5.79 (d, J=1.8 Hz, 1H), 4.52 (s, 2H), 1.24 (s, 9H); MS (ESI) ink (M+H⁺) 189.1.

Example 52

3-tert-Butyl-1H-indol-6-amine

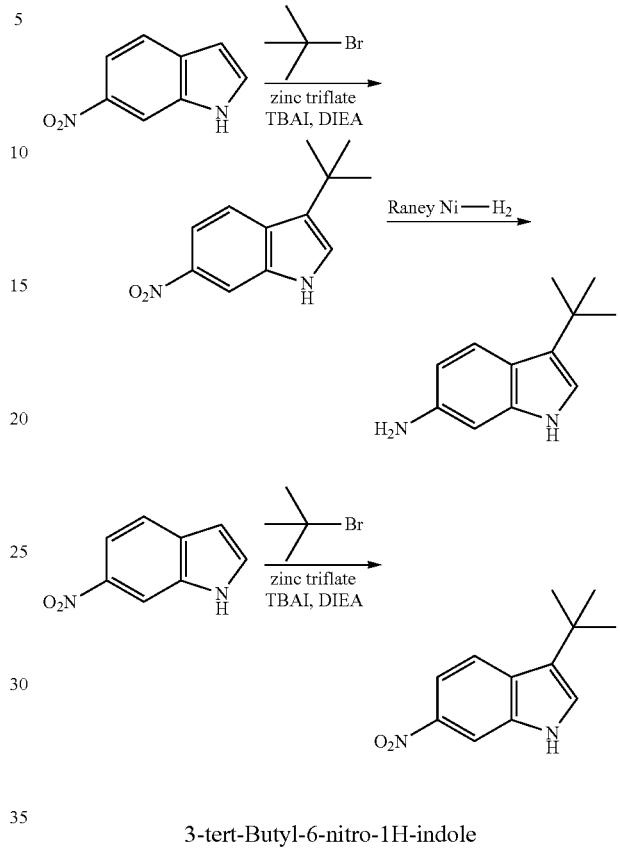

3-tert-Butyl-6-nitro-1H-indole

To a mixture of 6-nitroindole (1.0 g, 6.2 mmol), zinc triflate (2.1 g, 5.7 mmol), and TBAI (1.7 g, 5.2 mmol) in anhydrous toluene (11 mL) was added DIEA (1.5 g, 11 mmol) at room temperature under nitrogen. The reaction mixture was stirred for 10 min at 120° C., followed by the addition of t-butyl bromide (0.71 g, 5.2 mmol). The resulting mixture was stirred for 45 min at 120° C. The solid was filtered off and the filtrate was concentrated to dryness. The residue was purified by column chromatography on silica gel (petroleum ether/ethyl acetate=20:1) to give 3-tert-butyl-6-nitro-1H-indole (0.25 g, 19%) as a yellow solid. ¹H-NMR (CDCl₃) δ 8.32 (d, J=2.1 Hz, 1H), 8.00 (dd, J=2.1, 14.4 Hz, 1H), 7.85 (d, J=8.7 Hz, 1H), 7.25 (s, 1H), 1.46 (s, 9H).

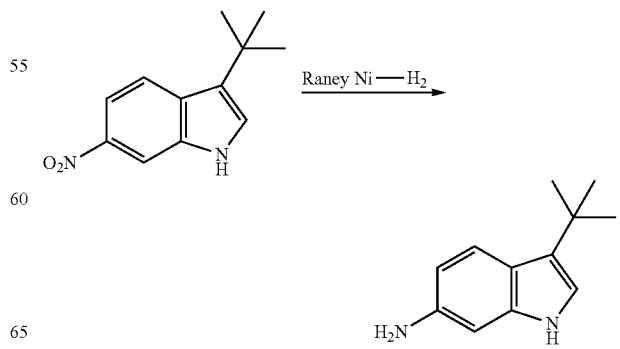

3-tert-Butyl-1H-indol-6-amine

A suspension of 3-tert-butyl-6-nitro-1H-indole (3.0 g, 14 mmol) and Raney Nickel (0.5 g) was hydrogenated under H$_2$ (1 atm) at room temperature for 3 h. The catalyst was filtered off and the filtrate was concentrated to dryness. The residue was purified by column on silica gel (petroleum ether/ethyl acetate=4:1) to give 3-tert-butyl-1H-indol-6-amine (2.0 g, 77%) as a gray solid. $^1$H NMR (CDCl$_3$) δ 7.58 (m, 2H), 6.73 (d, J=1.2 Hz, 1H), 6.66 (s, 1H), 6.57 (dd, J=0.8, 8.6 Hz, 1H), 3.60 (br, 2H), 1.42 (s, 9H).

Example 53

5-(Trifluoromethyl)-1H-indol-6-amine

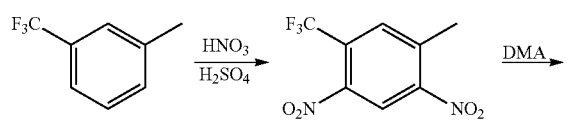

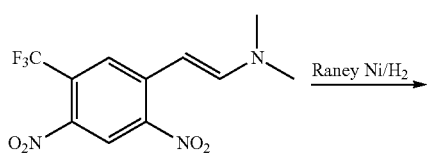

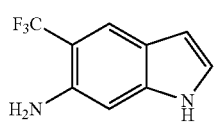

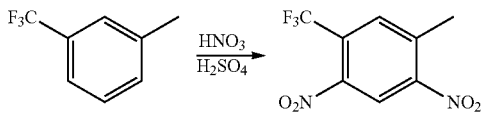

1-Methyl-2,4-dinitro-5-(trifluoromethyl)benzene

To a mixture of HNO$_3$ (98%, 30 mL) and H$_2$SO$_4$ (98%, 30 mL) was added dropwise 1-methyl-3-trifluoromethyl-benzene (10 g, 63 mmol) at 0° C. After addition, the mixture was stirred at rt for 30 min and was then poured into ice-water. The precipitate was filtered and washed with water to give 1-methyl-2,4-dinitro-5-trifluoromethyl-benzene (2.0 g, 13%).

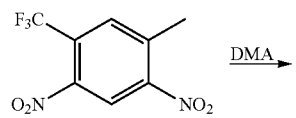

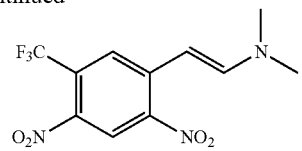

(E)-2-(2,4-Dinitro-5-(trifluoromethyl)phenyl)-N,N-dimethylethenamine

A mixture of 1-methyl-2,4-dinitro-5-trifluoromethyl-benzene (2.0 g, 8.0 mmol) and DMA (1.0 g, 8.2 mmol) in DMF (20 mL) was stirred at 100° C. for 30 min. The mixture was poured into ice-water and stirred for 1 h. The precipitate was filtered and washed with water to give (E)-2-(2,4-dinitro-5-(trifluoromethyl)phenyl)-N,N-dimethylethenamine (2.1 g, 86%).

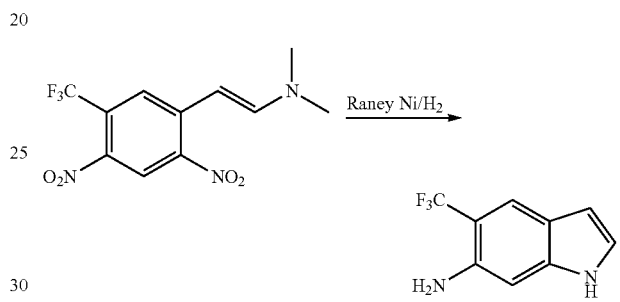

5-(Trifluoromethyl)-1H-indol-6-amine

A suspension of (E)-2-(2,4-dinitro-5-(trifluoromethyl)phenyl)-N,N-dimethylethenamine (2.1 g, 6.9 mmol) and Raney Nickel (1 g) in ethanol (80 mL) was stirred under H$_2$ (1 atm) at room temperature for 5 h. The catalyst was filtered off and the filtrate was concentrated to dryness. The residue was purified by column on silica gel to give 5-(trifluoromethyl)-1H-indol-6-amine (200 mg, 14%). $^1$H NMR (DMSO-d$_6$) δ 10.79 (br s, 1H), 7.55 (s, 1H), 7.12 (s, 1H), 6.78 (s, 1H), 6.27 (s, 1H), 4.92 (s, 2H); MS (ESI) m/e (M+H$^+$): 200.8.

Example 54

5-Ethyl-1H-indol-6-amine

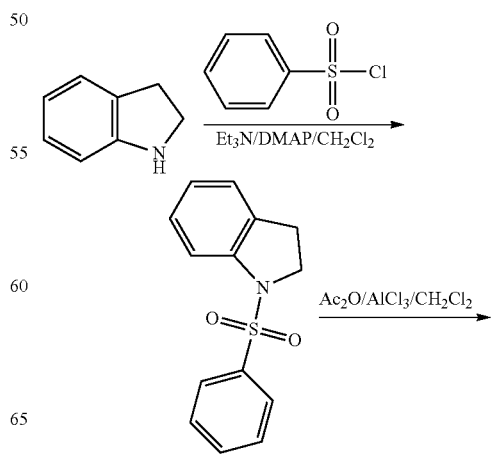

-continued

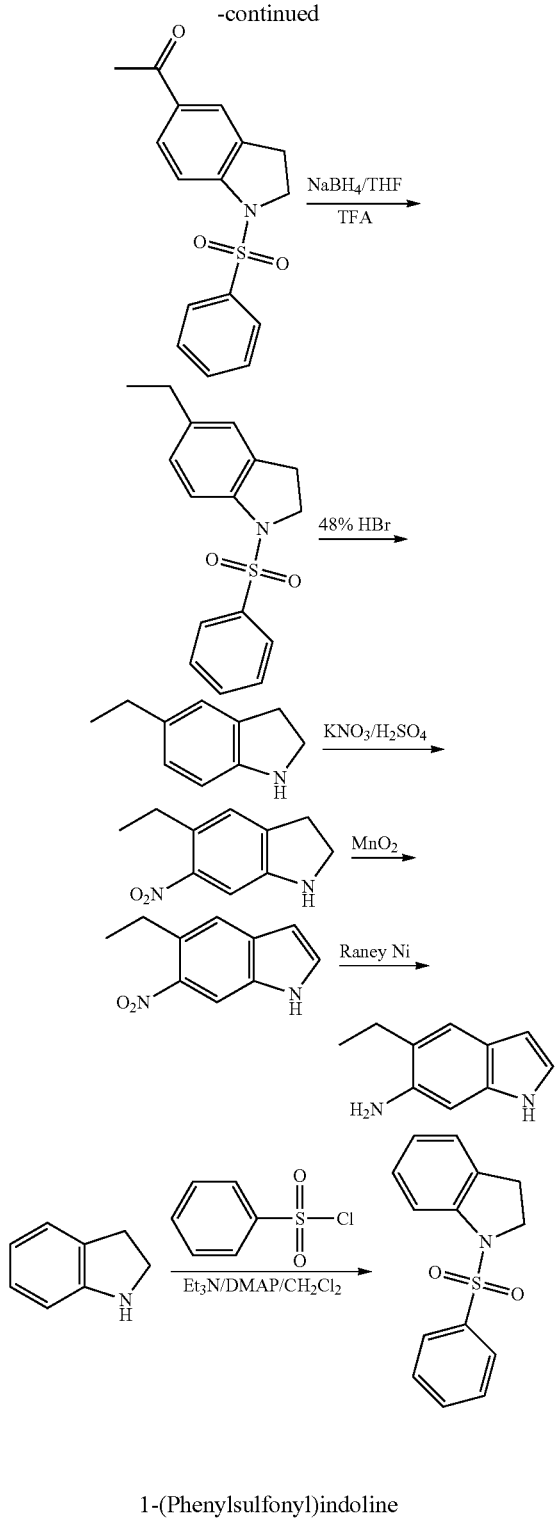

1-(Phenylsulfonyl)indoline

To a mixture of DMAP (1.5 g), benzenesulfonyl chloride (24.0 g, 136 mmol) and indoline (14.7 g, 124 mmol) in CH$_2$Cl$_2$ (200 mL) was added dropwise Et$_3$N (19.0 g, 186 mmol) at 0° C. The mixture was stirred at room temperature overnight. The organic layer was washed with water (2×), dried over Na$_2$SO$_4$ and concentrated to dryness under reduced pressure to obtain 1-(phenylsulfonyl)indoline (30.9 g, 96%).

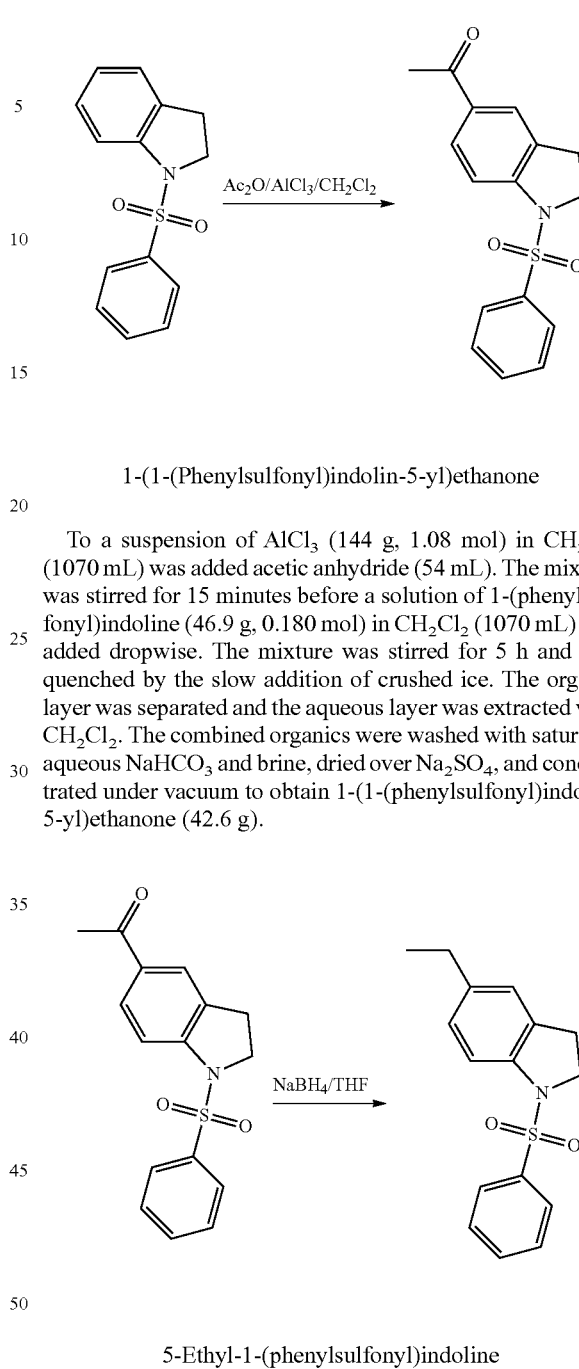

1-(1-(Phenylsulfonyl)indolin-5-yl)ethanone

To a suspension of AlCl$_3$ (144 g, 1.08 mol) in CH$_2$Cl$_2$ (1070 mL) was added acetic anhydride (54 mL). The mixture was stirred for 15 minutes before a solution of 1-(phenylsulfonyl)indoline (46.9 g, 0.180 mol) in CH$_2$Cl$_2$ (1070 mL) was added dropwise. The mixture was stirred for 5 h and was quenched by the slow addition of crushed ice. The organic layer was separated and the aqueous layer was extracted with CH$_2$Cl$_2$. The combined organics were washed with saturated aqueous NaHCO$_3$ and brine, dried over Na$_2$SO$_4$, and concentrated under vacuum to obtain 1-(1-(phenylsulfonyl)indolin-5-yl)ethanone (42.6 g).

5-Ethyl-1-(phenylsulfonyl)indoline

To TFA (1600 mL) at 0° C. was added sodium borohydride (64.0 g, 1.69 mol) over 1 h. To this mixture was added dropwise a solution of 1-(1-(phenylsulfonyl)indolin-5-yl)ethanone (40.0 g, 0.133 mol) in TFA (700 mL) over 1 h. The mixture was then stirred overnight at 25° C. After dilution with H$_2$O (1600 mL), the mixture was made basic by the addition of sodium hydroxide pellets at 0° C. The organic layer was separated and the aqueous layer was extracted with CH$_2$Cl$_2$. The combined organic layers were washed with brine, dried over Na$_2$SO$_4$ and concentrated under reduced pressure. The residue was purified by silica column to give 5-ethyl-1-(phenylsulfonyl)indoline (16.2 g, 47% over two steps).

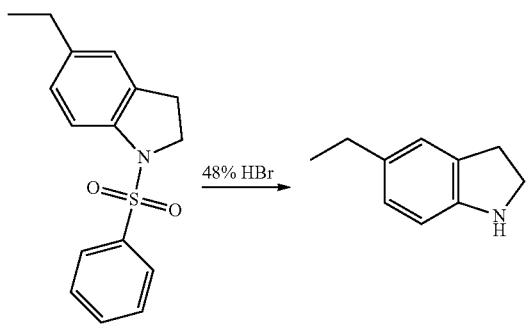 [SMILES: CCc1ccc2c(c1)CCN2S(=O)(=O)c1ccccc1 ; CCc1ccc2c(c1)CCN2]

5-Ethylindoline

A mixture of 5-ethyl-1-(phenylsulfonyl)indoline (15 g, 0.050 mol) in HBr (48%, 162 mL) was heated at reflux for 6 h. The mixture was basified with sat. NaOH to pH 9 and then it was extracted with ethyl acetate. The organic layer was washed with brine, dried over $Na_2SO_4$, and concentrated under reduced pressure. The residue was purified by silica column to give 5-ethylindoline (2.5 g, 32%).

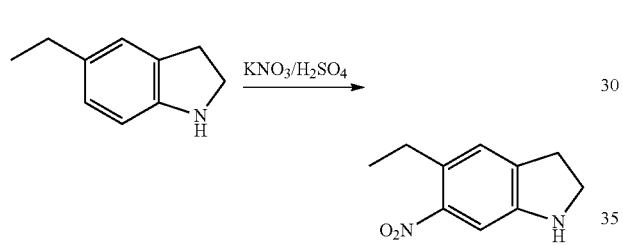

5-Ethyl-6-nitroindoline

To a solution of 5-ethylindoline (2.5 g, 17 mmol) in $H_2SO_4$ (98%, 20 mL) was slowly added $KNO_3$ (1.7 g, 17 mmol) at 0° C. The mixture was stirred at 0-10° C. for 10 minutes. The mixture was then carefully poured into ice, basified with NaOH solution to pH 9, and extracted with ethyl acetate. The combined extracts were washed with brine, dried over $Na_2SO_4$ and concentrated to dryness. The residue was purified by silica column to give 5-ethyl-6-nitroindoline (1.9 g, 58%).

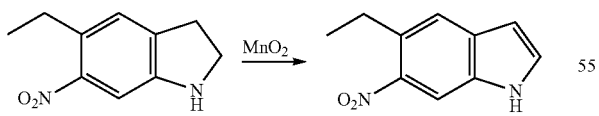

5-Ethyl-6-nitro-1H-indole

To a solution of 5-ethyl-6-nitroindoline (1.9 g, 9.9 mmol) in $CH_2Cl_2$ (30 mL) was added $MnO_2$ (4.0 g, 46 mmol). The mixture was stirred at ambient temperature for 8 h. The solid was filtered off and the filtrate was concentrated to dryness to give 5-ethyl-6-nitro-1H-indole (1.9 g).

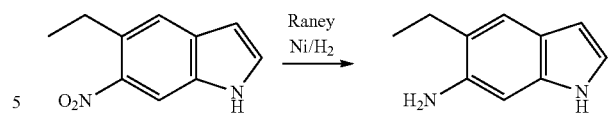

5-Ethyl-1H-indol-6-amine

A suspension of 5-ethyl-6-nitro-1H-indole (1.9 g, 10 mmol) and Raney Nickel (1 g) was hydrogenated under $H_2$ (1 atm) at room temperature for 2 h. The catalyst was filtered off and the filtrate was concentrated to dryness. The residue was purified by silica gel column to give 5-ethyl-1H-indol-6-amine (760 mg, 48% over two steps). $^1$H NMR ($CDCl_3$) δ 7.90 (br s, 1H), 7.41 (s, 1H), 7.00 (s, 1H), 6.78 (s, 2H), 6.39 (s, 1H), 3.39 (br s, 2H), 2.63 (q, J=7.2 Hz, 2H), 1.29 (t, J=6.9 Hz, 3H); MS (ESI) m/e (M+H$^+$) 161.1.

Example 55

Ethyl 6-amino-1H-indole-4-carboxylate

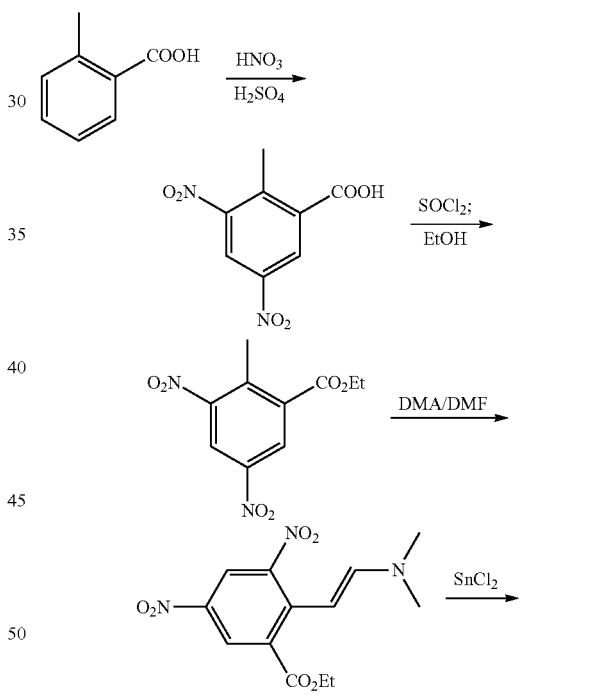

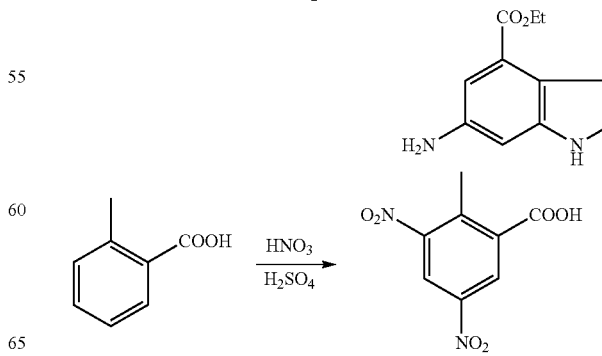

2-Methyl-3,5-dinitrobenzoic acid

To a mixture of HNO₃ (95%, 80 mL) and H₂SO₄ (98%, 80 mL) was slowly added 2-methylbenzic acid (50 g, 0.37 mol) at 0° C. After addition, the reaction mixture was stirred below 30° C. for 1.5 h. The mixture then was poured into ice-water and stirred for 15 min. The precipitate was filtered and washed with water to give 2-methyl-3,5-dinitrobenzoic acid (70 g, 84%).

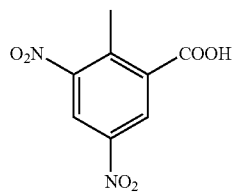

Ethyl 2-methyl-3,5-dinitrobenzoate

A mixture of 2-methyl-3,5-dinitrobenzoic acid (50 g, 0.22 mol) in SOCl₂ (80 mL) was heated at reflux for 4 h and then was concentrated to dryness. The residue was dissolved in CH₂Cl₂ (50 mL), to which EtOH (80 mL) was added and the mixture was stirred at room temperature for 1 h. The mixture was poured into ice-water and extracted with EtOAc (3×100 mL). The combined extracts were washed sat. Na₂CO₃ (80 mL), water (2×100 mL) and brine (100 mL), dried over Na₂SO₄ and concentrated to dryness to give ethyl 2-methyl-3,5-dinitrobenzoate (50 g, 88%)

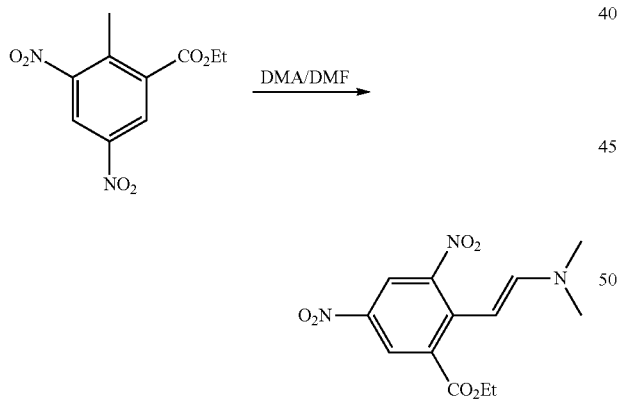

(E)-Ethyl 2-(2-(dimethylamino)vinyl)-3,5-dinitrobenzoate

A mixture of ethyl 2-methyl-3,5-dinitrobenzoate (35 g, 0.14 mol) and DMA (32 g, 0.27 mol) in DMF (200 mL) was heated at 100° C. for 5 h. The mixture was poured into ice-water and the precipitated solid was filtered and washed with water to give (E)-ethyl 2-(2-(dimethylamino)vinyl)-3,5-dinitrobenzoate (11 g, 48%)

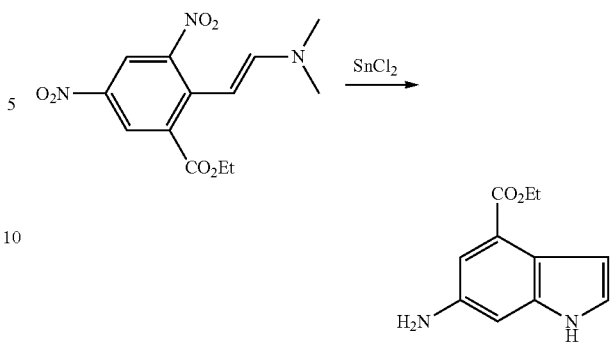

Ethyl 6-amino-1H-indole-4-carboxylate

A mixture of (E)-ethyl 2-(2-(dimethylamino)vinyl)-3,5-dinitrobenzoate (11 g, 0.037 mol) and SnCl₂ (83 g, 0.37 mol) in ethanol was heated at reflux for 4 h. The mixture was concentrated to dryness and the residue was poured into water and basified using sat. aq. Na₂CO₃ to pH 8. The precipitated solid was filtered and the filtrate was extracted with ethyl acetate (3×100 mL). The combined extracts were washed with water (2×100 mL) and brine (150 mL), dried over Na₂SO₄, and concentrated to dryness. The residue was purified by column on silica gel to give ethyl 6-amino-1H-indole-4-carboxylate (3.0 g, 40%). ¹H NMR (DMSO-d₆) δ 10.76 (br s, 1H), 7.11-7.14 (m, 2H), 6.81-6.82 (m, 1H), 6.67-6.68 (m, 1H), 4.94 (br s, 2H), 4.32-4.25 (q, J=7.2 Hz, 2H), 1.35-1.31 (t, J=7.2, 3 H); MS (ESI) m/e (M+H⁺) 205.0.

Example 56

5-Fluoro-1H-indol-6-amine

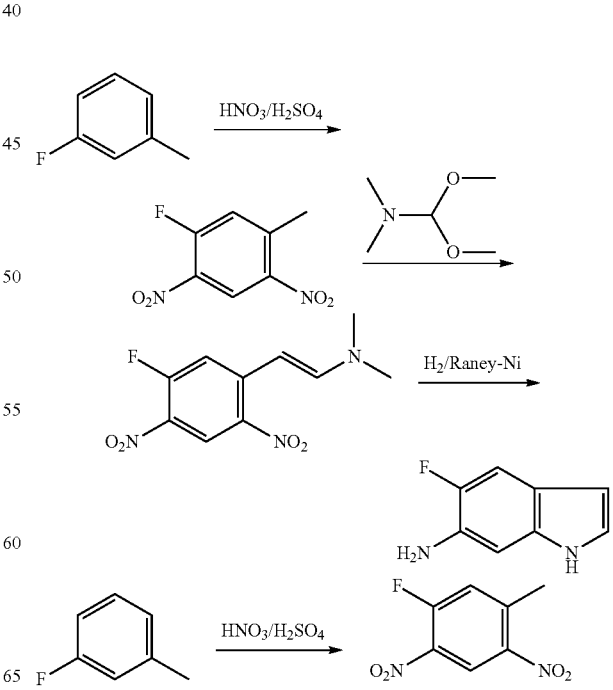

1-Fluoro-5-methyl-2,4-dinitrobenzene

To a stirred solution of HNO$_3$ (60 mL) and H$_2$SO$_4$ (80 mL) was added dropwise 1-fluoro-3-methylbenzene (28 g, 25 mmol) under ice-cooling at such a rate that the temperature did not rise above 35° C. The mixture was allowed to stir for 30 min at rt and was then poured into ice water (500 mL). The resulting precipitate (a mixture of 1-fluoro-5-methyl-2,4-dinitrobenzene and 1-fluoro-3-methyl-2,4-dinitrobenzene, 32 g, ca. 7:3 ratio) was collected by filtration and purified by recrystallization from 50 mL isopropyl ether to give pure 1-fluoro-5-methyl-2,4-dinitro-benzene as a white solid (18 g, 36%).

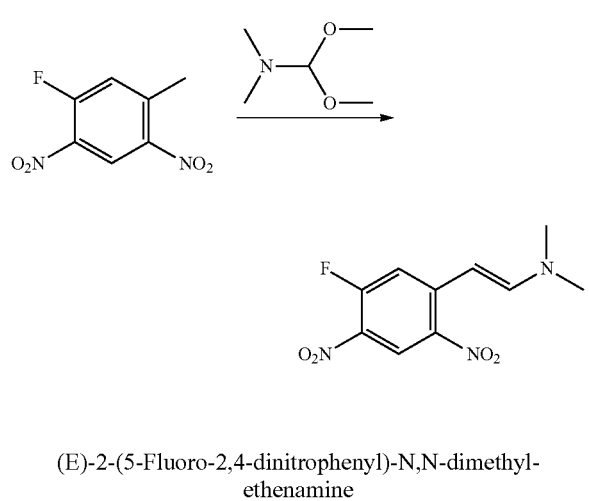

(E)-2-(5-Fluoro-2,4-dinitrophenyl)-N,N-dimethyl-ethenamine

A mixture of 1-fluoro-5-methyl-2,4-dinitro-benzene (10 g, 50 mmol), DMA (12 g, 100 mmol) and DMF (50 mL) was heated at 100° C. for 4 h. The solution was cooled and poured into water. The precipitated red solid was collected, washed with water, and dried to give (E)-2-(5-fluoro-2,4-dinitrophenyl)-N,N-dimethylethenamine (8.0 g, 63%).

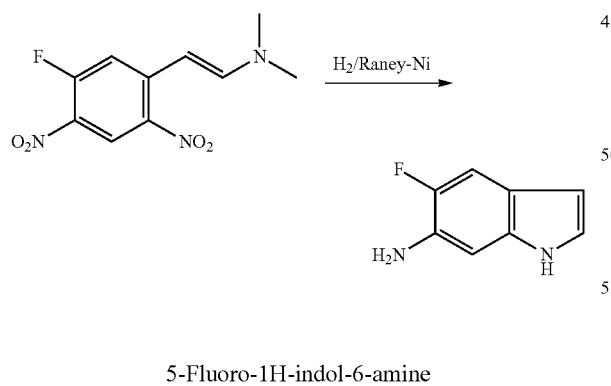

5-Fluoro-1H-indol-6-amine

A suspension of (E)-2-(5-fluoro-2,4-dinitrophenyl)-N,N-dimethylethenamine (8.0 g, 31 mmol) and Raney Nickel (8 g) in EtOH (80 mL) was stirred under H$_2$ (40 psi) at room temperature for 1 h. After filtration, the filtrate was concentrated and the residue was purified by column chromatography (petroleum ether/ethyl acetate=5/1) to give 5-fluoro-1H-indol-6-amine (1.0 g, 16%) as a brown solid. $^1$H NMR (DMSO-d$_6$) δ 10.56 (br s, 1H), 7.07 (d, J=12 Hz, 1H), 7.02 (m, 1H), 6.71 (d, J=8 Hz, 1H), 6.17 (s, 1H), 3.91 (br s, 2H); MS (ESI) m/e (M+H$^+$) 150.1.

Example 57

5-Chloro-1H-indol-6-amine

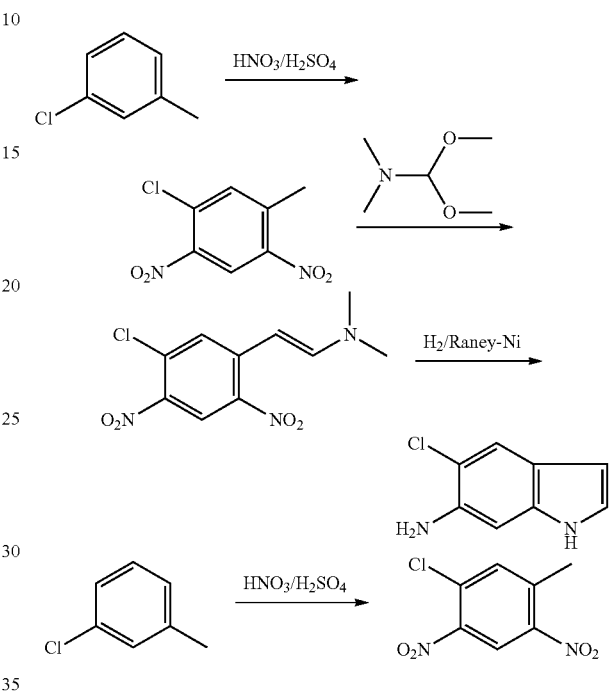

1-Chloro-5-methyl-2,4-dinitrobenzene

To a stirred solution of HNO$_3$ (55 mL) and H$_2$SO$_4$ (79 mL) was added dropwise 1-chloro-3-methylbenzene (25.3 g, 200 mmol) under ice-cooling at such a rate that the temperature did not rise above 35° C. The mixture was allowed to stir for 30 min at ambient temperature and was then poured into ice water (500 mL). The resulting precipitate was collected by filtration and purified by recrystallization to give 1-chloro-5-methyl-2,4-dinitrobenzene (26 g, 60%).

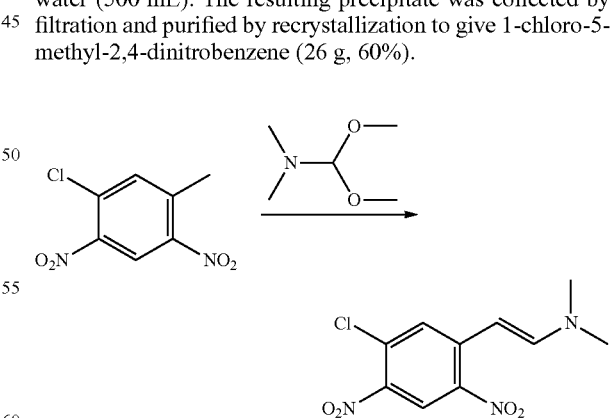

(E)-2-(5-Chloro-2,4-dinitrophenyl)-N,N-dimethyl-ethenamine

A mixture of 1-chloro-5-methyl-2,4-dinitro-benzene (11.6 g, 50.0 mmol), DMA (11.9 g, 100 mmol) in DMF (50 mL)

was heated at 100° C. for 4 h. The solution was cooled and poured into water. The precipitated red solid was collected by filtration, washed with water, and dried to give (E)-2-(5-chloro-2,4-dinitrophenyl)-N,N-dimethylethenamine (9.84 g, 72%).

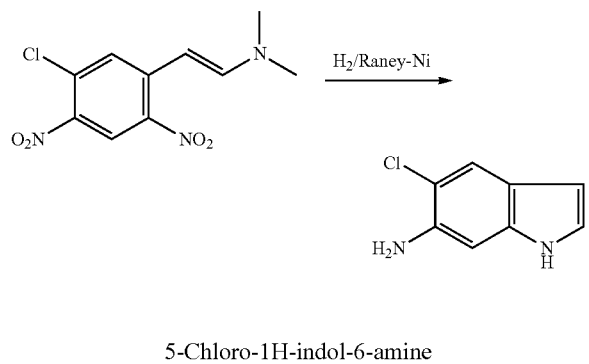

5-Chloro-1H-indol-6-amine

A suspension of (E)-2-(5-chloro-2,4-dinitrophenyl)-N,N-dimethylethenamine (9.8 g, 36 mmol) and Raney Nickel (9.8 g) in EtOH (140 mL) was stirred under H₂ (1 atm) at room temperature for 4 h. After filtration, the filtrate was concentrated and the residue was purified by column chromatograph (petroleum ether/ethyl acetate=10:1) to give 5-chloro-1H-indol-6-amine (0.97 g, 16%) as a gray powder. ¹H NMR (CDCl₃) δ 7.85 (br s, 1H), 7.52 (s, 1H), 7.03 (s, 1H), 6.79 (s, 1H), 6.34 (s, 1H), 3.91 (br s, 1H); MS (ESI) m/e (M+H⁺) 166.0.

Example 58

Ethyl 6-amino-1H-indole-7-carboxylate

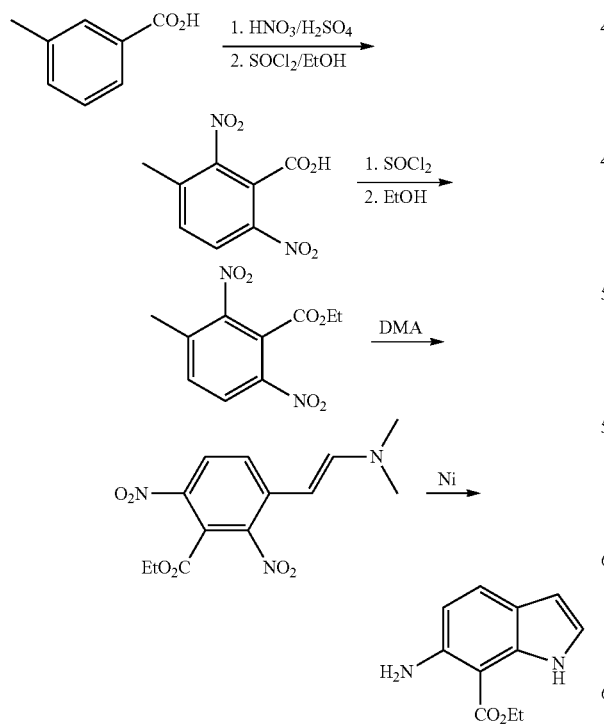

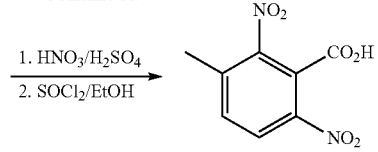

3-Methyl-2,6-dinitrobenzoic acid

To a mixture of HNO₃ (95%, 80 mL) and H₂SO₄ (98%, 80 mL) was slowly added 3-methylbenzic acid (50 g, 0.37 mol) at 0° C. After addition, the mixture was stirred below 30° C. for 1.5 hours. The mixture was then poured into ice-water and stirred for 15 min. The precipitate solid was filtered and washed with water to give a mixture of 3-methyl-2,6-dinitrobenzoic acid and 5-methyl-2,4-dinitrobenzoic acid (70 g, 84%). To a solution of this mixture (70 g, 0.31 mol) in EtOH (150 mL) was added dropwise SOCl₂ (54 g, 0.45 mol). The mixture was heated at reflux for 2 h before being concentrated to dryness under reduced pressure. The residue was partitioned between EtOAc (100 mL) and aq. Na₂CO₃ (10%, 120 mL). The organic layer was washed with brine (50 mL), dried over Na₂SO₄, and concentrated to dryness to obtain ethyl 5-methyl-2,4-dinitrobenzoate (20 g), which was placed aside. The aqueous layer was acidified by HCl to pH 2~3 and the precipitated solid was filtered, washed with water, and dried in air to give 3-methyl-2,6-dinitrobenzoic acid (39 g, 47%).

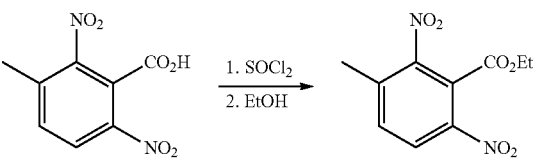 [SMILES: Cc1ccc([N+](=O)[O-])c(C(=O)O)c1[N+](=O)[O-] ; "2. EtOH" ; "1. SOCl2" ; CCOC(=O)c1c([N+](=O)[O-])ccc(C)c1[N+](=O)[O-]]

Ethyl 3-methyl-2,6-dinitrobenzoate

A mixture of 3-methyl-2,6-dinitrobenzoic acid (39 g, 0.15 mol) and SOCl₂ (80 mL) was heated at reflux 4 h. The excess SOCl₂ was evaporated off under reduced pressure and the residue was added dropwise to a solution of EtOH (100 mL) and Et₃N (50 mL). The mixture was stirred at 20° C. for 1 h and then concentrated to dryness. The residue was dissolved in EtOAc (100 mL), washed with Na₂CO₃ (10%, 40 mL×2), water (50 mL×2) and brine (50 mL), dried over Na₂SO₄ and concentrated to give ethyl 3-methyl-2,6-dinitrobenzoate (20 g, 53%).

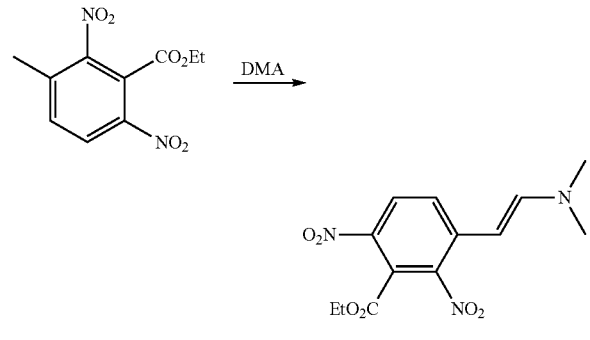

(E)-Ethyl 3-(2-(dimethylamino)vinyl)-2,6-dinitrobenzoate

A mixture of ethyl 3-methyl-2,6-dinitrobenzoate (35 g, 0.14 mol) and DMA (32 g, 0.27 mol) in DMF (200 mL) was heated at 100° C. for 5 h. The mixture was poured into ice water. The precipitated solid was filtered and washed with water to give (E)-ethyl 3-(2-(dimethylamino)vinyl)-2,6-dinitrobenzoate (25 g, 58%).

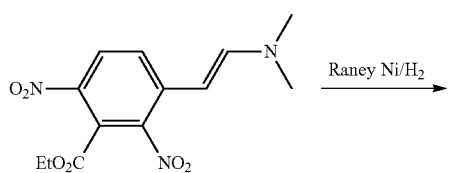

Ethyl 6-amino-1H-indole-7-carboxylate

A mixture of (E)-ethyl 3-(2-(dimethylamino)vinyl)-2,6-dinitrobenzoate (30 g, 0.097 mol) and Raney Nickel (10 g) in EtOH (1000 mL) was hydrogenated at room temperature under 50 psi for 2 h. The catalyst was filtered off and the filtrate was concentrated to dryness. The residue was purified by column on silica gel to give ethyl 6-amino-1H-indole-7-carboxylate as an off-white solid (3.2 g, 16%). $^1$H NMR (DMSO-$d_6$) δ 10.38 (s, 1H), 7.42 (d, J=8.7 Hz, 1H), 6.98 (t, J=3.0 Hz, 1H), 6.65 (s, 2H), 6.48 (d, J=8.7 Hz, 1H), 6.27-6.26 (m, 1H), 4.38 (q, J=7.2 Hz, 2H), 1.35 (t, J=7.2 Hz, 3H).

Example 59

Ethyl 6-amino-1H-indole-5-carboxylate

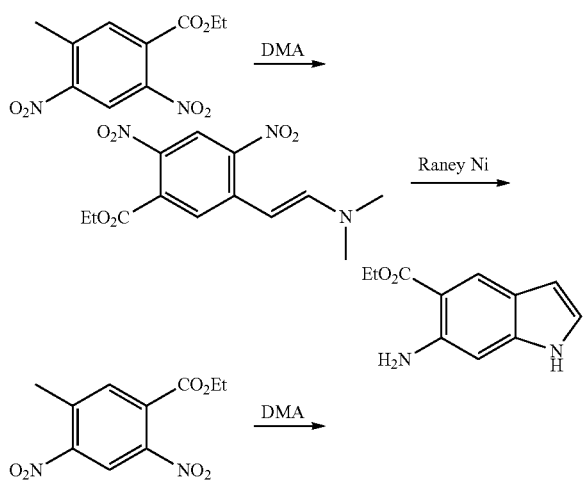

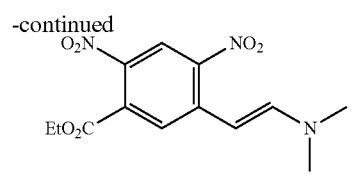

(E)-Ethyl 5-(2-(dimethylamino)vinyl)-2,4-dinitrobenzoate

A mixture of ethyl 5-methyl-2,4-dinitrobenzoate (39 g, 0.15 mol) and DMA (32 g, 0.27 mol) in DMF (200 mL) was heated at 100° C. for 5 h. The mixture was poured into ice water and the precipitated solid was filtered and washed with water to afford (E)-ethyl 542-(dimethylamino)vinyl)-2,4-dinitrobenzoate (15 g, 28%).

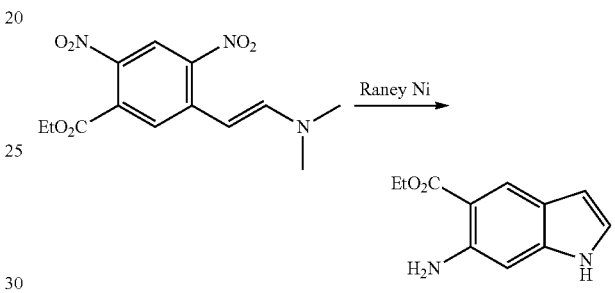

Ethyl 6-amino-1H-indole-5-carboxylate

A mixture of (E)-ethyl 5-(2-(dimethylamino)vinyl)-2,4-dinitrobenzoate (15 g, 0.050 mol) and Raney Nickel (5 g) in EtOH (500 mL) was hydrogenated at room temperature under 50 psi of hydrogen for 2 h. The catalyst was filtered off and the filtrate was concentrated to dryness. The residue was purified by column on silica gel to give ethyl 6-amino-1H-indole-5-carboxylate (3.0 g, 30%). $^1$H NMR (DMSO-$d_6$) δ 10.68 (s, 1H), 7.99 (s, 1H), 7.01-7.06 (m, 1H), 6.62 (s, 1H), 6.27-6.28 (m, 1H), 6.16 (s, 2H), 4.22 (q, J=7.2 Hz, 2H), 1.32-1.27 (t, J=7.2 Hz, 3H).

Example 60

5-tert-Butyl-1H-indol-6-amine

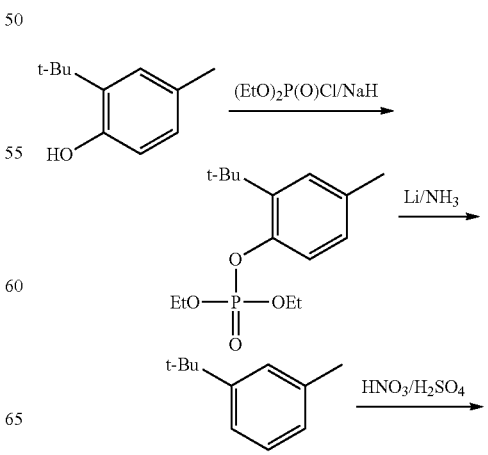

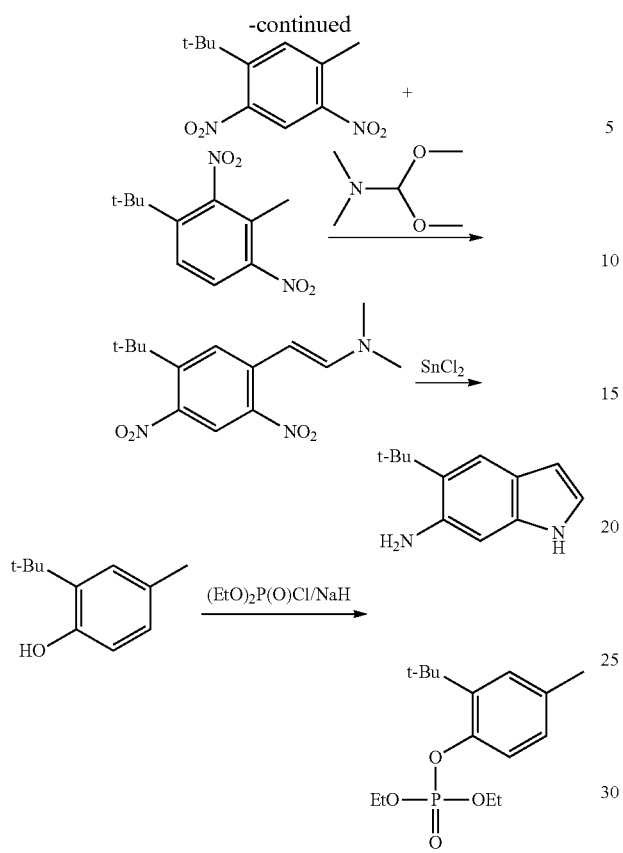

2-tert-Butyl-4-methylphenyl diethyl phosphate

To a suspension of NaH (60% in mineral oil, 8.4 g, 0.21 mol) in THF (200 mL) was added dropwise a solution of 2-tert-butyl-4-methylphenol (33 g, 0.20 mol) in THF (100 mL) at 0° C. The mixture was stirred at 0° C. for 15 min and then phosphorochloridic acid diethyl ester (37 g, 0.21 mol) was added dropwise at 0° C. After addition, the mixture was stirred at ambient temperature for 30 min. The reaction was quenched with sat. NH$_4$Cl (300 mL) and then extracted with Et$_2$O (350 mL×2). The combined organic layers were washed with brine, dried over anhydrous Na$_2$SO$_4$, and then evaporated under vacuum to give 2-tert-butyl-4-methylphenyl diethyl phosphate (contaminated with mineral oil) as a colorless oil (60 g, ~100%), which was used directly in the next step.

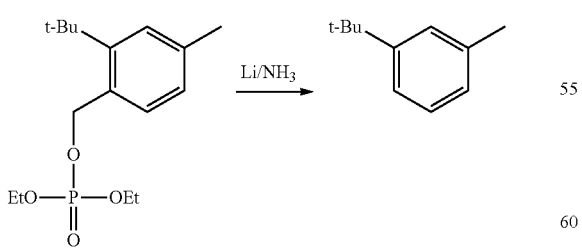

1-tert-Butyl-3-methylbenzene

To NH$_3$ (liquid, 1000 mL) was added a solution of 2-tert-butyl-4-methylphenyl diethyl phosphate (60 g, crude from last step, about 0.2 mol) in Et$_2$O (anhydrous, 500 mL) at −78° C. under N$_2$ atmosphere. Lithium metal was added to the solution in small pieces until the blue color persisted. The reaction mixture was stirred at −78° C. for 15 min and then was quenched with sat. NH$_4$Cl until the mixture turned colorless. Liquid NH$_3$ was evaporated and the residue was dissolved in water. The mixture was extracted with Et$_2$O (400 mL×2). The combined organics were dried over Na$_2$SO$_4$ and evaporated to give 1-tert-butyl-3-methylbenzene (contaminated with mineral oil) as a colorless oil (27 g, 91%), which was used directly in next step.

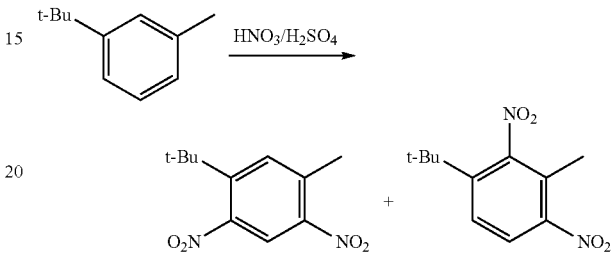

1-tert-Butyl-5-methyl-2,4-dinitrobenzene and 1-tert-butyl-3-methyl-2,4-dinitro-benzene To HNO$_3$ (95%, 14 mL) was added H$_2$SO$_4$ (98%, 20 mL) at 0° C. and then 1-tert-butyl-3-methylbenzene (7.4 g, ~50 mmol, crude from last step) dropwise to the with the temperature being kept below 30° C. The mixture was stirred at ambient temperature for 30 min, poured onto crushed ice (100 g), and extracted with EtOAc (50 mL×3). The combined organic layers were washed with water and brine, before being evaporated to give a brown oil, which was purified by column chromatography to give a mixture of 1-tert-butyl-5-methyl-2,4-dinitrobenzene and 1-tert-butyl-3-methyl-2,4-dinitrobenzene (2:1 by NMR) as a yellow oil (9.0 g, 61%).

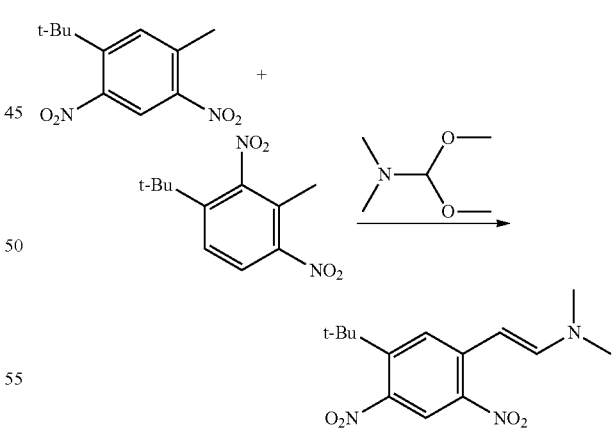

(E)-2-(5-tert-Butyl-2,4-dinitrophenyl)-N,N-dimethylethenamine

A mixture of 1-tert-butyl-5-methyl-2,4-dinitrobenzene and 1-tert-butyl-3-methyl-2,4-dinitrobenzene (9.0 g, 38 mmol, 2:1 by NMR) and DMA (5.4 g, 45 mmol) in DMF (50 mL) was heated at reflux for 2 h before being cooled to room temperature. The reaction mixture was poured into water-ice and extracted with EtOAc (50 mL×3). The combined organic layers were washed with water and brine, before being evaporated to give a brown oil, which was purified by column to give (E)-2-(5-tert-butyl-2,4-dinitrophenyl)-N,N-dimethyl-ethen-amine (5.0 g, 68%).

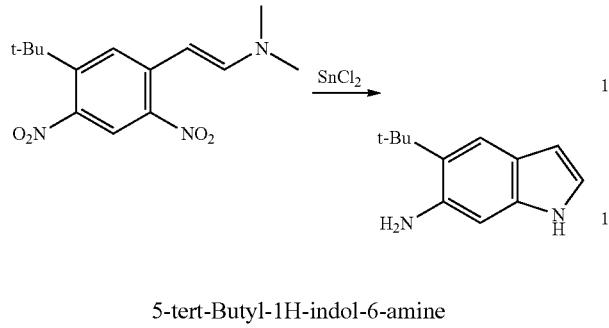

5-tert-Butyl-1H-indol-6-amine

A solution of (E)-2-(5-tert-butyl-2,4-dinitrophenyl)-N,N-dimethylethen-amine (5.3 g, 18 mmol) and tin (II) chloride dihydrate (37 g, 0.18 mol) in ethanol (200 mL) was heated at reflux overnight. The mixture was cooled to room temperature and the solvent was removed under vacuum. The residual slurry was diluted with water (500 mL) and was basified with 10% aq. $Na_2CO_3$ to pH 8. The resulting suspension was extracted with ethyl acetate (3×100 mL). The ethyl acetate extract was washed with water and brine, dried over $Na_2SO_4$, and concentrated. The residual solid was washed with $CH_2Cl_2$ to afford a yellow powder, which was purified by column chromatography to give 5-tert-butyl-1H-indol-6-amine (0.40 g, 12%). $^1$H NMR (DMSO, $d_6$) δ 10.34 (br s, 1H), 7.23 (s, 1H), 6.92 (s, 1H), 6.65 (s, 1H), 6.14 (s, 1H), 4.43 (br s, 2H), 2.48 (s, 9H); MS (ESI) m/e (M+H$^+$) 189.1.

General Procedure IV: Synthesis of acylaminoindoles

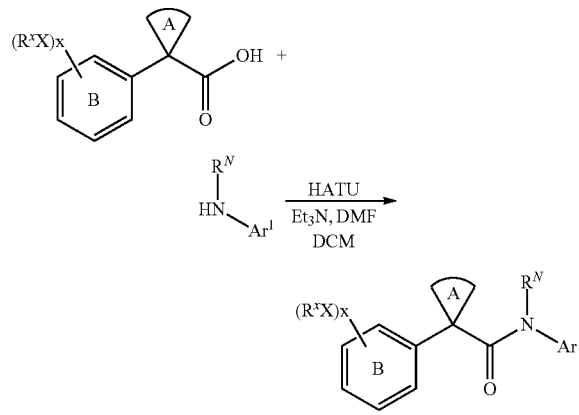

One equivalent of the appropriate carboxylic acid and one equivalent of the appropriate amine were dissolved in N,N-dimethylformamide (DMF) containing triethylamine (3 equivalents). O-(7-Azabenzotriazol-1-yl)-N,N,N',N'-tetramethyluronium hexafluorophosphate (HATU) was added and the solution was allowed to stir. The crude product was purified by reverse-phase preparative liquid chromatography to yield the pure product.

Example 61

N-(2-tert-Butyl-1H-indol-5-yl)-1-(4-methoxyphenyl)-cyclopropanecarboxamide

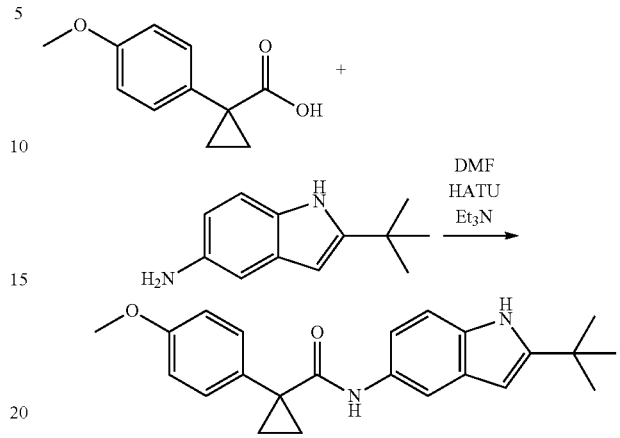

2-tert-Butyl-1H-indol-5-amine (19 mg, 0.10 mmol) and 1-(4-methoxyphenyl)-cyclopropanecarboxylic acid (19 mg, 0.10 mmol) were dissolved in N,N-dimethylformamide (1.00 mL) containing triethylamine (28 μL, 0.20 mmol). O-(7-Azabenzotriazol-1-yl)-N,N,N',N'-tetramethyluronium hexafluorophosphate (42 mg, 0.11 mmol) was added to the mixture and the resulting solution was allowed to stir for 3 hours. The crude reaction mixture was filtered and purified by reverse phase HPLC. ESI-MS m/z calc. 362.2. found 363.3 (M+1)$^+$; Retention time 3.48 minutes.

General Procedure V: Synthesis of Acylaminoindoles

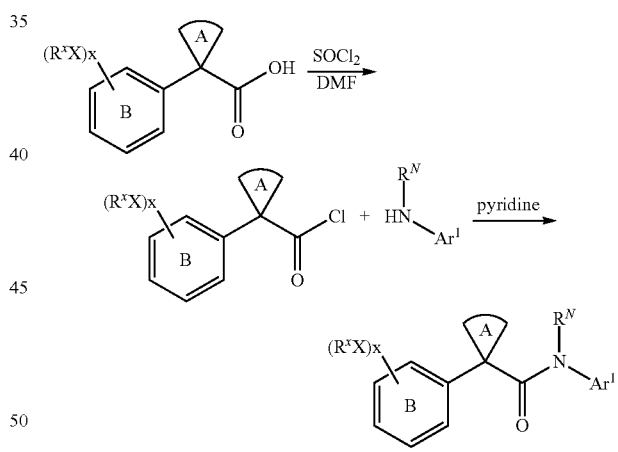

One equivalent of the appropriate carboxylic acid was placed in an oven-dried flask under nitrogen. A minimum (3 equivalents) of thionyl chloride and a catalytic amount of and N,N-dimethylformamide were added and the solution was allowed to stir for 20 minutes at 60° C. The excess thionyl chloride was removed under vacuum and the resulting solid was suspended in a minimum of anhydrous pyridine. This solution was slowly added to a stirred solution of one equivalent the appropriate amine dissolved in a minimum of anhydrous pyridine. The resulting mixture was allowed to stir for 15 hours at 110° C. The mixture was evaporated to dryness, suspended in dichloromethane, and then extracted three times with 1N HCl. The organic layer was then dried over sodium sulfate, evaporated to dryness, and then purified by column chromatography.

Example 62

Ethyl 5-(1-(benzo[d][1,3]dioxol-5-yl)cyclopropanecarboxamido)-1H-indole-2-carboxylate (Compd. 28)

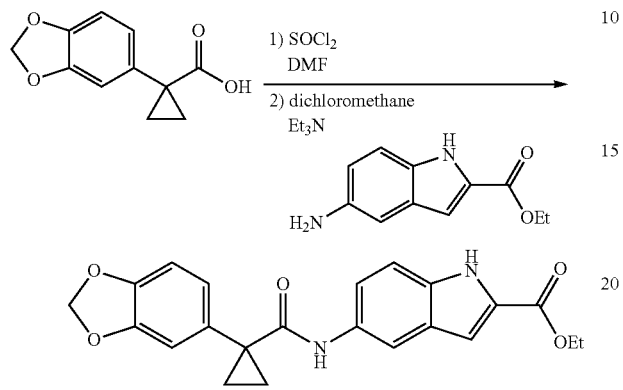

1-Benzo[1,3]dioxol-5-yl-cyclopropanecarboxylic acid (2.07 g, 10.0 mmol) was dissolved in thionyl chloride (2.2 mL) under $N_2$. N,N-dimethylformamide (0.3 mL) was added and the solution was allowed to stir for 30 minutes. The excess thionyl chloride was removed under vacuum and the resulting solid was dissolved in anhydrous dichloromethane (15 mL) containing triethylamine (2.8 mL, 20.0 mmol). Ethyl 5-amino-1H-indole-2-carboxylate (2.04 g, 10.0 mmol) in 15 mL of anhydrous dichloromethane was slowly added to the reaction. The resulting solution was allowed to stir for 1 hour. The reaction mixture was diluted to 50 mL with dichloromethane and washed three times with 50 mL of 1N HCl, saturated aqueous sodium bicarbonate, and saturated aqueous sodium chloride. The organic layer was dried over sodium sulfate and evaporated to dryness to yield ethyl 5-(1-(benzo[d][1,3]dioxol-5-yl)cyclopropanecarboxamido)-1H-indole-2-carboxylate as a gray solid (3.44 g, 88%). ESI-MS m/z calc. 392.4. found 393.1 (M+1)$^+$ Retention time 3.17 minutes. $^1$H NMR (400 MHz, DMSO-d6) δ 11.80 (s, 1H), 8.64 (s, 1H), 7.83 (m, 1H), 7.33-7.26 (m, 2H), 7.07 (m, 1H), 7.02 (m, 1H), 6.96-6.89 (m, 2H), 6.02 (s, 2H), 4.33 (q, J=7.1 Hz, 2H), 1.42-1.39 (m, 2H), 1.33 (t, J=7.1 Hz, 3H), 1.06-1.03 (m, 2H).

Example 63

1-(Benzo[d][1,3]dioxol-5-yl)-N-(2-tert-butyl-1H-indol-5-yl)cyclopropanecarboxamide

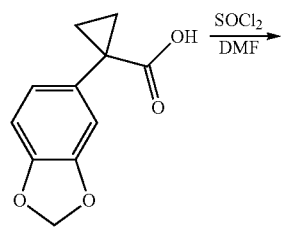

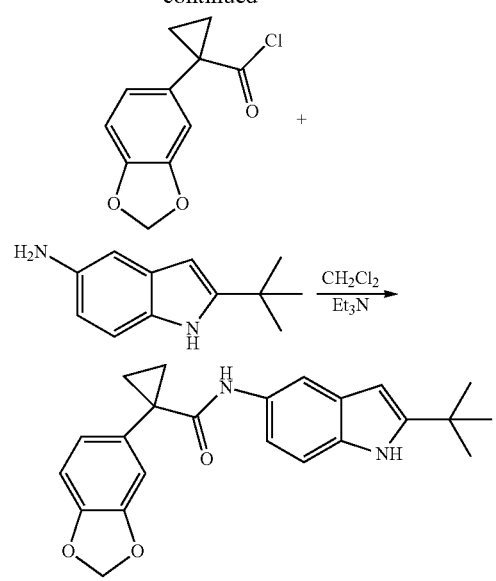

1-Benzo[1,3]dioxol-5-yl-cyclopropanecarboxylic acid (1.09 g, 5.30 mmol) was dissolved in 2 mL of thionyl chloride under nitrogen. A catalytic amount (0.3 mL) of N,N-dimethylformamide (DMF) was added and the reaction mixture was stirred for 30 minutes. The excess thionyl chloride was evaporated and the resulting residue was dissolved in 15 mL of dichloromethane. This solution was slowly added to a solution of 2-tert-butyl-1H-indol-5-amine (1.0 g, 5.3 mmol) in 10 mL of dichloromethane containing triethylamine (1.69 mL, 12.1 mmol). The resulting solution was allowed to stir for 10 minutes. The solvent was evaporated to dryness and the crude reaction mixture was purified by silica gel column chromatography using a gradient of 5-50% ethyl acetate in hexanes. The pure fractions were combined and evaporated to dryness to yield a pale pink powder (1.24 g 62%). ESI-MS m/z calc. 376.18. found 377.3 (M+1)$^+$. Retention time of 3.47 minutes. $^1$H NMR (400 MHz, DMSO) δ 10.77 (s, 1H), 8.39 (s, 1H), 7.56 (d, J=1.4 Hz, 1H), 7.15 (d, J=8.6 Hz, 1H), 7.05-6.87 (m, 4H), 6.03 (s, 3H), 1.44-1.37 (m, 2H), 1.33 (s, 9H), 1.05-1.00 (m, 2H).

Example 64

1-(Benzo[d][1,3]dioxol-5-yl)-N-(1-methyl-2-(1-methylcyclopropyl)-1H-indol-5-yl)cyclopropanecarboxamide

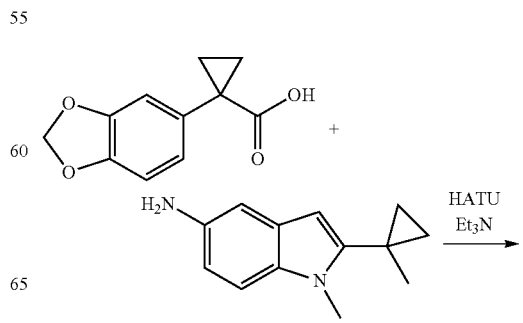

-continued

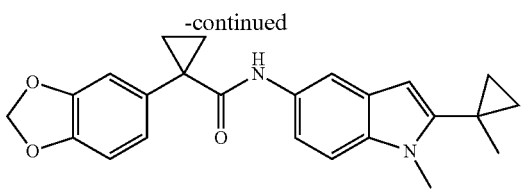

1-Methyl-2-(1-methylcyclopropyl)-1H-indol-5-amine (20.0 mg, 0.100 mmol) and 1-(benzo[d][1,3]dioxol-5-yl)cyclopropanecarboxylic acid (20.6 mg, 0.100 mmol) were dissolved in N,N-dimethylformamide (1 mL) containing triethylamine (42.1 µL, 0.300 mmol) and a magnetic stir bar. O-(7-Azabenzotriazol-1-yl)-N,N,N',N'-tetramethyluronium hexafluorophosphate (42 mg, 0.11 mmol) was added to the mixture and the resulting solution was allowed to stir for 6 h at 80° C. The crude product was then purified by preparative HPLC utilizing a gradient of 0-99% acetonitrile in water containing 0.05% trifluoroacetic acid to yield 1-(benzo[d][1,3]dioxol-5-yl)-N-(1-methyl-2-(1-methylcyclopropyl)-1H-indol-5-yl)cyclopropanecarboxamide. ESI-MS m/z calc. 388.2. found 389.2 (M+1)$^+$. Retention time of 3.05 minutes.

Example 65

1-(Benzo[d][1,3]dioxol-5-yl)-N-(1,1-dimethyl-2,3-dihydro-4H-pyrrolo[1,2-a]indol-7-yl)cyclopropanecarboxamide

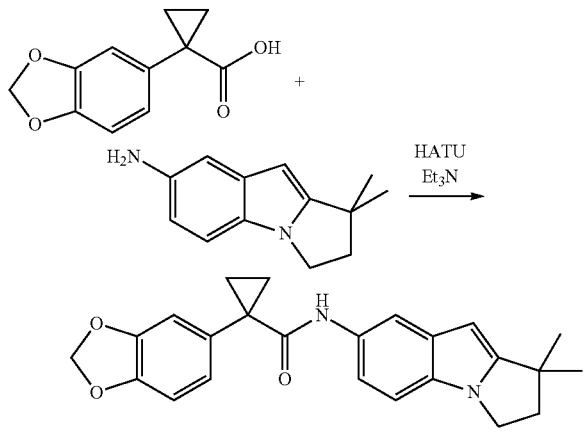

1,1-Dimethyl-2,3-dihydro-1H-pyrrolo[1,2-a]indol-7-amine (40.0 mg, 0.200 mmol) and 1-(benzo[d][1,3]dioxol-5-yl)cyclopropanecarboxylic acid (41.2 mg, 0.200 mmol) were dissolved in N,N-dimethylformamide (1 mL) containing triethylamine (84.2 µL, 0.600 mmol) and a magnetic stir bar. O-(7-Azabenzotriazol-1-yl)-N,N,N',N'-tetramethyluronium hexafluorophosphate (84 mg, 0.22 mmol) was added to the mixture and the resulting solution was allowed to stir for 5 minutes at room temperature. The crude product was then purified by preparative HPLC utilizing a gradient of 0-99% acetonitrile in water containing 0.05% trifluoroacetic acid to yield 1-(benzo[d][1,3]dioxol-5-yl)-N-(1,1-dimethyl-2,3-dihydro-1H-pyrrolo[1,2-a]-indol-7-yl)cyclopropanecarboxamide. ESI-MS m/z calc. 388.2. found 389.2 (M+1)$^+$. Retention time of 2.02 minutes. $^1$H NMR (400 MHz, DMSO-d6) δ 8.41 (s, 1H), 7.59 (d, J=1.8 Hz, 1H), 7.15 (d, J=8.6 Hz, 1H), 7.06-7.02 (m, 2H), 6.96-6.90 (m, 2H), 6.03 (s, 2H), 5.98 (d, J=0.7 Hz, 1H), 4.06 (t, J=6.8 Hz, 2H), 2.35 (t, J=6.8 Hz, 2H), 1.42-1.38 (m, 2H), 1.34 (s, 6H), 1.05-1.01 (m, 2H).

Example 66

Methyl 5-(1-(benzo[d][1,3]dioxol-5-yl)cyclopropanecarboxamido)-2-tert-butyl-1H-indole-7-carboxylate

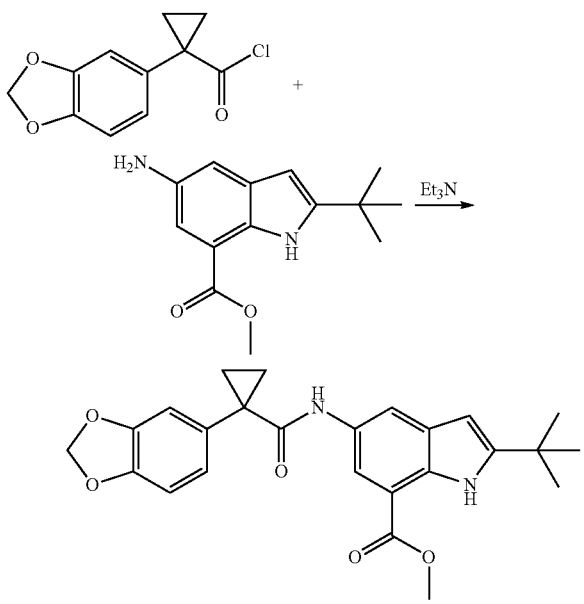

1-(Benzo[d][1,3]dioxol-5-yl)cyclopropanecarbonyl chloride (45 mg, 0.20 mmol) and methyl 5-amino-2-tert-butyl-1H-indole-7-carboxylate (49.3 mg, 0.200 mmol) were dissolved in N,N-dimethylformamide (2 mL) containing a magnetic stir bar and triethylamine (0.084 mL, 0.60 mmol). The resulting solution was allowed to stir for 10 minutes at room temperature. The crude product was then purified by preparative HPLC using a gradient of 0-99% acetonitrile in water containing 0.05% trifluoroacetic acid to yield methyl 5-(1-(benzo[d][1,3]dioxol-5-yl)cyclopropanecarboxamido)-2-tert-butyl-1H-indole-7-carboxylate. ESI-MS m/z calc. 434.2. found 435.5. (M+1)$^+$. Retention time of 2.12 minutes.

Example 67

1-(Benzo[d][1,3]dioxol-5-yl)-N-(2-(1-hydroxy-2-methylpropan-2-yl)-1H-indol-5-yl)cyclopropanecarboxamide

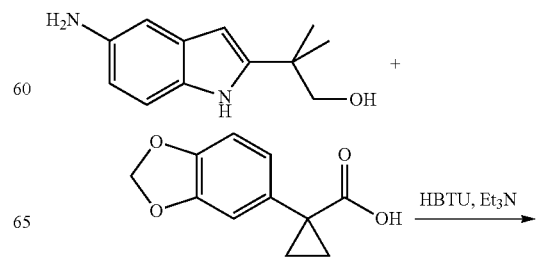

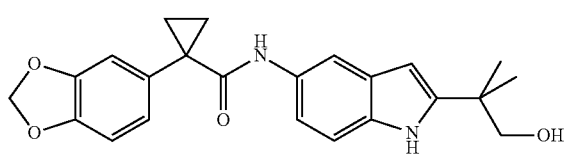

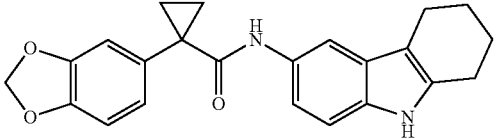

To a solution of 1-(benzo[d][1,3]dioxol-5-yl)cyclopropanecarboxylic acid (0.075 g, 0.36 mmol) in acetonitrile (1.5 mL) were added HBTU (0.138 g, 0.36 mmol) and Et₃N (152 µL, 1.09 mmol) at room temperature. The mixture was stirred at room temperature for 10 minutes before a solution of 2-(5-amino-1H-indol-2-yl)-2-methylpropan-1-ol (0.074 g, 0.36 mmol) in acetonitrile (1.94 mL) was added. After addition, the reaction mixture was stirred at room temperature for 3 h. The solvent was evaporated under reduced pressure and the residue was dissolved in dichloromethane. The organic layer was washed with 1 N HCl (1×3 mL) and saturated aqueous NaHCO₃ (1×3 mL). The organic layer was dried over Na₂SO₄, filtered and evaporated under reduced pressure. The crude material was purified by column chromatography on silica gel (ethyl acetate/hexane=1/1) to give 1-(benzo[d][1,3]dioxol-5-yl)-N-(2-(1-hydroxy-2-methylpropan-2-yl)-1H-indol-5-yl)cyclopropanecarboxamide (0.11 g, 75%). ¹H NMR (400 MHz, DMSO-d6) δ 10.64 (s, 1H), 8.38 (s, 1H), 7.55 (s, 1H), 7.15 (d, J=8.6 Hz, 1H), 7.04-6.90 (m, 411), 6.06 (s, 1H), 6.03 (s, 2H), 4.79 (t, J=2.7 Hz, 1H), 3.46 (d, J=0.0 Hz, 2H), 1.41-1.39 (m, 2H), 1.26 (s, 6H), 1.05-1.02 (m, 2H).

2,3,4,9-Tetrahydro-1H-carbazol-6-amine (81.8 mg, 0.439 mmol) and 1-(benzo[d][1,3]dioxol-5-yl)cyclopropanecarboxylic acid (90.4 mg, 0.439 mmol) were dissolved in acetonitrile (3 mL) containing diisopropylethylamine (0.230 mL, 1.32 mmol) and a magnetic stir bar. O-(7-Azabenzotriazol-1-yl)-N,N,N',N'-tetramethyluronium hexafluorophosphate (183 mg, 0.482 mmol) was added to the mixture and the resulting solution was allowed to stir for 16 h at 70° C. The solvent was evaporated and the crude product was then purified on 40 g of silica gel utilizing a gradient of 5-50% ethyl acetate in hexanes to yield 1-(benzo[d][1,3]dioxol-5-yl)-N-(2,3,4,9-tetrahydro-1H-carbazol-6-yl)cyclopropanecarboxamide as a beige powder (0.115 g, 70%) after drying. ESI-MS calc. 374.2. found 375.3 (M+1)⁺. Retention time of 3.43 minutes. ¹H NMR (400 MHz, DMSO-d6) δ 10.52 (s, 1H), 8.39 (s, 1H), 7.46 (d, J=1.8 Hz, 1H), 7.10-6.89 (m, 5H), 6.03 (s, 2H), 2.68-2.65 (m, 2H), 2.56-2.54 (m, 2H), 1.82-1.77 (m, 4H), 1.41-1.34 (m, 2H), 1.04-0.97 (m, 2H).

Example 69 tert-Butyl 4-(5-(1-(benzo[d][1,3]dioxol-5-yl)cyclopropanecarbox-amido)-1H-indol-2-yl)piperidine-1-carboxylate

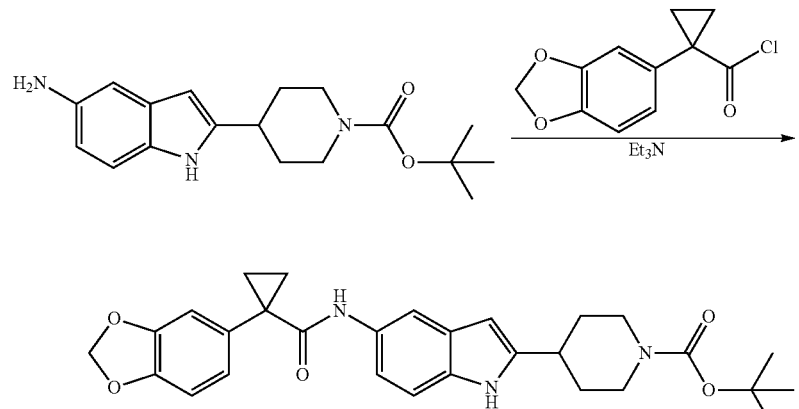

Example 67

1-(Benzo[d][1,3]dioxol-5-yl)-N-(2,3,4,9-tetrahydro-1H-carbazol-6-yl)cyclopropanecarboxamide

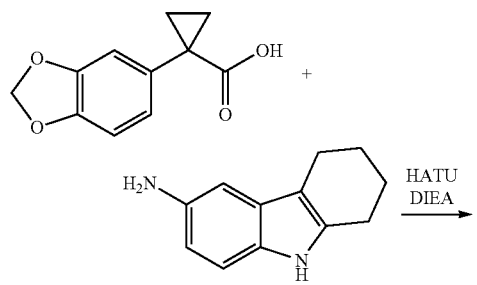

1-(Benzo[d][1,3]dioxol-5-yl)cyclopropanecarbonyl chloride (43 mg, 0.19 mmol) and tert-butyl 4-(5-amino-1H-indol-2-yl)piperidine-1-carboxylate (60 mg, 0.19 mmol) were dissolved in dichloromethane (1 mL) containing a magnetic stir bar and triethylamine (0.056 mL, 0.40 mmol). The resulting solution was allowed to stir for two days at room temperature. The crude product was then evaporated to dryness, dissolved in a minimum of N,N-dimethylformamide, and then purified by preparative HPLC using a gradient of 0-99% acetonitrile in water containing 0.05% trifluoroacetic acid to yield tert-butyl(benzo[d][1,3]dioxol-5-yl)cyclopropanecarboxamido)-1H-indol-2-yl)piperidine-1-carboxylate. ESI-MS m/z calc. 503.2. found 504.5. (M+1)⁺. Retention time of 1.99 minutes.

Example 70

Ethyl 2-(5-(1-(benzo[d][1,3]dioxol-5-yl)cyclopropanecarboxamido)-1H-indol-2-yl)propanoate

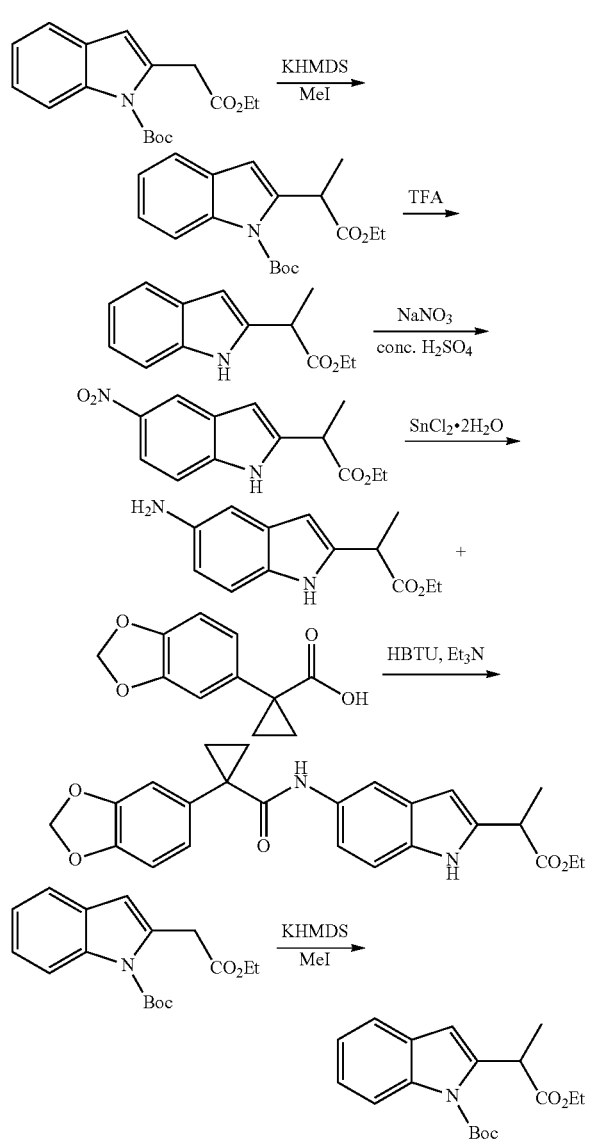

tert-Butyl 2-(1-ethoxy-1-oxopropan-2-yl)-1H-indole-1-carboxylate tert-Butyl 2-(2-ethoxy-2-oxoethyl)-1H-indole-1-carboxylate (3.0 g, 9.9 mmol) was added to anhydrous THF (29 mL) and cooled to −78° C. A 0.5M solution of potassium hexamethyldisilazane (20 mL, 9.9 mmol) was added slowly such that the internal temperature stayed below −60° C. Stirring was continued for 1 h at −78° C. Methyl iodide (727 μL, 11.7 mmol) was added to the mixture. The mixture was stirred for 30 minutes at room temperature. The mixture was quenched with sat. aq. ammonium chloride and partitioned between water and dichloromethane. The aqueous phase was extracted with dichloromethane and the combined organic phases were dried over Na$_2$SO$_4$ and evaporated under reduced pressure. The residue was purified by column chromatography on silica gel (ethylacetate/hexane=1/9) to give tert-butyl 2-(1-ethoxy-1-oxopropan-2-yl)-1H-indole-1-carboxylate (2.8 g, 88%).

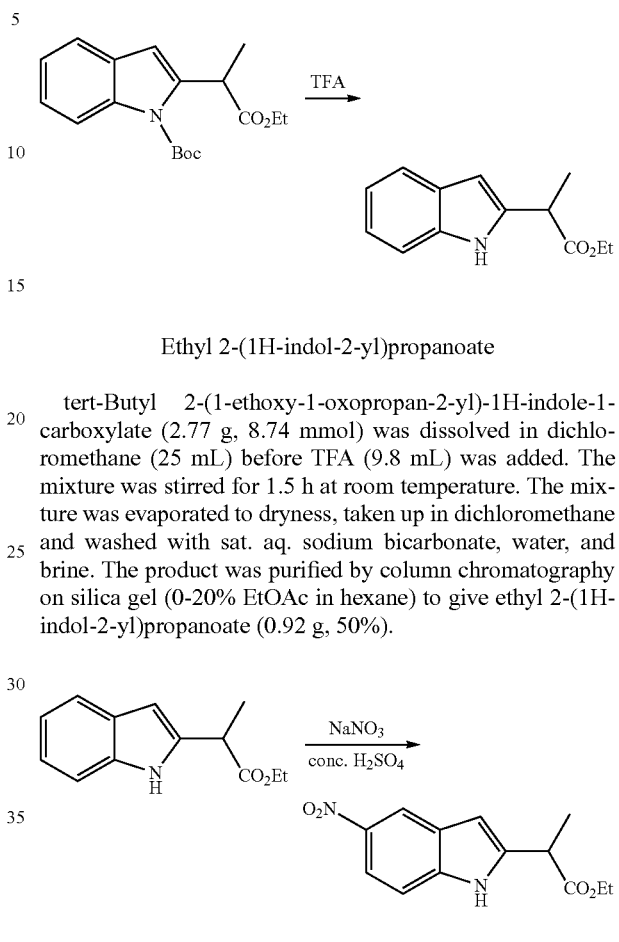

Ethyl 2-(1H-indol-2-yl)propanoate tert-Butyl 2-(1-ethoxy-1-oxopropan-2-yl)-1H-indole-1-carboxylate (2.77 g, 8.74 mmol) was dissolved in dichloromethane (25 mL) before TFA (9.8 mL) was added. The mixture was stirred for 1.5 h at room temperature. The mixture was evaporated to dryness, taken up in dichloromethane and washed with sat. aq. sodium bicarbonate, water, and brine. The product was purified by column chromatography on silica gel (0-20% EtOAc in hexane) to give ethyl 2-(1H-indol-2-yl)propanoate (0.92 g, 50%).

Ethyl 2-(5-nitro-1H-indol-2-yl)propanoate

Ethyl 2-(1H-indol-2-yl)propanoate (0.91 g, 4.2 mmol) was dissolved in concentrated sulfuric acid (3.9 mL) and cooled to −10° C. (salt/ice-mixture). A solution of sodium nitrate (0.36 g, 4.2 mmol) in concentrated sulfuric acid (7.8 mL) was added dropwise over 35 min. Stirring was continued for another 30 min at −10° C. The mixture was poured into ice and the product was extracted with ethyl acetate. The combined organic phases were washed with a small amount of sat. aq. sodium bicarbonate. The product was purified by column chromatography on silica gel (5-30% EtOAc in hexane) to give ethyl 2-(5-nitro-1H-indol-2-yl)propanoate (0.34 g, 31%).

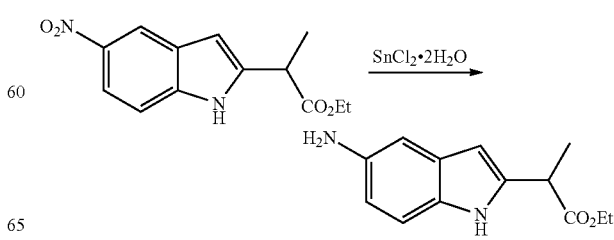

Ethyl 2-(5-amino-1H-indol-2-yl)propanoate

To a solution of ethyl 2-(5-nitro-1H-indol-2-yl)propanoate (0.10 g, 0.38 mmol) in ethanol (4 mL) was added tin chloride dihydrate (0.431 g, 1.91 mmol). The mixture was heated in the microwave at 120° C. for 1 h. The mixture was diluted with ethyl acetate before water and saturated aqueous NaHCO$_3$ were added. The reaction mixture was filtered through a plug of celite using ethyl acetate. The organic layer was separated from the aqueous layer. The organic layer was dried over Na$_2$SO$_4$, filtered and evaporated under reduced pressure to give ethyl 2-(5-amino-1H-indol-2-yl)propanoate (0.088 g, 99%).

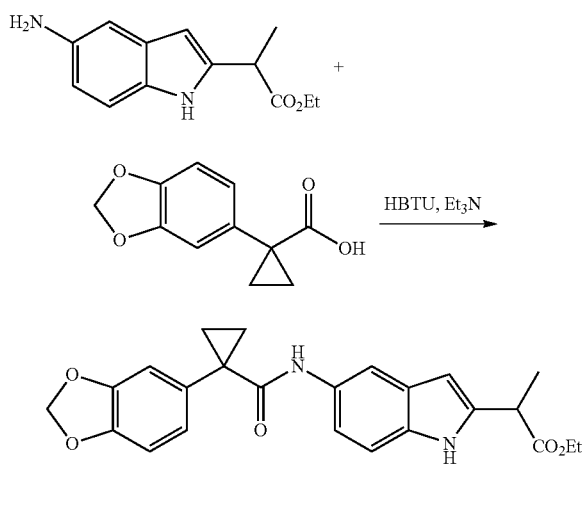

Ethyl 2-(5-(1-(benzo[d][1,3]dioxol-5-yl)cyclopropanecarboxamido)-1H-indol-2-yl)propanoate To a solution of 1-(benzo[d][1,3]dioxol-5-yl)cyclopropanecarboxylic acid (0.079 g, 0.384 mmol) in acetonitrile (1.5 mL) were added HBTU (0.146 g, 0.384 mmol) and Et$_3$N (160 µL, 1.15 mmol) at room temperature. The mixture was allowed to stir at room temperature for 10 min before a solution of ethyl 2-(5-amino-1H-indol-2-yl)propanoate (0.089 g, 0.384 mmol) in acetonitrile (2.16 mL) was added. After addition, the reaction mixture was stirred at room temperature for 2 h. The solvent was evaporated under reduced pressure and the residue was dissolved in dichloromethane. The organic layer was washed with 1 N HCl (1×3 mL) and then saturated aqueous NaHCO$_3$ (1×3 mL). The organic layer was dried over Na$_2$SO$_4$, filtered and evaporated under reduced pressure. The crude material was purified by column chromatography on silica gel (ethyl acetate/hexane=1/1) to give ethyl 2-(5-(1-(benzo[d][1,3]dioxol-5-yl)cyclopropanecarboxamido)-1H-indol-2-yl)propanoate (0.081 g, 50%). $^1$H NMR (400 MHz, CDCl$_3$) δ 8.51 (s, 1H), 7.67 (s, 1H), 7.23-7.19 (m, 2H), 7.04-7.01 (m, 3H), 6.89 (d, J=0.0 Hz, 1H), 6.28 (s, 1H), 6.06 (s, 2H), 4.25-4.17 (m, 2H), 3.91 (q, J=7.2 Hz, 1H), 1.72-1.70 (m, 2H), 1.61 (s, 2H), 1.29 (t, J=7.1 Hz, 4H), 1.13-1.11 (m, 2H).

Example 71 tert-Butyl 2-(5-(1-(benzo[d][1,3]dioxol-5-yl)cyclopropanecarbox-amido)-1H-indol-2-yl)-2-methylpropylcarbamate

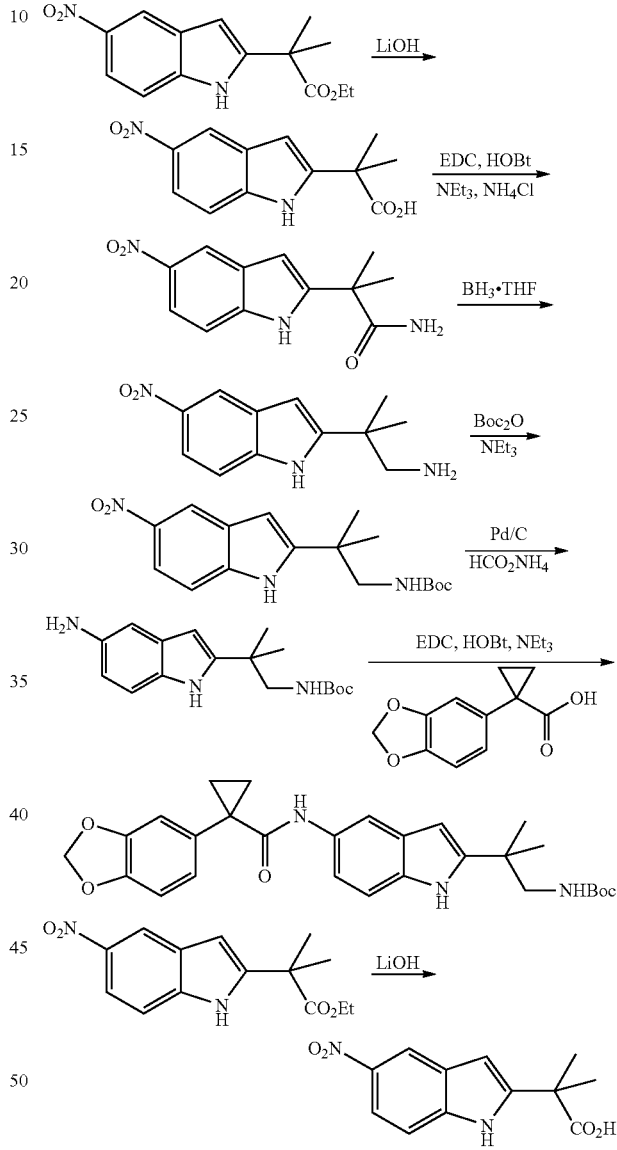

2-Methyl-2-(5-nitro-1H-indol-2-yl)propanoic acid

Ethyl 2-methyl-2-(5-nitro-1H-indol-2-yl)propanoate (4.60 g, 16.7 mmol) was dissolved in THF/water (2:1, 30 mL). LiOH.H$_2$O (1.40 g, 33.3 mmol) was added and the mixture was stirred at 50° C. for 3 h. The mixture was made acidic by the careful addition of 3N HCl. The product was extracted with ethylacetate and the combined organic phases were washed with brine and dried over magnesium sulfate to give 2-methyl-2-(5-nitro-1H-indol-2-yl)propanoic acid (4.15 g, 99%).

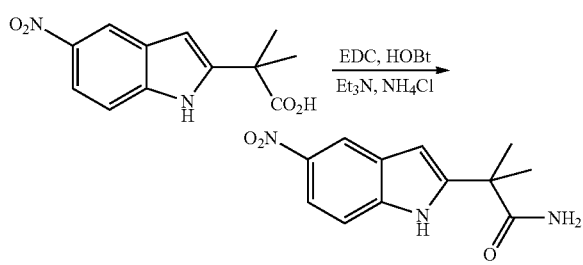

2-Methyl-2-(5-nitro-1H-indol-2-yl)propanamide

2-Methyl-2-(5-nitro-1H-indol-2-yl)-propanoic acid (4.12 g, 16.6 mmol) was dissolved in acetonitrile (80 mL). EDC (3.80 g, 0.020 mmol), HOBt (2.70 g, 0.020 mmol), Et$_3$N (6.9 mL, 0.050 mmol) and ammonium chloride (1.34 g, 0.025 mmol) were added and the mixture was stirred overnight at room temperature. Water was added and the mixture was extracted with ethylacetate. Combined organic phases were washed with brine, dried over magnesium sulfate and dried to give 2-methyl-2-(5-nitro-1H-indol-2-yl)propanamide (4.3 g, 99%).

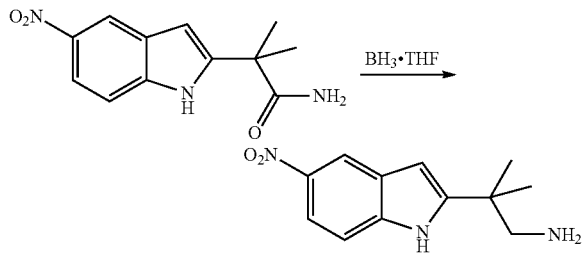

2-Methyl-2-(5-nitro-1H-indol-2-yl)propan-1-amine

2-Methyl-2-(5-nitro-1H-indol-2-yl)propanamide (200 mg, 0.81 mmol) was suspended in THF (5 ml) and cooled to 0° C. Borane-THF complex solution (1.0 M, 2.4 mL, 2.4 mmol) was added slowly and the mixture was allowed to stir overnight at room temperature. The mixture was cooled to 0° C. and carefully acidified with 3 N HCl. THF was evaporated off, water was added and the mixture was washed with ethylacetate. The aqueous layer was made alkaline with 50% NaOH and the mixture was extracted with ethylacetate. The combined organic layers were dried over magnesium sulfate, filtered and evaporated to give 2-methyl-2-(5-nitro-1H-indol-2-yl)propan-1-amine (82 mg, 43%).

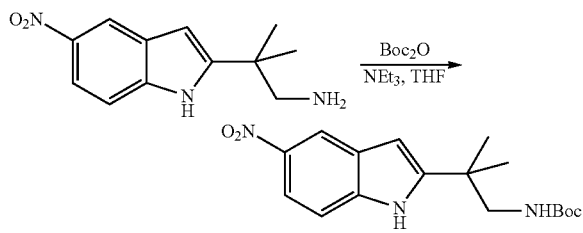

tert-Butyl 2-methyl-2-(5-nitro-1H-indol-2-yl)propylcarbamate

2-Methyl-2-(5-nitro-1H-indol-2-yl)propan-1-amine (137 mg, 0.587 mmol) was dissolved in THF (5 mL) and cooled to 0° C. Et$_3$N (82 µL, 0.59 mmol) and di-tert-butyl dicarbonate (129 mg, 0.587 mmol) were added and the mixture was stirred at room temperature overnight. Water was added and the mixture was extracted with ethylacetate. The residue was purified by silica gel chromatography (10-40% ethylacetate in hexane) to give tert-butyl 2-methyl-2-(5-nitro-1H-indol-2-yl)propylcarbamate (131 mg, 67%).

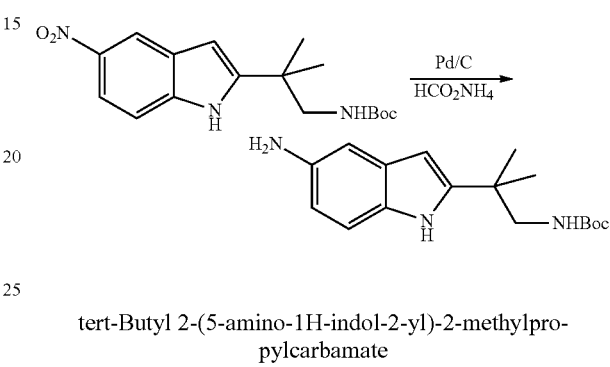

tert-Butyl 2-(5-amino-1H-indol-2-yl)-2-methylpropylcarbamate

To a solution of tert-butyl 2-methyl-2-(5-nitro-1H-indol-2-yl)propylcarbamate (80 mg, 0.24 mmol) in THF (9 mL) and water (2 mL) was added ammonium formate (60 mg, 0.96 mmol) followed by 10% Pd/C (50 mg). The mixture was stirred at room temperature for 45 minutes. Pd/C was filtered off and the organic solvent was removed by evaporation. The remaining aqueous phase was extracted with dichloromethane. The combined organic phases were dried over magnesium sulfate and evaporated to give tert-butyl 2-(5-amino-1H-indol-2-yl)-2-methylpropylcarbamate (58 mg, 80%).

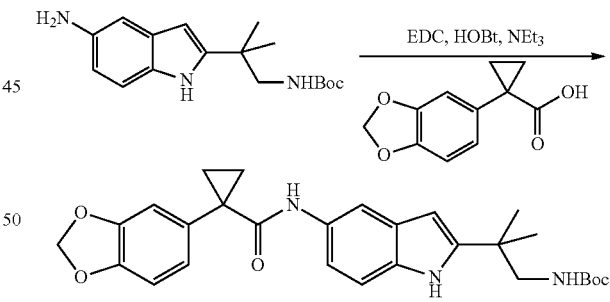

tert-Butyl 2-(5-(1-(benzo[d][1,3]dioxol-5-yl)cyclopropanecarboxamido)-1H-indol-2-yl)-2-methylpropylcarbamate tert-Butyl 2-(5-amino-1H-indol-2-yl)-2-methylpropylcarbamate (58 mg, 0.19 mmol), 1-(benzo[d][1,3]dioxol-6-yl) cyclopropanecarboxylic acid (47 mg, 0.23 mmol), EDC (45 mg, 0.23 mmol), HOBt (31 mg, 0.23 mmol) and Et$_3$N (80 µL, 0.57 mmol) were dissolved in DMF (4 mL) and stirred overnight at room temperature. The mixture was diluted with water and extracted with ethylacetate. The combined organic phases were dried over magnesium sulfate and evaporated to dryness. The residue was purified by silica gel chromatography (10-30% ethylacetate in hexane) to give tert-butyl 2-(5-(1-(benzo[d][1,3]dioxol-5-yl)cyclopropanecarboxamido)-1H-indol-2-yl)-2-methylpropyl-carbamate (88 mg, 94%). $^1$H NMR (400 MHz, CDCl$_3$) δ 8.32 (s, 1H), 7.62 (d, J=1.5 Hz, 1H), 7.18-7.16 (m, 2H), 7.02-6.94 (m, 3H), 6.85 (d, J=7.8 Hz, 1H), 6.19 (d, J=1.5 Hz, 1H), 6.02 (s, 2H), 4.54 (m, 1H), 3.33 (d, J=6.2 Hz, 2H), 1.68 (dd, J=3.7, 6.8 Hz, 2H), 1.36 (s, 9H), 1.35 (s, 6H), 1.09 (dd, J=3.7, 6.8 Hz, 2H).

Example 72

(R)—N-(2-tert-Butyl-1-(2,3-dihydroxypropyl)-1H-indol-5-yl)-1-(2,2-difluorobenzo[d][1,3]dioxol-5-yl)cyclopropanecarboxamide

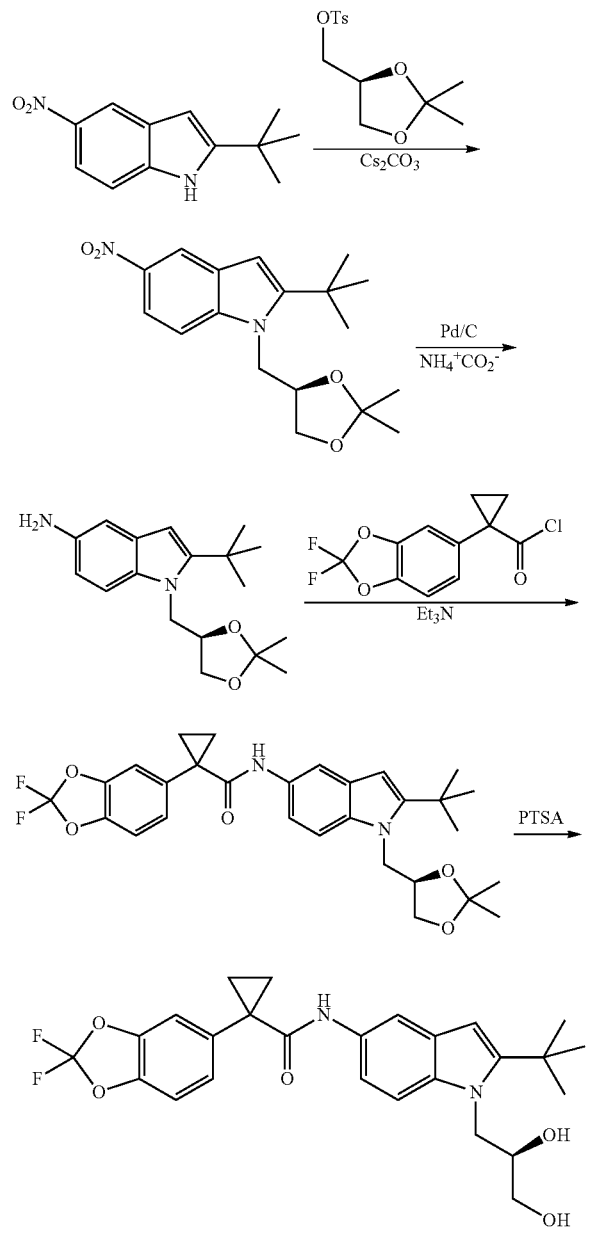

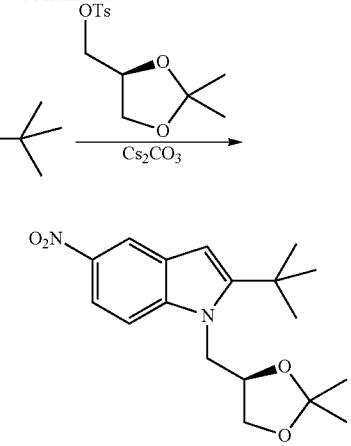

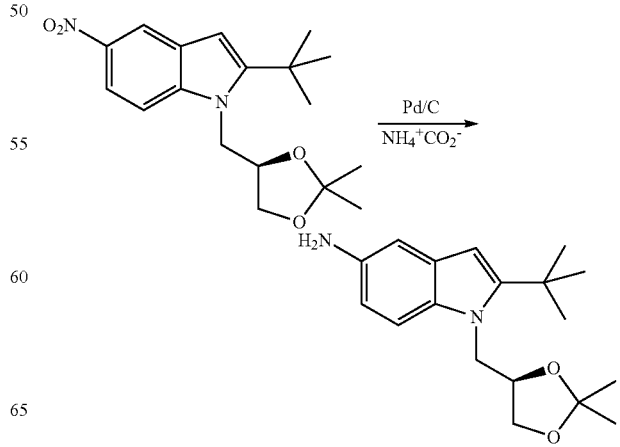

(R)-2-tert-Butyl-1-((2,2-dimethyl-1,3-dioxolan-4-yl)methyl)-5-nitro-1H-indole

To a stirred solution of (S)-(2,2-dimethyl-1,3-dioxolan-4-yl)methyl 4-methylbenzenesulfonate (1.58 g, 5.50 mmol) in anhydrous DMF (10 mL) under nitrogen gas was added 2-tert-butyl-5-nitro-1H-indole (1.00 g, 4.58 mmol) followed by Cs$_2$CO$_3$ (2.99 g, 9.16 mol). The mixture was stirred and heated at 80° C. under nitrogen gas. After 20 hours, 50% conversion was observed by LCMS. The reaction mixture was re-treated with Cs$_2$CO$_3$ (2.99 g, 9.16 mol) and (S)-(2,2-dimethyl-1,3-dioxolan-4-yl)methyl 4-methylbenzenesulfonate (1.58 g, 5.50 mmol) and heated at 80° C. for 24 hours. The reaction mixture was cooled to room temperature. The solids were filtered and washed with ethyl acetate and hexane (1:1). The layers were separated and the organic layer was washed with water (2×10 mL) and brine (2×10 mL). The organic layer was dried over Na$_2$SO$_4$, filtered and evaporated under reduced pressure. The residue was purified by column chromatography on silica gel (dichloromethane/hexane=1.5/1) to give (R)-2-tert-butyl-1-((2,2-dimethyl-1,3-dioxolan-4-yl)methyl)-5-nitro-1H-indole (1.0 g, 66%). $^1$H NMR (400 MHz, CDCl$_3$) δ 8.48 (d, J=2.2 Hz, 1H), 8.08 (dd, J=2.2, 9.1 Hz, 1H), 7.49 (d, J=9.1 Hz, 1H), 6.00 (s, 1H), 4.52-4.45 (m, 3H), 4.12 (dd, J=6.0, 8.6 Hz, 1H), 3.78 (dd, J=6.0, 8.6 Hz, 1H), 1.53 (s, 3H), 1.51 (s, 9H), 1.33 (s, 3H).

(R)-2-tert-Butyl-1-((2,2-dimethyl-1,3-dioxolan-4-yl)methyl-1H-indol-5-amine

To a stirred solution of (R)-2-tert-butyl-1-((2,2-dimethyl-1,3-dioxolan-4-yl)methyl)-5-nitro-1H-indole (1.0 g, 3.0 mmol) in ethanol (20 mL) and water (5 mL) was added ammonium formate (0.76 g, 12 mmol) followed by slow addition of 10% palladium on carbon (0.4 g). The mixture was stirred at room temperature for 1 h. The reaction mixture was filtered through a plug of celite and rinsed with ethyl acetate. The filtrate was evaporated under reduced pressure and the crude product was dissolved in ethyl acetate. The organic layer was washed with water (2×5 mL) and brine (2×5 mL). The organic layer was dried over $Na_2SO_4$, filtered and evaporated under reduced pressure to give (R)-2-tert-butyl-1-((2,2-dimethyl-1,3-dioxolan-4-yl)methyl-1H-indol-5-amine (0.89 g, 98%). $^1$H NMR (400 MHz, $CDCl_3$) δ 7.04 (d, J=4 Hz, 1H), 6.70 (d, J=2.2 Hz, 1H), 6.48 (dd, J=2.2, 8.6 Hz, 1H), 6.05 (s, 1H), 4.38-4.1 (m, 2H), 4.21 (dd, J=7.5, 16.5 Hz, 1H), 3.87 (dd, J=6.0, 8.6 Hz, 1H), 3.66 (dd, J=6.0, 8.6 Hz, 1H), 3.33 (br s, 2H), 1.40 (s, 3H), 1.34 (s, 9H), 1.25 (s, 3H).

N—((R)-2-tert-Butyl-1-((2,2-dimethyl-1,3-dioxolan-4-yl)methyl)-1H-indol-5-yl)-1-(2,2-difluorobenzo[d][1,3]dioxol-5-yl)cyclopropanecarboxamide To 1-(benzo[d][1,3]dioxol-5-yl)cyclopropanecarboxylic acid (0.73 g, 3.0 mmol) was added thionyl chloride (660 μL, 9.0 mmol) and DMF (20 μL) at room temperature. The mixture was stirred for 30 minutes before the excess thionyl chloride was evaporated under reduced pressure. To the resulting acid chloride, dichloromethane (6.0 mL) and $Et_3N$ (2.1 mL, 15 mmol) were added. A solution of (R)-2-tert-butyl-1-((2,2-dimethyl-1,3-dioxolan-4-yl)methyl-1H-indol-5-amine (3.0 mmol) in dichloromethane (3.0 mL) was added to the cooled acid chloride solution. After addition, the reaction mixture was stirred at room temperature for 45 minutes. The reaction mixture was filtered and the filtrate was evaporated under reduced pressure. The residue was purified by column chromatography on silica gel (ethyl acetate/hexane=3/7) to give N—((R)-2-tert-butyl-1-((2,2-dimethyl-1,3-dioxolan-4-yl)methyl)-1H-indol-5-yl)-1-(2,2-difluorobenzo[d][1,3]dioxol-5-yl)cyclopropanecarboxamide (1.33 g, 84%). $^1$H NMR (400 MHz, $CDCl_3$) δ 7.48 (d, J=2 Hz, 1H), 7.31 (dd, J=2, 8 Hz, 1H), 7.27 (dd, J=2, 8 Hz, 1H), 7.23 (d, J=8 Hz, 1H), 7.14 (d, J=8 Hz, 1H), 7.02 (dd, J=2, 8 Hz, 1H), 6.92 (br s, 1H), 6.22 (s, 1H), 4.38-4.05 (m, 3H), 3.91 (dd, J=5, 8 Hz, 1H), 3.75 (dd, J=5, 8 Hz, 1H), 2.33 (q, J=8 Hz, 2H), 1.42 (s, 3H), 1.37 (s, 9H), 1.22 (s, 3H), 1.10 (q, J=8 Hz, 2H).

N—((R)-2-tert-Butyl-1-((2,3-dihydroxypropyl)-1H-indol-5-yl)-1-(2,2-difluorobenzo-[d][1,3]dioxol-5-yl)cyclopropanecarboxamide To a stirred solution of N-(2-tert-butyl-1-((2,2-dimethyl-1,3-dioxolan-4-yl)methyl)-1H-indol-5-yl)-1-(2,2-difluorobenzo[d][1,3]dioxol-5-yl)cyclopropanecarboxamide (1.28 g, 2.43 mmol) in methanol (34 mL) and water (3.7 mL) was added para-toluenesulfonic acid-hydrate (1.87 g, 9.83 mmol). The reaction mixture was stirred and heated at 80° C. for 25 minutes. The solvent was evaporated under reduced pressure. The crude product was dissolved in ethyl acetate. The organic layer was washed with saturated aqueous $NaHCO_3$ (2×10 mL) and brine (2×10 mL). The organic layer was dried over $Na_2SO_4$, filtered and evaporated under reduced pressure. The residue was purified by column chromatography on silica gel (ethyl acetate/hexane=13/7) to give N—((R)-2-tert-butyl-1-2,3-dihydroxypropyl)-1H-indol-5-yl)-1-(2,2-difluorobenzo[d][1,3]dioxol-5-yl)cyclopropanecarboxamide (0.96 g, 81%). $^1$H NMR (400 MHz, $CDCl_3$) δ 7.50 (d, J=2 Hz, 1H), 7.31 (dd, J=2, 8 Hz, 1H), 7.27 (dd, J=2, 8 Hz, 1H), 7.23 (d, J=8 Hz, 1H), 7.14 (d, J=8 Hz, 1H), 7.02 (br s, 1H), 6.96 (dd, J=2, 8 Hz, 1H), 6.23 (s, 1H), 4.35 (dd, J=8, 15 Hz, 1H), 4.26 (dd, J=4, 15 Hz, 1H), 4.02-3.95 (m, 1H), 3.60 (dd, J=4, 11 Hz, 1H), 3.50 (dd, J=5, 11 Hz, 1H), 1.75 (q, J=8 Hz, 3H), 1.43 (s, 9H), 1.14 (q, J=8 Hz, 3H).

Example 73

3-(2-tert-Butyl-5-(1-(2,2-difluorobenzo[d][1,3]dioxol-5-yl)cyclopropanecarboxamido)-1H-indol-1-yl)-2-hydroxypropanoic acid

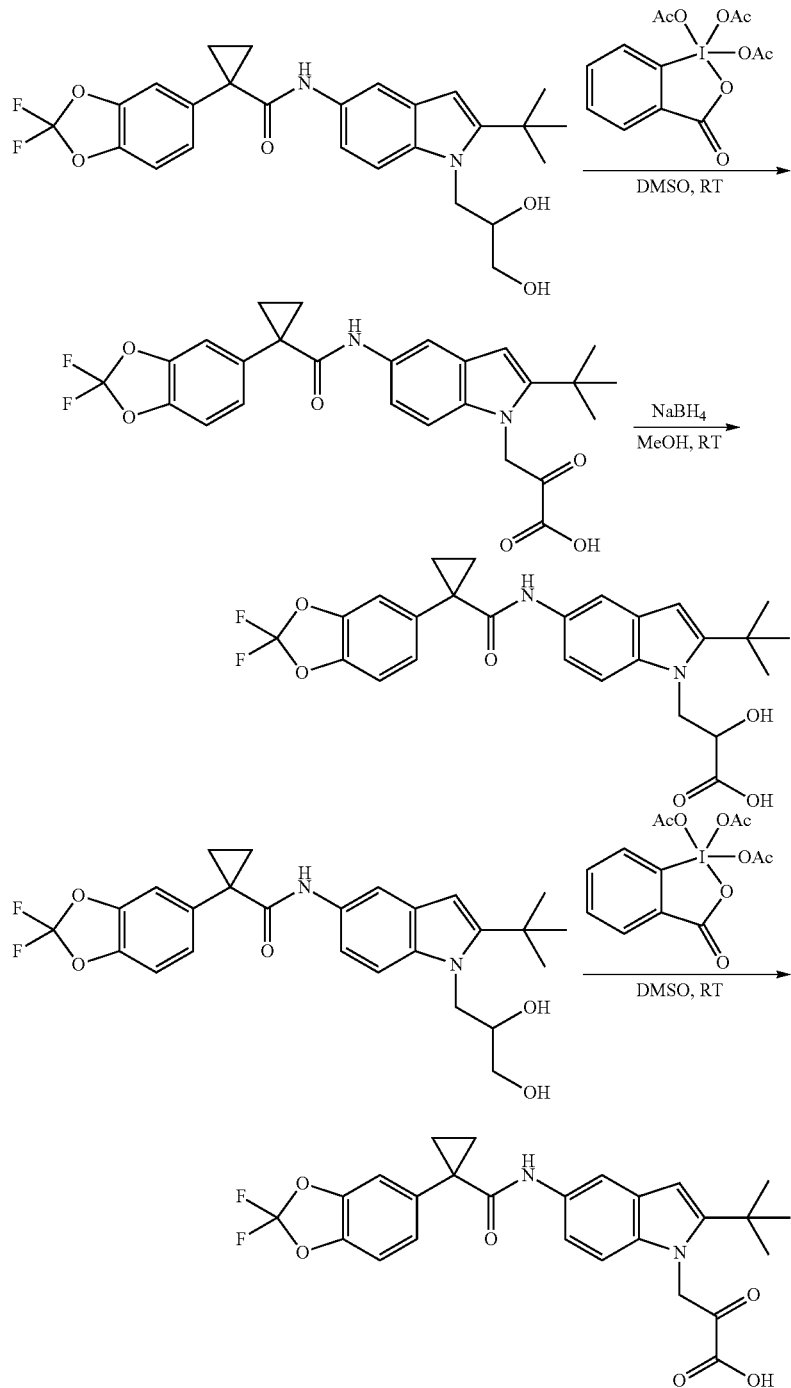

3-(2-tert-Butyl-5-(1-(2,2-difluorobenzo[d][1,3]dioxol-5-yl)cyclopropanecarbox-amido)-1H-indol-1-yl)-2-oxopropanoic acid To a solution of N-(2-tert-butyl-1-(2,3-dihydroxypropyl)-1H-indol-5-yl)-1-(2,2-difluorobenzo[d][1,3]dioxol-5-yl)cyclopropane-carboxamide (97 mg, 0.20 mmol) in DMSO (1 mL) was added Dess-Martin periodinane (130 mg, 0.30 mmol). The mixture was stirred at room temperature for 3 h. The solid was filtered off and washed with EtOAc. The filtrate was partitioned between EtOAc and water. The aqueous layer was extracted with EtOAc twice and the combined organic layers were washed with brine and dried over MgSO$_4$. After the removal of solvent, the residue was purified by preparative TLC to yield 3-(2-tert-butyl-5-(1-(2,2-difluorobenzo[d][1,3]dioxol-5-yl)cyclopropanecarboxamido)-1H-indol-1-yl)-2-oxopropanoic acid that was used without further purification.

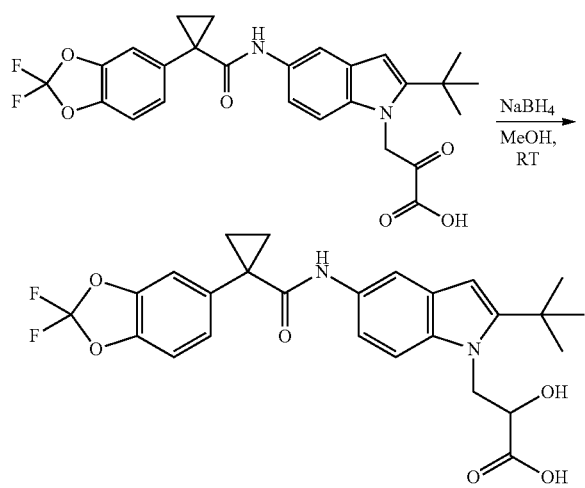

3-((2-tert-Butyl-5-(1-(2,2-difluorobenzo[d][1,3]dioxol-5-yl)cyclopropanecarbox-amido)-1H-indol-1-yl)-2-hydroxypropanoic acid To a solution of 3-(2-tert-butyl-5-(1-(2,2-difluorobenzo[d][1,3]dioxol-5-yl)cyclopropanecarboxamido)-1H-indol-1-yl)-2-oxopropanoic acid (50 mg, 0.10 mmol) in MeOH (1 mL) was added NaBH$_4$ (19 mg, 0.50 mmol) at 0° C. The mixture was stirred at room temperature for 15 min. The resulting mixture was partitioned between EtOAc and water. The aqueous layer was extracted with EtOAc twice and the combined organic layers were washed with brine and dried over anhydrous MgSO$_4$. After the removal of the solvent, the residue was taken up in DMSO and purified by preparative LC/MS to give 3-(2-tert-butyl-5-(1-(2,2-difluorobenzo[d][1,3]dioxol-5-yl)cyclopropanecarboxamido)-1H-indol-1-yl)-2-hydroxypropanoic acid. $^1$H NMR (400 MHz, CDCl$_3$) δ 7.36 (s), 7.27-7.23 (m, 2H), 7.15-7.11 (m, 2H), 6.94 (d, J=8.5 Hz, 1H), 6.23 (s, 1H), 4.71 (s, 3H), 4.59 (q, J=10.3 Hz, 1H), 4.40-4.33 (m, 2H), 1.70 (d, J=1.9 Hz, 2H), 1.15 (q, J=4.0 Hz, 2H). $^{13}$C NMR (400 MHz, CDCl$_3$) δ 173.6, 173.1, 150.7, 144.1, 143.6, 136.2, 135.4, 134.3, 131.7, 129.2, 129.0, 127.6, 126.7, 116.6, 114.2, 112.4, 110.4, 110.1, 99.7, 70.3, 48.5, 32.6, 30.9, 30.7, 16.8. MS (ESI) m/e (M+H$^+$) 501.2.

Example 74

(R)—N-(2-tert-Butyl-1-(2,3-dihydroxypropyl)-1H-indol-5-yl)-1-(2,2-dideuteriumbenzo[d][1,3]dioxol-5-yl)cyclopropanecarboxamide

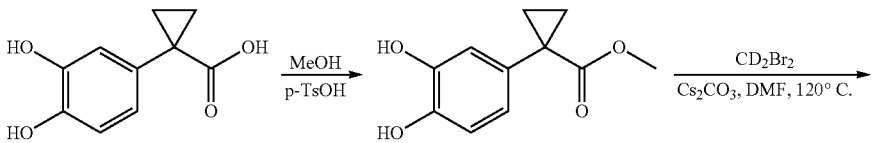

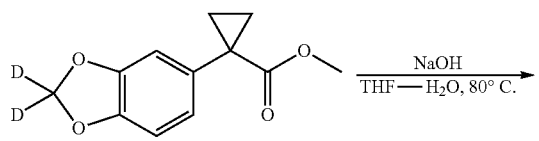

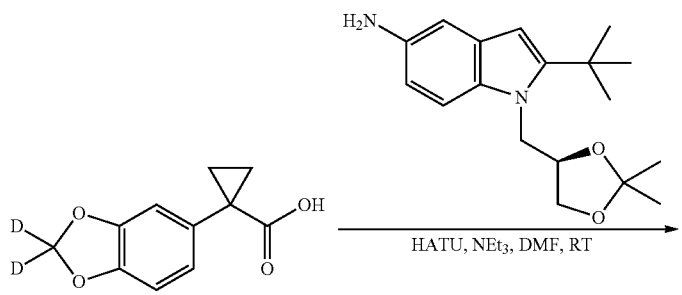

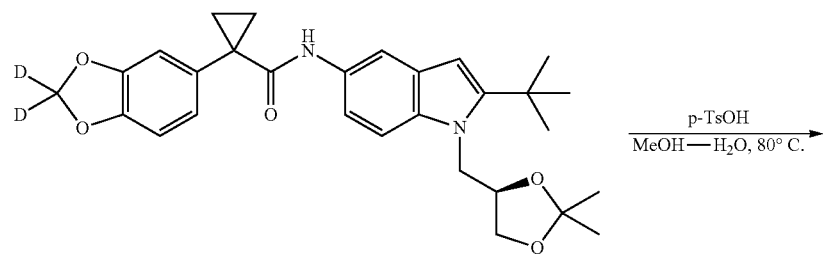

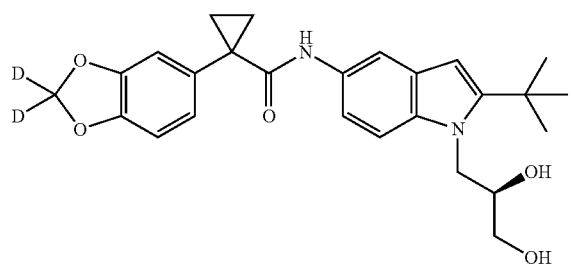

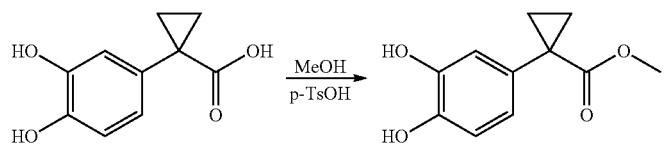

Methyl 1-(3,4-dihydroxyphenyl)cyclopropanecarboxylate

To a solution of 1-(3,4-dihydroxyphenyl)cyclopropanecarboxylic acid (190 mg, 1.0 mmol) in MeOH (3 mL) was added 4-methylbenzenesulfonic acid (19 mg, 0.10 mmol). The mixture was heated at 80° C. overnight. The reaction mixture was concentrated in vacuo and partitioned between EtOAc and water. The aqueous layer was extracted with EtOAc twice and the combined organic layers were washed with sat. NaHCO$_3$ and brine and dried over MgSO$_4$. After the removal of solvent, the residue was dried in vacuo to yield methyl 1-((3,4-dihydroxyphenyl)cyclopropanecarboxylate (190 mg, 91%) that was used without further purification. $^1$H NMR (400 MHz, DMSO-d$^6$) δ 6.76-6.71 (m, 2H), 6.66 (d, J=7.9 Hz, 1H), 3.56 (s, 3H), 1.50 (q, J=3.6 Hz, 2H), 1.08 (q, J=3.6 Hz, 2H).

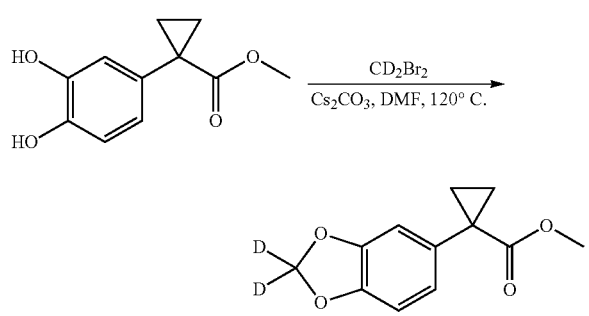

Methyl 1-(2,2-dideuteriumbenzo[d][1,3]dioxol-5-yl) cyclopropanecarboxylate

To a solution of methyl 1-(3,4-dihydroxyphenyl)cyclopropanecarboxylate (21 mg, 0.10 mmol) and CD$_2$Br$_2$ (35 mg, 0.20 mmol) in DMF (0.5 mL) was added Cs$_2$CO$_3$ (19 mg, 0.10 mmol). The mixture was heated at 120° C. for 30 min. The reaction mixture was partitioned between EtOAc and water. The aqueous layer was extracted with EtOAc twice and the combined organic layers were washed with 1N NaOH and brine before being dried over MgSO$_4$. After the removal of solvent, the residue was dried in vacuo to yield methyl 1-(2, 2-dideuteriumbenzo[d][1,3]dioxol-5-yl)cyclopropanecarboxylate (22 mg) that was used without further purification. $^1$H NMR (400 MHz, CDCl$_3$) δ 6.76-6.71 (m, 2H), 6.66 (d, J=7.9 Hz, 1H), 3.56 (s, 3H), 1.50 (q, J=3.6 Hz, 2H), 1.08 (q, J=3.6 Hz, 2H).

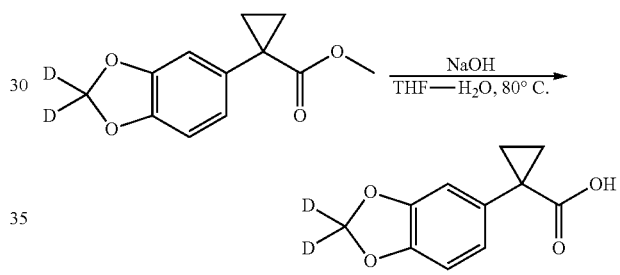

1-(2,2-Dideuteriumbenzo[d][1,3]dioxol-5-yl)cyclopropanecarboxylic acid

To a solution of methyl 1-(2,2-dideuteriumbenzo[d][1,3] dioxol-5-yl)cyclopropanecarboxylate (22 mg, 0.10 mmol) in THF (0.5 mL) was added NaOH (1N, 0.25 mL, 0.25 mmol). The mixture was heated at 80° C. for 2 h. The reaction mixture was partitioned between EtOAc and 1N NaOH. The aqueous layer was extracted with EtOAc twice, neutralized with 1N HCl and extracted with EtOAc twice. The combined organic layers were washed with brine and dried over MgSO$_4$. After the removal of solvent, the residue was dried in vacuo to yield 1-(2,2-dideuteriumbenzo[d][1,3]dioxol-5-yl)cyclopropanecarboxylic acid (21 mg) that was used without further purification.

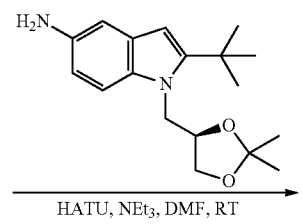

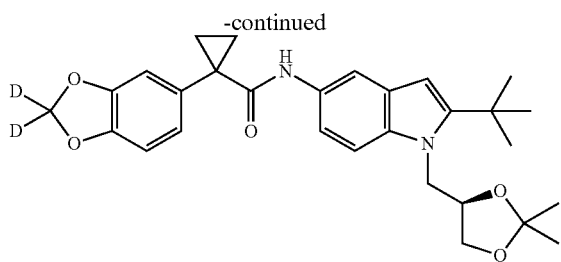

(R)—N-(2-tert-Butyl-1-((2,2-dimethyl-1,3-dioxolan-4-yl)methyl)-1H-indol-5-yl)-1-(2,2-dideuterium-benzo[d][1,3]dioxol-5-yl)cyclopropanecarboxamide To a solution of 1-(2,2-dideuteriumbenzo[d][1,3]dioxol-5-yl)cyclopropanecarboxylic acid (21 mg, 0.10 mmol), (R)-2-tert-butyl-1-((2,2-dimethyl-1,3-dioxolan-4-yl)methyl)-1H-indol-5-amine (30 mg, 0.10 mmol), HATU (42 mg, 0.11 mol) in DMF (1 mL) was added triethylamine (0.030 mL, 0.22 mmol). The mixture was heated at room temperature for 5 min. The reaction mixture was partitioned between EtOAc and water. The aqueous layer was extracted with EtOAc twice and the combined organic layers were washed with 1N NaOH, 1N HCl, and brine before being dried over MgSO₄. After the removal of solvent, the residue was purified by column chromatography (20-40% ethyl acetate/hexane) to yield (R)—N-(2-tert-butyl-1-((2,2-dimethyl-1,3-dioxolan-4-yl)methyl)-1H-indol-5-yl)-1-(2,2-dideuteriumbenzo[d][1,3]dioxol-5-yl)cyclopropanecarboxamide (24 mg, 49% from methyl 1-(3,4-dihydroxyphenyl)cyclopropanecarboxylate). MS (ESI) m/e (M+H⁺) 493.5.

mmol). The mixture was heated at 80° C. for 30 min. The reaction mixture was partitioned between EtOAc and water. The aqueous layer was extracted with EtOAc twice and the combined organic layers were washed with sat. NaHCO₃ and brine before being dried over MgSO₄. After the removal of solvent, the residue was purified by preparative HPLC to yield (R)—N-(2-tert-butyl-1-((2,2-dimethyl-1,3-dioxolan-4-yl)methyl)-1H-indol-5-yl)-1-(2,2-dideuteriumbenzo[d][1,3]dioxol-5-yl)cyclopropanecarboxamide (12 mg, 52%). ¹H NMR (400 MHz, CDCl₃) δ 7.44 (d, J=2.0 Hz, 1H), 7.14 (dd, J=22.8, 14.0 Hz, 2H), 6.95-6.89 (m, 2H), 6.78 (d, J=7.8 Hz, 1H), 6.14 (s, 1H), 4.28 (dd, J=15.1, 8.3 Hz, 1H), 4.19 (dd, J=15.1, 4.5 Hz, 1H), 4.05 (q, J=7.1 Hz, 1H), 3.55 (dd, J=11.3, 4.0 Hz, 1H), 3.45 (dd, J=11.3, 5.4 Hz, 1H), 1.60 (q, J=3.5 Hz, 2H), 1.35 (s, 9H), 1.02 (q, J=3.5 Hz, 2H). ¹³C NMR (400 MHz, CDCl₃) δ 171.4, 149.3, 147.1, 146.5, 134.8, 132.3, 129.2, 126.5, 123.6, 114.3, 111.4, 110.4, 109.0, 107.8, 98.5, 70.4, 63.1, 46.6, 31.6, 30.0, 29.8, 15.3. MS (ESI) m/e (M+H⁺) 453.5.

It is further noted that the mono-deuterated analogue for this compound can be synthesized by substitution the reagent CHDBR₂ for CD₂BR₂ and following the procedures described in example 74. Furthermore, mono-deuterated analogues of other compounds of the present invention can be synthesized by substituting the reagent CHDBR₂ for CD₂BR₂ and following the steps described herein.

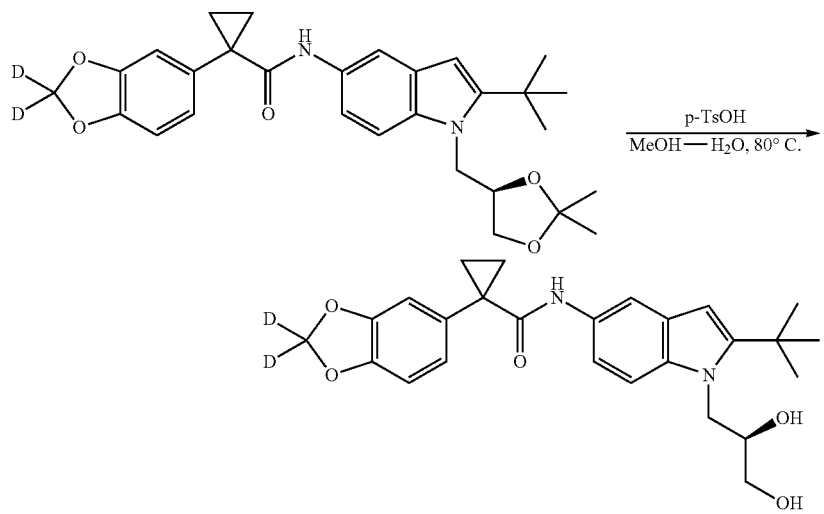

(R)—N-(2-tert-Butyl-1-(2,3-dihydroxypropyl)-1H-indol-5-yl)-1-(2,2-dideuteriumbenzo[d][1,3]dioxol-5-yl)cyclopropanecarboxamide To a solution of (R)—N-(2-tert-Butyl-1-((2,2-dimethyl-1,3-dioxolan-4-yl)methyl)-1H-indol-5-yl)-1-(2,2-dideuterium-benzo[d][1,3]dioxol-5-yl)cyclopropanecarboxamide (24 mg, 0.050 mmol), in methanol (0.5 mL) and water (0.05 mL) was added 4-methylbenzenesulfonic acid (2.0 mg, 0.010

Example 75

4-(5-(1-(Benzo[d][1,3]dioxol-5-yl)cyclopropanecarboxamido)-1H-indol-2-yl)-4-methylpentanoic acid

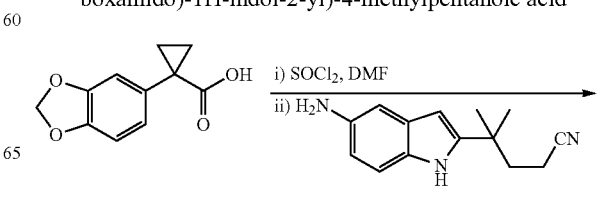

-continued

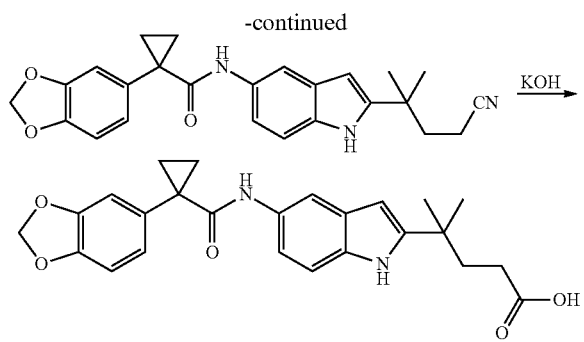

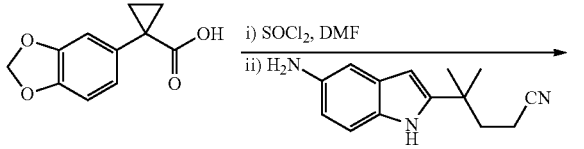

1-(Benzo[d][1,3]dioxol-5-yl)-N-(2-(4-cyano-2-methylbutan-2-yl)-1H-indol-5-yl)cyclopropanecarboxamide To 1-(benzo[d][1,3]dioxol-5-yl)cyclopropanecarboxylic acid (0.068 g, 0.33 mmol) was added thionyl chloride (72 µL, 0.99 mmol) and DMF (20 µL) at room temperature. The mixture was stirred for 30 minutes before the excess thionyl chloride was evaporated under reduced pressure. To the resulting acid chloride, dichloromethane (0.5 mL) and Et₃N (230 µL, 1.7 mmol) were added. A solution of 4-(5-amino-1H-indol-2-yl)-4-methylpentanenitrile (0.33 mmol) in dichloromethane (0.5 mL) was added to the acid chloride solution and the mixture was stirred at room temperature for 1.5 h. The resulting mixture was diluted with dichloromethane and washed with 1 N HCl (2×2 mL), saturated aqueous NaHCO₃ (2×2 mL) and brine (2×2 mL). The organic layer was dried over anhydrous Na₂SO₄ and evaporated under reduced pressure to give 1-(benzo[d][1,3]dioxol-5-yl)-N-(2-(4-cyano-2-methylbutan-2-yl)-1H-indol-5-yl)cyclopropanecarboxamide.

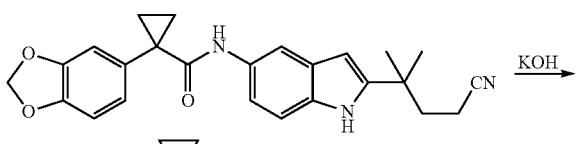

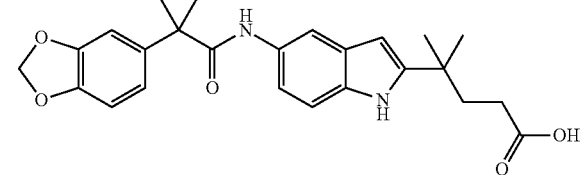

4-(5-(1-(Benzo[d][1,3]-dioxol-5-yl)cyclopropanecarboxamido)-1H-indol-2-yl)-4-methylpentanoic acid A mixture of 1-(benzo[d][1,3]dioxol-5-yl)-N-(2-(4-cyano-2-methylbutan-2-yl)-1H-indol-5-yl)cyclopropanecarboxamide (0.060 g, 0.15 mmol) and KOH (0.081 g, 1.5 mmol) in 50% EtOH/water (2 mL) was heated in the microwave at 100° C. for 1 h. The solvent was evaporated under reduced pressure. The crude product was dissolved in DMSO (1 mL), filtered, and purified by reverse phase preparative HPLC to give 4-(5-O-(benzo[d][1,3]dioxol-5-yl)cyclopropanecarboxamido)-1H-indol-2-yl)-4-methylpentanoic acid. ¹H NMR (400 MHz, DMSO-d6) δ 11.98 (s, 1H), 10.79 (s, 1H), 8.44 (s, 1H), 7.56 (s, 1H), 7.15 (d, J=8.6 Hz, 1H), 7.03-6.90 (m, 4H), 6.05 (s, 1H), 6.02 (s, 2H), 1.97-1.87 (m, 4H), 1.41-1.38 (m, 2H), 1.30 (s, 6H), 1.04-1.02 (m, 2H).

Example 76

1-(Benzo[d][1,3]dioxol-5-yl)-N-(2-(1-hydroxypropan-2-yl)-1H-indol-5-yl)cyclopropanecarboxamide

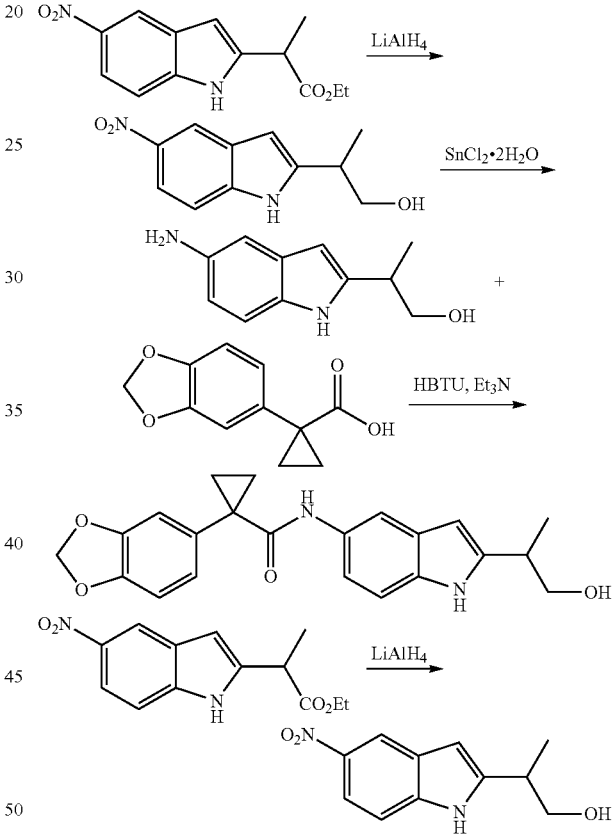

2-(5-Nitro-1H-indol-2-yl)propan-1-ol

To a cooled solution of LiAlH₄ (1.0 M in THF, 1.2 mL, 1.2 mmol) in THF (5.3 mL) at 0° C. was added a solution of ethyl 2-(5-nitro-1H-indol-2-yl)propanoate (0.20 g, 0.76 mmol) in THF (3.66 mL) dropwise. After addition, the mixture was allowed to warm up to room temperature and was stirred at room temperature for 3 h. The mixture was cooled to 0° C. Water (2 mL) was slowly added followed by careful addition of 15% NaOH (2 mL) and water (4 mL). The mixture was stirred at room temperature for 0.5 h and was then filtered through a short plug of celite using ethyl acetate. The organic layer was separated from the aqueous layer, dried over Na₂SO₄, filtered and evaporated under reduced pressure. The residue was purified by column chromatography on silica gel (ethyl acetate/hexane=1/1) to give 2-(5-nitro-1H-indol-2-yl)propan-1-ol (0.14 g, 81%).

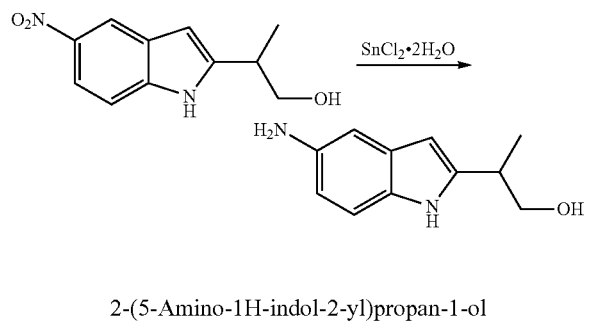

2-(5-Amino-1H-indol-2-yl)propan-1-ol

To a solution of 2-(5-nitro-1H-indol-2-yl)propan-1-ol (0.13 g, 0.60 mmol) in ethanol (5 mL) was added tin chloride dihydrate (0.67 g, 3.0 mmol). The mixture was heated in the microwave at 120° C. for 1 h. The mixture was diluted with ethyl acetate before water and saturated aqueous NaHCO$_3$ were added. The reaction mixture was filtered through a plug of celite using ethyl acetate. The organic layer was separated from the aqueous layer, dried over Na$_2$SO$_4$, filtered and evaporated under reduced pressure to give 2-(5-amino-1H-indol-2-yl)propan-1-ol (0.093 g, 82%).

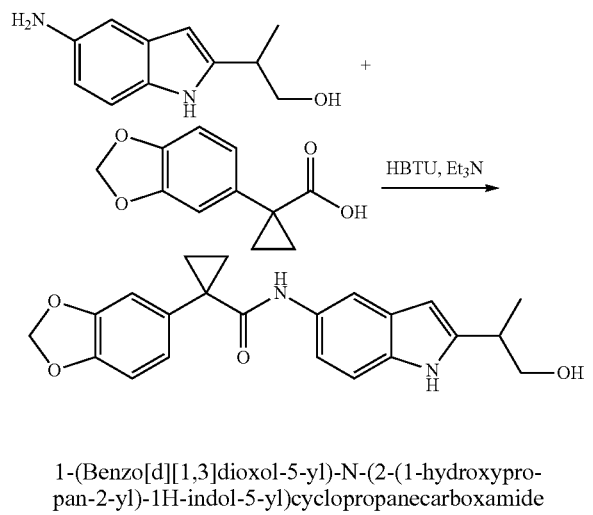

1-(Benzo[d][1,3]dioxol-5-yl)-N-(2-(1-hydroxypropan-2-yl)-1H-indol-5-yl)cyclopropanecarboxamide To a solution of 1-(benzo[d][1,3]dioxol-5-yl)cyclopropanecarboxylic acid (0.10 g, 0.49 mmol) in acetonitrile (2.0 mL) were added HBTU (0.185 g, 0.49 mmol) and Et$_3$N (205 µL, 1.47 mmol) at room temperature. The mixture was allowed to stir at room temperature for 10 minutes before a slurry of 2-(5-amino-1H-indol-2-yl)propan-1-ol (0.093 g, 0.49 mmol) in acetonitrile (2.7 mL) was added. After addition, the reaction mixture was stirred at room temperature for 5.5 h. The solvent was evaporated under reduced pressure and the residue was dissolved in dichloromethane. The organic layer was washed with 1 N HCl (1×3 mL) and saturated aqueous NaHCO$_3$ (1×3 mL). The organic layer was dried over Na$_2$SO$_4$, filtered and evaporated under reduced pressure. The crude material was purified by column chromatography on silica gel (ethyl acetate/hexane=13/7) to give 1-(benzo[d][1,3]dioxol-5-yl)-N-(2-(1-hydroxypropan-2-yl)-1H-indol-5-yl)cyclopropanecarboxamide (0.095 g, 51%). $^1$H NMR (400 MHz, DMSO-d6) δ 10.74 (s, 1H), 8.38 (s, 1H), 7.55 (s, 1H), 7.14 (d, J=8.6 Hz, 1H), 7.02-6.90 (m, 4H), 6.06 (s, 1H), 6.02 (s, 2H), 4.76 (t, J=5.3 Hz, 1H), 3.68-3.63 (m, 1H), 3.50-3.44 (m, 1H), 2.99-2.90 (m, 1H), 1.41-1.38 (m, 2H), 1.26 (d, J=7.0 Hz, 3H), 1.05-1.02 (m, 2H).

Example 77

1-(Benzo[d][1,3]dioxol-5-yl)-N-(2-tert-butyl-1H-indol-5-yl)-N-methylcyclopropanecarboxamide

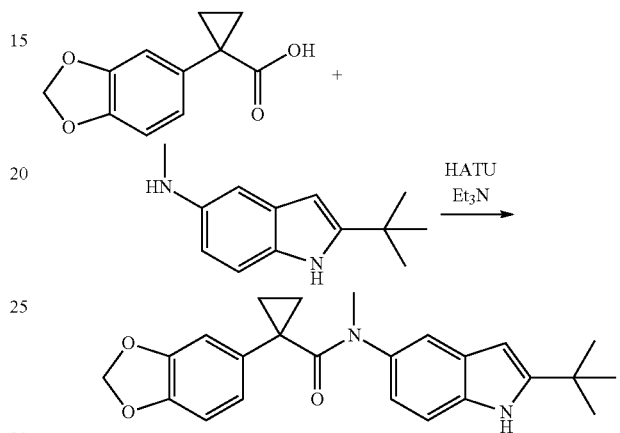

1-(Benzo[d][1,3]dioxol-5-yl)-N-(2-tert-butyl-1H-indol-5-yl)-N-methylcyclopropanecarboxamide 2-tert-Butyl-N-methyl-1H-indol-5-amine (20.2 mg, 0.100 mmol) and 1-(benzo[d][1,3]dioxol-5-yl)cyclopropanecarboxylic acid (20.6 mg, 0.100 mmol) were dissolved in N,N-dimethylformamide (1 mL) containing triethylamine (42.1 µL, 0.300 mmol) and a magnetic stir bar. O-(7-Azabenzotriazol-1-yl)-N,N,N',N'-tetramethyluronium hexafluorophosphate (42 mg, 0.11 mmol) was added to the mixture and the resulting solution was allowed to stir for 16 h at 80° C. The crude product was then purified by preparative HPLC utilizing a gradient of 0-99% acetonitrile in water containing 0.05% trifluoroacetic acid to yield 1-(benzo[d][1,3]dioxol-5-yl)-N-(2-tert-butyl-1H-indol-5-yl)-N-methylcyclopropanecarboxamide. ESI-MS m/z calc. 390.2. found 391.3 (M+1)$^+$. Retention time of 3.41 minutes.

Example 78

N-(2-tert-Butyl-1-methyl-1H-indol-5-yl)-1-(benzo[d][1,3]dioxol-6-yl)-N-methylcyclopropanecarboxamide

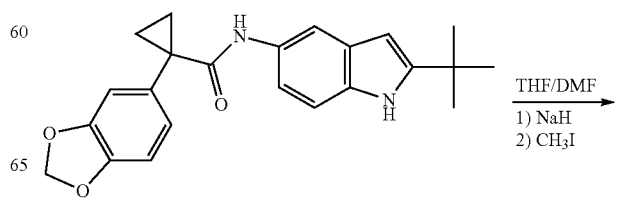

377
-continued

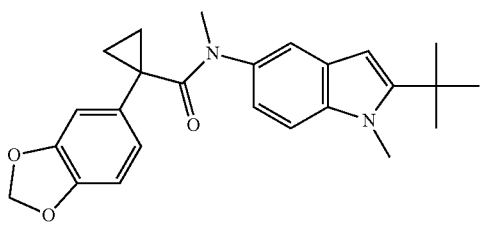

Sodium hydride (0.028 g, 0.70 mmol, 60% by weight dispersion in oil) was slowly added to a stirred solution of N-(2-tert-butyl-1H-indol-5-yl)-1-(benzo[d][1,3]dioxol-6-yl)cyclopropanecarboxamide (0.250 g, 0.664 mmol) in a mixture of 4.5 mL of anhydrous tetrahydrofuran (THF) and 0.5 mL of anhydrous N,N-dimethylformamide (DMF). The resulting suspension was allowed to stir for 2 minutes and then iodomethane (0.062 mL, 1.0 mmol) was added to the reaction mixture. Two additional aliquots of sodium hydride and iodomethane were required to consume all of the starting material which was monitored by LC/MS. The crude reaction product was evaporated to dryness, redissolved in a minimum of DMF and purified by preparative LC/MS chromatography to yield the pure product (0.0343 g, 13%) ESI-MS m/z calc. 404.2. found 405.3 (M+1)$^+$. Retention time of 3.65 minutes.

Example 79

1-(Benzo[d][1,3]dioxol-5-yl)-N-(2-(hydroxymethyl)-1H-indol-5-yl)cyclopropanecarboxamide

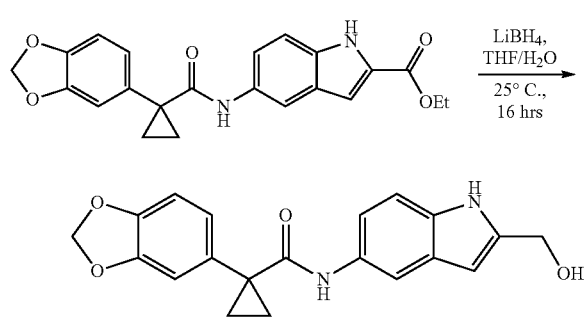 [SMILES: CCOC(=O)c1cc2cc(NC(=O)C3(c4ccc5c(c4)OCO5)CC3)ccc2[nH]1 ; O=C(Nc1ccc2[nH]c(CO)cc2c1)C1(c2ccc3c(c2)OCO3)CC1]

Ethyl 5-(1-(benzo[d][1,3]dioxol-5-yl)cyclopropanecarboxamido)-1H-indole-2-carboxylate (1.18 g, 3.0 mmol) was added to a solution of LiBH$_4$ (132 mg, 6.0 mmol) in THF (10 mL) and water (0.1 mL). The mixture was allowed to stir for 16 h at 25° C. before it was quenched with water (10 mL) and slowly made acidic by addition of 1 N HCl. The mixture was extracted with three 50-mL portions of ethyl acetate. The organic extracts were dried over Na$_2$SO$_4$ and evaporated to yield 1-(benzo[d][1,3]dioxol-5-yl)-N-(2-(hydroxymethyl)-1H-indol-5-yl)cyclopropanecarboxamide (770 mg, 73%). A small amount was further purified by reverse phase HPLC. ESI-MS m/z calc. 350.4. found 351.3 (M+1)$^+$; retention time 2.59 minutes.

378

Example 80

5-(1-(Benzo[d][1,3]dioxol-5-yl)cyclopropanecarboxamido)-N-tert-butyl-1H-indole-2-carboxamide

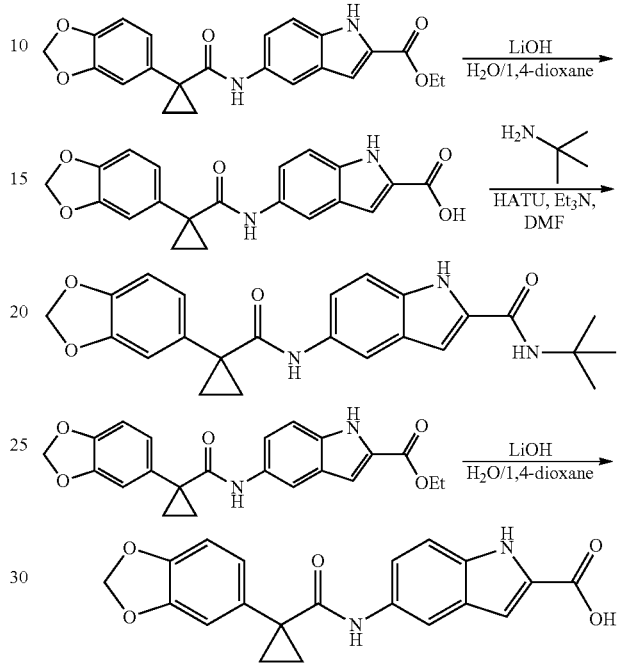

5-(1-(Benzo[d][1,3]dioxol-5-yl)cyclopropanecarboxamido)-1H-indole-2-carboxylic acid Ethyl 5-(1-(benzo[d][1,3]dioxol-5-yl)cyclopropanecarboxamido)-1H-indole-2-carboxylate (392 mg, 1.0 mmol) and LiOH (126 mg, 3 mmol) were dissolved in H$_2$O (5 mL) and 1,4-dioxane (3 mL). The mixture was heated in an oil bath at 100° C. for 24 hours before it was cooled to room temperature. The mixture was acidified with 1N HCl and it was extracted with three 20 mL portions of dichloromethane. The organic extracts were dried over Na$_2$SO$_4$ and evaporated to yield 5-(1-(benzo[d][1,3]-dioxol-5-yl)cyclopropanecarboxamido)-1H-indole-2-carboxylic acid (302 mg, 83%). A small amount was further purified by reverse phase HPLC. ESI-MS m/z calc. 364.1. found 365.1 (M+1)$^+$; retention time 2.70 minutes.

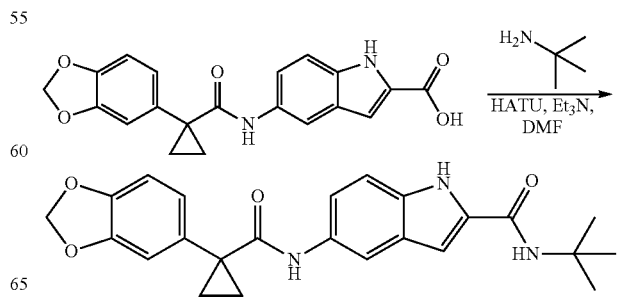

5-(1-(benzo[d][1,3]dioxol-5-yl)cyclopropanecarboxamido)-N-tert-butyl-1H-indole-2-carboxamide 5-(1-(Benzo[d][1,3]dioxol-5-yl)cyclopropane-carboxamido)-1H-indole-2-carboxylic acid (36 mg, 0.10 mmol) and 2-methylpropan-2-amine (8.8 mg, 0.12 mmol) were dissolved in N,N-dimethylformamide (1.0 mL) containing triethylamine (28 µL, 0.20 mmol). O-(7-Azabenzotriazol-1-yl)-N,N,N',N'-tetramethyluronium hexafluorophosphate (46 mg, 0.12 mmol) was added to the mixture and the resulting solution was allowed to stir for 3 hours. The mixture was filtered and purified by reverse phase HPLC to yield 5-(1-(benzo[d][1,3]dioxol-5-yl)cyclopropanecarboxamido)-N-tert-butyl-1H-indole-2-carboxamide. ESI-MS m/z calc. 419.2. found 420.3 (M+1)⁺; retention time 3.12 minutes.

Example 81

N-(3-Amino-2-tert-butyl-1H-indol-5-yl)-1-(benzo[d][1,3]dioxol-5-yl)cyclopropanecarboxamide

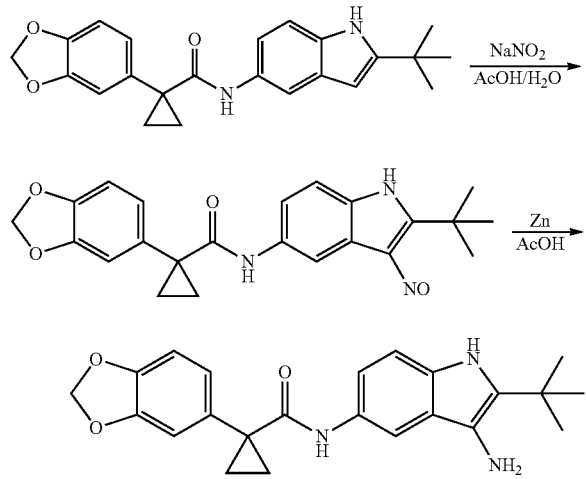

A solution of 1-(benzo[d][1,3]dioxol-5-yl)-N-(2-tert-butyl-1H-indol-5-yl)cyclopropane carboxamide (50 mg, 0.13 mmol) was dissolved in AcOH (2 mL) and warmed to 45° C. To the mixture was added a solution of NaNO₂ (9 mg) in H₂O (0.03 mL). The mixture was allowed to stir for 30 min at 45° C. before the precipitate was collected and washed with Et₂O. This material was used in the next step without further purification. To the crude material, 1-(benzo[d][1,3]dioxol-5-yl)-N-(2-tert-butyl-3-nitroso-1H-indol-5-yl)cyclopropanecarboxamide, was added AcOH (2 mL) and Zn dust (5 mg). The mixture was allowed to stir for 1 h at ambient temperature. EtOAc and H₂O were added to the mixture. The layers were separated and the organic layer was washed with sat. aq. NaHCO₃, dried over MgSO₄, and concentrated in vacuo. The residue was taken up in DMF (1 mL) and was purified using prep-HPLC. LCMS: m/z 392.3; retention time of 2.18 min.

Example 82

1-(Benzo[d][1,3]dioxol-5-yl)-N-(2-tert-butyl-3-(methylsulfonyl)-1H-indol-5-yl)cyclopropanecarboxamide

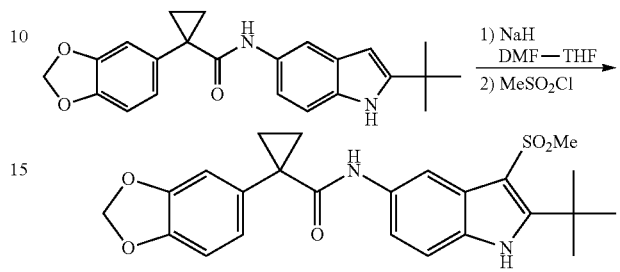

1-(Benzo[d][1,3]dioxol-5-yl)-N-(2-tert-butyl-3-(methylsulfonyl)-1H-indol-5-yl)cyclopropanecarboxamide To a solution of 1-(benzo[d][1,3]dioxol-5-yl)-N-(2-tert-butyl-1H-indol-5-yl)cyclopropanecarboxamide (120 mg, 0.31 mmol) in anhydrous DMF-THF (3.3 mL, 1:9) was added NaH (60% in mineral oil, 49 mg, 1.2 mmol) at room temperature. After 30 min under N₂, the suspension was cooled down to −15° C. and a solution of methanesulfonyl chloride (1.1 eq.) in DMF (0.5 mL) was added dropwise. The reaction mixture was stirred for 30 min at −15° C. then for 6 h at room temperature. Water (0.5 mL) was added at 0° C., solvent was removed, and the residue was diluted with MeOH, filtrated and purified by preparative HPLC to give 1-(Benzo[d][1,3]dioxol-5-yl)-N-(2-tert-butyl-3-(methylsulfonyl)-1H-indol-5-yl)cyclopropanecarboxamide. ¹H NMR (400 MHz, DMSO) δ 11.6 (s, 1H), 8.7 (s, 1H), 7.94 (d, J=1.7 Hz, 1H), 7.38 (d, J1=8.7 Hz, 1H), 7.33 (dd, J1=1.9 Hz, J2=8.7 Hz, 1H), 7.03 (d, J1=1.7 Hz, 1H), 6.95 (dd, J1=1.7 Hz, J2=8.0 Hz, 1H), 6.90 (d, J=8.0 Hz, 1H), 6.02 (s, 2H), 3.07 (s, 3H), 1.56-1.40 (m, 9H), 1.41 (dd, J1=4.0 Hz, J2=6.7 Hz, 2H), 1.03 (dd, J1=4.0 Hz, J2=6.7 Hz, 2H). MS (ESI) m/e (M+H⁺) 455.5.

Example 83

1-(Benzo[d][1,3]dioxol-5-yl)-N-(3-phenyl-1H-indol-5-yl)cyclopropane carboxamide

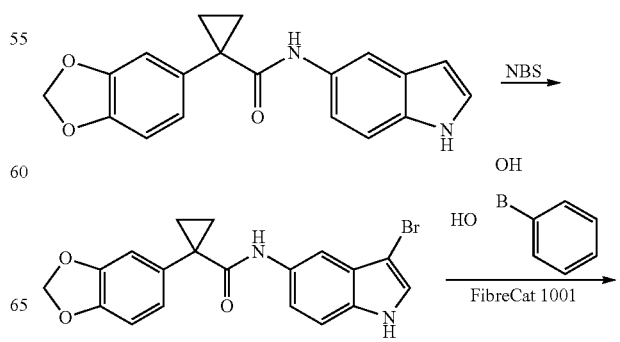

-continued

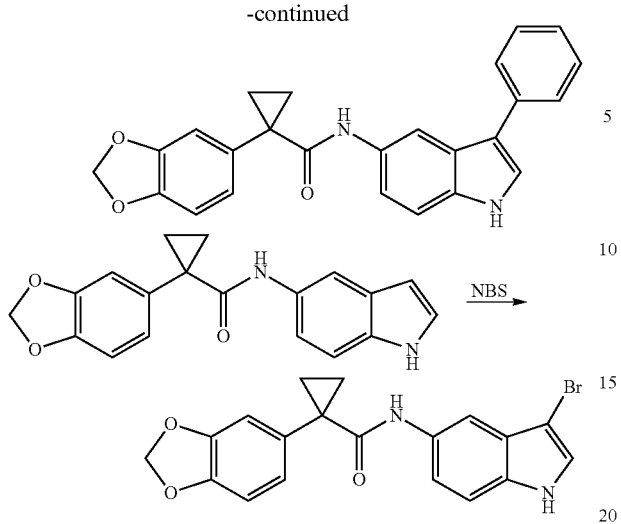

1-(Benzo[d][1,3]dioxol-5-yl)-N-(3-bromo-1H-indol-5-yl)cyclopropanecarboxamide

Freshly recrystallized N-bromosuccinimde (0.278 g, 1.56 mmol) was added portionwise to a solution of 1-(benzo[d][1,3]dioxol-5-yl)-N-(1H-indol-5-yl)cyclopropanecarboxamide (0.500 g, 1.56 mmol) in N,N-dimethylformamide (2 mL) over 2 minutes. The reaction mixture was protected from light and was stirred bar for 5 minutes. The resulting green solution was poured into 40 mL of water. The grey precipitate which formed was filtered and washed with water to yield 1-(benzo[d][1,3]dioxol-5-yl)-N-(3-bromo-1H-indol-5-yl)cyclopropanecarboxamide (0.564 g, 91%). ESI-MS m/z calc. 398.0. found 399.3 (M+1)+. Retention time of 3.38 minutes. $^1$H NMR (400 MHz, DMSO-d6) 11.37 (s, 1H), 8.71 (s, 1H), 7.67 (d, J=1.8 Hz, 1H), 7.50 (d, J=2.6 Hz, 1H), 7.29 (d, J=8.8 Hz, 1H), 7.22 (dd, J=2.0, 8.8 Hz, 1H), 7.02 (d, J=1.6 Hz, 1H), 6.96-6.88 (m, 2H), 6.03 (s, 2H), 1.43-1.40 (m, 2H), 1.09-1.04 (m, 2H).

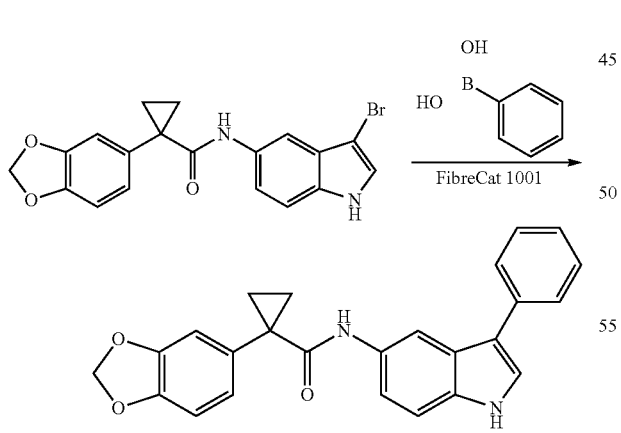

1-(Benzo[d][1,3]dioxol-5-yl)-N-(3-phenyl-1H-indol-5-yl)cyclopropanecarboxamide

Phenyl boronic acid (24.6 mg, 0.204 mmol) was added to a solution of 1-(benzo[d][1,3]-dioxol-5-yl)-N-(3-bromo-1H-indol-5-yl)cyclopropanecarboxamide (39.9 mg, 0.100 mmol) in ethanol (1 mL) containing FibreCat 1001 (6 mg) and 1M aqueous potassium carbonate (0.260 mL). The reaction mixture was then heated at 130° C. in a microwave reactor for 20 minutes. The crude product was then purified by preparative HPLC utilizing a gradient of 0-99% acetonitrile in water containing 0.05% trifluoroacetic acid to yield 1-(benzo[d][1,3]dioxol-5-yl)-N-(3-phenyl-1H-indol-5-yl)cyclopropane carboxamide. ESI-MS m/z calc. 396.2. found 397.3 (M+1)+. Retention time of 3.52 minutes. $^1$H NMR (400 MHz, DMSO-d6) δ 11.27 (d, J=1.9 Hz, 1H), 8.66 (s, 1H), 8.08 (d, J=1.6 Hz, 1H), 7.65-7.61 (m, 3H), 7.46-7.40 (m, 2H), 7.31 (d, J=8.7 Hz, 1H), 7.25-7.17 (m, 2H), 7.03 (d, J=1.6 Hz, 1H), 6.98-6.87 (m, 2H), 6.02 (s, 2H), 1.43-1.39 (m, 2H), 1.06-1.02 (m, 2H).

Example 84

1-(Benzo[d][1,3]dioxol-5-yl)-N-(2-tert-butyl-3-cyano-1H-indol-5-yl)cyclopropanecarboxamide

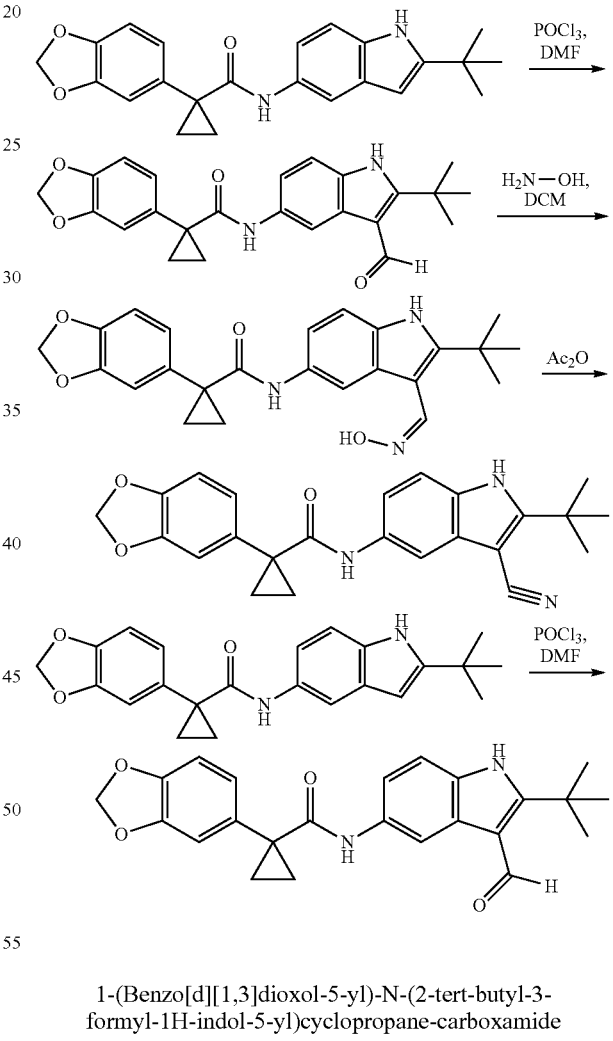

1-(Benzo[d][1,3]dioxol-5-yl)-N-(2-tert-butyl-3-formyl-1H-indol-5-yl)cyclopropane-carboxamide POCl$_3$ (12 g, 80 mmol) was added dropwise to DMF (40 mL) held at −20° C. After the addition was complete, the reaction mixture was allowed to MUM to 0° C. and was stirred for 1 h. 1-(Benzo[d][1,3]dioxol-5-yl)-N-(2-tert-butyl-1H-indol-5-yl)cyclopropanecarboxamide (3.0 g, 8.0 mmol) was added and the mixture was warmed to 25° C. After stirring for 30 minutes the reaction mixture was poured over ice and stirred for 2 h. The mixture was then heated at 100° C.

for 30 min. The mixture was cooled and the solid precipitate was collected and washed with water. The solid was then dissolved in 200 mL dichloromethane and washed with 200 mL of a saturated aq. NaHCO$_3$. The organics were dried over Na$_2$SO$_4$ and evaporated to yield 1-(benzo[d][1,3]dioxol-5-yl)-N-(2-tert-butyl-3-formyl-1H-indol-5-yl)cyclopropanecarboxamide (2.0 g, 61%). ESI-MS m/z calc. 404.5. found 405.5 (M+1)$^+$; retention time 3.30 minutes. $^1$H NMR (400 MHz, DMSO-d6) δ 11.48 (s, 1H), 10.39 (s, 1H), 8.72 (s, 1H), 8.21 (s, 1H), 7.35-7.31 (m, 2H), 7.04-7.03 (m, 1H), 6.97-6.90 (m, 2H), 6.03 (s, 2H), 1.53 (s, 9H), 1.42-1.39 (m, 2H), 1.05-1.03 (m, 2H).

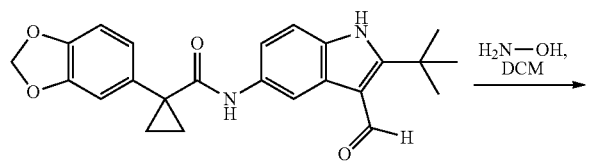

(Z)-1-(Benzo[d][1,3]dioxol-5-yl)-N-(2-tert-butyl-3-((hydroxyimino)methyl)-1H-indol-5-yl)cyclopropanecarboxamide To a solution of 1-(benzo[d][1,3]dioxol-5-yl)-N-(2-tert-butyl-3-formyl-1H-indol-5-yl)cyclopropanecarboxamide (100 mg, 0.25 mmol) in dichloromethane (5 mL) was added hydroxylamine hydrochloride (21 mg, 0.30 mmol). After stirring for 48 h, the mixture was evaporated to dryness and purified by column chromatography (0-100% ethyl acetate/hexanes) to yield (Z)-1-(benzo[d][1,3]dioxol-5-yl)-N-(2-tert-butyl-3-((hydroxyimino)methyl)-1H-indol-5-yl)cyclopropanecarboxamide (81 mg, 77%). ESI-MS m/z calc. 419.5. found 420.5 (M+1)$^+$; retention time 3.42 minutes. $^1$H NMR (400 MHz, DMSO-d6) δ 10.86 (s, 0.5H), 10.55 (s, 0.5H), 8.56-8.50 (m, 2H), 8.02 (m, 1H), 7.24-7.22 (m, 1H), 7.12-7.10 (m, 1H), 7.03 (m, 1H), 6.96-6.90 (m, 2H), 6.03 (s, 2H), 1.43 (s, 9H), 1.40-1.38 (m, 2H), 1.04-1.01 (m, 2H).

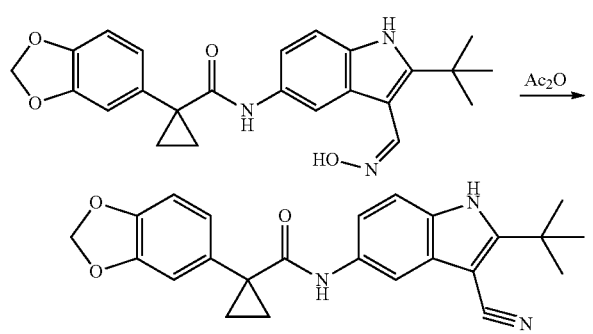

1-(Benzo[d][1,3]dioxol-5-yl)-N-(2-tert-butyl-3-cyano-1H-indol-5-yl)cyclopropane-carboxamide (Z)-1-(Benzo[d][1,3]dioxol-5-yl)-N-(2-tert-butyl-3-((hydroxyimino)-methyl)-1H-indol-5-yl)cyclopropanecarboxamide (39 mg, 0.090 mmol) was dissolved in acetic anhydride (1 mL) and heated at reflux for 3 h. The mixture was cooled in an ice bath and the precipitate was collected and washed with water. The solid was further dried under high vacuum to yield 1-(benzo[d][1,3]dioxol-5-yl)-N-(2-tert-butyl-3-cyano-1H-indol-5-yl)cyclopropanecarboxamide. ESI-MS m/z calc. 401.5. found 402.5 (M+1)$^+$; retention time 3.70 minutes. $^1$H NMR (400 MHz, DMSO-d6) δ 11.72 (s, 1H), 8.79 (s, 1H), 7.79 (s, 1H), 7.32 (m, 2H), 7.03-7.02 (m, 1H), 6.95-6.89 (m, 2H), 6.03 (s, 2H), 1.47 (s, 9H), 1.43-1.41 (m, 2H), 1.06-1.04 (m, 2H).

Example 85

1-(Benzo[d][1,3]dioxol-5-yl)-N-(2-tert-butyl-3-methyl-1H-indol-5-yl)cyclopropanecarboxamide

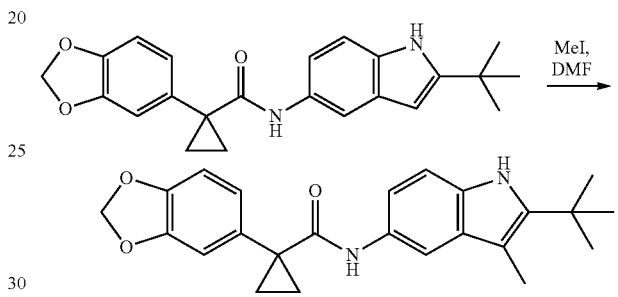

A solution of 1-(benzo[d][1,3]dioxol-5-yl)-N-(2-tert-butyl-1H-indol-5-yl)cyclopropanecarboxamide (75 mg, 0.20 mmol) and iodomethane (125 μL, 2.0 mmol) in N,N-dimethylformamide (1 mL) was heated at 120° C. in a sealed tube for 24 h. The reaction was filtered and purified by reverse phase HPLC. ESI-MS m/z calc. 390.5. found 391.3 (M+1)$^+$; retention time 2.04 minutes. $^1$H NMR (400 MHz, DMSO-d6) δ 10.30 (s, 1H), 8.39 (s, 1H), 7.51 (m, 1H), 7.13-7.11 (m, 1H), 7.03-6.90 (m, 4H), 6.03 (s, 2H), 2.25 (s, 3H), 1.40-1.38 (m, 11H), 1.03-1.01 (m, 2H).

Example 86

1-(Benzo[d][1,3]dioxol-5-yl)-N-(2-tert-butyl-3-(2-hydroxyethyl)-1H-indol-5-yl)cyclopropanecarboxamide

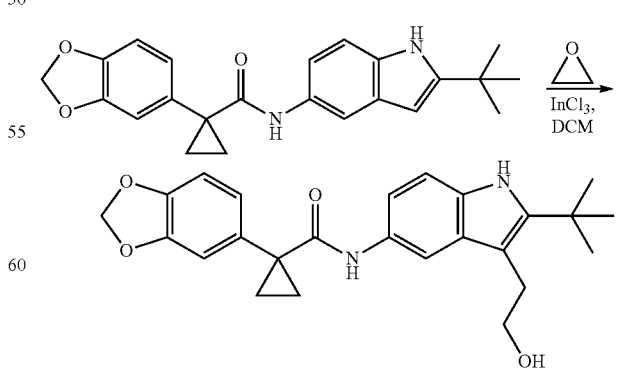

Approximately 100 μL of ethylene dioxide was condensed in a reaction tube at −78° C. A solution of 1-(benzo[d][1,3]

dioxol-5-yl)-N-(2-tert-butyl-1H-indol-5-yl)cyclopropan-ecarboxamide (200 mg, 0.50 mmol) and indium trichloride (20 mg, 0.10 mmol) in dichloromethane (2 mL) was added and the reaction mixture was irradiated in the microwave for 20 min at 100° C. The volatiles were removed and the residue was purified by column chromatography (0-100% ethyl acetate/hexanes) to give 1-(benzo[d][1,3]dioxol-5-yl)-N-(2-tert-butyl-3-(2-hydroxyethyl)-1H-indol-5-yl)cyclopropan-ecarboxamide (5 mg, 3%). ESI-MS m/z calc. 420.5. found 421.3 (M+1)$^+$; retention time 1.67 minutes. $^1$H NMR (400 MHz, CD$_3$CN) δ 8.78 (s, 1H), 7.40 (m, 1H), 7.33 (s, 1H), 7.08 (m, 1H), 6.95-6.87 (m, 3H), 6.79 (m, 1H), 5.91 (s, 2H), 3.51 (dd, J=5.9, 7.8 Hz, 2H), 2.92-2.88 (m, 2H), 2.64 (t, J=5.8 Hz, 1H), 1.50 (m, 2H), 1.41 (s, 9H), 1.06 (m, 2H).

Example 87

2-(5-(1-(Benzo[d][1,3]-dioxol-5-yl)cyclopropanecar-boxamido)-1H-indol-2-yl)acetic acid

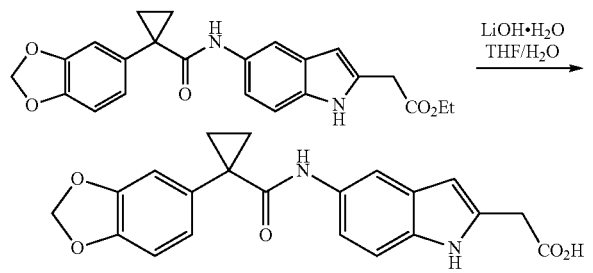

To a solution of ethyl 2-(5-(1-(benzo[d][1,3]dioxol-5-yl)cyclopropanecarboxamido)-1H-indol-2-yl)acetate (0.010 g, 0.025 mmol) in THF (0.3 mL) were added LiOH.H$_2$O (0.002 g, 0.05 mmol) and water (0.15 mL) were added. The mixture was stirred at room temperature for 2 h. dichloromethane (3 mL) was added to the reaction mixture and the organic layer was washed with 1 N HCl (2×1.5 mL) and water (2×1.5 mL). The organic layer was dried over Na$_2$SO$_4$ and filtered. The filtrate was evaporated under reduced pressure to give 2-(5-(1-(benzo[d][1,3]dioxol-5-yl)cyclopropanecarboxamido)-1H-indol-2-yl)-acetic acid. $^1$H NMR (400 MHz, DMSO-d6) δ 12.53 (s, 1H), 10.90 (s, 1H), 8.42 (s, 1H), 7.57 (s, 1H), 7.17 (d, J=8.6 Hz, 1H), 7.05-6.90 (m, 4H), 6.17 (s, 1H), 6.02 (s, 2H), 3.69 (s, 2H), 1.41-1.39 (m, 2H), 1.04-1.02 (m, 2H).

Example 88

5-(1-(Benzo[d][1,3]dioxol-5-yl)cyclopropanecar-boxamido)-2-tert-butyl-1H-indole-7-carboxylic acid

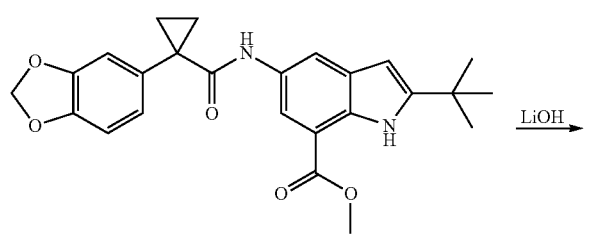

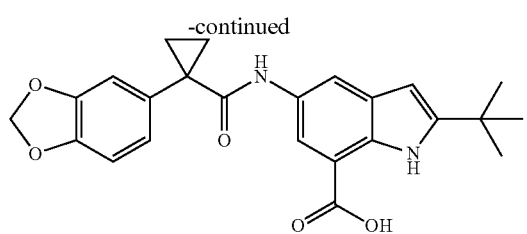

Methyl 5-(1-(benzo[d][1,3]dioxol-5-yl)cyclopropanecar-boxamido)-2-tert-butyl-1H-indole-7-carboxylate (30 mg, 0.069 mmol) was dissolved in a mixture of 1,4-dioxane (1.5 mL) and water (2 mL) containing a magnetic star bar and lithium hydroxide (30 mg, 0.71 mmol). The resulting solution was stirred at 70° C. for 45 minutes. The crude product was then acidified with 2.6 M hydrochloric acid and extracted three times with an equivalent volume of dichloromethane. The dichloromethane extracts were combined, dried over sodium sulfate, filtered, and evaporated to dryness. The residue was dissolved in a minimum of N,N-dimethylformamide and then purified by preparative HPLC using a gradient of 0-99%-acetonitrile in water containing 0.05% trifluoroacetic acid to yield 5-(1-(benzo[d][1,3]dioxol-5-yl)cyclopropan-ecarboxamido)-2-tert-butyl-1H-indole-7-carboxylic acid. ESI-MS m/z calc. 434.2. found 435.5. Retention time of 1.85 minutes. $^1$H NMR (400 MHz, DMSO-d6) δ 13.05 (s, 1H), 9.96 (d, J=1.6 Hz, 1H), 7.89 (d, J=1.9 Hz, 1H), 7.74 (d, J=2.0 Hz, 1H), 7.02 (d, J=1.6 Hz, 1H), 6.96-6.88 (m, 2H), 6.22 (d, J=2.3 Hz, 1H), 6.02 (s, 2H), 1.43-1.40 (m, 2H), 1.37 (s, 9H), 1.06-1.02 (m, 2H).

Example 89

1-(Benzo[d][1,3]dioxol-5-yl)-N-(2-tert-butyl-1-(1,3-dihydroxypropan-2-yl)-1H-indol-5-yl)cyclopropan-ecarboxamide

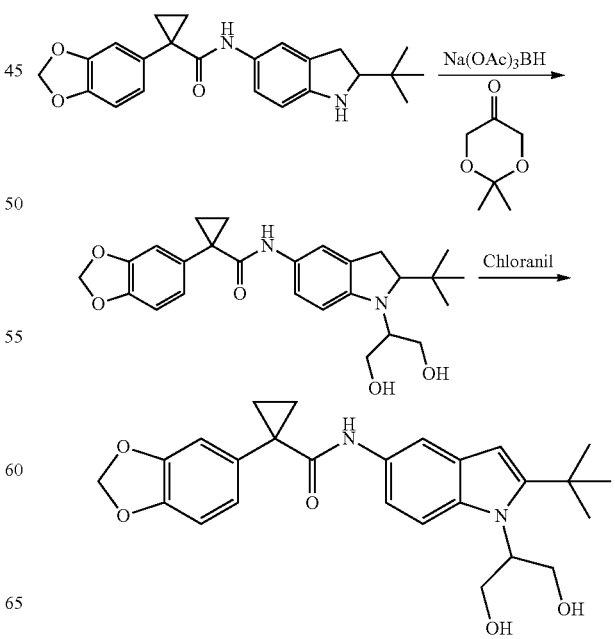

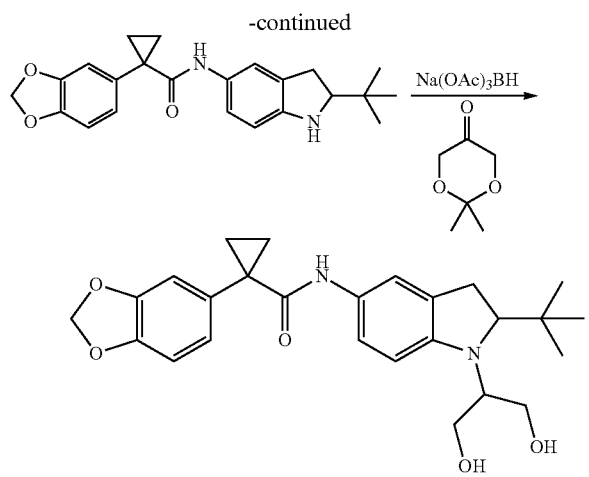

1-(Benzo[d][1,3]dioxol-5-yl)-N-(2-tert-butyl-1-(1,3-dihydroxypropan-2-yl)indolin-5-yl)cyclopropanecarboxamide 1-(Benzo[d][1,3]dioxol-5-yl)-N-(2-tert-butylindolin-5-yl)cyclopropanecarboxamide (50 mg, 0.13 mmol) was dissolved in dichloroethane (0.20 mL) and 2,2-dimethyl-1,3-dioxan-5-one (0.20 mL). Trifluoroacetic acid was added (0.039 mL) and the resulting solution was allowed to stir for 20 minutes. Sodium triacetoxyborohydride was added (55 mg, 0.26 mmol) and the reaction mixture was stirred for 30 minutes. The crude reaction mixture was then evaporated to dryness, dissolved in N,N-dimethylformamide and purified by preparative HPLC using a gradient of 0-99% acetonitrile in water containing 0.05% trifluoroacetic acid.

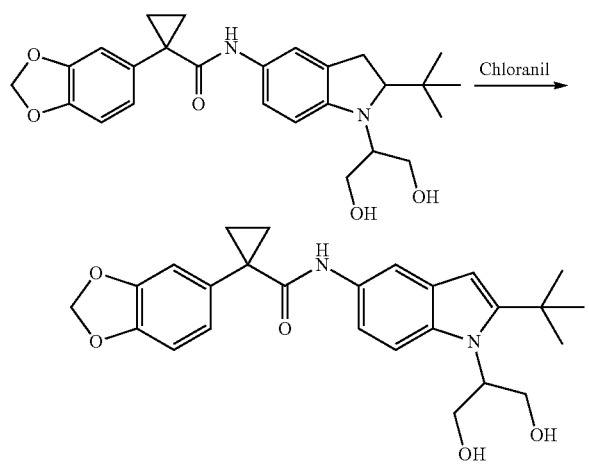

1-(Benzo[d][1,3]dioxol-5-yl)-N-(2-tert-butyl-1-(1,3-dihydroxypropan-2-yl)-1H-indol-5-yl)cyclopropanecarboxamide 1-(Benzo[d][1,3]dioxol-5-yl)-N-(2-tert-butyl-1-(1,3-dihydroxypropan-2-yl)indolin-5-yl)cyclopropanecarboxamide (40.3 mg, 0.0711 mmol as the trifluoracetic acid salt) was dissolved in toluene (1 mL). To the resulting solution was added 2,3,5,6-tetrachlorocyclohexa-2,5-diene-1,4-dione (35 mg, 0.14 mmol). The resulting suspension was heated at 100° C. in an oil bath for 10 minutes. The crude product was then evaporated to dryness, dissolved in a 1 mL of N,N-dimethylformamide and purified by purified by preparative HPLC using a gradient of 0-99% acetonitrile in water containing 0.05% trifluoroacetic acid to yield 1-(benzo[d][1,3]dioxol-5-yl)-N-(2-tert-butyl-1-(1,3-dihydroxypropan-2-yl)-1H-indol-5-yl)cyclopropanecarboxamide. ESI-MS m/z calc. 450.2. found 451.5 (M+1)⁺. Retention time of 1.59 minutes.

Example 90

N-(7-(Aminomethyl)-2-tert-butyl-1H-indol-5-yl)-1-(benzo[d][1,3]-dioxol-5-yl)cyclopropanecarboxamide

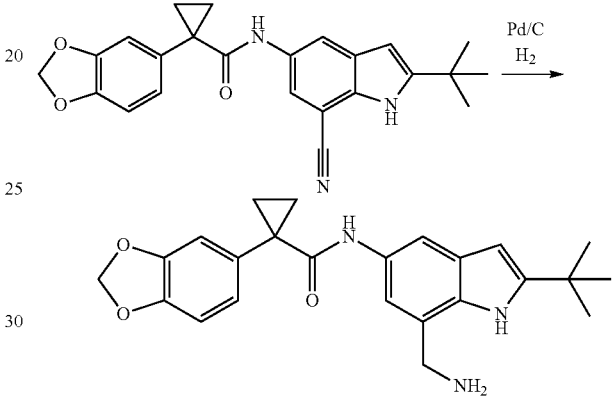

N-(7-(Aminomethyl)-2-tert-butyl-1H-indol-5-yl)-1-(benzo[d][1,3]dioxol-5-yl)cyclopropanecarboxamide 1-(Benzo[d][1,3]dioxol-5-yl)-N-(2-tert-butyl-7-cyano-1H-indol-5-yl)cyclopropanecarboxamide (375 mg, 0.934 mmol) was dissolved in 35 mL of ethyl acetate. The solution was recirculated through a continuous flow hydrogenation reactor containing 10% palladium on carbon at 100° C. under 100 bar of hydrogen for 8 h. The crude product was then evaporated to dryness and purified on 12 g of silica gel utilizing a gradient of 0-100% ethyl acetate (containing 0.5% triethylamine) in hexanes to yield N-(7-(aminomethyl)-2-tert-butyl-1H-indol-5-yl)-1-(benzo[d][1,3]-dioxol-5-yl)-cyclopropanecarboxamide (121 mg, 32%). ESI-MS m/z calc. 405.2. found 406.5 (M+1)⁺. Retention time of 1.48 minutes.

Example 91

5-(1-(Benzo[d][1,3]dioxol-5-yl)cyclopropanecarboxamido)-2-tert-butyl-1H-indole-7-carboxamide

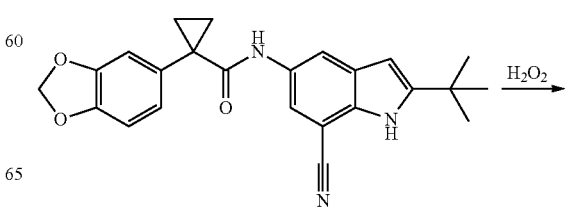

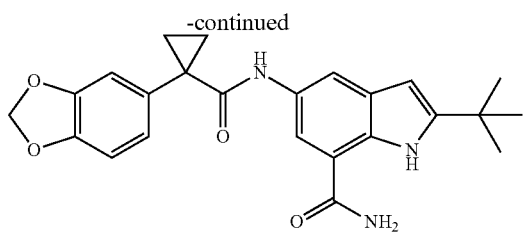

5-(1-(Benzo[d][1,3]dioxol-5-yl)cyclopropanecarboxamido)-2-tert-butyl-1H-indole-7-carboxamide 1-(Benzo[d][1,3]dioxol-5-yl)-N-(2-tert-butyl-7-cyano-1H-indol-5-yl)-cyclopropanecarboxamide (45 mg, 0.11 mmol) was suspended in a mixture of methanol (1.8 mL), 30% aqueous hydrogen peroxide (0.14 mL, 4.4 mmol) and 10% aqueous sodium hydroxide (0.150 mL). The resulting suspension was stirred for 72 h at room temperature. The hydrogen peroxide was then quenched with sodium sulfite. The reaction mixture was diluted with 0.5 mL of N,N-dimethylformamide, filtered, and purified by preparative HPLC using a gradient of 0-99% acetonitrile in water containing 0.05% trifluoroacetic acid to yield 5-(1-(benzo[d][1,3]dioxol-5-yl)cyclopropane-carboxamido)-2-tert-butyl-1H-indole-7-carboxamide. ESI-MS m/z calc. 419.2. found 420.3 (M+1)$^+$. Retention time of 1.74 minutes.

Example 92

1-(Benzo[d][1,3]dioxol-5-yl)-N-(2-tert-butyl-7-(methylsulfonamido-methyl)-1H-indol-5-yl)cyclopropanecarboxamide

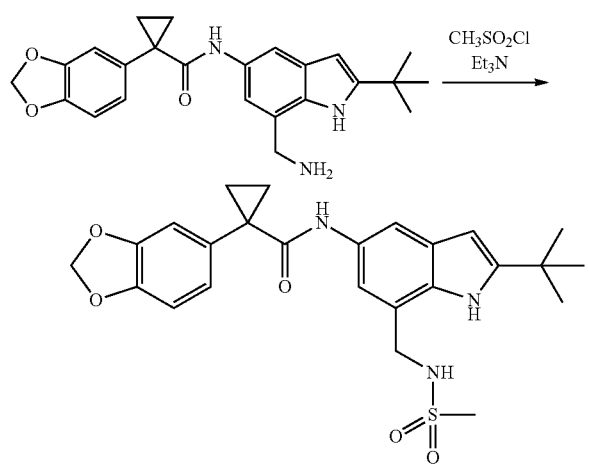

1-(Benzo[d][1,3]dioxol-5-yl)-N-(2-tert-butyl-7-(methylsulfonamidomethyl)-1H-indol-5-yl)cyclopropanecarboxamide N-(7-(Aminomethyl)-2-tert-butyl-1H-indol-5-yl)-1-(benzo[d][1,3]dioxol-5-yl)cyclopropanecarboxamide (20 mg, 0.049 mmol) was dissolved in DMF (0.5 mL) containing triethylamine (20.6 µL, 0.147 mmol) and a magnetic stir bar. Methanesulfonyl chloride (4.2 µL, 0.054 mmol) was then added to the reaction mixture. The reaction mixture was allowed to stir for 12 h at room temperature. The crude product was purified by preparative HPLC using a gradient of 0-99% acetonitrile in water containing 0.05% trifluoroacetic acid to yield 1-(benzo[d][1,3]dioxol-5-yl)-N-(2-tert-butyl-7-(methylsulfonamidomethyl)-1H-indol-5-yl)cyclopropanecarboxamide. ESI-MS m/z calc. 483.2. found 484.3 (M+1)$^+$. Retention time of 1.84 minutes.

Example 93

N-(7-(Acetamidomethyl)-2-tert-butyl-1H-indol-5-yl)-1-(benzo[d][1,3]-dioxol-5-yl)cyclopropanecarboxamide

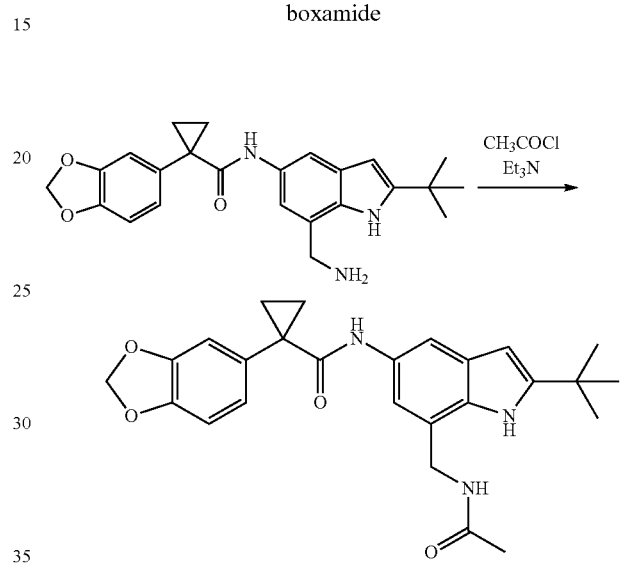

N-(7-(Aminomethyl)-2-tert-butyl-1H-indol-5-yl)-1-(benzo[d][1,3]dioxol-5-yl)cyclopropanecarboxamide (20 mg, 0.049 mmol) was dissolved in DMF (0.5 mL) containing triethylamine (20.6 µL, 0.147 mmol) and a magnetic stir bar. Acetyl chloride (4.2 µL, 0.054 mmol) was then added to the reaction mixture. The reaction mixture was allowed to stir for 16 h at room temperature. The crude product was purified by preparative HPLC using a gradient of 0-99% acetonitrile in water containing 0.05% trifluoroacetic acid to yield N-(7-(acetamidomethyl)-2-tert-butyl-1H-indol-5-yl)-1-(benzo[d][1,3]dioxol-5-yl)cyclopropanecarboxamide. ESI-MS m/z calc. 447.2. found 448.3 (M+1)$^+$. Retention time of 1.76 minutes.

Example 94

N-(1-Acetyl-2-tert-butyl-1H-indol-5-yl)-1-(benzo[d][1,3]dioxol-5-yl)-cyclopropanecarboxamide

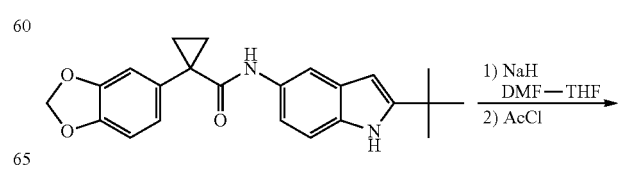

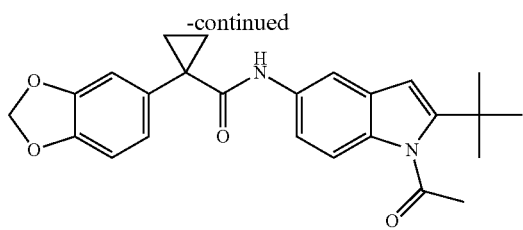

To a solution of 1-(benzo[d][1,3]dioxol-5-yl)-N-(2-tert-butyl-1H-indol-5-yl)cyclopropanecarboxamide (120 mg, 0.31 mmol) in anhydrous DMF-THF (3.3 mL, 1:9) was added NaH (60% in mineral oil, 49 mg, 1.2 mmol) at room temperature. After 30 min under $N_2$, the suspension was cooled down to −15° C. and a solution of acetyl chloride (1.1 eq.) in DMF (0.5 mL) was added dropwise. The reaction mixture was stirred for 30 min at −15° C. then for 6 h at room temperature. Water (0.5 mL) was added at 0° C., solvent was removed, and the residue was diluted with MeOH, filtrated and purified by preparative HPLC to give N-(1-acetyl-2-tert-butyl-1H-indol-5-yl)-1-(benzo[d][1,3]dioxol-5-yl)cyclo-propanecarboxamide. $^1$H NMR (400 MHz, DMSO) δ 8.9 (s, 1H), 7.74 (d, J=2.1 Hz, 1H), 7.54 (d, J=9.0 Hz, 1H), 7.28 (dd, J1=2.1 Hz, J2=9.0 Hz, 1H), 7.01 (d, J=1.5 Hz, 1H), 6.93 (dd, J1=1.7 Hz, J2=8.0 Hz, 1H), 6.89 (d, J=8.0 Hz, 1H), 6.54 (bs, 1H), 6.02 (s, 2H), 2.80 (s, 3H), 1.42-1.40 (m, 11H), 1.06-1.05 (m, 2H). MS (ESI) m/e (M+H$^+$) 419.3.

Example 95

N-(1-(2-Acetamidoethyl)-2-tert-butyl-6-fluoro-1H-indol-5-yl)-1-(2,2-difluorobenzo[d][1,3]dioxol-5-yl)cyclopropanecarboxamide

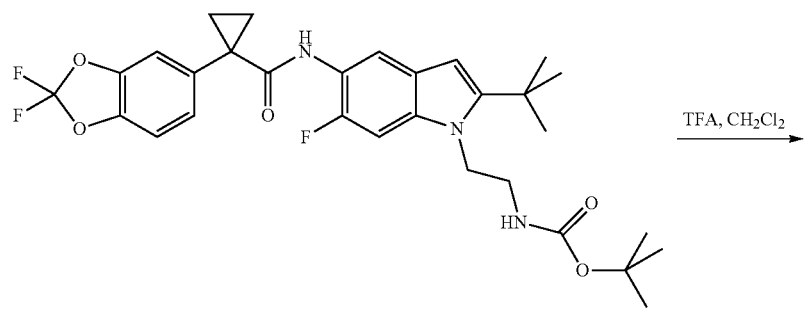

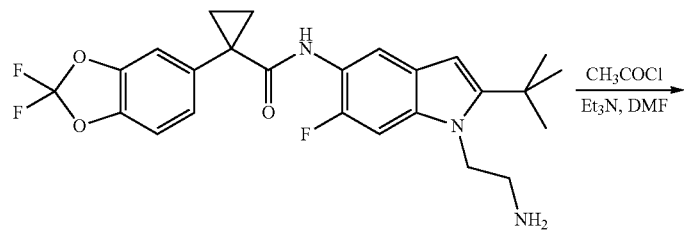

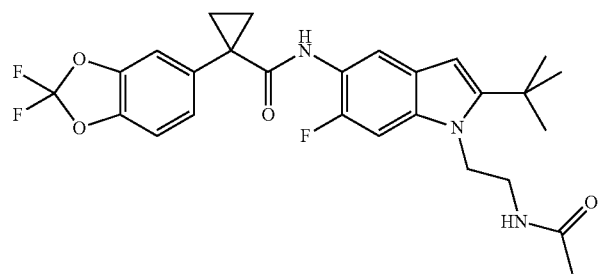

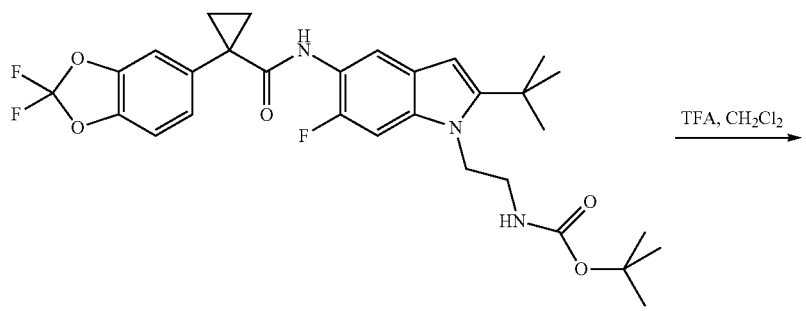

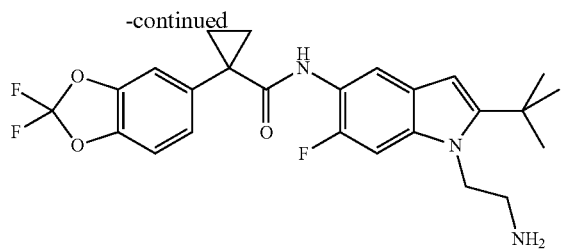

N-(1-(2-Aminoethyl)-2-tert-butyl-6-fluoro-1H-indol-5-yl)-1-(2,2-difluorobenzo-[d][1,3]dioxol-5-yl)cyclopropanecarboxamide To a solution of tert-butyl 2-(2-tert-butyl-5-(1-(2,2-difluorobenzo[d][1,3]dioxol-5-yl)cyclopropanecarboxamido)-6-fluoro-1H-indol-1-yl)ethylcarbamate (620 mg, 1.08 mmol) in CH$_2$Cl$_2$ (8 mL) was added TFA (2 mL). The reaction was stirred at room temperature for 1.5 h before being neutralized with solid NaHCO$_3$. The solution was partitioned between H$_2$O and CH$_2$Cl$_2$. The organic layer was dried over MgSO$_4$, filtered and concentrated to yield the product as a cream colored solid (365 mg, 71%). $^1$H NMR (400 MHz, DMSO-d6) δ 8.38 (s, 1H), 7.87 (br s, 3H, NH$_3^+$), 7.52 (s, 1H), 7.45-7.38 (m, 3H), 7.32 (dd, J=8.3, 1.5 Hz, 1H), 6.21 (s, 1H), 4.46 (m, 2H), 3.02 (m, 2H), 1.46 (m, 2H), 1.41 (s, 9H), 1.14 (m, 2H). HPLC ret. time 1.66 min, 10-99% CH$_3$CN, 3 min run; ESI-MS 474.4 m/z (M+H$^+$).

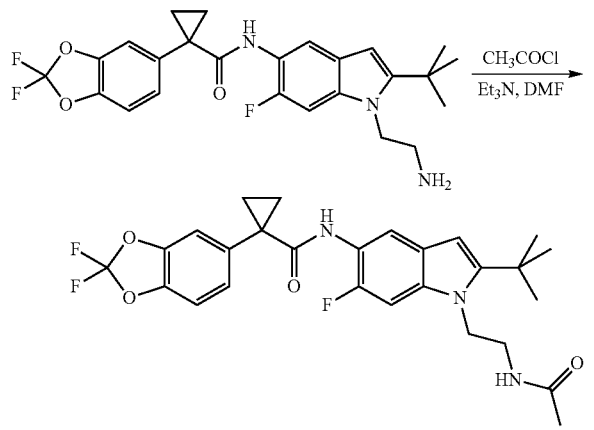

N-(1-(2-Acetamidoethyl)-2-tert-butyl-6-fluoro-1H-indol-5-yl)-1-(2,2-difluorobenzo[d][1,3]dioxol-5-yl)cyclopropanecarboxamide To a solution of N-(1-(2-aminoethyl)-2-tert-butyl-6-fluoro-1H-indol-5-yl)-1-(2,2-difluorobenzo[d][1,3]dioxol-5-yl)cyclopropane-carboxamide (47 mg, 0.10 mmol) and Et$_3$N (28 μL, 0.20 mmol) in DMF (1 mL) was added acetyl chloride (7.1 μL, 0.10 mmol). The mixture was stirred at room temperature for 1 h before being filtered and purified by reverse phase HPLC (10-99% CH$_3$CN/H$_2$O) to yield N-(1-(2-acetamidoethyl)-2-tert-butyl-6-fluoro-1H-indol-5-yl)-1-(2,2-difluorobenzo[d][1,3]dioxol-5-yl)cyclopropanecarboxamide. $^1$H NMR (400 MHz, DMSO-d6) δ 8.35 (s, 1H), 8.15 (t, J=5.9 Hz, 1H), 7.53 (s, 1H), 7.43-7.31 (m, 4H), 6.17 (s, 1H), 4.22 (m, 2H), 3.30 (m, 2H), 1.85 (s, 3H), 1.47 (m, 2H), 1.41 (s, 9H), 1.13 (m, 2H). HPLC ret. time 2.06 min, 10-99% CH$_3$CN, 3 min run; ESI-MS 516.4 m/z (M+H$^+$).

Example 96

1-(Benzo[d][1,3]dioxol-5-yl)-N-(2-tert-butyl-1-(2-hydroxy-3-methoxy-propyl)-1H-indol-5-yl)cyclopropenecarboxamide

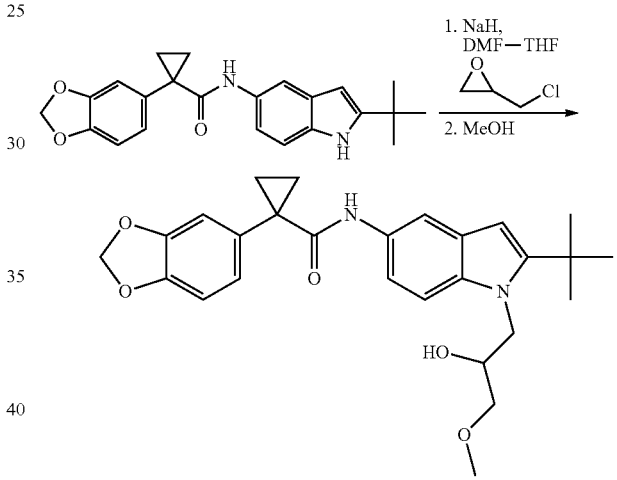

1-(Benzo[d][1,3]dioxol-5-yl)-N-(2-tert-butyl-1H-indol-5-yl)cyclopropanecarboxamide (320 mg, 0.84 mmol) was dissolved in a mixture composed of anhydrous DMF (0.5 mL) and anhydrous THF (5 mL) under N$_2$. NaH (60% in mineral oil, 120 mg, 3.0 mmol) was added at room temperature. After 30 min of stirring, the reaction mixture was cooled to −15° C. before a solution of epichlorohydrin (79 μL, 1.0 mmol) in anhydrous DMF (1 mL) was added dropwise. The reaction mixture was stirred for 15 min at −15° C., then for 8 h at room temperature. MeOH (1 mL) was added and the mixture was heated for 10 min at 105° C. in the microwave oven. The mixture was cooled, filtered and purified by preparative HPLC to give 1-(benzo[d][1,3]dioxol-5-yl)-N-(2-tert-butyl-1-(2-hydroxy-3-methoxy-propyl)-1H-indol-5-yl)cyclopropanecarboxamide. $^1$H NMR (400 MHz, DMSO-d6) δ 8.44 (s, 1H), 7.59 (d, J=1.9 Hz, 1H), 7.31 (d, J=8.9 Hz, 1H), 7.03 (dd, J=8.7, 1.9 Hz, 2H), 6.95 (dd, J=8.0, 1.7 Hz, 1H), 6.90 (d, J=8.0 Hz, 1H), 6.16 (s, 1H), 6.03 (s, 2H), 4.33 (dd, J=15.0, 4.0 Hz, 1H), 4.19 (dd, J=15.0, 8.1 Hz, 1H), 4.02 (ddd, J=8.7, 4.8 Hz, 1H), 3.41-3.32 (m, 2H), 3.30 (s, 3H), 1.41 (s, 9H), 1.41-1.38 (m, 2H), 1.03 (dd, J=6.7, 4.0 Hz, 2H). MS (ESI) m/e (M+H$^+$) 465.0.

Example 97

1-(Benzo[d][1,3]dioxol-5-yl)-N-(2-tert-butyl-1-(2-hydroxy-3-(methyl-amino)propyl)-1H-indol-5-yl)cyclopropanecarboxamide

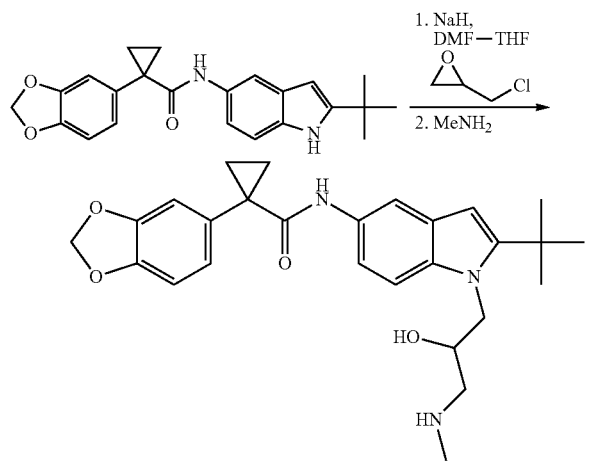

1-(Benzo[d][1,3]dioxol-5-yl)-N-(2-tert-butyl-1H-indol-5-yl)cyclopropanecarboxamide (320 mg, 0.84 mmol) was dissolved in a mixture composed of anhydrous DMF (0.5 mL) and anhydrous THF (5 mL) under $N_2$. NaH (60% in mineral oil, 120 mg, 3.0 mmol) was added at room temperature. After 30 min of stirring, the reaction mixture was cooled to −15° C. before a solution of epichlorohydrin (79 μL, 1.0 mmol) in anhydrous DMF (1 mL) was added dropwise. The reaction mixture was stirred for 15 min at −15° C., then for 8 h at room temperature. $MeNH_2$ (2.0 M in MeOH, 1.0 mL) was added and the mixture was heated for 10 min at 105° C. in the microwave oven. The mixture was cooled, filtered and purified by preparative HPLC to give 1-(benzo[d][1,3]dioxol-5-yl)-N-(2-tert-butyl-1-(2-hydroxy-3-(methylamino)propyl)-1H-indol-5-yl)cyclopropanecarboxamide. $^1$H NMR (400 MHz, DMSO-d6) δ 8.50 (s, 1H), 7.60-7.59 (m, 1H), 7.35 (dd, J=14.3, 8.9 Hz, 1H), 7.10 (d, J=8.8 Hz, 1H), 1H), 6.94 (dd, J=8.0, 1.6 Hz, 1H), 6.91 (d, J=7.9 Hz, 1H), 6.20 (d, J=2.3 Hz, 1H), 6.03 (s, 2H), 2.82 (d, J=4.7 Hz, 1H), 2.72 (d, J=4.7 Hz, 1H), 2.55 (dd, J=5.2, 5.2 Hz, 1H), 2.50 (s, 3H), 1.43 (s, 9H), 1.39 (dd, J=6.4, 3.7 Hz, 2H), 1.04 (dd, J=6.5, 3.9 Hz, 2H). MS (ESI) m/e (M+H$^+$) 464.0.

Example 98

(S)—N-(1-(3-Amino-2-hydroxypropyl)-2-tert-butyl-1H-indol-5-yl)-1-(2,2-difluorobenzo[d][1,3]dioxol-5-yl)cyclopropanecarboxamide

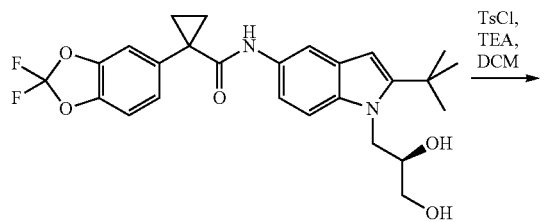

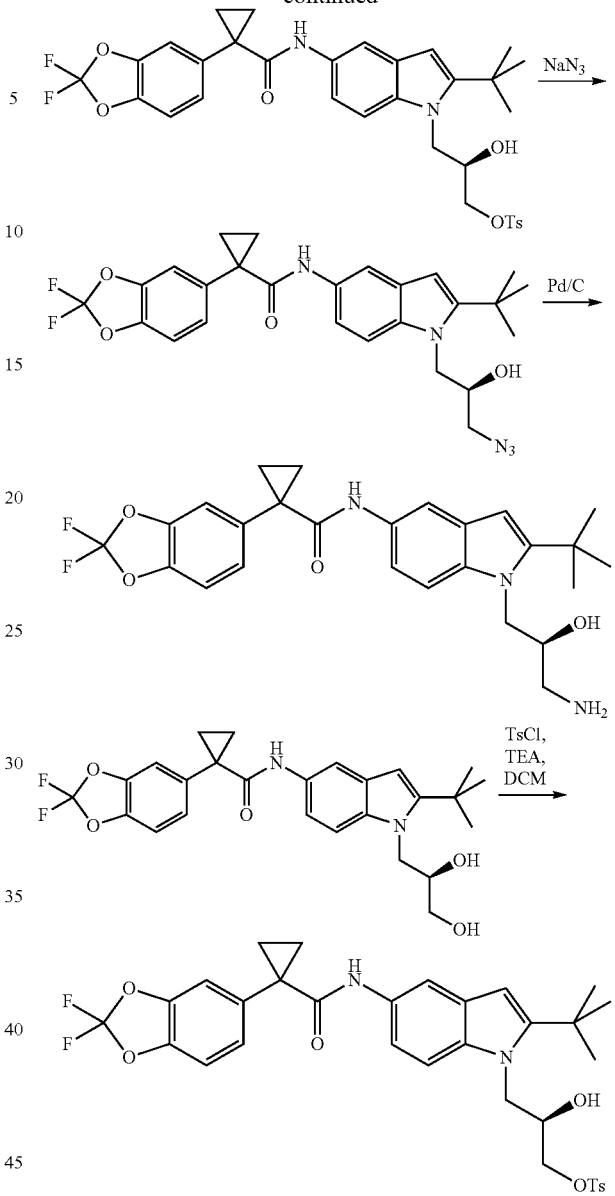

(R)-3-(2-tert-Butyl-5-(1-(2,2-difluorobenzo[d][1,3]dioxol-5-yl)cyclopropanecarbox-amido)-1H-indol-1-yl)-2-hydroxypropyl-4-methylbenzenesulfonate To a stirred solution of (R)—N-(2-tert-butyl-1-(2,3-dihydroxypropyl)-1H-indol-5-yl)-1-(2,2-difluoro-benzo[d][1,3]dioxol-5-yl)cyclopropanecarboxamide (3.0 g, 6.1 mmol) in dichloromethane (20 mL) was added triethylamine (2 mL) and para-toluenesulfonylchloride (1.3 g, 7.0 mmol). After 18 hours, the reaction mixture was partitioned between 10 mL of water and 10 mL of ethyl acetate. The organic layer was dried over magnesium sulfate, filtered and evaporated. The residue was purified using column chromatography on silica gel (0-60% ethyl acetate/hexane) providing (R)-3-(2-tert-butyl-5-(1-(2,2-difluorobenzo[d][1,3]-dioxol-5-yl)cyclopropanecarboxamido)-1H-indol-1-yl)-2-hydroxypropyl-4-methyl-benzenesulfonate (3.21 g, 86%). LC/MS (M+1)=641.2. $^1$H NMR (400 MHz, CDCl$_3$) δ 7.77 (d, 2H, J=16 Hz), 7.55 (d, 1H, J=2 Hz), 7.35 (d, 2H, J=16 Hz), 7.31 (m, 3H), 6.96 (s, 1H), 6.94 (dd, 1H, J=2, 8 Hz), 6.22 (s, 1H), 4.33 (m, 1H), 4.31 (dd, 1H, J=6, 15 Hz), 4.28 (dd, 1H, J=11, 15 Hz), 4.18 (m, 1H), 3.40 (dd, 1H, J=3, 6 Hz), 3.36 (dd, 1H, J=3, 6 Hz), 2.46 (s, 3H), 2.40 (br s, 1H), 1.74 (m, 2H), 1.40 (s, 9H), 1.11 (m, 2H).

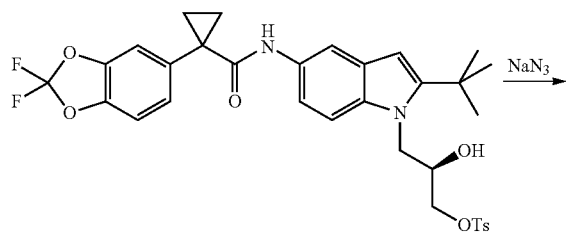

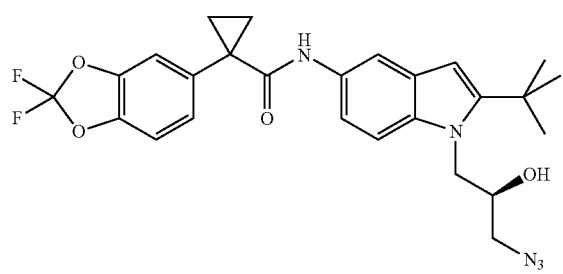

(R)—N-(1-(3-Azido-2-hydroxypropyl)-2-tert-butyl-1H-indol-5-yl)-1-(2,2-difluorobenzo[d][1,3]dioxol-5-yl)cyclopropanecarboxamide To a stirred solution (R)-3-(2-tert-butyl-5-(1-(2,2-difluorobenzo[d][1,3]dioxol-5-yl)cyclopropanecarboxamido)-1H-indol-1-yl)-2-hydroxypropyl-4-methylbenzenesulfonate (3.2 g, 5.0 mmol) in DMF (6 mL) was added sodium azide (2.0 g, 30 mmol). The reaction was heated at 80° C. for 2 h. The mixture was partitioned between 20 mL ethyl acetate and 20 mL water. The layers were separated and the organic layer was evaporated. The residue was purified using column chromatography (0-85% ethyl acetate/hexane) to give (R)—N-(1-(3-azido-2-hydroxypropyl)-2-tert-butyl-1H-indol-5-yl)-1-(2,2-difluorobenzo[d][1,3]dioxol-5-yl)-cyclopropanecarboxamide (2.48 g). LC/MS (M+1)=512.5. $^{1}$H NMR (400 MHz, CDCl$_{3}$) δ 7.55 (d, 1H, J=2 Hz), 7.31 (m, 3H), 6.96 (s, 1H), 6.94 (dd, 1H, J=2, 8 Hz), 6.22 (s, 1H), 4.33 (m, 1H), 4.31 (dd, 1H, J=6, 15 Hz), 4.28 (dd, 1H, J=11, 15 Hz), 4.18 (m, 1H), 3.40 (dd, 1H, J=3, 6 Hz), 3.36 (dd, 1H, J=3, 6 Hz), 2.40 (br s, 1H), 1.74 (m, 2H), 1.40 (s, 9H), 1.11 (m, 2H).

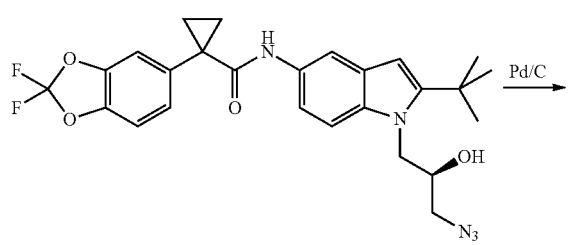

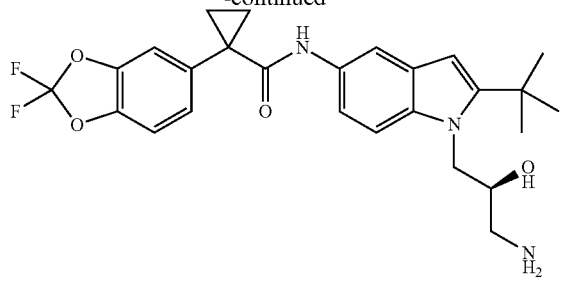

(S)—N-(1-(3-Amino-2-hydroxypropyl)-2-tert-butyl-1H-indol-5-yl)-1-(2,2-difluoro-benzo[d][1,3]dioxol-5-yl)cyclopropanecarboxamide To a stirred solution (R)—N-(1-(3-azido-2-hydroxypropyl)-2-tert-butyl-1H-indol-5-yl)-1-(2,2-difluorobenzo[d][1,3]dioxol-5-yl)cyclopropanecarboxamide (2.4 g, 4.0 mmol) in MeOH (25 mL) was added 5% Pd/C (2.4 g) under a Hydrogen gas filled balloon. After 18 h, the reaction mixture was filtered through celite and rinsed with 300 mL ethyl acetate. The organic layer was washed with 1 N HCl and evaporated to give (S)—N-(1-(3-amino-2-hydroxypropyl)-2-tert-butyl-1H-indol-5-yl)-1-(2,2-difluoro-benzo[d][1,3]-dioxol-5-yl)cyclopropane-carboxamide (1.37 g). MS (M+1)=486.5.

Example 99

(S)-Methyl 3-(2-tert-butyl-5-(1-(2,2-difluorobenzo[d][1,3]dioxol-5-yl)cyclopropanecarboxamido)-1H-indol-1-yl)-2-hydroxypropylcarbamate

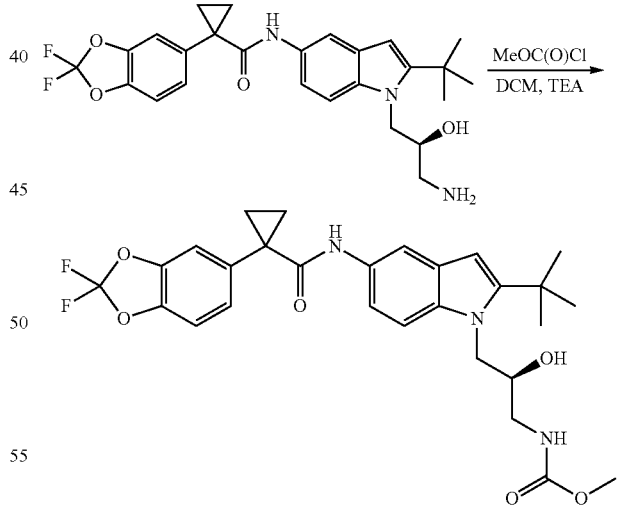

To a stirred solution (R)—N-(1-(3-amino-2-hydroxypropyl)-2-tert-butyl-1H-indol-5-yl)-1-(2,2-difluorobenzo[d][1,3]dioxol-5-yl)cyclopropanecarboxamide (0.10 g, 0.20 mmol) in methanol (1 mL) was added 2 drops of triethylamine and methylchloroformyl chloride (0.020 mL, 0.25 mmol). After 30 min, the reaction mixture was filtered and purified using reverse phase HPLC providing (S)-methyl 3-(2-tert-butyl-5-(1-(2,2-difluorobenzo[d][1,3]dioxol-5-yl)cyclo-propanecarboxamido)-1H-indol-1-yl)-2-hydroxypropylcarbamate. The retention time on a three minute run is 1.40 min. LC/MS (M+1)=544.3. $^1$H NMR (400 MHz, CDCl$_3$) δ 7.52 (d, 1H, J=2 Hz), 7.30 (dd, 1H, J=2, 8 Hz), 7.28 (m, 1H), 7.22 (d, 1H, J=8 Hz), 7.14 (d, 1H, J=8 Hz), 7.04 (br s, 1H), 6.97 (dd, 1H, J=2, 8 Hz), 6.24 (s, 1H), 5.19 (1H, br s), 4.31 (dd, 1H, J=6, 15 Hz), 4.28 (dd, 1H, J=11, 15 Hz), 4.18 (m, 1H), 3.70 (s, 3H), 3.40 (dd, 1H, J=3, 6 Hz), 3.36 (dd, 1H, J=3, 6 Hz), 3.26 (m, 1H), 1.74 (m, 2H), 1.40 (s, 9H), 1.11 (m, 2H).

Example 100

4-(5-(1-(Benzo[d][1,3]dioxol-5-yl)cyclopropanecarboxamido)-2-tert-butyl-1H-indol-1-yl)butanoic acid

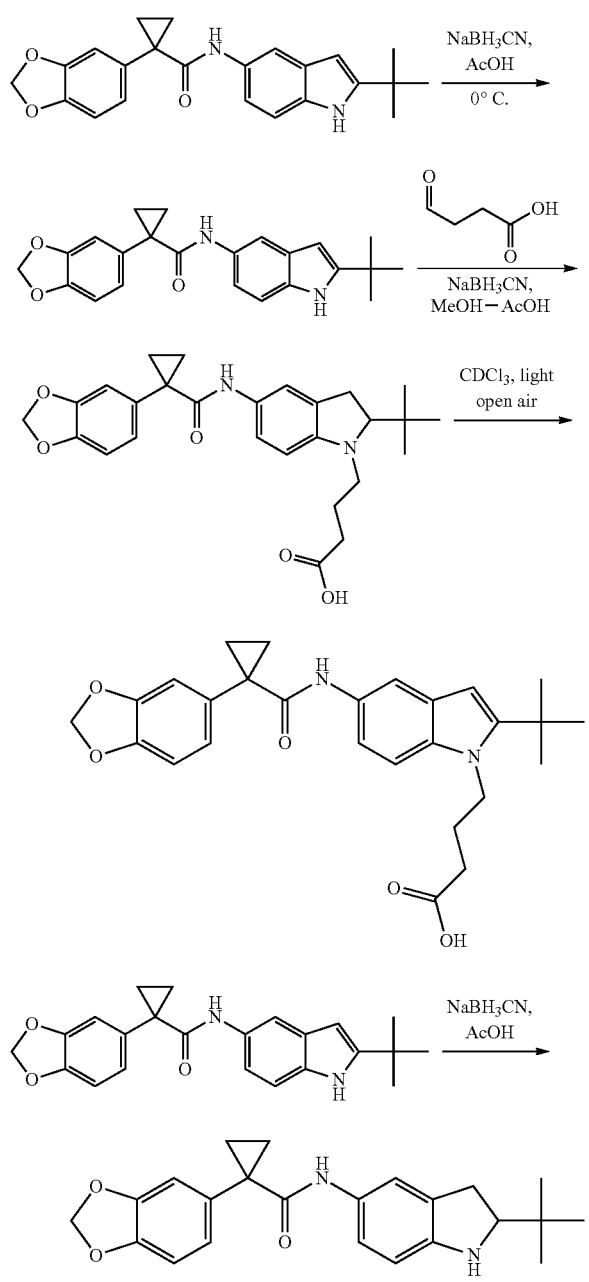

1-(Benzo[d][1,3]dioxol-5-yl)-N-(2-tert-butylindolin-5-yl)cyclopropanecarboxamide To a solution of 1-(benzo[d][1,3]dioxol-5-yl)-N-(2-tert-butyl-1H-indol-5-yl)cyclo-propanecarboxamide (851 mg, 2.26 mmol) in acetic acid (60 mL) was added NaBH$_3$CN (309 mg, 4.91 mmol) at 0° C. The reaction mixture was stirred for 5 min at room temperature after which no starting material could be detected by LCMS. The solvent was evaporated under reduced pressure and the residue was purified by column chromatography on silica gel (5-40% ethyl acetate/hexanes) to give 1-(benzo[d][1,3]dioxol-5-yl)-N-(2-tert-butylindolin-5-yl)cyclopropanecarboxamide (760 mg, 89%).

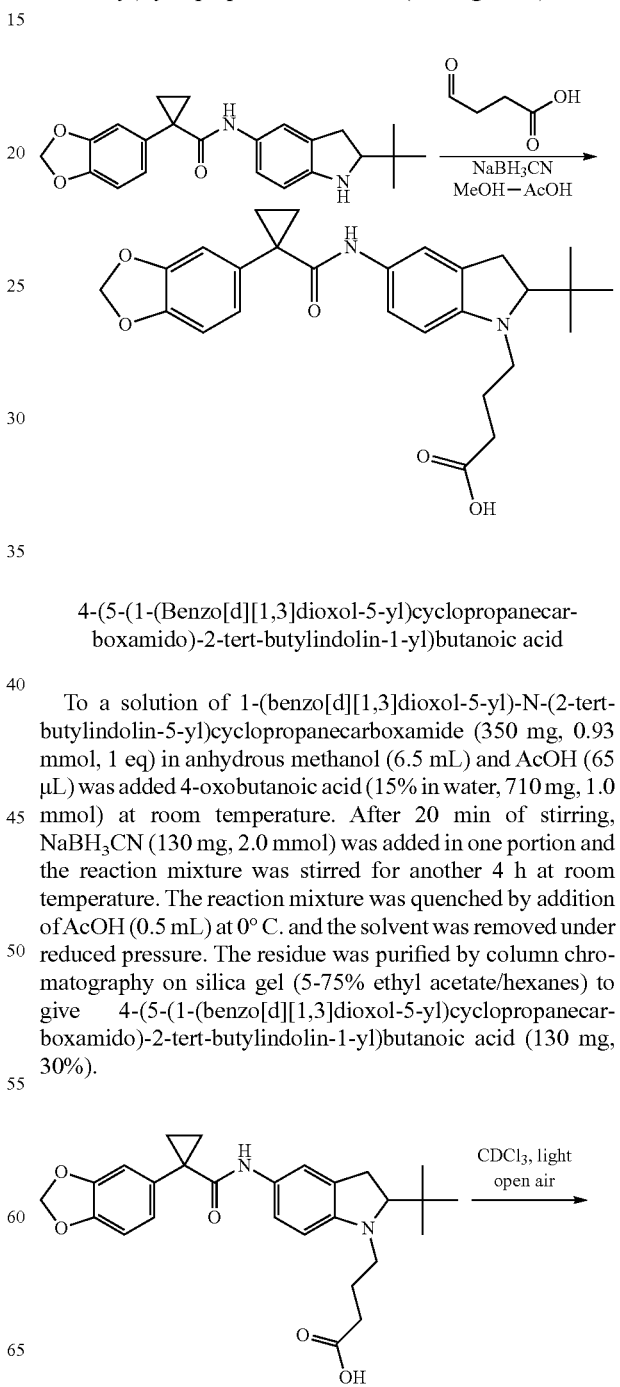

4-(5-(1-(Benzo[d][1,3]dioxol-5-yl)cyclopropanecarboxamido)-2-tert-butylindolin-1-yl)butanoic acid To a solution of 1-(benzo[d][1,3]dioxol-5-yl)-N-(2-tert-butylindolin-5-yl)cyclopropanecarboxamide (350 mg, 0.93 mmol, 1 eq) in anhydrous methanol (6.5 mL) and AcOH (65 μL) was added 4-oxobutanoic acid (15% in water, 710 mg, 1.0 mmol) at room temperature. After 20 min of stirring, NaBH$_3$CN (130 mg, 2.0 mmol) was added in one portion and the reaction mixture was stirred for another 4 h at room temperature. The reaction mixture was quenched by addition of AcOH (0.5 mL) at 0° C. and the solvent was removed under reduced pressure. The residue was purified by column chromatography on silica gel (5-75% ethyl acetate/hexanes) to give 4-(5-(1-(benzo[d][1,3]dioxol-5-yl)cyclopropanecarboxamido)-2-tert-butylindolin-1-yl)butanoic acid (130 mg, 30%).

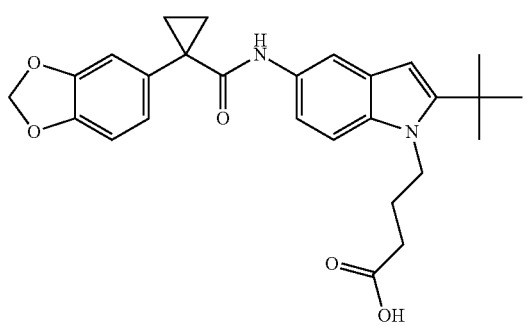

4-(5-(1-(Benzo[d][1,3]-dioxol-5-yl)cyclopropanecarboxamido)-2-tert-butyl-1H-indol-1-yl)butanoic acid 4-(5-(1-(Benzo[d][1,3]dioxol-5-yl)cyclopropanecarboxamido)-2-tert-butylindolin-1-yl)butanoic acid (130 mg, 0.28 mmol) was taken up in a mixture of acetonitrile-H$_2$O-TFA. The solvent was removed under reduced pressure and the residue obtained was dissolved in CDCl$_3$. After a brief exposition to daylight (5-10 min), the solution turned purple. The mixture was stirred open to the atmosphere at room temperature until complete disappearance of the starting material (8 h). Solvent was removed under reduced pressure and the residue was purified by reverse pharse HPLC to give 4-(5-(1-(benzo[d][1,3]dioxol-5-yl)cyclopropanecarboxamido)-2-tert-butyl-1H-indol-1-yl)butanoic acid. $^1$H NMR (400 MHz, CDCl$_3$) δ 7.52 (d, J=1.9 Hz, 1H), 7.18 (d, J=2.1 Hz, 1H), 7.16 (s, 1H), 7.03 (dd, J=9.4, 1.9 Hz, 1H), 7.00-6.98 (m, 2H), 6.85 (d, J=7.9 Hz, 1H), 6.16 (s, 1H), 6.02 (s, 2H), 4.29-4.24 (m, 2H), 2.48 (dd, J=6.9, 6.9 Hz, 2H), 2.12-2.04 (m, 2H), 1.69 (dd, J=6.8, 3.7 Hz, 2H), 1.43 (s, 9H), 1.09 (dd, J=6.8, 3.7 Hz, 2H). MS (ESI) m/e (M+H$^+$) 463.0.

Example 101

1-(Benzo[d][1,3]-dioxol-5-yl)-N-(2-tert-butyl-1-(4-(2-hydroxyethyl-amino)-4-oxobutyl)-1H-indol-5-yl)cyclopropanecarboxamide

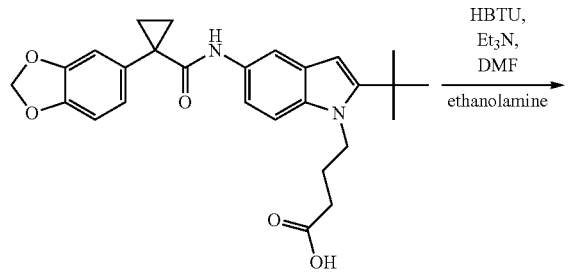

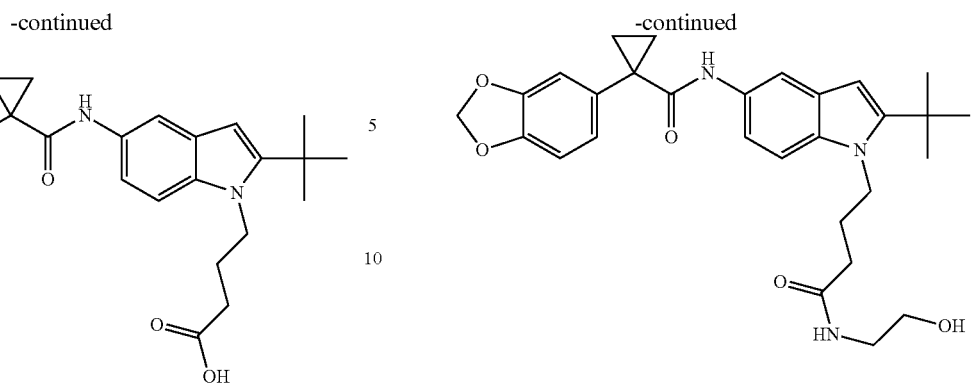

To a solution of 4-(5-(1-(benzo[d][1,3]dioxol-5-yl)cyclopropanecarboxamido)-2-tert-butyl-1H-indol-1-yl)butanoic acid (10 mg) in anhydrous DMF (0.25 mL) were successively added Et$_3$N (9.5 mL, 0.069 mmol) and HBTU (8.2 mg, 0.022 mmol). After stirring for 10 min at 60° C., ethanolamine (1.3 μL, 0.022 mmol) was added, and the mixture was stirred for another 4 h at 60° C. 1-(Benzo[d][1,3]dioxol-5-yl)-N-(2-tert-butyl-1-(4-(2-hydroxyethyl-amino)-4-oxobutyl)-1H-indol-5-yl)cyclopropanecarboxamide (5.8 mg, 64%) was obtained after purification by preparative HPLC. MS (ESI) m/e (M+H$^+$) 506.0.

Example 102

1-(Benzo[d][1,3]dioxol-5-yl)-N-(2-tert-butyl-1-(2-(dimethylamino)-2-oxoethyl)-1H-indol-5-yl)cyclopropanecarboxamide

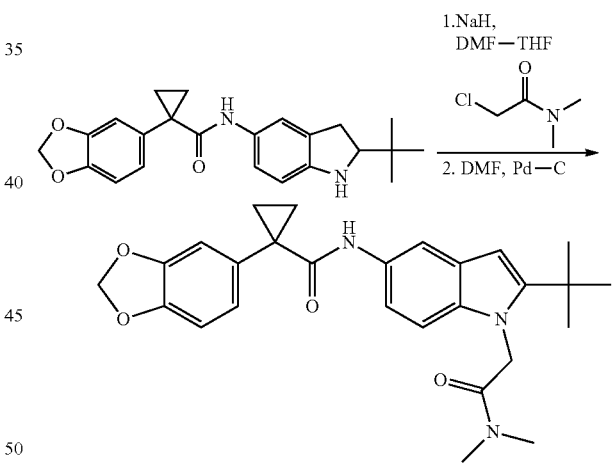

To a solution of 1-(benzo[d][1,3]dioxol-5-yl)-N-(2-tert-butylindolin-5-yl)cyclopropanecarboxamide (62 mg, 0.16 mmol) in anhydrous DMF (0.11 mL) and THF (1 mL) was added NaH (60% in mineral oil, 21 mg, 0.51 mmol) at room temperature under N$_2$. After 30 min of stirring, the reaction mixture was cooled to 0° C. and 2-chloro-N,N-dimethylacetamide (11 mL, 0.14 mmol) was added. The reaction mixture was stirred for 5 min at 0° C. and then for 10 h at room temperature. The mixture was purified by preparative HPLC and the resultant solid was dissolved in DMF (0.6 mL) in the presence of Pd—C (10 mg). The mixture was stirred open to the atmosphere overnight at room temperature. The reaction mixture was filtrated and purified by preparative HPLC providing 1-(benzo[d][1,3]dioxol-5-yl)-N-(2-tert-butyl-1-(2-(dimethylamino)-2-oxoethyl)-1H-indol-5-yl)cyclopropanecarboxamide. MS (ESI) m/e (M+H$^+$) 462.0.

Example 103

3-(2-tert-Butyl-5-(1-(2,2-difluorobenzo[d][1,3]dioxol-5-yl)cyclo-propanecarboxamido)-1H-indol-1-yl)propanoic acid

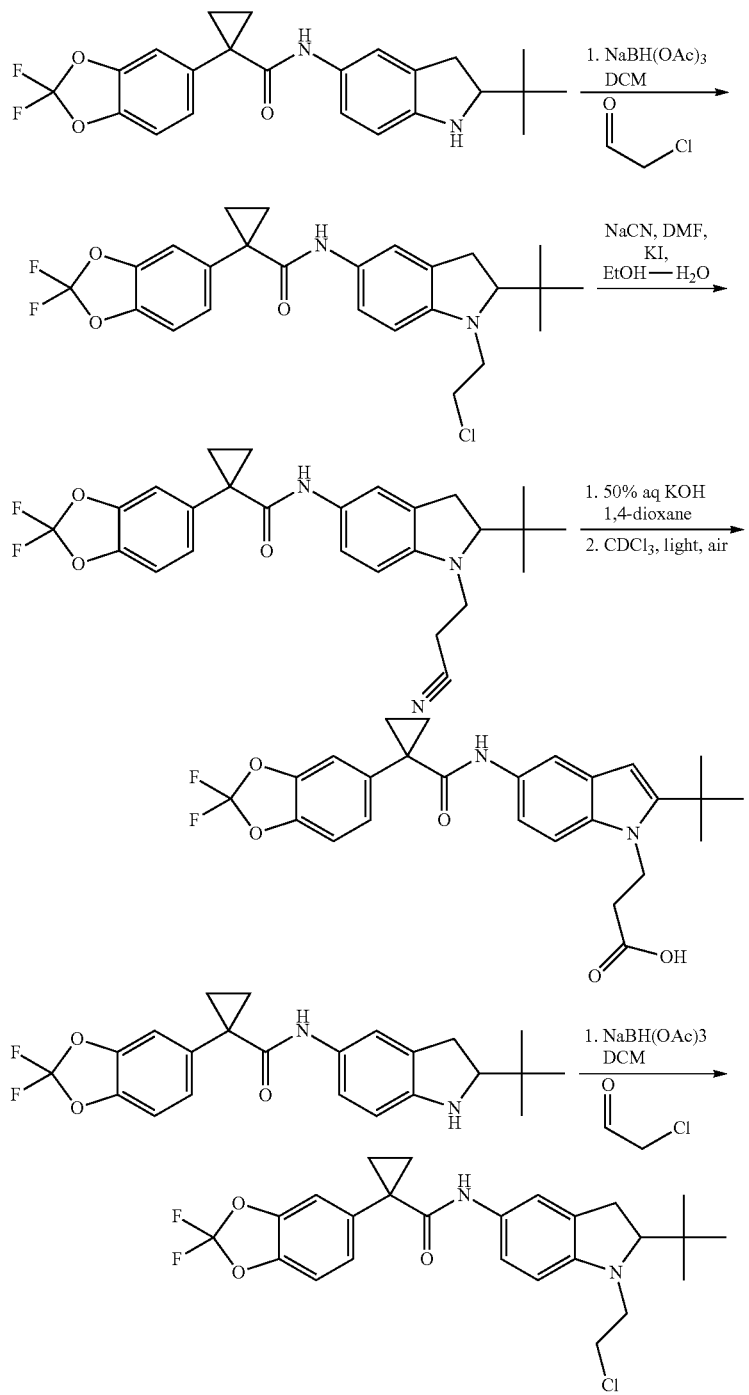

N-(2-tert-Butyl-1-(2-chloroethyl)indolin-5-yl)-1-(2,2-difluorobenzo[d][1,3]dioxol-5-yl)cyclopropanecarboxamide To a solution of N-(2-tert-butyl-1-(2-cyanoethyl)indolin-5-yl)-1-(2,2-difluorobenzo[d][1,3]dioxol-5-yl)cyclopropanecarboxamide (71 mg, 0.17 mmol) in anhydrous dichloromethane (1 mL) was added chloroacetaldehyde (53 µL, 0.41 mmol) at room temperature under $N_2$. After 20 min of stirring, $NaBH(OAc)_3$ (90 mg, 0.42 mmol) was added in two portions. The reaction mixture was stirred overnight at room temperature. The product was purified by column chromatography on silica gel (2-15% ethyl acetate/hexanes) providing N-(2-tert-butyl-1-(2-chloroethyl)indolin-5-yl)-1-(2,2-difluorobenzo[d][1,3]dioxol-5-yl)cyclopropanecarboxamide (51 mg, 63%).

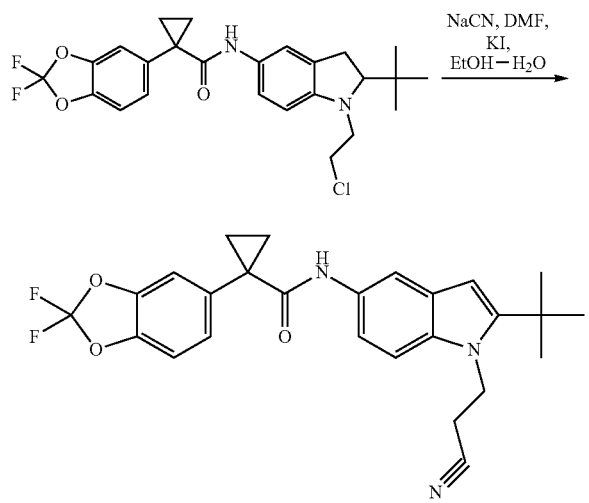

N-(2-tert-Butyl-1-(2-cyanoethyl)indolin-5-yl)-1-(2,2-difluorobenzo[d][1,3]dioxol-5-yl)cyclopropanecarboxamide N-(2-tert-butyl-1-(2-chloroethyl)indolin-5-yl)-1-(2,2-difluorobenzo[d][1,3]dioxol-5-yl)cyclopropanecarboxamide (51 mg), NaCN (16 mg, 0.32 mmol) and KI (cat) in EtOH (0.6 mL) and water (0.3 mL) were combined and heated at 110° C. for 30 min in the microwave. The solvent was removed under reduced pressure and the residue was purified by column chromatography on silica gel (2-15% ethyl acetate/hexanes) providing N-(2-tert-butyl-1-(2-cyanoethyl)indolin-5-yl)-1-(2,2-difluorobenzo[d][1,3]dioxol-5-yl)cyclopropanecarboxamide (24 mg, 48%).

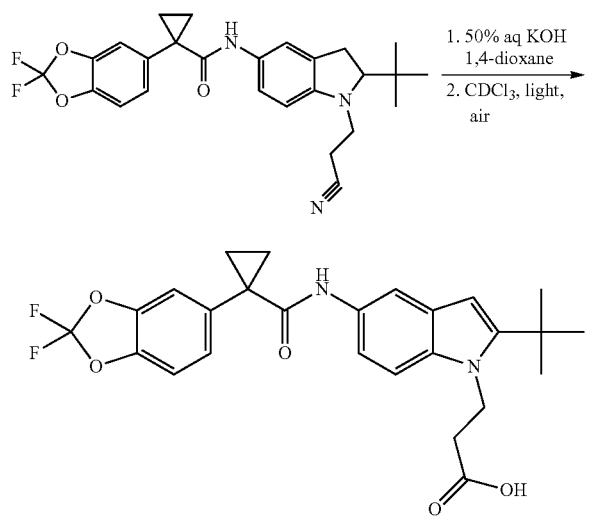

3-(2-tert-Butyl-5-(1-(2,2-difluorobenzo[d][1,3]dioxol-5-yl)cyclo-propanecarboxamido)-1H-indol-1-yl)propanoic acid N-(2-tert-butyl-1-(2-cyanoethyl)indolin-5-yl)-1-(2,2-difluorobenzo[d][1,3]dioxol-5-yl)cyclopropane-carboxamide (24 mg, 0.050 mmol) was taken up in 50% aq. KOH (0.5 mL) and 1,4-dioxane (1 mL). The mixture was heated at 125° C. for 2 h. The solvent was removed and the residue was purified by preparative HPLC. The residue was dissolved in CDCl₃ (1 mL) then briefly exposed to daylight. The purple solution that formed was stirred until complete disappearance of the starting material (1 h). The solvent was removed under reduced pressure and the residue was purified by preparative HPLC providing 3-(2-tert-butyl-5-(1-(2,2-difluorobenzo[d][1,3]dioxol-5-yl)cyclo-propanecarboxamido)-1H-indol-1-yl)propanoic acid. MS (ESI) m/e (M+H⁺) 485.0.

Example 104

1-(Benzo[d][1,3]dioxol-5-yl)-N-(2-tert-butyl-6-fluoro-1-(2-hydroxy-ethyl)-1H-indol-5-yl)cyclopropenecarboxamide

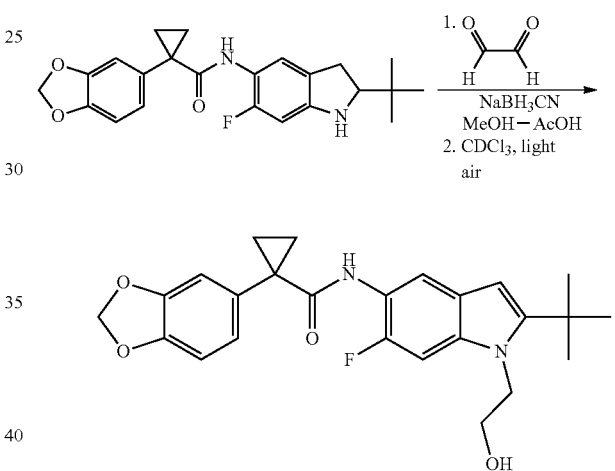

To a solution of 1-(benzo[d][1,3]dioxol-5-yl)-N-(2-tert-butyl-6-fluoroindolin-5-yl)cyclopropanecarboxamide (340 mg, 0.86 mmol) in anhydrous MeOH (5.7 mL) containing 1% of acetic acid was added glyoxal 40% in water (0.60 mL, 5.2 mmol) at room temperature under N₂. After 20 min of stirring, NaBH₃CN (120 mg, 1.9 mmol) was added in one portion and the reaction mixture was stirred overnight at room temperature. The solvent was removed under reduced pressure and the residue obtained was purified by column chromatography on silica gel (10-40% ethyl acetate/hexanes) providing a pale yellow oil which was treated with 50/50 CH₃CN—H₂O containing 0.05% TFA and CDCl₃. Solvent was removed under reduced pressure and the residue was purified by column chromatography on silica gel (20-35% ethyl acetate/hexanes) to give 1-(benzo[d][1,3]dioxol-5-yl)-N-(2-tert-butyl-6-fluoro-1-(2-hydroxyethyl)-1H-indol-5-yl)cyclopropanecarboxamide. ¹H NMR (400 MHz, CDCl₃) δ 8.02 (d, J=7.7 Hz, 1H), 7.30 (d, J=2.1 Hz, 1H), 6.93 (dd, J=1.6, 7.9 Hz, 1H), 6.90 (d, J=1.6 Hz, 1H), 6.90 (d, J=1.6 Hz, 1H), 6.78 (d, J=7.9 Hz, 1H), 6.08 (s, 1H), 5.92 (s, 2H), 4.21 (dd, J=6.9, 6.9 Hz, 2H), 3.68 (m, 2H), 2.28 (s, 1H), 1.60 (dd, J=3.7, 6.7 Hz, 2H), 1.35-1.32 (m, 9H), 1.04 (dd, J=3.7, 6.8 Hz, 2H). MS (ESI) m/e (M+H⁺) 439.0.

Example 105

1-(Benzo[d][1,3]dioxol-5-yl)-N-(2-tert-butyl-6-fluoro-1-(3-hydroxy-propyl)-1H-indol-5-yl)cyclopropanecarboxamide

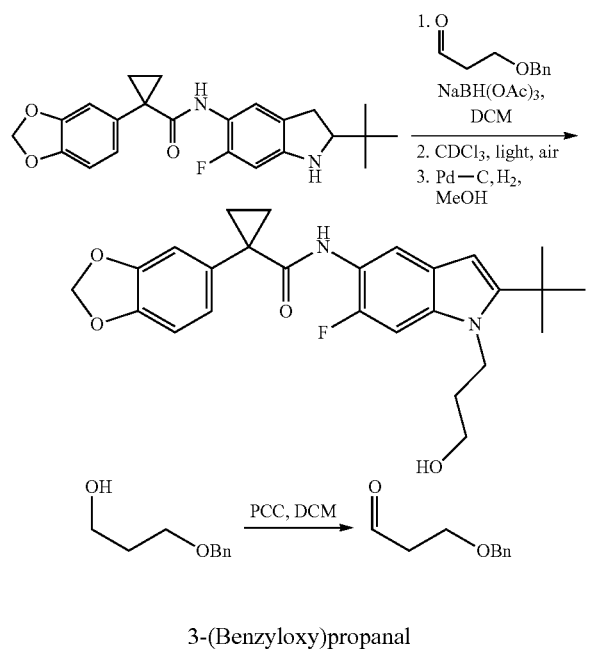

3-(Benzyloxy)propanal

To a suspension of PCC (606 mg, 2.82 mmol) in anhydrous dichloromethane (8 mL) at room temperature under N₂ was added a solution of 3-benzyloxy-1-propanol (310 mg, 1.88 mmol) in anhydrous dichloromethane. The reaction mixture was stirred overnight at room temperature, filtrated through Celite, and concentrated. The residue was purified by column chromatography on silica gel (1-10% ethyl acetate/hexanes) to give 3-(benzyloxy)propanal (243 mg, 79%).

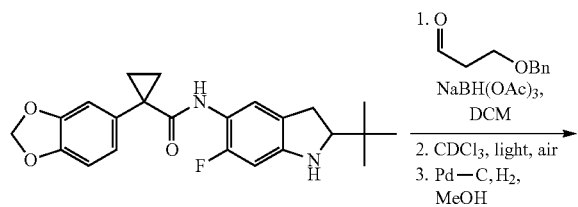

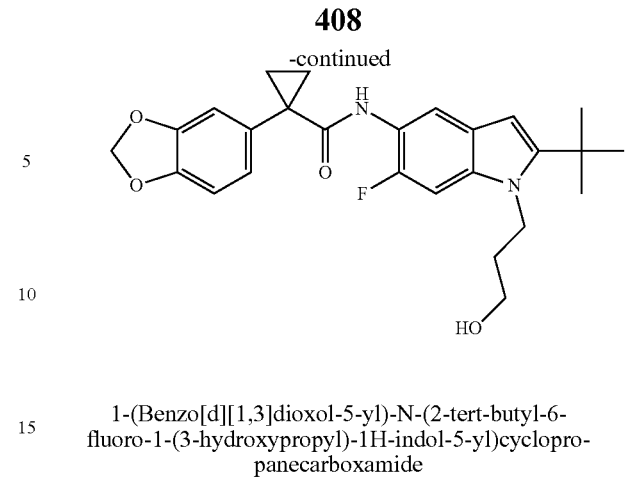

1-(Benzo[d][1,3]dioxol-5-yl)-N-(2-tert-butyl-6-fluoro-1-(3-hydroxypropyl)-1H-indol-5-yl)cyclopropanecarboxamide To a solution of 1-(benzo[d][1,3]dioxol-5-yl)-N-(2-tert-butyl-6-fluoroindolin-5-yl)cyclopropanecarboxamide (160 mg, 0.50 mmol) in anhydrous dichloromethane (3.4 mL) was added 3-(benzyloxy)propanal (160 mg, 0.98 mmol) at room temperature. After 10 min of stirring, NaBH(OAc)₃ (140 mg, 0.65 mmol) was added in one portion and the reaction mixture was stirred for 4 h at room temperature. The solvent was removed under reduced pressure and the residue was taken-up in a mixture of 50/50 CH₃CN—H₂O containing 0.05% TFA. The mixture was concentrated to dryness and the residue was dissolved in CDCl₃ (5 mL) and briefly exposed to daylight. The purple solution was stirred open to the atmosphere at room temperature for 2 h. The solvent was removed under reduced pressure and the residue was treated with Pd—C (10 mg) in MeOH (2 mL) under 1 atm of H₂ for 2 h. The catalyst was filtered through Celite and the solvent was removed under reduced pressure. The residue was purified by preparative TLC 30% ethyl acetate/hexanes to provide 1-(benzo[d][1,3]dioxol-5-yl)-N-(2-tert-butyl-6-fluoro-1-(3-hydroxypropyl)-1H-indol-5-yl)cyclopropanecarboxamide (18 mg, 8% from 1-(benzo[d][1,3]dioxol-5-yl)-N-(2-tert-butyl-6-fluoroindolin-5-yl)cyclopropane-carboxamide). ¹H NMR (400 MHz, CDCl₃) δ 8.11 (d, J=7.8 Hz, 1H), 7.31 (d, J=2.2 Hz, 1H), 6.94 (dd, J=7.9, 1.7 Hz, 1H), 6.91 (d, J=1.6 Hz, 1H), 6.85 (d, J=11.7 Hz, 1H), 6.79 (d, J=7.9 Hz, 1H), 6.10 (s, 1H), 5.94 (s, 2H), 4.25-4.21 (m, 2H), 3.70 (dd, J=5.7, 5.7 Hz, 2H), 1.93-1.86 (m, 2H), 1.61 (dd, J=6.8, 3.7 Hz, 2H), 1.35 (s, 9H), 1.04 (dd, J=6.8, 3.7 Hz, 2H). MS (ESI) m/e (M+H⁺) 453.0.

Example 106

N-(1-(2-Acetamidoethyl)-2-tert-butyl-1,1-indol-5-yl)-1-(benzo[d][1,3]-dioxol-5-yl)cyclopropanecarboxamide

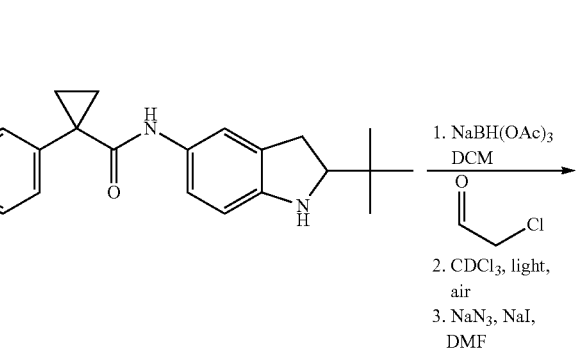

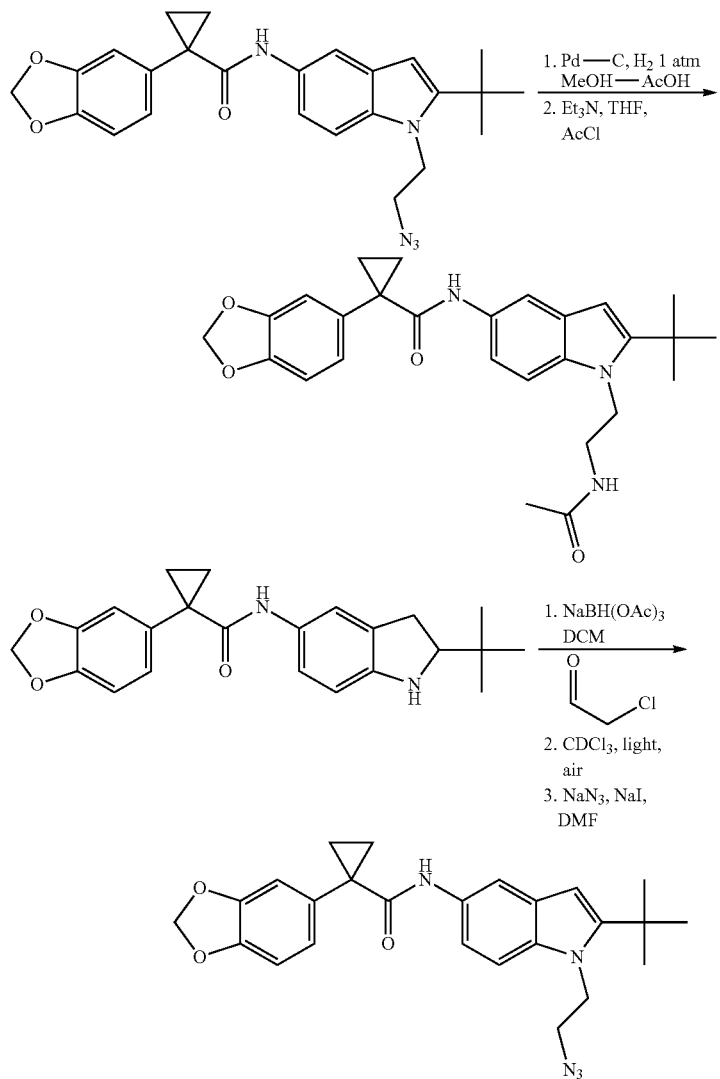

N-(1-(2-azidoethyl)-2-tert-butyl-1H-indol-5-yl)-1-(benzo[d][1,3]-dioxol-5-yl)-cyclopropanecarboxamide To a solution of 1-(benzo[d][1,3]dioxol-5-yl)-N-(2-tert-butylindolin-5-yl)cyclopropane-carboxamide (73 mg, 0.19 mmol) in anhydrous dichloromethane (1.2 mL) was added chloroacetaldehyde (60 µL, 0.24 mmol) at room temperature. After 10 min of stirring, NaBH(OAc)$_3$ (52 mg, 0.24 mmol) was added in one portion and the reaction mixture was stirred for another 30 min at room temperature. The solvent was removed under reduced pressure and the residue was purified by preparative HPLC to give the indoline, which oxidized to the corresponding indole when taken-up in CDCl$_3$. The resulting indole was treated with NaN$_3$ (58 mg, 0.89 mmol) and NaI (cat) in anhydrous DMF (0.8 mL) for 2 h at 85° C. The reaction mixture was purified by preparative HPLC providing N-(1-(2-azidoethyl)-2-tert-butyl-1H-indol-5-yl)-1-(benzo[d][1,3]dioxol-5-yl)cyclopropanecarboxamide (15 mg, 18% from 1-(benzo[d][1,3]dioxol-5-yl)-N-(2-tert-butyl-indolin-5-yl)cyclopropane-carboxamide).

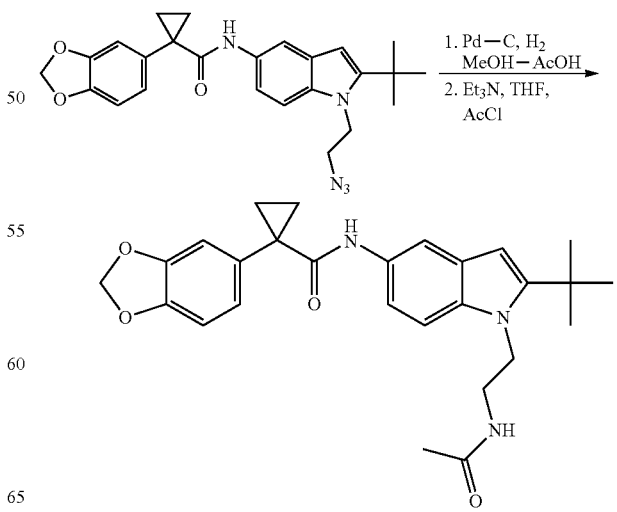

411

N-(1-(2-Acetamidoethyl)-2-tert-butyl-1H-indol-5-yl)-1-(benzo[d][1,3]-dioxol-5-yl)cyclopropanecarboxamide A solution of N-(1-(2-azidoethyl)-2-tert-butyl-1H-indol-5-yl)-1-(benzo[d][1,3]dioxol-5-yl)cyclopropanecarboxamide (13 mg, 0.029 mmol) in MeOH—AcOH (0.2 mL, 99:1) in the presence of Pd—C (2 mg) was stirred at room temperature under 1 atm of $H_2$ for 2 h, filtered through Celite, and concentrated under reduced pressure. The crude product was treated with AcCl (0.05 mL) and $Et_3N$ (0.05 mL) in anhydrous THF (0.2 mL) at 0° C. for 30 min and then 1 h at room temperature. The mixture was purified by preparative HPLC providing N-(1-(2-acetamidoethyl)-2-tert-butyl-1H-indol-5-yl)-1-(benzo[d][1,3]-dioxol-5-yl)cyclopropanecarboxamide. MS (ESI) m/e (M+H$^+$) 462.0.

Example 107

N-(2-tert-Butyl-1-(3-cyano-2-hydroxypropyl)-1H-indol-5-yl)-1-(2,2-difluorobenzo[d][1,3]dioxol-5-yl)cyclopropanecarboxamide

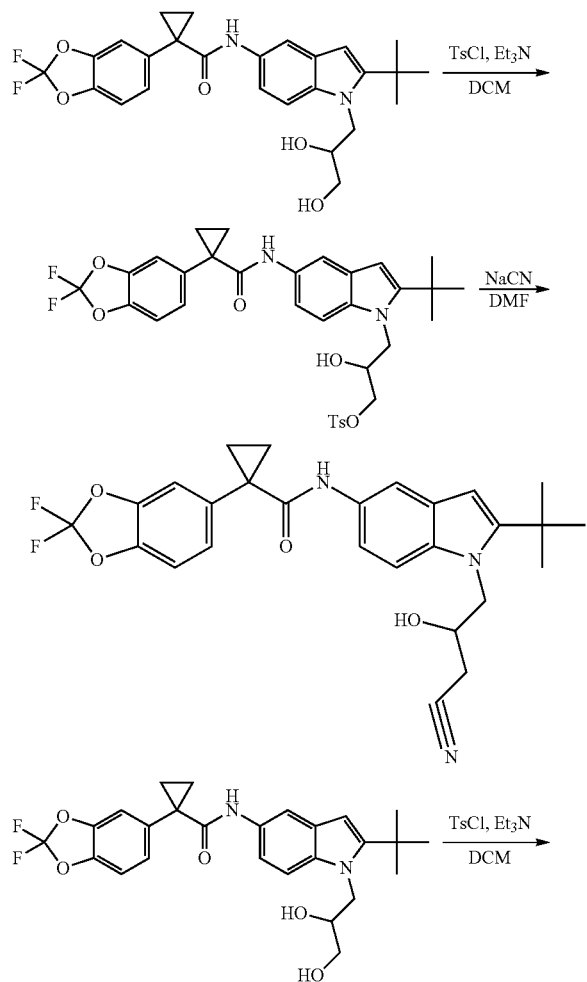

412

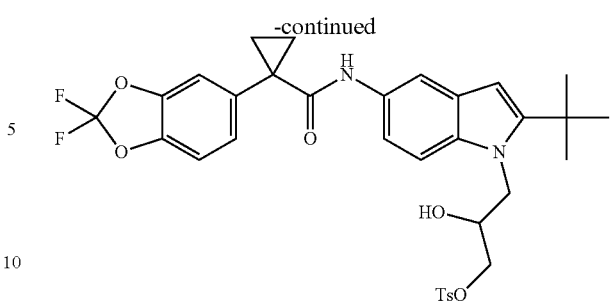

3-(2-tert-Butyl-5-(1-(2,2-difluorobenzo[d][1,3]dioxol-5-yl)cyclopropanecarbox-amido)-1H-indol-1-yl)-2-hydroxypropyl-4-methylbenzenesulfonate To a solution of N-(2-tert-butyl-1-(2,3-dihydroxypropyl)-1H-indol-5-yl)-1-(2,2-difluorobenzo[d][1,3]-dioxol-5-yl)cyclopropanecarboxamide (172 mg, 0.35 mmol) in anhydrous dichloromethane (1.4 mL) at 0° C. in the presence of $Et_3N$ (56 µL, 0.40 mmol) was added TsCl (71 mg, 0.37 mmol). The reaction mixture was stirred for 2 h at room temperature before being cooled to 0° C. and another portion of TsCl (71 mg, 0.37 mmol) was added. After 1 h of stirring at room temperature, the mixture was purified by column chromatography on silica gel (10-30% ethyl acetate/hexanes) providing 3-(2-tert-butyl-5-(1-(2,2-difluorobenzo[d][1,3]dioxol-5-yl)cyclopropanecarboxamido)-1H-indol-1-yl)-2-hydroxypropyl-4-methylbenzene-sulfonate (146 mg, 64%).

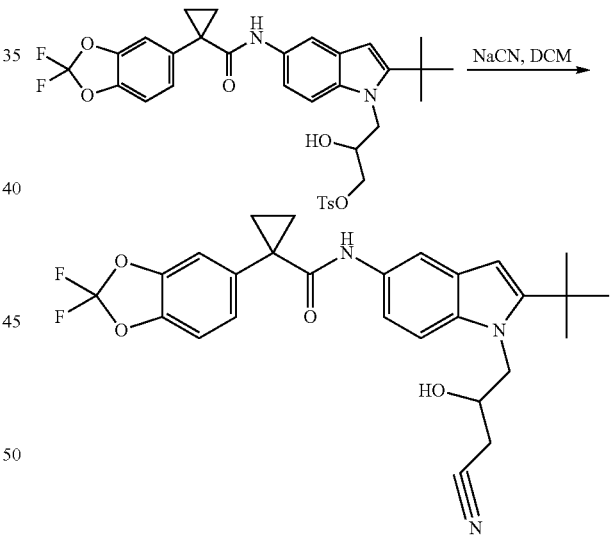

N-(2-tert-Butyl-1-(3-cyano-2-hydroxypropyl)-1H-indol-5-yl)-1-(2,2-difluorobenzo[d][1,3]dioxol-5-yl)cyclopropanecarboxamide N-(2-tert-Butyl-1-(3-cyano-2-hydroxypropyl)-1H-indol-5-yl)-1-(2,2-difluorobenzo[d][1,3]dioxol-5-yl)-cyclopropanecarboxamide (145 mg, 0.226 mmol) was treated with powdered NaCN (34 mg, 0.69 mmol) in anhydrous DMF (1.5 mL) at 85° C. for 2 h. The reaction mixture was cooled down to room temperature before it was diluted with dichloromethane (10 mL) and aq. sat. $NaHCO_3$ (10 mL). The organic phase was separated and the aqueous phase was extracted with dichloromethane (2×10 mL). The organic phases were combined, washed with brine, dried with sodium sulfate, filtered then concentrated. The residue was purified by column chromatography on silica gel (25-55% ethyl acetate/hexanes) providing N-(2-tert-butyl-1-(3-cyano-2-hydroxypropyl)-1H-indol-5-yl)-1-(2,2-difluorobenzo[d][1,3]dioxol-5-yl)cyclopropanecarboxamide (89 mg, 79%). $^1$H NMR (400 MHz, CDCl$_3$) δ 7.43 (d, J=1.9 Hz, 1H), 7.20-7.16 (m, 2H), 7.08 (d, J=8.8 Hz, 1H), 7.04 (d, J=8.2 Hz, 1H), 6.94 (s, 1H), 6.88 (dd, J=8.7, 2.0 Hz, 1H), 6.16 (s, 1H), 4.32-4.19 (m, 3H), 2.83 (s, 1H), 2.40 (dd, J=5.2, 5.2 Hz, 2H), 1.62 (dd, J=6.6, 3.6 Hz, 2H), 1.35 (s, 9H), 1.04 (dd, J=6.9, 3.9 Hz, 2H). MS (ESI) m/e (M+H$^+$) 496.0.

Example 108

N-(2-tert-Butyl-1-(2-hydroxy-3-(2H-tetrazol-5-yl)propyl)-1H-indol-5-yl)-1-(2,2-difluorobenzo[d][1,3]dioxol-5-yl)cyclopropanecarboxamide

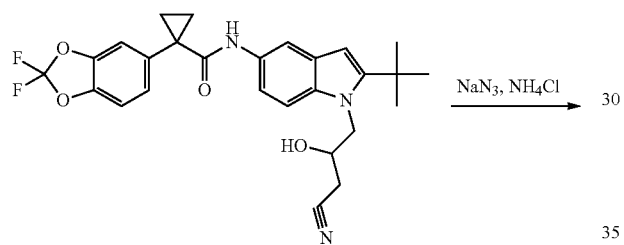

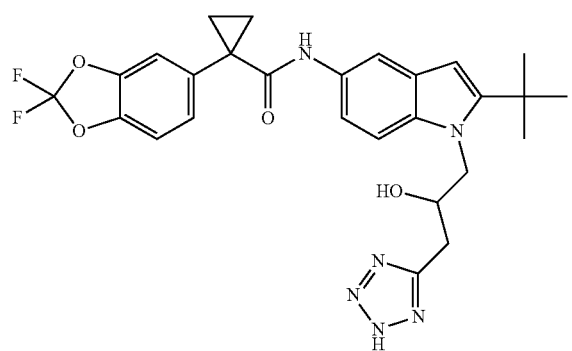

To a solution of N-(2-tert-butyl-1-(3-cyano-2-hydroxypropyl)-1H-indol-5-yl)-1-(2,2-difluorobenzo[d][1,3]dioxol-5-yl)cyclopropanecarboxamide (27 mg, 0.054 mmol) in anhydrous DMF (1.2 mL) were successively added NH$_4$Cl (35 mg, 0.65 mmol) and NaN$_3$ (43 mg, 0.65 mmol) at room temperature. The reaction mixture was stirred for 4 h at 110° C. in the microwave, at which stage 50% of the starting material was converted to the desired product. The reaction mixture was purified by preparative HPLC to provide N-(2-tert-butyl-1-(2-hydroxy-3-(2H-tetrazol-5-yl)propyl)-1H-indol-5-yl)-1-(2,2-difluorobenzo[d][1,3]dioxol-5-yl)cyclopropanecarboxamide. MS (ESI) m/e (M+H$^+$) 539.0.

Example 109

4-(2-tert-Butyl-5-(1-(2,2-difluorobenzo[d][1,3]dioxol-5-yl)cyclo-propanecarboxamido)-1H-indol-1-yl)-3-hydroxybutanoic acid

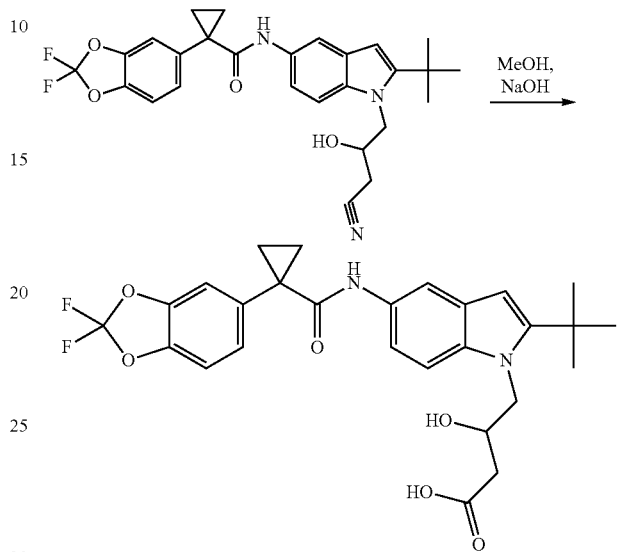

A solution of N-(2-tert-butyl-1-(3-cyano-2-hydroxypropyl)-1H-indol-5-yl)-1-(2,2-difluorobenzo[d][1,3]dioxol-5-yl)cyclopropanecarboxamide (14 mg, 0.028 mmol) in methanol (0.8 mL) and 4 M NaOH (0.8 mL) was stirred at 60° C. for 4 h. The reaction mixture was neutralized with 4 M HCl and concentrated. The residue was purified by preparative HPLC to provide 4-(2-tert-butyl-5-(1-(2,2-difluorobenzo[d][1,3]dioxol-5-yl)cyclopropanecarboxamido)-1H-indol-1-yl)-3-hydroxybutanoic acid. MS (ESI) m/e (M+H$^+$) 515.0.

Example 110

N-(1-(2-(2H-Tetrazol-5-yl)ethyl)-2-tert-butyl-1H-indol-5-yl)-1-(benzo[d][1,3]dioxol-5-yl)cyclopropanecarboxamide

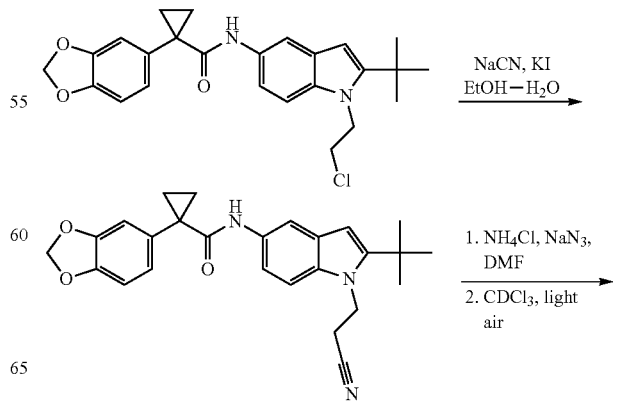

415

-continued

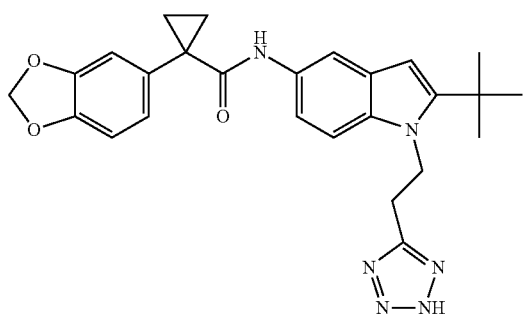

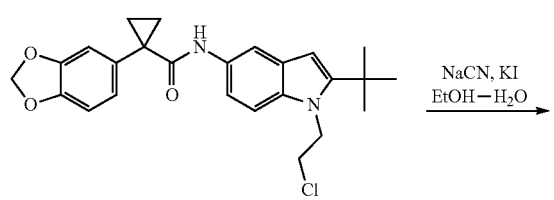

NaCN, KI
EtOH—H₂O

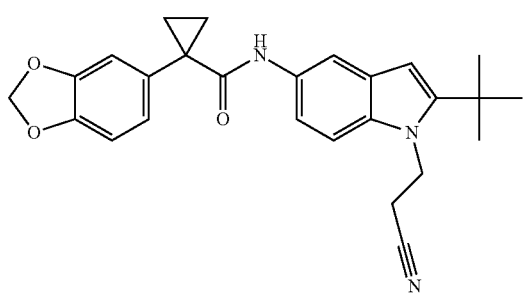

1-(Benzo[d][1,3]dioxol-5-yl)-N-(2-tert-butyl-1-(2-cyanoethyl)indolin-5-yl)-cyclopropanecarboxamide To a solution of 1-(benzo[d][1,3]dioxol-5-yl)-N-(2-tert-butyl-1-(2-chloroethyl)indolin-5-yl)cyclopropanecarboxamide (66 mg, 0.15 mmol) in ethanol (0.8 mL) and water (0.4 mL) were added NaCN (22 mg, 0.45 mmol) and KI (cat) at room temperature. The reaction mixture was stirred for 30 min at 110° C. in the microwave before being purified by column chromatography on silica gel (5-15% ethyl acetate/hexanes) to provide 1-(benzo[d][1,3]dioxol-5-yl)-N-(2-tert-butyl-1-(2-cyano-ethyl)indolin-5-yl)cyclopropanecarboxamide (50 mg, 77%).

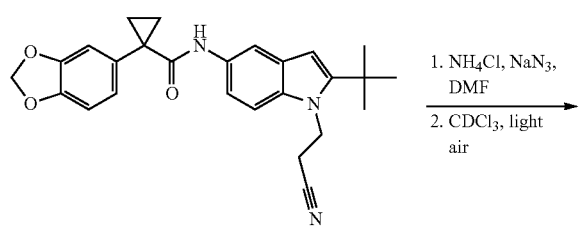

1. NH₄Cl, NaN₃, DMF
2. CDCl₃, light air

416

-continued

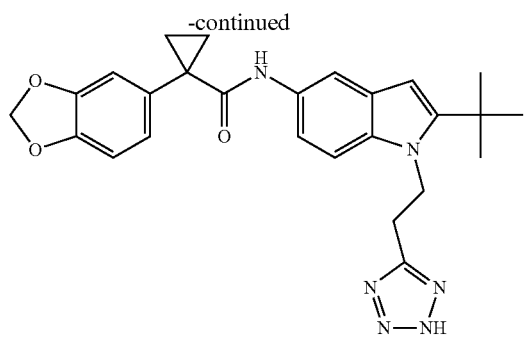

N-(1-(2-(2H-Tetrazol-5-yl)ethyl)-2-tert-butyl-1H-indol-5-yl)-1-(benzo[d][1,3]dioxol-5-yl)cyclopropanecarboxamide To a solution of 1-(benzo[d][1,3]dioxol-5-yl)-N-(2-tert-butyl-1-(2-cyano-ethyl)indolin-5-yl)cyclopropanecarboxamide (50 mg, 0.12 mmol) in anhydrous DMF (2.6 mL) was added NH₄Cl (230 mg, 4.3 mmol) and NaN₃ (280 mg, 4.3 mmol). The reaction mixture was stirred for 30 min at 110° C. in the microwave, filtrated, and purified by preparative HPLC. The solid residue was dissolved in CDCl₃ (3 mL) and briefly (2 to 4 min) exposed to daylight, which initiated a color change (purple). After 2 h of stirring open to the atmosphere at room temperature, the solvent was removed and the residue was purified by preparative HPLC to give N-(1-(2-(2H-tetrazol-5-yl)ethyl)-2-tert-butyl-1H-indol-5-yl)-1-(benzo[d][1,3]dioxol-5-yl)cyclopropanecarboxamide. MS (ESI) m/e (M+H⁺) 473.0.

Example 111

1-(Benzo[d][1,3]dioxol-5-yl)-N-(2-tert-butyl-6-fluoro-1-((tetrahydro-2H-pyran-3-yl)methyl)-1H-indol-5-yl)cyclopropanecarboxamide

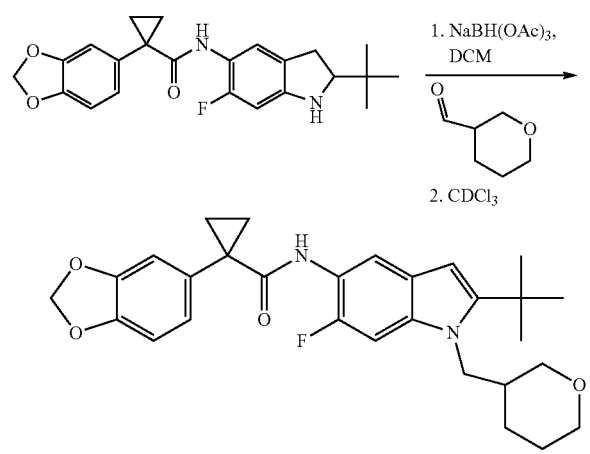

1. NaBH(OAc)₃, DCM
2. CDCl₃

To a solution of 1-(benzo[d][1,3]dioxol-5-yl)-N-(2-tert-butyl-6-fluoroindolin-5-yl)cyclopropane-carboxamide (150 mg, 0.38 mmol) in anhydrous dichloromethane (2.3 mL) at room temperature under N₂ was added tetrahydropyran-3-carbaldehyde (54 mg, 0.47 mmol). After 20 min of stirring, NaBH(OAc)₃ (110 mg, 0.51 mmol) was added in one portion at room temperature. The reaction mixture was stirred for 6 h at room temperature before being purified by column chromatography on silica gel (5-20% ethyl acetate/hexanes) to provide 1-(benzo[d][1,3]dioxol-5-yl)-N-(2-tert-butyl-6-fluoro-1-((tetrahydro-2H-pyran-3-yl)methyl)indolin-5-yl)cyclopropanecarboxamide (95 mg, 50%). CDCl₃ was added to the indoline and the solution was allowed to stir overnight at ambient temperature. The solution was concentrated to give 1-(benzo[d][1,3]dioxol-5-yl)-N-(2-tert-butyl-6-fluoro-1-((tetrahydro-2H-pyran-3-yl)methyl)-1H-indol-5-yl)cyclopropanecarboxamide. MS (ESI) m/e (M+H⁺) 493.0.

Example 112

1-(Benzo[d][1,3]dioxol-5-yl)-N-(2-(2-hydroxypropan-2-yl)-1H-indol-5-yl)cyclopropanecarboxamide

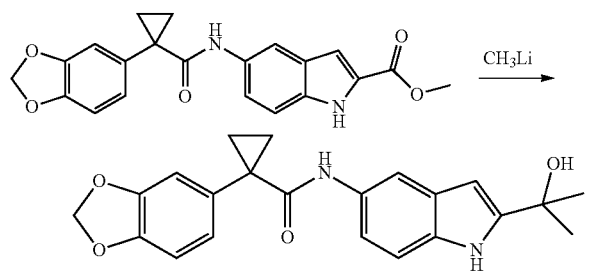

Methyl 5-(1-(benzo[d][1,3]dioxol-5-yl)cyclopropane-carboxamido)-1H-indole-2-carboxylate (100 mg, 0.255 mmol) was dissolved in anhydrous tetrahydrofuran (2 mL) under an argon atmosphere. The solution was cooled to 0° C. in an ice water bath before methyllithium (0.85 mL, 1.6 M in diethyl ether) was added by syringe. The mixture was allowed to warm to room temperature. The crude product was then partitioned between a saturated aqueous solution of sodium chloride (5 mL) and dichloromethane (5 mL). The organic layers were combined, dried over sodium sulfate, filtered, evaporated to dryness, and purified on 12 g of silica gel utilizing a gradient of 20-80% ethyl acetate in hexanes to yield 1-(benzo[d][1,3]dioxol-5-yl)-N-(2-(2-hydroxypropan-2-yl)-1H-indol-5-yl)cyclopropanecarboxamide (35 mg, 36%) as a white solid. ESI-MS m/z calc. 378.2. found 379.1 (M+1)⁺. Retention time of 2.18 minutes. ¹H NMR (400 MHz, DMSO-d6) δ 10.78 (s, 1H), 8.39 (s, 1H), 7.57 (d, J=1.7 Hz, 1H), 7.17 (d, J=8.6 Hz, 1H), 7.03-6.90 (m, 4H), 6.12 (d, J=1.5 Hz, 1H), 6.03 (s, 2H), 5.18 (s, 1H), 1.50 (s, 6H), 1.41-1.38 (m, 2H), 1.05-0.97 (m, 2H).

Example 113

N-(2-(1-Amino-2-methylpropan-2-yl)-1H-indol-5-yl)-1-(benzo[d][1,3]-dioxol-5-yl)cyclopropanecarboxamide

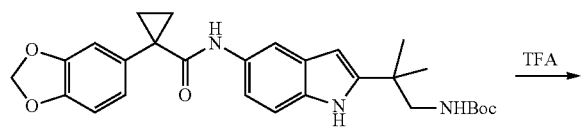

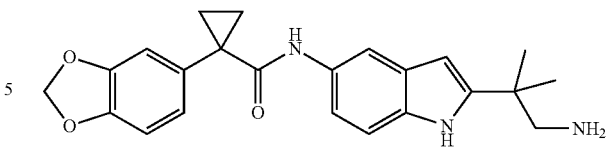

Trifluoroacetic acid (0.75 mL) was added to a solution of tert-butyl 2-(5-(1-(benzo[d][1,3]dioxol-5-yl)cyclopropanecarboxamido)-1H-indol-2-yl)-2-methylpropylcarbamate (77 mg, 0.16 mmol) in dichloromethane (3 mL) and the mixture was stirred at room temperature for 1.5 h. The mixture was evaporated, dissolved in dichloromethane, washed with saturated sodium bicarbonate solution, dried over magnesium sulfate and evaporated to dryness to give N-(2-(1-amino-2-methylpropan-2-yl)-1H-indol-5-yl)-1-(benzo[d][1,3]dioxol-5-yl)cyclopropanecarboxamide (53 mg, 86%). ¹H NMR (400 MHz, CDCl₃) δ 9.58 (s, 1H), 7.60 (d, J=1.6 Hz, 1H), 7.18-7.15 (m, 2H), 7.02-6.94 (m, 3H), 6.85 (d, J=7.8 Hz, 1H), 6.14 (d, J=1.2 Hz, 1H), 6.02 (s, 2H), 2.84 (s, 2H), 1.68 (dd, J=3.6, 6.7 Hz, 2H), 1.32 (s, 6H), 1.08 (dd, J=3.7, 6.8 Hz, 2H).

Example 114

1-(Benzo[d][1,3]dioxol-5-yl)-N-(2-(1-(dimethylamino)-2-methyl-propan-2-yl)-1H-indol-5-yl)cyclopropanecarboxamide

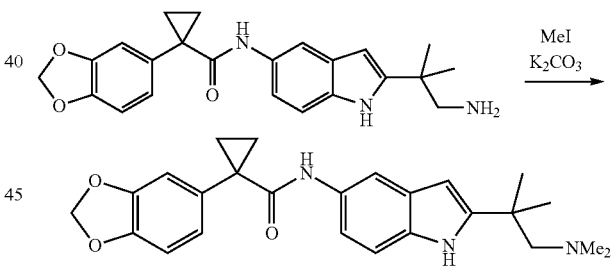

To a solution of N-(2-(1-amino-2-methylpropan-2-yl)-1H-indol-5-yl)-1-(benzo[d][1,3]dioxol-5-yl)cyclopropanecarboxamide (20 mg, 0.051 mmol) in DMF (1 mL) was added potassium carbonate (35 mg, 0.26 mmol) and iodomethane (7.0 µL, 0.11 mmol). The mixture was stirred for 2 h. Water was added and the mixture was extracted with dichloromethane. Combined organic phases were dried over magnesium sulfate, evaporated, coevaporated with toluene (3×) and purified by silica gel chromatography (0-30% EtOAc in hexane) to give 1-(benzo[d][1,3]dioxol-5-yl)-N-(2-(1-(dimethylamino)-2-methylpropan-2-yl)-1H-indol-5-yl)cyclopropanecarboxamide (7 mg, 33%). ¹H NMR (400 MHz, CDCl₃) δ 9.74 (s, 1H), 7.58 (d, J=1.9 Hz, 1H), 7.20 (d, J=8.6 Hz, 1H), 7.15 (s, 1H), 7.01-6.95 (m, 3H), 6.85 (d, J=7.9 Hz, 1H), 6.10 (d, J=0.9 Hz, 1H), 6.02 (s, 2H), 2.43 (s, 2H), 2.24 (s, 6H), 1.68 (dd, J=3.7, 6.7 Hz, 2H), 1.33 (s, 6H), 1.08 (dd, J=3.7, 6.8 Hz, 2H).

Example 115

N-(2-(1-Acetamido-2-methylpropan-2-yl)-1H-indol-5-yl)-1-(benzo[d][1,3]-dioxol-5-yl)cyclopropanecarboxamide

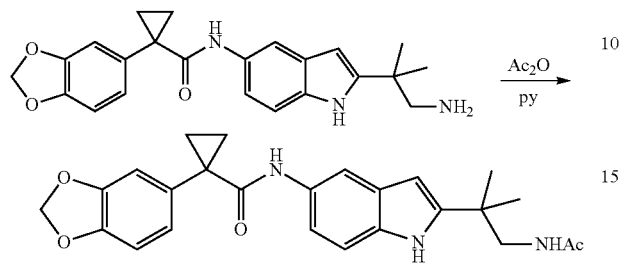

To a solution of N-(2-(1-amino-2-methylpropan-2-yl)-1H-indol-5-yl)-1-(benzo[d][1,3]-dioxol-5-yl)cyclopropanecarboxamide (21 mg, 0.054 mmol) in dichloromethane (1 mL) was added pyridine (14 µL, 0.16 mmol) followed by acetic anhydride (6.0 µL, 0.059 mmol). The mixture was stirred for 2 h. Water was added and the mixture was extracted with dichloromethane, evaporated, coevaporated with toluene (3×) and purified by silica gel chromatography (60-100% ethylacetate in hexane) to give N-(2-(1-acetamido-2-methylpropan-2-yl)-1H-indol-5-yl)-1-(benzo[d][1,3]-dioxol-5-yl)cyclopropanecarboxamide (17 mg, 73%). $^1$H NMR (400 MHz, DMSO) δ 10.79 (s, 1H), 8.39 (s, 1H), 7.66 (t, J=6.2 Hz, 1H), 7.56 (d, J=1.7 Hz, 1H), 7.18-7.14 (m, 1H), 7.02-6.89 (m, 4H), 6.08 (d, J=1.5 Hz, 1H), 6.03 (s, 2H), 3.31 (d, J=6.2 Hz, 2H), 1.80 (s, 3H), 1.41-1.38 (m, 2H), 1.26 (s, 6H), 1.04-1.01 (m, 2H).

Example 116

1-(Benzo[d][1,3]dioxol-5-yl)-N-(2-(2-methyl-4-(1H-tetrazol-5-yl)butan-2-yl)-1H-indol-5-yl)cyclopropanecarboxamide

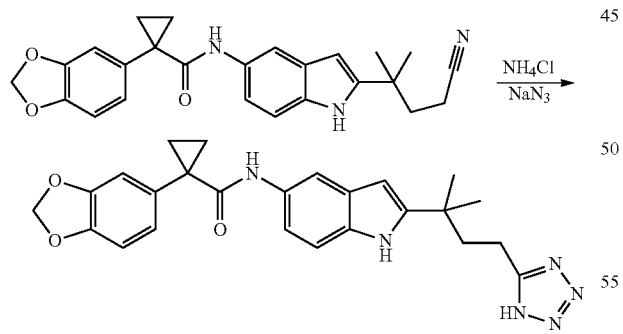

1-(Benzo[d][1,3]dioxol-5-yl)-N-(2-(4-cyano-2-methylbutan-2-yl)-1H-indol-5-yl)cyclopropanecarboxamide (83 mg, 0.20 mmol) was dissolved in N,N-dimethylformamide (1 mL) containing ammonium chloride (128 mg, 2.41 mmol), sodium azide (156 mg, 2.40 mmol), and a magnetic stir bar. The reaction mixture was heated at 110° C. for 40 minutes in a microwave reactor. The crude product was filtered and then purified by preparative HPLC using a gradient of 0-99% acetonitrile in water containing 0.05% trifluoroacetic acid to yield 1-(benzo[d][1,3]dioxol-5-yl)-N-(2-(2-methyl-4-(1H-tetrazol-5-yl)butan-2-yl)-1H-indol-5-yl)cyclopropanecarboxamide. ESI-MS m/z calc. 458.2. found 459.2 (M+1)$^+$. Retention time of 1.53 minutes. $^1$H NMR (400 MHz, CD$_3$CN) 9.23 (s, 1H), 7.51-7.48 (m, 2H), 7.19 (d, J=8.6 Hz, 1H), 7.06-7.03 (m, 2H), 6.95-6.89 (m, 2H), 6.17 (dd, J=0.7, 2.2 Hz, 1H), 6.02 (s, 2H), 2.61-2.57 (m, 2H), 2.07-2.03 (m, 2H), 1.55-1.51 (m, 2H), 1.39 (s, 6H), 1.12-1.09 (m, 2H).

Example 117

1-(Benzo[d][1,3]dioxol-5-yl)-N-(2-(piperidin-2-yl)-1H-indol-5-yl)cyclopropanecarboxamide

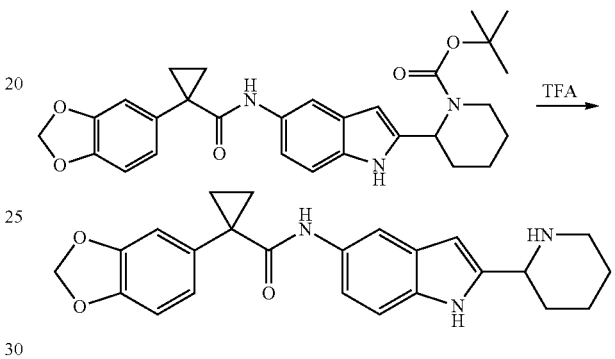

tert-Butyl 2-(5-(1-(benzo[d][1,3]dioxol-5-yl)cyclo-propanecarboxamido)-1H-indol-2-yl)piperidine-1-carboxylate (55 mg, 0.11 mmol) was dissolved in dichloromethane (2.5 mL) containing trifluoroacetic acid (1 mL). The reaction mixture was stirred for 6 h at room temperature. The crude product was purified by preparative HPLC using a gradient of 0-99% acetonitrile in water containing 0.05% trifluoroacetic acid to yield 1-(benzo[d][1,3]dioxol-5-yl)-N-(2-(piperidin-2-yl)-1H-indol-5-yl)cyclopropanecarboxamide. ESI-MS m/z calc. 403.2. found 404.4 (M+1)$^+$. Retention time of 0.95 minutes.

Example 118

5-tert-Butyl-1H-indol-6-ylamine

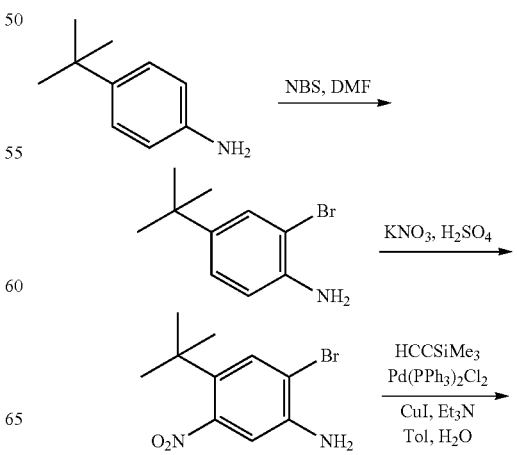

421

-continued

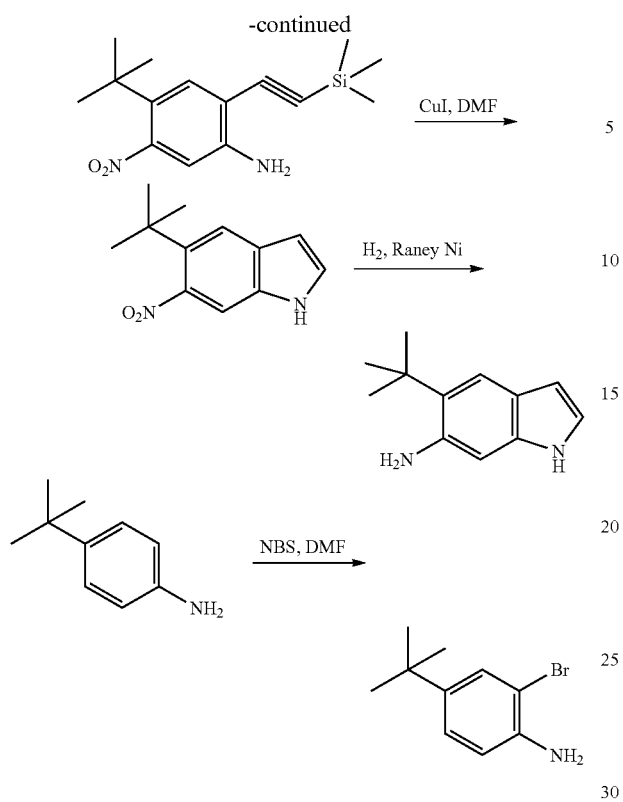

2-Bromo-4-tert-butyl-phenylamine

To a solution of 4-tert-Butyl-phenylamine (447 g, 3.00 mol) in DMF (500 mL) was added dropwise NBS (531 g, 3.00 mol) in DMF (500 mL) at room temperature. Upon completion, the reaction mixture was diluted with water and extracted with EtOAc. The organic layer was washed with water, brine, dried over $Na_2SO_4$ and concentrated. The crude product was directly used in the next step without further purification.

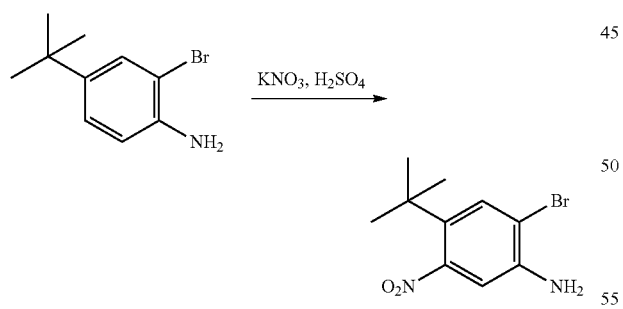

2-Bromo-4-tert-butyl-5-nitro-phenylamine

2-Bromo-4-tert-butyl-phenylamine (160 g, 0.71 mol) was added dropwise to $H_2SO_4$ (410 mL) at room temperature to yield a clear solution. This clear solution was then cooled down to −5 to −10° C. A solution of $KNO_3$ (83 g, 0.82 mol) in $H_2SO_4$ (410 mL) was added dropwise while the temperature was maintained between −5 to −10° C. Upon completion, the reaction mixture was poured into ice/water and extracted with EtOAc. The combined organic layers were washed with 5%

422

$Na_2CO_3$ and brine, dried over $Na_2SO_4$ and concentrated. The residue was purified by a column chromatography (ethyl acetate/petroleum ether 1:10) to give 2-bromo-4-tert-butyl-5-nitro-phenylamine as a yellow solid (150 g, 78%).

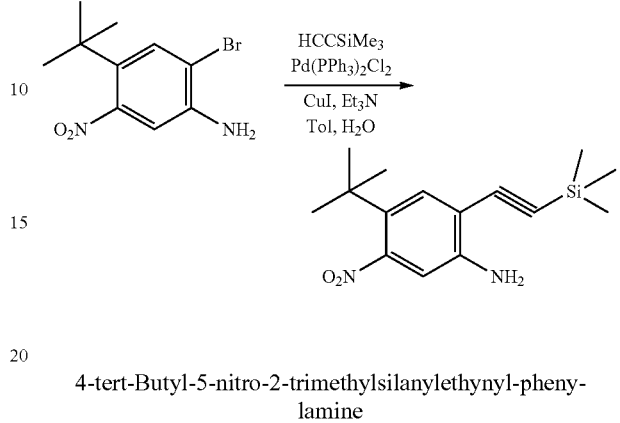

4-tert-Butyl-5-nitro-2-trimethylsilanylethynyl-phenylamine

To a mixture of 2-bromo-4-tert-butyl-5-nitro-phenylamine (27.3 g, 100 mmol) in toluene (200 mL) and water (100 mL) was added $Et_3N$ (27.9 mL, 200 mmol), $Pd(PPh_3)_2Cl_2$ (2.11 g, 3.00 mmol), CuI (950 mg, 0.500 mmol) and trimethylsilyl acetylene (21.2 mL, 150 mmol) under a nitrogen atmosphere. The reaction mixture was heated at 70° C. in a sealed pressure flask for 2.5 h., cooled down to room temperature and filtered through a short plug of Celite. The filter cake was washed with EtOAc. The combined filtrate was washed with 5% $NH_4OH$ solution and water, dried over $Na_2SO_4$ and concentrated. The crude product was purified by column chromatography (0-10% ethyl acetate/petroleum ether) to provide 4-tert-butyl-5-nitro-2-trimethylsilanylethynyl-phenylamine as a brown viscous liquid (25 g, 81%).

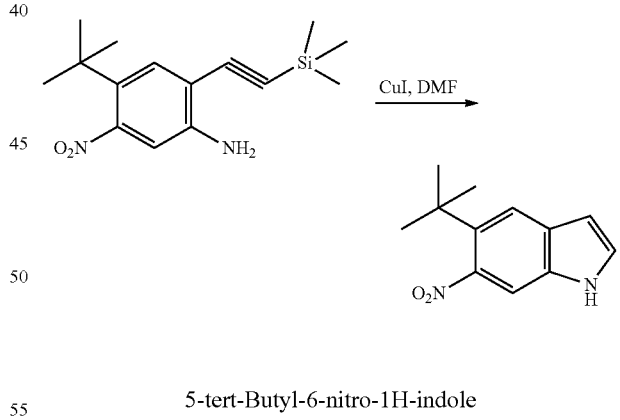

5-tert-Butyl-6-nitro-1H-indole

To a solution of 4-tert-butyl-5-nitro-2-trimethylsilanylethynyl-phenylamine (25 g, 86 mmol) in DMF (100 mL) was added CuI (8.2 g, 43 mmol) under a nitrogen atmosphere. The mixture was heated at 135° C. in a sealed pressure flask overnight, cooled down to room temperature and filtered through a short plug of Celite. The filter cake was washed with EtOAc. The combined filtrate was washed with water, dried over $Na_2SO_4$ and concentrated. The crude product was purified by column chromatography (10-20% ethyl aetate/hexane) to provide 5-tert-butyl-6-nitro-1H-indole as a yellow solid (13 g, 69%).

5-tert-Butyl-1H-indol-6-ylamine

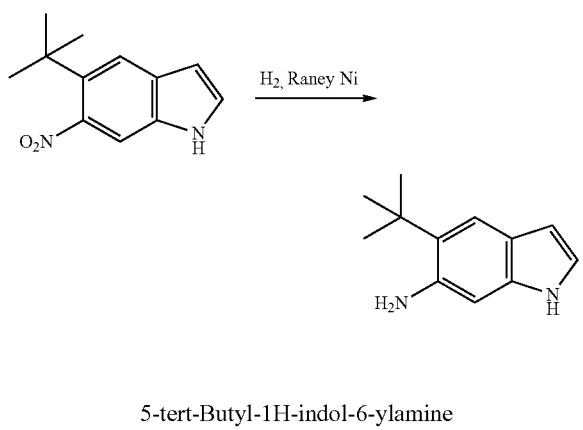

Raney Nickel (3 g) was added to 5-tert-butyl-6-nitro-1H-indole (15 g, 67 mmol) in methanol (100 mL). The mixture was stirred under hydrogen (1 atm) at 30° C. for 3 h. The catalyst was filtered off. The filtrate was dried over Na₂SO₄ and concentrated. The crude dark brown viscous oil was purified by column chromatography (10-20% ethyl acetate/petroleum ether) to give 5-tert-butyl-1H-indol-6-ylamine as a gray solid (11 g, 87%). $^1$H NMR (300 MHz, DMSO-d6) δ 10.3 (br s, 1H), 7.2 (s, 1H), 6.9 (m, 1H), 6.6 (s, 1H), 6.1 (m, 1H), 4.4 (br s, 2H), 1.3 (s, 9H).

1-(2,3-Dihydro-1H-inden-5-yl)cyclopropanecarboxylic acid

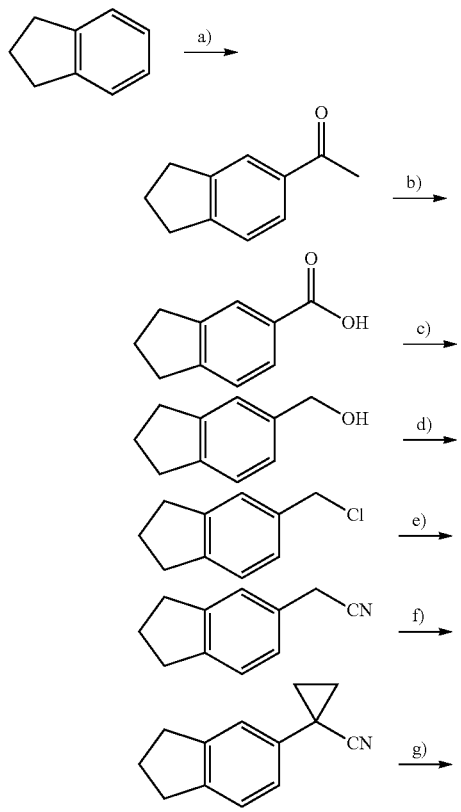

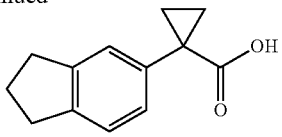

a) Ac₂O, AlCl₃, CH₂Cl₂; b) NaClO; c) LiAlH₄, THF, -78° C.; d) SOCl₂ CHCl₃; e) NaCN, DMSO; f) BrCH₂CH₂Cl, NaOH, Bu₄NBr, toluene; g) NaOH Step a: 1-(2,3-Dihydro-1H-inden-6-yl)ethanone A mixture of 2,3-dihydro-1H-indene (100.0 g, 0.85 mol) and acetic anhydride (104.2 g, 1.35 mol) was added dropwise to a slurry of AlCl₃ (272.0 g, 2.04 mol) in CH₂Cl₂ (1000 ml) at 0° C. over a period of 3 h. The reaction mixture was stirred at room temperature under a nitrogen atmosphere for 15 h. Then the reaction mixture was poured into ice water (500 mL) and extracted with ethyl acetate (500 mL×3). The combined organic layers were washed with brine (500 mL), dried over Na₂SO₄ and evaporated in vacuo. The residue that was purified by column chromatography (petroleum ether:ethyl acetate=20:1) to give the product (120.0 g, 88%). $^1$H NMR (400 MHz, CDCl₃) δ 2.08-2.15 (m, 2H), 2.58 (s, 3H), 2.95 (t, J=7.2, 4 H), 7.28 (d, J=8.0, 1H), 7.75 (d, J=8.0, 1H) 7.82 (s, 1H).

Step b: 2,3-dihydro-1H-indene-5-carboxylic acid

To a stirred aqueous sodium hypochlorite solution (2230 ml, 1.80 mmol, 6%) at 55° C. was added 1-(2,3-dihydro-1H-inden-6-yl)ethanone (120.0 g, 0.75 mol) and the mixture was stirred at 55° C. for 2 h. After cooling to room temperature, saturated NaHCO₃ solution was added until the solution became clear. The produced precipitate was filtered, washed several times with water and dried to afford the desired product (120.0 g, 99%). $^1$H NMR (CDCl₃, 300 MHz) δ 2.07-2.17 (m, 2H), 2.96 (t, J=7.5 Hz, 4H), 7.30 (d, J=7.8, 1H), 7.91 (d, J=7.8, 1H), 7.96 (s, 1H).

Step c: (2,3-dihydro-1H-inden-5-yl)methanol

To a stirred solution of LAH (72.8 g, 1.92 mol) in THF (2.5 L) at 0° C. was slowly added 2,3-dihydro-1H-indene-5-carboxylic acid (100.0 g, 0.62 mol). The reaction mixture was stirred at 0° C. for 1 h. Then the reaction was quenched with H₂O (72 ml) and NaOH (68 ml, 20%). The mixture was filtered and the organic layer was dried over Na₂SO₄, evaporated in vacuo and the residue was purified by column chromatography (petroleum ether:ethyl acetate=10:1) to give the desired product (82.0 g, 90%). $^1$H NMR (CDCl₃, 300 MHz); δ 2.03-2.13 (m, 2H), 2.91 (t, J=7.5 Hz, 4H), 4.64 (s, 2H), 7.13 (d, J=7.5, 1H), 7.18-7.24 (m, 2H).

Step d: 5-(chloromethyl)-2,3-dihydro-1H-indene

Thionyl chloride (120 ml, 1.65 mol) was added drop-wise to a rapidly stirred mixture of (2,3-dihydro-1H-inden-5-yl)methanol (81.4 g, 0.55 mol) in chloroform (500 ml) at 0° C. After the addition was complete, the resulting mixture was allowed to warm to room temperature and the stirring was continued for an additional 12 h. The chloroform was evaporated under reduced pressure to give a residue, that was purified by column chromatography (petroleum ether:ethyl acetate=15:1) to afford 5-(chloromethyl)-2,3-dihydro-1H-indene (90.5 g, 99%). $^1$H NMR (300 MHz, CDCl$_3$) δ 2.06-2.19 (m, 4H), 2.93 (t, J=7.5, 4H), 4.54 (s, 2H), 7.15-7.31 (m, 3H).

Step e: 2-(2,3-dihydro-1H-inden-5-yl)acetonitrile

To a stirred solution of 5-(chloromethyl)-2,3-dihydro-1H-indene (90.0 g, 0.54 mol) in DMSO (500 ml) was added sodium cyanide (54.0 g, 1.08 mol) at 0° C. portion wise. The reaction mixture was then stirred at room temperature for 3 hours. The reaction was quenched with water (1000 ml), extracted with ethyl acetate (3×250 mL). The combined organic layers were washed with brine, dried over Na$_2$SO$_4$ and evaporated in vacuo to afford 2-(2,3-dihydro-1H-inden-5-yl)acetonitrile (82.2 g, 97%), that was used in the next step without further purification.

Step f: 1-(2,3-dihydro-1H-inden-6-yl)cyclopropanecarbonitrile

To a stirred solution of 2-(2,3-dihydro-1H-inden-5-yl)acetonitrile (50.0 g, 0.32 mol) in toluene (150 mL) was added sodium hydroxide (300 mL, 50 percent in water W/W), 1-bromo-2-chloroethane (92.6 ml, 1.12 mol) and (n-Bu)$_4$NBr (5 g, 15.51 mmol). The mixture was heated at 60° C. overnight. After cooling to room temperature, the reaction mixture was diluted with water (400 mL) and extracted with EtOAc (3×200 mL). The combined organic extracts were washed with brine, dried over Na$_2$SO$_4$, filtered and concentrated under vacuum and purified by column chromatography (petroleum ether:ethyl acetate=10:1) to yield 1-(2,3-dihydro-1H-inden-6-yl)cyclopropanecarbonitrile (9.3 g, 16%). $^1$H NMR (CDCl$_3$, 300 MHz) δ 1.35-1.38 (m, 2H), 1.66-1.69 (m, 2H), 2.05-2.13 (m, 2H), 2.87-294 (m, 4H), 7.07-7.22 (m, 3H).

Step g: 1-(2,3-dihydro-1H-inden-6-yl)cyclopropanecarboxylic acid

To a stirred 1-(2,3-dihydro-1H-inden-6-yl)cyclopropanecarbonitrile (9.3 g, 50.8 mmol) in methanol (40 mL) was added a solution of 150 mL of sodium hydroxide (25% NaOH w/w in water). The mixture was heated at 100° C. for 8 hours. After cooling to room temperature, the reaction mixture was poured over ice-water (0° C.), the pH was adjusted to pH=4 with hydrogen chloride (1 N) and the mixture was extracted with dichloromethane (3×100 mL). The combined organic layers were dried over Na$_2$SO$_4$ and evaporated under vacuum. The residue that was purified by column chromatography (petroleum ether:ethyl acetate=5:1) to give 1-(2,3-dihydro-1H-inden-6-yl)cyclopropanecarboxylic acid (4.8 g, 47%). $^1$H NMR (CDCl$_3$, 400 MHz) δ 1.23-1.26 (m, 2H), 1.62-1.65 (m, 2H), 2.03-210 (m, 2H), 2.81-2.91 (m, 4H), 7.11-7.21 (m, 3H).

5-Amino-2-tert-butyl-1H-indole-4-carbonitrile

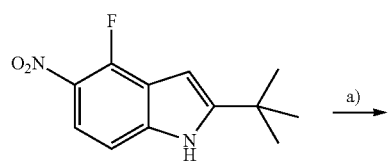

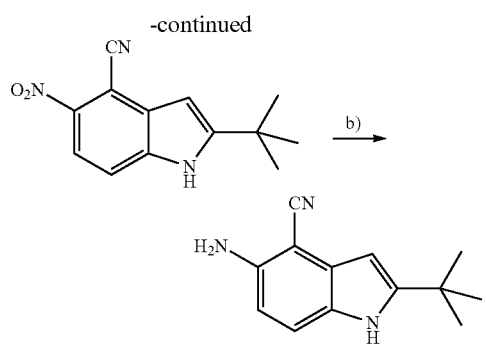

a) KCN, DMSO; b) Pd/C, EtOAc

Step a: 2-tert-butyl-5-nitro-1H-indole-4-carbonitrile

To a solution of 2-tert-butyl-4-fluoro-5-nitro-1H-indole (4.0 g, 17 mmol) in DMSO (30 mL) was added KCN (3.4 g, 51 mmol). The mixture was stirred at 70° C. for 3 hours, and poured into water (80 mL) and extracted with ethyl acetate (50 mL×3). The combined organic layers were washed with brine, dried over anhydrous Na$_2$SO$_4$ and concentrated under vacuum. The residue was purified by column chromatography on silica gel (7% EtOAc in petroleum ether) to afford 2-tert-butyl-5-nitro-1H-indole-4-carbonitrile (2.2 g, 53%). $^1$H NMR (DMSO, 300 MHz) δ 12.23 (br s, 1H), 8.09 (d, J=9.0 Hz, 1H), 7.75 (d, J=9.0 Hz, 1H), 6.50 (s, 1H), 1.38 (s, 9H). MS (ESI) m/z: 244.2 [M+H$^+$].

Step b: 5-amino-2-tert-butyl-1H-indole-4-carbonitrile

To a solution of 2-tert-butyl-5-nitro-1H-indole-4-carbonitrile (550 mg, 2.3 mmol) in EtOAc (10 mL) was added Raney Ni (0.1 g) under a nitrogen atmosphere. The mixture was stirred under hydrogen atmosphere (1 atm) at room temperature for 1 h. The catalyst was filtered over Celite and the filtrate was evaporated in vacuo to afford 5-amino-2-tert-butyl-1H-indole-4-carbonitrile (250 mg, 51%). $^1$H NMR (DMSO, 300 MHz) δ 10.93 (br s, 1H), 7.25 (d, J=8.7 Hz, 1H), 6.49 (d, J=8.7 Hz, 1H), 5.94 (d, J=2.1 Hz, 1H), 5.40 (br s, 2H), 1.30 (s, 9H). MS (ESI) m/z: 214.0 [M+H$^+$].

N-(2-tert-butyl-4-cyano-1H-indol-5-yl)-1-(2,2-difluorobenzo[d][1,3]dioxol-5-yl)cyclopropanecarboxamide

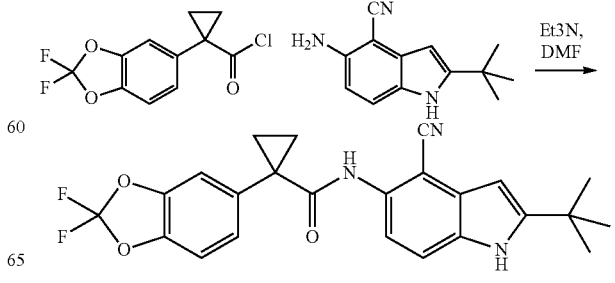

Step a: N-(2-tert-butyl-4-cyano-1H-indol-5-yl)-1-(2,2-difluorobenzo[d][1,3]dioxol-5-yl)cyclopropanecarboxamide 1-(2,2-difluorobenzo[d][1,3]dioxol-5-yl)cyclopropanecarbonyl chloride (26 mg, 0.1 mmol) was added to a solution of 5-amino-2-tert-butyl-1H-indole-4-carbonitrile (21 mg, 0.1 mmol) and triethylamine (41.7 µL, 0.3 mmol) in DMF (1 mL). The reaction was stirred at room temperature overnight, then filtered and purified by reverse-phase HPLC to yield the product, N-(2-tert-butyl-4-cyano-1H-indol-5-yl)-1-(2,2-difluorobenzo[d][1,3]dioxol-5-yl)cyclopropanecarboxamide. ESI-MS m/z calc. 437.2. found 438.7 (M+1)⁺. Retention time 2.10 minutes. ¹H NMR (400 MHz, DMSO-d6) δ 11.48 (s, 1H), 8.88 (s, 1H), 7.52 (d, J=8.5 Hz, 2H), 7.41 (d, J=8.3 Hz, 1H), 7.32 (dd, J=1.5, 8.3 Hz, 1H), 7.03 (d, J=8.6 Hz, 1H), 6.21 (d, J=1.8 Hz, 1H), 1.51-1.49 (m, 2H), 1.36 (s, 9H), 1.18-1.16 (m, 2H).

N-(2-tert-butyl-4-cyano-1-(2-hydroxyethyl)-1H-indol-5-yl)-1-(2,2-difluorobenzo[d][1,3]dioxol-5-yl)cyclopropanecarboxamide

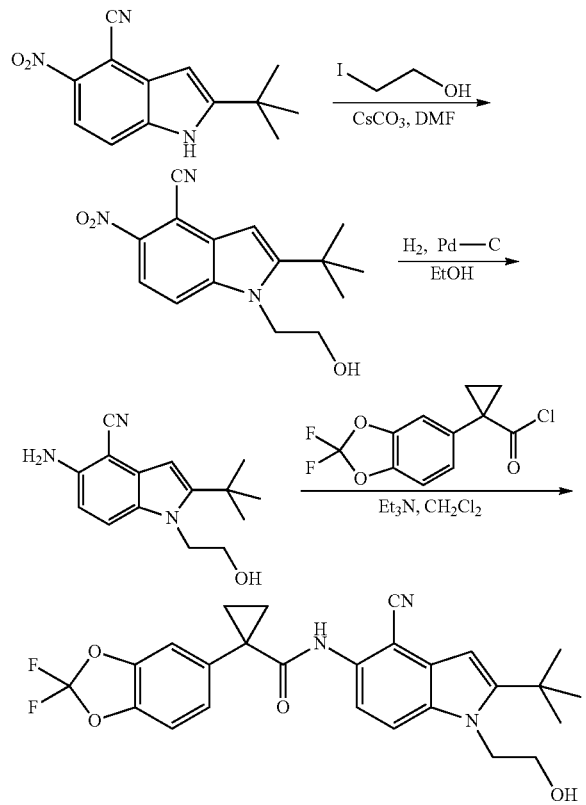

Step a: 2-tert-butyl-1-(2-hydroxyethyl)-5-nitro-1H-indole-4-carbonitrile

A mixture of 2-tert-butyl-5-nitro-1H-indole-4-carbonitrile (200 mg, 0.82 mmol), 2-iodoethanol (77 µL, 0.98 mmol), cesium carbonate (534 mg, 1.64 mmol) and DMF (1.3 mL) was heated to 90° C. overnight. Then more 2-iodoethanol (77 µL, 0.98 mmol) was added and the reaction was stirred at 90° C. for 3 days. The reaction mixture was partitioned between ethyl acetate and water. The aqueous layer was washed with ethyl acetate and then the combined ethyl acetate layers were washed with water (×3) and brine, dried over MgSO₄ and concentrated. The residue was purified by column chromatography (50-100% CH₂Cl₂-Hexanes) to yield the product as a yellow solid (180 mg, ~25% purity by NMR, product co-elutes with the indole starting material). ESI-MS m/z calc. 287.1. found 288.5 (M+1)⁺. Retention time 1.59 minutes. ¹H NMR (400 MHz, DMSO-d6) δ 12.23 (s, 1H), 8.14 (d, J=9.1 Hz, 1H), 8.02 (d, J=9.1 Hz, 1H), 6.60 (s, 1H), 5.10 (t, J=5.5 Hz, 1H), 4.55 (t, J=6.3 Hz, 2H), 3.78-3.73 (m, 2H) and 1.49 (s, 9H) ppm.

Step b: 5-amino-2-tert-butyl-1-(2-hydroxyethyl)-1H-indole-4-carbonitrile

To a solution of 2-tert-butyl-1-(2-hydroxyethyl)-5-nitro-1H-indole-4-carbonitrile (180 mg, 0.63 mmol) in ethanol (6 mL) under N₂ atmosphere was added Pd—C (5% wt, 18 mg). The reaction was flushed with N₂ (g) and then with H₂ (g) and stirred under H₂ (atm) at room temperature for 1.5 hours. The reaction was filtered over Celite and concentrated to yield the product (150 mg, 93%). ESI-MS m/z calc. 257.2. found 258.5 (M+1)⁺. Retention time 1.26 minutes.

Step c: N-(2-tert-butyl-4-cyano-1-(2-hydroxyethyl)-1H-indol-5-yl)-1-(2,2-difluorobenzo[d][1,3]dioxol-5-yl)cyclopropanecarboxamide 1-(2,2-difluorobenzo[d][1,3]dioxol-5-yl)cyclopropanecarbonyl chloride (196 mg, 0.75 mmol) was added to a solution of 5-amino-2-tert-butyl-1-(2-hydroxyethyl)-1H-indole-4-carbonitrile (150 mg, 0.58 mmol) and triethylamine (242 µL, 1.74 mmol) in dichloromethane (2 mL). The reaction was stirred at room temperature overnight. The reaction mixture was diluted with dichloromethane and extracted with 1N HCl solution (×2), saturated NaHCO₃ solution (×2), brine, dried over MgSO₄, filtered and concentrated. The residue was dissolved in DMSO and purified by reverse-phase HPLC to yield the product, N-(2-tert-butyl-4-cyano-1-(2-hydroxyethyl)-1H-indol-5-yl)-1-(2,2-difluorobenzo[d][1,3]dioxol-5-yl)cyclopropanecarboxamide. ESI-MS m/z calc. 481.2. found 482.5 (M+1)⁺. Retention time 1.99 minutes. ¹H NMR (400 MHz, DMSO-d6) δ 8.93 (s, 1H), 7.71 (d, J=8.8 Hz, 1H), 7.51 (s, 1H), 7.42 (d, J=8.3 Hz, 1H), 7.33 (d, J=1.6 Hz, 1H), 7.08 (d, J=8.8 Hz, 1H), 6.28 (s, 1H), 5.05 (t, J=5.6 Hz, 1H), 4.42 (t, J=6.8 Hz, 2H), 3.70-3.65 (m, 2H), 1.51-1.48 (m, 2H), 1.44 (s, 9H), 1.19-1.16 (m, 2H).

2-(2-tert-butyl-5-(1-(2,2-difluorobenzo[d][1,3]dioxol-5-yl)cyclopropanecarboxamido)-6-fluoro-1H-indol-1-yl)-N,N,N-trimethylethanaminium chloride

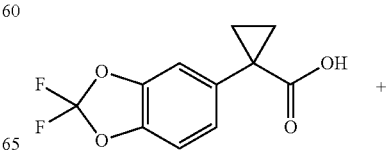 +

429
-continued

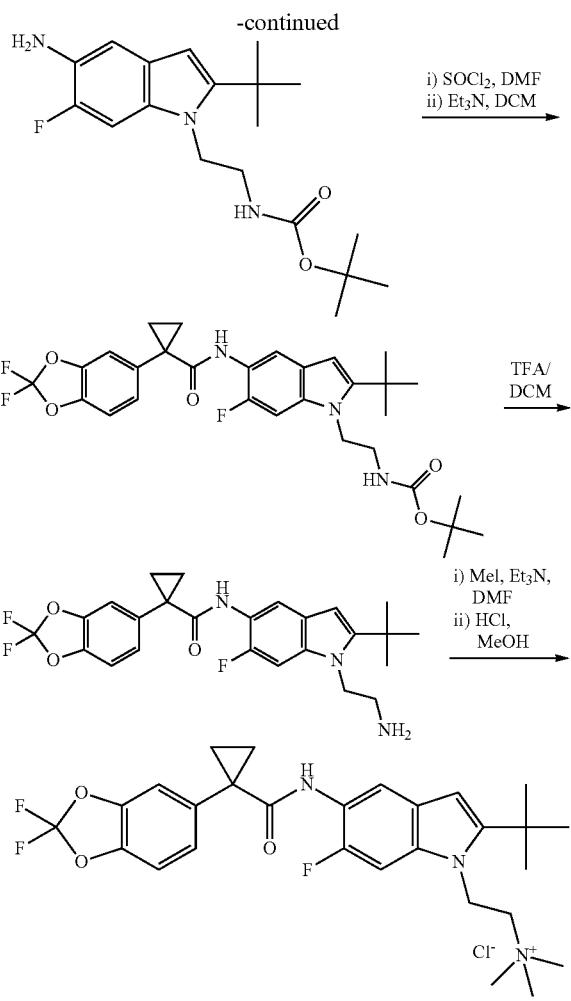

Step a: tert-Butyl 2-(2-tert-butyl-5-(1-(2,2-difluorobenzo[d][1,3]dioxol-5-yl)cyclopropanecarboxamido)-6-fluoro-1H-indol-1-yl)ethylcarbamate To 1-(2,2-difluorobenzo[d][1,3]dioxol-5-yl)cyclopropanecarboxylic acid (90.14 mg, 0.3722 mmol) in thionyl chloride (81.28 µL, 1.117 mmol) was added N,N-dimethyl formamide (8.204 µL, 0.1064 mmol). The reaction mixture was stirred at room temperature for 30 minutes before excess thionyl chloride and N,N-dimethyl formamide were removed in vacuo to yield the acid chloride. The acid chloride was then dissolved in dichloromethane (1.5 mL) and added slowly to a solution of tert-butyl 2-(5-amino-2-tert-butyl-6-fluoro-1H-indol-1-yl)ethylcarbamate (156.1 mg, 0.4467 mmol) and triethylamine (155.6 µL, 1.117 mmol) in dichloromethane (1.5 mL). The resulting reaction mixture was stirred at room temperature for 21 hours. The reaction mixture was diluted with dichloromethane (5 mL) and washed with 1N aqueous HCl (5 mL) and a saturated aqueous NaHCO₃ solution (5 mL). The organic layer was dried over Na₂SO₄, filtered and evaporated under reduced pressure. The crude product was purified by column chromatography on silica gel (0-30% ethyl acetate in hexane) to yield tert-butyl 2-(2-tert-butyl-5-(1-(2,2-difluorobenzo[d][1,3]dioxol-5-yl)cyclopropanecarboxamido)-6-fluoro-1H-indol-1-yl)ethylcarbamate as a white solid (140 mg, 66%). ESI-MS m/z calc. 573.2. found 574.7 (M+1)⁺. Retention time 2.41 minutes. ¹H NMR (400.0 MHz, DMSO) d 8.35 (s, 1H), 7.53 (s, 1H), 7.44-7.41 (m, 2H), 7.34-7.29 (m, 2H), 7.13-7.10 (m, 1H), 6.17 (s, 1H), 4.24-4.20 (m, 2H), 3.20-3.17 (m, 2H), 1.48-1.45 (m, 2H), 1.41 (s, 18H) and 1.15-1.12 (m, 2H) ppm.

Step b: N-(1-(2-aminoethyl)-2-tert-butyl-6-fluoro-1H-indol-5-yl)-1-(2,2-difluorobenzo[d][1,3]dioxol-5-yl)cyclopropanecarboxamide To a solution of tert-butyl 2-(2-tert-butyl-5-(1-(2,2-difluorobenzo[d][1,3]dioxol-5-yl)cyclopropanecarboxamido)-6-fluoro-1H-indol-1-yl)ethylcarbamate (137.5 mg, 0.24 mmol) in dichloromethane (1.8 mL) was added trifluoroacetic acid (444 µL, 5.8 mmol) and the mixture was stirred at room temperature for 1 hour. The reaction was diluted with dichloromethane and washed with saturated aqueous NaHCO₃ solution (3 mL) and brine (3 mL). The organic layer was dried over Na₂SO₄, filtered and evaporated under reduced pressure. The crude product was purified by column chromatography on silica gel (0-10% methanol in dichloromethane) to yield N-(1-(2-aminoethyl)-2-tert-butyl-6-fluoro-1H-indol-5-yl)-1-(2,2-difluorobenzo[d][1,3]dioxol-5-yl)cyclopropanecarboxamide as a white solid (93.7 mg, 82%). ESI-MS m/z calc. 473.19. found 474.5 (M+1)⁺. Retention time 1.61 minutes.

Step c: 2-(2-tert-butyl-5-(1-(2,2-difluorobenzo[d][1,3]dioxol-5-yl)cyclopropanecarboxamido)-6-fluoro-1H-indol-1-yl)-N,N,N-trimethylethanaminium chloride To a clear solution of N-(1-(2-aminoethyl)-2-tert-butyl-6-fluoro-1H-indol-5-yl)-1-(2,2-difluorobenzo[d][1,3]dioxol-5-yl)cyclopropanecarboxamide (50 mg, 0.1056 mmol) in N,N-dimethyl formamide (1 mL), methyl iodide (336.8 mg, 147.7 µL, 2.37 mmol) and triethylamine (106.9 mg, 147.2 µL, 1.05 mmol) were added and the mixture was heated at 80° C. for 2 hours. The crude product was purified by reverse phase preparative HPLC. 22 mg of this product were dissolved in 1.25 M HCl in methanol (112 µL, 0.14 mmol) and heated at 60° C. for 1 hour. The reaction was cooled to room temperature. The product was first dried and then dissolved in dichloromethane and dried again. This procedure was repeated four times to yield 2-(2-tert-butyl-5-(1-(2,2-difluorobenzo[d][1,3]dioxol-5-yl)cyclopropanecarboxamido)-6-fluoro-1H-indol-1-yl)-N,N,N-trimethylethanaminium chloride. ESI-MS m/z calc. 516.25. found 516.7 (M+1)⁺. Retention time 1.69 minutes. ¹H NMR (400.0 MHz, DMSO) d 8.43 (s, 1H), 7.53 (s, 1H), 7.45-7.41 (m, 2H), 7.36-7.31 (m, 2H), 6.27 (s, 1H), 4.74-4.70 (m, 2H), 3.57-3.53 (m, 2H), 3.29 (s, 9H), 1.48-1.42 (m, 11H), and 1.15 (dd, J=3.9, 6.8 Hz, 2H) ppm.

2-(4-(Tert-butyldimethylsilyloxy)-2-methylbutan-2-yl)-6-fluoro-5-nitro-1H-indole

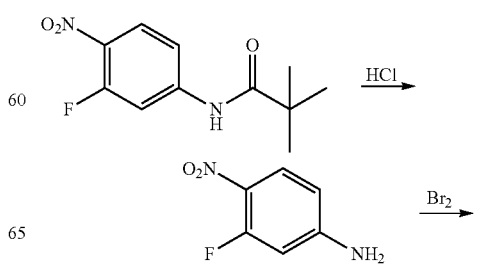

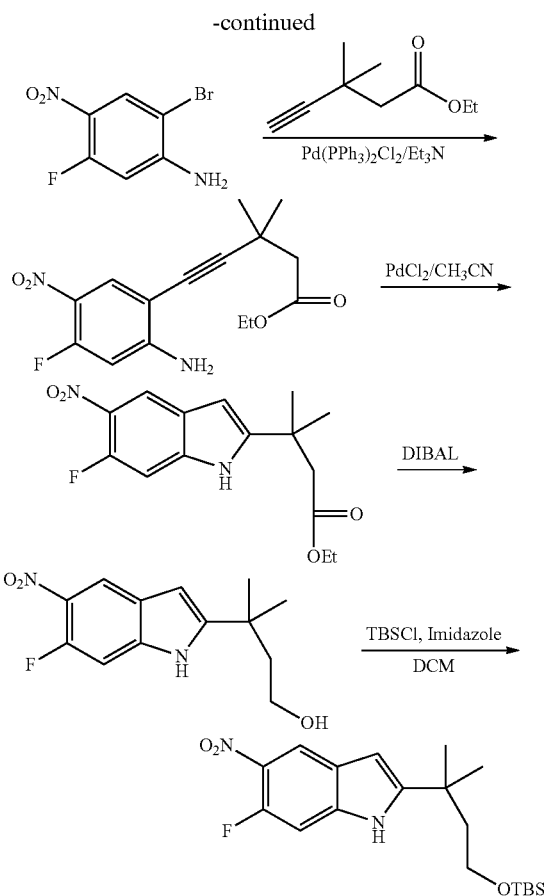

Step a: 3-fluoro-4-nitroaniline

A mixture of N-(3-fluoro-4-nitro-phenyl)-2,2-dimethyl-propionamide (87.0 g, 0.36 mol) in CH$_2$Cl$_2$ (400 mL) and 6N hydrochloric acid (800 mL) was heated to reflux for 2 hours. The reaction mixture was cooled to room temperature. The reaction mixture was diluted with 1000 mL of ethyl acetate and potassium carbonate (500.0 g) was added portion wise. The aqueous solution was separated and the organic layer was washed with brine and dried over anhydrous Na$_2$SO$_4$. The solvent was removed by evaporation under reduced pressure; the residue was purified by column chromatography on silica gel (petroleum ether/ethyl acetate 30:1) to afford 3-fluoro-4-nitroaniline (56.0 g, 99%). $^1$H NMR (300 MHz, CDCl$_3$) δ 8.07 (t, J=8.7 Hz, 1H), 7.86 (dd, J=2.1, 13.2 Hz 1H), 7.59 (brs, 2H), 7.22 (s, 1H).

Step b: 2-bromo-5-fluoro-4-nitroaniline

To a solution of 3-fluoro-4-nitroaniline (56 g, 0.36 mol) in acetic acid (500 mL) was added drop-wise bromine (17.7 mL, 0.36 mol) over 1 hour. The reaction mixture was stirred for 1 hour at 0-5° C. in an ice bath. The reaction mixture was basified with saturated Na$_2$CO$_3$ and extracted with ethyl acetate (200 mL×3). The combined organic layers were washed with brine, dried over anhydrous Na$_2$SO$_4$, filtered and concentrated under reduced pressure to yield a residue that was purified by column chromatography on silica gel (petroleum ether/ethyl acetate 10:1) to give the 2-bromo-5-fluoro-4-nitroaniline (45.6 g, 84%) as a yellow solid. $^1$H NMR (400 MHz, CDCl$_3$) δ 8.29 (d, J=7.6 Hz, 1H), 653 (d, J=12.4 Hz, 1H), 4.94 (br s, 2H).

Step c: ethyl 5-(2-amino-4-fluoro-5-nitrophenyl)-3,3-dimethylpent-4-ynoate

To a solution of 2-bromo-5-fluoro-4-nitroaniline (45.7 g, 0.19 mol) and ethyl 3,3-dimethylpent-4-ynoate (88.3 g, 0.57 mol) in Et$_3$N (700 mL) was added Pd(PPh$_3$)$_2$Cl$_2$ (13.8 g, 0.02 mol) and CuI (3.6 g, 0.02 mol) under N$_2$. The reaction mixture was stirred at 70° C. for 8 hours. The reaction mixture was diluted with 500 mL of ethyl acetate and 1500 mL of water. The organic layer was separated and the aqueous phase was extracted with ethyl acetate (500 mL×3), the combined organic layers were washed with brine and dried over anhydrous Na$_2$SO$_4$, filtered and evaporated under reduced pressure and the residue was purified by column chromatography on silica gel (petroleum ether/ethyl acetate 10:1) to give ethyl-5-(2-amino-4-fluoro-5-nitrophenyl)-3,3-dimethyl-pent-4-ynoate (34.5 g, 57%). $^1$H NMR (300 MHz, CDCl$_3$) δ 8.05 (d, J=8.1 Hz, 1H), 6.36 (d, J=13.2 Hz, 1H), 5.60 (brs, 2H), 4.16 (q, J=7.2 Hz, 2H), 2.51 (s, 2H), 1.40 (s, 6H), 1.28 (t, J=7.2 Hz, 3H).

Step d: ethyl 3-(6-fluoro-5-nitro-1H-indol-2-yl)-3-methylbutanoate

To a mixture of ethyl 5-(2-amino-4-fluoro-5-nitrophenyl)-3,3-dimethylpent-4-ynoate (34.5 g, 0.11 mol) and PdCl$_2$ (10.4 g, 58.6 nmol) in CH$_3$CN (350 mL) was heated to reflux for 1.5 hours. The reaction mixture was cooled down to room temperature. Ethyl acetate (300 mL) was added, the precipitate was filtered off and washed with methanol. The filtrate was concentrated under reduced pressure and the residue was purified by column chromatography on silica gel (petroleum ether/ethyl acetate 40:1) to give ethyl 3-(6-fluoro-5-nitro-1H-indol-2-yl)-3-methylbutanoate (34.0 g, 98%) as a deep yellow solid. $^1$H NMR (300 MHz, CDCl$_3$) δ 10.11 (brs, 1H), 8.30 (d, J=7.2 Hz, 1H), 7.14 (d, J=11.7 Hz, 1H), 6.35 (d, J=1.5 Hz, 1H), 4.17 (q, J=7.2 Hz, 2H), 2.69 (s, 2H), 1.51 (s, 6H), 1.25 (t, J=7.2 Hz, 3H).

Step e: 3-(6-fluoro-5-nitro-1H-indol-2-yl)-3-methylbutan-1-ol

To a solution of ethyl 3-(6-fluoro-5-nitro-1H-indol-2-yl)-3-methylbutanoate (34 g, 0.11 mol) in dry CH$_2$Cl$_2$ (400 mL) was added drop-wise DIBAL-H (283.4 mL, 0.27 mol) over 2 hours at −78° C. The reaction mixture was stirred for 10 hours at −78° C. and then quenched by adding water (200 mL). The precipitate was filtered off and washed with methanol. The filtrate was extracted with CH$_2$Cl$_2$ (200 mL×3), the combined organic layers were washed with brine, dried over anhydrous Na$_2$SO$_4$ and concentrated under reduced pressure. The residue was purified by column chromatography on silica gel (petroleum ether/ethyl acetate 50:1) to give 3-(6-fluoro-5-nitro-1H-indol-2-yl)-3-methylbutan-1-ol (6.6 g, 22%). $^1$H NMR (400 MHz, CDCl$_3$) δ 9.35 (brs, 1H), 8.30 (d, J=7.6 Hz, 1H), 7.11 (d, J=12.0 Hz, 1H), 6.35 (d, J=1.2 Hz, 1H), 3.74 (t, J=6.4 Hz, 2H), 1.9 (t, J=6.4 Hz, 2H), 1.4 (s, 6H).

Step f: 2-(4-(tert-butyldimethylsilyloxy)-2-methylbutan-2-yl)-6-fluoro-5-nitro-1H-indole To a solution of 3-(6-fluoro-5-nitro-1H-indol-2-yl)-3-methylbutan-1-ol (6.6 g, 25 mmol) in CH$_2$Cl$_2$ (80 mL) was added TBSCl (3.7 g, 25 nmol) and imidazole (4.2 g, 62 nmol) at 0° C. The reaction mixture was stirred at room temperature for 12 hours. The precipitate was filtered off and washed with the methanol. The filtrate was concentrated under reduced pressure. The residue was purified by column chromatography on silica gel (petroleum ether/ethyl acetate 10:1) to give the desired product as a brown solid (5.0 g, 53%). $^1$H NMR (300 MHz, CDCl$_3$) δ 9.80 (brs, 1H), 8.30 (d, J=7.2 Hz, 1H), 7.05 (d, J=11.7 Hz, 1H), 6.33 (t, J=1.2 Hz, 1H), 3.7 (t, J=6.0 Hz, 2H), 1.91 (t, J=6.0 Hz, 2H), 1.42 (s, 6H), 0.94 (s, 9H), 0.12 (s, 6H). MS (ESI) m/z (M+H$^+$): 381.1.

Benzyl 2,2-dimethylbut-3-ynoate

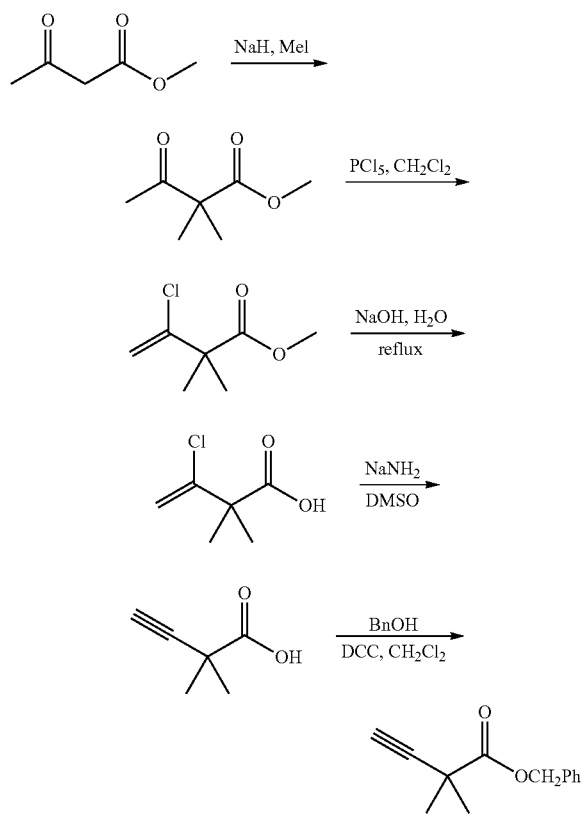

Step a: methyl 2,2-dimethyl-3-oxobutanoate

To a suspension of NaH (28.5 g, 0.718 mol, 60%) in THF (270 mL) was added dropwise a solution of 3-oxo-butyric acid methyl ester (78.6 g, 0.677 mol) in THF (70 mL) at 0° C. The mixture was stirred for 0.5 hours at 0° C. MeI (99.0 g, 0.698 mol) was added dropwise at 0° C. The resultant mixture was warmed to room temperature and stirred for 1 hour. NaH (28.5 g, 0.718 mol, 60%) was added in portions at 0° C. and the resulting mixture was continued to stir for 0.5 h at 0° C. MeI (99.0 g, 0.698 mol) was then added dropwise at 0° C. The reaction mixture was warmed to room temperature and stirred overnight. The mixture was poured into ice water. The organic layer was separated. The aqueous phase was extracted with EtOAc (300 mL×3). The combined organic layers were dried and evaporated under reduced pressure to give methyl 2,2-dimethyl-3-oxobutanoate (52 g, 53%), which was used directly in the next step.

Step b: methyl 3-chloro-2,2-dimethylbut-3-enoate

To a suspension of PCl$_5$ (161 g, 0.772 mol) in dichloromethane (600 mL) was added dropwise methyl 2,2-dimethyl-3-oxobutanoate (52 g, 0.361 mol, crude from last step) at 0° C., followed by the addition of approximately 20 drops of dry DMF. The mixture was heated at reflux overnight. After cooling, the reaction mixture was slowly poured into ice water. The organic layer was separated and the aqueous phase was extracted with dichloromethane (300 mL×3). The combined organic layers were washed with saturated aqueous NaHCO$_3$ solution and dried over anhydrous Na$_2$SO$_4$. The solvent was evaporated to give the product, methyl 3-chloro-2,2-dimethylbut-3-enoate which was used without further purification (47 g, 82%).

Step c: 3-chloro-2,2-dimethylbut-3-enoic acid

A mixture of methyl 3-chloro-2,2-dimethylbut-3-enoate (42.0 g, 0.26 mol) and NaOH (12.4 g, 0.31 mol) in water (300 mL) was heated at reflux overnight. After cooling, the reaction mixture was extracted with ether. The organic layer contained 20 g of methyl 3-chloro-2,2-dimethylbut-3-enoate (48% recovered). The aqueous layer was acidified with cold 20% HCl solution and was extracted with ether (250 mL×3). The combined organic layers were dried and evaporated under reduced pressure to give 3-chloro-2,2-dimethylbut-3-enoic acid (17 g, 44%), which was used directly in the next step.

Step d: 2,2-dimethylbut-3-ynoic acid

To a three-neck flask (500 mL) was added NaNH$_2$ (17.8 g, 0.458 mmol, pellets) and DMSO (50 mL). The mixture was stirred at room temperature until no more NH$_3$ (g) was given off. A solution of 3-chloro-2,2-dimethylbut-3-enoic acid (17.0 g, 114 mmol) in DMSO (50 mL) was added dropwise at 0° C. The mixture was warmed and stirred at 50° C. for 5 hours, then stirred at room temperature overnight. The mixture was poured into cold 20% HCl solution, and then extracted three times with ether. The ether extracts were dried over anhydrous Na$_2$SO$_4$ and concentrated to give a 6:1 ratio of starting material and alkyne product. The residue was re-dried using ether and Na$_2$SO$_4$ and re-subjected to the reaction conditions above. The reaction mixture was worked up in the same manner to provide 2,2-dimethylbut-3-ynoic acid (12.0 g, 94%).

benzyl 2,2-dimethylbut-3-ynoate

To a stirred solution of 2,2-dimethylbut-3-ynoic acid (87.7 g, 0.782 mmol) and benzyl alcohol (114.6 g, 0.938 mol) in dichloromethane (800 mL) was added DCC (193.5 g, 0.938 mmol) at −20° C. The reaction mixture was stirred at room temperature overnight and then the solvent was evaporated in vacuo. The residue was purified by chromatography on silica gel (2% ethyl acetate in petroleum ether as eluant) to afford benzyl 2,2-dimethylbut-3-ynoate (100 g, 59% yield). $^1$H NMR (CDCl$_3$, 400 MHz) δ 7.37-7.36 (m, 5H), 5.19 (s, 2H), 2.28 (s, 1H), 1.52 (s, 6H).

2-(1-(Tert-butyldimethylsilyloxy)-2-methylpropan-2-yl)-6-fluoro-5-nitro-1H-indole

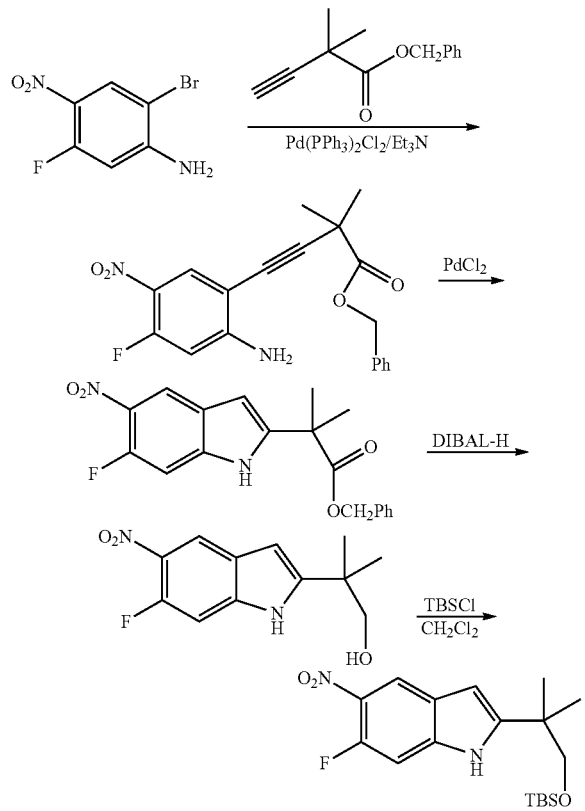

Step a: benzyl 4-(2-amino-4-fluoro-5-nitrophenyl)-2,2-dimethylbut-3-ynoate

To a solution of 2-bromo-5-fluoro-4-nitroaniline (23.0 g, 0.1 mol) in Et$_3$N (250 mL) was added benzoic 2,2-dimethylbut-3-ynoic anhydride (59.0 g, 0.29 mol), CuI (1.85 g) and Pd(PPh$_3$)$_2$Cl$_2$ (2.3 g) at room temperature. The mixture was stirred at 80° C. overnight. After cooling to room temperature, the reaction was quenched with water and the aqueous layer was extracted with ethyl acetate (100 mL×3). The combined organic layer was dried over anhydrous Na$_2$SO$_4$, the solvent was evaporated in vacuo. The residue was purified by chromatography on silica gel (10% ethyl acetate in petroleum ether) to give benzyl 4-(2-amino-4-fluoro-5-nitrophenyl)-2,2-dimethylbut-3-ynoate (20.0 g, 56%). $^1$H NMR (400 MHz, CDCl$_3$) 8.05 (d, J=8.4 Hz, 1H), 7.39-7.38 (m, 5H), 6.33 (d, J=13.2 Hz, 1H), 5.20 (s, 2H), 4.89 (br s, 2H), 1.61 (s, 6H).

Step b: benzyl 2-(6-fluoro-5-nitro-1H-indol-2-yl)-2-methylpropanoate

To a solution of benzyl 4-(2-amino-4-fluoro-5-nitrophenyl)-2,2-dimethylbut-3-ynoate (20.0 g, 56 mmol) in acetonitrile (100 mL) was added PdCl$_2$ (5.0 g, 28 mmol) at room temperature. The mixture was stirred at 80° C. overnight. The mixture was filtered off and the solvent was evaporated in vacuo, the residue was purified by chromatography on silica gel (10% EtOAc in petroleum ether) to give benzyl 2-(6-fluoro-5-nitro-1H-indol-2-yl)-2-methylpropanoate (18.0 g, 90%). $^1$H NMR (300 MHz, CDCl$_3$) 8.96 (br s, 1H), 8.33 (d, J=7.2 Hz, 1H) 7.35-7.28 (m, 5H) 7.08 (d, J=11.7 Hz, 1H), 6.47 (s, 1H), 5.18 (s, 2H) 1.69 (s, 6H).

Step c: 2-(6-fluoro-5-nitro-1H-indol-2-yl)-2-methylpropan-1-ol

To a solution of benzyl 2-(6-fluoro-5-nitro-1H-indol-2-yl)-2-methylpropanoate (18.0 g, 0.05 mol) in CH$_2$Cl$_2$ (100 mL) was added DIBAL-H (12 mL) at −78° C. The mixture was stirred for 1 h at that temperature and was warmed to room temperature. The reaction was quenched with water and the aqueous layer was extracted with EtOAc (100 mL×3). The combined organic layers were dried over anhydrous Na$_2$SO$_4$, the solvent was evaporated in vacuo. The residue was purified by chromatography on silica gel (10% EtOAc in petroleum ether) to give 2-(6-fluoro-5-nitro-1H-indol-2-yl)-2-methylpropan-1-ol (10.0 g, 77%). $^1$H NMR (300 MHz, CDCl$_3$) 9.37 (s, 1H), 8.32 (d, J=7.2 Hz, 1H), 7.11 (d, J=11.7 Hz, 1H), 6.36 (s, 1H), 3.73 (d, J=5.1 Hz 2H), 1.97 (t, J=5.1 Hz, 1H), 1.39 (s, 6H).

Step d: 2-(1-(tert-butyldimethylsilyloxy)-2-methylpropan-2-yl)-6-fluoro-5-nitro-1H-indole To a stirred solution of 2-(6-fluoro-5-nitro-1H-indol-2-yl)-2-methylpropan-1-ol (10.0 g) in CH$_2$Cl$_2$ was added TBSCl (8.9 g), imidazole (8.1 g, 0.12 mol) at room temperature. The mixture was stirred overnight. The solvent was evaporated in vacuo and the residue was purified by chromatography on silica gel (10% EtOAc in petroleum ether) to give 2-(1-(tert-butyldimethylsilyloxy)-2-methylpropan-2-yl)-6-fluoro-5-nitro-1H-indole (5.3 g, 38%). $^1$H NMR (300 MHz, CDCl$_3$) 9.51 (s, 1H), 8.31 (d, J=7.5 Hz, 1H), 7.02 (d, J=11.7 Hz, 1H), 6.32 (s, 1H), 3.63 (s, 2H), 1.35 (s, 6H), 0.99 (s, 9H), 0.11 (s, 6H).

6-fluoro-1,1-dimethyl-7-nitro-2,3-dihydro-1H-pyrrolo[1,2-a]indole, (R)-3-(1-((2,2-dimethyl-1,3-dioxolan-4-yl)methyl)-6-fluoro-5-nitro-1H-indol-2-yl)-3-methylbutan-1-ol, 2-(4-(((R)-2,2-dimethyl-1,3-dioxolan-4-yl)methoxy)-2-methylbutan-2-yl)-1-(((R)-2,2-dimethyl-1,3-dioxolan-4-yl)methyl)-6-fluoro-5-nitro-1H-indole, 3-(6-fluoro-5-nitro-1H-indol-2-yl)-3-methylbutan-1-ol and (R)-2-(4-((2,2-dimethyl-1,3-dioxolan-4-yl)methoxy)-2-methylbutan-2-yl)-6-fluoro-5-nitro-4H-indole

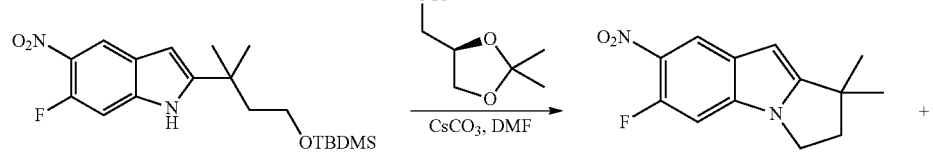

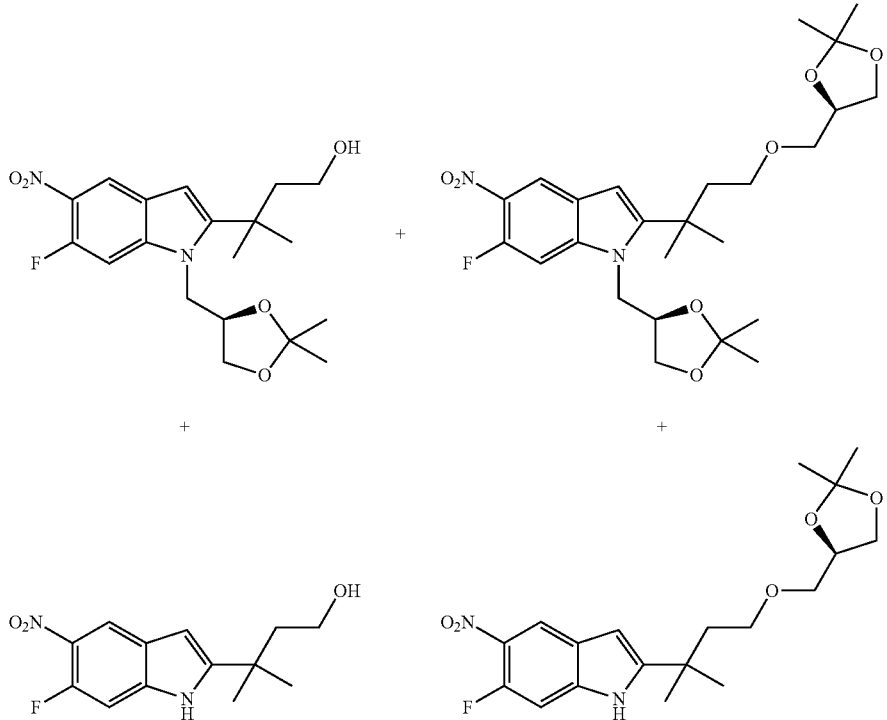

Step a: 6-fluoro-1,1-dimethyl-7-nitro-2,3-dihydro-1H-pyrrolo[1,2-a]indole, (R)-3-(1-((2,2-dimethyl-1,3-dioxolan-4-yl)methyl)-6-fluoro-5-nitro-1H-indol-2-yl)-3-methylbutan-1-ol, 2-(4-(aR)-2,2-dimethyl-1,3-dioxolan-4-yl)methoxy)-2-methylbutan-2-yl)-1-(((R)-2,2-dimethyl-1,3-dioxolan-4-yl)methyl)-6-fluoro-5-nitro-1H-indole, 3-(6-fluoro-5-nitro-1H-indol-2-yl)-3-methylbutan-1-ol and (R)-2-(4-((2,2-dimethyl-1,3-dioxolan-4-yl)methoxy)-2-methylbutan-2-yl)-6-fluoro-5-nitro-1H-indole To a solution of 2-(4-(tert-butyldimethylsilyloxy)-2-methylbutan-2-yl)-6-fluoro-5-nitro-1H-indole (1.9 g, 5.0 mmol) and (S)-(2,2-dimethyl-1,3-dioxolan-4-yl)methyl 4-methylbenzenesulfonate (2.86 g, 10.0 mmol) in DMF (10 mL) was added $Cs_2CO_3$ (4.88 g, 15.0 mmol). The mixture was heated at 90° C. for 24 hours. The reaction was partitioned between ethyl acetate and water. The aqueous layer was extracted with ethyl acetate and the combined organic layers were washed with brine and dried over $MgSO_4$. After the removal of solvent, the residue was purified by column chromatography (10-50% ethyl acetate-hexane) to afford 6-fluoro-1,1-dimethyl-7-nitro-2,3-dihydro-1H-pyrrolo[1,2-a]indole (600 mg, 48%). ESI-MS m/z calc. 248.1. found 249.2 $(M+1)^+$. Retention time 2.00 minutes; 2-(4-(((R)-2,2-dimethyl-1,3-dioxolan-4-yl)methoxy)-2-methylbutan-2-yl)-1-(((R)-2,2-dimethyl-1,3-dioxolan-4-yl)methyl)-6-fluoro-5-nitro-1H-indole (270 mg, containing some (R)-2-(4-((2,2-dimethyl-1,3-dioxolan-4-yl)methoxy)-2-methylbutan-2-yl)-6-fluoro-5-nitro-1H-indole). ESI-MS m/z calc. 494.2 and 380.2. found 495.4 and 381.4 $(M+1)^+$. Retention time 2.12 and 1.92 minutes; (R)-3-(1-((2,2-dimethyl-1,3-dioxolan-4-yl)methyl)-6-fluoro-5-nitro-1H-indol-2-yl)-3-methylbutan-1-ol (1.0 g, containing some 3-(6-fluoro-5-nitro-1H-indol-2-yl)-3-methylbutan-1-ol). ESI-MS m/z calc. 380.2 and 266.1. found 381.2 and 267.2 $(M+1)^+$. Retention time 1.74 and 1.48 minutes.

(R)-2-(1-((2,2-dimethyl-1,3-dioxolan-4-yl)methyl)-6-fluoro-5-nitro-1H-indol-2-yl)-2-methylpropan-1-ol and 3-(6-fluoro-5-nitro-1H-indol-2-yl)-3-methylbutan-1-ol

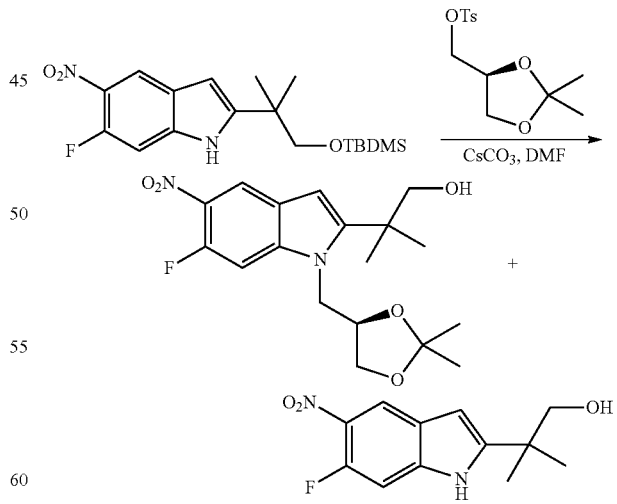

A mixture containing (R)-2-(1-((2,2-dimethyl-1,3-dioxolan-4-yl)methyl)-6-fluoro-5-nitro-1H-indol-2-yl)-2-methylpropan-1-ol and 3-(6-fluoro-5-nitro-1H-indol-2-yl)-3-methylbutan-1-ol was obtained following the procedure shown above starting from 2-(1-(tert-butyldimethylsilyloxy)-2-methylpropan-2-yl)-6-fluoro-5-nitro-1H-indole. (R)-2-(1-((2,2-dimethyl-1,3-dioxolan-4-yl)methyl)-6-fluoro-5-nitro-1H-indol-2-yl)-2-methylpropan-1-ol, ESI-MS m/z calc. 366.2. found 367.2 (M+1)+. Retention time 1.71 minutes; 3-(6-fluoro-5-nitro-1H-indol-2-yl)-3-methylbutan-1-ol, ESI-MS m/z calc. 252.1. found 253.4 (M+1)+. Retention time 1.42 minutes.

1-(2,2-difluorobenzo[d][1,3]dioxol-5-yl)-N-(6-fluoro-1,1-dimethyl-2,3-dihydro-1H-pyrrolo[1,2-a]indol-7-yl)cyclopropanecarboxamide

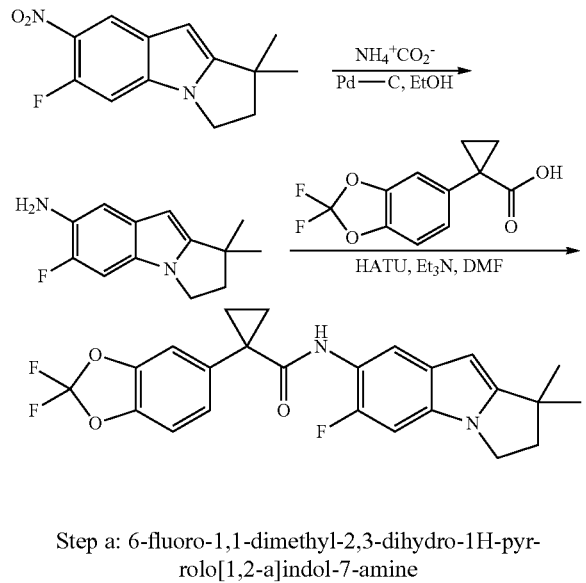

Step a: 6-fluoro-1,1-dimethyl-2,3-dihydro-1H-pyrrolo[1,2-a]indol-7-amine

To a solution of 6-fluoro-1,1-dimethyl-7-nitro-2,3-dihydro-1H-pyrrolo[1,2-a]indole (600 mg, 2.4 mmol) in ethanol (15 mL) was added ammonium formate (600 mg, 9.5 mmol) and Pd/C (10%, 129 mg, 0.12 mmol). The mixture was refluxed for 10 min. The Pd catalyst was removed via filtration through Celite and washed with ethanol. The filtrate was concentrated and purified by column chromatography (20-40% ethyl acetate-hexanes) to provide 6-fluoro-1,1-dimethyl-2,3-dihydro-1H-pyrrolo[1,2-a]indol-7-amine (260 mg, 49%). ESI-MS m/z calc. 218.1. found 219.2 (M+1)+. Retention time 1.01 minutes.

Step b: 1-(2,2-difluorobenzo[d][1,3]dioxol-5-yl)-N-(6-fluoro-1,1-dimethyl-2,3-dihydro-1H-pyrrolo[1,2-a]indol-7-yl)cyclopropanecarboxamide To a mixture of 1-(2,2-difluorobenzo[d][1,3]dioxol-5-yl)cyclopropanecarboxylic acid (346 mg, 1.4 mmol), 6-fluoro-1,1-dimethyl-2,3-dihydro-1H-pyrrolo[1,2-a]indol-7-amine (260 mg, 1.2 mmol) and HATU (543 mg, 1.4 mmol) in DMF (5 mL) was added triethylamine (0.40 mL, 2.9 mmol). The reaction was stirred at room temperature overnight and then partitioned between ethyl acetate and water. The aqueous layer was extracted with ethyl acetate and the combined organic layers were washed with brine and dried over MgSO4. After the removal of solvent, the residue was purified by column chromatography (10-20% ethyl acetate-hexanes) to afford 1-(2,2-difluorobenzo[d][1,3]dioxol-5-yl)-N-(6-fluoro-1,1-dimethyl-2,3-dihydro-1H-pyrrolo[1,2-a]indol-7-yl)cyclopropanecarboxamide (342 mg, 65%). ESI-MS m/z calc. 442.2. found 443.5 (M+1)+. Retention time 2.30 minutes. 1H NMR (400 MHz, DMSO-d6) δ 8.20 (d, J=7.6 Hz, 1H), 7.30-7.25 (m, 3H), 7.20 (m, 1H), 7.12 (d, J=8.2 Hz, 1H), 6.84 (d, J=11.1 Hz, 1H), 6.01 (d, J=0.5 Hz, 1H), 3.98 (t, J=6.8 Hz, 2H), 2.37 (t, J=6.8 Hz, 2H), 1.75 (dd, J=3.8, 6.9 Hz, 2H), 1.37 (s, 6H) and 1.14 (dd, J=3.9, 6.9 Hz, 2H) ppm.

(R)-1-(2,2-difluorobenzo[d][1,3]dioxol-5-yl)-N-(1-(2,3-dihydroxypropyl)-6-fluoro-2-(4-hydroxy-2-methylbutan-2-yl)-1H-indol-5-yl)cyclopropanecarboxamide

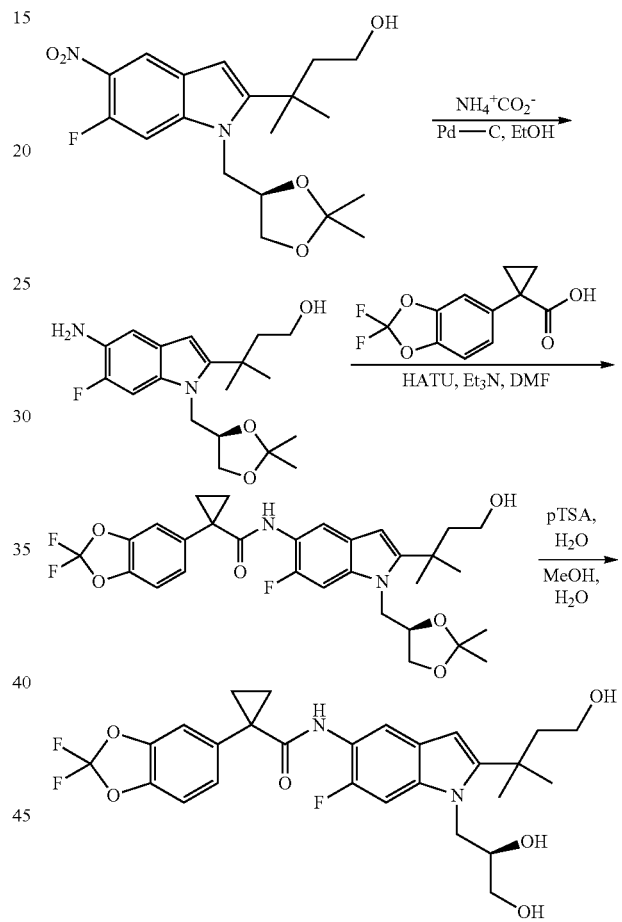

Step a: (R)-3-(5-amino-1-((2,2-dimethyl-1,3-dioxolan-4-yl)methyl)-6-fluoro-1H-indol-2-yl)-3-methylbutan-1-ol To a solution of (R)-3-(1-((2,2-dimethyl-1,3-dioxolan-4-yl)methyl)-6-fluoro-5-nitro-1H-indol-2-yl)-3-methylbutan-1-ol containing some 3-(6-fluoro-5-nitro-1H-indol-2-yl)-3-methylbutan-1-ol (500 mg, 1.3 mmol) in ethanol (10 mL) was added ammonium formate (500 mg, 7.9 mmol) and Pd/C (10%, 139 mg, 0.13 mmol). The mixture was refluxed for 5 min. The Pd catalyst was removed via filtration through Celite and washed with ethanol. The filtrate was evaporated to dryness and purified by column chromatography (30-50% ethyl acetate-hexanes) to provide (R)-3-(5-amino-1-((2,2-dimethyl-1,3-dioxolan-4-yl)methyl)-6-fluoro-1H-indol-2-yl)-3-methylbutan-1-ol (220 mg, 48%, contains some 3-(5-amino- 6-fluoro-1H-indol-2-yl)-3-methylbutan-1-ol). ESI-MS m/z calc. 350.2 found 351.4 (M+1)⁺. Retention time 0.94 minutes.

Step b: (R)-1-(2,2-difluorobenzo[d][1,3]dioxol-5-yl)-N-(1-((2,2-dimethyl-1,3-dioxolan-4-yl)methyl)-6-fluoro-2-(4-hydroxy-2-methylbutan-2-yl)-1H-indol-5-yl)cyclopropanecarboxamide To a mixture of 1-(2,2-difluorobenzo[d][1,3]dioxol-5-yl)cyclopropanecarboxylic acid (183 mg, 0.75 mmol), (R)-3-(5-amino-1-((2,2-dimethyl-1,3-dioxolan-4-yl)methyl)-6-fluoro-1H-indol-2-yl)-3-methylbutan-1-ol containing some 3-(5-amino-6-fluoro-1H-indol-2-yl)-3-methylbutan-1-ol (220 mg, 0.63 mmol) and HATU (287 mg, 0.75 mmol) in DMF (3.0 mL) was added triethylamine (0.21 mL, 1.5 mmol). The reaction was stirred at room temperature overnight and then partitioned between ethyl acetate and water. The aqueous layer was extracted with ethyl acetate and the combined organic layers were washed with brine and dried over MgSO₄. After the removal of solvent, the residue was purified by column chromatography (20-40% ethyl acetate-hexanes) to afford (R)-1-(2,2-difluorobenzo[d][1,3]dioxol-5-yl)-N-(1-((2,2-dimethyl-1,3-dioxolan-4-yl)methyl)-6-fluoro-2-(4-hydroxy-2-methylbutan-2-yl)-1H-indol-5-yl)cyclopropanecarboxamide (315 mg, 87%, contains some 1-(2,2-difluorobenzo[d][1,3]dioxol-5-yl)-N-(6-fluoro-2-(4-hydroxy-2-methylbutan-2-yl)-1H-indol-5-yl)cyclopropanecarboxamide). ESI-MS m/z calc. 574.2 found 575.7 (M+1)⁺. Retention time 2.08 minutes.

Step c: (R)-1-(2,2-difluorobenzo[d][1,3]dioxol-5-yl)-N-(1-(2,3-dihydroxypropyl)-6-fluoro-2-(4-hydroxy-2-methylbutan-2-yl)-1H-indol-5-yl)cyclopropanecarboxamide To a solution of (R)-1-(2,2-difluorobenzo[d][1,3]dioxol-5-yl)-N-(1-((2,2-dimethyl-1,3-dioxolan-4-yl)methyl)-6-fluoro-2-(4-hydroxy-2-methylbutan-2-yl)-1H-indol-5-yl)cyclopropanecarboxamide containing some 1-(2,2-difluorobenzo[d][1,3]dioxol-5-yl)-N-(6-fluoro-2-(4-hydroxy-2-methylbutan-2-yl)-1H-indol-5-yl)cyclopropanecarboxamide (315 mg, 0.55 mmol) in methanol (3 mL) and water (0.3 mL) was added p-TsOH.H₂O (21 mg, 0.11 mmol). The mixture was heated at 80° C. for 30 minutes. The reaction was partitioned between ethyl acetate and water and the aqueous layer was extracted with ethyl acetate twice. The combined organic layers were washed with saturated. NaHCO₃ solution and brine and dried over MgSO₄. After the removal of solvent, the residue was purified by column chromatography (20-80% ethyl acetate-hexanes) to provide (R)-1-(2,2-difluorobenzo[d][1,3]dioxol-5-yl)-N-(1-(2,3-dihydroxypropyl)-6-fluoro-2-(4-hydroxy-2-methylbutan-2-yl)-1H-indol-5-yl)cyclopropanecarboxamide (92 mg, 31%). ESI-MS m/z calc. 534.2. found 535.5 (M+1)⁺. Retention time 1.72 minutes. ¹H NMR (400 MHz, DMSO-d6) δ 8.32 (s, 1H), 7.53 (d, J=1.0 Hz, 1H), 7.43-7.31 (m, 4H), 6.17 (s, 1H), 4.97-4.92 (m, 2H), 4.41 (dd, J=2.4, 15.0 Hz, 1H), 4.23 (t, J=5.0 Hz, 1H), 4.08 (dd, J=8.6, 15.1 Hz, 1H), 3.87 (s, 1H), 3.48-3.44 (m, 1H), 3.41-3.33 (m, 1H), 3.20 (dd, J=7.4, 12.7 Hz, 2H), 1.94-1.90 (m, 2H), 1.48-1.45 (m, 2H), 1.42 (s, 3H), 1.41 (s, 3H) and 1.15-1.12 (m, 2H) ppm.

1-(2,2-difluorobenzo[d][1,3]dioxol-5-yl)-N-(2-(4-((S)-2,3-dihydroxypropoxy)-2-methylbutan-2-yl)-1-(R)-2,3-dihydroxypropyl)-6-fluoro-1H-indol-5-yl)cyclopropanecarboxamide and (S)-1-(2,2-difluorobenzo[d][1,3]dioxol-5-yl)-N-(2-(4-(2,3-dihydroxypropoxy)-2-methylbutan-2-yl)-6-fluoro-1H-indol-5-yl)cyclopropanecarboxamide

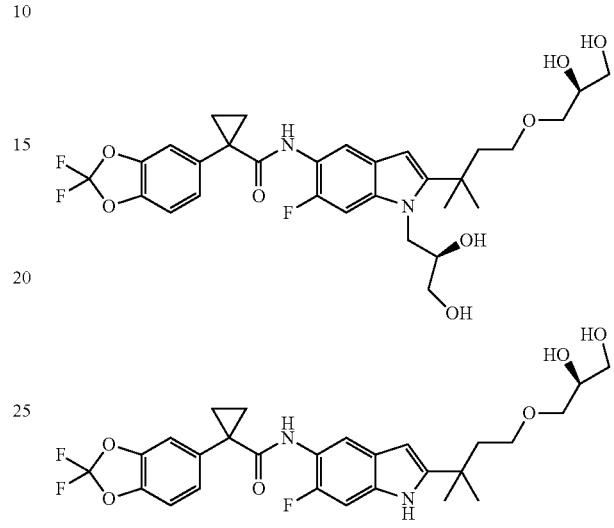

1-(2,2-difluorobenzo[d][1,3]dioxol-5-yl)-N-(2-(4-((S)-2,3-dihydroxypropoxy)-2-methylbutan-2-yl)-1-((R)-2,3-dihydroxypropyl)-6-fluoro-1H-indol-5-yl)cyclopropanecarboxamide and (S)-1-(2,2-difluorobenzo[d][1,3]dioxol-5-yl)-N-(2-(4-(2,3-dihydroxypropoxy)-2-methylbutan-2-yl)-6-fluoro-1H-indol-5-yl)cyclopropanecarboxamide 1-(2,2-difluorobenzo[d][1,3]dioxol-5-yl)-N-(2-(4-((S)-2,3-dihydroxypropoxy)-2-methylbutan-2-yl)-1-(R)-2,3-dihydroxypropyl)-6-fluoro-1H-indol-5-yl)cyclopropanecarboxamide and (S)-1-(2,2-difluorobenzo[d][1,3]dioxol-5-yl)-N-(2-(4-(2,3-dihydroxypropoxy)-2-methylbutan-2-yl)-6-fluoro-1H-indol-5-yl)cyclopropanecarboxamide were made following a scheme similar as shown above starting from 2-(4-(((R)-2,2-dimethyl-1,3-dioxolan-4-yl)methoxy)-2-methylbutan-2-yl)-1-(((R)-2,2-dimethyl-1,3-dioxolan-4-yl)methyl)-6-fluoro-5-nitro-1H-indole containing some (R)-2-(4-(((2,2-dimethyl-1,3-dioxolan-4-yl)methoxy)-2-methylbutan-2-yl)-6-fluoro-5-nitro-1H-indole). 1-(2,2-difluorobenzo[d][1,3]dioxol-5-yl)-N-(2-(4-((S)-2,3-dihydroxypropoxy)-2-methylbutan-2-yl)-1-(R)-2,3-dihydroxypropyl)-6-fluoro-1H-indol-5-yl)cyclopropanecarboxamide, ESI-MS m/z calc. 608.2. found 609.5 (M+1)⁺. Retention time 1.67 minutes. ¹H NMR (400 MHz, DMSO-d6) δ 8.32 (s, 1H), 7.53 (s, 1H), 7.43-7.31 (m, 4H), 6.19 (s, 1H), 4.95-4.93 (m, 2H), 4.51 (d, J=5.0 Hz, 1H), 4.42-4.39 (m, 2H), 4.10-4.04 (m, 1H), 3.86 (s, 1H), 3.49-3.43 (m, 2H), 3.41-3.33 (m, 1H), 3.30-3.10 (m, 6H), 2.02-1.97 (m, 2H), 1.48-1.42 (m, 8H) and 1.13 (dd, J=4.0, 6.7 Hz, 2H) ppm; (S)-1-(2,2-difluorobenzo[d][1,3]dioxol-5-yl)-N-(2-(4-(2,3-dihydroxypropoxy)-2-methylbutan-2-yl)-6-fluoro-1H-indol-5-yl)cyclopropanecarboxamide, ESI-MS m/z calc. 534.2. found 535.5 (M+1)⁺. Retention time 1.81 minutes. ¹H NMR (400 MHz, DMSO-d6) δ 10.91 (d, J=1.5 Hz, 1H), 8.30 (s, 1H), 7.53 (s, 1H), 7.42-7.33 (m, 3H), 7.03 (d, J=10.9 Hz, 1H), 6.07 (d, J=1.6 Hz, 1H), 4.56 (d, J=5.0 Hz, 1H), 4.43 (t, J=5.7 Hz, 1H), 3.51-3.46 (m, 1H), 3.31-3.13 (m, 6H), 1.88 (t, J=7.3 Hz, 2H), 1.48-1.45 (m, 2H), 1.31 (s, 6H) and 1.15-1.12 (m, 2H) ppm.

1-(2,2-difluorobenzo[d][1,3]dioxol-5-yl)-N-(6-fluoro-2-(1-hydroxy-2-methylpropan-2-yl)-1H-indol-5-yl)cyclopropanecarboxamide

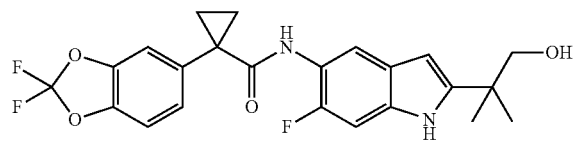 [SMILES: CC(C)(CO)c1cc2cc(NC(=O)C3(c4ccc5c(c4)OC(F)(F)O5)CC3)c(F)cc2[nH]1]

1-(2,2-difluorobenzo[d][1,3]dioxol-5-yl)-N-(6-fluoro-2-(1-hydroxy-2-methylpropan-2-yl)-1H-indol-5-yl)cyclopropanecarboxamide 1-(2,2-difluorobenzo[d][1,3]dioxol-5-yl)-N-(6-fluoro-2-(1-hydroxy-2-methylpropan-2-yl)-1H-indol-5-yl)cyclopropanecarboxamide was made following the scheme shown above starting from a mixture containing (R)-2-(1-((2,2-dimethyl-1,3-dioxolan-4-yl)methyl)-6-fluoro-5-nitro-1H-indol-2-yl)-2-methylpropan-1-ol and 3-(6-fluoro-5-nitro-1H-indol-2-yl)-3-methylbutan-1-ol. ESI-MS m/z calc. 446.2. found 447.5 (M+1)$^+$. Retention time 1.88 minutes. $^1$H NMR (400 MHz, CDCl$_3$) δ 8.68 (s, 1H), 8.20 (d, J=7.7 Hz, 1H), 7.30-7.21 (m, 3H), 7.12 (d, J=8.2 Hz, 1H), 6.94 (d, J=11.2 Hz, 1H), 6.18 (s, 1H), 3.64 (s, 2H), 1.75 (dd, J=3.8, 6.8 Hz, 2H), 1.34 (s, 6H) and 1.14 (dd, J=3.9, 6.9 Hz, 2H) ppm.

(R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide

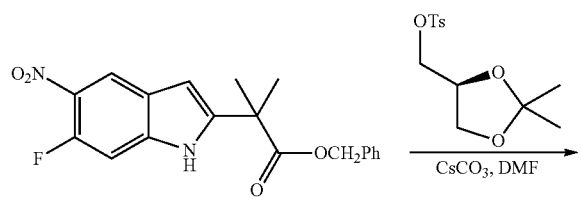

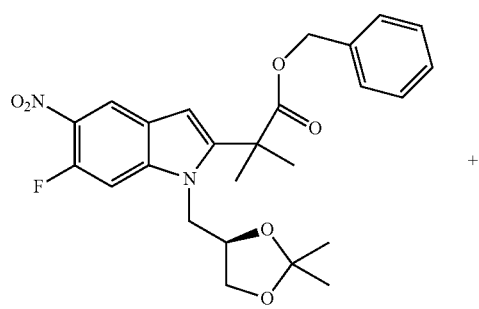

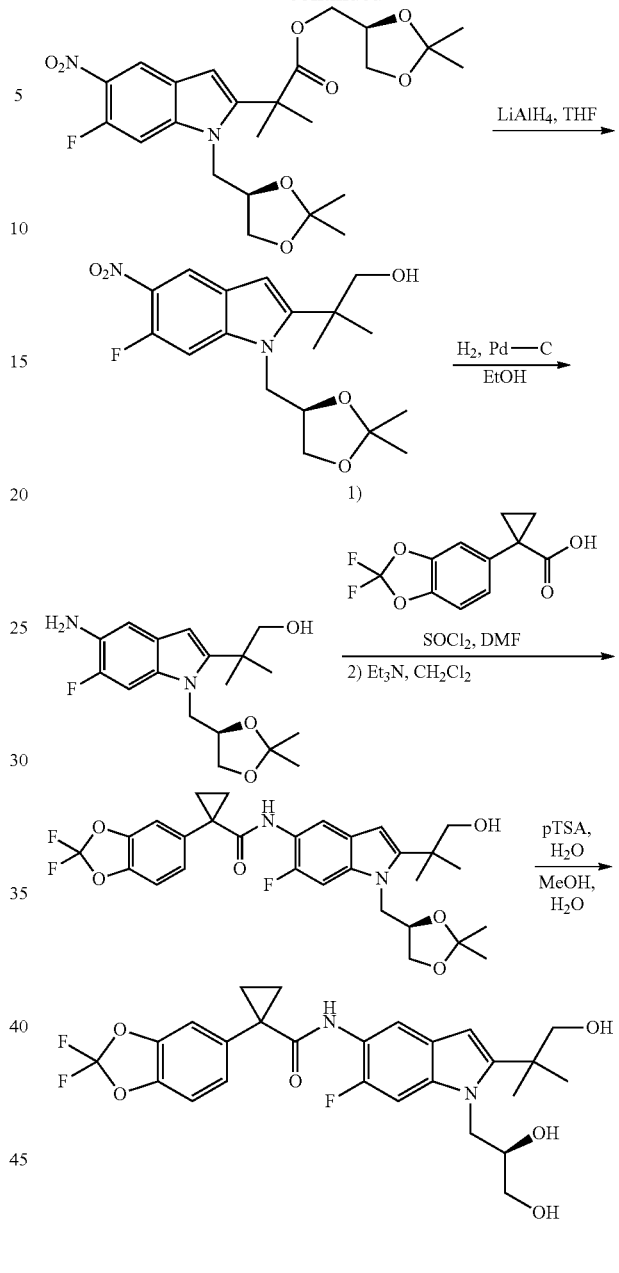

Step a: (R)-Benzyl 2-(1-((2,2-dimethyl-1,3-dioxolan-4-yl)methyl)-6-fluoro-5-nitro-1H-indol-2-yl)-2-methylpropanoate and ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate Cesium carbonate (8.23 g, 25.3 mmol) was added to a mixture of benzyl 2-(6-fluoro-5-nitro-1H-indol-2-yl)-2-methylpropanoate (3.0 g, 8.4 mmol) and (S)-(2,2-dimethyl-1,3-dioxolan-4-yl)methyl 4-methylbenzenesulfonate (7.23 g, 25.3 mmol) in DMF (17 mL). The reaction was stirred at 80° C. for 46 hours under nitrogen atmosphere. The mixture was then partitioned between ethyl acetate and water. The aqueous layer was extracted with ethyl acetate. The combined ethyl acetate layers were washed with brine, dried over MgSO$_4$, filtered and concentrated. The crude product, a viscous brown oil which contains both of the products shown above, was taken directly to the next step without further purification. (R)-Benzyl 2-(1-(2,2-dimethyl-1,3-dioxolan-4-yl)methyl)-6-fluoro-5-nitro-1H-indol-2-yl)-2-methylpropanoate, ESI-MS m/z calc. 470.2. found 471.5 (M+1)$^+$. Retention time 2.20 minutes. ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate, ESI-MS m/z calc. 494.5. found 495.7 (M+1)$^+$. Retention time 2.01 minutes.

Step b: (R)-2-(1-((2,2-dimethyl-1,3-dioxolan-4-yl)methyl)-6-fluoro-5-nitro-1H-indol-2-yl)-2-methyl-propan-1-ol To the crude reaction mixture obtained in step (a) was dissolved in THF (42 mL) and cooled in an ice-water bath. LiAlH$_4$ (16.8 mL of 1 M solution, 16.8 mmol) was added drop-wise. After the addition was complete, the reaction was stirred for an additional 5 minutes. The reaction was quenched by adding water (1 mL), two NaOH solution (1 mL) and then water (3 mL). The mixture was filtered over Celite, and the solids were washed with THF and ethyl acetate. The filtrate was concentrated and purified by column chromatography (30-60% ethyl acetate-hexanes) to obtain the product as a brown oil (2.68 g, 87% over 2 steps). ESI-MS m/z calc. 366.4. found 367.3 (M+1)$^+$. Retention time 1.68 minutes. $^1$H NMR (400 MHz, DMSO-d6) δ 8.34 (d, J=7.6 Hz, 1H), 7.65 (d, J=13.4 Hz, 1H), 6.57 (s, 1H), 4.94 (t, J=5.4 Hz, 1H), 4.64-4.60 (m, 1H), 4.52-4.42 (m, 2H), 4.16-4.14 (m, 1H), 3.76-3.74 (m, 1H), 3.63-3.53 (m, 2H), 1.42 (s, 3H), 1.38-1.36 (m, 6H) and 1.19 (s, 3H) ppm Step c: (R)-2-(5-amino-1-((2,2-dimethyl-1,3-dioxolan-4-yl)methyl)-6-fluoro-1H-indol-2-yl)-2-methyl-propan-1-ol (R)-2-(1-((2,2-dimethyl-1,3-dioxolan-4-yl)methyl)-6-fluoro-5-nitro-1H-indol-2-yl)-2-methylpropan-1-ol (2.5 g, 6.82 mmol) was dissolved ethanol (70 mL) and the reaction was flushed with N$_2$. Then Pd—C (250 mg, 5% wt) was added. The reaction was flushed with nitrogen again and then stirred under H$_2$ (atm). After 2.5 hours only partial conversion to the product was observed by LCMS. The reaction was filtered through Celite and concentrated. The residue was re-subjected to the conditions above. After 2 hours LCMS indicated complete conversion to product. The reaction mixture was filtered through Celite. The filtrate was concentrated to yield the product as a black solid (1.82 g, 79%). ESI-MS m/z calc. 336.2. found 337.5 (M+1)$^+$. Retention time 0.86 minutes. $^1$H NMR (400 MHz, DMSO-d6) δ 7.17 (d, J=12.6 Hz, 1H), 6.76 (d, J=9.0 Hz, 1H), 6.03 (s, 1H), 4.79-4.76 (m, 1H), 4.46 (s, 2H), 4.37-4.31 (m, 3H), 4.06 (dd, J=6.1, 8.3 Hz, 1H), 3.70-3.67 (m, 1H), 3.55-3.52 (m, 2H), 1.41 (s, 3H), 1.32 (s, 6H) and 1.21 (s, 3H) ppm.

Step d: (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide DMF (3 drops) was added to a stirring mixture of 1-(2,2-difluorobenzo[d][1,3]dioxol-5-yl)cyclopropanecarboxylic acid (1.87 g, 7.7 mmol) and thionyl chloride (1.30 mL, 17.9 mmol). After 1 hour a clear solution had formed. The solution was concentrated under vacuum and then toluene (3 mL) was added and the mixture was concentrated again. The toluene step was repeated once more and the residue was placed on high vacuum for 10 minutes. The acid chloride was then dissolved in dichloromethane (10 mL) and added to a mixture of (R)-2-(5-amino-1-((2,2-dimethyl-1,3-dioxolan-4-yl)methyl)-6-fluoro-1H-indol-2-yl)-2-methylpropan-1-ol (1.8 g, 5.4 mmol) and triethylamine (2.24 mL, 16.1 mmol) in dichloromethane (45 mL). The reaction was stirred at room temperature for 1 hour. The reaction was washed with 1N HCl solution, saturated NaHCO$_3$ solution and brine, dried over MgSO$_4$ and concentrated to yield the product as a black foamy solid (3 g, 100%). ESI-MS m/z calc. 560.6. found 561.7 (M+1)$^+$. Retention time 2.05 minutes. $^1$H NMR (400 MHz, DMSO-d6) δ 8.31 (s, 1H), 7.53 (s, 1H), 7.42-7.40 (m, 2H), 7.34-7.30 (m, 3H), 6.24 (s, 1H), 4.51-4.48 (m, 1H), 4.39-4.34 (m, 2H), 4.08 (dd, J=6.0, 8.3 Hz, 1H), 3.69 (t, J=7.6 Hz, 1H), 3.58-3.51 (m, 2H), 1.48-1.45 (m, 2H), 1.39 (s, 3H), 1.34-1.33 (m, 6H), 1.18 (s, 3H) and 1.14-1.12 (m, 2H) ppm Step e: (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropan-ecarboxamide (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide (3.0 g, 5.4 mmol) was dissolved in methanol (52 mL). Water (5.2 mL) was added followed by p-TsOH.H$_2$O (204 mg, 1.1 mmol). The reaction was heated at 80° C. for 45 minutes. The solution was concentrated and then partitioned between ethyl acetate and saturated NaHCO$_3$ solution. The ethyl acetate layer was dried over MgSO$_4$ and concentrated. The residue was purified by column chromatography (50-100% ethyl acetate-hexanes) to yield the product as a cream colored foamy solid. (1.3 g, 47%, ee>98% by SFC). ESI-MS m/z calc. 520.5. found 521.7 (M+1)$^+$. Retention time 1.69 minutes. $^1$H NMR (400 MHz, DMSO-d6) δ 8.31 (s, 1H), 7.53 (s, 1H), 7.42-7.38 (m, 2H), 7.33-7.30 (m, 2H), 6.22 (s, 1H), 5.01 (d, J=5.2 Hz, 1H), 4.90 (t, J=5.5 Hz, 1H), 4.75 (t, J=5.8 Hz, 1H), 4.40 (dd, J=2.6, 15.1 Hz, 1H), 4.10 (dd, J=8.7, 15.1 Hz, 1H), 3.90 (s, 1H), 3.65-3.54 (m, 2H), 3.48-3.33 (m, 2H), 1.48-1.45 (m, 2H), 1.35 (s, 3H), 1.32 (s, 3H) and 1.14-1.11 (m, 2H) ppm.

(S)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide

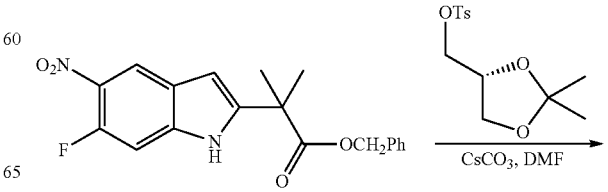

447
-continued

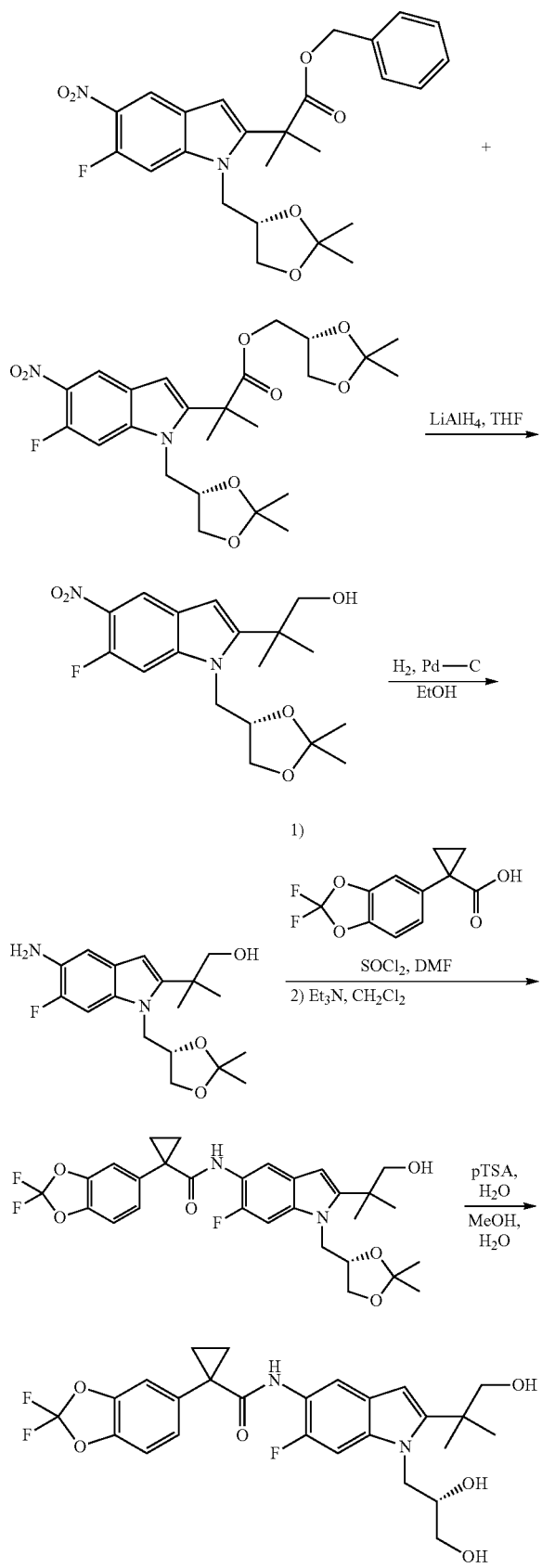

1)

448

Step a: (S)-Benzyl 2-(1-((2,2-dimethyl-1,3-dioxolan-4-yl)methyl)-6-fluoro-5-nitro-1H-indol-2-yl)-2-methylpropanoate and ((R)-2,2-Dimethyl-1,3-dioxolan-4-yl)methyl 2-(1-(((S)-2,2-dimethyl-1,3-dioxolan-4-yl)methyl)-6-fluoro-5-nitro-1H-indol-2-yl)-2-methylpropanoate Cesium carbonate (2.74 g, 8.4 mmol) was added to a mixture of benzyl 2-(6-fluoro-5-nitro-1H-indol-2-yl)-2-methylpropanoate (1.0 g, 2.8 mmol) and (S)-(2,2-dimethyl-1,3-dioxolan-4-yl)methyl 4-methylbenzenesulfonate (3.21 g, 11.2 mmol) in DMF (5.6 mL). The reaction was stirred at 80° C. for 64 hours under nitrogen atmosphere. The mixture was then partitioned between ethyl acetate and water. The aqueous layer was extracted with ethyl acetate. The combined ethyl acetate layers were washed with brine, dried over $MgSO_4$, filtered and concentrated. The crude product, a viscous brown oil which contains both of the products shown above, was taken directly to the next step without further purification. (S)-Benzyl 2-(1-((2,2-dimethyl-1,3-dioxolan-4-yl)methyl)-6-fluoro-5-nitro-1H-indol-2-yl)-2-methylpropanoate, ESI-MS m/z calc. 470.2. found 471.5 $(M+1)^+$. Retention time 2.22 minutes. ((R)-2,2-Dimethyl-1,3-dioxolan-4-yl)methyl 2-(1-(((S)-2,2-dimethyl-1,3-dioxolan-4-yl)methyl)-6-fluoro-5-nitro-1H-indol-2-yl)-2-methylpropanoate, ESI-MS m/z calc. 494.5. found 495.5 $(M+1)^+$. Retention time 2.03 minutes.

Step b: (S)-2-(1-((2,2-Dimethyl-1,3-dioxolan-4-yl)methyl)-6-fluoro-5-nitro-1H-indol-2-yl)-2-methylpropan-1-ol The mixture of crude reaction mixture of (S)-benzyl 2-(1-((2,2-dimethyl-1,3-dioxolan-4-yl)methyl)-6-fluoro-5-nitro-1H-indol-2-yl)-2-methylpropanoate and ((R)-2,2-dimethyl-1,3-dioxolan-4-yl)methyl 2-(1-(((S)-2,2-dimethyl-1,3-dioxolan-4-yl)methyl)-6-fluoro-5-nitro-1H-indol-2-yl)-2-methylpropanoate was dissolved in THF (15 mL) and cooled in an ice-water bath. $LiAlH_4$ (2.8 mL of 1 M solution, 2.8 mmol) was added dropwise. After addition was complete the reaction was stirred for 5 minutes. The reaction was quenched by adding water (0.5 mL), 15% NaOH solution (0.5 mL) and then water (1.5 mL). The mixture was filtered over Celite, and the solids were washed with THF and ethyl acetate. The filtrate was concentrated and purified by column chromatography (30-60% ethyl acetate-hexanes) to obtain the product as a brown oil (505 mg, 49% over 2 steps). ESI-MS m/z calc. 366.4. found 367.3 $(M+1)^+$. Retention time 1.68 minutes. $^1H$ NMR (400 MHz, DMSO-d6) δ 8.34 (d, J=7.6 Hz, 1H), 7.65 (d, J=13.5 Hz, 1H), 6.57 (s, 1H), 4.94 (t, J=5.4 Hz, 1H), 4.64-4.60 (m, 1H), 4.52-4.42 (m, 2H), 4.14 (dd, J=6.2, 8.4 Hz, 1H), 3.74 (dd, J=7.0, 8.3 Hz, 1H), 3.63-3.53 (m, 2H), 1.42 (s, 3H), 1.37 (m, 6H) and 1.19 (s, 3H) ppm.

Step c: (S)-2-(5-amino-1-((2,2-dimethyl-1,3-dioxolan-4-yl)methyl)-6-fluoro-1H-indol-2-yl)-2-methylpropan-1-ol (S)-2-(1-((2,2-dimethyl-1,3-dioxolan-4-yl)methyl)-6-fluoro-5-nitro-1H-indol-2-yl)-2-methylpropan-1-ol (500 mg, 1.4 mmol) was dissolved ethanol (15 mL) and the reaction was flushed with $N_2$. Then Pd—C (50 mg, 5% wt) was added. The reaction was flushed with nitrogen again and then stirred under $H_2$ (atm). After 1 hour only partial conversion to the product was observed by LCMS. The reaction was filtered through Celite and concentrated. The residue was resubjected to the conditions above. After 1 hour LCMS indicated complete conversion to product. The reaction mixture was filtered through Celite. The filtrate was concentrated to yield the product as a black solid (420 mg, 91%). ESI-MS m/z calc. 336.2. found 337.5 (M+1)+. Retention time 0.90 minutes. ¹H NMR (400 MHz, DMSO-d6) δ 7.17 (d, J=12.6 Hz, 1H), 6.76 (d, J=9.0 Hz, 1H), 6.03 (s, 1H), 4.78 (br s, 1H), 4.46 (s, 2H), 4.41-4.27 (m, 3H), 4.06 (dd, J=6.1, 8.3 Hz, 1H), 3.70-3.67 (m, 1H), 3.53 (dd, J=10.7, 17.2 Hz, 2H), 1.40 (s, 3H), 1.32 (s, 6H) and 1.21 (s, 3H) ppm.

Step d: (S)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide DMF (3 drops) was added to a stirring mixture of 1-(2,2-difluorobenzo[d][1,3]dioxol-5-yl)cyclopropanecarboxylic acid (187 mg, 0.8 mmol) and thionyl chloride (0.13 mL, 1.8 mmol). After 30 minutes a clear solution had formed. A small amount was mixed piperidine to test that the acid chloride had been formed. The solution was concentrated on the rotovap and then toluene (1 mL) was added and the mixture was concentrated again. The toluene step was repeated once more and the residue was placed on high vacuum for 10 minutes. The acid chloride was then dissolved in dichloromethane (2 mL) and added to a mixture of (S)-2-(5-amino-1-((2,2-dimethyl-1,3-dioxolan-4-yl)methyl)-6-fluoro-1H-indol-2-yl)-2-methylpropan-1-ol (200 mg, 0.6 mmol) and triethylamine (0.25 mL, 1.8 mmol) in dichloromethane (4 mL). The reaction was stirred at room temperature for 45 minutes. The reaction was washed with 1N HCl solution, saturated NaHCO₃ solution and brine, dried over MgSO₄ and concentrated to yield the product as a black foamy solid (320 mg, 96%). ESI-MS m/z calc. 560.6. found 561.5 (M+1)+. Retention time 2.05 minutes. ¹H NMR (400 MHz, DMSO-d6) δ 8.31 (s, 1H), 7.53 (s, 1H), 7.42-7.40 (m, 2H), 7.34-7.30 (m, 3H), 6.24 (s, 1H), 4.84 (t, J=5.5 Hz, 1H), 4.51-4.46 (m, 1H), 4.41-4.32 (m, 2H), 4.08 (dd, J=6.0, 8.3 Hz, 1H), 3.71-3.67 (m, 1H), 3.58-3.50 (m, 2H), 1.48-1.45 (m, 2H), 1.40 (s, 3H), 1.34-1.33 (m, 6H), 1.18 (s, 3H) and 1.14-1.12 (m, 2H) ppm.

Step e: (S)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (S)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide (290 g, 0.5 mmol) was dissolved in methanol (5 mL). Water (0.5 mL) was added followed by p-TsOH.H₂O (20 mg, 0.1 mmol). The reaction was heated at 80° C. for 45 minutes. The solution was then partitioned between ethyl acetate and saturated NaHCO₃ solution. The ethyl acetate layer was dried over MgSO₄ and concentrated. The residue was purified by column chromatography (50-100% ethyl acetate-hexanes) to yield the product as a cream colored foamy solid. (146 mg, 54%, ee>97% by SFC). ESI-MS m/z calc. 520.5. found 521.5 (M+1)+. Retention time 1.67 minutes. ¹H NMR (400 MHz, DMSO-d6) δ 8.31 (s, 1H), 7.53 (d, J=1.1 Hz, 1H), 7.42-7.37 (m, 2H), 7.33-7.30 (m, 2H), 6.22 (s, 1H), 5.01 (d, J=5.0 Hz, 1H), 4.91 (t, J=5.5 Hz, 1H), 4.75 (t, J=5.8 Hz, 1H), 4.42-4.38 (m, 1H), 4.10 (dd, J=8.8, 15.1 Hz, 1H), 3.90 (s, 1H), 3.64-3.54 (m, 2H), 3.48-3.33 (m, 2H), 1.48-1.45 (m, 2H), 1.35 (s, 3H), 1.32 (s, 3H) and 1.14-1.11 (m, 2H) ppm.

(R)-1-(benzo[d][1,3]-dioxol-5-yl)-N-(2-tert-butyl-1-(2,3-dihydroxypropyl)-6-fluoro-1H-indol-5-yl)cyclopropanecarboxamide

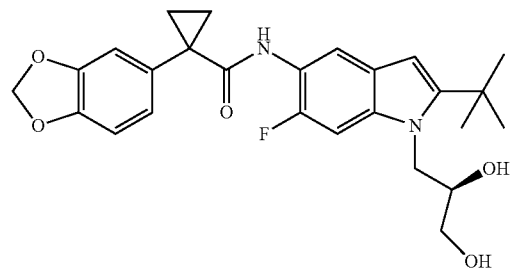 [SMILES: CC(C)(C)c1cc2cc(NC(=O)C3(c4ccc5c(c4)OCO5)CC3)c(F)cc2n1C[C@@H](O)CO]

(R)-1-(benzo[d][1,3]dioxol-5-yl)-N-(2-tert-butyl-1-(2,3-dihydroxypropyl)-6-fluoro-1H-indol-5-yl)cyclopropanecarboxamide was prepared using an experimental procedure similar to example 72 from 1-(benzo[d][1,3]dioxol-5-yl)cyclopropanecarboxylic acid and 2-tert-butyl-6-fluoro-5-nitro-1H-indole.

(S)-1-(benzo[d][1,3]dioxol-5-yl)-N-(2-tert-butyl-1-(2,3-dihydroxypropyl)-6-fluoro-1H-indol-5-yl)cyclopropanecarboxamide

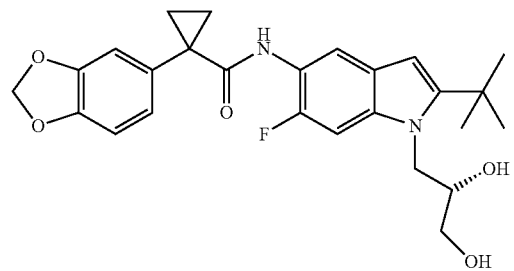

(S)-1-(benzo[d][1,3]dioxol-5-yl)-N-(2-tert-butyl-1-(2,3-dihydroxypropyl)-6-fluoro-1H-indol-5-yl)cyclopropanecarboxamide was prepared using an experimental procedure similar to Example 72 from 1-(benzo[d][1,3]dioxol-5-yl)cyclopropanecarboxylic acid and 2-tert-butyl-6-fluoro-5-nitro-1H-indol.

(R)—N-(2-tert-butyl-1-(2,3-dihydroxypropyl)-1H-indol-5-yl)-1-(3,4-dihydroxyphenyl)cyclopropanecarboxamide

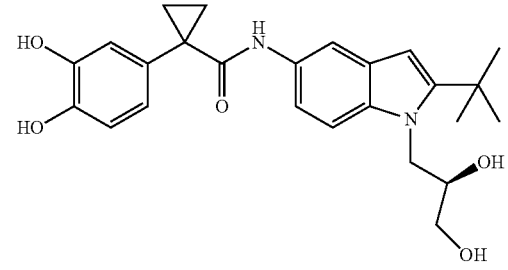 [SMILES: CC(C)(C)c1cc2cc(NC(=O)C3(c4ccc(O)c(O)c4)CC3)ccc2n1C[C@@H](O)CO]

(R)—N-(2-tert-butyl-1-(2,3-dihydroxypropyl)-1H-indol-5-yl)-1-(3,4-dihydroxyphenyl)cyclopropanecarboxamide was prepared using an experimental procedure similar to Example 72 from 1-(3,4-dihydroxyphenyl)cyclopropanecarboxylic acid and 2-tert-butyl-5-nitro-1H-indole.

(R)—N-(2-tert-butyl-1-(2,3-dihydroxypropyl)-1H-indol-5-yl)-1-(2,3-dihydro-1H-inden-5-yl)cyclopropanecarboxamide

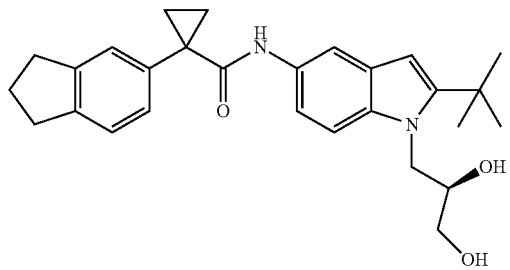 [SMILES: CC(C)(C)c1cc2cc(NC(=O)C3(c4ccc5c(c4)CCC5)CC3)ccc2n1C[C@@H](O)CO]

(R)—N-(2-tert-butyl-1-(2,3-dihydroxypropyl)-1H-indol-5-yl)-1-(2,3-dihydro-1H-inden-5-yl)cyclopropanecarboxamide was prepared using an experimental procedure similar to Example 72 from 1-(2,3-dihydro-1H-inden-5-yl)cyclopropanecarboxylic acid and 2-tert-butyl-5-nitro-1H-indole.

A person skilled in the chemical arts can use the examples and schemes along with known synthetic methodologies to synthesize compounds of the present invention, including the compounds in Table 3, below.

TABLE 3

Physical data of exemplary compounds.

| Compound No. | LC/MS M + 1 | LC/RT Min | NMR |
|---|---|---|---|
| 1 | 373.3 | 2.49 | |
| 2 | 469.4 | 3.99 | |
| 3 | 381.3 | 3.69 | |
| 4 | 448.3 | 1.75 | |
| 5 | 389.3 | 3.3 | |
| 6 | 463 | 1.87 | |
| 7 | 363.3 | 3.7 | |
| 8 | 405.5 | 3.87 | |
| 9 | 487.3 | 2.12 | H NMR (400 MHz, DMSO-d6) 8.65 (s, 1H), 7.55 (d, J = 1.7 Hz, 1H), 7.49 (d, J = 1.4 Hz, 1H), 7.38 (d, J = 8.3 Hz, 1H), 7.30-7.25 (m, 2H), 7.08 (dd, J = 8.8, 1.9 Hz, 1H), 6.11 (s, 1H), 4.31 (t, J = 7.4 Hz, 2H), 3.64 (t, J = 7.3 Hz, 2H), 3.20 (t, J = 7.6 Hz, 2H), 1.92 (t, J = 7.6 Hz, 2H), 1.45 (m, 2H), 1.39 (s, 6H), 1.10 (m, 2H) |
| 10 | 388 | 3.34 | |
| 11 | 452.3 | 2.51 | |
| 12 | 527 | 2.36 | |
| 13 | 498 | 1.85 | |
| 14 | 404.5 | 1.18 | |
| 15 | 369.2 | 3.81 | |
| 16 | 419.2 | 2.24 | |
| 17 | 389.2 | 2.02 | H NMR (400 MHz, DMSO) 8.41 (s, 1H), 7.59 (d, J = 1.8 Hz, 1H), 7.15 (d, J = 8.6 Hz, 1H), 7.06-7.02 (m, 2H), 6.96-6.90 (m, 3H), 6.03 (s, 2H), 5.98 (d, J = 0.7 Hz, 1H), 4.06 (t, J = 6.8 Hz, 2H), 2.35 (t, J = 6.8 Hz, 2H), 1.42-1.38 (m, 2H), 1.34 (s, 6H), 1.05-1.01 (m, 2H) |
| 18 | 395.3 | 3.6 | H NMR (400 MHz, DMSO) 10.91 (s, 1H), 7.99 (s, 1H), 7.67 (d, J = 7.7 Hz, 1H), 7.08-6.92 (m, 4H), 6.09-6.03 (m, 3H), 1.47-1.42 (m, 2H), 1.31 (d, J = 7.3 Hz, 9H), 1.09-1.05 (m, 2H) |
| 19 | 457.2 | 1.97 | H NMR (400 MHz, CD3CN) 7.50 (d, J = 1.9 Hz, 1H), 7.41 (d, J = 1.6 Hz, 2H), 7.36 (dd, J = 1.7, 8.3 Hz, 1H), 7.29-7.24 (m, 2H), 7.02 (dd, J = 2.1, 8.8 Hz, 1H), 6.24 (s, 1H), 4.40 (t, J = 7.1 Hz, 2H), 3.80 (t, J = 7.1 Hz, 2H), 1.59-1.55 (m, 2H), 1.50 (s, 9H), 1.15-1.12 (m, 2H) |
| 20 | 375.5 | 3.71 | |
| 21 | 496 | 206 | |
| 22 | 421.14 | 1.53 | |
| 23 | 363.3 | 3.62 | |
| 24 | 378.5 | 2.66 | |
| 25 | 417.5 | 3.53 | |
| 26 | 454.3 | 3.18 | |
| 27 | 596.2 | 2.58 | |
| 28 | 379.3 | 2.92 | |
| 29 | 481 | 1.69 | |
| 30 | 504.2 | 1.95 | |
| 31 | 517 | 1.92 | |
| 32 | 403.5 | 3.5 | H NMR (400 MHz, DMSO) 10.76 (s, 1H), 8.72 (s, 1H), 7.79 (d, J = 2.3 Hz, 1H), 7.62 (dd, J = 2.4, 8.6 Hz, 1H), 7.55 (d, J = 1.5 Hz, 1H), 7.14 (d, J = 8.6 Hz, 1H), 7.05-7.01 (m, 2H), 6.03 (d, J = 1.6 Hz, 1H), 4.54 (t, J = 6.4 Hz, 2H), 2.79 (t, J = 6.4 Hz, 2H), 1.44 (m, 2H), 1.32 (s, 9H), 1.03 (m, 2H) |
| 33 | 321.3 | 2.98 | |
| 34 | 450.2 | 2.02 | |
| 35 | 395.1 | 3.59 | |
| 36 | 509 | 2.01 | |
| 37 | 447.2 | 2.02 | |
| 38 | 379.1 | 2.16 | H NMR (400 MHz, DMSO) 10.78 (s, 1H), 8.39 (s, 1H), 7.57 (d, J = 1.7 Hz, 1H), 7.17 (d, J = 8.6 Hz, 1H), 7.03-6.90 (m, 4H), 6.12 (d, J = 1.5 Hz, 1H), 6.03 (s, 2H), 5.18 (s, 1H), 1.50 (s, 6H), 1.41-1.38 (m, 2H), 1.05-0.97 (m, 2H) |
| 39 | 373.3 | 3.74 | |
| 40 | 372.8 | 3.8 | |
| 41 | 397.3 | 3.41 | H NMR (400 MHz, DMSO) 11.44 (s, 1H), 8.52 (s, 1H), 7.85 (d, J = 1.2 Hz, 2H), 7.71 (d, J = 1.7 Hz, 1H), 7.47-7.43 (m, 2H), 7.32-7.26 (m, 2H), 7.12 (dd, J = 2.0, 8.7 Hz, 1H), 7.04 (d, J = 1.6 Hz, 1H), 6.97-6.90 (m, 2H), 6.84 (d, J = 1.3 Hz, 1H), 6.03 (s, 2H), 1.43-1.40 (m, 2H), 1.07-1.03 (m, 2H) |
| 42 | 505.3 | 2.23 | H NMR (400 MHz, DMSO-d6) 8.33 (s, 1H), 7.52 (s, 1H), 7.42-7.39 (m, 2H), 7.33-7.25 (m, 2H), 6.14 (s, 1H), 4.99 (s, 1H), 4.31-4.27 (m, 3H), 3.64 (t, J = 7.0 Hz, 2H), 3.20 (t, J = 7.6 Hz, 2H), 1.91 (t, J = 7.6 Hz, 2H), 1.46 (m, 2H), 1.39 (s, 6H), 1.13 (m, 2H) |
| 43 | 505.4 | 1.97 | |
| 44 | 407.7 | 1.76 | H NMR (400 MHz, DMSO) 10.31 (s, 1H), 8.34 (s, 1H), 7.53 (d, J = 1.8 Hz, 1H), 7.03 (d, J = 1.6 Hz, 1H), 6.97-6.90 (m, 3H), 6.05-6.03 (m, 3H), 4.72 (s, 2H), 1.40-1.38 (m, 2H), 1.34 (s, 9H), 1.04-1.00 (m, 2H) |
| 45 | 497.2 | 2.26 | |
| 46 | 391.3 | 3.41 | |
| 47 | 377.5 | 3.48 | |
| 48 | 427.5 | 4.09 | |
| 49 | 402.2 | 3.06 | |

TABLE 3-continued

Physical data of exemplary compounds.

| | | | |
|---|---|---|---|
| 50 | 421.1 | 1.81 | |
| 51 | 407.5 | 3.34 | |
| 52 | 464.3 | 2.87 | |
| 53 | 405.3 | 3.65 | |
| 54 | 375 | 1.84 | |
| 55 | 505.4 | 1.96 | |
| 56 | 335.3 | 3.18 | |
| 57 | 445.2 | 3.27 | |
| 58 | 491 | 1.88 | |
| 59 | 478 | 1.98 | |
| 60 | 413.3 | 3.95 | |
| 61 | 402.5 | 3.71 | |
| 62 | 393.3 | 1.98 | |
| 63 | 407.2 | 2.91 | |
| 64 | 505.4 | 1.98 | |
| 65 | 377.5 | 3.53 | |
| 66 | 417.5 | 4.06 | |
| 67 | 333.3 | 3.53 | |
| 68 | 397.3 | 3.86 | |
| 69 | 506 | 1.67 | |
| 70 | 501 | 2.1 | |
| 71 | 335.3 | 3.22 | |
| 72 | 487 | 1.93 | |
| 73 | 417.5 | 3.88 | |
| 74 | 395 | 1.95 | |
| 75 | 548 | 1.64 | |
| 76 | 418.3 | 2.9 | |
| 77 | 377.3 | 3.87 | |
| 78 | 363.3 | 3.48 | |
| 79 | 476 | 1.8 | |
| 80 | 447.3 | 2.18 | |
| 81 | 492.4 | 2 | |
| 82 | 564.3 | 1.35 | |
| 83 | 467.3 | 1.72 | |
| 84 | 445.2 | 3.08 | |
| 85 | 389.5 | 3.86 | |
| 86 | 374.3 | 3.11 | |
| 87 | 435 | 3.87 | |
| 88 | 465 | 1.89 | |
| 89 | 411.3 | 3.89 | |
| 90 | 449.3 | 3.92 | |
| 91 | 393.3 | 3.12 | |
| 92 | 469.6 | 1.75 | |
| 93 | 476.5 | 2.88 | |
| 94 | 377.5 | 3.41 | |
| 95 | 375.3 | 3.43 | H NMR (400 MHz, DMSO) 10.52 (s, 1H), 8.39 (s, 1H), 7.46 (d, J = 1.8 Hz, 1H), 7.10-6.89 (m, 5H), 6.03 (s, 2H), 2.68-2.65 (m, 2H), 2.56-2.54 (m, 2H), 1.82-1.77 (m, 4H), 1.41-1.34 (m, 2H), 1.04-0.97 (m, 2H) |
| 96 | 346.1 | 3.1 | |
| 97 | 367.3 | 3.72 | |
| 98 | 440.3 | 3.26 | |
| 99 | 393.1 | 3.18 | H NMR (400 MHz, DMSO-d6) 11.80 (s, 1H), 8.64 (s, 1H), 7.83 (m, 1H), 7.33-7.26 (m, 2H), 7.07 (m, 1H), 7.02 (m, 1H), 6.96-6.89 (m, 2H), 6.02 (s, 2H), 4.33 (q, J = 7.1 Hz, 2H), 1.42-1.39 (m, 2H), 1.33 (t, J = 7.1 Hz, 3H), 1.06-1.03 (m, 2H) |
| 100 | 421.3 | 1.85 | H NMR (400 MHz, DMSO) 13.05 (s, 1H), 9.96 (d, J = 1.6 Hz, 1H), 7.89 (d, J = 1.9 Hz, 1H), 7.74 (d, J = 2.0 Hz, 1H), 7.02 (d, J = 1.6 Hz, 1H), 6.96-6.88 (m, 2H), 6.22 (d, J = 2.3 Hz, 1H), 6.02 (s, 2H), 1.43-1.40 (m, 2H), 1.37 (s, 9H), 1.06-1.02 (m, 2H) |
| 101 | 387.5 | 2.51 | |
| 102 | 479 | 3.95 | |
| 103 | 420.3 | 3.12 | |
| 104 | 469.5 | 3.97 | |
| 105 | 391.3 | 2.04 | |
| 106 | 375.2 | 2.82 | |
| 107 | 349.3 | 3.33 | |
| 108 | 503.3 | 1.88 | |
| 109 | 451.5 | 1.59 | |
| 110 | 361.5 | 3.7 | |
| 111 | 391.3 | 3.65 | |
| 112 | 335.3 | 3.03 | |
| 113 | 496.5 | 1.68 | |
| 114 | 381.5 | 3.72 | |
| 115 | 390.3 | 3.22 | |
| 116 | 397.3 | 3.52 | H NMR (400 MHz, DMSO-d6) 11.27 (d, J = 1.9 Hz, 1H), 8.66 (s, 1H), 8.08 (d, J = 1.6 Hz, 1H), 7.65-7.61 (m, 3H), 7.46-7.40 (m, 2H), 7.31 (d, J = 8.7 Hz, 1H), 7.25-7.17 (m, 2H), 7.03 (d, J = 1.6 Hz, 1H), 6.98-6.87 (m, 2H), 6.02 (s, 2H), 1.43-1.39 (m, 2H), 1.06-1.02 (m, 2H) |
| 117 | 377.5 | 3.77 | |
| 118 | 515.3 | 2.3 | |
| 119 | 381.3 | 3.8 | |
| 120 | 464.2 | 2.1 | |
| 121 | 465 | 1.74 | |
| 122 | 395.2 | 3.74 | |
| 123 | 383.3 | 3.52 | |
| 124 | 388.5 | 3.56 | |
| 125 | 411.3 | 3.85 | |
| 126 | 459.2 | 1.53 | H NMR (400 MHz, CD3CN) 9.23 (s, 1H), 7.51-7.48 (m, 2H), 7.19 (d, J = 8.6 Hz, 1H), 7.06-7.03 (m, 2H), 6.95-6.89 (m, 2H), 6.17 (dd, J = 0.7, 2.2 Hz, 1H), 6.02 (s, 2H), 2.61-2.57 (m, 2H), 2.07-2.03 (m, 2H), 1.55-1.51 (m, 2H), 1.39 (s, 6H), 1.12-1.09 (m, 2H) |
| 127 | 408.5 | 2.48 | |
| 128 | 393 | 3.26 | |
| 129 | 420.2 | 2.16 | |
| 130 | 406.3 | 2.88 | |
| 131 | 473.3 | 4.22 | |
| 132 | 417.3 | 3.8 | |
| 133 | 465 | 1.74 | |
| 134 | 464.3 | 2.91 | |
| 135 | 347.3 | 3.42 | |
| 136 | 511 | 2.35 | |
| 137 | 455.5 | 3.29 | |
| 138 | 393.3 | 3.54 | |
| 139 | 335.1 | 3.08 | |
| 140 | 434.5 | 2.35 | |
| 141 | 381.3 | 2.91 | |
| 142 | 431.5 | 3.97 | |
| 143 | 539 | 1.89 | |
| 144 | 515 | 1.89 | |
| 145 | 407.5 | 3.6 | |
| 146 | 379.5 | 1.51 | |
| 147 | 409.3 | 4 | |
| 148 | 392.2 | 1.22 | |
| 149 | 375.3 | 3.37 | |
| 150 | 377.3 | 3.61 | |
| 151 | 377.22 | 3.96 | |
| 152 | 504.5 | 1.99 | |
| 153 | 393.1 | 3.47 | |
| 154 | 363.3 | 3.52 | |
| 155 | 321.3 | 3.13 | |
| 156 | 407.5 | 3.2 | |
| 157 | 406.3 | 1.43 | |
| 158 | 379.3 | 1.89 | |
| 159 | 451 | 3.34 | |
| 160 | 375.3 | 3.82 | |
| 161 | 355.1 | 3.32 | |
| 162 | 475 | 2.06 | |
| 163 | 437.2 | 2.35 | |
| 164 | 379.2 | 2.76 | |
| 165 | 462 | 3.44 | |
| 166 | 465.2 | 2.15 | |
| 167 | 455.2 | 2.45 | |
| 168 | 451 | 1.65 | |
| 169 | 528 | 1.71 | |
| 170 | 374.3 | 3.4 | |
| 171 | 449.5 | 1.95 | |
| 172 | 381.3 | 3.8 | |
| 173 | 346.3 | 2.93 | |
| 174 | 483.1 | 2.25 | |

TABLE 3-continued

Physical data of exemplary compounds.

| # | Mass | RT | NMR |
|---|------|-----|-----|
| 175 | 411.2 | 3.85 | |
| 176 | 431.5 | 4.02 | |
| 177 | 485.5 | 4.02 | |
| 178 | 528.5 | 1.18 | |
| 179 | 473 | 1.79 | |
| 180 | 479 | 2.15 | |
| 181 | 387.5 | 2.56 | |
| 182 | 365.3 | 3.13 | |
| 183 | 493 | 2.3 | |
| 184 | 461.3 | 2.4 | H NMR (400 MHz, DMSO-d6) 10.89 (s, 1H), 8.29 (s, 1H), 7.52 (s, 1H), 7.42-7.37 (m, 2H), 7.32 (dd, J = 8.3, 1.4 Hz, 1H), 7.01 (d, J = 10.9 Hz, 1H), 6.05 (d, J = 1.7 Hz, 1H), 4.29 (t, J = 5.0 Hz, 1H), 3.23 (m, 2H), 1.81 (t, J = 7.7 Hz, 2H), 1.46 (m, 2H), 1.29 (s, 6H), 1.13 (m, 2H) |
| 185 | 377.5 | 3.63 | |
| 186 | 464 | 1.46 | |
| 187 | 339.1 | 3.2 | |
| 188 | 435.5 | 1.64 | |
| 189 | 392.3 | 2.18 | |
| 190 | 435.5 | 3.67 | H NMR (400 MHz, DMSO) 11.83 (s, 1H), 10.76 (s, 1H), 8.53 (s, 1H), 7.93 (d, J = 1.8 Hz, 1H), 7.60 (dd, J = 2.3, 8.5 Hz, 1H), 7.53 (d, J = 1.4 Hz, 1H), 7.14 (d, J = 8.6 Hz, 1H), 7.02-6.97 (m, 2H), 6.02 (d, J = 1.5 Hz, 1H), 3.71 (t, J = 6.2 Hz, 2H), 3.37 (t, J = 6.2 Hz, 2H), 3.25 (s, 3H), 1.44 (m, 2H), 1.32 (s, 9H), 1.08 (m, 2H) |
| 191 | 421.3 | 3.32 | |
| 192 | 404.4 | 0.95 | |
| 193 | 451 | 1.71 | |
| 194 | 465 | 1.69 | |
| 195 | 434.2 | 2.29 | |
| 196 | 363.3 | 3.4 | |
| 197 | 501 | 1.91 | |
| 198 | 411.2 | 3.14 | |
| 199 | 439 | 1.89 | |
| 200 | 434.4 | 1.53 | |
| 201 | 462 | 3.22 | |
| 202 | 351.3 | 2.59 | |
| 203 | 495.2 | 2.71 | |
| 204 | 435 | 3.94 | |
| 205 | 397.3 | 3.69 | |
| 206 | 493 | 2.26 | |
| 207 | 487 | 1.87 | |
| 208 | 391.3 | 2.94 | |
| 209 | 397.2 | 3.3 | |
| 210 | 487.2 | 1.85 | H NMR (400 MHz, CD3CN) 7.50 (d, J = 2.0 Hz, 1H), 7.41 (d, J = 1.6 Hz, 2H), 7.37-7.32 (m, 2H), 7.25 (d, J = 8.3 Hz, 1H), 6.98 (dd, J = 2.1, 8.8 Hz, 1H), 6.27 (d, J = 0.6 Hz, 1H), 4.40-4.28 (m, 2H), 4.12-4.06 (m, 1H), 3.59-3.51 (m, 2H), 1.59-1.50 (m, 2H), 1.47 (s, 9H), 1.15-1.12 (m, 2H) |
| 211 | 381.3 | 3.69 | |
| 212 | 461 | 2.04 | |
| 213 | 469 | 1.72 | |
| 214 | 363.3 | 3.48 | |
| 215 | 432.3 | 3.07 | |
| 216 | 403.5 | 3.94 | |
| 217 | 420.4 | 1.27 | |
| 218 | 475 | 2.2 | |
| 219 | 484.3 | 1.84 | |
| 220 | 419.3 | 3.87 | |
| 221 | 486.3 | 0.91 | |
| 222 | 391.3 | 3.01 | |
| 223 | 398.3 | 1.3 | |
| 224 | 349.2 | 2.54 | |
| 225 | 375.5 | 3.74 | |
| 226 | 377.5 | 3.47 | H NMR (400 MHz, DMSO-d6) 10.76 (s, 1H), 8.39 (s, 1H), 7.55 (s, 1H), 7.15-7.13 (m, 1H), 7.03-6.89 (m, 4H), 6.03 (m, 3H), 1.41-1.38 (m, 2H), 1.32 (s, 9H), 1.04-1.01 (m, 2H) |
| 227 | 393.3 | 2.03 | |
| 228 | 398.3 | 1.24 | |
| 229 | 487.2 | 1.78 | |
| 230 | 361.1 | 3.47 | |
| 231 | 435.5 | 2.12 | |
| 232 | 321.3 | 2.91 | |
| 233 | 413.3 | 3.77 | |
| 234 | 393.3 | 1.58 | |
| 235 | 465 | 1.92 | |
| 236 | 361.3 | 3.18 | |
| 237 | 421 | 1.8 | |
| 238 | 405.5 | 3.79 | |
| 239 | 544.3 | 1.4 | |
| 240 | 405.3 | 3.9 | |
| 241 | 462 | 1.74 | |
| 242 | 550 | 1.68 | |
| 243 | 395.2 | 1.98 | |
| 244 | 517.3 | 1.94 | |
| 245 | 372.2 | 3.59 | |
| 246 | 361.3 | 3.58 | |
| 247 | 490 | 1.95 | |
| 248 | 407.3 | 1.52 | H NMR (400 MHz, DMSO) 10.74 (d, J = 1.2 Hz, 1H), 8.40 (s, 1H), 7.54 (d, J = 1.8 Hz, 1H), 7.15 (d, J = 8.6 Hz, 1H), 7.03-6.90 (m, 4H), 6.03-6.00 (m, 3H), 3.26-3.22 (m, 2H), 1.85-1.80 (m, 2H), 1.41-1.38 (m, 2H), 1.31 (s, 6H), 1.05-1.01 (m, 2H) |
| 249 | 393.3 | 3.32 | |
| 250 | 406.2 | 2.08 | |
| 251 | 511 | 2.39 | |
| 252 | 379.3 | 3.3 | |
| 253 | 383 | 3.46 | |
| 254 | 401.2 | 3.26 | |
| 255 | 398.3 | 1.38 | |
| 256 | 512.5 | 1.96 | |
| 257 | 389.2 | 3.05 | |
| 258 | 321.3 | 3.02 | |
| 259 | 392.1 | 2.74 | |
| 260 | 462 | 1.81 | |
| 261 | 453 | 1.91 | |
| 262 | 349.3 | 3.22 | |
| 263 | 391.1 | 3.67 | H NMR (400 MHz, DMSO) 1.01-1.05 (dd, J = 4.0, 6.7 Hz, 2H), 1.41-1.39 (m, 11H), 3.81 (s, 3H), 6.03 (s, 2H), 6.15 (s, 1H), 6.96-6.90 (m, 2H), 7.02 (d, J = 1.6 Hz, 1H), 7.09 (dd, J = 2.0, 8.8 Hz, 1H), 7.25 (d, J = 8.8 Hz, 1H), 7.60 (d, J = 1.9 Hz, 1H), 8.46 (s, 1H) |
| 264 | 421.3 | 1.66 | H NMR (400 MHz, CD3CN) 8.78 (s, 1H), 7.40 (m, 1H), 7.33 (s, 1H), 7.08 (m, 1H), 6.95-6.87 (m, 3H), 6.79 (m, 1H), 5.91 (s, 2H), 3.51 (dd, J = 5.9, 7.8 Hz, 2H), 2.92-2.88 (m, 2H), 2.64 (t, J = 5.8 Hz, 1H), 1.50 (m, 2H), 1.41 (s, 9H), 1.06 (m, 2H) |
| 265 | 475 | 2.15 | |
| 266 | 347.3 | 3.32 | |
| 267 | 420.5 | 1.81 | |
| 268 | 416.2 | 1.76 | |
| 269 | 485 | 2.06 | |
| 270 | 395.3 | 3.89 | |
| 271 | 492 | 1.59 | |
| 272 | 405.5 | 3.96 | |
| 273 | 547.2 | 1.65 | |
| 274 | 631.6 | 1.91 | |
| 275 | 590.4 | 2.02 | |
| 276 | 465.7 | 1.79 | |
| 277 | 411.3 | 2.14 | |
| 278 | 385.3 | 1.99 | |
| 279 | 425.3 | 2.19 | |
| 280 | 473.2 | 1.74 | |
| 281 | 469.4 | 2.02 | H NMR (400 MHz, DMSO) 8.82 (s, 1H), 7.84 (d, J = 1.7 Hz, 1H), 7.55-7.51 |

TABLE 3-continued

Physical data of exemplary compounds.

| Cmpd. No. | LC/MS M + 1 | LC/RT Min | NMR |
|---|---|---|---|
| | | | (m, 2H), 7.40-7.35 (m, 2H), 7.29 (dd, J = 1.7, 8.3 Hz, 1H), 7.04 (s, 1H), 4.98 (t, J = 5.6 Hz, 1H), 4.27 (t, J = 6.1 Hz, 2H), 3.67 (q, J = 6.0 Hz, 2H), 1.48 (dd, J = 4.0, 6.7 Hz, 2H), 1.13 (dd, J = 4.1, 6.8 Hz, 2H) |
| 282 | 644.4 | 1.83 | |
| 283 | 544.6 | 1.97 | |
| 284 | 465.4 | 1.56 | |
| 285 | 485.2 | 1.8 | |
| 286 | 475.2 | 1.87 | |
| 287 | 564.2 | 1.95 | |
| 288 | 512.5 | 1.89 | H NMR (400 MHz, DMSO) 8.77 (s, 1H), 7.97 (s, 1H), 7.51 (s, 1H), 7.43-7.40 (m, 2H), 7.33 (d, J = 8.2 Hz, 1H), 6.36 (s, 1H), 4.99-4.97 (m, 2H), 4.52 (d, J = 13.1 Hz, 1H), 4.21 (dd, J = 9.2, 15.2 Hz, 1H), 3.86 (m, 1H), 3.51-3.36 (m, 2H), 1.51-1.48 (m, 2H), 1.43 (s, 9H), 1.17-1.15 (m, 2H) |
| 289 | 437.3 | 1.6 | |
| 290 | 499.5 | 1.81 | H NMR (400 MHz, DMSO) 8.82 (s, 1H), 7.83 (d, J = 1.7 Hz, 1H), 7.55-7.50 (m, 2H), 7.39-7.28 (m, 3H), 7.03 (s, 1H), 4.97 (d, J = 5.6 Hz, 1H), 4.83 (t, J = 5.6 Hz, 1H), 4.33 (dd, J = 3.4, 15.1 Hz, 1H), 4.09 (dd, J = 8.7, 15.1 Hz, 1H), 3.80-3.78 (m, 1H), 3.43-3.38 (m, 1H), 3.35-3.30 (m, 1H), 1.49-1.46 (m, 2H), 1.14-1.11 (m, 2H) |
| 291 | 455.4 | 2.02 | H NMR (400 MHz, DMSO) 8.62 (s, 1H), 7.56 (s, 1H), 7.50 (s, 1H), 7.38 (d, J = 8.3 Hz, 1H), 7.29 (dd, J = 1.5, 8.3 Hz, 1H), 7.23 (d, J = 8.7 Hz, 1H), 7.06 (dd, J = 1.7, 8.7 Hz, 1H), 6.19 (s, 1H), 4.86 (t, J = 5.4 Hz, 1H), 4.03 (t, J = 6.1 Hz, 2H), 3.73 (qn, J = 8.5 Hz, 1H), 3.57 (q, J = 5.9 Hz, 2H), 2.39-2.33 (m, 2H), 2.18-1.98 (m, 3H), 1.88-1.81 (m, 1H), 1.47-1.44 (m, 2H), 1.11-1.09 (m, 2H) |
| 292 | 578.4 | 1.99 | |
| 293 | 630.4 | 1.8 | |
| 294 | 443.4 | 1.98 | H NMR (400 MHz, DMSO) 8.62 (s, 1H), 7.55 (d, J = 1.8 Hz, 1H), 7.50 (d, J = 1.5 Hz, 1H), 7.38 (d, J = 8.3 Hz, 1H), 7.30-7.24 (m, 2H), 7.05 (dd, J = 2.0, 8.8 Hz, 1H), 6.13 (s, 1H), 4.88 (t, J = 5.5 Hz, 1H), 4.14 (t, J = 6.1 Hz, 2H), 3.61 (m, 2H), 3.21 (septet, J = 6.8 Hz, 1H), 1.47-1.44 (m, 2H), 1.26 (d, J = 6.8 Hz, 6H), 1.11-1.08 (m, 2H) |
| 295 | 482.3 | 2 | H NMR (400 MHz, DMSO) 8.78 (s, 1H), 7.92 (s, 1H), 7.51 (s, 1H), 7.45 (s, 1H), 7.41 (d, J = 8.3 Hz, 1H), 7.33 (d, J = 8.4 Hz, 1H), 6.34 (s, 1H), 5.01 (t, J = 5.7 Hz, 1H), 4.41 (t, J = 6.6 Hz, 2H), 3.68 (m, 2H), 1.51-1.47 (m, 2H), 1.42 (s, 9H), 1.19-1.15 (m, 2H) |
| 296 | 438.7 | 2.12 | H NMR (400 MHz, DMSO) 11.43 (s, 1H), 8.74 (s, 1H), 7.63 (s, 1H), 7.51 (s, 1H), 7.45-7.40 (m, 2H), 7.33 (dd, J = 1.4, 8.3 Hz, 1H), 6.25 (d, J = 1.5 Hz, 1H), 1.51-1.48 (m, 2H), 1.34 (s, 9H), 1.17-1.14 (m, 2H) |
| 297 | 449.3 | 1.6 | |
| 298 | 517.5 | 1.64 | |
| 299 | 391.5 | 2.05 | |
| 300 | 449.3 | 1.59 | |
| 301 | 501.2 | 1.93 | |
| 302 | 503.5 | 1.63 | |
| 303 | 437.3 | 1.6 | |
| 304 | 425.1 | 2.04 | H NMR (400 MHz, DMSO) 12.16 (s, 1H), 8.80 (s, 1H), 7.83 (s, 1H), 7.51 (d, J = 1.4 Hz, 1H), 7.39-7.28 (m, 4H), 6.95 (s, 1H), 1.48 (dd, J = 4.0, 6.6 Hz, 2H), 1.13 (dd, J = 4.0, 6.7 Hz, 2H) |
| 305 | 459.2 | 1.67 | |
| 306 | 558.4 | 2.05 | |
| 307 | 447.5 | 1.93 | |
| 308 | 516.7 | 1.69 | $^1$H NMR (400 MHz, DMSO-d6) δ 8.32 (s, 1H), 7.53 (s, 1H), 7.43-7.31 (m, 4H), 6.19 (s, 1H), 4.95-4.93 (m, 2H), 4.51 (d, J = 5.0 Hz, 1H), 4.42-4.39 (m, 2H), 4.10-4.04 (m, 1H), 3.86 (s, 1H), 3.49-3.43 (m, 2H), 3.41-3.33 (m, 1H), 3.30-3.10 (m, 6H), 2.02-1.97 (m, 2H), 1.48-1.42 (m, 8H) and 1.13 (dd, J = 4.0, 6.7 Hz, 2H) ppm |
| 309 | 535.7 | 1.79 | 1H NMR (400.0 MHz, DMSO) δ 8.43 (s, 1H), 7.53 (s, 1H), 7.45-7.41 (m, 2H), 7.36-7.31 (m, 2H), 6.27 (s, 1H), 4.74-4.70 (m, 2H), 3.57-3.53 (m, 2H), 3.29 (s, 9H), 1.48-1.42 (m, 11H), and 1.15 (dd, J = 3.9, 6.8 Hz, 2H) ppm. |
| 310 | 609.5 | 1.64 | |
| 311 | 535.7 | 1.7 | $^1$H NMR (400 MHz, DMSO-d6) δ 8.32 (s, 1H), 7.53 (d, J = 1.0 Hz, 1H), 7.43-7.31 (m, 4H), 6.17 (s, 1H), 4.97-4.92 (m, 2H), 4.41 (dd, J = 2.4, 15.0 Hz, 1H), 4.23 (t, J = 5.0 Hz, 1H), 4.08 (dd, J = 8.6, 15.1 Hz, 1H), 3.87 (s, 1H), 3.48-3.44 (m, 1H), 3.41-3.33 (m, 1H), 3.20 (dd, J = 7.4, 12.7 Hz, 2H), 1.94-1.90 (m, 2H), 1.48-1.45 (m, 2H), 1.42 (s, 3H), 1.41 (s, 3H) and 1.15-1.12 (m, 2H) ppm. |
| 312 | 443 | 2.31 | $^1$H NMR (400 MHz, DMSO-d6) δ 8.93 (s, 1H), 7.71 (d, J = 8.8 Hz, 1H), 7.51 (s, 1H), 7.42 (d, J = 8.3 Hz, 1H), 7.33 (d, J = 1.6 Hz, 1H), 7.08 (d, J = 8.8 Hz, 1H), 6.28 (s, 1H), 5.05 (t, J = 5.6 Hz, 1H), 4.42 (t, J = 6.8 Hz, 2H), 3.70-3.65 (m, 2H), 1.51-1.48 (m, 2H), 1.44 (s, 9H), 1.19-1.16 (m, 2H) ppm |
| 313 | 521.5 | 1.69 | 1H NMR (400.0 MHz, CD3CN) δ 7.69 (d, J = 7.7 Hz, 1H), 7.44 (d, J = 1.6 Hz, 1H), 7.39 (dd, J = 1.7, 8.3 Hz, 1H), 7.31 (s, 1H), 7.27 (d, J = 8.3 Hz, 1H), 7.20 (d, J = 12.0 Hz, 1H), 6.34 (s, 1H), 4.32 (d, J = 6.8 Hz, 2H), 4.15-4.09 (m, 1H), 3.89 (dd, J = 6.0, 11.5 Hz, 1H), 3.63-3.52 (m, 3H), 3.42 (d, J = 4.6 Hz, 1H), 3.21 (dd, J = 6.2, 7.2 Hz, 1H), 3.04 (t, J = 5.8 Hz, 1H), 1.59 (dd, J = 3.8, 6.8 Hz, 2H), 1.44 (s, 3H), 1.33 (s, 3H) and 1.18 (dd, J = 3.7, 6.8 Hz, 2H) ppm |
| 314 | 447.5 | 1.86 | $^1$H NMR (400 MHz, DMSO-d6) δ 8.20 (d, J = 7.6 Hz, 1H), 7.30-7.25 (m, 3H), 7.20 (m, 1H), 7.12 (d, J = 8.2 Hz, 1H), 6.84 (d, J = 11.1 Hz, 1H), 6.01 (d, J = 0.5 Hz, 1H), 3.98 (t, J = 6.8 Hz, 2H), 2.37 (t, J = 6.8 Hz, 2H), 1.75 (dd, J = 3.8, 6.9 Hz, 2H), 1.37 (s, 6H) and 1.14 (dd, J = 3.9, 6.9 Hz, 2H) ppm. |
| 315 | 482.5 | 1.99 | H NMR (400 MHz, DMSO) 8.93 (s, 1H), 7.71 (d, J = 8.8 Hz, 1H), 7.51 (s, 1H), 7.42 (d, J = 8.3 Hz, 1H), 7.33 |

TABLE 3-continued

Physical data of exemplary compounds.

| | | | |
|---|---|---|---|
| | | | (d, J = 1.6 Hz, 1H), 7.08 (d, J = 8.8 Hz, 1H), 6.28 (s, 1H), 5.05 (t, J = 5.6 Hz, 1H), 4.42 (t, J = 6.8 Hz, 2H), 3.70-3.65 (m, 2H), 1.51-1.48 (m, 2H), 1.44 (s, 9H), 1.19-1.16 (m, 2H) |
| 316 | 438.7 | 2.1 | H NMR (400 MHz, DMSO) 11.48 (s, 1H), 8.88 (s, 1H), 7.52 (d, J = 8.5 Hz, 2H), 7.41 (d, J = 8.3 Hz, 1H), 7.32 (dd, J = 1.5, 8.3 Hz, 1H), 7.03 (d, J = 8.6 Hz, 1H), 6.21 (d, J = 1.8 Hz, 1H), 1.51-1.49 (m, 2H), 1.36 (s, 9H), 1.18-1.16 (m, 2H) ppm. |
| 317 | 439.4 | 1.36 | |
| 318 | 469.016 | 1.66 | |
| 319 | 469.016 | 1.66 | |
| 320 | 465.7 | 1.79 | H NMR (400 MHz, DMSO) 9.26 (s, 1H), 7.65 (d, J = 1.9 Hz, 1H), 7.49 (d, J = 8.7 Hz, 2H), 7.36 (d, J = 8.9 Hz, 1H), 7.11 (dd, J = 1.9, 8.9 Hz, 1H), 6.89 (d, J = 8.8 Hz, 2H), 6.14 (s, 1H), 4.42-4.37 (m, 1H), 4.16-4.10 (m, 1H), 3.90-3.88 (m, 1H), 3.73 (s, 3H), 3.46-3.42 (m, 2H), 1.41 (s, 9H), 1.36 (d, J = 5.0 Hz, 1H), 1.21 (s, 3H), 0.99 (d, J = 5.0 Hz, 1H), 0.84 (s, 3H) |
| 321 | 391.5 | 2.05 | H NMR (400 MHz, DMSO) 10.73 (s, 1H), 9.23 (s, 1H), 7.61 (d, J = 1.5 Hz, 1H), 7.49 (d, J = 8.8 Hz, 2H), 7.13 (s, 1H), 7.10 (d, J = 1.9 Hz, 1H), 6.88 (d, J = 8.8 Hz, 2H), 6.02 (d, J = 1.8 Hz, 1H), 3.73 (s, 3H), 1.36 (d, J = 5.0 Hz, 1H), 1.31 (s, 9H), 1.22 (s, 3H), 0.98 (d, J = 5.0 Hz, 1H), 0.84 (s, 3H) |
| 322 | 521.5 | 1.67 | 1H NMR (400.0 MHz, DMSO) d 8.31 (s, 1H), 7.53 (d, J = 1.1 Hz, 1H), 7.42-7.37 (m, 2H), 7.33-7.30 (m, 2H), 6.22 (s, 1H), 5.01 (d, J = 5.0 Hz, 1H), 4.91 (t, J = 5.5 Hz, 1H), 4.75 (t, J = 5.8 Hz, 1H), 4.42-4.38 (m, 1H), 4.10 (dd, J = 8.8, 15.1 Hz, 1H), 3.90 (s, 1H), 3.64-3.54 (m, 2H), 3.48-3.33 (m, 2H), 1.48-1.45 (m, 2H), 1.35 (s, 3H), 1.32 (s, 3H) and 1.14-1.11 (m, 2H) ppm |

Assays for Detecting and Measuring ΔF508-CFTR Correction Properties of Compounds Membrane potential optical methods for assaying ΔF508-CFTR modulation properties of compounds.

The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Correction Compounds

To identify small molecules that correct the trafficking defect associated with ΔF508-CFTR; a single-addition HTS assay format was developed. Assay Plates containing cells are incubated for ~2-4 hours in tissue culture incubator at 37° C., 5% $CO_2$, 90% humidity. Cells are then ready for compound exposure after adhering to the bottom of the assay plates.

The cells were incubated in serum-free medium for 16-24 hrs in tissue culture incubator at 37° C., 5% $CO_2$, 90% humidity in the presence or absence (negative control) of test compound. The cells were subsequently rinsed 3× with Krebs Ringers solution and loaded with a voltage sensing redistribution dye. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation and the resulting membrane depolarization was optically monitored using voltage sensor dyes.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl⁻ ion gradient in conjunction with channel activation with forskolin in a single liquid addition step using a fluoresecent plate reader such as FLIPR III after the cells have previously been treated with potentiator compounds (or DMSO vehicle control) and subsequently loaded with a redistribution dye.

Solutions:

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 are substituted with gluconate salts.

Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours.

Electrophysiological Assays for assaying ΔF508-CFTR modulation properties of compounds.

1. Ussing Chamber Assay

Ussing chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) *In Vitro Cell. Dev. Biol.* 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Ussing chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, IA). Briefly, HBE were examined under voltage-clamp recording conditions ($V_{hold}$=0 mV) at 37° C. The basolateral solution contained (in mM) 145 NaCl, 0.83 $K_2HPO_4$, 3.3

KH$_2$PO$_4$, 1.2 MgCl$_2$, 1.2 CaCl$_2$, 10 Glucose, 10 HEPES (pH adjusted to 7.35 with NaOH) and the apical solution contained (in mM) 145 NaGluconate, 1.2 MgCl$_2$, 1.2 CaCl$_2$, 10 glucose, 10 HEPES (pH adjusted to 7.35 with NaOH).

Identification of Correction Compounds

Typical protocol utilized a basolateral to apical membrane Cl$^-$ concentration gradient. To set up this gradient, normal ringer was used on the basolateral membrane, whereas apical NaCl was replaced by equimolar sodium gluconate (titrated to pH 7.4 with NaOH) to give a large Cl$^-$ concentration gradient across the epithelium. All experiments were performed with intact monolayers. To fully activate ΔF508-CFTR, forskolin (10 μM), PDE inhibitor, IBMX (100 μM) and CFTR potentiator, genistein (50 μM) were added to the apical side.

As observed in other cell types, incubation at low temperatures of FRT cells and human bronchial epithelial cells isolated from diseased CF patients (CF-HBE) expressing ΔF508-CFTR increases the functional density of CFTR in the plasma membrane. To determine the activity of correction compounds, the cells were incubated with test compound for 24-48 hours at 37° C. and were subsequently washed 3× prior to recording. The cAMP- and genistein-mediated I$_{SC}$ in compound-treated cells was normalized to 37° C. controls and expressed as percentage activity of CFTR activity in wt-HBE. Preincubation of the cells with the correction compound significantly increased the cAMP- and genistein-mediated I$_{SC}$ compared to the 37° C. controls.

Identification of Potentiator Compounds

Typical protocol utilized a basolateral to apical membrane CF concentration gradient. To set up this gradient, normal ringers was used on the basolateral membrane, whereas apical NaCl was replaced by equimolar sodium gluconate (titrated to pH 7.4 with NaOH) to give a large CF concentration gradient across the epithelium. Forskolin (10 μM) and all test compounds were added to the apical side of the cell culture inserts. The efficacy of the putative ΔF508-CFTR potentiators was compared to that of the known potentiator, genistein.

2. Patch-clamp Recordings

Total CF current in ΔF508-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 MgCl$_2$, 2 CaCl$_2$, 10 EGTA, 10 HEPES, and 240 μg/ml amphotericin-B (pH adjusted to 7.35 with HCl). The extracellular medium contained (in mM) 150 NMDG-Cl, 2 MgCl$_2$, 2 CaCl$_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 μM forskolin and 20 μM genistein were added to the bath and the current-voltage relation was monitored every 30 sec.

Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 μM of correction compounds significantly increased the cAMP- and genistein-dependent current compared to the 37° C. controls.

Identification of Potentiator Compounds

The ability of ΔF508-CFTR potentiators to increase the macroscopic ΔF508-CFTR current (I$_{\Delta F508}$) in NIH3T3 cells stably expressing ΔF508-CFTR was also investigated using perforated-patch-recording techniques. The potentiators identified from the optical assays evoked a dose-dependent increase in IΔ$_{F508}$ with similar potency and efficacy observed in the optical assays. In all cells examined, the reversal potential before and during potentiator application was around −30 mV, which is the calculated E$_{Cl}$ (−28 mV).

Cell Culture

NIH3T3 mouse fibroblasts stably expressing ΔF508-CFTR are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) *Nature* 354, 526-528) using an Axopatch 200B patch-clamp amplifier (Axon Instruments Inc.). The pipette contained (in mM): 150 NMDG, 150 aspartic acid, 5 CaCl$_2$, 2 MgCl$_2$, and 10 HEPES (pH adjusted to 7.35 with Tris base). The bath contained (in mM): 150 NMDG-Cl, 2 MgCl$_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability (P$_o$) were determined from 120 sec of channel activity. The P$_o$ was determined using the Bio-Patch software or from the relationship P$_o$=I/i(N), where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

The compounds of Table 1 were found to exhibit Correction activity as measured in the assay described above.

Compounds of the invention are useful as modulators of ATP binding cassette transporters. Using the procedures described above, the activities, i.e., EC50s, of compounds of the present invention have been measured to be from about 3.8 nM to about 13.5 μM. Furthermore, using those methods described above, the efficacies of compounds of the present invention have been measured to be from about 35% to about 110%.

In Table 4, the following meanings apply:

EC50: "+++" means <2 uM; "++" means between 2 uM to 5 uM; "+" means between 5 uM to 25 uM.

% Efficacy: "+" means <25%; "++" means between 25% and 100%; "+++" means >100%.

TABLE 4

| Cmpd. No. | EC50 | Binned EC50 | Max Efficacy | Binned Max Efficacy |
|---|---|---|---|---|
| 307 | 0.981 | +++ | 160 | +++ |
| 308 | 3.095 | ++ | 100 | +++ |
| 309 | 0.0381 | +++ | 122 | +++ |
| 310 | 0.1595 | +++ | 120.5 | +++ |
| 311 | 0.08175 | +++ | 126 | +++ |
| 312 | 0.181 | +++ | 117.5 | +++ |
| 313 | 0.2835 | +++ | 102 | +++ |
| 314 | 0.2285 | +++ | 124.5 | +++ |
| 315 | 0.272 | +++ | 106 | +++ |
| 316 | 0.285 | +++ | 126.5 | +++ |
| 317 | 4.525 | ++ | 65.5 | ++ |

TABLE 4-continued

| Cmpd. No. | EC50 | Binned EC50 | Max Efficacy | Binned Max Efficacy |
|---|---|---|---|---|
| 318 | 0.06595 | +++ | 132 | +++ |
| 319 | 0.03905 | +++ | 125.5 | +++ |
| 320 | 4.315 | ++ | 94 | ++ |
| 321 | 1.81 | +++ | 76 | ++ |
| 322 | | | | None |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of treating male infertility or pancreatic insufficiency in a patient, comprising the step of administering to said patient a compound which is:

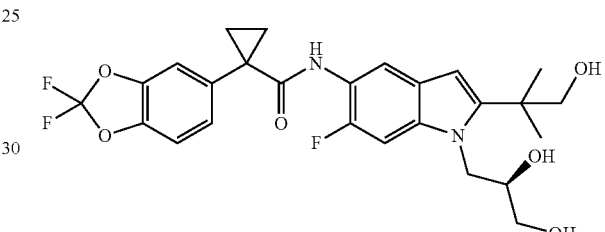

or a pharmaceutically acceptable salt thereof.

2. The method of claim 1, wherein the patient has male infertility.

3. The method of claim 1, wherein the patient has pancreatic insufficiency.

* * * * *